United States Patent
Umetani et al.

(10) Patent No.: US 10,299,477 B2
(45) Date of Patent: May 28, 2019

(54) PYRIDONE COMPOUNDS AND AGRICULTURAL AND HORTICULTURAL FUNGICIDES CONTAINING SAID COMPOUNDS AS ACTIVE INGREDIENT

(71) Applicant: MITSUI CHEMICALS AGRO, INC., Chuo-ku, Tokyo (JP)

(72) Inventors: Hideki Umetani, Ritto (JP); Hideaki Ikishima, Chiba (JP); Ryohei Naito, Moriyama (JP); Toshiyuki Kouno, Chiba (JP); Takeshi Fukumoto, Chiba (JP); Satoshi Yutani, Kusatsu (JP); Toshiaki Ohara, Moriyama (JP); Akihiro Nishida, Chiba (JP)

(73) Assignee: MITSUI CHEMICALS AGRO, INC., Chuo-Ku, Tokyo (JP)

( * ) Notice: Subject to any disclaimer, the term of this patent is extended or adjusted under 35 U.S.C. 154(b) by 0 days.

(21) Appl. No.: 15/765,809

(22) PCT Filed: Oct. 6, 2016

(86) PCT No.: PCT/JP2016/079723
§ 371 (c)(1),
(2) Date: Apr. 4, 2018

(87) PCT Pub. No.: WO2017/061525
PCT Pub. Date: Apr. 13, 2017

(65) Prior Publication Data
US 2018/0279614 A1    Oct. 4, 2018

(30) Foreign Application Priority Data
Oct. 9, 2015  (JP) ................. 2015-201578

(51) Int. Cl.
| | | |
|---|---|---|
| *C07F 7/12* | (2006.01) |
| *A01N 43/40* | (2006.01) |
| *A01N 47/02* | (2006.01) |
| *A01N 47/40* | (2006.01) |
| *A01N 55/00* | (2006.01) |
| *C07D 211/84* | (2006.01) |
| *C07D 211/86* | (2006.01) |
| *C07D 213/64* | (2006.01) |
| *C07D 213/70* | (2006.01) |
| *C07D 401/04* | (2006.01) |
| *C07D 405/12* | (2006.01) |

(52) U.S. Cl.
CPC ............ *A01N 43/40* (2013.01); *A01N 47/02* (2013.01); *A01N 47/40* (2013.01); *A01N 55/00* (2013.01); *C07D 211/84* (2013.01); *C07D 211/86* (2013.01); *C07D 213/64* (2013.01); *C07D 213/70* (2013.01); *C07D 401/04* (2013.01); *C07D 405/12* (2013.01); *C07F 7/12* (2013.01)

(58) Field of Classification Search
None
See application file for complete search history.

(56) References Cited

U.S. PATENT DOCUMENTS

| 6,200,982 B1 | 3/2001 | Collins et al. |
| 2001/0018438 A1 | 8/2001 | Collins et al. |
| 2005/0182103 A1 | 8/2005 | Finke et al. |
| 2008/0269279 A1 | 10/2008 | Clements et al. |

FOREIGN PATENT DOCUMENTS

| EP | 0 308 020 A2 | 3/1989 |
| JP | H01-128969 A | 5/1989 |
| JP | H02-121970 A | 5/1990 |
| JP | 2002-503244 A | 1/2002 |
| JP | 2005-531520 A | 10/2005 |
| JP | 2010-523665 A | 7/2010 |
| WO | WO 98/55480 A1 | 12/1998 |

OTHER PUBLICATIONS

Yu et al, Organic Letters, vol. 16, pp. 2146-2149 (Year: 2014).*
International Search Report (PCT/ISA/210) dated Jan. 10, 2017, by the Japanese Patent Office as the International Searching Authority for International Application No. PCT/JP2016/079723.
Written Opinion (PCT/ISA/237) dated Jan. 10, 2017, by the Japanese Patent Office as the International Searching Authority for International Application No. PCT/JP2016/079723.

* cited by examiner

*Primary Examiner* — Zinna Northington Davis
(74) *Attorney, Agent, or Firm* — Buchanan, Ingersoll & Rooney PC

(57) ABSTRACT

A compound represented by Formula (1) or a salt thereof is provided. R1 represents a C1-C6 alkyl group optionally substituted, a C1-C6 haloalkyl group or the like, R2 represents a halogen atom, a C1-C6 alkyl group optionally substituted, a C1-C6 alkyloxy group optionally substituted or the like, R3 represents a hydrogen atom, a halgenatom, C1-C6 alkyl group optionally substituted or the like, n represents an integer of 0 to 5, X represents an oxygen atom or a sulfur atom, Y represents a phenyl group or a pyridyl group that is substituted with substituent at an ortho position, and the bond with a broken line indicates a double bond or a single bond.

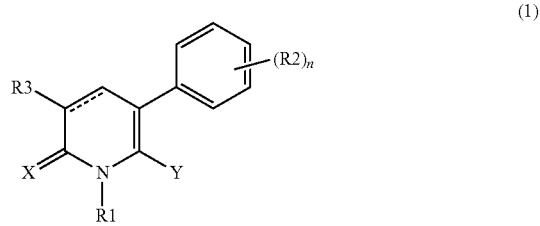

7 Claims, No Drawings

PYRIDONE COMPOUNDS AND AGRICULTURAL AND HORTICULTURAL FUNGICIDES CONTAINING SAID COMPOUNDS AS ACTIVE INGREDIENT

TECHNICAL FIELD

The present invention relates to pyridone compounds, and pesticides containing the compounds as an active ingredient.

BACKGROUND ART

The protection of agricultural and horticultural crops from diseases is important to ensure stable agricultural production, and various fungicides are used for this purpose. However, fungi become resistant to fungicides over years, and thus novel fungicides that are effective not only to drug-sensitive fungi but also to drug-resistant fungi are demanded.

Regarding 1,3,5,6-substituted-2-pyridone compounds, for example, 1,3,5,6-substituted-2-pyridone compounds having an aryl group or a heteroaryl group at the 3-position are disclosed as GABA alpha 2/3 ligands (see, for example, WO 98/55480). Further, 1,3,5,6-substituted-2-pyridone compounds having a carboxyl group at the 3-position are disclosed as bacterial infection treatment agents (see, for example, EP Patent No. 0308020).

CITATION LIST

Patent Literature

Patent Literature 1: WO 98/55480
Patent Literature 2: EP Patent No. 0308020

SUMMARY OF INVENTION

Technical Problem

The compounds disclosed in WO 98/55480 and EP Patent No. 0308020 differ from the compounds of the present invention in the substituent at the 3-position. That is, such compounds disclosed have chemical structures different from those according to the present invention. Further, the compounds described in the above patent literatures are used for pharmaceutical purposes, and thus belong to a different technical field from the agricultural and horticultural fungicides according to the present invention.

An object of the present invention is to provide novel compounds effective as agricultural and horticultural fungicides.

Solution to Problem

To achieve the above object, the present inventors have extensively studied 1,3,5,6-substituted-2-pyridone compounds and 1,5,6-substituted-2-pyridone compounds. As a result, the present inventors have found that those compounds which have an ortho-substituted aryl group or heteroaryl group introduced at the 6-position in the 2-pyridone skeleton exhibit an excellent activity in the treatment or prevention of plant diseases, thus completing the present invention.

Specifically, the present invention resides in the following aspects.

[1] A compound represented by Formula (1), or a salt thereof:

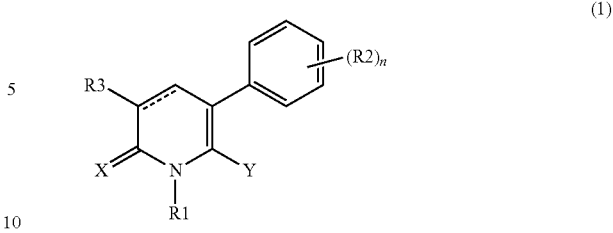

[wherein R1 represents a hydroxy group,
a cyano group,
a C1-C6 alkyl group optionally substituted with substituent A,
a C1-C6 haloalkyl group,
a C3-C8 cycloalkyl group optionally substituted with substituent A,
a C2-C6 alkenyl group optionally substituted with substituent A,
a C2-C6 haloalkenyl group,
a C2-C6 alkynyl group optionally substituted with substituent A,
a C2-C6 haloalkynyl group,
a C1-C6 alkoxy group optionally substituted with substituent A,
a C1-C6 haloalkoxy group,
a C3-C8 cycloalkoxy group optionally substituted with substituent A,
a C2-C6 alkenyloxy group optionally substituted with substituent A,
a C2-C6 haloalkenyloxy group,
a C3-C6 alkynyloxy group optionally substituted with substituent A,
a C3-C6 haloalkynyloxy group, or
an R10R11N— (wherein R10 and R11 each independently represents a hydrogen atom or a C1-C6 alkyl group);
R2 represents a halogen atom,
a hydroxy group,
a cyano group,
a nitro group,
a C1-C6 alkyl group optionally substituted with substituent B,
a C1-C6 haloalkyl group,
a C3-C8 cycloalkyl group optionally substituted with substituent B,
a C2-C6 alkenyl group optionally substituted with substituent B,
a C2-C6 haloalkenyl group,
a C2-C6 alkynyl group optionally substituted with substituent B,
a C2-C6 haloalkynyl group,
a C1-C6 alkoxy group optionally substituted with substituent B,
a C1-C6 haloalkoxy group,
a C3-C8 cycloalkoxy group optionally substituted with substituent B,
a C2-C6 alkenyloxy group optionally substituted with substituent B,
a C2-C6 haloalkenyloxy group,
a C3-C6 alkynyloxy group optionally substituted with substituent B,
a C3-C6 haloalkynyloxy group,
an R20C(=O)— (wherein R20 represents a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or an R21R22N— (wherein R21 and R22 each independently represents a hydrogen atom, a C1-C6 alkyl group optionally substituted with substituent B1, a C1-C6 haloalkyl group or a C3-C8 cycloalkyl group, or R21 and R22 in combination with the nitrogen atom to which they are bonded form an aziridinyl group, an azetidinyl group, a pyrrolidinyl group, a piperidinyl group, a homopiperidinyl group or an azocanyl group)), an R20C(=O)O— (wherein R20 is the same as defined hereinabove), a 3 to 6-membered ring group containing 1 to 2 oxygen atoms, an R23-L2- (wherein R23 represents a C1-C6 alkyl group or a C1-C6 haloalkyl group, and L2 represents S, SO or $SO_2$), an R21R22N— (wherein R21 and R22 are the same as defined hereinabove), or an R24C(=O)N(R25)- (wherein R24 represents a hydrogen atom, a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or an R21R22N— (wherein R21 and R22 are the same as defined hereinabove), and R25 represents a hydrogen atom, a C1-C6 alkyl group optionally substituted with substituent B1, a C1-C6 haloalkyl group or a C3-C8 cycloalkyl group);

R3 represents a hydrogen atom, a halogen atom, a nitro group, a C1-C6 alkyl group optionally substituted with substituent C, a C1-C6 haloalkyl group, a C3-C8 cycloalkyl group optionally substituted with substituent C, a C1-C6 alkoxy group optionally substituted with substituent C, a C1-C6 haloalkoxy group, a C2-C6 alkenyl group optionally substituted with substituent C, a C2-C6 haloalkenyl group, a C2-C6 alkynyl group optionally substituted with substituent C, a C2-C6 haloalkynyl group, an R30-L3- (wherein R30 has the same definition as R23, and L3 has the same definition as L2), an R31R32N— (wherein R31 and R32 have the same definition as R21 and R22), or an R33C(=O)— (wherein R33 represents a C1-C6 alkyl group, a C1-C6 haloalkyl group or a C3-C8 cycloalkyl group);

n represents an integer of 0 to 5 (with the proviso that when n is 2 or greater, the two or more R2's represent independent substituents);

X represents an oxygen atom or a sulfur atom;

Y represents a phenyl group, a pyridyl group, a pyridazinyl group, a pyrimidinyl group, a pyrazinyl group, a triazinyl group, a tetrazinyl group, a thienyl group, a thiazolyl group, an isothiazolyl group or a thiadiazolyl group, the phenyl group is substituted with substituent D at an ortho position and is further substituted with 0 to 4 independent substituents D1 appropriately, the pyridyl group, the pyrazinyl group, the pyrimidinyl group, the pyridazinyl group, the triazinyl group or the tetrazinyl group is substituted with substituent D at an ortho position and is further substituted with 0 to 3 independent substituents D1 appropriately, the thienyl group, the thiazolyl group, the isothiazolyl group or the thiadiazolyl group is substituted with substituent D at an ortho position and is further substituted with 0 to 2 independent substituents D1 appropriately;

the bond with a broken line indicates a double bond or a single bond, the substituent A is at least one selected from the group consisting of:

a hydroxy group, a cyano group, a C3-C8 cycloalkyl group, a C1-C6 alkoxy group, a C1-C6 haloalkoxy group, a C3-C8 cycloalkoxy group, an R12R13N— (wherein R12 and R13 each independently represents a hydrogen atom, a C1-C6 alkyl group, a C1-C6 haloalkyl group or a C3-C8 cycloalkyl group, or R12 and R13 in combination with the nitrogen atom to which they are bonded form an aziridinyl group, an azetidinyl group, a pyrrolidinyl group, a piperidinyl group, a homopiperidinyl group or an azocanyl group), and an R14-L1- (wherein R14 represents a C1-C6 alkyl group or a C1-C6 haloalkyl group, and L1 represents S, SO or $SO_2$);

the substituent B is at least one selected from the group consisting of:

a hydroxy group, a cyano group, a C3-C8 cycloalkyl group, a C1-C6 alkoxy group, a C1-C6 haloalkoxy group, a C3-C8 cycloalkoxy group, a C2-C6 alkoxyalkoxy group, an R21R22N— (wherein R21 and R22 are the same as defined hereinabove), an R23-L2- (wherein R23 and L2 are the same as defined hereinabove), an R26R27R28Si— (wherein R26, R27 and R28 each independently represents a C1-C6 alkyl group), an R26R27R28Si—($CH_2$)s-O— (wherein s represents an integer of 1 to 3, and R26, R27 and R28 are the same as defined hereinabove), an R20C(=O)— (wherein R20 is the same as defined hereinabove) and a 3 to 6-membered ring group containing 1 to 2 oxygen atoms;

the substituent B1 is at least one selected from the group consisting of:

a cyano group, a C1-C6 alkoxy group, a C1-C6 haloalkoxy group and a C3-C8 cycloalkoxy group;

the substituent C is at least one selected from the group consisting of:

a hydroxy group, a cyano group, a C3-C8 cycloalkyl group, a C1-C6 alkoxy group, a C1-C6 haloalkoxy group, a C3-C8 cycloalkoxy group, an R31R32N— (wherein R31 and R32 have the same definition as R21 and R22) and an R30-L3- (wherein R30 has the same definition as R14, and L3 has the same definition as L1);

the substituent D is at least one selected from the group consisting of:

a halogen atom, a C1-C6 alkyl group, a C1-C6 haloalkyl group, a C1-C6 alkoxy group and a C1-C6 haloalkoxy group; and the substituent D1 is at least one selected from the group consisting of:

a hydroxy group, a halogen atom, a C1-C6 alkyl group, a C1-C6 haloalkyl group, a C3-C8 cycloalkyl group, a C1-C6 alkoxy group, a C1-C6 haloalkoxy group and a C3-C8 cycloalkoxy group].

[2] The compound or salt thereof described in [1], wherein

R1 represents a cyano group, a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A, or an R10R11N— (wherein R10 and R11 each independently represents a hydrogen atom or a C1-C6 alkyl group);

R2 represents a halogen atom, a hydroxy group, a cyano group, a C1-C6 alkyl group optionally substituted with substituent B, a C1-C6 haloalkyl group, a C1-C6 alkoxy group optionally substituted with substituent B, a C1-C6 haloalkoxy group, a C3-C8 cycloalkoxy group optionally substituted with substituent B, a C2-C6 alkenyloxy group optionally substituted with substituent B, a C3-C6 alkynyloxy group optionally substituted with substituent B, an R20C(=O)O— (wherein R20 represents a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or an R21R22N— (wherein R21 and R22 each independently represents a hydrogen atom, a C1-C6 alkyl group optionally substituted with substituent B1, a C1-C6 haloalkyl group or a C3-C8 cycloalkyl group, or R21 and R22 in combination with the nitrogen atom to which they are bonded form an aziridinyl group, an azetidinyl group, a pyrrolidinyl group, a piperidinyl group, a homopiperidinyl group or an azocanyl group), or an R23-L2- (wherein R23 represents a C1-C6 alkyl group or a C1-C6 haloalkyl group, and L2 represents S, SO or SO$_2$);

R3 represents a hydrogen atom, a halogen atom, a C1-C6 alkyl group optionally substituted with substituent C, a C3-C8 cycloalkyl group optionally substituted with substituent C, a C1-C6 alkoxy group optionally substituted with substituent C, a C2-C6 alkynyl group optionally substituted with substituent C, or an R30-L3- (wherein R30 has the same definition as R23, and L3 has the same definition as L2);

Y represents a phenyl group or a pyridyl group, the phenyl group is substituted with substituent D at an ortho position and is further substituted with 0 to 4 independent substituents D1 appropriately, and the pyridyl group is substituted with substituent D at an ortho position and is further substituted with 0 to 3 independent substituents D1 appropriately.

[3] The compound or salt thereof described in [2], wherein

R1 represents a C1-C6 alkyl group optionally substituted with substituent A, or a C1-C6 haloalkyl group;

R2 represents a halogen atom, a C1-C6 alkyl group optionally substituted with substituent B, or a C1-C6 alkoxy group optionally substituted with substituent B; and R3 represents a hydrogen atom, a halogen atom, or a C1-C6 alkyl group optionally substituted with substituent C.

[4] A compound represented by Formula (2), or a salt thereof:

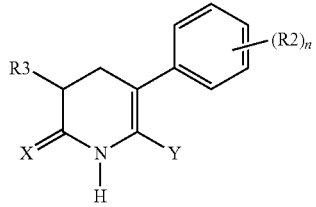

(2)

[wherein R2 represents a halogen atom, a hydroxy group, a cyano group, a nitro group, a C1-C6 alkyl group optionally substituted with substituent B, a C1-C6 haloalkyl group, a C3-C8 cycloalkyl group optionally substituted with substituent B, a C2-C6 alkenyl group optionally substituted with substituent B, a C2-C6 haloalkenyl group, a C2-C6 alkynyl group optionally substituted with substituent B, a C2-C6 haloalkynyl group, a C1-C6 alkoxy group optionally substituted with substituent B, a C1-C6 haloalkoxy group, a C3-C8 cycloalkoxy group optionally substituted with substituent B, a C2-C6 alkenyloxy group optionally substituted with substituent B, a C2-C6 haloalkenyloxy group, a C3-C6 alkynyloxy group optionally substituted with substituent B, a C3-C6 haloalkynyloxy group, an R20C(=O)— (wherein R20 represents a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or an R21R22N— (wherein R21 and R22 each independently represents a hydrogen atom, a C1-C6 alkyl group optionally substituted with substituent B1, a C1-C6 haloalkyl group or a C3-C8 cycloalkyl group, or R21 and R22 in combination with the nitrogen atom to which they are bonded form an aziridinyl group, an azetidinyl group, a pyrrolidinyl group, a piperidinyl group, a homopiperidinyl group or an azocanyl group)), an R20C(=O)O— (wherein R20 is the same as defined hereinabove), a 3 to 6-membered ring group containing 1 to 2 oxygen atoms, an R23-L2- (wherein R23 represents a C1-C6 alkyl group or a C1-C6 haloalkyl group, and L2 represents S, SO or SO$_2$), an R21R22N— (wherein R21 and R22 are the same as defined hereinabove), or an R24C(=O)N(R25)- (wherein R24 represents a hydrogen atom, a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or an R21R22N— (wherein R21 and R22 are the same as defined hereinabove), and R25 represents a hydrogen atom, a C1-C6 alkyl group optionally substituted with substituent B1, a C1-C6 haloalkyl group or a C3-C8 cycloalkyl group);

R3 represents a hydrogen atom,
a halogen atom,
a nitro group,
a C1-C6 alkyl group optionally substituted with substituent C,
a C1-C6 haloalkyl group,
a C3-C8 cycloalkyl group optionally substituted with substituent C,
a C1-C6 alkoxy group optionally substituted with substituent C,
a C1-C6 haloalkoxy group,
a C2-C6 alkenyl group optionally substituted with substituent C,
a C2-C6 haloalkenyl group,
a C2-C6 alkynyl group optionally substituted with substituent C,
a C2-C6 haloalkynyl group,
an R30-L3- (wherein R30 has the same definition as R23, and L3 has the same definition as L2),
an R31R32N— (wherein R31 and R32 have the same definition as R21 and R22), or
an R33C(=O)— (wherein R33 represents a C1-C6 alkyl group, a C1-C6 haloalkyl group or a C3-C8 cycloalkyl group);
n represents an integer of 0 to 5 (with the proviso that when n is 2 or greater, the two or more R2's represent independent substituents);
X represents an oxygen atom or a sulfur atom;
Y represents a phenyl group, a pyridyl group, a pyridazinyl group, a pyrimidinyl group, a pyrazinyl group, a triazinyl group, a tetrazinyl group, a thienyl group, a thiazolyl group, an isothiazolyl group or a thiadiazolyl group,
the phenyl group is substituted with substituent D at an ortho position and is further substituted with 0 to 4 independent substituents D1 appropriately, the pyridyl group, the pyrazinyl group, the pyrimidinyl group, the pyridazinyl group, the triazinyl group or the tetrazinyl group is substituted with substituent D at an ortho position and is further substituted with 0 to 3 independent substituents D1 appropriately, and the thienyl group, the thiazolyl group, the isothiazolyl group or the thiadiazolyl group is substituted with substituent D at an ortho position and is further substituted with 0 to 2 independent substituents D1 appropriately,
the substituent B is at least one selected from the group consisting of:
a hydroxy group, a cyano group, a C3-C8 cycloalkyl group, a C1-C6 alkoxy group, a C1-C6 haloalkoxy group, a C3-C8 cycloalkoxy group, a C2-C6 alkoxyalkoxy group, an R21R22N— (wherein R21 and R22 are the same as defined hereinabove), an R23-L2- (wherein R23 and L2 are the same as defined hereinabove), an R26R27R28Si— (wherein R26, R27 and R28 each independently represents a C1-C6 alkyl group), an R26R27R28Si—(CH$_2$)s-O— (wherein s represents an integer of 1 to 3, and R26, R27 and R28 are the same as defined hereinabove), an R20C(=O)— (wherein R20 is the same as defined hereinabove) and a 3 to 6-membered ring group containing 1 to 2 oxygen atoms;
the substituent B1 is at least one selected from the group consisting of:
a cyano group, a C1-C6 alkoxy group, a C1-C6 haloalkoxy group and a C3-C8 cycloalkoxy group;
the substituent C is at least one selected from the group consisting of:
a hydroxy group, a cyano group, a C3-C8 cycloalkyl group, a C1-C6 alkoxy group, a C1-C6 haloalkoxy group, a C3-C8 cycloalkoxy group, an R31R32N— (wherein R31 and R32 have the same definition as R21 and R22) and an R30-L3- (wherein R30 has the same definition as R23, and L3 has the same definition as L2);
the substituent D is at least one selected from the group consisting of:
a halogen atoms, a C1-C6 alkyl group, a C1-C6 haloalkyl group, a C1-C6 alkoxy group and a C1-C6 haloalkoxy group; and
the substituent D1 is at least one selected from the group consisting of:
a hydroxy group, a halogen atoms, a C1-C6 alkyl group, a C1-C6 haloalkyl group, a C3-C8 cycloalkyl group, a C1-C6 alkoxy group, a C1-C6 haloalkoxy group and a C3-C8 cycloalkoxy group].

[5] An agricultural and horticultural pest control agent including the compound or salt thereof described in [1] as an active ingredient.

[6] An agricultural and horticultural fungicide including the compound or salt thereof described in [1] as an active ingredient.

[7] A method for treating or preventing a plant disease, including applying the agricultural and horticultural pest control agent described in [5] to a plant, a plant seed, or a soil for plant cultivation.

Advantageous Effects of Invention

The novel compounds provided according to the present invention are effective as agricultural and horticultural fungicides.

DESCRIPTION OF EMBODIMENTS

Hereinbelow, embodiments for carrying out the present invention will be described in detail.

The terminologies used in the claims and the specification are understood in accordance with the definitions which are generally used in the art unless otherwise specified.

The symbols used in the specification indicate the following:

DMF: N,N-dimethylformamide, THF: tetrahydrofuran, Me: methyl group, Et: ethyl group, Pr: propyl group, Bu: butyl group, Pentyl: pentyl group, Hexyl: hexyl group, Ac: acetyl group, Ph: phenyl group, Py: pyridyl group, i: iso, sec: secondary, t: tertiary, c: cyclo, =: double bond, and ≡: triple bond. In the columns in the tables, a simple hyphen "-" indicates that no substituents are present, and Pr, Bu, Pentyl and Hexyl used without any prefix indicate that the respective groups have a normal form.

The definitions of the phrases and terminologies used in the specification will be explained below.

The term Cx-Cy indicates that the group or compound has as many carbon atoms as indicated by a number between x and y inclusive.

The phrase "optionally substituted" means that the group or compound may be substituted or unsubstituted. The absence of indication of the number of substituents means that there is only one substituent.

The term C1-C6 alkyl group indicates a linear or branched such group, and is a methyl group, an ethyl group, a propyl group, an isopropyl group, a butyl group, an isobutyl group, a sec-butyl group, a t-butyl group, a pentyl group, an isopentyl group, a 2-methylbutyl group, a neopentyl group, a 1-ethylpropyl group, a hexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2- dimethylbutyl group, a 1,3-dimethylbutyl group, a 2,3-dimethylbutyl group or a 2-ethylbutyl group.

The halogen atom is a fluorine atom, a chlorine atom, a bromine atom or an iodine atom.

The term C1-C6 haloalkyl group indicates a group resulting from the substitution of the aforementioned C1-C6 alkyl group with a halogen atom in place of any hydrogen atom. When the group is substituted with two or more halogen atoms, these halogen atoms may be the same as or different from one another, and the number of such substitutions is not particularly limited as long as the group can exist as a substituent. Specific examples of the C1-C6 haloalkyl group include monofluoromethyl group, difluoromethyl group, trifluoromethyl group, monochloromethyl group, monobromomethyl group, monoiodomethyl group, chlorodifluoromethyl group, bromodifluoromethyl group, 1-fluoroethyl group, 2-fluoroethyl group, 1,1-difluoroethyl group, 2,2-difluoroethyl group, 2,2,2-trifluoroethyl group, 1,1,2,2-tetrafluoroethyl group, pentafluoroethyl group, 2,2,2-trichloroethyl group, 3,3-difluoropropyl group, 3,3,3-trifluoropropyl group, heptafluoropropyl group, heptafluoroisopropyl group, 2,2,2-trifluoro-1-(trifluoromethyl)ethyl group, nonafluorobutyl group, nonafluoro-sec-butyl group, 3,3,4,4,5,5,5-heptafluoropentyl group, undecafluoropentyl group, tridecafluorohexyl group and the like.

The term C3-C8 cycloalkyl group indicates a cyclopropyl group, a cyclobutyl group, a cyclopentyl group, a cyclohexyl group, a cycloheptyl group or a cyclooctyl group.

The term C2-C6 alkenyl group indicates a linear or branched, unsaturated hydrocarbon group having one, or two or more double bonds. When the group has geometric isomeric forms, the group may be either the E-isomer or the Z-isomer, or may be a mixture of the E-isomer and the Z-isomer in an appropriate ratio without limitation as long as the number of carbon atoms falls in the specific range. Specific examples of the C2-C6 alkenyl group include vinyl group, 1-propenyl group, allyl group, 1-butenyl group, 2-butenyl group, 3-butenyl group, 1-pentenyl group, 2-pentenyl group, 3-pentenyl group, 4-pentenyl group, 3-methyl-2-butenyl group, 1-hexenyl group, 2-hexenyl group, 3-hexenyl group, 4-hexenyl group, 5-hexenyl group, 4-methyl-3-pentenyl group, 3-methyl-2-pentenyl group and the like.

The term C2-C6 haloalkenyl group indicates a group resulting from the substitution of the aforementioned C2-C6 alkenyl group with a halogen atom in place of any hydrogen atom. When the group is substituted with two or more halogen atoms, these halogen atoms may be the same as or different from one another, and the number of such substitutions is not particularly limited as long as the group can exist as a substituent. Specific examples of the C2-C6 haloalkenyl group include 2-fluorovinyl group, 2,2-difluorovinyl group, 2,2-dichlorovinyl group, 3-fluoroallyl group, 3,3-difluoroallyl group, 3,3-dichloroallyl group, 4,4-difluoro-3-butenyl group, 5,5-difluoro-4-pentenyl group, 6,6-difluoro-5-hexenyl group and the like.

The term C2-C6 alkynyl group indicates a linear or branched, unsaturated hydrocarbon group having one, or two or more triple bonds. Specific examples of the C2-C6 alkynyl group include ethynyl group, 1-propynyl group, propargyl group, 1-butynyl group, 2-butynyl group, 3-butynyl group, 1-pentynyl group, 2-pentynyl group, 3-pentynyl group, 4-pentynyl group, 1,1-dimethyl-2-propynyl group, 1-hexynyl group, 2-hexynyl group, 3-hexynyl group, 4-hexynyl group, 5-hexynyl group and the like.

The term C2-C6 haloalkynyl group indicates a group resulting from the substitution of the aforementioned C2-C6 alkynyl group with a halogen atom in place of any hydrogen atom. When the group is substituted with two or more halogen atoms, these halogen atoms may be the same as or different from one another, and the number of such substitutions is not particularly limited as long as the group can exist as a substituent. Specific examples of the C2-C6 haloalkynyl group include 2-fluoroethynyl group, 2-chloroethynyl group, 2-bromoethynyl group, 2-iodoethynyl group, 3,3-difluoro-1-propynyl group, 3-chloro-3,3-difluoro-1-propynyl group, 3-bromo-3,3-difluoro-1-propynyl group, 3,3,3-trifluoro-1-propynyl group, 4,4-difluoro-1-butynyl group, 4,4-difluoro-2-butynyl group, 4-chloro-4,4-difluoro-1-butynyl group, 4-chloro-4,4-difluoro-2-butynyl group, 4-bromo-4,4-difluoro-1-butynyl group, 4-bromo-4,4-difluoro-2-butynyl group, 4,4,4-trifluoro-1-butynyl group, 4,4,4-trifluoro-2-butynyl group, 5,5-difluoro-3-pentynyl group, 5-chloro-5,5-difluoro-3-pentynyl group, 5-bromo-5,5-difluoro-3-pentynyl group, 5,5,5-trifluoro-3-pentynyl group, 6,6-difluoro-4-hexynyl group, 6-chloro-6,6-difluoro-4-hexynyl group, 6-bromo-6,6-difluoro-4-hexynyl group, 6,6,6-trifluoro-4-hexynyl group and the like.

The term C1-C6 alkoxy group indicates a group resulting from the bonding of an oxygen atom to the C1-C6 alkyl group. Specific examples of the C1-C6 alkoxy group include methoxy group, ethoxy group, propyloxy group, isopropyloxy group, butoxy group, isobutoxy group, sec-butoxy group, t-butoxy group, pentyloxy group, isopentyloxy group, 2-methylbutoxy group, neopentyloxy group, 1-ethylpropyloxy group, hexyloxy group, 4-methylpentyloxy group, 3-methylpentyloxy group, 2-methylpentyloxy group, 1-methylpentyloxy group, 3,3-dimethylbutoxy group, 2,2-dimethylbutoxy group, 1,1-dimethylbutoxy group, 1,2-dimethylbutoxy group, 1,3-dimethylbutoxy group, 2,3-dimethylbutoxy group and 2-ethylbutoxy group.

The term C1-C6 haloalkoxy group indicates a group resulting from the substitution of the aforementioned C1-C6 alkoxy group with a halogen atom in place of any hydrogen atom. When the group is substituted with two or more halogen atoms, these halogen atoms may be the same as or different from one another, and the number of such substitutions is not particularly limited as long as the group can exist as a substituent. Specific examples of the C1-C6 alkoxy group include difluoromethoxy group, trifluoromethoxy group, chlorodifluoromethoxy group, bromodifluoromethoxy group, 2-fluoroethoxy group, 2,2-difluoroethoxy group, 2,2,2-trifluoroethoxy group, 1,1,2,2-tetrafluoroethoxy group, pentafluoroethoxy group, 2,2,2-trichloroethoxy group, 3,3-difluoropropyloxy group, 3,3,3-trifluoropropyloxy group, heptafluoropropyloxy group, heptafluoroisopropyloxy group, 2,2,2-trifluoro-1-(trifluoromethyl)-ethoxy group, nonafluorobutoxy group, nonafluoro-sec-butoxy group, 3,3,4,4,5,5,5-heptafluoropentyloxy group, undecafluoropentyloxy group, tridecafluorohexyloxy group and the like.

The term C3-C8 cycloalkoxy group indicates a group resulting from the bonding of an oxygen atom to the C3-C8 cycloalkyl group. Specific examples of the C3-C8 cycloalkoxy group include cyclopropyloxy group, cyclobutoxy group, cyclopentyloxy group, cyclohexyloxy group, cycloheptyloxy group and cyclooctyloxy group.

The term C2-C6 alkenyloxy group indicates a group resulting from the bonding of an oxygen atom to the C2-C6 alkenyl group. When the group has geometric isomeric forms, the group may be either the E-isomer or the Z-isomer, or may be a mixture of the E-isomer and the Z-isomer in an appropriate ratio without limitation as long as the number of carbon atoms falls in the specific range. Specific examples of the C2-C6 alkenyloxy group include vinyloxy group, 1-propenyloxy group, allyloxy group, 1-butenyloxy group, 2-butenyloxy group, 3-butenyloxy group, 1-pentenyloxy group, 2-pentenyloxy group, 3-pentenyloxy group, 4-pentenyloxy group, 3-methyl-2-butenyloxy group, 1-hexenyloxy group, 2-hexenyloxy group, 3-hexenyloxy group, 4-hexenyloxy group, 5-hexenyloxy group, 4-methyl-3-pentenyloxy group, 3-methyl-2-pentenyloxy group and the like.

The term C2-C6 haloalkenyloxy group indicates a group resulting from the substitution of the aforementioned C2-C6 alkenyloxy group with a halogen atom in place of any hydrogen atom. When the group is substituted with two or more halogen atoms, these halogen atoms may be the same as or different from one another, and the number of such substitutions is not particularly limited as long as the group can exist as a substituent. Specific examples of the C2-C6 haloalkenyloxy group include 2-fluorovinyloxy group, 2,2-difluorovinyloxy group, 2,2-dichlorovinyloxy group, 3,3-difluoroallyloxy group, 3,3-dichloroallyloxy group, 4,4-difluoro-3-butenyloxy group, 5,5-difluoro-4-pentenyloxy group, 6,6-difluoro-5-hexenyloxy group and the like.

The term C3-C6 alkynyloxy group indicates a group resulting from the bonding of an oxygen atom to a C3-C6 alkynyl group that belongs to the aforementioned C2-C6 alkynyl group. Specific examples of the C3-C6 alkynyloxy group include propargyloxy group, 2-butynyloxy group, 3-butynyloxy group, 2-pentynyloxy group, 3-pentynyloxy group, 4-pentynyloxy group, 1,1-dimethyl-2-propynyloxy group, 2-hexynyloxy group, 3-hexynyloxy group, 4-hexynyloxy group, 5-hexynyloxy group and the like.

The term C3-C6 haloalkynyloxy group indicates a group resulting from the substitution of the aforementioned C3-C6 alkynyloxy group with a halogen atom in place of any hydrogen atom. When the group is substituted with two or more halogen atoms, these halogen atoms may be the same as or different from one another, and the number of such substitutions is not particularly limited as long as the group can exist as a substituent. Specific examples of the C3-C6 haloalkynyloxy group include 1,1-difluoro-2-propynyloxy group, 4,4-difluoro-2-butynyloxy group, 4-chloro-4,4-difluoro-2-butynyloxy group, 4-bromo-4,4-difluoro-2-butynyloxy group, 4,4,4-trifluoro-2-butynyloxy group, 5,5-difluoro-3-pentynyloxy group, 5-chloro-5,5-difluoro-3-pentynyloxy group, 5-bromo-5,5-difluoro-3-pentynyloxy group, 5,5,5-trifluoro-3-pentynyloxy group, 6,6-difluoro-4-hexynyloxy group, 6-chloro-6,6-difluoro-4-hexynyloxy group, 6-bromo-6,6-difluoro-4-hexynyloxy group, 6,6,6-trifluoro-4-hexynyloxy group and the like.

The term C2-C6 alkoxyalkoxy group indicates a group resulting from the substitution of a C1-C5 alkoxy group that belongs to the aforementioned C1-C6 alkoxy group with a C1-C5 alkoxy group in place of any hydrogen atom. The substitution is not particularly limited as long as the total number of carbon atoms falls in the specific range. Specific examples of the C2-C6 alkoxyalkoxy group include methoxymethoxy group, ethoxymethoxy group, propyloxymethoxy group, isopropyloxymethoxy group, methoxyethoxy group, ethoxyethoxy group, propyloxyethoxy group, isopropyloxyethoxy group, methoxypropyloxy group, ethoxypropyloxy group, propyloxypropyloxy group, isopropyloxypropyloxy group and the like.

Specific examples of the 3 to 6-membered ring group containing 1 to 2 oxygen atoms include 1,2-epoxyethanyl group, oxetanyl group, oxoranyl group, oxanyl group, 1,3-dioxoranyl group, 1,3-dioxanyl group, 1,4-dioxanyl group and the like.

The pyridone compounds of the present invention include those compounds represented by Formula (1) below and salts thereof.

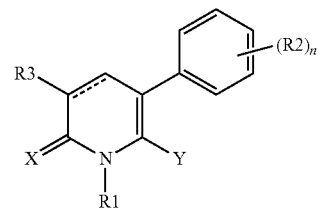

(1)

Hereinbelow, Formula (1) will be described.

R1 in Formula (1) is a hydroxy group, a cyano group, a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A, a C2-C6 haloalkynyl group, a C1-C6 alkoxy group optionally substituted with substituent A, a C1-C6 haloalkoxy group, a C3-C8 cycloalkoxy group optionally substituted with substituent A, a C2-C6 alkenyloxy group optionally substituted with substituent A, a C2-C6 haloalkenyloxy group, a C3-C6 alkynyloxy group optionally substituted with substituent A, a C3-C6 haloalkynyloxy group, or an R10R11N— (wherein R10 and R11 each independently represents a hydrogen atom or a C1-C6 alkyl group).

In particular, R1 is preferably a cyano group, a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A, or an R10R11N— (wherein R10 and R11 are the same as defined hereinabove), or is particularly preferably a C1-C6 alkyl group optionally substituted with substituent A, or a C1-C6 haloalkyl group.

The term "substituent A" in Formula (1) represents at least one selected from the group consisting of a hydroxy group, a cyano group, a C3-C8 cycloalkyl group, a C1-C6 alkoxy group, a C1-C6 haloalkoxy group, a C3-C8 cycloalkoxy group, an R12R13N— (wherein R12 and R13 each independently represents a hydrogen atom, a C1-C6 alkyl group, a C1-C6 haloalkyl group or a C3-C8 cycloalkyl group, or R12 and R13 in combination with the nitrogen atom to which they are bonded form an aziridinyl group, an azetidinyl group, a pyrrolidinyl group, a piperidinyl group, a homopiperidinyl group or an azocanyl group), and an R14-L1- (wherein R14 represents a C1-C6 alkyl group or a C1-C6 haloalkyl group, and L1 represents S, SO or $SO_2$).

In particular, the substituent A is preferably a cyano group, a C1-C6 alkoxy group or an R14-L1- (wherein R14 and L1 are the same as defined hereinabove), or is particularly preferably a cyano group or a C1-C6 alkoxy group.

Preferred specific examples of the substituents A include a hydroxy group; a cyano group;

a C3-C8 cycloalkyl group such as cyclopropyl group, cyclobutyl group, cyclopentyl group and cyclohexyl group;

a C1-C6 alkoxy group such as methoxy group, ethoxy group, propyloxy group and isopropyloxy group;

a C1-C6 haloalkoxy group such as difluoromethoxy group, trifluoromethoxy group, 2,2-difluoroethoxy group, 2,2,2-trifluoroethoxy group, 3,3-difluoropropyloxy group and 3,3,3-trifluoropropyloxy group;

a C3-C8 cycloalkoxy group such as cyclopropyloxy group, cyclobutoxy group, cyclopentyloxy group and cyclohexyloxy group;

an R12R13N— (wherein R12 and R13 are the same as defined hereinabove) such as amino group, dimethylamino group, ethylmethylamino group and diethylamino group; and an R14-L1- (wherein R14 and L1 are the same as defined hereinabove) such as methylthio group, methanesulfinyl group, methanesulfonyl group, trifluoromethylthio group, trifluoromethanesulfinyl group and trifluoromethanesulfonyl group.

More preferred specific examples of the substituents A include a hydroxy group; a cyano group;

a C3-C8 cycloalkyl group such as cyclopropyl group and cyclobutyl group;

a C1-C6 alkoxy group such as methoxy group and ethoxy group;

a C1-C6 haloalkoxy group such as difluoromethoxy group, trifluoromethoxy group, 2,2-difluoroethoxy group and 2,2,2-trifluoroethoxy group;

a C3-C8 cycloalkoxy group such as cyclopropyloxy group and cyclobutoxy group;

an R12R13N— (wherein R12 and R13 are the same as defined hereinabove) such as dimethylamino group, ethylmethylamino group and diethylamino group; and an R14-L1- (wherein R14 and L1 are the same as defined hereinabove) such as methylthio group, methanesulfinyl group and methanesulfonyl group.

R1 in Formula (1) may represent a hydroxy group or a cyano group.

The C1-C6 alkyl group in the "C1-C6 alkyl group optionally substituted with substituent A" represented by R1 in Formula (1) is the same as defined hereinabove, and is preferably a methyl group, an ethyl group, a propyl group, an isopropyl group, a butyl group or an isobutyl group, and more preferably a methyl group or an ethyl group. When the group is substituted with substituent A, the substituent A substitutes for any hydrogen atom in the C1-C6 alkyl group.

The "C1-C6 haloalkyl group" represented by R1 in Formula (1) is the same as defined hereinabove, and is preferably a 2-fluoroethyl group, a 2,2-difluoroethyl group, a 2,2,2-trifluoroethyl group, a 3,3-difluoropropyl group or a 3,3,3-trifluoropropyl group, and more preferably a 2-fluoroethyl group, a 2,2-difluoroethyl group or a 2,2,2-trifluoroethyl group.

The C3-C8 cycloalkyl group in the "C3-C8 cycloalkyl group optionally substituted with substituent A" represented by R1 in Formula (1) is the same as defined hereinabove, and is preferably a cyclopropyl group, a cyclobutyl group, a cyclopentyl group or a cyclohexyl group, and more preferably a cyclopropyl group or a cyclobutyl group. When the group is substituted with substituent A, the substituent A substitutes for any hydrogen atom in the C3-C8 cycloalkyl group.

The C2-C6 alkenyl group in the "C2-C6 alkenyl group optionally substituted with substituent A" represented by R1 in Formula (1) is the same as defined hereinabove, and is preferably a vinyl group, a 1-propenyl group or an allyl group, and more preferably a vinyl group or an allyl group. When the group is substituted with substituent A, the substituent A substitutes for any hydrogen atom in the C2-C6 alkenyl group.

The "C2-C6 haloalkenyl group" represented by R1 in Formula (1) is the same as defined hereinabove, and is preferably a 2-fluorovinyl group, a 2,2-difluorovinyl group, a 3-fluoroallyl group or a 3,3-difluoroallyl group, and more preferably a 2-fluorovinyl group or a 2,2-difluorovinyl group.

The C2-C6 alkynyl group in the "C2-C6 alkynyl group optionally substituted with substituent A" represented by R1 in Formula (1) is the same as defined hereinabove, and is preferably a propargyl group, a 2-butynyl group or a 3-butynyl group, and more preferably a propargyl group. When the group is substituted with substituent A, the substituent A substitutes for any hydrogen atom in the C2-C6 alkynyl group.

The "C2-C6 haloalkynyl group" represented by R1 in Formula (1) is the same as defined hereinabove, and is preferably a 4,4-difluoro-2-butynyl group, a 4-chloro-4,4-difluoro-2-butynyl group, a 4-bromo-4,4-difluoro-2-butynyl group or a 4,4,4-trifluoro-2-butynyl group, and more preferably a 4,4-difluoro-2-butynyl group or a 4,4,4-trifluoro-2-butynyl group.

The C1-C6 alkoxy group in the "C1-C6 alkoxy group optionally substituted with substituent A" represented by R1 in Formula (1) is the same as defined hereinabove, and is preferably a methoxy group, an ethoxy group, a propyloxy group, an isopropyloxy group, a butoxy group or an isobutoxy group, and more preferably a methoxy group or an ethoxy group. When the group is substituted with substituent A, the substituent A substitutes for any hydrogen atom in the C1-C6 alkoxy group.

The "C1-C6 haloalkoxy group" represented by R1 in Formula (1) is the same as defined hereinabove, and is preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group, and more preferably a difluoromethoxy group, a trifluoromethoxy group, a 2,2-difluoroethoxy group or a 2,2,2-trifluoroethoxy group.

The C3-C8 cycloalkoxy group in the "C3-C8 cycloalkoxy group optionally substituted with substituent A" represented by R1 in Formula (1) is the same as defined hereinabove, and is preferably a cyclopropyloxy group, a cyclobutoxy group, a cyclopentyloxy group or a cyclohexyloxy group, and more preferably a cyclopropyloxy group or a cyclobutoxy group. When the group is substituted with substituent A, the substituent A substitutes for any hydrogen atom in the C3-C8 cycloalkoxy group.

The C2-C6 alkenyloxy group in the "C2-C6 alkenyloxy group optionally substituted with substituent A" represented by R1 in Formula (1) is the same as defined hereinabove, and is preferably a vinyloxy group, a 1-propenyloxy group or an allyloxy group, and more preferably a vinyloxy group. When the group is substituted with substituent A, the substituent A substitutes for any hydrogen atom in the C2-C6 alkenyloxy group.

The "C2-C6 haloalkenyloxy group" represented by R1 in Formula (1) is the same as defined hereinabove, and is preferably a 2-fluorovinyloxy group, a 2,2-difluorovinyloxy group, a 3-fluoroallyloxy group or a 3,3-difluoroallyloxy group, and more preferably a 2-fluorovinyloxy group or a 2,2-difluorovinyloxy group.

The C3-C6 alkynyloxy group in the "C3-C6 alkynyloxy group optionally substituted with substituent A" represented by R1 in Formula (1) is the same as defined hereinabove, and is preferably a propargyloxy group, a 2-butynyloxy group or a 3-butynyloxy group, and more preferably a propargyloxy group. When the group is substituted with substituent A, the substituent A substitutes for any hydrogen atom in the C3-C6 alkynyloxy group.

The "C3-C6 haloalkynyloxy group" represented by R1 in Formula (1) is the same as defined hereinabove, and is preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group, and more preferably a 4,4-difluoro-2-butynyloxy group or a 4,4,4-trifluoro-2-butynyloxy group.

The C1-C6 alkyl group in the "R10R11N—" (wherein R10 and R11 each independently represents a hydrogen atom or a C1-C6 alkyl group) represented by R1 in Formula (1) is the same as defined hereinabove. The "R10R11N—" may be preferably an amino group, a dimethylamino group, an ethylmethylamino group or a diethylamino group, and more preferably an amino group or a dimethylamino group.

R2 represents a halogen atom, a hydroxy group, a cyano group, a nitro group, a C1-C6 alkyl group optionally substituted with substituent B, a C1-C6 haloalkyl group, a C3-C8 cycloalkyl group optionally substituted with substituent B, a C2-C6 alkenyl group optionally substituted with substituent B, a C2-C6 haloalkenyl group, a C2-C6 alkynyl group optionally substituted with substituent B, a C2-C6 haloalkynyl group, a C1-C6 alkoxy group optionally substituted with substituent B, a C1-C6 haloalkoxy group, a C3-C8 cycloalkoxy group optionally substituted with substituent B, a C2-C6 alkenyloxy group optionally substituted with substituent B, a C2-C6 haloalkenyloxy group, a C3-C6 alkynyloxy group optionally substituted with substituent B, a C3-C6 haloalkynyloxy group, an R20C(=O)— (wherein R20 is a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or an R21R22N— (wherein R21 and R22 each independently represents a hydrogen atom, a C1-C6 alkyl group optionally substituted with substituent B1, a C1-C6 haloalkyl group or a C3-C8 cycloalkyl group, or R21 and R22 in combination with the nitrogen atom to which they are bonded form an aziridinyl group, an azetidinyl group, a pyrrolidinyl group, a piperidinyl group, a homopiperidinyl group or an azocanyl group)), an R20C(=O)O— (wherein R20 is the same as defined hereinabove), a 3 to 6-membered ring group containing 1 to 2 oxygen atoms, an R23-L2- (wherein R23 is a C1-C6 alkyl group or a C1-C6 haloalkyl group, and L2 is S, SO or SO$_2$), an R21R22N— (wherein R21 and R22 are the same as defined hereinabove), or an R24C(=O)N(R25)- (wherein R24 is a hydrogen atom, a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or an R21R22N— (wherein R21 and R22 are the same as defined hereinabove), and R25 is a hydrogen atom, a C1-C6 alkyl group optionally substituted with substituent B1, a C1-C6 haloalkyl group or a C3-C8 cycloalkyl group).

In particular, R2 is preferably a halogen atom, a hydroxy group, a cyano group, a C1-C6 alkyl group optionally substituted with substituent B, a C1-C6 haloalkyl group, a C1-C6 alkoxy group optionally substituted with substituent B, a C1-C6 haloalkoxy group, a C3-C8 cycloalkoxy group optionally substituted with substituent B, a C2-C6 alkenyloxy group optionally substituted with substituent B, a C3-C6 alkynyloxy group optionally substituted with substituent B, an R20C(=O)O— (wherein R20 is the same as defined hereinabove), or an R23-L2- (wherein R23 and L2 are the same as defined hereinabove), or is particularly preferably a halogen atom, a C1-C6 alkyl group optionally substituted with substituent B, or a C1-C6 alkoxy group optionally substituted with substituent B.

The "substituent B" in Formula (1) represents at least one selected from the group consisting of a hydroxy group, a cyano group, a C3-C8 cycloalkyl group, a C1-C6 alkoxy group, a C1-C6 haloalkoxy group, a C3-C8 cycloalkoxy group, a C2-C6 alkoxyalkoxy group, an R21R22N— (wherein R21 and R22 are the same as defined hereinabove), an R23-L2- (wherein R23 and L2 are the same as defined hereinabove), an R26R27R28Si— (wherein R26, R27 and R28 each independently represents a C1-C6 alkyl group), an R26R27R28Si—(CH$_2$)s-O— (wherein s represents an integer of 1 to 3, and R26, R27 and R28 are the same as defined hereinabove), an R20C(=O)— (wherein R20 has the same definition as R20 described hereinabove), and a 3 to 6-membered ring group containing 1 to 2 oxygen atoms.

In particular, the substituent B is preferably a cyano group, a C3-C8 cycloalkyl group, a C1-C6 alkoxy group, a C2-C6 alkoxyalkoxy group, an R23-L2- (wherein R23 and L2 are the same as defined hereinabove), R26R27R28Si— (wherein R26, R27 and R28 are the same as defined hereinabove), R26R27R28Si—(CH$_2$)s-O— (wherein s, R26, R27 and R28 are the same as defined hereinabove), R20C(=O)— (wherein R20 is the same as defined hereinabove), or a 3 to 6-membered ring group containing 1 to 2 oxygen atoms, or is particularly preferably a cyano group or a C1-C6 alkoxy group.

Preferred specific examples of the substituents B include a hydroxy group; a cyano group;

a C3-C8 cycloalkyl group such as cyclopropyl group, cyclobutyl group, cyclopentyl group and cyclohexyl group;

a C1-C6 alkoxy group such as methoxy group, ethoxy group, propyloxy group, isopropyloxy group, butoxy group and isobutoxy group; a C1-C6 haloalkoxy group such as difluoromethoxy group, trifluoromethoxy group, 2,2-difluoroethoxy group, 2,2,2-trifluoroethoxy group, 3,3-difluoropropyloxy group and 3,3,3-trifluoropropyloxy group;

a C3-C8 cycloalkoxy group such as cyclopropyloxy group, cyclobutoxy group, cyclopentyloxy group and cyclohexyloxy group; a C2-C6 alkoxyalkoxy group such as methoxymethoxy group, ethoxymethoxy group, methoxyethoxy group, ethoxyethoxy group and methoxypropyloxy group;

an R21R22N— (wherein R21 and R22 are the same as defined hereinabove) such as amino group, dimethylamino group, ethylmethylamino group, diethylamino group, pyrrolidinyl group and piperidinyl group;

an R23-L2- (wherein R23 and L2 are the same as defined hereinabove) such as methylthio group, methanesulfinyl group, methanesulfonyl group, trifluoromethylthio group, trifluoromethanesulfinyl group and trifluoromethanesulfonyl group;

an R26R27R28Si— (wherein R26, R27 and R28 are the same as defined hereinabove) such as trimethylsilyl group and triethylsilyl group;

an R26R27R28Si—(CH$_2$)s-O— (wherein s, R26, R27 and R28 are the same as defined hereinabove) such as 2-(trimethylsilyl)ethoxy group and 2-(triethylsilyl)ethoxy group;

an R20C(=O)— (wherein R20 is the same as defined hereinabove) such as acetyl group, propionyl group, difluoroacetyl group, trifluoroacetyl group, cyclopropanecarbonyl group, methoxycarbonyl group, ethoxycarbonyl group, 2,2-difluoroethoxycarbonyl group, 3,3,3-trifluoropropyloxycarbonyl group, cyclopropyloxycarbonyl group, aminocarbonyl group, dimethylaminocarbonyl group, ethylmethylaminocarbonyl group, diethylaminocarbonyl group, pyrrolidinylcarbonyl group and piperidinylcarbonyl group; and a 3 to 6-membered ring group containing 1 to 2 oxygen atoms such as oxoranyl group, oxanyl group, 1,3-dioxoranyl group and 1,3-dioxanyl group.

More preferred specific examples of the substituents B include a hydroxy group; a cyano group;

a C3-C8 cycloalkyl group such as cyclopropyl group and cyclobutyl group;

a C1-C6 alkoxy group such as methoxy group and ethoxy group;

a C1-C6 haloalkoxy group such as difluoromethoxy group, trifluoromethoxy group, 2,2-difluoroethoxy group and 2,2,2-trifluoroethoxy group;

a C3-C8 cycloalkoxy group such as cyclopropyloxy group and cyclobutoxy group;

a C2-C6 alkoxyalkoxy group such as methoxymethoxy group, ethoxymethoxy group, methoxyethoxy group and ethoxyethoxy group;

an R21R22N— (wherein R21 and R22 are the same as defined hereinabove) such as dimethylamino group, ethylmethylamino group and diethylamino group;

an R23-L2- (wherein R23 and L2 are the same as defined hereinabove) such as methylthio group, methanesulfinyl group and methanesulfonyl group;

an R26R27R28Si— (wherein R26, R27 and R28 are the same as defined hereinabove) such as trimethylsilyl group;

an R26R27R28Si—(CH$_2$)s-O— (wherein s, R26, R27 and R28 are the same as defined hereinabove) such as 2-(trimethylsilyl)ethoxy group;

an R20C(=O)— (wherein R20 is the same as defined hereinabove) such as acetyl group, difluoroacetyl group, trifluoroacetyl group, methoxycarbonyl group, ethoxycarbonyl group, aminocarbonyl group, dimethylaminocarbonyl group, ethylmethylaminocarbonyl group and diethylaminocarbonyl group; and a 3 to 6-membered ring group containing 1 to 2 oxygen atoms such as 1,3-dioxoranyl group and 1,3-dioxanyl group.

The "substituent B1" in Formula (1) represents at least one selected from the group consisting of a cyano group, a C1-C6 alkoxy group, a C1-C6 haloalkoxy group and a C3-C8 cycloalkoxy group. In particular, the substituent B1 is preferably a cyano group or a C1-C6 alkoxy group.

Preferred specific examples of the substituents B1 include a cyano group;

a C1-C6 alkoxy group such as methoxy group, ethoxy group, propyloxy group, isopropyloxy group, butoxy group and isobutoxy group;

a C1-C6 haloalkoxy group such as difluoromethoxy group, trifluoromethoxy group, 2,2-difluoroethoxy group, 2,2,2-trifluoroethoxy group, 3,3-difluoropropyloxy group and 3,3,3-trifluoropropyloxy group; and a C3-C8 cycloalkoxy group such as cyclopropyloxy group, cyclobutoxy group, cyclopentyloxy group and cyclohexyloxy group.

More preferred specific examples of the substituents B1 include a cyano group;

a C1-C6 alkoxy group such as methoxy group and ethoxy group;

a C1-C6 haloalkoxy group such as difluoromethoxy group, trifluoromethoxy group, 2,2-difluoroethoxy group and 2,2,2-trifluoroethoxy group; and a C3-C8 cycloalkoxy group such as cyclopropyloxy group and cyclobutoxy group.

The halogen atom represented by R2 in Formula (1) is the same as defined hereinabove.

R2 in Formula (1) may represent a hydroxy group, a cyano group or a nitro group.

The C1-C6 alkyl group in the "C1-C6 alkyl group optionally substituted with substituent B" represented by R2 in Formula (1) is the same as defined hereinabove, and is preferably a methyl group, an ethyl group, a propyl group, an isopropyl group, a butyl group or an isobutyl group, and more preferably a methyl group, an ethyl group, a propyl group or an isopropyl group. When the group is substituted with substituent B, the substituent B substitutes for any hydrogen atom in the C1-C6 alkyl group.

The "C1-C6 haloalkyl group" represented by R2 in Formula (1) is the same as defined hereinabove, and is preferably a difluoromethyl group, a trifluoromethyl group, 2,2-difluoroethyl group, a 2,2,2-trifluoroethyl group, a 3,3-difluoropropyl group or a 3,3,3-trifluoropropyl group, and more preferably a difluoromethyl group, a trifluoromethyl group, a 2,2-difluoroethyl group or a 2,2,2-trifluoroethyl group.

The C3-C8 cycloalkyl group in the "C3-C8 cycloalkyl group optionally substituted with substituent B" represented by R2 in Formula (1) is the same as defined hereinabove, and is preferably a cyclopropyl group, a cyclobutyl group, a cyclopentyl group or a cyclohexyl group, and more preferably a cyclopropyl group or a cyclobutyl group. When the group is substituted with substituent B, the substituent B substitutes for any hydrogen atom in the C3-C8 cycloalkyl group.

The C2-C6 alkenyl group in the "C2-C6 alkenyl group optionally substituted with substituent B" represented by R2 in Formula (1) is the same as defined hereinabove, and is preferably a vinyl group, a 1-propenyl group, an allyl group, a 1-butenyl group, a 2-butenyl group or a 3-butenyl group, and more preferably a vinyl group, a 1-propenyl group or an allyl group. When the group is substituted with substituent B, the substituent B substitutes for any hydrogen atom in the C2-C6 alkenyl group.

The "C2-C6 haloalkenyl group" represented by R2 in Formula (1) is the same as defined hereinabove, and is preferably a 2-fluorovinyl group, a 2,2-difluorovinyl group, a 2,2-dichlorovinyl group, a 3-fluoroallyl group, a 3,3-difluoroallyl group or a 3,3-dichloroallyl group, and more preferably a 2-fluorovinyl group or a 2,2-difluorovinyl group.

The C2-C6 alkynyl group in the "C2-C6 alkynyl group optionally substituted with substituent B" represented by R2 in Formula (1) is the same as defined hereinabove, and is preferably an ethynyl group, a 1-propynyl group, a propargyl group, a 1-butynyl group, a 2-butynyl group or a 3-butynyl group, and more preferably an ethynyl group, a 1-propynyl group or a propargyl group. When the group is substituted with substituent B, the substituent B substitutes for any hydrogen atom in the C2-C6 alkynyl group.

The "C2-C6 haloalkynyl group" represented by R2 in Formula (1) is the same as defined hereinabove, and is preferably a 3,3-difluoro-1-propynyl group, a 3,3,3-trifluoro-1-propynyl group, a 4,4-difluoro-1-butynyl group, a 4,4-difluoro-2-butynyl group, a 4,4,4-trifluoro-1-butynyl group or a 4,4,4-trifluoro-2-butynyl group, and more preferably a 3,3-difluoro-1-propynyl group or a 3,3,3-trifluoro-1-propynyl group.

The C1-C6 alkoxy group in the "C1-C6 alkoxy group optionally substituted with substituent B" represented by R2 in Formula (1) is the same as defined hereinabove, and is preferably a methoxy group, an ethoxy group, a propyloxy group, an isopropyloxy group, a butoxy group, an isobutoxy group or a pentyloxy group, and more preferably a methoxy group, an ethoxy group, a propyloxy group, an isopropyloxy group, a butoxy group or a pentyloxy group. When the group is substituted with substituent B, the substituent B substitutes for any hydrogen atom in the C1-C6 alkoxy group.

The "C1-C6 haloalkoxy group" represented by R2 in Formula (1) is the same as defined hereinabove, and is preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group, and more preferably a difluoromethoxy group, a trifluoromethoxy group, a 2,2-difluoroethoxy group or a 2,2,2-trifluoroethoxy group.

The C3-C8 cycloalkoxy group in the "C3-C8 cycloalkoxy group optionally substituted with substituent B" represented by R2 in Formula (1) is the same as defined hereinabove, and is preferably a cyclopropyloxy group, a cyclobutoxy group, a cyclopentyloxy group or a cyclohexyloxy group, and more preferably a cyclopropyloxy group or a cyclobutoxy group. When the group is substituted with substituent B, the substituent B substitutes for any hydrogen atom in the C3-C8 cycloalkoxy group.

The C2-C6 alkenyloxy group in the "C2-C6 alkenyloxy group optionally substituted with substituent B" represented by R2 in Formula (1) is the same as defined hereinabove, and is preferably a vinyloxy group, a 1-propenyloxy group, an allyloxy group, a 1-butenyloxy group, a 2-butenyloxy group or a 3-butenyloxy group, and more preferably a vinyloxy group, a 1-propenyloxy group or an allyloxy group. When the group is substituted with substituent B, the substituent B substitutes for any hydrogen atom in the C2-C6 alkenyloxy group.

The "C2-C6 haloalkenyloxy group" represented by R2 in Formula (1) is the same as defined hereinabove, and is preferably a 2-fluorovinyloxy group, a 2,2-difluorovinyloxy group, a 2,2-dichlorovinyloxy group, a 3-fluoroallyloxy group, a 3,3-difluoroallyloxy group or a 3,3-dichloroallyloxy group, and more preferably a 2-fluorovinyloxy group or a 2,2-difluorovinyloxy group.

The C3-C6 alkynyloxy group in the "C3-C6 alkynyloxy group optionally substituted with substituent B" represented by R2 in Formula (1) is the same as defined hereinabove, and is preferably a propargyloxy group, a 2-butynyloxy group or a 3-butynyloxy group, and more preferably a propargyloxy group. When the group is substituted with substituent B, the substituent B substitutes for any hydrogen atom in the C3-C6 alkynyloxy group.

The "C3-C6 haloalkynyloxy group" represented by R2 in Formula (1) is the same as defined hereinabove, and is preferably a 4,4-difluoro-2-butynyloxy group, a 4-chloro-4,4-difluoro-2-butynyloxy group, a 4-bromo-4,4-difluoro-2-butynyloxy group or a 4,4,4-trifluoro-2-butynyloxy group, and more preferably a 4,4-difluoro-2-butynyloxy group or a 4,4,4-trifluoro-2-butynyloxy group.

The definitions in "R20C(=O)—" (wherein R20 represents a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or an R21R22N— (wherein R21 and R22 each independently represents a hydrogen atom, a C1-C6 alkyl group optionally substituted with substituent B1, a C1-C6 haloalkyl group or a C3-C8 cycloalkyl group, or R21 and R22 in combination with the nitrogen atom to which they are bonded form an aziridinyl group, an azetidinyl group, a pyrrolidinyl group, a piperidinyl group, a homopiperidinyl group or an azocanyl group)) represented by R2 in Formula (1) are the same as described hereinabove. Examples of the "R20C(=O)—" include preferably an acetyl group, a propionyl group, a difluoroacetyl group, a trifluoroacetyl group, a cyclopropanecarbonyl group, a methoxycarbonyl group, an ethoxycarbonyl group, a 2,2-difluoroethoxycarbonyl group, a 2,2,2-trifluoroethoxycarbonyl group, a cyclopropyloxycarbonyl group, an aminocarbonyl group, a dimethylaminocarbonyl group, an ethylmethylaminocarbonyl group, a diethylaminocarbonyl group, a pyrrolidinylcarbonyl group and a piperidinylcarbonyl group, and more preferably an acetyl group, a difluoroacetyl group, a trifluoroacetyl group, a methoxycarbonyl group, an ethoxycarbonyl group, an aminocarbonyl group, a dimethylaminocarbonyl group, an ethylmethylaminocarbonyl group and a diethylaminocarbonyl group.

R20 in "R20C(=O)O—" represented by R2 in Formula (1) is the same as defined hereinabove. Examples of the "R20C(=O)O—" include preferably an acetyloxy group, a propionyloxy group, a difluoroacetyloxy group, a trifluoroacetyloxy group, a cyclopropanecarbonyloxy group, a methoxycarbonyloxy group, an ethoxycarbonyloxy group, a 2,2-difluoroethoxycarbonyloxy group, a 2,2,2-trifluoroethoxycarbonyloxy group, a cyclopropyloxycarbonyloxy group, an aminocarbonyloxy group, a dimethylaminocarbonyloxy group, an ethylmethylaminocarbonyloxy group, a diethylaminocarbonyloxy group, a pyrrolidinylcarbonyloxy group and a piperidinylcarbonyloxy group, and more preferably an acetyloxy group, a difluoroacetyloxy group, a trifluoroacetyloxy group, a methoxycarbonyloxy group, an ethoxycarbonyloxy group, an aminocarbonyloxy group, a dimethylaminocarbonyloxy group, an ethylmethylaminocarbonyloxy group and a diethylaminocarbonyloxy group.

The "3 to 6-membered ring group containing 1 to 2 oxygen atoms" represented by R2 in Formula (1) is the same as defined hereinabove, and is preferably an oxoranyl group, an oxanyl group, a 1,3-dioxoranyl group or a 1,3-dioxanyl group, and more preferably a 1,3-dioxoranyl group or a 1,3-dioxanyl group.

The definitions in "R23-L2-" (wherein R23 represents a C1-C6 alkyl group or a C1-C6 haloalkyl group, and L2 represents S, SO or $SO_2$) represented by R2 in Formula (1) are the same as described hereinabove. Examples of the "R23-L2-" include preferably a methylthio group, a methanesulfinyl group, a methanesulfonyl group, a trifluoromethylthio group, a trifluoromethanesulfinyl group, a trifluoromethanesulfonyl group, a (chloromethyl)thio group, a (chloromethane)sulfinyl group or a (chloromethane)sulfonyl group, and more preferably a methylthio group, a methanesulfinyl group, a methanesulfonyl group, a (chloromethyl)thio group, a (chloromethane)sulfinyl group and a (chloromethane)sulfonyl group.

R21 and R22 in the "R21R22N—" represented by R2 in Formula (1) are the same as defined hereinabove. Examples of the "R21R22N—" include preferably an amino group, a dimethylamino group, an ethylmethylamino group, a diethylamino group, a pyrrolidinyl group and a piperidinyl group, and more preferably a dimethylarnino group, an ethylmethylamino group and a diethylamino group.

The definitions in "R24C(=O)N(R25)-" (wherein R24 represents a hydrogen atom, a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or an R21R22N— (wherein R21 and R22 are the same as defined hereinabove), and R25 represents a hydrogen atom, a C1-C6 alkyl group optionally substituted with substituent B1, a C1-C6 haloalkyl group or a C3-C8 cycloalkyl group) represented by R2 in Formula (1) are the same as described hereinabove. Examples of R24 include preferably a hydrogen atom, a methyl group, an ethyl group, a difluoromethyl group, a trifluoromethyl group, a cyclopropyl group, a methoxy group, an ethoxy group, 2,2-difluoroethoxy, a 2,2,2-trifluoroethoxy group, a cyclopropyloxy group, an amino group, a dimethylamino group, an ethylmethylamino group, a diethylamino group, a pyrrolidinyl group and a piperidinyl group, and more preferably a hydrogen atom, a methyl group, a difluoromethyl group, a trifluoromethyl group, a methoxy group, an ethoxy group, an amino group, a dimethylamino group, an ethylmethylamino group and a diethylamino group. Examples of R25 include preferably a hydrogen atom, a methyl group, an ethyl group, a propyl group, a methoxymethyl group, an ethoxymethyl group, a methoxyethyl group, an ethoxyethyl group, a cyanomethyl group, a 2-cyanoethyl group, a 2,2-difluoroethyl group, a 2,2,2-trifluoroethyl group and a cyclopropyl group, and more preferably a hydrogen atom, a methyl group, an ethyl group, a methoxymethyl group, an ethoxymethyl group, a methoxyethyl group, an ethoxyethyl group, a cyanomethyl group, a 2,2-difluoroethyl group and a 2,2,2-trifluoroethyl group.

The letter n in Formula (1) is an integer of 0 to 5. When n is 2 or greater, the two or more R2's represent independent substituents which may be the same as or different from one another and are selected appropriately.

R3 in Formula (1) represents a hydrogen atom, a halogen atom, a nitro group, a C1-C6 alkyl group optionally substituted with substituent C, a C1-C6 haloalkyl group, a C3-C8 cycloalkyl group optionally substituted with substituent C, a C1-C6 alkoxy group optionally substituted with substituent C, a C1-C6 haloalkoxy group, a C2-C6 alkenyl group optionally substituted with substituent C, a C2-C6 haloalkenyl group, a C2-C6 alkynyl group optionally substituted with substituent C, a C2-C6 haloalkynyl group, an R30-L3- (wherein R30 has the same definition as R23, and L3 has the same definition as L2), an R31R32N— (wherein R31 and R32 have the same definition as R21 and R22), or an R33C(=O)— (wherein R33 represents a C1-C6 alkyl group, a C1-C6 haloalkyl group or a C3-C8 cycloalkyl group).

In particular, R3 is preferably a hydrogen atom, a halogen atom, a C1-C6 alkyl group optionally substituted with substituent C, a C3-C8 cycloalkyl group optionally substituted with substituent C, a C1-C6 alkoxy group optionally substituted with substituent C, a C2-C6 alkynyl group optionally substituted with substituent C, or an R30-L3- (wherein R30 and L3 are the same as defined hereinabove), or is particularly preferably a hydrogen atom, a halogen atom or a C1-C6 alkyl group optionally substituted with substituent C.

The "substituent C" in Formula (1) represents at least one selected from the group consisting of a hydroxy group, a cyano group, a C3-C8 cycloalkyl group, a C1-C6 alkoxy group, a C1-C6 haloalkoxy group, a C3-C8 cycloalkoxy group, an R31R32N— (wherein R31 and R32 have the same definition as R21 and R22), and an R30-L3- (wherein R30 has the same definition as R14, and L3 has the same definition as L1). In particular, the substituent C is preferably a cyano group, a C1-C6 alkoxy group or an R30-L3- (wherein R30 and L3 are the same as defined hereinabove), or is particularly preferably a cyano group or a C1-C6 alkoxy group.

Preferred specific examples of the substituents C include a hydroxy group; a cyano group;

a C3-C8 cycloalkyl group such as cyclopropyl group, cyclobutyl group, cyclopentyl group and cyclohexyl group;

a C1-C6 alkoxy group such as methoxy group, ethoxy group, propyloxy group, isopropyloxy group, butoxy group and isobutoxy group;

a C1-C6 haloalkoxy group such as difluoromethoxy group, trifluoromethoxy group, 2,2-difluoroethoxy group, 2,2,2-trifluoroethoxy group, 3,3-difluoropropyloxy group and 3,3,3-trifluoropropyloxy group;

a C3-C8 cycloalkoxy group such as cyclopropyloxy group, cyclobutoxy group, cyclopentyloxy group and cyclohexyloxy group;

an R31R32N— (wherein R31 and R32 have the same definition as R21 and R22) such as amino group, dimethylamino group, ethylmethylamino group, diethylamino group, pyrrolidinyl group and piperidinyl group; and an R30-L3- (wherein R30 has the same definition as R14, and L3 has the same definition as L1) such as methylthio group, methanesulfinyl group, methanesulfonyl group, trifluoromethylthio group, trifluoromethanesulfinyl group and trifluoromethanesulfonyl group.

More preferred specific examples of the substituents C include a hydroxy group; a cyano group;

a C3-C8 cycloalkyl group such as cyclopropyl group and cyclobutyl group;

a C1-C6 alkoxy group such as methoxy group and ethoxy group;

a C1-C6 haloalkoxy group such as difluoromethoxy group, trifluoromethoxy group, 2,2-difluoroethoxy group and 2,2,2-trifluoroethoxy group;

a C3-C8 cycloalkoxy group such as cyclopropyloxy group and cyclobutoxy group;

an R31R32N— (wherein R31 and R32 are the same as defined hereinabove) such as dimethylamino group, ethylmethylamino group and diethylamino group; and an R30-L3- (wherein R30 and L3 are the same as defined hereinabove) such as methylthio group, methanesulfinyl group and methanesulfonyl group.

R3 in Formula (1) may represent a hydrogen atom or a nitro group.

The "halogen atom" represented by R3 in Formula (1) is the same as defined hereinabove.

The C1-C6 alkyl group in the "C1-C6 alkyl group optionally substituted with substituent C" represented by R3 in Formula (1) is the same as defined hereinabove, and is preferably a methyl group, an ethyl group, a propyl group, an isopropyl group, a butyl group or an isobutyl group, and more preferably a methyl group, an ethyl group or a propyl group. When the group is substituted with substituent C, the substituent C substitutes for any hydrogen atom in the C1-C6 alkyl group.

The "C1-C6 haloalkyl group" represented by R3 in Formula (1) is the same as defined hereinabove, and is preferably a difluoromethyl group, a trifluoromethyl group, a 2,2-difluoroethyl group, a 2,2,2-trifluoroethyl group, a 3,3-difluoropropyl group or a 3,3,3-trifluoropropyl group, and more preferably a difluoromethyl group, a trifluoromethyl group, a 2,2-difluoroethyl group or a 2,2,2-trifluoroethyl group.

The C3-C8 cycloalkyl group in the "C3-C8 cycloalkyl group optionally substituted with substituent C" represented by R3 in Formula (1) is the same as defined hereinabove, and is preferably a cyclopropyl group, a cyclobutyl group, a cyclopentyl group or a cyclohexyl group, and more preferably a cyclopropyl group or a cyclobutyl group. When the group is substituted with substituent C, the substituent C substitutes for any hydrogen atom in the C3-C8 cycloalkyl group.

The C1-C6 alkoxy group in the "C1-C6 alkoxy group optionally substituted with substituent C" represented by R3 in Formula (1) is the same as defined hereinabove, and is preferably a methoxy group, an ethoxy group, a propyloxy group, an isopropyloxy group, a butoxy group or an isobutoxy group, and more preferably a methoxy group, an ethoxy group, a propyloxy group or an isopropyloxy group. When the group is substituted with substituent C, the substituent C substitutes for any hydrogen atom in the C1-C6 alkoxy group.

The "C1-C6 haloalkoxy group" represented by R3 in Formula (1) is the same as defined hereinabove, and is preferably a difluoromethoxy group, a trifluoromethoxy group, a 2,2-difluoroethoxy group, a 2,2,2-trifluoroethoxy group, a 3,3-difluoropropyloxy group or a 3,3,3-trifluoropropyloxy group, and more preferably a difluoromethoxy group, a trifluoromethoxy group, a 2,2-difluoroethoxy group or a 2,2,2-trifluoroethoxy group.

The C2-C6 alkenyl group in the "C2-C6 alkenyl group optionally substituted with substituent C" represented by R3 in Formula (1) is the same as defined hereinabove, and is preferably a vinyl group, a 1-propenyl group, an allyl group, a 1-butenyl group, a 2-butenyl group or a 3-butenyl group, and more preferably a vinyl group, a 1-propenyl group or an ally! group. When the group is substituted with substituent C, the substituent C substitutes for any hydrogen atom in the C2-C6 alkenyl group:

The "C2-C6 haloalkenyl group" represented by R3 in Formula (1) is the same as defined hereinabove, and is preferably a 2-fluorovinyl group, a 2,2-difluorovinyl group, a 2,2-dichlorovinyl group, a 3-fluoroallyl group, a 3,3-difluoroallyl group or a 3,3-dichloroallyl group, and more preferably a 2-fluorovinyl group or a 2,2-difluorovinyl group.

The C2-C6 alkynyl group in the "C2-C6 alkynyl group optionally substituted with substituent C" represented by R3 in Formula (1) is the same as defined hereinabove, and is preferably an ethynyl group, a 1-propynyl group, a propargyl group, a 1-butynyl group, a 2-butynyl group or a 3-butynyl group, and more preferably an ethynyl group, a 1-propynyl group or a propargyl group. When the group is substituted with substituent C, the substituent C substitutes for any hydrogen atom in the C2-C6 alkynyl group.

The "C2-C6 haloalkynyl group" represented by R3 in Formula (1) is the same as defined hereinabove, and is preferably a 3,3-difluoro-1-propynyl group, a 3,3,3-trifluoro-1-propynyl group, a 4,4-difluoro-1-butynyl group, a 4,4-difluoro-2-butyryl group, a 4,4,4-trifluoro-1-butynyl group or a 4,4,4-trifluoro-2-butynyl group, and more preferably a 3,3-difluoro-1-propynyl group or a 3,3,3-trifluoro-1-propynyl group.

R30 in the "R30-L3-" represented by R3 in Formula (1) has the same definition as R23, and L3 has the same definition as L2. Examples of the "R30-L3-" include preferably a methylthio group, a methanesulfinyl group, a methanesulfonyl group, a trifluoromethylthio group, a trifluoromethanesulfinyl group and a trifluoromethanesulfonyl group, and more preferably a methylthio group, a methanesulfinyl group and a methanesulfonyl group.

R31 and R32 in the "R31R32N-" represented by R3 in Formula (1) have the same definition as R21 and R22, and is preferably each an amino group, a dimethylamino group, an ethylmethylamino group, a diethylamino group, a pyrrolidinyl group or a piperidinyl group, and more preferably a dimethylamino group, an ethylmethylamino group or a diethylamino group.

The definitions in "R33C(=O)—" (wherein R33 represents a C1-C6 alkyl group, a C1-C6 haloalkyl group or a C3-C8 cycloalkyl group) represented by R3 in Formula (1) are the same as described hereinabove. Examples of the "R33C(=O)—" include preferably an acetyl group, a propionyl group, a difluoroacetyl group, a trifluoroacetyl group and a cyclopropanecarbonyl group, and more preferably an acetyl group, a difluoroacetyl group and a trifluoroacetyl group.

X in Formula (1) represents an oxygen atom or a sulfur atom. Preferably, X is an oxygen atom.

Y in Formula (1) represents a phenyl group, a pyridyl group, a pyridazinyl group, a pyrimidinyl group, a pyrazinyl group, a triazinyl group, a tetrazinyl group, a thienyl group, a thiazolyl group, an isothiazolyl group or a thiadiazolyl group.

The phenyl group is substituted with substituent D at an ortho position and is further substituted with 0 to 4 independent substituents D1 appropriately.

The pyridyl group, the pyridazinyl group, the pyrimidinyl group, the pyrazinyl group, the triazinyl group or the tetrazinyl group is substituted with substituent D at an ortho position and is further substituted with 0 to 3 independent substituents D1 appropriately.

The thienyl group, the thiazolyl group, the isothiazolyl group or the thiadiazolyl group is substituted with substituent D at an ortho position and is further substituted with 0 to 2 independent substituents D1 appropriately.

The "substituent D" in Formula (1) represents at least one selected from the group consisting of a halogen atom, a C1-C6 alkyl group, a C1-C6 haloalkyl group, a C1-C6 alkoxy group and a C1-C6 haloalkoxy group.

In particular, the substituent D is preferably a halogen atom or a C1-C6 alkyl group, or is particularly preferably a halogen atom.

Preferred specific examples of the substituents D include:

a halogen atom such as fluorine atom, chlorine atom, bromine atom and iodine atom;

a C1-C6 alkyl group such as methyl group, ethyl group and propyl group;

a C1-C6 haloalkyl group such as difluoromethyl group, trifluoromethyl group, 2,2-difluoroethyl group and 2,2,2-trifluoroethyl group;

a C1-C6 alkoxy group such as methoxy group, ethoxy group, propyloxy group, isopropyloxy group, butoxy group, isobutoxy group and t-butoxy group; and a C1-C6 haloalkoxy group such as difluoromethoxy group, trifluoromethoxy group, 2,2-difluoroethoxy group, 2,2,2-trifluoroethoxy group, 3,3-difluoropropyloxy group and 3,3,3-trifluoropropyloxy group.

More preferred specific examples of the substituents D include:

a halogen atom such as fluorine atom, chlorine atom and bromine atom;

a C1-C6 alkyl group such as methyl group and ethyl group;

a C1-C6 alkoxy group such as methoxy group, ethoxy group, propyloxy group and isopropyloxy group; and a C1-C6 haloalkoxy group such as difluoromethoxy group, trifluoromethoxy group, 2,2-difluoroethoxy group and 2,2,2-trifluoroethoxy group.

The "substituent D1" in Formula (1) represents at least one selected from the group consisting of a hydroxy group, a halogen atom, a C1-C6 alkyl group, a C1-C6 haloalkyl group, a C3-C8 cycloalkyl group, a C1-C6 alkoxy group, a C1-C6 haloalkoxy group and a C3-C8 cycloalkoxy group.

In particular, the substituent D1 is preferably a hydroxy group, a halogen atom, a C1-C6 alkyl group, a C1-C6 alkoxy group or a C1-C6 haloalkyl group, and more preferably a halogen atom, a C1-C6 alkyl group, a C1-C6 alkoxy group or a C1-C6 haloalkoxy group.

Preferred specific examples of the substituents D1 include a hydroxy group;

a halogen atom such as fluorine atom, chlorine atom, bromine atom and iodine atom;

a C1-C6 alkyl group such as methyl group, ethyl group and propyl group;

a C1-C6 haloalkyl group such as difluoromethyl group, trifluoromethyl group, 2,2-difluoroethyl group and 2,2,2-trifluoroethyl group;

a C3-C8 cycloalkyl group such as cyclopropyl group, cyclobutyl group, cyclopentyl group and cyclohexyl group;

a C1-C6 alkoxy group such as methoxy group, ethoxy group, propyloxy group, isopropyloxy group, butoxy group, isobutoxy group and t-butoxy group;

a C1-C6 haloalkoxy group such as difluoromethoxy group, trifluoromethoxy group, 2,2-difluoroethoxy group, 2,2,2-trifluoroethoxy group, 3,3-difluoropropyloxy group and 3,3,3-trifluoropropyloxy group; and a C3-C8 cycloalkoxy group such as cyclopropyloxy group, cyclobutoxy group, cyclopentyloxy group and cyclohexyloxy group.

More preferred specific examples of the substituents D1 include a hydroxy group;

a halogen atom such as fluorine atom, chlorine atom and bromine atom;

a C1-C6 alkyl group such as methyl group and ethyl group;

a C1-C6 haloalkyl group such as difluoromethyl group and trifluoromethyl group;

a C3-C8 cycloalkyl group such as cyclopropyl group and cyclobutyl group;

a C1-C6 alkoxy group such as methoxy group, ethoxy group, propyloxy group and isopropyloxy group;

a C1-C6 haloalkoxy group such as difluoromethoxy group, trifluoromethoxy group, 2,2-difluoroethoxy group and 2,2,2-trifluoroethoxy group; and a C3-C8 cycloalkoxy group such as cyclopropyloxy group and cyclobutoxy group.

Hereinbelow, specific examples of Y in Formula (1) will be described in detail.

A) When Y is a phenyl group, Y indicates a partial structure represented by Formula (a):

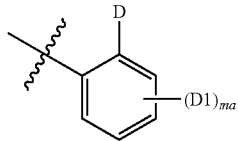

(a)

wherein D and D1 are the same as defined hereinabove, and ma represents an integer of 0 to 4.

The letter ma in Formula (a) represents an integer of 0 to 4.

When ma in Formula (a) is 2 or greater, the two or more D1's represent independent substituents which may be the same as or different from one another and may be selected appropriately.

In the specification, when Y is a phenyl group, the ortho position indicates the position in the phenyl group at which there is the substituent D as illustrated in Formula (a).

The phenyl group having the substituent D at the ortho position satisfies the characteristics of the invention.

Some preferred combinations represented by Formula (a) are 2-D-6-D1-phenyl group, 2-D-4-D1-phenyl group and 2-D-4-D1-6-D1-phenyl group. Here, for example, "2-D-6-D1-phenyl group" indicates a disubstituted phenyl group having substituent D at the 2-position and substituent D1 at the 6-position. The same applies hereinafter.

B) When Y is a pyridyl group, a pyridazinyl group, a pyrimidinyl group, a pyrazinyl group, a triazinyl group or a tetrazinyl group, Y indicates a partial structure represented by Formula (b):

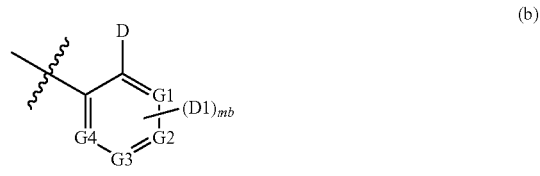

(b)

wherein D and D1 are the same as defined hereinabove, and mb is an integer of 0 to 3.

G1, G2, G3 and G4 in Formula (b) each independently represents a carbon atom or a nitrogen atom. At least one of G1, G2, G3 and G4 is a nitrogen atom. Preferably, G1, G2, G3 and G4 are such that any one of G1, G2, G3 and G4 is a nitrogen atom, namely, the structure is a pyridyl group.

The letter mb in Formula (b) represents an integer of 0 to 3.

When mb in Formula (b) is 2 or greater, the two or more D1's represent independent substituents which may be the same as or different from one another and may be selected appropriately.

In the specification, when Y is a pyridyl group, a pyridazinyl group, a pyrimidinyl group, a pyrazinyl group, a triazinyl group or a tetrazinyl group, the ortho position indicates the position in the 6-membered ring at which there is the substituent D as illustrated in Formula (b).

Specific examples of the partial structures of Formula (b) are illustrated below.

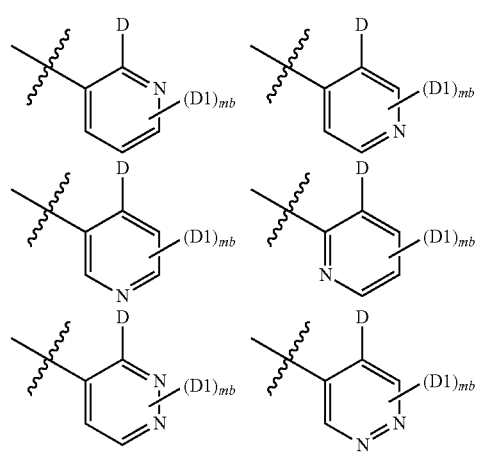

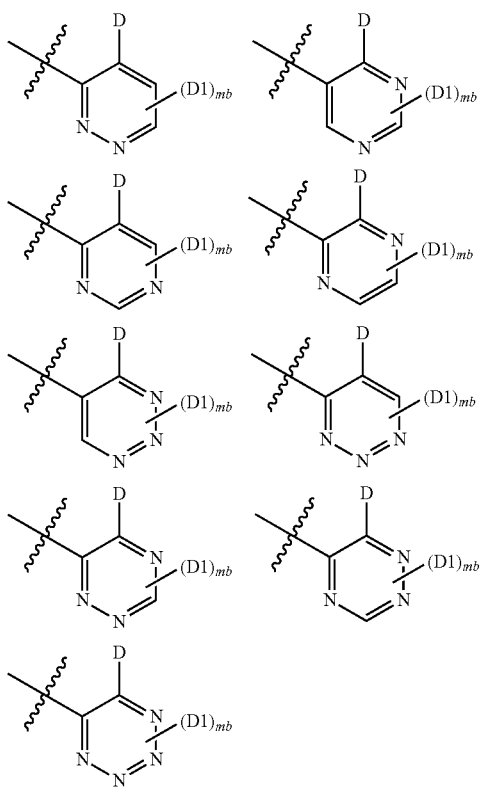

The pyridyl group, the pyridazinyl group, the pyrimidinyl group, the pyrazinyl group, the triazinyl group or the tetrazinyl group having the substituent D at the ortho position satisfies the characteristics of the invention.

Some preferred combinations represented by Formula (b) are 3-D-2-pyridyl group, 3-D-5-D1-2-pyridyl group, 2-D-3-pyridyl group, 2-D-4-D1-3-pyridyl group, 2-D-6-D1-3-pyridyl group, 2-D-4-D1-6-D1-3-pyridyl group, 4-D-3-pyridyl group, 4-D-2-D1-3-pyridyl group, 4-D-6-D1-3-pyridyl group, 4-D-2-D1-6-D1-3-pyridyl group, 3-D-4-pyridyl group and 3-D-5-D1-4-pyridyl group.

C) When Y is a thienyl group, a thiazolyl group, an isothiazolyl group or a thiadiazolyl group, Y indicates a partial structure represented by Formula (c-1):

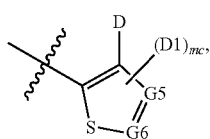

Formula (c-2):

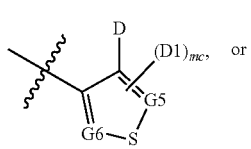

Formula (c-3):

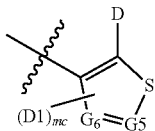

wherein D and D1 are the same as defined hereinabove, and mc is an integer of 0 to 2.

G5 and G6 in Formula (c-1), Formula (c-2) and Formula (c-3) each independently represents a carbon atom or a nitrogen atom.

The letter mc in Formula (c-1), Formula (c-2) and Formula (c-3) represents an integer of 0 to 2.

When mc in Formula (c-1), Formula (c-2) and Formula (c-3) is 2, the two D1's represent independent substituents which may be the same as or different from each other and may be selected appropriately.

In the specification, when Y is a thienyl group, a thiazolyl group, an isothiazolyl group or a thiadiazolyl group, the ortho position indicates the position in the 5-membered ring at which there is the substituent D as illustrated in Formula (c-1), Formula (c-2) and Formula (c-3).

Specific examples of the partial structures of Formula (c-1) are illustrated below.

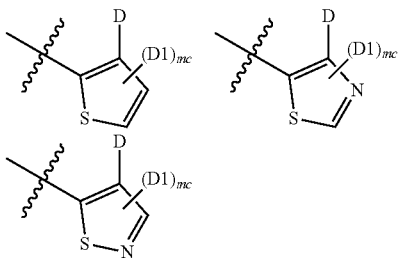

Specific examples of the partial structures of Formula (c-2) are illustrated below.

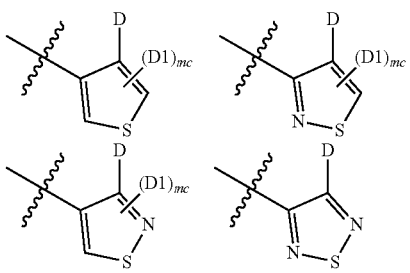

Specific examples of the substituents forming the partial structures of Formula (c-3) are illustrated below.

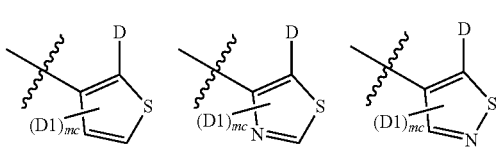

The thienyl group, the thiazolyl group, the isothiazolyl group or the thiadiazolyl group having the substituent D at the ortho position satisfies the characteristics of the invention.

Formula (1) includes a bond indicated with a broken line, as represented by: ⸺ The bond indicated with a broken line in Formula (1) represents a double bond or a single bond.

When the bond indicated with a broken line in Formula (1) is a double bond, the compound or salt thereof is represented by Formula (1a):

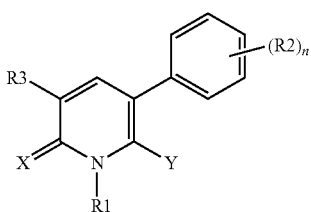

(1a)

In the formula, R1, R2, R3, X, Y and n are the same as defined in Formula (1).

When the bond indicated with a broken line in Formula (1) is a single bond, the compound or salt thereof is represented by Formula (1b):

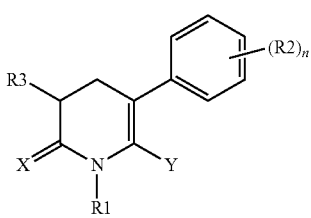

(1b)

In the formula, R1, R2, R3, X, Y and n are the same as defined in Formula (1).

When R3 in Formula (1b) is a substituent other than hydrogen, the compound is either the R-isomer or the S-isomer, or a mixture of the R-isomer and the S-isomer in an appropriate ratio.

The compound represented by Formula (1) may have one or two chiral axes. In this case, the compound is a single isomer or a mixture of isomers in an appropriate ratio without limitation.

The compound represented by Formula (1) may have a chiral atom. In this case, the compound is a single isomer or a mixture of isomers in an appropriate ratio without limitation.

The compound represented by Formula (1) may have geometric isomeric forms. In this case, the compound is a single isomer or a mixture of isomers in an appropriate ratio without limitation.

The compound represented by Formula (1) may form a salt. Examples include acid salts such as of hydrochloric acid, sulfuric acid, acetic acid, fumaric acid and maleic acid, and metal salts such as of sodium, potassium and calcium. However, the salts are not particularly limited as long as they are usable as agricultural and horticultural fungicides.

Next, some specific compounds according to the present invention are shown by combinations of the structural formulas illustrated in Table 1 and (R2)n described in Table 2. Those compounds are only illustrative and the scope of the invention is not limited to such compounds.

TABLE 1

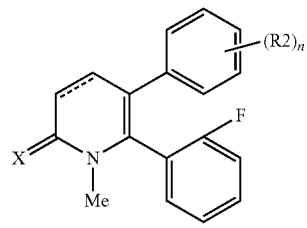

P-1

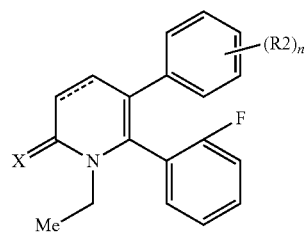

P-2

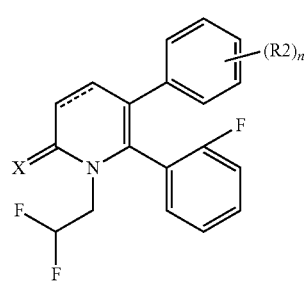

P-3

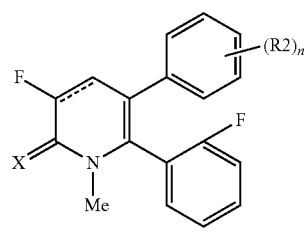

P-4

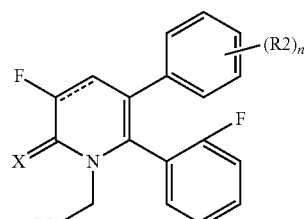

P-5

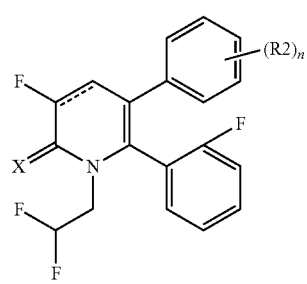

P-6

TABLE 1-continued
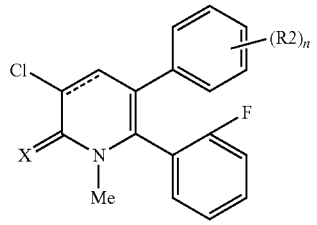 P-7
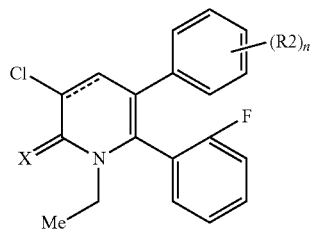 P-8
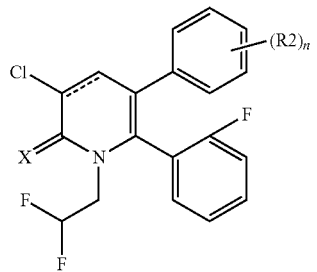 P-9
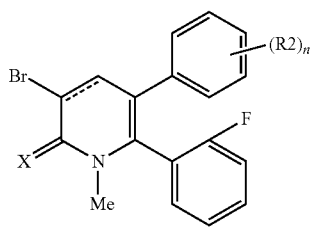 P-10
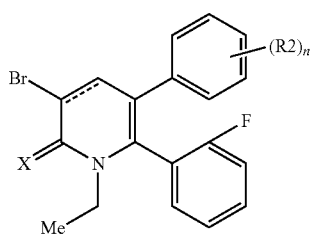 P-11
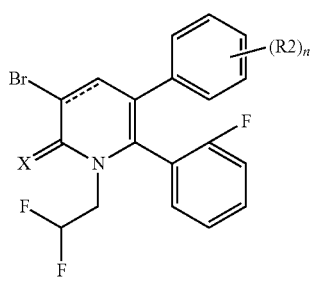 P-12
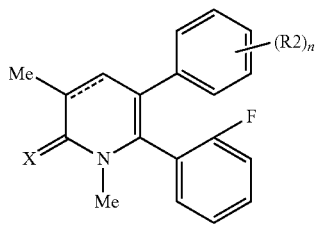 P-13
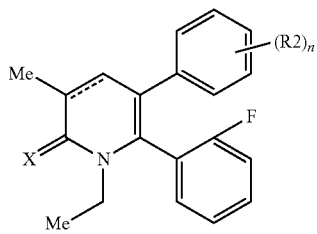 P-14
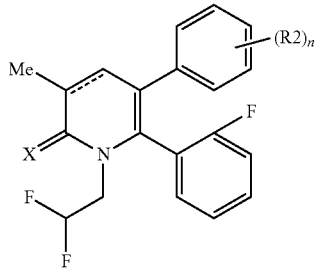 P-15
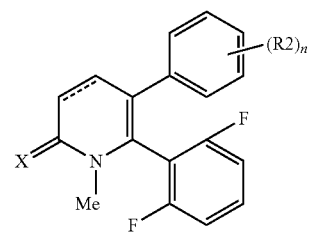 P-16
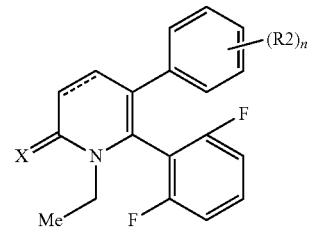 P-17
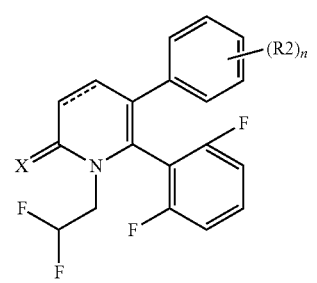 P-18

TABLE 1-continued
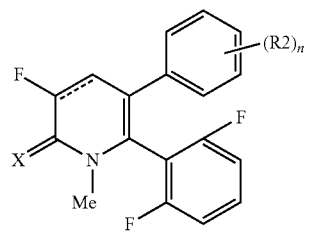 P-19
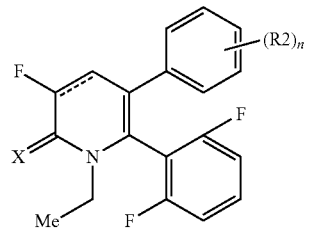 P-20
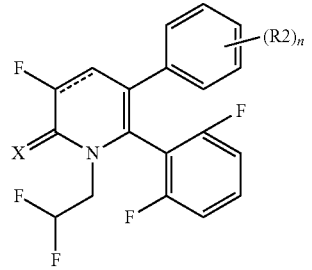 P-21
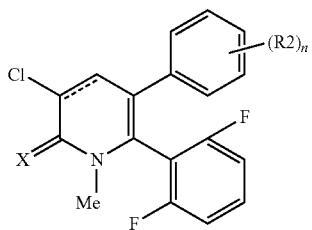 P-22
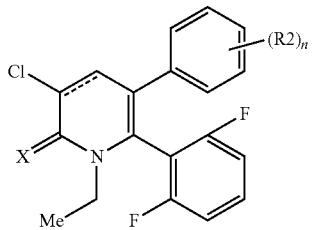 P-23
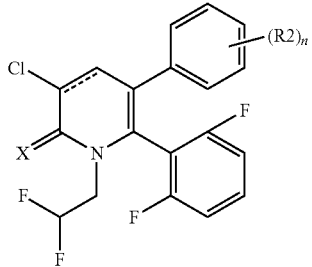 P-24
TABLE 1-continued
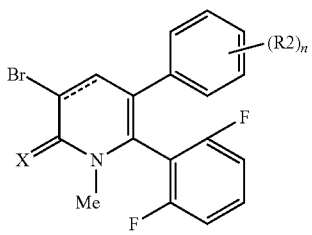 P-25
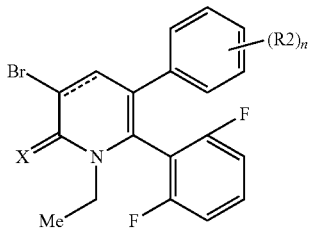 P-26
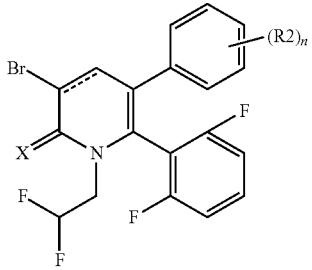 P-27
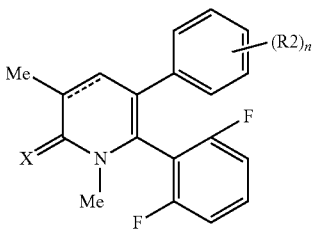 P-28
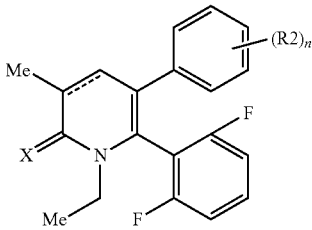 P-29
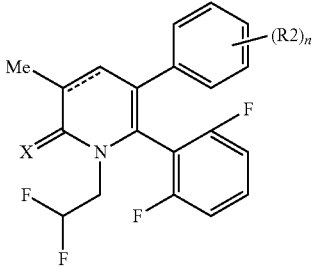 P-30

TABLE 1-continued
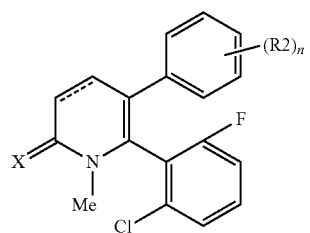 P-31
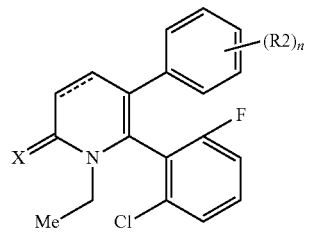 P-32
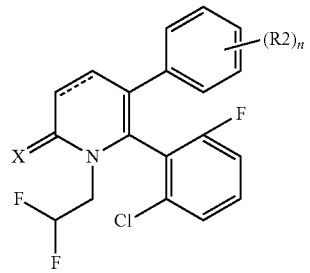 P-33
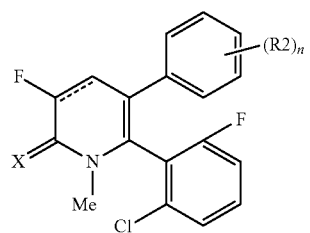 P-34
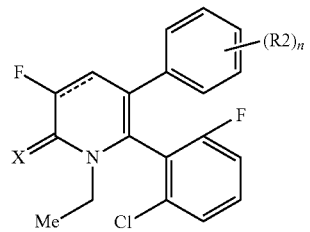 P-35
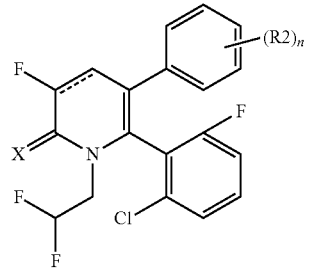 P-36
TABLE 1-continued
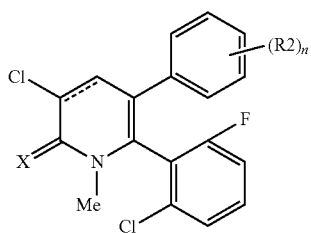 P-37
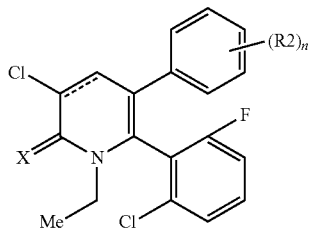 P-38
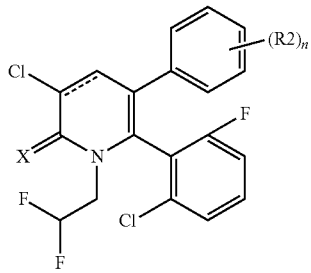 P-39
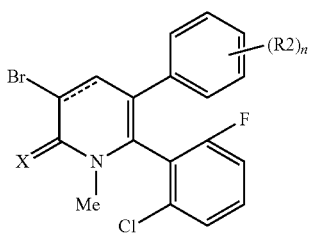 P-40
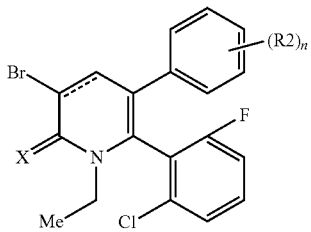 P-41
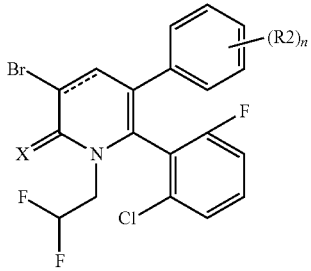 P-42

TABLE 1-continued
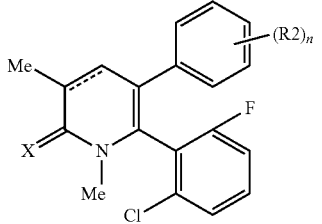 P-43
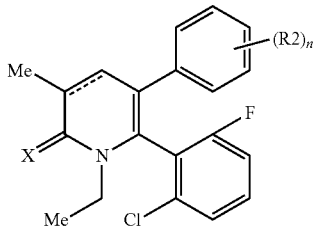 P-44
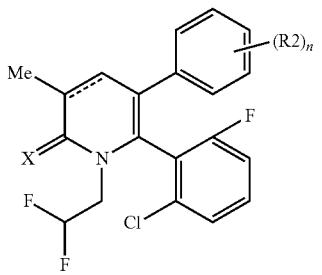 P-45
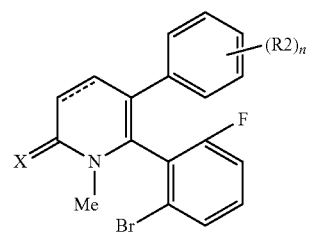 P-46
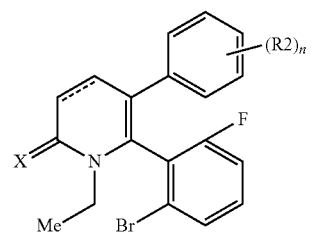 P-47
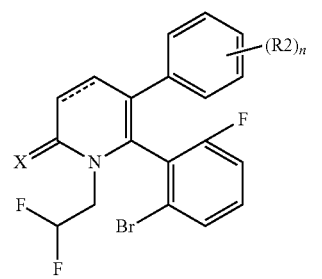 P-48
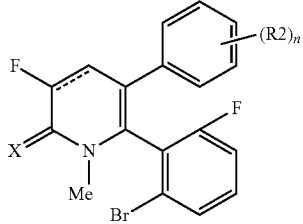 P-49
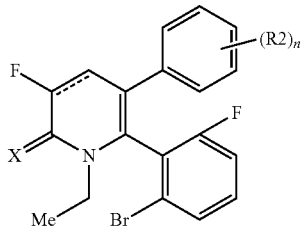 P-50
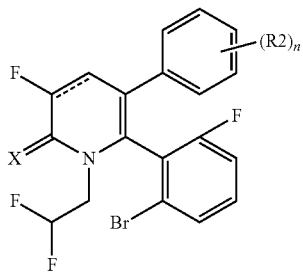 P-51
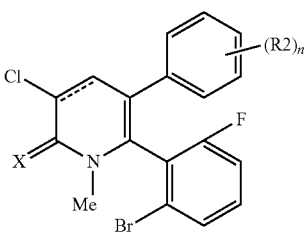 P-52
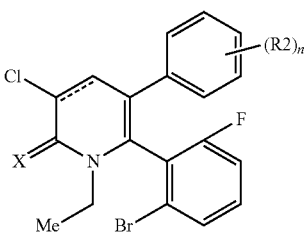 P-53
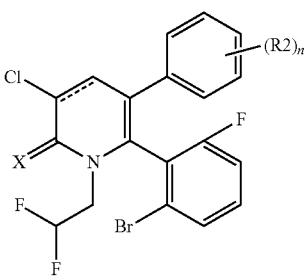 P-54

TABLE 1-continued
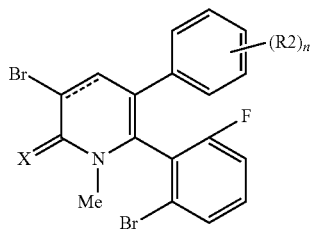 P-55
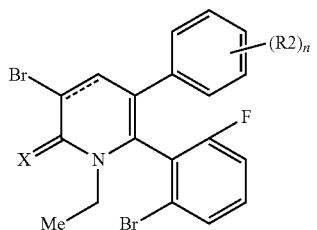 P-56
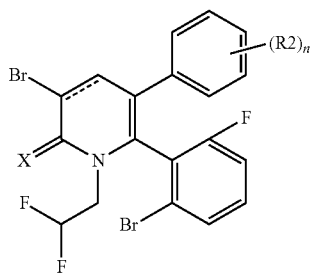 P-57
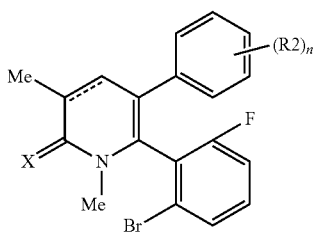 P-58
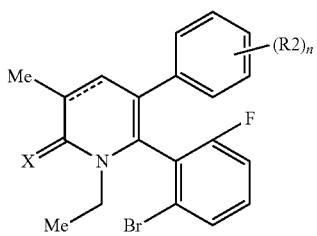 P-59
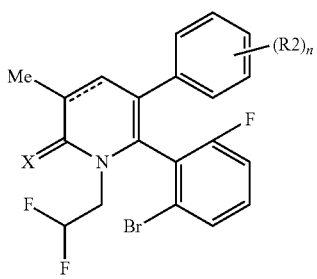 P-60
TABLE 1-continued
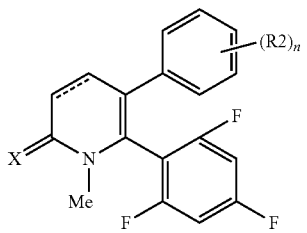 P-61
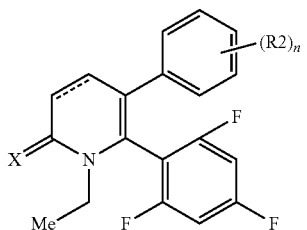 P-62
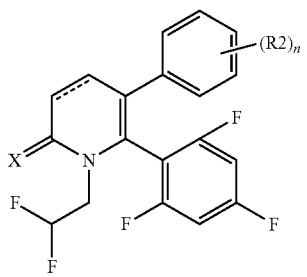 P-63
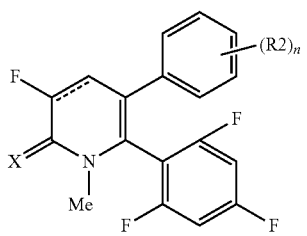 P-64
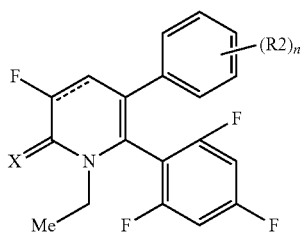 P-65
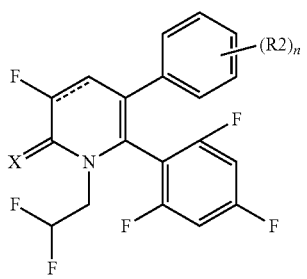 P-66

TABLE 1-continued
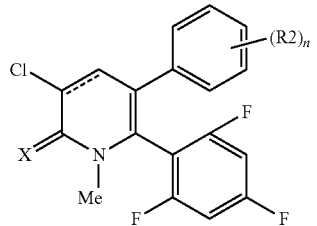 P-67
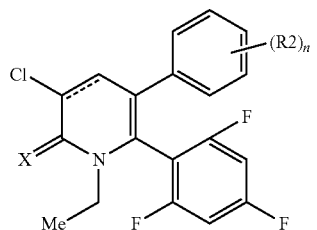 P-68
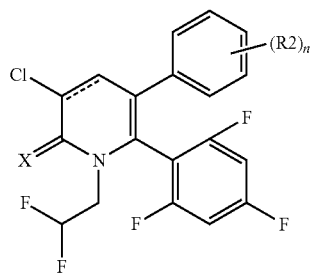 P-69
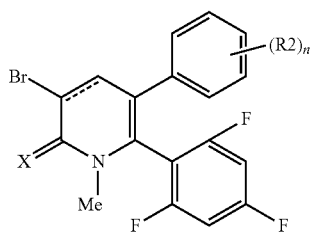 P-70
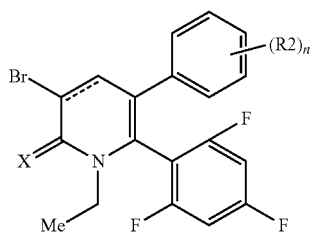 P-71
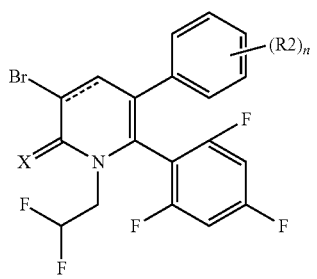 P-72
TABLE 1-continued
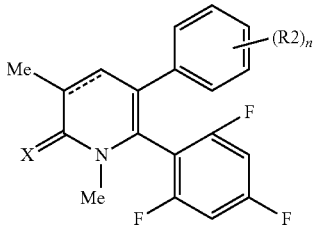 P-73
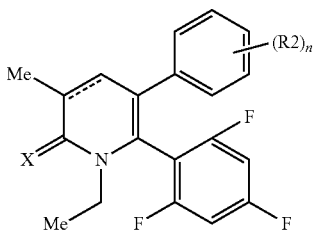 P-74
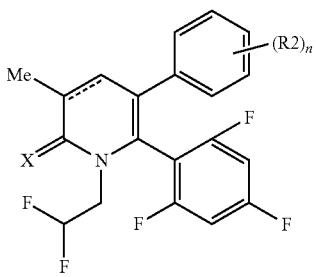 P-75
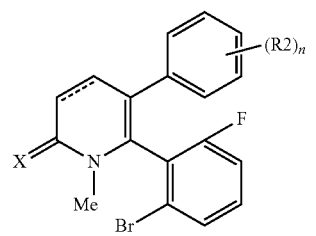 P-76
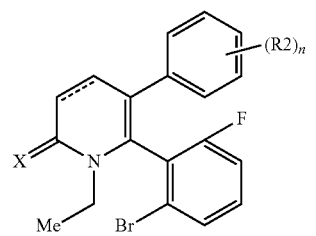 P-77
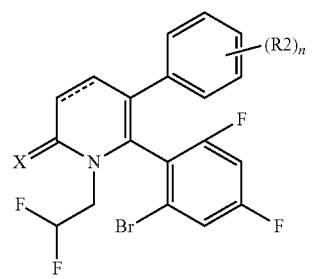 P-78

TABLE 1-continued
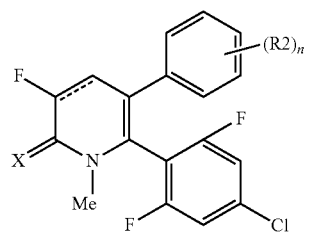 P-79
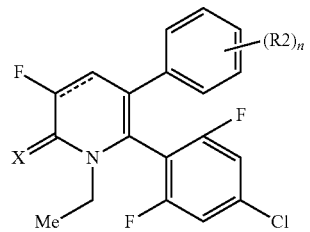 P-80
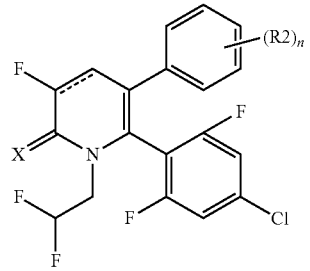 P-81
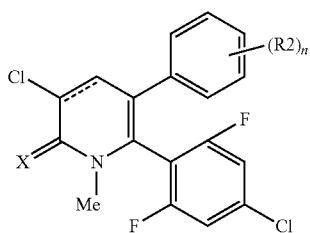 P-82
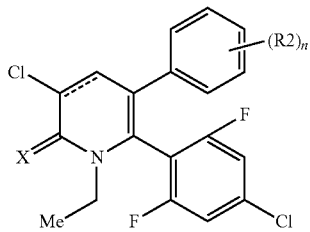 P-83
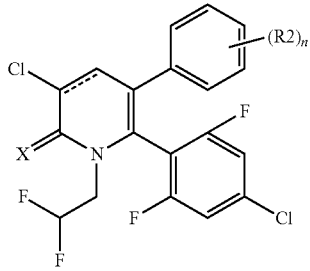 P-84
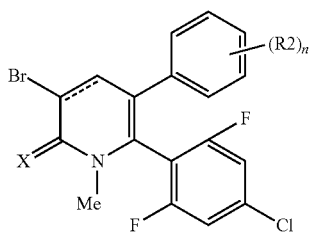 P-85
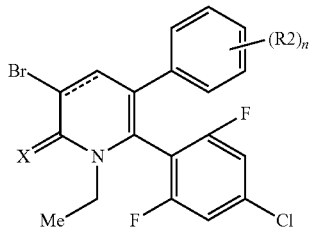 P-86
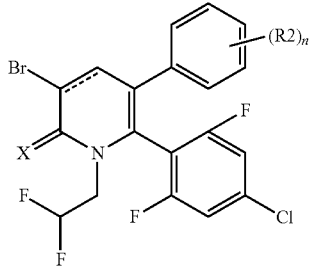 P-87
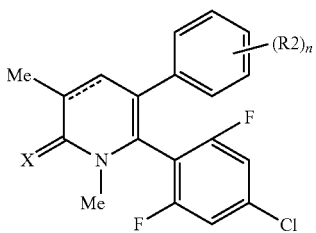 P-88
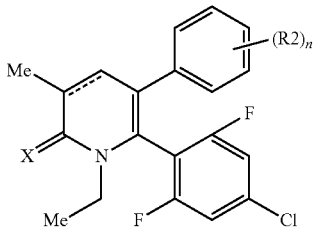 P-89
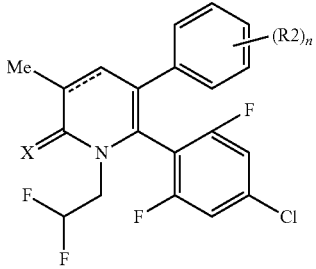 P-90

TABLE 1-continued
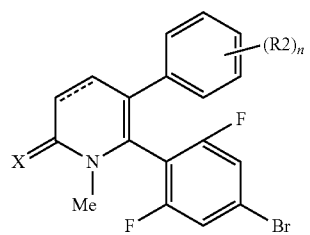 P-91
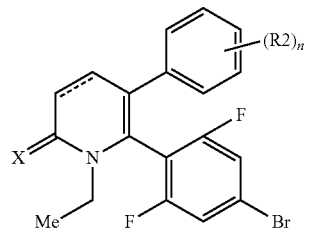 P-92
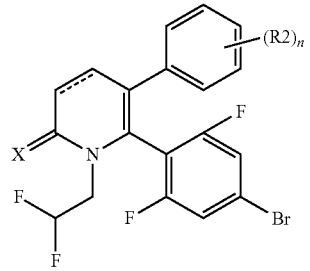 P-93
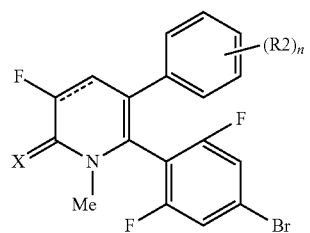 P-94
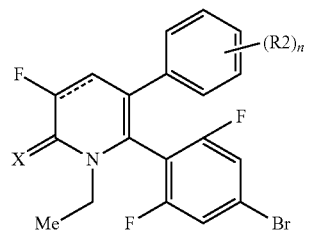 P-95
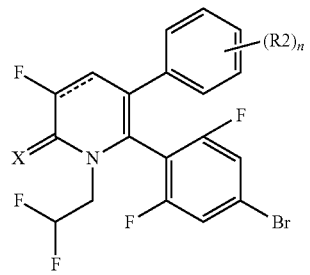 P-96
TABLE 1-continued
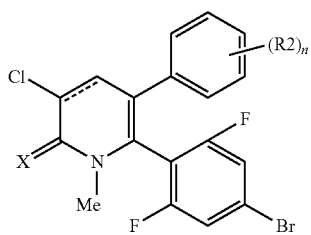 P-97
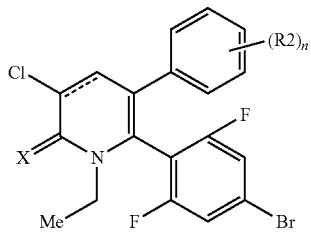 P-98
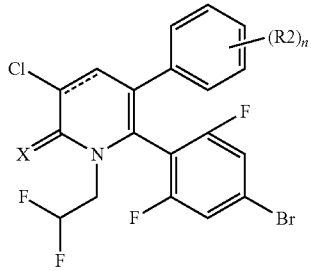 P-99
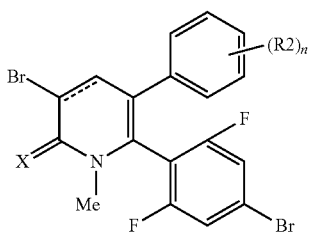 P-100
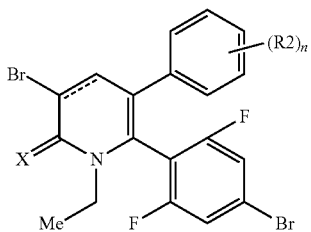 P-101
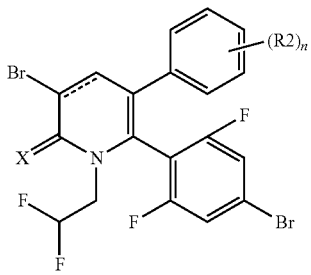 P-102

TABLE 1-continued

| Compound | Structure |
|---|---|
| P-103 | (structure shown) |
| P-104 | (structure shown) |
| P-105 | (structure shown) |
| P-106 | (structure shown) |
| P-107 | (structure shown) |
| P-108 | (structure shown) |
| P-109 | (structure shown) |
| P-110 | (structure shown) |
| P-111 | (structure shown) |
| P-112 | (structure shown) |
| P-113 | (structure shown) |
| P-114 | (structure shown) |

TABLE 1-continued
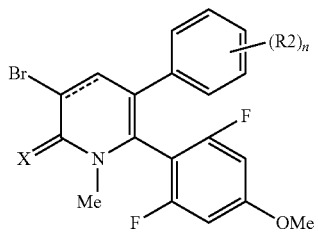 P-115
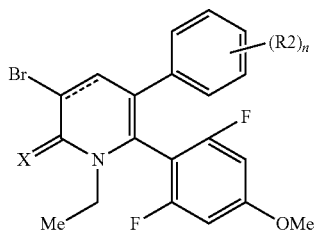 P-116
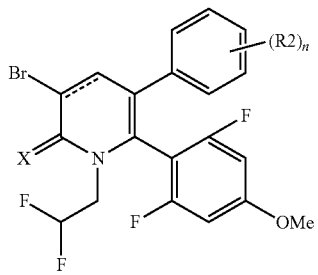 P-117
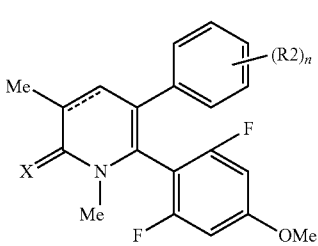 P-118
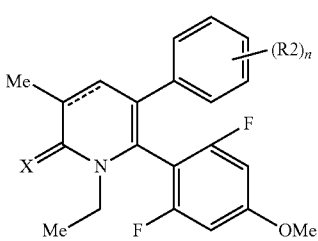 P-119
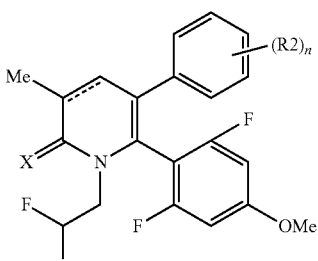 P-120
TABLE 1-continued
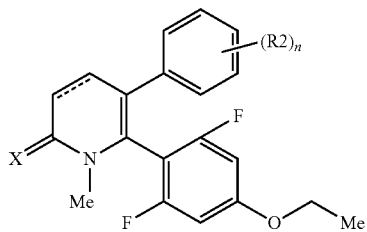 P-121
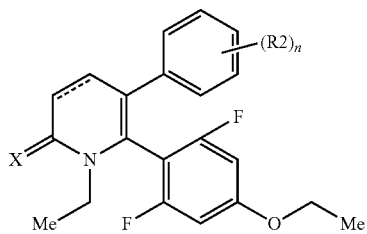 P-122
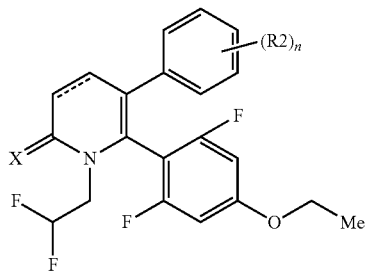 P-123
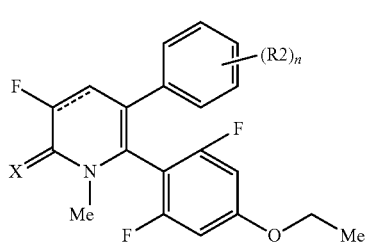 P-124
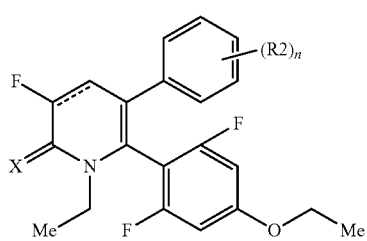 P-125
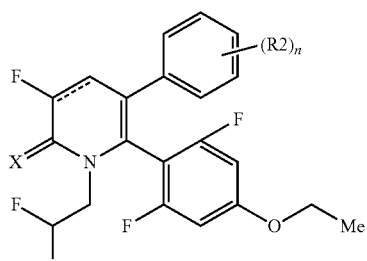 P-126

TABLE 1-continued

| Structure | ID |
|---|---|
| (chlorine, phenyl-R2n, F, OEt, F, N-Me pyridinone) | P-127 |
| (chlorine, phenyl-R2n, F, OEt, F, N-Et pyridinone) | P-128 |
| (chlorine, phenyl-R2n, F, OEt, F, N-CH2CHF2 pyridinone) | P-129 |
| (bromine, phenyl-R2n, F, OEt, F, N-Me pyridinone) | P-130 |
| (bromine, phenyl-R2n, F, OEt, F, N-Et pyridinone) | P-131 |
| (bromine, phenyl-R2n, F, OEt, F, N-CH2CHF2 pyridinone) | P-132 |
| (Me, phenyl-R2n, F, OEt, F, N-Me pyridinone) | P-133 |
| (Me, phenyl-R2n, F, OEt, F, N-Et pyridinone) | P-134 |
| (Me, phenyl-R2n, F, OEt, F, N-CH2CHF2 pyridinone) | P-135 |
| (phenyl-R2n, Cl-pyridine, N-Me pyridinone) | P-136 |
| (phenyl-R2n, Cl-pyridine, N-Et pyridinone) | P-137 |
| (phenyl-R2n, Cl-pyridine, N-CH2CHF2 pyridinone) | P-138 |

TABLE 1-continued
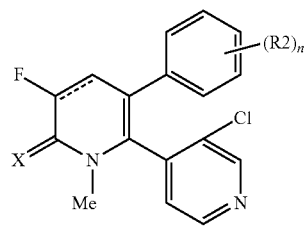 P-139
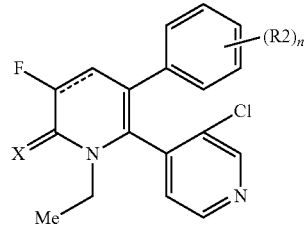 P-140
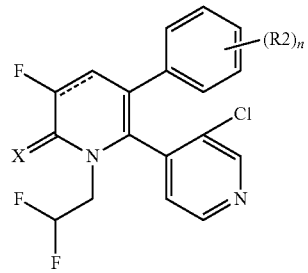 P-141
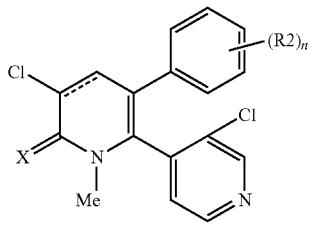 P-142
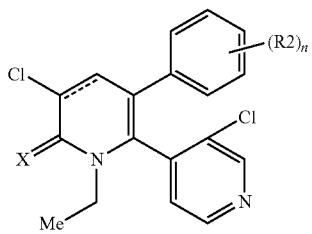 P-143
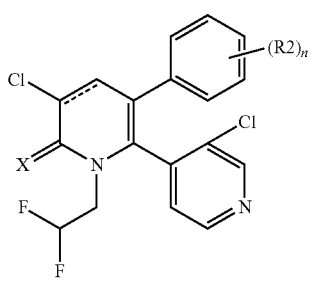 P-144
TABLE 1-continued
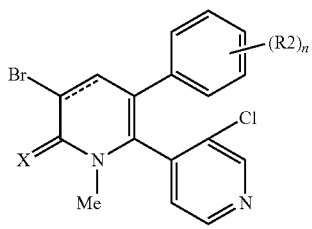 P-145
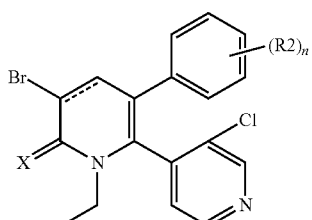 P-146
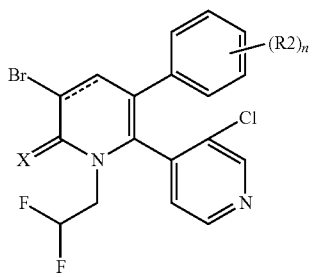 P-147
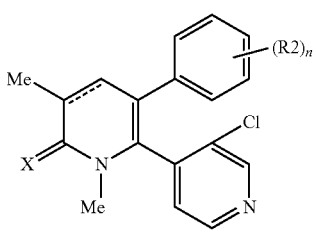 P-148
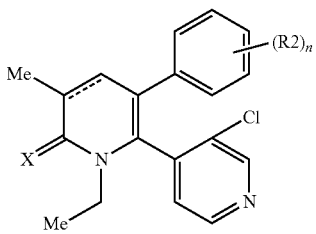 P-149
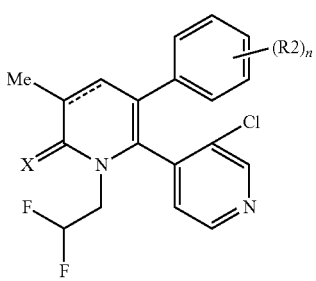 P-150

TABLE 1-continued
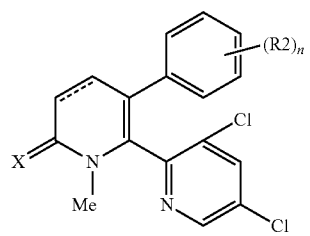 P-151
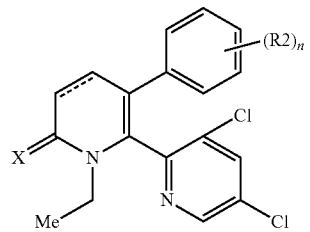 P-152
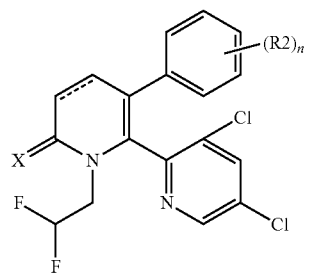 P-153
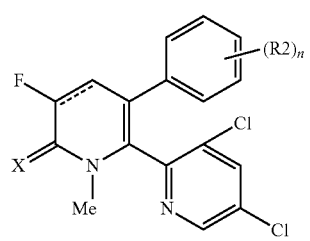 P-154
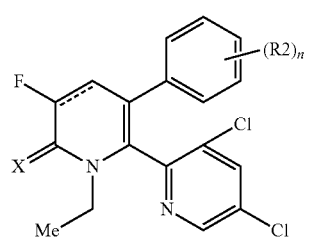 P-155
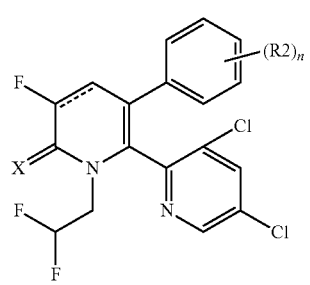 P-156
TABLE 1-continued
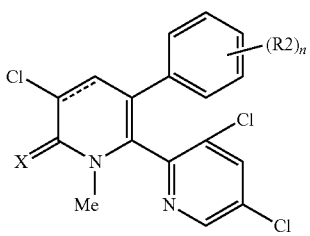 P-157
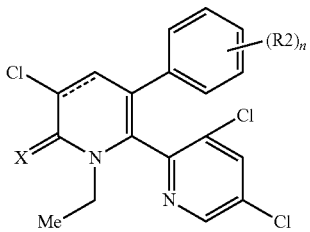 P-158
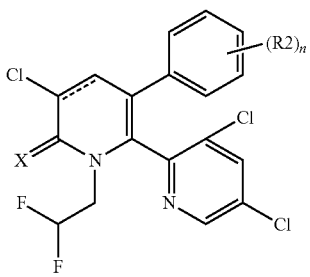 P-159
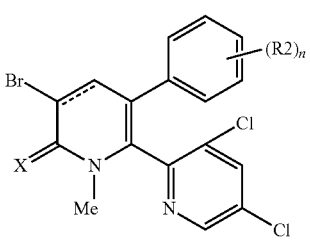 P-160
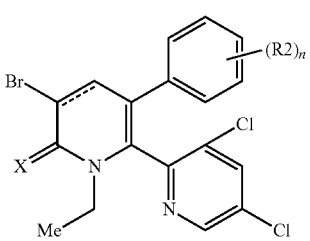 P-161
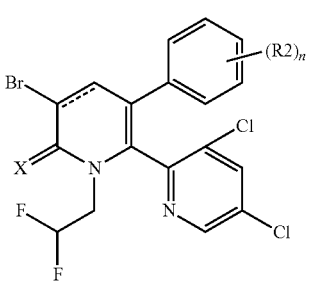 P-162

TABLE 1-continued
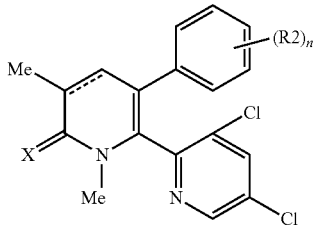 P-163
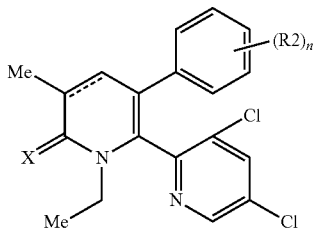 P-164
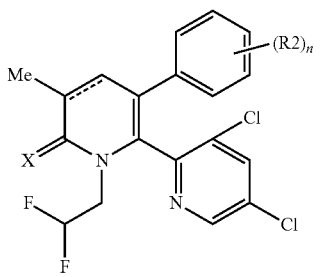 P-165
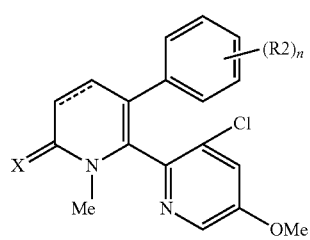 P-166
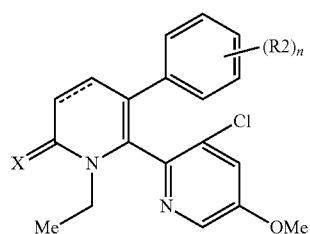 P-167
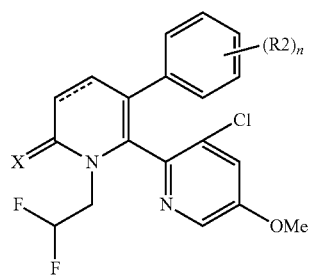 P-168
TABLE 1-continued
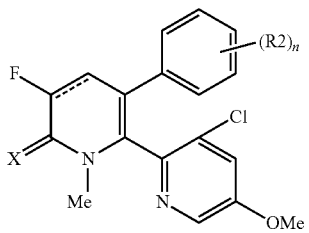 P-169
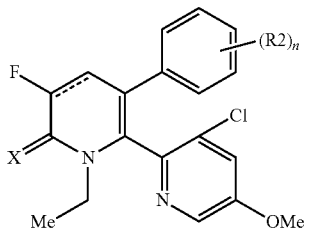 P-170
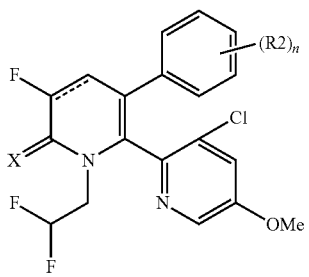 P-171
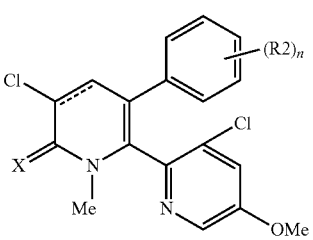 P-172
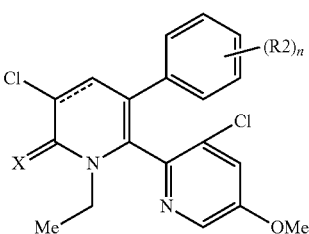 P-173
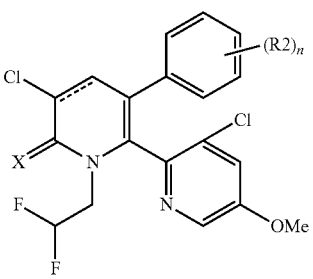 P-174

TABLE 1-continued
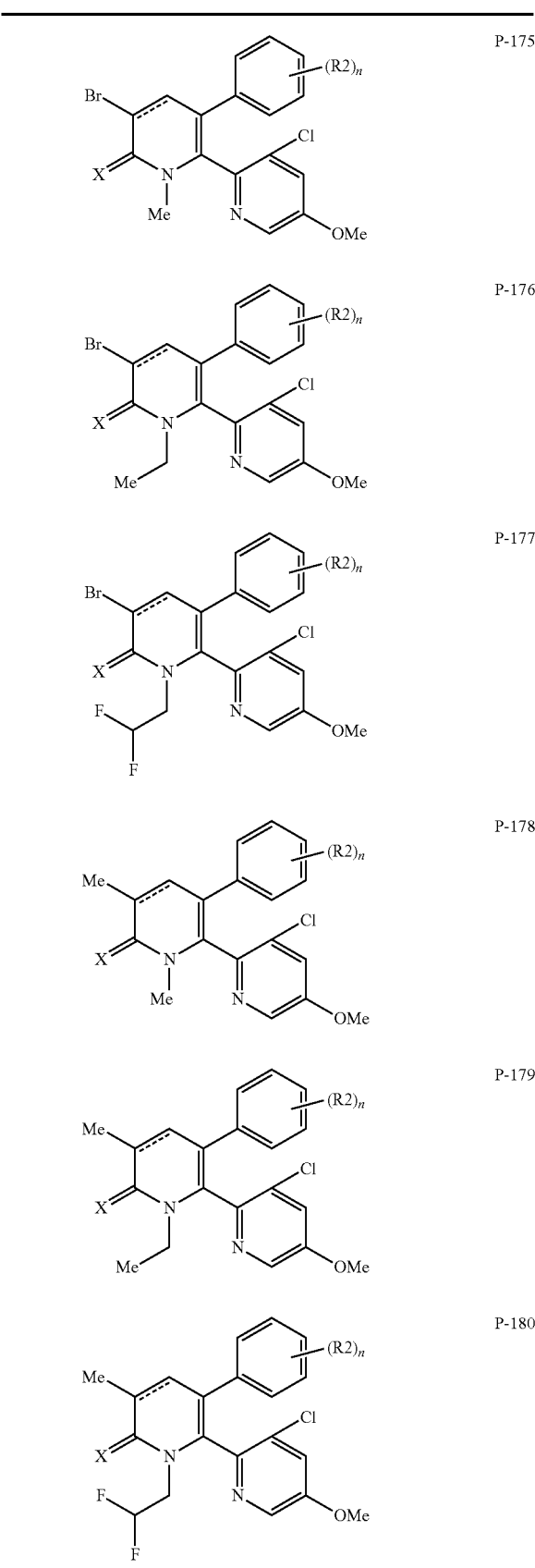
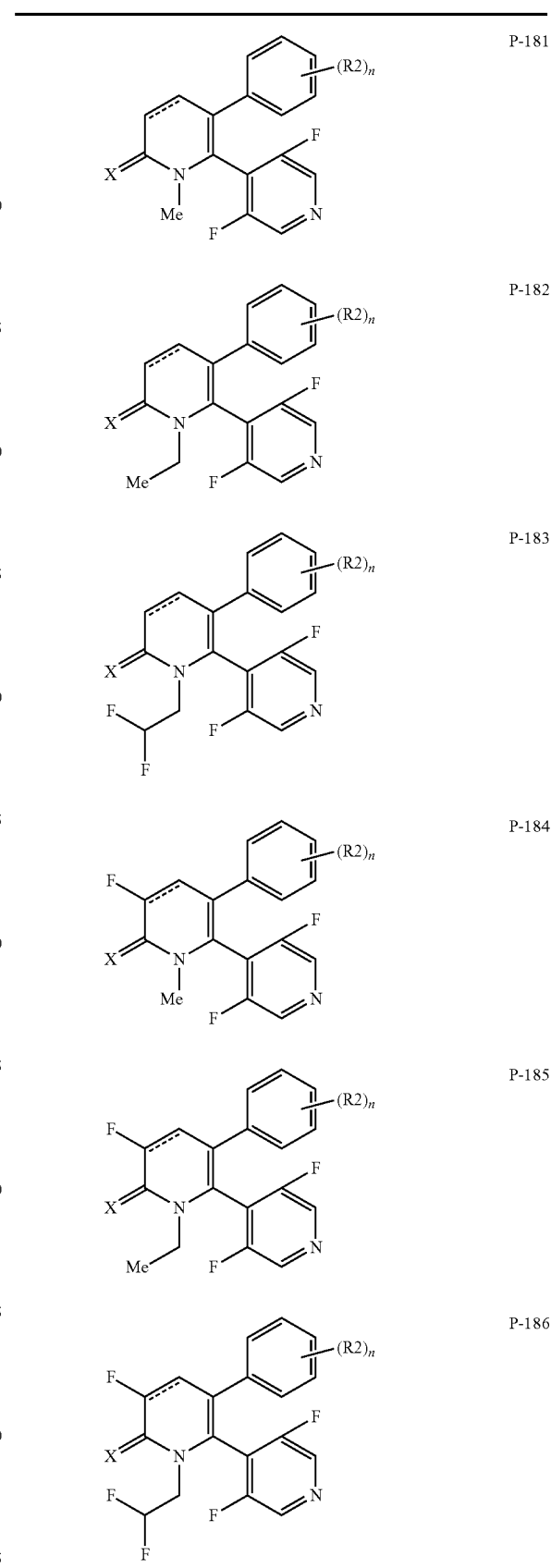

TABLE 1-continued
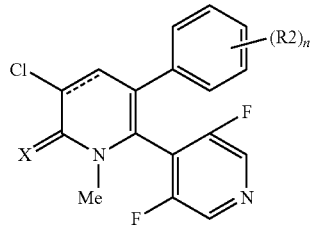 P-187
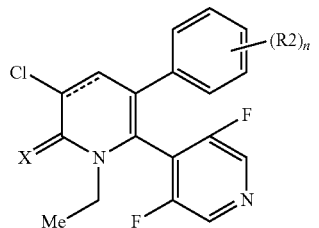 P-188
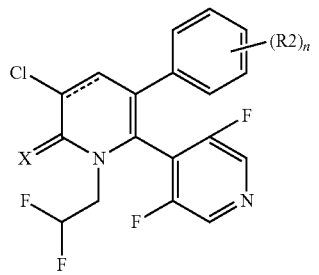 P-189
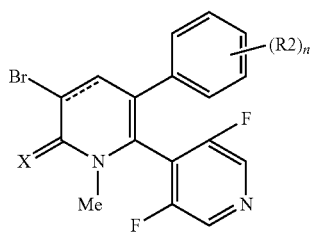 P-190
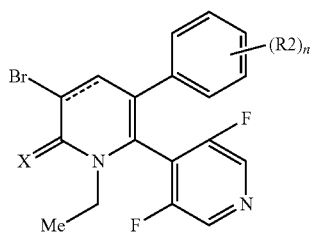 P-191
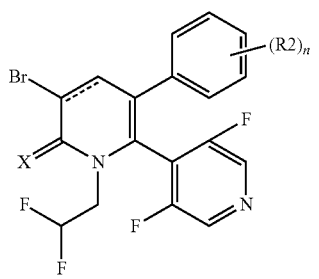 P-192
TABLE 1-continued
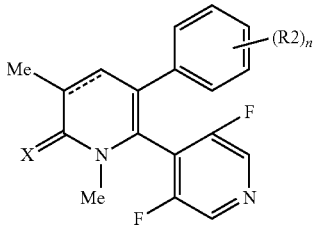 P-193
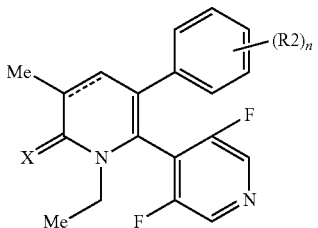 P-194
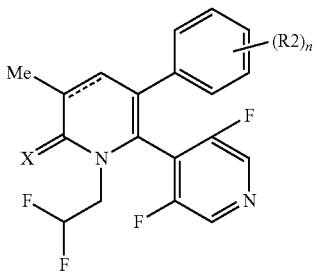 P-195
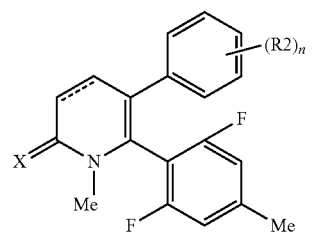 P-196
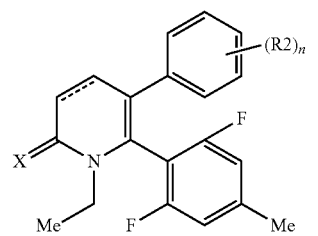 P-197
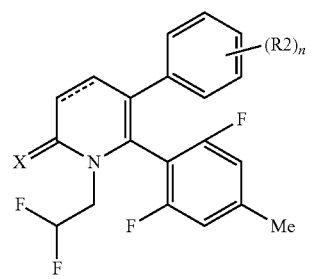 P-198

TABLE 1-continued
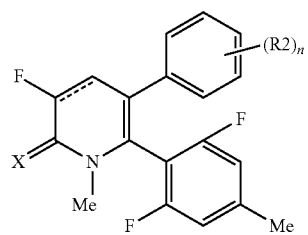 P-199
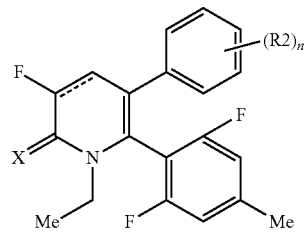 P-200
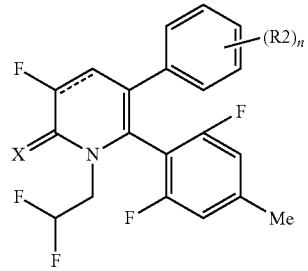 P-201
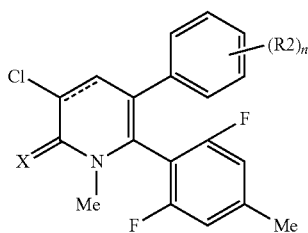 P-202
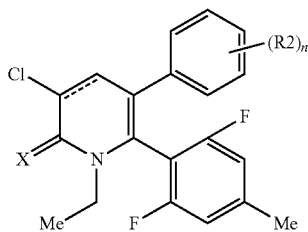 P-203
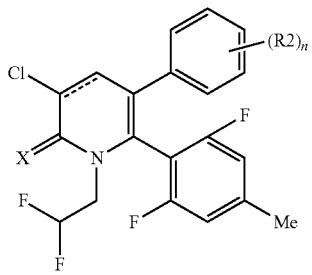 P-204
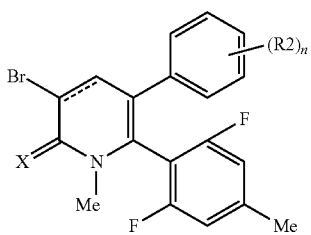 P-205
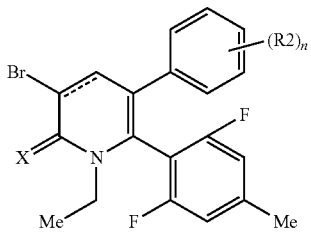 P-206
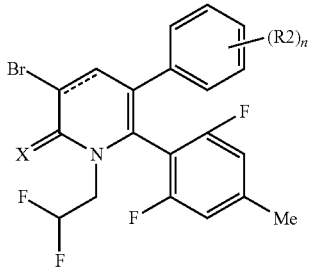 P-207
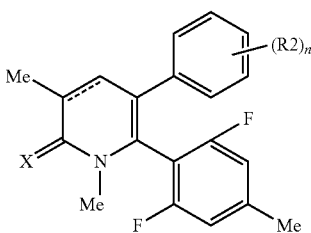 P-208
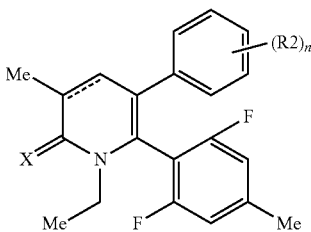 P-209
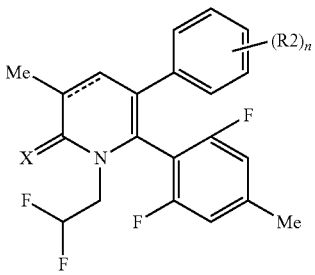 P-210

TABLE 1-continued
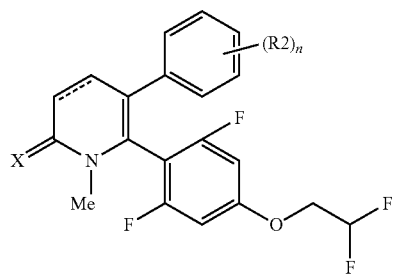 P-211
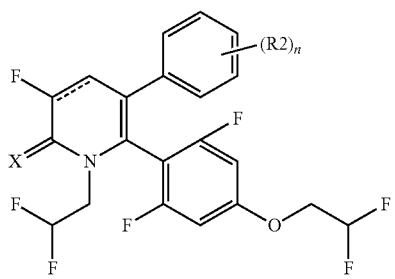 P-216
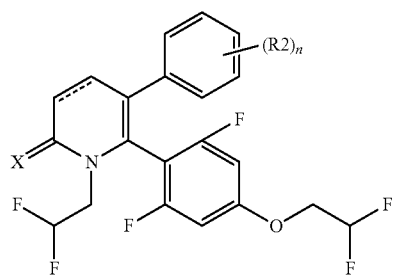 P-212
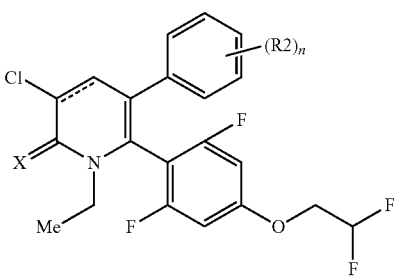 P-217
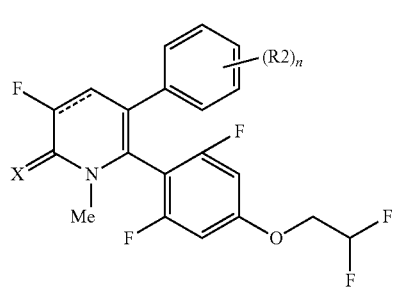 P-213
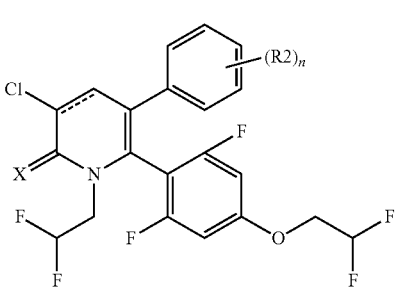 P-218
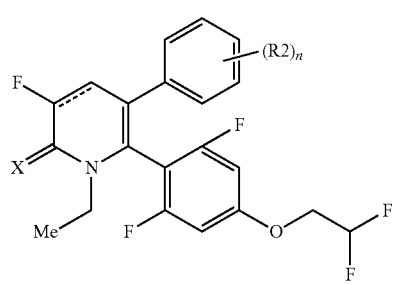 P-214
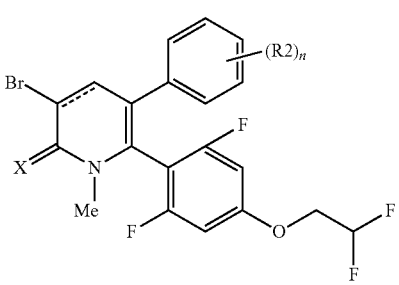 P-219
P-215
P-220

TABLE 1-continued
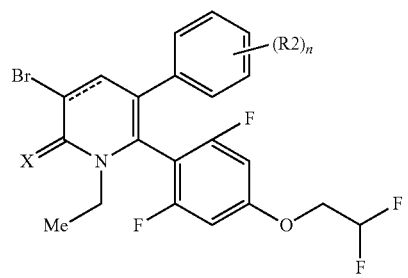
P-221
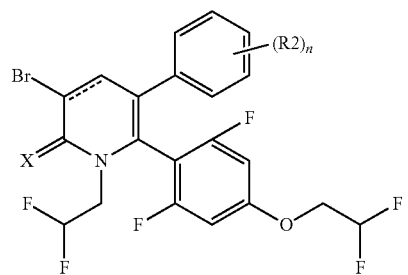
P-222
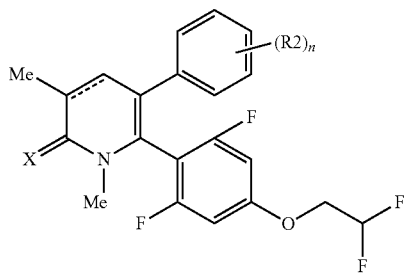
P-223
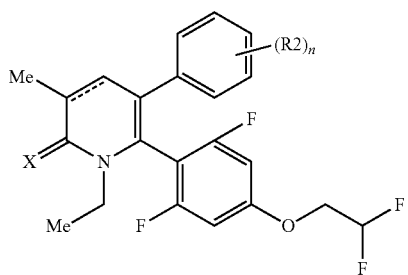
P-224
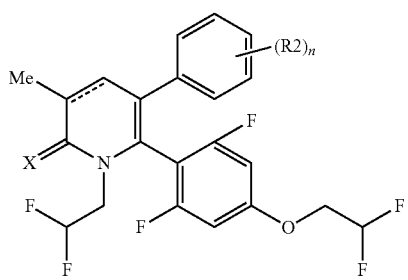
P-225
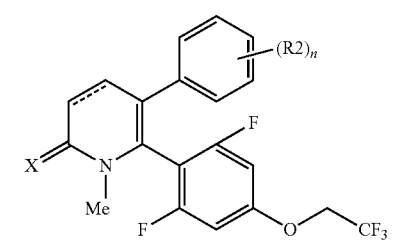
P-226
TABLE 1-continued
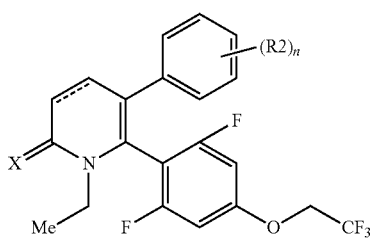
P-227
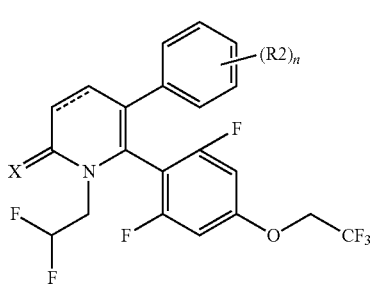
P-228
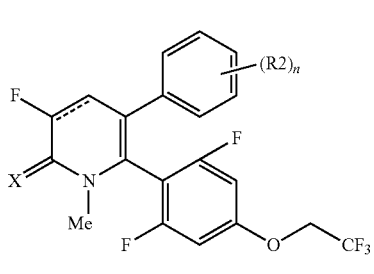
P-229
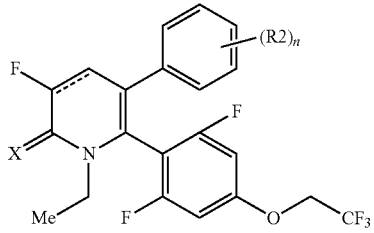
P-230
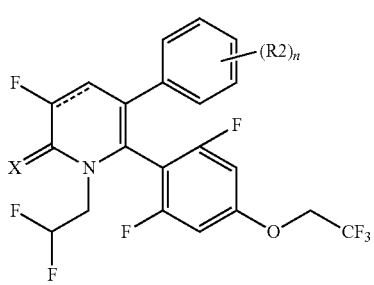
P-231
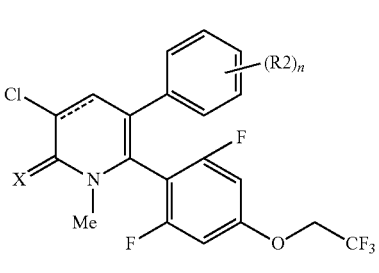
P-232

TABLE 1-continued
P-233 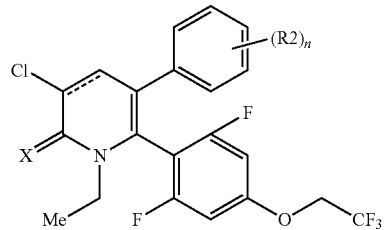
P-234 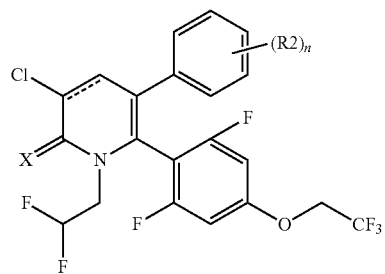
P-235 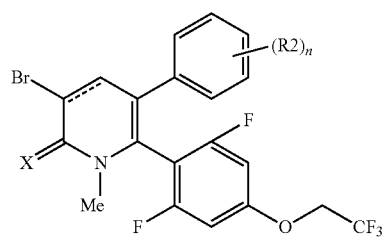
P-236 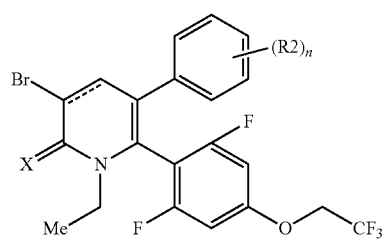
P-237 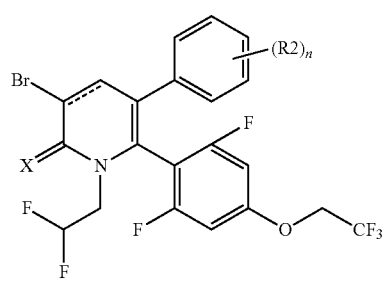
P-238 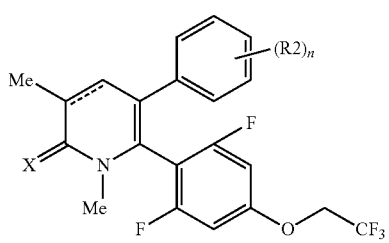
TABLE 1-continued
P-239 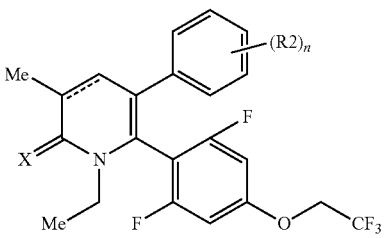
P-240 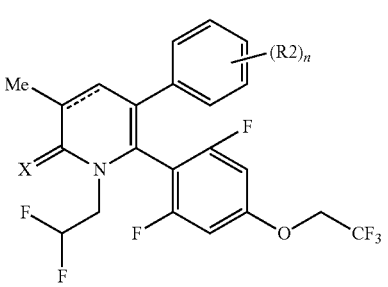
P-241 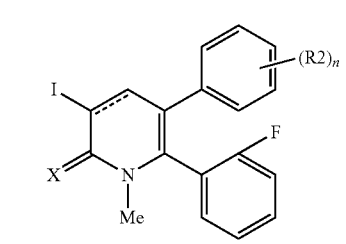
P-242 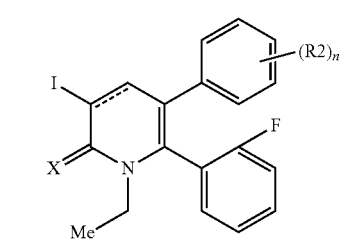
P-243 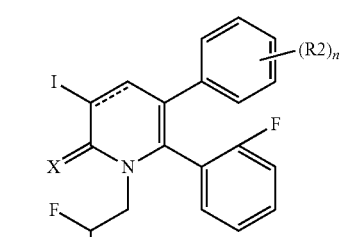
P-244 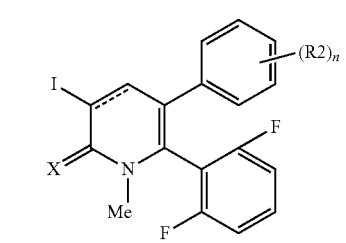

TABLE 1-continued
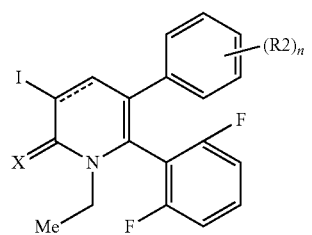 P-245
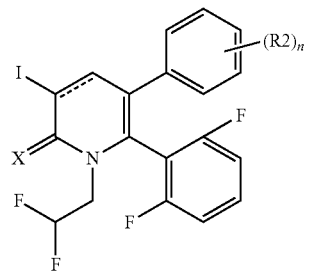 P-246
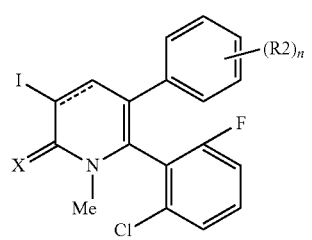 P-247
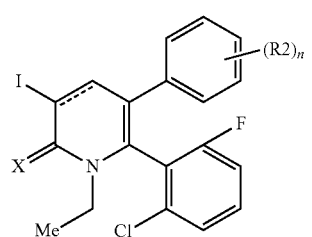 P-248
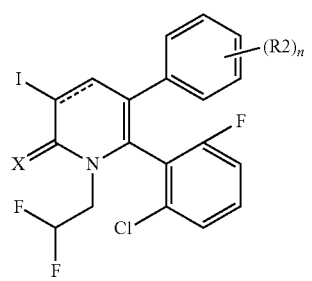 P-249
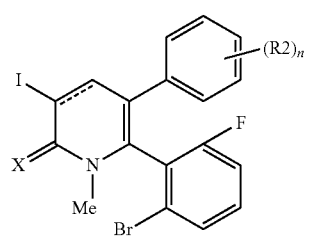 P-250
TABLE 1-continued
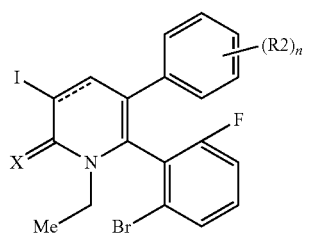 P-251
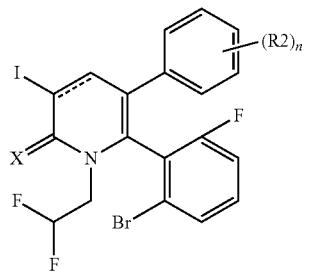 P-252
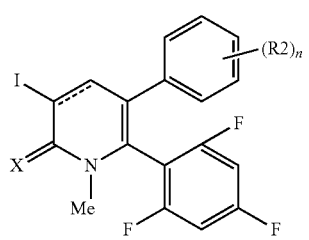 P-253
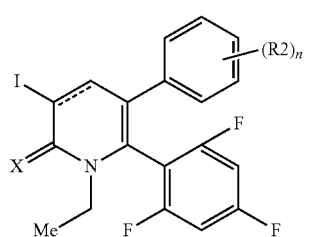 P-254
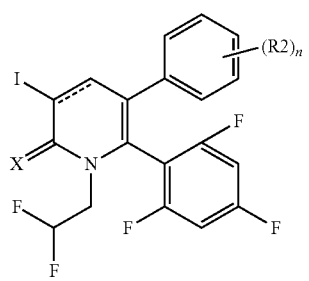 P-255
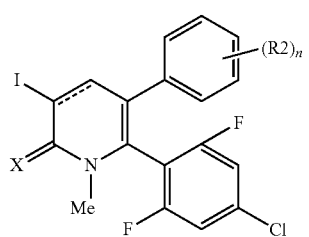 P-256

TABLE 1-continued
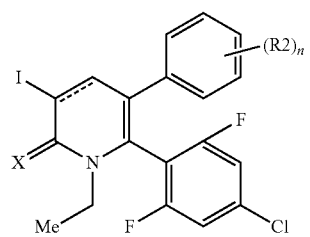 P-257
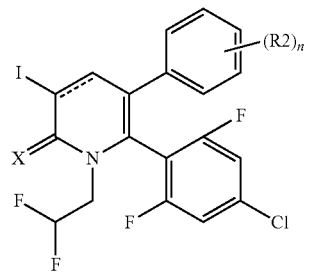 P-258
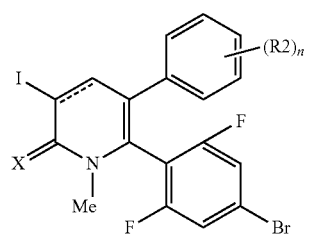 P-259
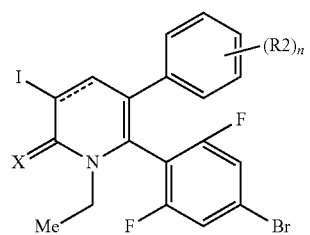 P-260
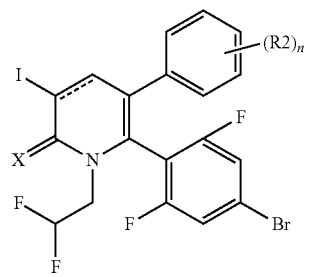 P-261
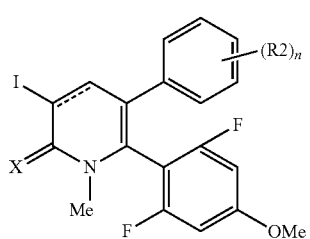 P-262
TABLE 1-continued
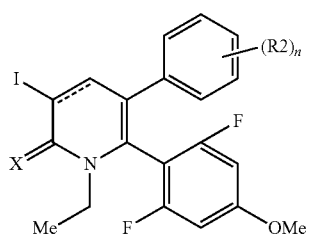 P-263
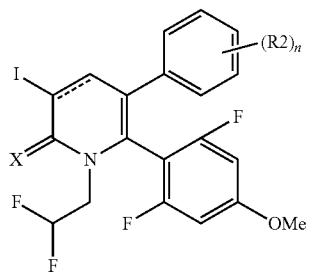 P-264
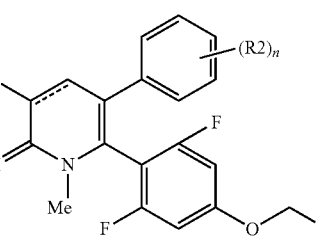 P-265
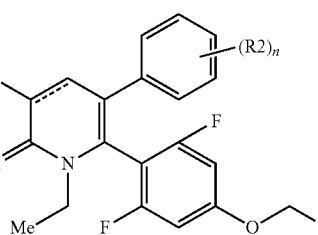 P-266
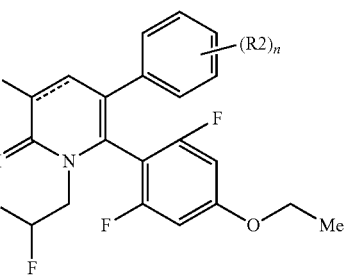 P-267
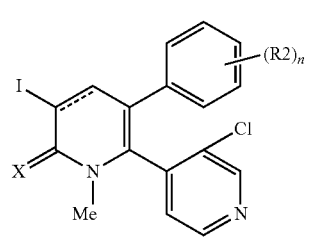 P-268

TABLE 1-continued
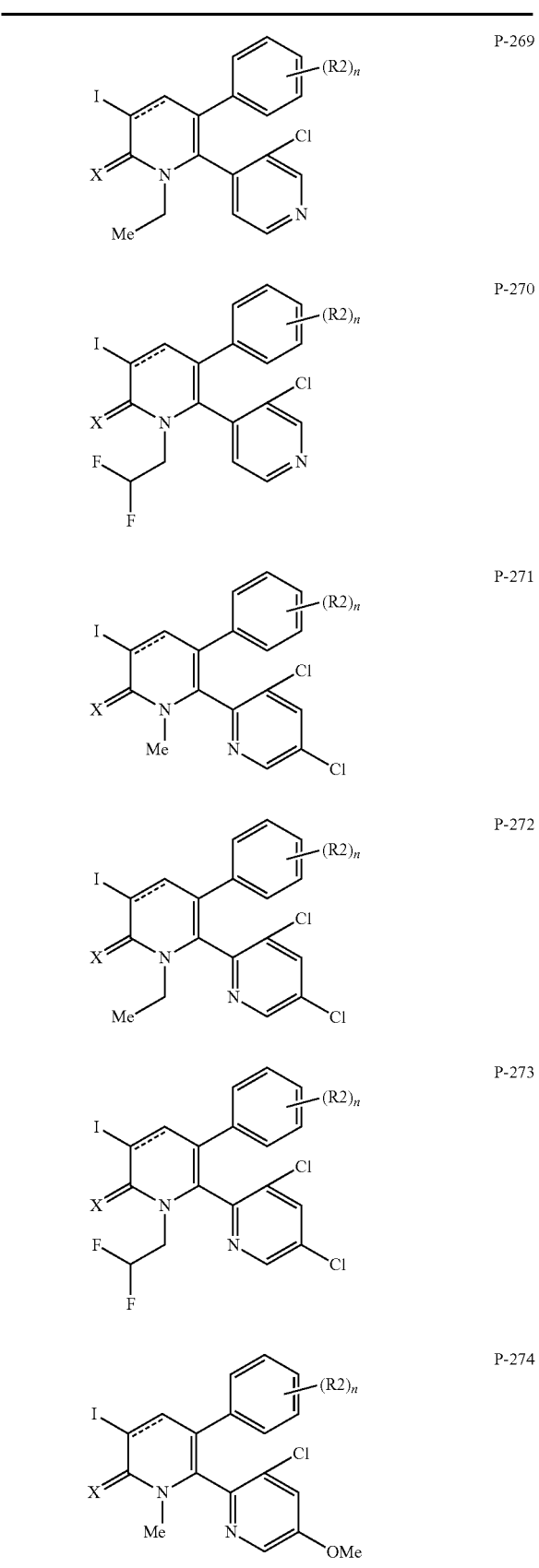
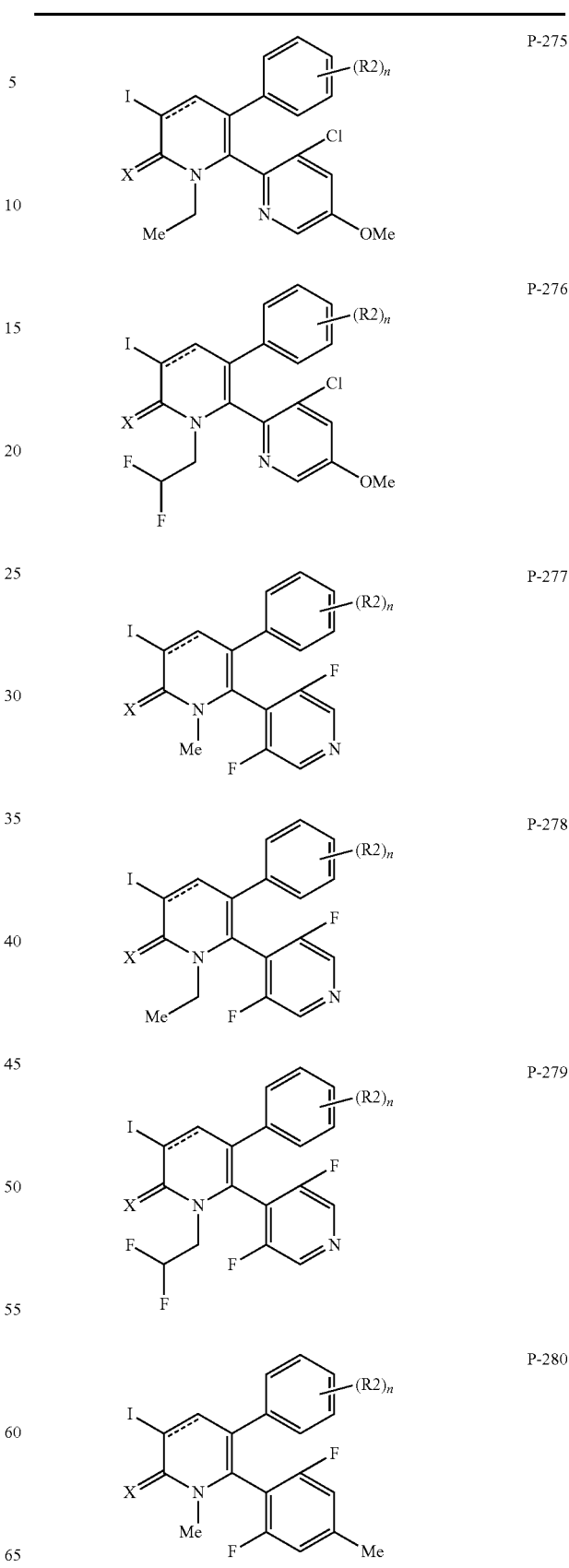

TABLE 1-continued

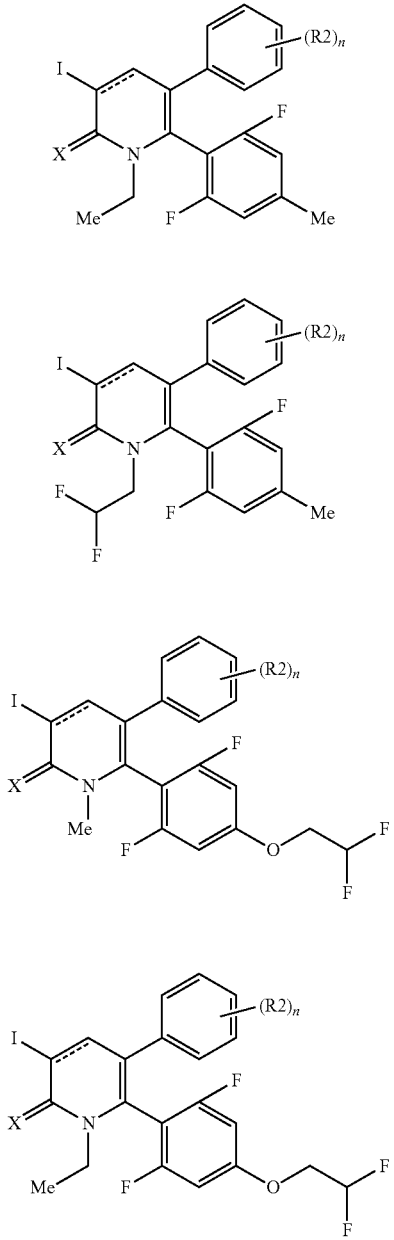

P-281

P-282

P-283

P-284

P-285

P-286

P-287

P-288

In the following, for example, the term "2-F—" in Table 2 indicates that a fluorine atom is bonded to the 2-position of the phenyl group to which (R2)n is bonded, the term "2-F-3-HO—" indicates that a fluorine atom is bonded to the 2-position and a hydroxy group at the 3-position, and the term "2,3-di-F" indicates that fluorine atoms are bonded to the 2- and 3-positions. This also applies to other similar expressions.

TABLE 2

| No. | (R2)n | No. | (R2)n | No. | (R2)n |
|---|---|---|---|---|---|
| 1 | —(Unsubstituted) | 2 | 2-F— | 3 | 3-F— |
| 4 | 4-F— | 5 | 2-Cl— | 6 | 3-Cl— |
| 7 | 4-Cl— | 8 | 2-Br— | 9 | 3-Br— |
| 10 | 4-Br— | 11 | 2-I— | 12 | 3-I— |
| 13 | 4-I— | 14 | 2-HO— | 15 | 3-HO— |
| 16 | 4-HO— | 17 | 2-N≡C— | 18 | 3-N≡C— |
| 19 | 4-N≡C— | 20 | 2-O$_2$N— | 21 | 3-O$_2$N— |
| 22 | 4-O$_2$N— | 23 | 2-Me— | 24 | 3-Me— |
| 25 | 4-Me— | 26 | 2-Et— | 27 | 3-Et— |
| 28 | 4-Et— | 29 | 2-Pr— | 30 | 3-Pr— |
| 31 | 4-Pr— | 32 | 2-iPr— | 33 | 3-iPr— |
| 34 | 4-iPr— | 35 | 2-N=CH$_2$— | 36 | 3-N=CH$_2$— |
| 37 | 4-N=CH$_2$— | 38 | 2-N=CCH$_2$CH$_2$— | 39 | 3-N=CCH$_2$CH$_2$— |

TABLE 2-continued

| No. | (R2)n | No. | (R2)n | No. | (R2)n |
|---|---|---|---|---|---|
| 40 | 4-N≡CCH₂CH₂— | 41 | 2-cPrCH₂— | 42 | 3-cPrCH₂— |
| 43 | 4-cPrCH₂— | 44 | 2-cBuCH₂— | 45 | 3-cBuCH₂— |
| 46 | 4-cBuCH₂— | 47 | 2-MeOCH₂— | 48 | 3-MeOCH₂— |
| 49 | 4-MeOCH₂— | 50 | 2-MeOCH₂CH₂— | 51 | 3-MeOCH₂CH₂— |
| 52 | 4-MeOCH₂CH₂— | 53 | 2-MeOCH₂CH₂CH₂— | 54 | 3-MeOCH₂CH₂CH₂— |
| 55 | 4-MeOCH₂CH₂CH₂— | 56 | 2-EtOCH₂— | 57 | 3-EtOCH₂— |
| 58 | 4-EtOCH₂— | 59 | 2-EtOCH₂CH₂— | 60 | 3-EtOCH₂CH₂— |
| 61 | 4-EtOCH₂CH₂— | 62 | 2-cPrOCH₂— | 63 | 3-cPrOCH₂— |
| 64 | 4-cPrOCH₂— | 65 | 2-F₃COCH₂— | 66 | 3-F₃COCH₂— |
| 67 | 4-F₃COCH₂— | 68 | 2-F₂CHOCH₂— | 69 | 3-F₂CHOCH₂— |
| 70 | 4-F₂CHOCH₂— | 71 | 2-MeOCH₂OCH₂— | 72 | 3-MeOCH₂OCH₂— |
| 73 | 4-MeOCH₂CH₂OCH₂— | 74 | 2-Me₂NCH₂— | 75 | 3-Me₂NCH₂— |
| 76 | 4-Me₂NCH₂— | 77 | 2-MeSCH₂— | 78 | 3-MeSCH₂— |
| 79 | 4-MeSCH₂— | 80 | 2-MeS(O)CH₂— | 81 | 3-MeS(O)CH₂— |
| 82 | 4-MeS(O)CH₂— | 83 | 2-MeSO₂CH₂— | 84 | 3-MeSO₂CH₂— |
| 85 | 4-MeSO₂CH₂— | 86 | 2-cPr— | 87 | 3-cPr— |
| 88 | 4-cPr— | 89 | 2-cBu— | 90 | 3-cBu— |
| 91 | 4-cBu— | 92 | 2-F₃C— | 93 | 3-F₃C— |
| 94 | 4-F₃C— | 95 | 2-F₂CH— | 96 | 3-F₂CH— |
| 97 | 4-F₂CH— | 98 | 2-H₂C=CH— | 99 | 3-H₂C=CH— |
| 100 | 4-H₂C=CH— | 101 | 2-H₂C=CHCH₂— | 102 | 3-H₂C=CHCH₂— |
| 103 | 4-H₂C=CHCH₂— | 104 | 2-F₂C=CH— | 105 | 3-F₂C=CH— |
| 106 | 4-F₂C=CH— | 107 | 2-F₂C=CHCH₂— | 108 | 3-F₂C=CHCH₂— |
| 109 | 4-F₂C=CHCH₂— | 110 | 2-HC≡C— | 111 | 3-HC≡C— |
| 112 | 4-HC≡C— | 113 | 2-HC≡CCH₂— | 114 | 3-HC≡CCH₂— |
| 115 | 4-HC≡CCH₂— | 116 | 2-F₃CC≡C— | 117 | 3-F₃CC≡C— |
| 118 | 4-F₃CC≡C— | 119 | 2-F₃CC≡CCH₂— | 120 | 3-F₃CC≡CCH₂— |
| 121 | 4-F₃CC≡CCH₂— | 122 | 2-MeO— | 123 | 3-MeO— |
| 124 | 4-MeO— | 125 | 2-EtO— | 126 | 3-EtO— |
| 127 | 4-EtO— | 128 | 2-PrO— | 129 | 3-PrO— |
| 130 | 4-PrO— | 131 | 2-iPrO— | 132 | 3-iPrO— |
| 133 | 4-iPrO— | 134 | 2-BuO— | 135 | 3-BuO— |
| 136 | 4-BuO— | 137 | 2-iBuO— | 138 | 3-iBuO— |
| 139 | 4-iBuO— | 140 | 2-PentylO— | 141 | 3-PentylO— |
| 142 | 4-PentylO— | 143 | 2-N≡CCH₂O— | 144 | 3-N≡CCH₂O— |
| 145 | 4-N≡CCH₂O— | 146 | 2-N≡CCH₂CH₂O— | 147 | 3-N≡CCH₂CH₂O— |
| 148 | 4-N≡CCH₂CH₂O— | 149 | 2-cPrCH₂O— | 150 | 3-cPrCH₂O— |
| 151 | 4-cPrCH₂O— | 152 | 2-cBuCH₂O— | 153 | 3-cBuCH₂O— |
| 154 | 4-cBuCH₂O— | 155 | 2-cPentylCH₂O— | 156 | 3-cPentylCH₂O— |
| 157 | 4-cPentylCH₂O— | 158 | 2-cHexylCH₂O— | 159 | 3-cHexylCH₂O— |
| 160 | 4-cHexylCH₂O— | 161 | 2-MeOCH₂O— | 162 | 3-MeOCH₂O— |
| 163 | 4-MeOCH₂O— | 164 | 2-EtOCH₂O— | 165 | 3-EtOCH₂O— |
| 166 | 4-EtOCH₂O— | 167 | 2-MeOCH₂CH₂O— | 168 | 3-MeOCH₂CH₂O— |
| 169 | 4-MeOCH₂CH₂O— | 170 | 2-MeOCH₂CH₂CH₂O— | 171 | 3-MeOCH₂CH₂CH₂O— |
| 172 | 4-MeOCH₂CH₂CH₂O— | 173 | 2-MeOCH₂CH₂OCH₂O— | 174 | 3-MeOCH₂CH₂OCH₂O— |
| 175 | 4-MeOCH₂CH₂OCH₂O— | 176 | 2-MeSCH₂O— | 177 | 3-MeSCH₂O— |
| 178 | 4-MeSCH₂O— | 179 | 2-MeS(O)CH₂O— | 180 | 3-MeS(O)CH₂O— |
| 181 | 4-MeS(O)CH₂O— | 182 | 2-MeSO₂CH₂O— | 183 | 3-MeSO₂CH₂O— |
| 184 | 4-MeSO₂CH₂O— | 185 | 2-Me₃SiCH₂O— | 186 | 3-Me₃SiCH₂O— |
| 187 | 4-Me₃SiCH₂O— | 188 | 2-Me₃SiCH₂CH₂O— | 189 | 3-Me₃SiCH₂CH₂O— |
| 190 | 4-Me₃SiCH₂CH₂O— | 191 | 2-Me₃SiCH₂CH₂CH₂O— | 192 | 3-Me₃SiCH₂CH₂CH₂O— |
| 193 | 4-Me₃SiCH₂CH₂CH₂O— | 194 | 2-AcCH₂O— | 195 | 3-AcCH₂O— |
| 196 | 4-AcCH₂O— | 197 | 2-MeOC(=O)CH₂O— | 198 | 3-MeOC(=O)CH₂O— |
| 199 | 4-MeOC(=O)CH₂O— | 200 | 2-EtOC(=O)CH₂O— | 201 | 3-EtOC(=O)CH₂O— |
| 202 | 4-EtOC(=O)CH₂O— | 203 | 2-(1,3-dioxolan-2-yl)CH₂O— | 204 | 3-(1,3-dioxolan-2-yl)CH₂O— |
| 205 | 4-(1,3-dioxolan-2-yl)CH₂O— | 206 | 2-(1,3-dioxolan-2-yl)CH₂CH₂O— | 207 | 3-(1,3-dioxolan-2-yl)CH₂CH₂O— |
| 208 | 4-(1,3-dioxolan-2-yl)CH₂CH₂O— | 209 | 2-(1,3-dioxan-2-yl)CH₂O— | 210 | 3-(1,3-dioxan-2-yl)CH₂O— |
| 211 | 4-(1,3-dioxan-2-yl)CH₂O— | 212 | 2-(1,3-dioxan-2-yl)CH₂CH₂O— | 213 | 3-(1,3-dioxan-2-yl)CH₂CH₂O— |
| 214 | 4-(1,3-dioxan-2-yl)CH₂CH₂O— | 215 | 2-cPrO— | 216 | 3-cPrO— |
| 217 | 4-cPrO— | 218 | 2-cBuO— | 219 | 3-cBuO— |
| 220 | 4-cBuO— | 221 | 2-cPentylO— | 222 | 3-cPentylO— |
| 223 | 4-cPentylO— | 224 | 2-cHexylO— | 225 | 3-cHexylO— |
| 226 | 4-cHexylO— | 227 | 2-F₃CO— | 228 | 3-F₃CO— |
| 229 | 4-F₃CO— | 230 | 2-F₂CHO— | 231 | 3-F₂CHO— |
| 232 | 4-F₂CHO— | 233 | 2-F₃CCH₂O— | 234 | 3-F₃CCH₂O— |
| 235 | 4-F₃CCH₂O— | 236 | 2-F₂CHCH₂O— | 237 | 3-F₂CHCH₂O— |
| 238 | 4-F₂CHCH₂O— | 239 | 2-H₂C=CHCH₂O— | 240 | 3-H₂C=CHCH₂O— |
| 241 | 4-H₂C=CHCH₂O— | 242 | 2-HC≡CCH₂O— | 243 | 3-HC≡CCH₂O— |
| 244 | 4-HC≡CCH₂O— | 245 | 2-Ac | 246 | 3-Ac |
| 247 | 4-Ac | 248 | 2-MeOC(=O)— | 249 | 3-MeOC(=O)— |
| 250 | 4-MeOC(=O)— | 251 | 2-EtOC(=O)— | 252 | 3-EtOC(=O)— |
| 253 | 4-EtOC(=O)— | 254 | 2-AcO— | 255 | 3-AcO— |
| 256 | 4-AcO— | 257 | 2-MeOC(=O)O— | 258 | 3-MeOC(=O)O— |

TABLE 2-continued

| No. | (R2)n | No. | (R2)n | No. | (R2)n |
|---|---|---|---|---|---|
| 259 | 4-MeOC(=O)O— | 260 | 2-EtOC(=O)O— | 261 | 3-EtOC(=O)O— |
| 262 | 4-EtOC(=O)O— | 263 | 2-(1,3-dioxolan-2-yl)- | 264 | 3-(1,3-dioxolan-2-yl)- |
| 265 | 4-(1,3-dioxolan-2-yl)- | 266 | 2-(1,3-dioxan-2-yl)- | 267 | 3-(1,3-dioxan-2-yl)- |
| 268 | 4-(1,3-dioxan-2-yl)- | 269 | 2-MeS— | 270 | 3-MeS— |
| 271 | 4-MeS— | 272 | 2-MeS(O)— | 273 | 3-MeS(O)— |
| 274 | 4-MeS(O)— | 275 | 2-MeSO$_2$— | 276 | 3-MeSO$_2$— |
| 277 | 4-MeSO$_2$— | 278 | 2-ClCH$_2$S— | 279 | 3-ClCH$_2$S— |
| 280 | 4-ClCH$_2$S— | 281 | 2-ClCH$_2$S(O)— | 282 | 3-ClCH$_2$S(O)— |
| 283 | 4-ClCH$_2$S(O)— | 284 | 2-ClCH$_2$SO$_2$— | 285 | 3-ClCH$_2$SO$_2$— |
| 286 | 4-ClCH$_2$SO$_2$— | 287 | 2-F-3-HO— | 288 | 2-F-4-HO— |
| 289 | 2-F-5-HO— | 290 | 2-F-6-HO— | 291 | 2-Cl-3-HO— |
| 292 | 2-Cl-4-HO— | 293 | 2-Cl-5-HO— | 294 | 2-Cl-6-HO— |
| 295 | 2-Br-3-HO— | 296 | 2-Br-4-HO— | 297 | 2-Br-5-HO— |
| 298 | 2-Br-6-HO— | 299 | 2-I-3-HO— | 300 | 2-I-4-HO— |
| 301 | 2-I-5-HO— | 302 | 2-I-6-HO— | 303 | 2-Me-3-HO— |
| 304 | 2-Me-4-HO— | 305 | 2-Me-5-HO— | 306 | 2-Me-6-HO— |
| 307 | 2,3-di-F— | 308 | 2,4-di-F— | 309 | 2,5-di-F— |
| 310 | 2,6-di-F— | 311 | 2-Cl-3-F— | 312 | 2-Cl-4-F— |
| 313 | 2-Cl-5-F— | 314 | 2-Cl-6-F— | 315 | 2-Br-3-F— |
| 316 | 2-Br-4-F— | 317 | 2-Br-5-F— | 318 | 2-Br-6-F— |
| 319 | 3-F-2-I— | 320 | 4-F-2-I— | 321 | 5-F-2-I— |
| 322 | 6-F-2-I— | 323 | 3-F-2-Me— | 324 | 4-F-2-Me— |
| 325 | 5-F-2-Me— | 326 | 6-F-2-Me— | 327 | 3-Cl-2-F— |
| 328 | 4-Cl-2-F— | 329 | 5-Cl-2-F— | 330 | 6-Cl-2-F— |
| 331 | 2,3-di-Cl— | 332 | 2,4-di-Cl— | 333 | 2,5-di-Cl— |
| 334 | 2,6-di-Cl— | 335 | 2-Br-3-Cl— | 336 | 2-Br-4-Cl— |
| 337 | 2-Br-5-Cl— | 338 | 2-Br-6-Cl— | 339 | 3-Cl-2-I— |
| 340 | 4-Cl-2-I— | 341 | 5-Cl-2-I— | 342 | 6-Cl-2-I— |
| 343 | 3-Cl-2-Me— | 344 | 4-Cl-2-Me— | 345 | 5-Cl-2-Me— |
| 346 | 6-Cl-2-Me— | 347 | 3-Br-2-F— | 348 | 4-Br-2-F— |
| 349 | 5-Br-2-F— | 350 | 6-Br-2-F— | 351 | 3-Br-2-Cl— |
| 352 | 4-Br-2-Cl— | 353 | 5-Br-2-Cl— | 354 | 6-Br-2-Cl— |
| 355 | 2,3-di-Br— | 356 | 2,4-di-Br— | 357 | 2,5-di-Br— |
| 358 | 2,6-di-Br— | 359 | 3-Br-2-I— | 360 | 4-Br-2-I— |
| 361 | 5-Br-2-I— | 362 | 6-Br-2-I— | 363 | 3-Br-2-Me— |
| 364 | 4-Br-2-Me— | 365 | 5-Br-2-Me— | 366 | 6-Br-2-Me— |
| 367 | 2-F-3-I— | 368 | 2-F-4-I— | 369 | 2-F-5-I— |
| 370 | 2-F-6-I— | 371 | 2-Cl-3-I— | 372 | 2-Cl-4-I— |
| 373 | 2-Cl-5-I— | 374 | 2-Cl-6-I— | 375 | 2-Br-3-I— |
| 376 | 2-Br-4-I— | 377 | 2-Br-5-I— | 378 | 2-Br-6-I— |
| 379 | 2,3-di-I— | 380 | 2,4-di-I— | 381 | 2,5-di-I— |
| 382 | 2,6-di-I— | 383 | 2-Me-3-I— | 384 | 2-Me-4-I— |
| 385 | 2-Me-5-I— | 386 | 2-Me-6-I— | 387 | 2-F-3-N≡C— |
| 388 | 2-F-4-N≡C— | 389 | 2-F-5-N≡C— | 390 | 2-F-6-N≡C— |
| 391 | 2-Cl-3-N≡C— | 392 | 2-Cl-4-N≡C— | 393 | 2-Cl-5-N≡C— |
| 394 | 2-Cl-6-N≡C— | 395 | 2-Br-3-N≡C— | 396 | 2-Br-4-N≡C— |
| 397 | 2-Br-5-N≡C— | 398 | 2-Br-6-N≡C— | 399 | 2-I-3-N≡C— |
| 400 | 2-I-4-N≡C— | 401 | 2-I-5-N≡C— | 402 | 2-I-6-N≡C— |
| 403 | 2-Me-3-N≡C— | 404 | 2-Me-4-N≡C— | 405 | 2-Me-5-N≡C— |
| 406 | 2-Me-6-N≡C— | 407 | 2-F-3-O$_2$N— | 408 | 2-F-4-O$_2$N— |
| 409 | 2-F-5-O$_2$N— | 410 | 2-F-6-O$_2$N— | 411 | 2-Cl-3-O$_2$N— |
| 412 | 2-Cl-4-O$_2$N— | 413 | 2-Cl-5-O$_2$N— | 414 | 2-Cl-6-O$_2$N— |
| 415 | 2-Br-3-O$_2$N— | 416 | 2-Br-4-O$_2$N— | 417 | 2-Br-5-O$_2$N— |
| 418 | 2-Br-6-O$_2$N— | 419 | 2-I-3-O$_2$N— | 420 | 2-I-4-O$_2$N— |
| 421 | 2-I-5-O$_2$N— | 422 | 2-I-6-O$_2$N— | 423 | 2-Me-3-O$_2$N— |
| 424 | 2-Me-4-O$_2$N— | 425 | 2-Me-5-O$_2$N— | 426 | 2-Me-6-O$_2$N— |
| 427 | 2-F-3-Me— | 428 | 2-F-4-Me— | 429 | 2-F-5-Me— |
| 430 | 2-F-6-Me— | 431 | 2-Cl-3-Me— | 432 | 2-Cl-4-Me— |
| 433 | 2-Cl-5-Me— | 434 | 2-Cl-6-Me— | 435 | 2-Br-3-Me— |
| 436 | 2-Br-4-Me— | 437 | 2-Br-5-Me— | 438 | 2-Br-6-Me— |
| 439 | 2-I-3-Me— | 440 | 2-I-4-Me— | 441 | 2-I-5-Me— |
| 442 | 2-I-6-Me— | 443 | 2,3-di-Me— | 444 | 2,4-di-Me— |
| 445 | 2,5-di-Me— | 446 | 2,6-di-Me— | 447 | 2-F-3-Et— |
| 448 | 2-F-4-Et— | 449 | 2-F-5-Et— | 450 | 2-F-6-Et— |
| 451 | 2-Cl-3-Et— | 452 | 2-Cl-4-Et— | 453 | 2-Cl-5-Et— |
| 454 | 2-Cl-6-Et— | 455 | 2-Br-3-Et— | 456 | 2-Br-4-Et— |
| 457 | 2-Br-5-Et— | 458 | 2-Br-6-Et— | 459 | 2-I-3-Et— |
| 460 | 2-I-4-Et— | 461 | 2-I-5-Et— | 462 | 2-I-6-Et— |
| 463 | 2-Me-3-Et— | 464 | 2-Me-4-Et— | 465 | 2-Me-5-Et— |
| 466 | 2-Me-6-Et— | 467 | 2-F-3-Pr— | 468 | 2-F-4-Pr— |
| 469 | 2-F-5-Pr— | 470 | 2-F-6-Pr— | 471 | 2-Cl-3-Pr— |
| 472 | 2-Cl-4-Pr— | 473 | 2-Cl-5-Pr— | 474 | 2-Cl-6-Pr— |
| 475 | 2-Br-3-Pr— | 476 | 2-Br-4-Pr— | 477 | 2-Br-5-Pr— |
| 478 | 2-Br-6-Pr— | 479 | 2-I-3-Pr— | 480 | 2-I-4-Pr— |
| 481 | 2-I-5-Pr— | 482 | 2-I-6-Pr— | 483 | 2-Me-3-Pr— |
| 484 | 2-Me-4-Pr— | 485 | 2-Me-5-Pr— | 486 | 2-Me-6-Pr— |
| 487 | 2-F-3-iPr— | 488 | 2-F-4-iPr— | 489 | 2-F-5-iPr— |
| 490 | 2-F-6-iPr— | 491 | 2-Cl-3-iPr— | 492 | 2-Cl-4-iPr— |

TABLE 2-continued

| No. | (R2)n | No. | (R2)n | No. | (R2)n |
|---|---|---|---|---|---|
| 493 | 2-Cl-5-iPr— | 494 | 2-Cl-6-iPr— | 495 | 2-Br-3-iPr— |
| 496 | 2-Br-4-iPr— | 497 | 2-Br-5-iPr— | 498 | 2-Br-6-iPr— |
| 499 | 2-I-3-iPr— | 500 | 2-I-4-iPr— | 501 | 2-I-5-iPr— |
| 502 | 2-I-6-iPr— | 503 | 2-Me-3-iPr— | 504 | 2-Me-4-iPr— |
| 505 | 2-Me-5-iPr— | 506 | 2-Me-6-iPr— | 507 | 2-F-3-N=CCH$_2$— |
| 508 | 2-F-4-N=CCH$_2$— | 509 | 2-F-5-N=CCH$_2$— | 510 | 2-F-6-N=CCH$_2$— |
| 511 | 2-Cl-3-N=CCH$_2$— | 512 | 2-Cl-4-N=CCH$_2$— | 513 | 2-Cl-5-N=CCH$_2$— |
| 514 | 2-Cl-6-N=CCH$_2$— | 515 | 2-Br-3-N=CCH$_2$— | 516 | 2-Br-4-N=CCH$_2$— |
| 517 | 2-Br-5-N=CCH$_2$— | 518 | 2-Br-6-N=CCH$_2$— | 519 | 2-I-3-N=CCH$_2$— |
| 520 | 2-I-4-N=CCH$_2$— | 521 | 2-I-5-N=CCH$_2$— | 522 | 2-I-6-N=CCH$_2$— |
| 523 | 2-Me-3-N=CCH$_2$— | 524 | 2-Me-4-N=CCH$_2$— | 525 | 2-Me-5-N=CCH$_2$— |
| 526 | 2-Me-6-N=CCH$_2$— | 527 | 2-F-3-N=CCH$_2$CH$_2$— | 528 | 2-F-4-N=CCH$_2$CH$_2$— |
| 529 | 2-F-5-N=CCH$_2$CH$_2$— | 530 | 2-F-6-N=CCH$_2$CH$_2$— | 531 | 2-Cl-3-N=CCH$_2$CH$_2$— |
| 532 | 2-Cl-4-N=CCH$_2$CH$_2$— | 533 | 2-Cl-5-N=CCH$_2$CH$_2$— | 534 | 2-Cl-6-N=CCH$_2$CH$_2$— |
| 535 | 2-Br-3-N=CCH$_2$CH$_2$— | 536 | 2-Br-4-N=CCH$_2$CH$_2$— | 537 | 2-Br-5-N=CCH$_2$CH$_2$— |
| 538 | 2-Br-6-N=CCH$_2$CH$_2$— | 539 | 2-I-3-N=CCH$_2$CH$_2$— | 540 | 2-I-4-N=CCH$_2$CH$_2$— |
| 541 | 2-I-5-N=CCH$_2$CH$_2$— | 542 | 2-I-6-N=CCH$_2$CH$_2$— | 543 | 2-Me-3-N=CCH$_2$CH$_2$— |
| 544 | 2-Me-4-N=CCH$_2$CH$_2$— | 545 | 2-Me-5-N=CCH$_2$CH$_2$— | 546 | 2-Me-6-N=CCH$_2$CH$_2$— |
| 547 | 2-F-3-cPrCH$_2$— | 548 | 2-F-4-cPrCH$_2$— | 549 | 2-F-5-cPrCH$_2$— |
| 550 | 2-F-6-cPrCH$_2$— | 551 | 2-Cl-3-cPrCH$_2$— | 552 | 2-Cl-4-cPrCH$_2$— |
| 553 | 2-Cl-5-cPrCH$_2$— | 554 | 2-Cl-6-cPrCH$_2$— | 555 | 2-Br-3-cPrCH$_2$— |
| 556 | 2-Br-4-cPrCH$_2$— | 557 | 2-Br-5-cPrCH$_2$— | 558 | 2-Br-6-cPrCH$_2$— |
| 559 | 2-I-3-cPrCH$_2$— | 560 | 2-I-4-cPrCH$_2$— | 561 | 2-I-5-cPrCH$_2$— |
| 562 | 2-I-6-cPrCH$_2$— | 563 | 2-Me-3-cPrCH$_2$— | 564 | 2-Me-4-cPrCH$_2$— |
| 565 | 2-Me-5-cPrCH$_2$— | 566 | 2-Me-6-cPrCH$_2$— | 567 | 2-F-3-cBuCH$_2$— |
| 568 | 2-F-4-cBuCH$_2$— | 569 | 2-F-5-cBuCH$_2$— | 570 | 2-F-6-cBuCH$_2$— |
| 571 | 2-Cl-3-cBuCH$_2$— | 572 | 2-Cl-4-cBuCH$_2$— | 573 | 2-Cl-5-cBuCH$_2$— |
| 574 | 2-Cl-6-cBuCH$_2$— | 575 | 2-Br-3-cBuCH$_2$— | 576 | 2-Br-4-cBuCH$_2$— |
| 577 | 2-Br-5-cBuCH$_2$— | 578 | 2-Br-6-cBuCH$_2$— | 579 | 2-I-3-cBuCH$_2$— |
| 580 | 2-I-4-cBuCH$_2$— | 581 | 2-I-5-cBuCH$_2$— | 582 | 2-I-6-cBuCH$_2$— |
| 583 | 2-Me-3-cBuCH$_2$— | 584 | 2-Me-4-cBuCH$_2$— | 585 | 2-Me-5-cBuCH$_2$— |
| 586 | 2-Me-6-cBuCH$_2$— | 587 | 2-F-3-MeOCH$_2$— | 588 | 2-F-4-MeOCH$_2$— |
| 589 | 2-F-5-MeOCH$_2$— | 590 | 2-F-6-MeOCH$_2$— | 591 | 2-Cl-3-MeOCH$_2$— |
| 592 | 2-Cl-4-MeOCH$_2$— | 593 | 2-Cl-5-MeOCH$_2$— | 594 | 2-Cl-6-MeOCH$_2$— |
| 595 | 2-Br-3-MeOCH$_2$— | 596 | 2-Br-4-MeOCH$_2$— | 597 | 2-Br-5-MeOCH$_2$— |
| 598 | 2-Br-6-MeOCH$_2$— | 599 | 2-I-3-MeOCH$_2$— | 600 | 2-I-4-MeOCH$_2$— |
| 601 | 2-I-5-MeOCH$_2$— | 602 | 2-I-6-MeOCH$_2$— | 603 | 2-Me-3-MeOCH$_2$— |
| 604 | 2-Me-4-MeOCH$_2$— | 605 | 2-Me-5-MeOCH$_2$— | 606 | 2-Me-6-MeOCH$_2$— |
| 607 | 2-F-3-MeOCH$_2$CH$_2$— | 608 | 2-F-4-MeOCH$_2$CH$_2$— | 609 | 2-F-5-MeOCH$_2$CH$_2$— |
| 610 | 2-F-6-MeOCH$_2$CH$_2$— | 611 | 2-Cl-3-MeOCH$_2$CH$_2$— | 612 | 2-Cl-4-MeOCH$_2$CH$_2$— |
| 613 | 2-Cl-5-MeOCH$_2$CH$_2$— | 614 | 2-Cl-6-MeOCH$_2$CH$_2$— | 615 | 2-Br-3-MeOCH$_2$CH$_2$— |
| 616 | 2-Br-4-MeOCH$_2$CH$_2$— | 617 | 2-Br-5-MeOCH$_2$CH$_2$— | 618 | 2-Br-6-MeOCH$_2$CH$_2$— |
| 619 | 2-I-3-MeOCH$_2$CH$_2$— | 620 | 2-I-4-MeOCH$_2$CH$_2$— | 621 | 2-I-5-MeOCH$_2$CH$_2$— |
| 622 | 2-I-6-MeOCH$_2$CH$_2$— | 623 | 2-Me-3-MeOCH$_2$CH$_2$— | 624 | 2-Me-4-MeOCH$_2$CH$_2$— |
| 625 | 2-Me-5-MeOCH$_2$CH$_2$— | 626 | 2-Me-6-MeOCH$_2$CH$_2$— | 627 | 2-F-3-MeOCH$_2$CH$_2$CH$_2$— |
| 628 | 2-F-4-MeOCH$_2$CH$_2$CH$_2$— | 629 | 2-F-5-MeOCH$_2$CH$_2$CH$_2$— | 630 | 2-F-6-MeOCH$_2$CH$_2$CH$_2$— |
| 631 | 2-Cl-3-MeOCH$_2$CH$_2$CH$_2$— | 632 | 2-Cl-4-MeOCH$_2$CH$_2$CH$_2$— | 633 | 2-Cl-5-MeOCH$_2$CH$_2$CH$_2$— |
| 634 | 2-Cl-6-MeOCH$_2$CH$_2$CH$_2$— | 635 | 2-Br-3-MeOCH$_2$CH$_2$CH$_2$— | 636 | 2-Br-4-MeOCH$_2$CH$_2$CH$_2$— |
| 637 | 2-Br-5-MeOCH$_2$CH$_2$CH$_2$— | 638 | 2-Br-6-MeOCH$_2$CH$_2$CH$_2$— | 639 | 2-I-3-MeOCH$_2$CH$_2$CH$_2$— |
| 640 | 2-I-4-MeOCH$_2$CH$_2$CH$_2$— | 641 | 2-I-5-MeOCH$_2$CH$_2$CH$_2$— | 642 | 2-I-6-MeOCH$_2$CH$_2$CH$_2$— |
| 643 | 2-Me-3-MeOCH$_2$CH$_2$CH$_2$— | 644 | 2-Me-4-MeOCH$_2$CH$_2$CH$_2$— | 645 | 2-Me-5-MeOCH$_2$CH$_2$CH$_2$— |
| 646 | 2-Me-6-MeOCH$_2$CH$_2$CH$_2$— | 647 | 2-F-3-EtOCH$_2$— | 648 | 2-F-4-EtOCH$_2$— |
| 649 | 2-F-5-EtOCH$_2$— | 650 | 2-F-6-EtOCH$_2$— | 651 | 2-Cl-3-EtOCH$_2$— |
| 652 | 2-Cl-4-EtOCH$_2$— | 653 | 2-Cl-5-EtOCH$_2$— | 654 | 2-Cl-6-EtOCH$_2$— |
| 655 | 2-Br-3-EtOCH$_2$— | 656 | 2-Br-4-EtOCH$_2$— | 657 | 2-Br-5-EtOCH$_2$— |
| 658 | 2-Br-6-EtOCH$_2$— | 659 | 2-I-3-EtOCH$_2$— | 660 | 2-I-4-EtOCH$_2$— |
| 661 | 2-I-5-EtOCH$_2$— | 662 | 2-I-6-EtOCH$_2$— | 663 | 2-Me-3-EtOCH$_2$— |
| 664 | 2-Me-4-EtOCH$_2$— | 665 | 2-Me-5-EtOCH$_2$— | 666 | 2-Me-6-EtOCH$_2$— |
| 667 | 2-F-3-EtOCH$_2$CH$_2$— | 668 | 2-F-4-EtOCH$_2$CH$_2$— | 669 | 2-F-5-EtOCH$_2$CH$_2$— |
| 670 | 2-F-6-EtOCH$_2$CH$_2$— | 671 | 2-Cl-3-EtOCH$_2$CH$_2$— | 672 | 2-Cl-4-EtOCH$_2$CH$_2$— |
| 673 | 2-Cl-5-EtOCH$_2$CH$_2$— | 674 | 2-Cl-6-EtOCH$_2$CH$_2$— | 675 | 2-Br-3-EtOCH$_2$CH$_2$— |
| 676 | 2-Br-4-EtOCH$_2$CH$_2$— | 677 | 2-Br-5-EtOCH$_2$CH$_2$— | 678 | 2-Br-6-EtOCH$_2$CH$_2$— |
| 679 | 2-I-3-EtOCH$_2$CH$_2$— | 680 | 2-I-4-EtOCH$_2$CH$_2$— | 681 | 2-I-5-EtOCH$_2$CH$_2$— |
| 682 | 2-I-6-EtOCH$_2$CH$_2$— | 683 | 2-Me-3-EtOCH$_2$CH$_2$— | 684 | 2-Me-4-EtOCH$_2$CH$_2$— |
| 685 | 2-Me-5-EtOCH$_2$CH$_2$— | 686 | 2-Me-6-EtOCH$_2$CH$_2$— | 687 | 2-F-3-cPrOCH$_2$— |
| 688 | 2-F-4-cPrOCH$_2$— | 689 | 2-F-5-cPrOCH$_2$— | 690 | 2-F-6-cPrOCH$_2$— |
| 691 | 2-Cl-3-cPrOCH$_2$— | 692 | 2-Cl-4-cPrOCH$_2$— | 693 | 2-Cl-5-cPrOCH$_2$— |
| 694 | 2-Cl-6-cPrOCH$_2$— | 695 | 2-Br-3-cPrOCH$_2$— | 696 | 2-Br-4-cPrOCH$_2$— |
| 697 | 2-Br-5-cPrOCH$_2$— | 698 | 2-Br-6-cPrOCH$_2$— | 699 | 2-I-3-cPrOCH$_2$— |
| 700 | 2-I-4-cPrOCH$_2$— | 701 | 2-I-5-cPrOCH$_2$— | 702 | 2-I-6-cPrOCH$_2$— |
| 703 | 2-Me-3-cPrOCH$_2$— | 704 | 2-Me-4-cPrOCH$_2$— | 705 | 2-Me-5-cPrOCH$_2$— |

TABLE 2-continued

| No. | (R2)n | No. | (R2)n | No. | (R2)n |
|---|---|---|---|---|---|
| 706 | 2-Me-6-cPrOCH$_2$— | 707 | 2-F-3-F$_3$COCH$_2$— | 708 | 2-F-4-F$_3$COCH$_2$— |
| 709 | 2-F-5-F$_3$COCH$_2$— | 710 | 2-F-6-F$_3$COCH$_2$— | 711 | 2-Cl-3-F$_3$COCH$_2$— |
| 712 | 2-Cl-4-F$_3$COCH$_2$— | 713 | 2-Cl-5-F$_3$COCH$_2$— | 714 | 2-Cl-6-F$_3$COCH$_2$— |
| 715 | 2-Br-3-F$_3$COCH$_2$— | 716 | 2-Br-4-F$_3$COCH$_2$— | 717 | 2-Br-5-F$_3$COCH$_2$— |
| 718 | 2-Br-6-F$_3$COCH$_2$— | 719 | 2-I-3-F$_3$COCH$_2$— | 720 | 2-I-4-F$_3$COCH$_2$— |
| 721 | 2-I-5-F$_3$COCH$_2$— | 722 | 2-I-6-F$_3$COCH$_2$— | 723 | 2-Me-3-F$_3$COCH$_2$— |
| 724 | 2-Me-4-F$_3$COCH$_2$— | 725 | 2-Me-5-F$_3$COCH$_2$— | 726 | 2-Me-6-F$_3$COCH$_2$— |
| 727 | 2-F-3-F$_2$CHOCH$_2$— | 728 | 2-F-4-F$_2$CHOCH$_2$— | 729 | 2-F-5-F$_2$CHOCH$_2$— |
| 730 | 2-F-6-F$_2$CHOCH$_2$— | 731 | 2-Cl-3-F$_2$CHOCH$_2$— | 732 | 2-Cl-4-F$_2$CHOCH$_2$— |
| 733 | 2-Cl-5-F$_2$CHOCH$_2$— | 734 | 2-Cl-6-F$_2$CHOCH$_2$— | 735 | 2-Br-3-F$_2$CHOCH$_2$— |
| 736 | 2-Br-4-F$_2$CHOCH$_2$— | 737 | 2-Br-5-F$_2$CHOCH$_2$— | 738 | 2-Br-6-F$_2$CHOCH$_2$— |
| 739 | 2-I-3-F$_2$CHOCH$_2$— | 740 | 2-I-4-F$_2$CHOCH$_2$— | 741 | 2-I-5-F$_2$CHOCH$_2$— |
| 742 | 2-I-6-F$_2$CHOCH$_2$— | 743 | 2-Me-3-F$_2$CHOCH$_2$— | 744 | 2-Me-4-F$_2$CHOCH$_2$— |
| 745 | 2-Me-5-F$_2$CHOCH$_2$— | 746 | 2-Me-6-F$_2$CHOCH$_2$— | 747 | 2-F-3-MeOCH$_2$CH$_2$OCH$_2$— |
| 748 | 2-F-4-MeOCH$_2$CH$_2$OCH$_2$— | 749 | 2-F-5-MeOCH$_2$CH$_2$OCH$_2$— | 750 | 2-F-6-MeOCH$_2$CH$_2$OCH$_2$— |
| 751 | 2-Cl-3-MeOCH$_2$CH$_2$OCH$_2$— | 752 | 2-Cl-4-MeOCH$_2$CH$_2$OCH$_2$— | 753 | 2-Cl-5-MeOCH$_2$CH$_2$OCH$_2$— |
| 754 | 2-Cl-6-MeOCH$_2$CH$_2$OCH$_2$— | 755 | 2-Br-3-MeOCH$_2$CH$_2$OCH$_2$— | 756 | 2-Br-4-MeOCH$_2$CH$_2$OCH$_2$— |
| 757 | 2-Br-5-MeOCH$_2$CH$_2$OCH$_2$— | 758 | 2-Br-6-MeOCH$_2$CH$_2$OCH$_2$— | 759 | 2-I-3-MeOCH$_2$CH$_2$OCH$_2$— |
| 760 | 2-I-4-MeOCH$_2$CH$_2$OCH$_2$— | 761 | 2-I-5-MeOCH$_2$CH$_2$OCH$_2$— | 762 | 2-I-6-MeOCH$_2$CH$_2$OCH$_2$— |
| 763 | 2-Me-3-MeOCH$_2$CH$_2$OCH$_2$— | 764 | 2-Me-4-MeOCH$_2$CH$_2$OCH$_2$— | 765 | 2-Me-5-MeOCH$_2$CH$_2$OCH$_2$— |
| 766 | 2-Me-6-MeOCH$_2$CH$_2$OCH$_2$— | 767 | 2-F-3-Me$_2$NCH$_2$— | 768 | 2-F-4-Me$_2$NCH$_2$— |
| 769 | 2-F-5-Me$_2$NCH$_2$— | 770 | 2-F-6-Me$_2$NCH$_2$— | 771 | 2-Cl-3-Me$_2$NCH$_2$— |
| 772 | 2-Cl-4-Me$_2$NCH$_2$— | 773 | 2-Cl-5-Me$_2$NCH$_2$— | 774 | 2-Cl-6-Me$_2$NCH$_2$— |
| 775 | 2-Br-3-Me$_2$NCH$_2$— | 776 | 2-Br-4-Me$_2$NCH$_2$— | 777 | 2-Br-5-Me$_2$NCH$_2$— |
| 778 | 2-Br-6-Me$_2$NCH$_2$— | 779 | 2-I-3-Me$_2$NCH$_2$— | 780 | 2-I-4-Me$_2$NCH$_2$— |
| 781 | 2-I-5-Me$_2$NCH$_2$— | 782 | 2-I-6-Me$_2$NCH$_2$— | 783 | 2-Me-3-Me$_2$NCH$_2$— |
| 784 | 2-Me-4-Me$_2$NCH$_2$— | 785 | 2-Me-5-Me$_2$NCH$_2$— | 786 | 2-Me-6-Me$_2$NCH$_2$— |
| 787 | 2-F-3-MeSCH$_2$— | 788 | 2-F-4-MeSCH$_2$— | 789 | 2-F-5-MeSCH$_2$— |
| 790 | 2-F-6-MeSCH$_2$— | 791 | 2-Cl-3-MeSCH$_2$— | 792 | 2-Cl-4-MeSCH$_2$— |
| 793 | 2-Cl-5-MeSCH$_2$— | 794 | 2-Cl-6-MeSCH$_2$— | 795 | 2-Br-3-MeSCH$_2$— |
| 796 | 2-Br-4-MeSCH$_2$— | 797 | 2-Br-5-MeSCH$_2$— | 798 | 2-Br-6-MeSCH$_2$— |
| 799 | 2-I-3-MeSCH$_2$— | 800 | 2-I-4-MeSCH$_2$— | 801 | 2-I-5-MeSCH$_2$— |
| 802 | 2-I-6-MeSCH$_2$— | 803 | 2-Me-3-MeSCH$_2$— | 804 | 2-Me-4-MeSCH$_2$— |
| 805 | 2-Me-5-MeSCH$_2$— | 806 | 2-Me-6-MeSCH$_2$— | 807 | 2-F-3-MeS(O)CH$_2$— |
| 808 | 2-F-4-MeS(O)CH$_2$— | 809 | 2-F-5-MeS(O)CH$_2$— | 810 | 2-F-6-MeS(O)CH$_2$— |
| 811 | 2-Cl-3-MeS(O)CH$_2$— | 812 | 2-Cl-4-MeS(O)CH$_2$— | 813 | 2-Cl-5-MeS(O)CH$_2$— |
| 814 | 2-Cl-6-MeS(O)CH$_2$— | 815 | 2-Br-3-MeS(O)CH$_2$— | 816 | 2-Br-4-MeS(O)CH$_2$— |
| 817 | 2-Br-5-MeS(O)CH$_2$— | 818 | 2-Br-6-MeS(O)CH$_2$— | 819 | 2-I-3-MeS(O)CH$_2$— |
| 820 | 2-I-4-MeS(O)CH$_2$— | 821 | 2-I-5-MeS(O)CH$_2$— | 822 | 2-I-6-MeS(O)CH$_2$— |
| 823 | 2-Me-3-MeS(O)CH$_2$— | 824 | 2-Me-4-MeS(O)CH$_2$— | 825 | 2-Me-5-MeS(O)CH$_2$— |
| 826 | 2-Me-6-MeS(O)CH$_2$— | 827 | 2-F-3-MeSO$_2$CH$_2$— | 828 | 2-F-4-MeSO$_2$CH$_2$— |
| 829 | 2-F-5-MeSO$_2$CH$_2$— | 830 | 2-F-6-MeSO$_2$CH$_2$— | 831 | 2-Cl-3-MeSO$_2$CH$_2$— |
| 832 | 2-Cl-4-MeSO$_2$CH$_2$— | 833 | 2-Cl-5-MeSO$_2$CH$_2$— | 834 | 2-Cl-6-MeSO$_2$CH$_2$— |
| 835 | 2-Br-3-MeSO$_2$CH$_2$— | 836 | 2-Br-4-MeSO$_2$CH$_2$— | 837 | 2-Br-5-MeSO$_2$CH$_2$— |
| 838 | 2-Br-6-MeSO$_2$CH$_2$— | 839 | 2-I-3-MeSO$_2$CH$_2$— | 840 | 2-I-4-MeSO$_2$CH$_2$— |
| 841 | 2-I-5-MeSO$_2$CH$_2$— | 842 | 2-I-6-MeSO$_2$CH$_2$— | 843 | 2-Me-3-MeSO$_2$CH$_2$— |
| 844 | 2-Me-4-MeSO$_2$CH$_2$— | 845 | 2-Me-5-MeSO$_2$CH$_2$— | 846 | 2-Me-6-MeSO$_2$CH$_2$— |
| 847 | 2-F-3-cPr— | 848 | 2-F-4-cPr— | 849 | 2-F-5-cPr— |
| 850 | 2-F-6-cPr— | 851 | 2-Cl-3-cPr— | 852 | 2-Cl-4-cPr— |
| 853 | 2-Cl-5-cPr— | 854 | 2-Cl-6-cPr— | 855 | 2-Br-3-cPr— |
| 856 | 2-Br-4-cPr— | 857 | 2-Br-5-cPr— | 858 | 2-Br-6-cPr— |
| 859 | 2-I-3-cPr— | 860 | 2-I-4-cPr— | 861 | 2-I-5-cPr— |
| 862 | 2-I-6-cPr— | 863 | 2-Me-3-cPr— | 864 | 2-Me-4-cPr— |
| 865 | 2-Me-5-cPr— | 866 | 2-Me-6-cPr— | 867 | 2-F-3-cBu— |
| 868 | 2-F-4-cBu— | 869 | 2-F-5-cBu— | 870 | 2-F-6-cBu— |
| 871 | 2-Cl-3-cBu— | 872 | 2-Cl-4-cBu— | 873 | 2-Cl-5-cBu— |
| 874 | 2-Cl-6-cBu— | 875 | 2-Br-3-cBu— | 876 | 2-Br-4-cBu— |
| 877 | 2-Br-5-cBu— | 878 | 2-Br-6-cBu— | 879 | 2-I-3-cBu— |
| 880 | 2-I-4-cBu— | 881 | 2-I-5-cBu— | 882 | 2-I-6-cBu— |
| 883 | 2-Me-3-cBu— | 884 | 2-Me-4-cBu— | 885 | 2-Me-5-cBu— |
| 886 | 2-Me-6-cBu— | 887 | 2-F-3-F$_3$C— | 888 | 2-F-4-F$_3$C— |
| 889 | 2-F-5-F$_3$C— | 890 | 2-F-6-F$_3$C— | 891 | 2-Cl-3-F$_3$C— |
| 892 | 2-Cl-4-F$_3$C— | 893 | 2-Cl-5-F$_3$C— | 894 | 2-Cl-6-F$_3$C— |
| 895 | 2-Br-3-F$_3$C— | 896 | 2-Br-4-F$_3$C— | 897 | 2-Br-5-F$_3$C— |
| 898 | 2-Br-6-F$_3$C— | 899 | 2-I-3-F$_3$C— | 900 | 2-I-4-F$_3$C— |
| 901 | 2-I-5-F$_3$C— | 902 | 2-I-6-F$_3$C— | 903 | 2-Me-3-F$_3$C— |
| 904 | 2-Me-4-F$_3$C— | 905 | 2-Me-5-F$_3$C— | 906 | 2-Me-6-F$_3$C— |
| 907 | 2-F-3-F$_2$CH— | 908 | 2-F-4-F$_2$CH— | 909 | 2-F-5-F$_2$CH— |
| 910 | 2-F-6-F$_2$CH— | 911 | 2-Cl-3-F$_2$CH— | 912 | 2-Cl-4-F$_2$CH— |
| 913 | 2-Cl-5-F$_2$CH— | 914 | 2-Cl-6-F$_2$CH— | 915 | 2-Br-3-F$_2$CH— |

TABLE 2-continued

| No. | (R2)n | No. | (R2)n | No. | (R2)n |
|---|---|---|---|---|---|
| 916 | 2-Br-4-F$_2$CH— | 917 | 2-Br-5-F$_2$CH— | 918 | 2-Br-6-F$_2$CH— |
| 919 | 2-I-3-F$_2$CH— | 920 | 2-I-4-F$_2$CH— | 921 | 2-I-5-F$_2$CH— |
| 922 | 2-I-6-F$_2$CH— | 923 | 2-Me-3-F$_2$CH— | 924 | 2-Me-4-F$_2$CH— |
| 925 | 2-Me-5-F$_2$CH— | 926 | 2-Me-6-F$_2$CH— | 927 | 2-F-3-H$_2$C=CH— |
| 928 | 2-F-4-H$_2$C=CH— | 929 | 2-F-5-H$_2$C=CH— | 930 | 2-F-6-H$_2$C=CH— |
| 931 | 2-Cl-3-H$_2$C=CH— | 932 | 2-Cl-4-H$_2$C=CH— | 933 | 2-Cl-5-H$_2$C=CH— |
| 934 | 2-Cl-6-H$_2$C=CH— | 935 | 2-Br-3-H$_2$C=CH— | 936 | 2-Br-4-H$_2$C=CH— |
| 937 | 2-Br-5-H$_2$C=CH— | 938 | 2-Br-6-H$_2$C=CH— | 939 | 2-I-3-H$_2$C=CH— |
| 940 | 2-I-4-H$_2$C=CH— | 941 | 2-I-5-H$_2$C=CH— | 942 | 2-I-6-H$_2$C=CH— |
| 943 | 2-Me-3-H$_2$C=CH— | 944 | 2-Me-4-H$_2$C=CH— | 945 | 2-Me-5-H$_2$C=CH— |
| 946 | 2-Me-6-H$_2$C=CH— | 947 | 2-F-3-H$_2$C=CHCH$_2$— | 948 | 2-F-4-H$_2$C=CHCH$_2$— |
| 949 | 2-F-5-H$_2$C=CHCH$_2$— | 950 | 2-F-6-H$_2$C=CHCH$_2$— | 951 | 2-Cl-3-H$_2$C=CHCH$_2$— |
| 952 | 2-Cl-4-H$_2$C=CHCH$_2$— | 953 | 2-Cl-5-H$_2$C=CHCH$_2$— | 954 | 2-Cl-6-H$_2$C=CHCH$_2$— |
| 955 | 2-Br-3-H$_2$C=CHCH$_2$— | 956 | 2-Br-4-H$_2$C=CHCH$_2$— | 957 | 2-Br-5-H$_2$C=CHCH$_2$— |
| 958 | 2-Br-6-H$_2$C=CHCH$_2$— | 959 | 2-I-3-H$_2$C=CHCH$_2$— | 960 | 2-I-4-H$_2$C=CHCH$_2$— |
| 961 | 2-I-5-H$_2$C=CHCH$_2$— | 962 | 2-I-6-H$_2$C=CHCH$_2$— | 963 | 2-Me-3-H$_2$C=CHCH$_2$— |
| 964 | 2-Me-4-H$_2$C=CHCH$_2$— | 965 | 2-Me-5-H$_2$C=CHCH$_2$— | 966 | 2-Me-6-H$_2$C=CHCH$_2$— |
| 967 | 2-F-3-F$_2$C=CH— | 968 | 2-F-4-F$_2$C=CH— | 969 | 2-F-5-F$_2$C=CH— |
| 970 | 2-F-6-F$_2$C=CH— | 971 | 2-Cl-3-F$_2$C=CH— | 972 | 2-Cl-4-F$_2$C=CH— |
| 973 | 2-Cl-5-F$_2$C=CH— | 974 | 2-Cl-6-F$_2$C=CH— | 975 | 2-Br-3-F$_2$C=CH— |
| 976 | 2-Br-4-F$_2$C=CH— | 977 | 2-Br-5-F$_2$C=CH— | 978 | 2-Br-6-F$_2$C=CH— |
| 979 | 2-I-3-F$_2$C=CH— | 980 | 2-I-4-F$_2$C=CH— | 981 | 2-I-5-F$_2$C=CH— |
| 982 | 2-I-6-F$_2$C=CH— | 983 | 2-Me-3-F$_2$C=CH— | 984 | 2-Me-4-F$_2$C=CH— |
| 985 | 2-Me-5-F$_2$C=CH— | 986 | 2-Me-6-F$_2$C=CH— | 987 | 2-F-3-F$_2$C=CHCH$_2$— |
| 988 | 2-F-4-F$_2$C=CHCH$_2$— | 989 | 2-F-5-F$_2$C=CHCH$_2$— | 990 | 2-F-6-F$_2$C=CHCH$_2$— |
| 991 | 2-Cl-3-F$_2$C=CHCH$_2$— | 992 | 2-Cl-4-F$_2$C=CHCH$_2$— | 993 | 2-Cl-5-F$_2$C=CHCH$_2$— |
| 994 | 2-Cl-6-F$_2$C=CHCH$_2$— | 995 | 2-Br-3-F$_2$C=CHCH$_2$— | 996 | 2-Br-4-F$_2$C=CHCH$_2$— |
| 997 | 2-Br-5-F$_2$C=CHCH$_2$— | 998 | 2-Br-6-F$_2$C=CHCH$_2$— | 999 | 2-I-3-F$_2$C=CHCH$_2$— |
| 1000 | 2-I-4-F$_2$C=CHCH$_2$— | 1001 | 2-I-5-F$_2$C=CHCH$_2$— | 1002 | 2-I-6-F$_2$C=CHCH$_2$— |
| 1003 | 2-Me-3-F$_2$C=CHCH$_2$— | 1004 | 2-Me-4-F$_2$C=CHCH$_2$— | 1005 | 2-Me-5-F$_2$C=CHCH$_2$— |
| 1006 | 2-Me-6-F$_2$C=CHCH$_2$— | 1007 | 2-F-3-HC≡C— | 1008 | 2-F-4-HC≡C— |
| 1009 | 2-F-5-HC≡C— | 1010 | 2-F-6-HC≡C— | 1011 | 2-Cl-3-HC≡C— |
| 1012 | 2-Cl-4-HC≡C— | 1013 | 2-Cl-5-HC≡C— | 1014 | 2-Cl-6-HC≡C— |
| 1015 | 2-Br-3-HC≡C— | 1016 | 2-Br-4-HC≡C— | 1017 | 2-Br-5-HC≡C— |
| 1018 | 2-Br-6-HC≡C— | 1019 | 2-I-3-HC≡C— | 1020 | 2-I-4-HC≡C— |
| 1021 | 2-I-5-HC≡C— | 1022 | 2-I-6-HC≡C— | 1023 | 2-Me-3-HC≡C— |
| 1024 | 2-Me-4-HC≡C— | 1025 | 2-Me-5-HC≡C— | 1026 | 2-Me-6-HC≡C— |
| 1027 | 2-F-3-HC≡CCH$_2$— | 1028 | 2-F-4-HC≡CCH$_2$— | 1029 | 2-F-5-HC≡CCH$_2$— |
| 1030 | 2-F-6-HC≡CCH$_2$— | 1031 | 2-Cl-3-HC≡CCH$_2$— | 1032 | 2-Cl-4-HC≡CCH$_2$— |
| 1033 | 2-Cl-5-HC≡CCH$_2$— | 1034 | 2-Cl-6-HC≡CCH$_2$— | 1035 | 2-Br-3-HC≡CCH$_2$— |
| 1036 | 2-Br-4-HC≡CCH$_2$— | 1037 | 2-Br-5-HC≡CCH$_2$— | 1038 | 2-Br-6-HC≡CCH$_2$— |
| 1039 | 2-I-3-HC≡CCH$_2$— | 1040 | 2-I-4-HC≡CCH$_2$— | 1041 | 2-I-5-HC≡CCH$_2$— |
| 1042 | 2-I-6-HC≡CCH$_2$— | 1043 | 2-Me-3-HC≡CCH$_2$— | 1044 | 2-Me-4-HC≡CCH$_2$— |
| 1045 | 2-Me-5-HC≡CCH$_2$— | 1046 | 2-Me-6-HC≡CCH$_2$— | 1047 | 2-F-3-F$_3$CC≡C— |
| 1048 | 2-F-4-F$_3$CC≡C— | 1049 | 2-F-5-F$_3$CC≡C— | 1050 | 2-F-6-F$_3$CC≡C— |
| 1051 | 2-Cl-3-F$_3$CC≡C— | 1052 | 2-Cl-4-F$_3$CC≡C— | 1053 | 2-Cl-5-F$_3$CC≡C— |
| 1054 | 2-Cl-6-F$_3$CC≡C— | 1055 | 2-Br-3-F$_3$CC≡C— | 1056 | 2-Br-4-F$_3$CC≡C— |
| 1057 | 2-Br-5-F$_3$CC≡C— | 1058 | 2-Br-6-F$_3$CC≡C— | 1059 | 2-I-3-F$_3$CC≡C— |
| 1060 | 2-I-4-F$_3$CC≡C— | 1061 | 2-I-5-F$_3$CC≡C— | 1062 | 2-I-6-F$_3$CC≡C— |
| 1063 | 2-Me-3-F$_3$CC≡C— | 1064 | 2-Me-4-F$_3$CC≡C— | 1065 | 2-Me-5-F$_3$CC≡C— |
| 1066 | 2-Me-6-F$_3$CC≡C— | 1067 | 2-F-3-F$_3$CC≡CCH$_2$— | 1068 | 2-F-4-F$_3$CC≡CCH$_2$— |
| 1069 | 2-F-5-F$_3$CC≡CCH$_2$— | 1070 | 2-F-6-F$_3$CC≡CCH$_2$— | 1071 | 2-Cl-3-F$_3$CC≡CCH$_2$— |
| 1072 | 2-Cl-4-F$_3$CC≡CCH$_2$— | 1073 | 2-Cl-5-F$_3$CC≡CCH$_2$— | 1074 | 2-Cl-6-F$_3$CC≡CCH$_2$— |
| 1075 | 2-Br-3-F$_3$CC≡CCH$_2$— | 1076 | 2-Br-4-F$_3$CC≡CCH$_2$— | 1077 | 2-Br-5-F$_3$CC≡CCH$_2$— |
| 1078 | 2-Br-6-F$_3$CC≡CCH$_2$— | 1079 | 2-I-3-F$_3$CC≡CCH$_2$— | 1080 | 2-I-4-F$_3$CC≡CCH$_2$— |
| 1081 | 2-I-5-F$_3$CC≡CCH$_2$— | 1082 | 2-I-6-F$_3$CC≡CCH$_2$— | 1083 | 2-Me-3-F$_3$CC≡CCH$_2$— |
| 1084 | 2-Me-4-F$_3$CC≡CCH$_2$— | 1085 | 2-Me-5-F$_3$CC≡CCH$_2$— | 1086 | 2-Me-6-F$_3$CC≡CCH$_2$— |
| 1087 | 2-F-3-MeO— | 1088 | 2-F-4-MeO— | 1089 | 2-F-5-MeO— |
| 1090 | 2-F-6-MeO— | 1091 | 2-Cl-3-MeO— | 1092 | 2-Cl-4-MeO— |
| 1093 | 2-Cl-5-MeO— | 1094 | 2-Cl-6-MeO— | 1095 | 2-Br-3-MeO— |
| 1096 | 2-Br-4-MeO— | 1097 | 2-Br-5-MeO— | 1098 | 2-Br-6-MeO— |
| 1099 | 2-I-3-MeO— | 1100 | 2-I-4-MeO— | 1101 | 2-I-5-MeO— |
| 1102 | 2-I-6-MeO— | 1103 | 2-Me-3-MeO— | 1104 | 2-Me-4-MeO— |
| 1105 | 2-Me-5-MeO— | 1106 | 2-Me-6-MeO— | 1107 | 2-F-3-EtO— |
| 1108 | 2-F-4-EtO— | 1109 | 2-F-5-EtO— | 1110 | 2-F-6-EtO— |
| 1111 | 2-Cl-3-EtO— | 1112 | 2-Cl-4-EtO— | 1113 | 2-Cl-5-EtO— |
| 1114 | 2-Cl-6-EtO— | 1115 | 2-Br-3-EtO— | 1116 | 2-Br-4-EtO— |
| 1117 | 2-Br-5-EtO— | 1118 | 2-Br-6-EtO— | 1119 | 2-I-3-EtO— |
| 1120 | 2-I-4-EtO— | 1121 | 2-I-5-EtO— | 1122 | 2-I-6-EtO— |
| 1123 | 2-Me-3-EtO— | 1124 | 2-Me-4-EtO— | 1125 | 2-Me-5-EtO— |
| 1126 | 2-Me-6-EtO— | 1127 | 2-F-3-PrO— | 1128 | 2-F-4-PrO— |
| 1129 | 2-F-5-PrO— | 1130 | 2-F-6-PrO— | 1131 | 2-Cl-3-PrO— |
| 1132 | 2-Cl-4-PrO— | 1133 | 2-Cl-5-PrO— | 1134 | 2-Cl-6-PrO— |
| 1135 | 2-Br-3-PrO— | 1136 | 2-Br-4-PrO— | 1137 | 2-Br-5-PrO— |
| 1138 | 2-Br-6-PrO— | 1139 | 2-I-3-PrO— | 1140 | 2-I-4-PrO— |
| 1141 | 2-I-5-PrO— | 1142 | 2-I-6-PrO— | 1143 | 2-Me-3-PrO— |
| 1144 | 2-Me-4-PrO— | 1145 | 2-Me-5-PrO— | 1146 | 2-Me-6-PrO— |
| 1147 | 2-F-3-iPrO— | 1148 | 2-F-4-iPrO— | 1149 | 2-F-5-iPrO— |

TABLE 2-continued

| No. | (R2)n | No. | (R2)n | No. | (R2)n |
|---|---|---|---|---|---|
| 1150 | 2-F-6-iPrO— | 1151 | 2-Cl-3-iPrO— | 1152 | 2-Cl-4-iPrO— |
| 1153 | 2-Cl-5-iPrO— | 1154 | 2-Cl-6-iPrO— | 1155 | 2-Br-3-iPrO— |
| 1156 | 2-Br-4-iPrO— | 1157 | 2-Br-5-iPrO— | 1158 | 2-Br-6-iPrO— |
| 1159 | 2-I-3-iPrO— | 1160 | 2-I-4-iPrO— | 1161 | 2-I-5-iPrO— |
| 1162 | 2-I-6-iPrO— | 1163 | 2-Me-3-iPrO— | 1164 | 2-Me-4-iPrO— |
| 1165 | 2-Me-5-iPrO— | 1166 | 2-Me-6-iPrO— | 1167 | 2-F-3-BuO— |
| 1168 | 2-F-4-BuO— | 1169 | 2-F-5-BuO— | 1170 | 2-F-6-BuO— |
| 1171 | 2-Cl-3-BuO— | 1172 | 2-Cl-4-BuO— | 1173 | 2-Cl-5-BuO— |
| 1174 | 2-Cl-6-BuO— | 1175 | 2-Br-3-BuO— | 1176 | 2-Br-4-BuO— |
| 1177 | 2-Br-5-BuO— | 1178 | 2-Br-6-BuO— | 1179 | 2-I-3-BuO— |
| 1180 | 2-I-4-BuO— | 1181 | 2-I-5-BuO— | 1182 | 2-I-6-BuO— |
| 1183 | 2-Me-3-BuO— | 1184 | 2-Me-4-BuO— | 1185 | 2-Me-5-BuO— |
| 1186 | 2-Me-6-BuO— | 1187 | 2-F-3-iBuO— | 1188 | 2-F-4-iBuO— |
| 1189 | 2-F-5-iBuO— | 1190 | 2-F-6-iBuO— | 1191 | 2-Cl-3-iBuO— |
| 1192 | 2-Cl-4-iBuO— | 1193 | 2-Cl-5-iBuO— | 1194 | 2-Cl-6-iBuO— |
| 1195 | 2-Br-3-iBuO— | 1196 | 2-Br-4-iBuO— | 1197 | 2-Br-5-iBuO— |
| 1198 | 2-Br-6-iBuO— | 1199 | 2-I-3-iBuO— | 1200 | 2-I-4-iBuO— |
| 1201 | 2-I-5-iBuO— | 1202 | 2-I-6-iBuO— | 1203 | 2-Me-3-iBuO— |
| 1204 | 2-Me-4-iBuO— | 1205 | 2-Me-5-iBuO— | 1206 | 2-Me-6-iBuO— |
| 1207 | 2-F-3-PentylO— | 1208 | 2-F-4-PentylO— | 1209 | 2-F-5-PentylO— |
| 1210 | 2-F-6-PentylO— | 1211 | 2-Cl-3-PentylO— | 1212 | 2-Cl-4-PentylO— |
| 1213 | 2-Cl-5-PentylO— | 1214 | 2-Cl-6-PentylO— | 1215 | 2-Br-3-PentylO— |
| 1216 | 2-Br-4-PentylO— | 1217 | 2-Br-5-PentylO— | 1218 | 2-Br-6-PentylO— |
| 1219 | 2-I-3-PentylO— | 1220 | 2-I-4-PentylO— | 1221 | 2-I-5-PentylO— |
| 1222 | 2-I-6-PentylO— | 1223 | 2-Me-3-PentylO— | 1224 | 2-Me-4-PentylO— |
| 1225 | 2-Me-5-PentylO— | 1226 | 2-Me-6-PentylO— | 1227 | 2-F-3-N=CCH$_2$O— |
| 1228 | 2-F-4-N=CCH$_2$O— | 1229 | 2-F-5-N=CCH$_2$O— | 1230 | 2-F-6-N=CCH$_2$O— |
| 1231 | 2-Cl-3-N=CCH$_2$O— | 1232 | 2-Cl-4-N=CCH$_2$O— | 1233 | 2-Cl-5-N=CCH$_2$O— |
| 1234 | 2-Cl-6-N=CCH$_2$O— | 1235 | 2-Br-3-N=CCH$_2$O— | 1236 | 2-Br-4-N=CCH$_2$O— |
| 1237 | 2-Br-5-N=CCH$_2$O— | 1238 | 2-Br-6-N=CCH$_2$O— | 1239 | 2-I-3-N=CCH$_2$O— |
| 1240 | 2-I-4-N=CCH$_2$O— | 1241 | 2-I-5-N=CCH$_2$O— | 1242 | 2-I-6-N=CCH$_2$O— |
| 1243 | 2-Me-3-N=CCH$_2$O— | 1244 | 2-Me-4-N=CCH$_2$O— | 1245 | 2-Me-5-N=CCH$_2$O— |
| 1246 | 2-Me-6-N=CCH$_2$O— | 1247 | 2-F-3-N=CCH$_2$CH$_2$O— | 1248 | 2-F-4-N=CCH$_2$CH$_2$O— |
| 1249 | 2-F-5-N=CCH$_2$CH$_2$O— | 1250 | 2-F-6-N=CCH$_2$CH$_2$O— | 1251 | 2-Cl-3-N=CCH$_2$CH$_2$O— |
| 1252 | 2-Cl-4-N=CCH$_2$CH$_2$O— | 1253 | 2-Cl-5-N=CCH$_2$CH$_2$O— | 1254 | 2-Cl-6-N=CCH$_2$CH$_2$O— |
| 1255 | 2-Br-3-N=CCH$_2$CH$_2$O— | 1256 | 2-Br-4-N=CCH$_2$CH$_2$O— | 1257 | 2-Br-5-N=CCH$_2$CH$_2$O— |
| 1258 | 2-Br-6-N=CCH$_2$CH$_2$O— | 1259 | 2-I-3-N=CCH$_2$CH$_2$O— | 1260 | 2-I-4-N=CCH$_2$CH$_2$O— |
| 1261 | 2-I-5-N=CCH$_2$CH$_2$O— | 1262 | 2-I-6-N=CCH$_2$CH$_2$O— | 1263 | 2-Me-3-N=CCH$_2$CH$_2$O— |
| 1264 | 2-Me-4-N=CCH$_2$CH$_2$O— | 1265 | 2-Me-5-N=CCH$_2$CH$_2$O— | 1266 | 2-Me-6-N=CCH$_2$CH$_2$O— |
| 1267 | 2-F-3-cPrCH$_2$O— | 1268 | 2-F-4-cPrCH$_2$O— | 1269 | 2-F-5-cPrCH$_2$O— |
| 1270 | 2-F-6-cPrCH$_2$O— | 1271 | 2-Cl-3-cPrCH$_2$O— | 1272 | 2-Cl-4-cPrCH$_2$O— |
| 1273 | 2-Cl-5-cPrCH$_2$O— | 1274 | 2-Cl-6-cPrCH$_2$O— | 1275 | 2-Br-3-cPrCH$_2$O— |
| 1276 | 2-Br-4-cPrCH$_2$O— | 1277 | 2-Br-5-cPrCH$_2$O— | 1278 | 2-Br-6-cPrCH$_2$O— |
| 1279 | 2-I-3-cPrCH$_2$O— | 1280 | 2-I-4-cPrCH$_2$O— | 1281 | 2-I-5-cPrCH$_2$O— |
| 1282 | 2-I-6-cPrCH$_2$O— | 1283 | 2-Me-3-cPrCH$_2$O— | 1284 | 2-Me-4-cPrCH$_2$O— |
| 1285 | 2-Me-5-cPrCH$_2$O— | 1286 | 2-Me-6-cPrCH$_2$O— | 1287 | 2-F-3-cBuCH$_2$O— |
| 1288 | 2-F-4-cBuCH$_2$O— | 1289 | 2-F-5-cBuCH$_2$O— | 1290 | 2-F-6-cBuCH$_2$O— |
| 1291 | 2-Cl-3-cBuCH$_2$O— | 1292 | 2-Cl-4-cBuCH$_2$O— | 1293 | 2-Cl-5-cBuCH$_2$O— |
| 1294 | 2-Cl-6-cBuCH$_2$O— | 1295 | 2-Br-3-cBuCH$_2$O— | 1296 | 2-Br-4-cBuCH$_2$O— |
| 1297 | 2-Br-5-cBuCH$_2$O— | 1298 | 2-Br-6-cBuCH$_2$O— | 1299 | 2-I-3-cBuCH$_2$O— |
| 1300 | 2-I-4-cBuCH$_2$O— | 1301 | 2-I-5-cBuCH$_2$O— | 1302 | 2-I-6-cBuCH$_2$O— |
| 1303 | 2-Me-3-cBuCH$_2$O— | 1304 | 2-Me-4-cBuCH$_2$O— | 1305 | 2-Me-5-cBuCH$_2$O— |
| 1306 | 2-Me-6-cBuCH$_2$O— | 1307 | 2-F-3-cPentylCH$_2$O— | 1308 | 2-F-4-cPentylCH$_2$O— |
| 1309 | 2-F-5-cPentylCH$_2$O— | 1310 | 2-F-6-cPentylCH$_2$O— | 1311 | 2-Cl-3-cPentylCH$_2$O— |
| 1312 | 2-Cl-4-cPentylCH$_2$O— | 1313 | 2-Cl-5-cPentylCH$_2$O— | 1314 | 2-Cl-6-cPentylCH$_2$O— |
| 1315 | 2-Br-3-cPentylCH$_2$O— | 1316 | 2-Br-4-cPentylCH$_2$O— | 1317 | 2-Br-5-cPentylCH$_2$O— |
| 1318 | 2-Br-6-cPentylCH$_2$O— | 1319 | 2-I-3-cPentylCH$_2$O— | 1320 | 2-I-4-cPentylCH$_2$O— |
| 1321 | 2-I-5-cPentylCH$_2$O— | 1322 | 2-I-6-cPentylCH$_2$O— | 1323 | 2-Me-3-cPentylCH$_2$O— |
| 1324 | 2-Me-4-cPentylCH$_2$O— | 1325 | 2-Me-5-cPentylCH$_2$O— | 1326 | 2-Me-6-cPentylCH$_2$O— |
| 1327 | 2-F-3-cHexylCH$_2$O— | 1328 | 2-F-4-cHexylCH$_2$O— | 1329 | 2-F-5-cHexylCH$_2$O— |
| 1330 | 2-F-6-cHexylCH$_2$O— | 1331 | 2-Cl-3-cHexylCH$_2$O— | 1332 | 2-Cl-4-cHexylCH$_2$O— |
| 1333 | 2-Cl-5-cHexylCH$_2$O— | 1334 | 2-Cl-6-cHexylCH$_2$O— | 1335 | 2-Br-3-cHexylCH$_2$O— |
| 1336 | 2-Br-4-cHexylCH$_2$O— | 1337 | 2-Br-5-cHexylCH$_2$O— | 1338 | 2-Br-6-cHexylCH$_2$O— |
| 1339 | 2-I-3-cHexylCH$_2$O— | 1340 | 2-I-4-cHexylCH$_2$O— | 1341 | 2-I-5-cHexylCH$_2$O— |
| 1342 | 2-I-6-cHexylCH$_2$O— | 1343 | 2-Me-3-cHexylCH$_2$O— | 1344 | 2-Me-4-cHexylCH$_2$O— |
| 1345 | 2-Me-5-cHexylCH$_2$O— | 1346 | 2-Me-6-cHexylCH$_2$O— | 1347 | 2-F-3-MeOCH$_2$O— |
| 1348 | 2-F-4-MeOCH$_2$O— | 1349 | 2-F-5-MeOCH$_2$O— | 1350 | 2-F-6-MeOCH$_2$O— |
| 1351 | 2-Cl-3-MeOCH$_2$O— | 1352 | 2-Cl-4-MeOCH$_2$O— | 1353 | 2-Cl-5-MeOCH$_2$O— |
| 1354 | 2-Cl-6-MeOCH$_2$O— | 1355 | 2-Br-3-MeOCH$_2$O— | 1356 | 2-Br-4-MeOCH$_2$O— |
| 1357 | 2-Br-5-MeOCH$_2$O— | 1358 | 2-Br-6-MeOCH$_2$O— | 1359 | 2-I-3-MeOCH$_2$O— |
| 1360 | 2-I-4-MeOCH$_2$O— | 1361 | 2-I-5-MeOCH$_2$O— | 1362 | 2-I-6-MeOCH$_2$O— |
| 1363 | 2-Me-3-MeOCH$_2$O— | 1364 | 2-Me-4-MeOCH$_2$O— | 1365 | 2-Me-5-MeOCH$_2$O— |
| 1366 | 2-Me-6-MeOCH$_2$O— | 1367 | 2-F-3-EtOCH$_2$O— | 1368 | 2-F-4-EtOCH$_2$O— |
| 1369 | 2-F-5-EtOCH$_2$O— | 1370 | 2-F-6-EtOCH$_2$O— | 1371 | 2-Cl-3-EtOCH$_2$O— |
| 1372 | 2-Cl-4-EtOCH$_2$O— | 1373 | 2-Cl-5-EtOCH$_2$O— | 1374 | 2-Cl-6-EtOCH$_2$O— |
| 1375 | 2-Br-3-EtOCH$_2$O— | 1376 | 2-Br-4-EtOCH$_2$O— | 1377 | 2-Br-5-EtOCH$_2$O— |
| 1378 | 2-Br-6-EtOCH$_2$O— | 1379 | 2-I-3-EtOCH$_2$O— | 1380 | 2-I-4-EtOCH$_2$O— |
| 1381 | 2-I-5-EtOCH$_2$O— | 1382 | 2-I-6-EtOCH$_2$O— | 1383 | 2-Me-3-EtOCH$_2$O— |

TABLE 2-continued

| No. | (R2)n | No. | (R2)n | No. | (R2)n |
|---|---|---|---|---|---|
| 1384 | 2-Me-4-EtOCH$_2$O— | 1385 | 2-Me-5-EtOCH$_2$O— | 1386 | 2-Me-6-EtOCH$_2$O— |
| 1387 | 2-F-3-MeOCH$_2$CH$_2$O— | 1388 | 2-F-4-MeOCH$_2$CH$_2$O— | 1389 | 2-F-5-MeOCH$_2$CH$_2$O— |
| 1390 | 2-F-6-MeOCH$_2$CH$_2$O— | 1391 | 2-Cl-3-MeOCH$_2$CH$_2$O— | 1392 | 2-Cl-4-MeOCH$_2$CH$_2$O— |
| 1393 | 2-Cl-5-MeOCH$_2$CH$_2$O— | 1394 | 2-Cl-6-MeOCH$_2$CH$_2$O— | 1395 | 2-Br-3-MeOCH$_2$CH$_2$O— |
| 1396 | 2-Br-4-MeOCH$_2$CH$_2$O— | 1397 | 2-Br-5-MeOCH$_2$CH$_2$O— | 1398 | 2-Br-6-MeOCH$_2$CH$_2$O— |
| 1399 | 2-I-3-MeOCH$_2$CH$_2$O— | 1400 | 2-I-4-MeOCH$_2$CH$_2$O— | 1401 | 2-I-5-MeOCH$_2$CH$_2$O— |
| 1402 | 2-I-6-MeOCH$_2$CH$_2$O— | 1403 | 2-Me-3-MeOCH$_2$CH$_2$O— | 1404 | 2-Me-4-MeOCH$_2$CH$_2$O— |
| 1405 | 2-Me-5-MeOCH$_2$CH$_2$O— | 1406 | 2-Me-6-MeOCH$_2$CH$_2$O— | 1407 | 2-F-3-MeOCH$_2$CH$_2$CH$_2$O— |
| 1408 | 2-F-4-MeOCH$_2$CH$_2$CH$_2$O— | 1409 | 2-F-5-MeOCH$_2$CH$_2$CH$_2$O— | 1410 | 2-F-6-MeOCH$_2$CH$_2$CH$_2$O— |
| 1411 | 2-Cl-3-MeOCH$_2$CH$_2$CH$_2$O— | 1412 | 2-Cl-4-MeOCH$_2$CH$_2$CH$_2$O— | 1413 | 2-Cl-5-MeOCH$_2$CH$_2$CH$_2$O— |
| 1414 | 2-Cl-6-MeOCH$_2$CH$_2$CH$_2$O— | 1415 | 2-Br-3-MeOCH$_2$CH$_2$CH$_2$O— | 1416 | 2-Br-4-MeOCH$_2$CH$_2$CH$_2$O— |
| 1417 | 2-Br-5-MeOCH$_2$CH$_2$CH$_2$O— | 1418 | 2-Br-6-MeOCH$_2$CH$_2$CH$_2$O— | 1419 | 2-I-3-MeOCH$_2$CH$_2$CH$_2$O— |
| 1420 | 2-I-4-MeOCH$_2$CH$_2$CH$_2$O— | 1421 | 2-I-5-MeOCH$_2$CH$_2$CH$_2$O— | 1422 | 2-I-6-MeOCH$_2$CH$_2$CH$_2$O— |
| 1423 | 2-Me-3-MeOCH$_2$CH$_2$CH$_2$O— | 1424 | 2-Me-4-MeOCH$_2$CH$_2$CH$_2$O— | 1425 | 2-Me-5-MeOCH$_2$CH$_2$CH$_2$O— |
| 1426 | 2-Me-6-MeOCH$_2$CH$_2$CH$_2$O— | 1427 | 2-F-3-MeOCH$_2$CH$_2$OCH$_2$O— | 1428 | 2-F-4-MeOCH$_2$CH$_2$OCH$_2$O— |
| 1429 | 2-F-5-MeOCH$_2$CH$_2$OCH$_2$O— | 1430 | 2-F-6-MeOCH$_2$CH$_2$OCH$_2$O— | 1431 | 2-Cl-3-MeOCH$_2$CH$_2$OCH$_2$O— |
| 1432 | 2-Cl-4-MeOCH$_2$CH$_2$OCH$_2$O— | 1433 | 2-Cl-5-MeOCH$_2$CH$_2$OCH$_2$O— | 1434 | 2-Cl-6-MeOCH$_2$CH$_2$OCH$_2$O— |
| 1435 | 2-Br-3-MeOCH$_2$CH$_2$OCH$_2$O— | 1436 | 2-Br-4-MeOCH$_2$CH$_2$OCH$_2$O— | 1437 | 2-Br-5-MeOCH$_2$CH$_2$OCH$_2$O— |
| 1438 | 2-Br-6-MeOCH$_2$CH$_2$OCH$_2$O— | 1439 | 2-I-3-MeOCH$_2$CH$_2$OCH$_2$O— | 1440 | 2-I-4-MeOCH$_2$CH$_2$OCH$_2$O— |
| 1441 | 2-I-5-MeOCH$_2$CH$_2$OCH$_2$O— | 1442 | 2-I-6-MeOCH$_2$CH$_2$OCH$_2$O— | 1443 | 2-Me-3-MeOCH$_2$CH$_2$OCH$_2$O— |
| 1444 | 2-Me-4-MeOCH$_2$CH$_2$OCH$_2$O— | 1445 | 2-Me-5-MeOCH$_2$CH$_2$OCH$_2$O— | 1446 | 2-Me-6-MeOCH$_2$CH$_2$OCH$_2$O— |
| 1447 | 2-F-3-MeSCH$_2$O— | 1448 | 2-F-4-MeSCH$_2$O— | 1449 | 2-F-5-MeSCH$_2$O— |
| 1450 | 2-F-6-MeSCH$_2$O— | 1451 | 2-Cl-3-MeSCH$_2$O— | 1452 | 2-Cl-4-MeSCH$_2$O— |
| 1453 | 2-Cl-5-MeSCH$_2$O— | 1454 | 2-Cl-6-MeSCH$_2$O— | 1455 | 2-Br-3-MeSCH$_2$O— |
| 1456 | 2-Br-4-MeSCH$_2$O— | 1457 | 2-Br-5-MeSCH$_2$O— | 1458 | 2-Br-6-MeSCH$_2$O— |
| 1459 | 2-I-3-MeSCH$_2$O— | 1460 | 2-I-4-MeSCH$_2$O— | 1461 | 2-I-5-MeSCH$_2$O— |
| 1462 | 2-I-6-MeSCH$_2$O— | 1463 | 2-Me-3-MeSCH$_2$O— | 1464 | 2-Me-4-MeSCH$_2$O— |
| 1465 | 2-Me-5-MeSCH$_2$O— | 1466 | 2-Me-6-MeSCH$_2$O— | 1467 | 2-F-3-MeS(O)CH$_2$O— |
| 1468 | 2-F-4-MeS(O)CH$_2$O— | 1469 | 2-F-5-MeS(O)CH$_2$O— | 1470 | 2-F-6-MeS(O)CH$_2$O— |
| 1471 | 2-Cl-3-MeS(O)CH$_2$O— | 1472 | 2-Cl-4-MeS(O)CH$_2$O— | 1473 | 2-Cl-5-MeS(O)CH$_2$O— |
| 1474 | 2-Cl-6-MeS(O)CH$_2$O— | 1475 | 2-Br-3-MeS(O)CH$_2$O— | 1476 | 2-Br-4-MeS(O)CH$_2$O— |
| 1477 | 2-Br-5-MeS(O)CH$_2$O— | 1478 | 2-Br-6-MeS(O)CH$_2$O— | 1479 | 2-I-3-MeS(O)CH$_2$O— |
| 1480 | 2-I-4-MeS(O)CH$_2$O— | 1481 | 2-I-5-MeS(O)CH$_2$O— | 1482 | 2-I-6-MeS(O)CH$_2$O— |
| 1483 | 2-Me-3-MeS(O)CH$_2$O— | 1484 | 2-Me-4-MeS(O)CH$_2$O— | 1485 | 2-Me-5-MeS(O)CH$_2$O— |
| 1486 | 2-Me-6-MeS(O)CH$_2$O— | 1487 | 2-F-3-MeSO$_2$CH$_2$O— | 1488 | 2-F-4-MeSO$_2$CH$_2$O— |
| 1489 | 2-F-5-MeSO$_2$CH$_2$O— | 1490 | 2-F-6-MeSO$_2$CH$_2$O— | 1491 | 2-Cl-3-MeSO$_2$CH$_2$O— |
| 1492 | 2-Cl-4-MeSO$_2$CH$_2$O— | 1493 | 2-Cl-5-MeSO$_2$CH$_2$O— | 1494 | 2-Cl-6-MeSO$_2$CH$_2$O— |
| 1495 | 2-Br-3-MeSO$_2$CH$_2$O— | 1496 | 2-Br-4-MeSO$_2$CH$_2$O— | 1497 | 2-Br-5-MeSO$_2$CH$_2$O— |
| 1498 | 2-Br-6-MeSO$_2$CH$_2$O— | 1499 | 2-I-3-MeSO$_2$CH$_2$O— | 1500 | 2-I-4-MeSO$_2$CH$_2$O— |
| 1501 | 2-I-5-MeSO$_2$CH$_2$O— | 1502 | 2-I-6-MeSO$_2$CH$_2$O— | 1503 | 2-Me-3-MeSO$_2$CH$_2$O— |
| 1504 | 2-Me-4-MeSO$_2$CH$_2$O— | 1505 | 2-Me-5-MeSO$_2$CH$_2$O— | 1506 | 2-Me-6-MeSO$_2$CH$_2$O— |
| 1507 | 2-F-3-Me$_3$SiCH$_2$O— | 1508 | 2-F-4-Me$_3$SiCH$_2$O— | 1509 | 2-F-5-Me$_3$SiCH$_2$O— |
| 1510 | 2-F-6-Me$_3$SiCH$_2$O— | 1511 | 2-Cl-3-Me$_3$SiCH$_2$O— | 1512 | 2-Cl-4-Me$_3$SiCH$_2$O— |
| 1513 | 2-Cl-5-Me$_3$SiCH$_2$O— | 1514 | 2-Cl-6-Me$_3$SiCH$_2$O— | 1515 | 2-Br-3-Me$_3$SiCH$_2$O— |
| 1516 | 2-Br-4-Me$_3$SiCH$_2$O— | 1517 | 2-Br-5-Me$_3$SiCH$_2$O— | 1518 | 2-Br-6-Me$_3$SiCH$_2$O— |
| 1519 | 2-I-3-Me$_3$SiCH$_2$O— | 1520 | 2-I-4-Me$_3$SiCH$_2$O— | 1521 | 2-I-5-Me$_3$SiCH$_2$O— |
| 1522 | 2-I-6-Me$_3$SiCH$_2$O— | 1523 | 2-Me-3-Me$_3$SiCH$_2$O— | 1524 | 2-Me-4-Me$_3$SiCH$_2$O— |
| 1525 | 2-Me-5-Me$_3$SiCH$_2$O— | 1526 | 2-Me-6-Me$_3$SiCH$_2$O— | 1527 | 2-F-3-Me$_3$SiCH$_2$CH$_2$O— |
| 1528 | 2-F-4-Me$_3$SiCH$_2$CH$_2$O— | 1529 | 2-F-5-Me$_3$SiCH$_2$CH$_2$O— | 1530 | 2-F-6-Me$_3$SiCH$_2$CH$_2$O— |
| 1531 | 2-Cl-3-Me$_3$SiCH$_2$CH$_2$O— | 1532 | 2-Cl-4-Me$_3$SiCH$_2$CH$_2$O— | 1533 | 2-Cl-5-Me$_3$SiCH$_2$CH$_2$O— |
| 1534 | 2-Cl-6-Me$_3$SiCH$_2$CH$_2$O— | 1535 | 2-Br-3-Me$_3$SiCH$_2$CH$_2$O— | 1536 | 2-Br-4-Me$_3$SiCH$_2$CH$_2$O— |
| 1537 | 2-Br-5-Me$_3$SiCH$_2$CH$_2$O— | 1538 | 2-Br-6-Me$_3$SiCH$_2$CH$_2$O— | 1539 | 2-I-3-Me$_3$SiCH$_2$CH$_2$O— |
| 1540 | 2-I-4-Me$_3$SiCH$_2$CH$_2$O— | 1541 | 2-I-5-Me$_3$SiCH$_2$CH$_2$O— | 1542 | 2-I-6-Me$_3$SiCH$_2$CH$_2$O— |
| 1543 | 2-Me-3-Me$_3$SiCH$_2$CH$_2$O— | 1544 | 2-Me-4-Me$_3$SiCH$_2$CH$_2$O— | 1545 | 2-Me-5-Me$_3$SiCH$_2$CH$_2$O— |
| 1546 | 2-Me-6-Me$_3$SiCH$_2$CH$_2$O— | 1547 | 2-F-3-Me$_3$SiCH$_2$CH$_2$CH$_2$O— | 1548 | 2-F-4-Me$_3$SiCH$_2$CH$_2$CH$_2$O— |
| 1549 | 2-F-5-Me$_3$SiCH$_2$CH$_2$CH$_2$O— | 1550 | 2-F-6-Me$_3$SiCH$_2$CH$_2$CH$_2$O— | 1551 | 2-Cl-3-Me$_3$SiCH$_2$CH$_2$CH$_2$O— |
| 1552 | 2-Cl-4-Me$_3$SiCH$_2$CH$_2$CH$_2$O— | 1553 | 2-Cl-5-Me$_3$SiCH$_2$CH$_2$CH$_2$O— | 1554 | 2-Cl-6-Me$_3$SiCH$_2$CH$_2$CH$_2$O— |
| 1555 | 2-Br-3-Me$_3$SiCH$_2$CH$_2$CH$_2$O— | 1556 | 2-Br-4-Me$_3$SiCH$_2$CH$_2$CH$_2$O— | 1557 | 2-Br-5-Me$_3$SiCH$_2$CH$_2$CH$_2$O— |

TABLE 2-continued

| No. | (R2)n | No. | (R2)n | No. | (R2)n |
|---|---|---|---|---|---|
| 1558 | 2-Br-6-Me$_3$SiCH$_2$CH$_2$O— | 1559 | 2-I-3-Me$_3$SiCH$_2$CH$_2$O— | 1560 | 2-I-3-Me$_3$SiCH$_2$CH$_2$O— |
| 1561 | 2-I-5-Me$_3$SiCH$_2$CH$_2$O— | 1562 | 2-I-6-Me$_3$SiCH$_2$CH$_2$O— | 1563 | 2-Me-3-Me$_3$SiCH$_2$CH$_2$O— |
| 1564 | 2-Me-4-Me$_3$SiCH$_2$CH$_2$O— | 1565 | 2-Me-5-Me$_3$SiCH$_2$CH$_2$O— | 1566 | 2-Me-6-Me$_3$SiCH$_2$CH$_2$O— |
| 1567 | 2-F-3-AcCH$_2$O— | 1568 | 2-F-4-AcCH$_2$O— | 1569 | 2-F-5-AcCH$_2$O— |
| 1570 | 2-F-6-AcCH$_2$O— | 1571 | 2-Cl-3-AcCH$_2$O— | 1572 | 2-Cl-4-AcCH$_2$O— |
| 1573 | 2-Cl-5-AcCH$_2$O— | 1574 | 2-Cl-6-AcCH$_2$O— | 1575 | 2-Br-3-AcCH$_2$O— |
| 1576 | 2-Br-4-AcCH$_2$O— | 1577 | 2-Br-5-AcCH$_2$O— | 1578 | 2-Br-6-AcCH$_2$O— |
| 1579 | 2-I-3-AcCH$_2$O— | 1580 | 2-I-4-AcCH$_2$O— | 1581 | 2-I-5-AcCH$_2$O— |
| 1582 | 2-I-6-AcCH$_2$O— | 1583 | 2-Me-3-AcCH$_2$O— | 1584 | 2-Me-4-AcCH$_2$O— |
| 1585 | 2-Me-5-AcCH$_2$O— | 1586 | 2-Me-6-AcCH$_2$O— | 1587 | 2-F-3-MeOC(=O)CH$_2$O— |
| 1588 | 2-F-4-MeOC(=O)CH$_2$O— | 1589 | 2-F-5-MeOC(=O)CH$_2$O— | 1590 | 2-F-6-MeOC(=O)CH$_2$O— |
| 1591 | 2-Cl-3-MeOC(=O)CH$_2$O— | 1592 | 2-Cl-4-MeOC(=O)CH$_2$O— | 1593 | 2-Cl-5-MeOC(=O)CH$_2$O— |
| 1594 | 2-Cl-6-MeOC(=O)CH$_2$O— | 1595 | 2-Br-3-MeOC(=O)CH$_2$O— | 1596 | 2-Br-4-MeOC(=O)CH$_2$O— |
| 1597 | 2-Br-5-MeOC(=O)CH$_2$O— | 1598 | 2-Br-6-MeOC(=O)CH$_2$O— | 1599 | 2-I-3-MeOC(=O)CH$_2$O— |
| 1600 | 2-I-4-MeOC(=O)CH$_2$O— | 1601 | 2-I-5-MeOC(=O)CH$_2$O— | 1602 | 2-I-6-MeOC(=O)CH$_2$O— |
| 1603 | 2-Me-3-MeOC(=O)CH$_2$O— | 1604 | 2-Me-4-MeOC(=O)CH$_2$O— | 1605 | 2-Me-5-MeOC(=O)CH$_2$O— |
| 1606 | 2-Me-6-MeOC(=O)CH$_2$O— | 1607 | 2-F-3-EtOC(=O)CH$_2$O— | 1608 | 2-F-4-EtOC(=O)CH$_2$O— |
| 1609 | 2-F-5-EtOC(=O)CH$_2$O— | 1610 | 2-F-6-EtOC(=O)CH$_2$O— | 1611 | 2-Cl-3-EtOC(=O)CH$_2$O— |
| 1612 | 2-Cl-4-EtOC(=O)CH$_2$O— | 1613 | 2-Cl-5-EtOC(=O)CH$_2$O— | 1614 | 2-Cl-6-EtOC(=O)CH$_2$O— |
| 1615 | 2-Br-3-EtOC(=O)CH$_2$O— | 1616 | 2-Br-4-EtOC(=O)CH$_2$O— | 1617 | 2-Br-5-EtOC(=O)CH$_2$O— |
| 1618 | 2-Br-6-EtOC(=O)CH$_2$O— | 1619 | 2-I-3-EtOC(=O)CH$_2$O— | 1620 | 2-I-4-EtOC(=O)CH$_2$O— |
| 1621 | 2-I-5-EtOC(=O)CH$_2$O— | 1622 | 2-I-6-EtOC(=O)CH$_2$O— | 1623 | 2-Me-3-EtOC(=O)CH$_2$O— |
| 1624 | 2-Me-4-EtOC(=O)CH$_2$O— | 1625 | 2-Me-5-EtOC(=O)CH$_2$O— | 1626 | 2-Me-6-EtOC(=O)CH$_2$O— |
| 1627 | 2-F-3-(1,3-dioxolan-2-yl)CH$_2$O— | 1628 | 2-F-4-(1,3-dioxolan-2-yl)CH$_2$O— | 1629 | 2-F-5-(1,3-dioxolan-2-yl)CH$_2$O— |
| 1630 | 2-F-6-(1,3-dioxolan-2-yl)CH$_2$O— | 1631 | 2-Cl-3-(1,3-dioxolan-2-yl)CH$_2$O— | 1632 | 2-Cl-4-(1,3-dioxolan-2-yl)CH$_2$O— |
| 1633 | 2-Cl-5-(1,3-dioxolan-2-yl)CH$_2$O— | 1634 | 2-Cl-6-(1,3-dioxolan-2-yl)CH$_2$O— | 1635 | 2-Br-3-(1,3-dioxolan-2-yl)CH$_2$O— |
| 1636 | 2-Br-4-(1,3-dioxolan-2-yl)CH$_2$O— | 1637 | 2-Br-5-(1,3-dioxolan-2-yl)CH$_2$O— | 1638 | 2-Br-6-(1,3-dioxolan-2-yl)CH$_2$O— |
| 1639 | 2-I-3-(1,3-dioxolan-2-yl)CH$_2$O— | 1640 | 2-I-4-(1,3-dioxolan-2-yl)CH$_2$O— | 1641 | 2-I-5-(1,3-dioxolan-2-yl)CH$_2$O— |
| 1642 | 2-I-6-(1,3-dioxolan-2-yl)CH$_2$O— | 1643 | 2-Me-3-(1,3-dioxolan-2-yl)CH$_2$O— | 1644 | 2-Me-4-(1,3-dioxolan-2-yl)CH$_2$O— |
| 1645 | 2-Me-5-(1,3-dioxolan-2-yl)CH$_2$O— | 1646 | 2-Me-6-(1,3-dioxolan-2-yl)CH$_2$O— | 1647 | 2-F-3-(1,3-dioxolan-2-yl)CH$_2$CH$_2$O— |
| 1648 | 2-F-4-(1,3-dioxolan-2-yl)CH$_2$CH$_2$O— | 1649 | 2-F-5-(1,3-dioxolan-2-yl)CH$_2$CH$_2$O— | 1650 | 2-F-6-(1,3-dioxolan-2-yl)CH$_2$CH$_2$O— |
| 1651 | 2-Cl-3-(1,3-dioxolan-2-yl)CH$_2$CH$_2$O— | 1652 | 2-Cl-4-(1,3-dioxolan-2-yl)CH$_2$CH$_2$O— | 1653 | 2-Cl-5-(1,3-dioxolan-2-yl)CH$_2$CH$_2$O— |
| 1654 | 2-Cl-6-(1,3-dioxolan-2-yl)CH$_2$CH$_2$O— | 1655 | 2-Br-3-(1,3-dioxolan-2-yl)CH$_2$CH$_2$O— | 1656 | 2-Br-4-(1,3-dioxolan-2-yl)CH$_2$CH$_2$O— |
| 1657 | 2-Br-5-(1,3-dioxolan-2-yl)CH$_2$CH$_2$O— | 1658 | 2-Br-6-(1,3-dioxolan-2-yl)CH$_2$CH$_2$O— | 1659 | 2-I-3-(1,3-dioxolan-2-yl)CH$_2$CH$_2$O— |
| 1660 | 2-I-4-(1,3-dioxolan-2-yl)CH$_2$CH$_2$O— | 1661 | 2-I-5-(1,3-dioxolan-2-yl)CH$_2$CH$_2$O— | 1662 | 2-I-6-(1,3-dioxolan-2-yl)CH$_2$CH$_2$O— |
| 1663 | 2-Me-3-(1,3-dioxolan-2-yl)CH$_2$CH$_2$O— | 1664 | 2-Me-4-(1,3-dioxolan-2-yl)CH$_2$CH$_2$O— | 1665 | 2-Me-5-(1,3-dioxolan-2-yl)CH$_2$CH$_2$O— |
| 1666 | 2-Me-6-(1,3-dioxolan-2-yl)CH$_2$CH$_2$O— | 1667 | 2-F-3-(1,3-dioxan-2-yl)CH$_2$O— | 1668 | 2-F-4-(1,3-dioxan-2-yl)CH$_2$O— |
| 1669 | 2-F-5-(1,3-dioxan-2-yl)CH$_2$O— | 1670 | 2-F-6-(1,3-dioxan-2-yl)CH$_2$O— | 1671 | 2-Cl-3-(1,3-dioxan-2-yl)CH$_2$O— |
| 1672 | 2-Cl-4-(1,3-dioxan-2-yl)CH$_2$O— | 1673 | 2-Cl-5-(1,3-dioxan-2-yl)CH$_2$O— | 1674 | 2-Cl-6-(1,3-dioxan-2-yl)CH$_2$O— |
| 1675 | 2-Br-3-(1,3-dioxan-2-yl)CH$_2$O— | 1676 | 2-Br-4-(1,3-dioxan-2-yl)CH$_2$O— | 1677 | 2-Br-5-(1,3-dioxan-2-yl)CH$_2$O— |
| 1678 | 2-Br-6-(1,3-dioxan-2-yl)CH$_2$O— | 1679 | 2-I-3-(1,3-dioxan-2-yl)CH$_2$O— | 1680 | 2-I-4-(1,3-dioxan-2-yl)CH$_2$O— |
| 1681 | 2-I-5-(1,3-dioxan-2-yl)CH$_2$O— | 1682 | 2-I-6-(1,3-dioxan-2-yl)CH$_2$O— | 1683 | 2-Me-3-(1,3-dioxan-2-yl)CH$_2$O— |

TABLE 2-continued

| No. | (R2)n | No. | (R2)n | No. | (R2)n |
|---|---|---|---|---|---|
| 1684 | 2-Me-4-(1,3-dioxan-2-yl)CH$_2$O— | 1685 | 2-Me-5-(1,3-dioxan-2-yl)CH$_2$O— | 1686 | 2-Me-6-(1,3-dioxan-2-yl)CH$_2$O— |
| 1687 | 2-F-3-(1,3-dioxan-2-yl)CH$_2$CH$_2$O— | 1688 | 2-F-4-(1,3-dioxan-2-yl)CH$_2$CH$_2$O— | 1689 | 2-F-5-(1,3-dioxan-2-yl)CH$_2$CH$_2$O— |
| 1690 | 2-F-6-(1,3-dioxan-2-yl)CH$_2$CH$_2$O— | 1691 | 2-Cl-3-(1,3-dioxan-2-yl)CH$_2$CH$_2$O— | 1692 | 2-Cl-4-(1,3-dioxan-2-yl)CH$_2$CH$_2$O— |
| 1693 | 2-Cl-5-(1,3-dioxan-2-yl)CH$_2$CH$_2$O— | 1694 | 2-Cl-6-(1,3-dioxan-2-yl)CH$_2$CH$_2$O— | 1695 | 2-Br-3-(1,3-dioxan-2-yl)CH$_2$CH$_2$O— |
| 1696 | 2-Br-4-(1,3-dioxan-2-yl)CH$_2$CH$_2$O— | 1697 | 2-Br-5-(1,3-dioxan-2-yl)CH$_2$CH$_2$O— | 1698 | 2-Br-6-(1,3-dioxan-2-yl)CH$_2$CH$_2$O— |
| 1699 | 2-I-3-(1,3-dioxan-2-yl)CH$_2$CH$_2$O— | 1700 | 2-I-4-(1,3-dioxan-2-yl)CH$_2$CH$_2$O— | 1701 | 2-I-5-(1,3-dioxan-2-yl)CH$_2$CH$_2$O— |
| 1702 | 2-I-6-(1,3-dioxan-2-yl)CH$_2$CH$_2$O— | 1703 | 2-Me-3-(1,3-dioxan-2-yl)CH$_2$CH$_2$O— | 1704 | 2-Me-4-(1,3-dioxan-2-yl)CH$_2$CH$_2$O— |
| 1705 | 2-Me-5-(1,3-dioxan-2-yl)CH$_2$CH$_2$O— | 1706 | 2-Me-6-(1,3-dioxan-2-yl)CH$_2$CH$_2$O— | 1707 | 2-F-3-cPrO— |
| 1708 | 2-F-4-cPrO— | 1709 | 2-F-5-cPrO— | 1710 | 2-F-6-cPrO— |
| 1711 | 2-Cl-3-cPrO— | 1712 | 2-Cl-4-cPrO— | 1713 | 2-Cl-5-cPrO— |
| 1714 | 2-Cl-6-cPrO— | 1715 | 2-Br-3-cPrO— | 1716 | 2-Br-4-cPrO— |
| 1717 | 2-Br-5-cPrO— | 1718 | 2-Br-6-cPrO— | 1719 | 2-I-3-cPrO— |
| 1720 | 2-I-4-cPrO— | 1721 | 2-I-5-cPrO— | 1722 | 2-I-6-cPrO— |
| 1723 | 2-Me-3-cPrO— | 1724 | 2-Me-4-cPrO— | 1725 | 2-Me-5-cPrO— |
| 1726 | 2-Me-6-cPrO— | 1727 | 2-F-3-cBuO— | 1728 | 2-F-4-cBuO— |
| 1729 | 2-F-5-cBuO— | 1730 | 2-F-6-cBuO— | 1731 | 2-Cl-3-cBuO— |
| 1732 | 2-Cl-4-cBuO— | 1733 | 2-Cl-5-cBuO— | 1734 | 2-Cl-6-cBuO— |
| 1735 | 2-Br-3-cBuO— | 1736 | 2-Br-4-cBuO— | 1737 | 2-Br-5-cBuO— |
| 1738 | 2-Br-6-cBuO— | 1739 | 2-I-3-cBuO— | 1740 | 2-I-4-cBuO— |
| 1741 | 2-I-5-cBuO— | 1742 | 2-I-6-cBuO— | 1743 | 2-Me-3-cBuO— |
| 1744 | 2-Me-4-cBuO— | 1745 | 2-Me-5-cBuO— | 1746 | 2-Me-6-cBuO— |
| 1747 | 2-F-3-cPentylO— | 1748 | 2-F-4-cPentylO— | 1749 | 2-F-5-cPentylO— |
| 1750 | 2-F-6-cPentylO— | 1751 | 2-Cl-3-cPentylO— | 1752 | 2-Cl-4-cPentylO— |
| 1753 | 2-Cl-5-cPentylO— | 1754 | 2-Cl-6-cPentylO— | 1755 | 2-Br-3-cPentylO— |
| 1756 | 2-Br-4-cPentylO— | 1757 | 2-Br-5-cPentylO— | 1758 | 2-Br-6-cPentylO— |
| 1759 | 2-I-3-cPentylO— | 1760 | 2-I-4-cPentylO— | 1761 | 2-I-5-cPentylO— |
| 1762 | 2-I-6-cPentylO— | 1763 | 2-Me-3-cPentylO— | 1764 | 2-Me-4-cPentylO— |
| 1765 | 2-Me-5-cPentylO— | 1766 | 2-Me-6-cPentylO— | 1767 | 2-F-3-cHexylO— |
| 1768 | 2-F-4-cHexylO— | 1769 | 2-F-5-cHexylO— | 1770 | 2-F-6-cHexylO— |
| 1771 | 2-Cl-3-cHexylO— | 1772 | 2-Cl-4-cHexylO— | 1773 | 2-Cl-5-cHexylO— |
| 1774 | 2-Cl-6-cHexylO— | 1775 | 2-Br-3-cHexylO— | 1776 | 2-Br-4-cHexylO— |
| 1777 | 2-Br-5-cHexylO— | 1778 | 2-Br-6-cHexylO— | 1779 | 2-I-3-cHexylO— |
| 1780 | 2-I-4-cHexylO— | 1781 | 2-I-5-cHexylO— | 1782 | 2-I-6-cHexylO— |
| 1783 | 2-Me-3-cHexylO— | 1784 | 2-Me-4-cHexylO— | 1785 | 2-Me-5-cHexylO— |
| 1786 | 2-Me-6-cHexylO— | 1787 | 2-F-3-F$_3$CO— | 1788 | 2-F-4-F$_3$CO— |
| 1789 | 2-F-5-F$_3$CO— | 1790 | 2-F-6-F$_3$CO— | 1791 | 2-Cl-3-F$_3$CO— |
| 1792 | 2-Cl-4-F$_3$CO— | 1793 | 2-Cl-5-F$_3$CO— | 1794 | 2-Cl-6-F$_3$CO— |
| 1795 | 2-Br-3-F$_3$CO— | 1796 | 2-Br-4-F$_3$CO— | 1797 | 2-Br-5-F$_3$CO— |
| 1798 | 2-Br-6-F$_3$CO— | 1799 | 2-I-3-F$_3$CO— | 1800 | 2-I-4-F$_3$CO— |
| 1801 | 2-I-5-F$_3$CO— | 1802 | 2-I-6-F$_3$CO— | 1803 | 2-Me-3-F$_3$CO— |
| 1804 | 2-Me-4-F$_3$CO— | 1805 | 2-Me-5-F$_3$CO— | 1806 | 2-Me-6-F$_3$CO— |
| 1807 | 2-F-3-F$_2$CHO— | 1808 | 2-F-4-F$_2$CHO— | 1809 | 2-F-5-F$_2$CHO— |
| 1810 | 2-F-6-F$_2$CHO— | 1811 | 2-Cl-3-F$_2$CHO— | 1812 | 2-Cl-4-F$_2$CHO— |
| 1813 | 2-Cl-5-F$_2$CHO— | 1814 | 2-Cl-6-F$_2$CHO— | 1815 | 2-Br-3-F$_2$CHO— |
| 1816 | 2-Br-4-F$_2$CHO— | 1817 | 2-Br-5-F$_2$CHO— | 1818 | 2-Br-6-F$_2$CHO— |
| 1819 | 2-I-3-F$_2$CHO— | 1820 | 2-I-4-F$_2$CHO— | 1821 | 2-I-5-F$_2$CHO— |
| 1822 | 2-I-6-F$_2$CHO— | 1823 | 2-Me-3-F$_2$CHO— | 1824 | 2-Me-4-F$_2$CHO— |
| 1825 | 2-Me-5-F$_2$CHO— | 1826 | 2-Me-6-F$_2$CHO— | 1827 | 2-F-3-F$_3$CCH$_2$O— |
| 1828 | 2-F-4-F$_3$CCH$_2$O— | 1829 | 2-F-5-F$_3$CCH$_2$O— | 1830 | 2-F-6-F$_3$CCH$_2$O— |
| 1831 | 2-Cl-3-F$_3$CCH$_2$O— | 1832 | 2-Cl-4-F$_3$CCH$_2$O— | 1833 | 2-Cl-5-F$_3$CCH$_2$O— |
| 1834 | 2-Cl-6-F$_3$CCH$_2$O— | 1835 | 2-Br-3-F$_3$CCH$_2$O— | 1836 | 2-Br-4-F$_3$CCH$_2$O— |
| 1837 | 2-Br-5-F$_3$CCH$_2$O— | 1838 | 2-Br-6-F$_3$CCH$_2$O— | 1839 | 2-I-3-F$_3$CCH$_2$O— |
| 1840 | 2-I-4-F$_3$CCH$_2$O— | 1841 | 2-I-5-F$_3$CCH$_2$O— | 1842 | 2-I-6-F$_3$CCH$_2$O— |
| 1843 | 2-Me-3-F$_3$CCH$_2$O— | 1844 | 2-Me-4-F$_3$CCH$_2$O— | 1845 | 2-Me-5-F$_3$CCH$_2$O— |
| 1846 | 2-Me-6-F$_3$CCH$_2$O— | 1847 | 2-F-3-F$_2$CHCH$_2$O— | 1848 | 2-F-4-F$_2$CHCH$_2$O— |
| 1849 | 2-F-5-F$_2$CHCH$_2$O— | 1850 | 2-F-6-F$_2$CHCH$_2$O— | 1851 | 2-Cl-3-F$_2$CHCH$_2$O— |
| 1852 | 2-Cl-4-F$_2$CHCH$_2$O— | 1853 | 2-Cl-5-F$_2$CHCH$_2$O— | 1854 | 2-Cl-6-F$_2$CHCH$_2$O— |
| 1855 | 2-Br-3-F$_2$CHCH$_2$O— | 1856 | 2-Br-4-F$_2$CHCH$_2$O— | 1857 | 2-Br-5-F$_2$CHCH$_2$O— |
| 1858 | 2-Br-6-F$_2$CHCH$_2$O— | 1859 | 2-I-3-F$_2$CHCH$_2$O— | 1860 | 2-I-4-F$_2$CHCH$_2$O— |
| 1861 | 2-I-5-F$_2$CHCH$_2$O— | 1862 | 2-I-6-F$_2$CHCH$_2$O— | 1863 | 2-Me-3-F$_2$CHCH$_2$O— |
| 1864 | 2-Me-4-F$_2$CHCH$_2$O— | 1865 | 2-Me-5-F$_2$CHCH$_2$O— | 1866 | 2-Me-6-F$_2$CHCH$_2$O— |
| 1867 | 2-F-3-H$_2$C=CHCH$_2$O— | 1868 | 2-F-4-H$_2$C=CHCH$_2$O— | 1869 | 2-F-5-H$_2$C=CHCH$_2$O— |
| 1870 | 2-F-6-H$_2$C=CHCH$_2$O— | 1871 | 2-Cl-3-H$_2$C=CHCH$_2$O— | 1872 | 2-Cl-4-H$_2$C=CHCH$_2$O— |
| 1873 | 2-Cl-5-H$_2$C=CHCH$_2$O— | 1874 | 2-Cl-6-H$_2$C=CHCH$_2$O— | 1875 | 2-Br-3-H$_2$C=CHCH$_2$O— |
| 1876 | 2-Br-4-H$_2$C=CHCH$_2$O— | 1877 | 2-Br-5-H$_2$C=CHCH$_2$O— | 1878 | 2-Br-6-H$_2$C=CHCH$_2$O— |
| 1879 | 2-I-3-H$_2$C=CHCH$_2$O— | 1880 | 2-I-4-H$_2$C=CHCH$_2$O— | 1881 | 2-I-5-H$_2$C=CHCH$_2$O— |
| 1882 | 2-I-6-H$_2$C=CHCH$_2$O— | 1883 | 2-Me-3-H$_2$C=CHCH$_2$O— | 1884 | 2-Me-4-H$_2$C=CHCH$_2$O— |
| 1885 | 2-Me-5-H$_2$C=CHCH$_2$O— | 1886 | 2-Me-6-H$_2$C=CHCH$_2$O— | 1887 | 2-F-3-HC≡CCH$_2$O— |
| 1888 | 2-F-4-HC≡CCH$_2$O— | 1889 | 2-F-5-HC≡CCH$_2$O— | 1890 | 2-F-6-HC≡CCH$_2$O— |
| 1891 | 2-Cl-3-HC≡CCH$_2$O— | 1892 | 2-Cl-4-HC≡CCH$_2$O— | 1893 | 2-Cl-5-HC≡CCH$_2$O— |

TABLE 2-continued

| No. | (R2)n | No. | (R2)n | No. | (R2)n |
|---|---|---|---|---|---|
| 1894 | 2-Cl-6-HC≡CCH$_2$O— | 1895 | 2-Br-3-HC≡CCH$_2$O— | 1896 | 2-Br-4-HC≡CCH$_2$O— |
| 1897 | 2-Br-5-HC≡CCH$_2$O— | 1898 | 2-Br-6-HC≡CCH$_2$O— | 1899 | 2-I-3-HC≡CCH$_2$O— |
| 1900 | 2-I-4-HC≡CCH$_2$O— | 1901 | 2-I-5-HC≡CCH$_2$O— | 1902 | 2-I-6-HC≡CCH$_2$O— |
| 1903 | 2-Me-3-HC≡CCH$_2$O— | 1904 | 2-Me-4-HC≡CCH$_2$O— | 1905 | 2-Me-5-HC≡CCH$_2$O— |
| 1906 | 2-Me-6-HC≡CCH$_2$O— | 1907 | 2-F-3-Ac— | 1908 | 2-F-4-Ac— |
| 1909 | 2-F-5-Ac— | 1910 | 2-F-6-Ac— | 1911 | 2-Cl-3-Ac— |
| 1912 | 2-Cl-4-Ac— | 1913 | 2-Cl-5-Ac— | 1914 | 2-Cl-6-Ac— |
| 1915 | 2-Br-3-Ac— | 1916 | 2-Br-4-Ac— | 1917 | 2-Br-5-Ac— |
| 1918 | 2-Br-6-Ac— | 1919 | 2-I-3-Ac— | 1920 | 2-I-4-Ac— |
| 1921 | 2-I-5-Ac— | 1922 | 2-I-6-Ac— | 1923 | 2-Me-3-Ac— |
| 1924 | 2-Me-4-Ac— | 1925 | 2-Me-5-Ac— | 1926 | 2-Me-6-Ac— |
| 1927 | 2-F-3-MeOC(═O)— | 1928 | 2-F-4-MeOC(═O)— | 1929 | 2-F-5-MeOC(═O)— |
| 1930 | 2-F-6-MeOC(═O)— | 1931 | 2-Cl-3-MeOC(═O)— | 1932 | 2-Cl-4-MeOC(═O)— |
| 1933 | 2-Cl-5-MeOC(═O)— | 1934 | 2-Cl-6-MeOC(═O)— | 1935 | 2-Br-3-MeOC(═O)— |
| 1936 | 2-Br-4-MeOC(═O)— | 1937 | 2-Br-5-MeOC(═O)— | 1938 | 2-Br-6-MeOC(═O)— |
| 1939 | 2-I-3-MeOC(═O)— | 1940 | 2-I-4-MeOC(═O)— | 1941 | 2-I-5-MeOC(═O)— |
| 1942 | 2-I-6-MeOC(═O)— | 1943 | 2-Me-3-MeOC(═O)— | 1944 | 2-Me-4-MeOC(═O)— |
| 1945 | 2-Me-5-MeOC(═O)— | 1946 | 2-Me-6-MeOC(═O)— | 1947 | 2-F-3-EtOC(═O)— |
| 1948 | 2-F-4-EtOC(═O)— | 1949 | 2-F-5-EtOC(═O)— | 1950 | 2-F-6-EtOC(═O)— |
| 1951 | 2-Cl-3-EtOC(═O)— | 1952 | 2-Cl-4-EtOC(═O)— | 1953 | 2-Cl-5-EtOC(═O)— |
| 1954 | 2-Cl-6-EtOC(═O)— | 1955 | 2-Br-3-EtOC(═O)— | 1956 | 2-Br-4-EtOC(═O)— |
| 1957 | 2-Br-5-EtOC(═O)— | 1958 | 2-Br-6-EtOC(═O)— | 1959 | 2-I-3-EtOC(═O)— |
| 1960 | 2-I-4-EtOC(═O)— | 1961 | 2-I-5-EtOC(═O)— | 1962 | 2-I-6-EtOC(═O)— |
| 1963 | 2-Me-3-EtOC(═O)— | 1964 | 2-Me-4-EtOC(═O)— | 1965 | 2-Me-5-EtOC(═O)— |
| 1966 | 2-Me-6-EtOC(═O)— | 1967 | 2-F-3-AcO— | 1968 | 2-F-4-AcO— |
| 1969 | 2-F-5-AcO— | 1970 | 2-F-6-AcO— | 1971 | 2-Cl-3-AcO— |
| 1972 | 2-Cl-4-AcO— | 1973 | 2-Cl-5-AcO— | 1974 | 2-Cl-6-AcO— |
| 1975 | 2-Br-3-AcO— | 1976 | 2-Br-4-AcO— | 1977 | 2-Br-5-AcO— |
| 1978 | 2-Br-6-AcO— | 1979 | 2-I-3-AcO— | 1980 | 2-I-4-AcO— |
| 1981 | 2-I-5-AcO— | 1982 | 2-I-6-AcO— | 1983 | 2-Me-3-AcO— |
| 1984 | 2-Me-4-AcO— | 1985 | 2-Me-5-AcO— | 1986 | 2-Me-6-AcO— |
| 1987 | 2-F-3-MeOC(═O)O— | 1988 | 2-F-4-MeOC(═O)O— | 1989 | 2-F-5-MeOC(═O)O— |
| 1990 | 2-F-6-MeOC(═O)O— | 1991 | 2-Cl-3-MeOC(═O)O— | 1992 | 2-Cl-4-MeOC(═O)O— |
| 1993 | 2-Cl-5-MeOC(═O)O— | 1994 | 2-Cl-6-MeOC(═O)O— | 1995 | 2-Br-3-MeOC(═O)O— |
| 1996 | 2-Br-4-MeOC(═O)O— | 1997 | 2-Br-5-MeOC(═O)O— | 1998 | 2-Br-6-MeOC(═O)O— |
| 1999 | 2-I-3-MeOC(═O)O— | 2000 | 2-I-4-MeOC(═O)O— | 2001 | 2-I-5-MeOC(═O)O— |
| 2002 | 2-I-6-MeOC(═O)O— | 2003 | 2-Me-3-MeOC(═O)O— | 2004 | 2-Me-4-MeOC(═O)O— |
| 2005 | 2-Me-5-MeOC(═O)O— | 2006 | 2-Me-6-MeOC(═O)O— | 2007 | 2-F-3-EtOC(═O)O— |
| 2008 | 2-F-4-EtOC(═O)O— | 2009 | 2-F-5-EtOC(═O)O— | 2010 | 2-F-6-EtOC(═O)O— |
| 2011 | 2-Cl-3-EtOC(═O)O— | 2012 | 2-Cl-4-EtOC(═O)O— | 2013 | 2-Cl-5-EtOC(═O)O— |
| 2014 | 2-Cl-6-EtOC(═O)O— | 2015 | 2-Br-3-EtOC(═O)O— | 2016 | 2-Br-4-EtOC(═O)O— |
| 2017 | 2-Br-5-EtOC(═O)O— | 2018 | 2-Br-6-EtOC(═O)O— | 2019 | 2-I-3-EtOC(═O)O— |
| 2020 | 2-I-4-EtOC(═O)O— | 2021 | 2-I-5-EtOC(═O)O— | 2022 | 2-I-6-EtOC(═O)O— |
| 2023 | 2-Me-3-EtOC(═O)O— | 2024 | 2-Me-4-EtOC(═O)O— | 2025 | 2-Me-5-EtOC(═O)O— |
| 2026 | 2-Me-6-EtOC(═O)O— | 2027 | 2-F-3-(1,3-dioxolan-2-yl)- | 2028 | 2-F-4-(1,3-dioxolan-2-yl)- |
| 2029 | 2-F-5-(1,3-dioxolan-2-yl)- | 2030 | 2-F-6-(1,3-dioxolan-2-yl)- | 2031 | 2-Cl-3-(1,3-dioxolan-2-yl)- |
| 2032 | 2-Cl-4-(1,3-dioxolan-2-yl)- | 2033 | 2-Cl-5-(1,3-dioxolan-2-yl)- | 2034 | 2-Cl-6-(1,3-dioxolan-2-yl)- |
| 2035 | 2-Br-3-(1,3-dioxolan-2-yl)- | 2036 | 2-Br-4-(1,3-dioxolan-2-yl)- | 2037 | 2-Br-5-(1,3-dioxolan-2-yl)- |
| 2038 | 2-Br-6-(1,3-dioxolan-2-yl)- | 2039 | 2-I-3-(1,3-dioxolan-2-yl)- | 2040 | 2-I-4-(1,3-dioxolan-2-yl)- |
| 2041 | 2-I-5-(1,3-dioxolan-2-yl)- | 2042 | 2-I-6-(1,3-dioxolan-2-yl)- | 2043 | 2-Me-3-(1,3-dioxolan-2-yl)- |
| 2044 | 2-Me-4-(1,3-dioxolan-2-yl)- | 2045 | 2-Me-5-(1,3-dioxolan-2-yl)- | 2046 | 2-Me-6-(1,3-dioxolan-2-yl)- |
| 2047 | 2-F-3-(1,3-dioxan-2-yl)- | 2048 | 2-F-4-(1,3-dioxan-2-yl)- | 2049 | 2-F-5-(1,3-dioxan-2-yl)- |
| 2050 | 2-F-6-(1,3-dioxan-2-yl)- | 2051 | 2-Cl-3-(1,3-dioxan-2-yl)- | 2052 | 2-Cl-4-(1,3-dioxan-2-yl)- |
| 2053 | 2-Cl-5-(1,3-dioxan-2-yl)- | 2054 | 2-Cl-6-(1,3-dioxan-2-yl)- | 2055 | 2-Br-3-(1,3-dioxan-2-yl)- |
| 2056 | 2-Br-4-(1,3-dioxan-2-yl)- | 2057 | 2-Br-5-(1,3-dioxan-2-yl)- | 2058 | 2-Br-6-(1,3-dioxan-2-yl)- |
| 2059 | 2-I-3-(1,3-dioxan-2-yl)- | 2060 | 2-I-4-(1,3-dioxan-2-yl)- | 2061 | 2-I-5-(1,3-dioxan-2-yl)- |
| 2062 | 2-I-6-(1,3-dioxan-2-yl)- | 2063 | 2-Me-3-(1,3-dioxan-2-yl)- | 2064 | 2-Me-4-(1,3-dioxan-2-yl)- |
| 2065 | 2-Me-5-(1,3-dioxan-2-yl)- | 2066 | 2-Me-6-(1,3-dioxan-2-yl)- | 2067 | 2-F-3-MeS— |
| 2068 | 2-F-4-MeS— | 2069 | 2-F-5-MeS— | 2070 | 2-F-6-MeS— |
| 2071 | 2-Cl-3-MeS— | 2072 | 2-Cl-4-MeS— | 2073 | 2-Cl-5-MeS— |
| 2074 | 2-Cl-6-MeS— | 2075 | 2-Br-3-MeS— | 2076 | 2-Br-4-MeS— |
| 2077 | 2-Br-5-MeS— | 2078 | 2-Br-6-MeS— | 2079 | 2-I-3-MeS— |
| 2080 | 2-I-4-MeS— | 2081 | 2-I-5-MeS— | 2082 | 2-I-6-MeS— |
| 2083 | 2-Me-3-MeS— | 2084 | 2-Me-4-MeS— | 2085 | 2-Me-5-MeS— |
| 2086 | 2-Me-6-MeS— | 2087 | 2-F-3-MeS(O)— | 2088 | 2-F-4-MeS(O)— |
| 2089 | 2-F-5-MeS(O)— | 2090 | 2-F-6-MeS(O)— | 2091 | 2-Cl-3-MeS(O)— |

TABLE 2-continued

| No. | (R2)n | No. | (R2)n | No. | (R2)n |
|---|---|---|---|---|---|
| 2092 | 2-Cl-4-MeS(O)— | 2093 | 2-Cl-5-MeS(O)— | 2094 | 2-Cl-6-MeS(O)— |
| 2095 | 2-Br-3-MeS(O)— | 2096 | 2-Br-4-MeS(O)— | 2097 | 2-Br-5-MeS(O)— |
| 2098 | 2-Br-6-MeS(O)— | 2099 | 2-I-3-MeS(O)— | 2100 | 2-I-4-MeS(O)— |
| 2101 | 2-I-5-MeS(O)— | 2102 | 2-I-6-MeS(O)— | 2103 | 2-Me-3-MeS(O)— |
| 2104 | 2-Me-4-MeS(O)— | 2105 | 2-Me-5-MeS(O)— | 2106 | 2-Me-6-MeS(O)— |
| 2107 | 2-F-3-MeSO$_2$— | 2108 | 2-F-4-MeSO$_2$— | 2109 | 2-F-5-MeSO$_2$— |
| 2110 | 2-F-6-MeSO$_2$— | 2111 | 2-Cl-3-MeSO$_2$— | 2112 | 2-Cl-4-MeSO$_2$— |
| 2113 | 2-Cl-5-MeSO$_2$— | 2114 | 2-Cl-6-MeSO$_2$— | 2115 | 2-Br-3-MeSO$_2$— |
| 2116 | 2-Br-4-MeSO$_2$— | 2117 | 2-Br-5-MeSO$_2$— | 2118 | 2-Br-6-MeSO$_2$— |
| 2119 | 2-I-3-MeSO$_2$— | 2120 | 2-I-4-MeSO$_2$— | 2121 | 2-I-5-MeSO$_2$— |
| 2122 | 2-I-6-MeSO$_2$— | 2123 | 2-Me-3-MeSO$_2$— | 2124 | 2-Me-4-MeSO$_2$— |
| 2125 | 2-Me-5-MeSO$_2$— | 2126 | 2-Me-6-MeSO$_2$— | 2127 | 2-F-3-ClCH$_2$S— |
| 2128 | 2-F-4-ClCH$_2$S— | 2129 | 2-F-5-ClCH$_2$S— | 2130 | 2-F-6-ClCH$_2$S— |
| 2131 | 2-Cl-3-ClCH$_2$S— | 2132 | 2-Cl-4-ClCH$_2$S— | 2133 | 2-Cl-5-ClCH$_2$S— |
| 2134 | 2-Cl-6-ClCH$_2$S— | 2135 | 2-Br-3-ClCH$_2$S— | 2136 | 2-Br-4-ClCH$_2$S— |
| 2137 | 2-Br-5-ClCH$_2$S— | 2138 | 2-Br-6-ClCH$_2$S— | 2139 | 2-I-3-ClCH$_2$S— |
| 2140 | 2-I-4-ClCH$_2$S— | 2141 | 2-I-5-ClCH$_2$S— | 2142 | 2-I-6-ClCH$_2$S— |
| 2143 | 2-Me-3-ClCH$_2$S— | 2144 | 2-Me-4-ClCH$_2$S— | 2145 | 2-Me-5-ClCH$_2$S— |
| 2146 | 2-Me-6-ClCH$_2$S— | 2147 | 2-F-3-ClCH$_2$S(O)— | 2148 | 2-F-4-ClCH$_2$S(O)— |
| 2149 | 2-F-5-ClCH$_2$S(O)— | 2150 | 2-F-6-ClCH$_2$S(O)— | 2151 | 2-Cl-3-ClCH$_2$S(O)— |
| 2152 | 2-Cl-4-ClCH$_2$S(O)— | 2153 | 2-Cl-5-ClCH$_2$S(O)— | 2154 | 2-Cl-6-ClCH$_2$S(O)— |
| 2155 | 2-Br-3-ClCH$_2$S(O)— | 2156 | 2-Br-4-ClCH$_2$S(O)— | 2157 | 2-Br-5-ClCH$_2$S(O)— |
| 2158 | 2-Br-6-ClCH$_2$S(O)— | 2159 | 2-I-3-ClCH$_2$S(O)— | 2160 | 2-I-4-ClCH$_2$S(O)— |
| 2161 | 2-I-5-ClCH$_2$S(O)— | 2162 | 2-I-6-ClCH$_2$S(O)— | 2163 | 2-Me-3-ClCH$_2$S(O)— |
| 2164 | 2-Me-4-ClCH$_2$S(O)— | 2165 | 2-Me-5-ClCH$_2$S(O)— | 2166 | 2-Me-6-ClCH$_2$S(O)— |
| 2167 | 2-F-3-ClCH$_2$SO$_2$— | 2168 | 2-F-4-ClCH$_2$SO$_2$— | 2169 | 2-F-5-ClCH$_2$SO$_2$— |
| 2170 | 2-F-6-ClCH$_2$SO$_2$— | 2171 | 2-Cl-3-ClCH$_2$SO$_2$— | 2172 | 2-Cl-4-ClCH$_2$SO$_2$— |
| 2173 | 2-Cl-5-ClCH$_2$SO$_2$— | 2174 | 2-Cl-6-ClCH$_2$SO$_2$— | 2175 | 2-Br-3-ClCH$_2$SO$_2$— |
| 2176 | 2-Br-4-ClCH$_2$SO$_2$— | 2177 | 2-Br-5-ClCH$_2$SO$_2$— | 2178 | 2-Br-6-ClCH$_2$SO$_2$— |
| 2179 | 2-I-3-ClCH$_2$SO$_2$— | 2180 | 2-I-4-ClCH$_2$SO$_2$— | 2181 | 2-I-5-ClCH$_2$SO$_2$— |
| 2182 | 2-I-6-ClCH$_2$SO$_2$— | 2183 | 2-Me-3-ClCH$_2$SO$_2$— | 2184 | 2-Me-4-ClCH$_2$SO$_2$— |
| 2185 | 2-Me-5-ClCH$_2$SO$_2$— | 2186 | 2-Me-6-ClCH$_2$SO$_2$— | 2187 | 3,5-di-MeO— |
| 2188 | 3,5-di-EtO— | 2189 | 3,5-di-F— | 2190 | 3,5-di-Cl— |
| 2191 | 3,5-di-Br— | 2192 | 3,5-di-I— | 2193 | 3,5-di-Me— |
| 2194 | 3-F-5-Me— | 2195 | 3-Cl-5-Me— | 2196 | 3-Br-5-Me— |
| 2197 | 3-I-5-Me— | 2198 | 3-F-5-MeO— | 2199 | 3-Cl-5-MeO— |
| 2200 | 3-Br-5-MeO— | 2201 | 3-I-5-MeO— | 2202 | 5-F-3-EtO— |
| 2203 | 3-Cl-5-EtO— | 2204 | 3-Br-5-EtO— | 2205 | 5-I-3-EtO— |
| 2206 | 3-F-5-N=CCH$_2$O— | 2207 | 3-Cl-5-N=CCH$_2$O— | 2208 | 3-Br-5-N=CCH$_2$O— |
| 2209 | 3-I-5-N=CCH$_2$O— | 2210 | 3-F-5-MeOCH$_2$O— | 2211 | 3-Cl-5-MeOCH$_2$O— |
| 2212 | 3-Br-5-MeOCH$_2$O— | 2213 | 3-I-5-MeOCH$_2$O— | 2214 | 5-F-2-MeO— |
| 2215 | 5-Cl-2-MeO— | 2216 | 5-Br-2-MeO— | 2217 | 5-I-2-MeO— |
| 2218 | 5-Me-2-MeO— | 2219 | 2-F-3,5-di-MeO— | 2220 | 2-F-3,5-di-EtO— |
| 2221 | 2,3,5-tri-F— | 2222 | 2-F-3,5-di-Cl— | 2223 | 3,5-di-Br-2-F— |
| 2224 | 2-F-3,5-di-I— | 2225 | 2-F-3,5-di-Me— | 2226 | 2,3-di-F-5-Me— |
| 2227 | 2,5-di-F-3-Me— | 2228 | 3-Cl-2-F-5-Me— | 2229 | 5-Cl-2-F-3-Me— |
| 2230 | 3-Br-2-F-5-Me— | 2231 | 5-Br-2-F-3-Me— | 2232 | 2-F-3-I-5-Me— |
| 2233 | 2-F-5-I-3-Me— | 2234 | 2,3-di-F-5-MeO— | 2235 | 2,5-di-F-3-MeO— |
| 2236 | 3-Cl-2-F-5-MeO— | 2237 | 5-Cl-2-F-3-MeO— | 2238 | 3-Br-2-F-5-MeO— |
| 2239 | 5-Br-2-F-3-MeO— | 2240 | 2-F-3-I-5-MeO— | 2241 | 2-F-5-I-3-MeO— |
| 2242 | 2,3-di-F-5-EtO— | 2243 | 2,5-di-F-3-EtO— | 2244 | 3-Cl-2-F-5-EtO— |
| 2245 | 5-Cl-2-F-3-EtO— | 2246 | 3-Br-2-F-5-EtO— | 2247 | 5-Br-2-F-3-EtO— |
| 2248 | 2-F-3-I-5-EtO— | 2249 | 2-F-5-I-3-EtO— | 2250 | 2,3-di-F-5-N=CCH$_2$O— |
| 2251 | 2,5-di-F-3-N=CCH$_2$O— | 2252 | 3-Cl-2-F-5-N=CCH$_2$O— | 2253 | 5-Cl-2-F-3-N=CCH$_2$O— |
| 2254 | 3-Br-2-F-5-N=CCH$_2$O— | 2255 | 5-Br-2-F-3-N=CCH$_2$O— | 2256 | 2-F-3-I-5-N=CCH$_2$O— |
| 2257 | 2-F-5-I-3-N=CCH$_2$O— | 2258 | 2,3-di-F-5-MeOCH$_2$O— | 2259 | 2,5-di-F-3-MeOCH$_2$O— |
| 2260 | 3-Cl-2-F-5-MeOCH$_2$O— | 2261 | 5-Cl-2-F-3-MeOCH$_2$O— | 2262 | 3-Br-2-F-5-MeOCH$_2$O— |
| 2263 | 5-Br-2-F-3-MeOCH$_2$O— | 2264 | 2-F-3-I-5-MeOCH$_2$O— | 2265 | 2-F-5-I-3-MeOCH$_2$O— |
| 2266 | 2-Cl-3,5-di-MeO— | 2267 | 2-Cl-3,5-di-EtO— | 2268 | 2-Cl-3,5-di-F— |
| 2269 | 2,3,5-tri-Cl— | 2270 | 3,5-di-Br-2-Cl— | 2271 | 2-Cl-3,5-di-I— |
| 2272 | 2-Cl-3,5-di-Me— | 2273 | 2-Cl-3-F-5-Me— | 2274 | 2-Cl-5-F-3-Me— |
| 2275 | 2,3-di-Cl-5-Me— | 2276 | 2,5-di-Cl-3-Me— | 2277 | 3-Br-2-Cl-5-Me— |
| 2278 | 5-Br-2-Cl-3-Me— | 2279 | 2-Cl-3-I-5-Me— | 2280 | 2-Cl-5-I-3-Me— |
| 2281 | 2-Cl-3-F-5-MeO— | 2282 | 2-Cl-5-F-3-MeO— | 2283 | 2,3-di-Cl-5-MeO— |
| 2284 | 2,5-di-Cl-3-MeO— | 2285 | 3-Br-2-Cl-5-MeO— | 2286 | 5-Br-2-Cl-3-MeO— |
| 2287 | 2-Cl-3-I-5-MeO— | 2288 | 2-Cl-5-I-3-MeO— | 2289 | 2-Cl-3-F-5-EtO— |
| 2290 | 2-Cl-5-F-3-EtO— | 2291 | 2,3-di-Cl-5-EtO— | 2292 | 2,5-di-Cl-3-EtO— |
| 2293 | 3-Br-2-Cl-5-EtO— | 2294 | 5-Br-2-Cl-3-EtO— | 2295 | 2-Cl-3-I-5-EtO— |
| 2296 | 2-Cl-5-I-3-EtO— | 2297 | 2-Cl-3-F-5-N=CCH$_2$O— | 2298 | 2-Cl-5-F-3-N=CCH$_2$O— |
| 2299 | 2,3-di-Cl-5-N=CCH$_2$O— | 2300 | 2,5-di-Cl-3-N=CCH$_2$O— | 2301 | 3-Br-2-Cl-5-N=CCH$_2$O— |
| 2302 | 5-Br-2-Cl-3-N=CCH$_2$O— | 2303 | 2-Cl-3-I-5-N=CCH$_2$O— | 2304 | 2-Cl-5-I-3-N=CCH$_2$O— |
| 2305 | 2-Cl-3-F-5-MeOCH$_2$O— | 2306 | 2-Cl-5-F-3-MeOCH$_2$O— | 2307 | 2,3-di-Cl-5-MeOCH$_2$O— |
| 2308 | 2,5-di-Cl-3-MeOCH$_2$O— | 2309 | 3-Br-2-Cl-5-MeOCH$_2$O— | 2310 | 5-Br-2-Cl-3-MeOCH$_2$O— |
| 2311 | 2-Cl-3-I-5-MeOCH$_2$O— | 2312 | 2-Cl-5-I-3-MeOCH$_2$O— | 2313 | 2-Br-3,5-di-MeO— |
| 2314 | 2-Br-3,5-di-EtO— | 2315 | 2-Br-3,5-di-F— | 2316 | 2-Br-3,5-di-Cl— |
| 2317 | 2,3,5-tri-Br— | 2318 | 2-Br-3,5-di-I— | 2319 | 2-Br-3,5-di-Me— |
| 2320 | 2-Br-3-F-5-Me— | 2321 | 2-Br-5-F-3-Me— | 2322 | 2-Br-3-Cl-5-Me— |
| 2323 | 2-Br-5-Cl-3-Me— | 2324 | 2,3-di-Br-5-Me— | 2325 | 2,5-di-Br-3-Me— |

TABLE 2-continued

| No. | (R2)n | No. | (R2)n | No. | (R2)n |
|---|---|---|---|---|---|
| 2326 | 2-Br-3-I-5-Me— | 2327 | 2-Br-5-I-3-Me— | 2328 | 2-Br-3-F-5-MeO— |
| 2329 | 2-Br-5-F-3-MeO— | 2330 | 2-Br-3-Cl-5-MeO— | 2331 | 2-Br-5-Cl-3-MeO— |
| 2332 | 2,3-di-Br-5-MeO— | 2333 | 2,5-di-Br-3-MeO— | 2334 | 2-Br-3-I-5-MeO— |
| 2335 | 2-Br-5-I-3-MeO— | 2336 | 2-Br-3-F-5-EtO— | 2337 | 2-Br-5-F-3-EtO— |
| 2338 | 2-Br-3-Cl-5-EtO— | 2339 | 2-Br-5-Cl-3-EtO— | 2340 | 2,3-di-Br-5-EtO— |
| 2341 | 2,5-di-Br-3-EtO— | 2342 | 2-Br-3-I-5-EtO— | 2343 | 2-Br-5-I-3-EtO— |
| 2344 | 2-Br-3-F-5-N=CCH$_2$O— | 2345 | 2-Br-5-F-3-N=CCH$_2$O— | 2346 | 2-Br-3-Cl-5-N=CCH$_2$O— |
| 2347 | 2-Br-5-Cl-3-N=CCH$_2$O— | 2348 | 2,3-di-Br-5-N=CCH$_2$O— | 2349 | 2,5-di-Br-3-N=CCH$_2$O— |
| 2350 | 2-Br-3-I-5-N=CCH$_2$O— | 2351 | 2-Br-5-I-3-N=CCH$_2$O— | 2352 | 2-Br-3-F-5-MeOCH$_2$O— |
| 2353 | 2-Br-5-F-3-MeOCH$_2$O— | 2354 | 2-Br-3-Cl-5-MeOCH$_2$O— | 2355 | 2-Br-5-Cl-3-MeOCH$_2$O— |
| 2356 | 2,3-di-Br-5-MeOCH$_2$O— | 2357 | 2,5-di-Br-3-MeOCH$_2$O— | 2358 | 2-Br-3-I-5-MeOCH$_2$O— |
| 2359 | 2-Br-5-I-3-MeOCH$_2$O— | 2360 | 2-I-3,5-di-MeO— | 2361 | 2-I-3,5-di-EtO— |
| 2362 | 3,5-di-F-2-I— | 2363 | 3,5-di-Cl-2-I— | 2364 | 3,5-di-Br-2-I— |
| 2365 | 2,3,5-Tri-I— | 2366 | 3,5-di-Me-2-I— | 2367 | 3-F-2-I-5-Me— |
| 2368 | 5-F-2-I-3-Me— | 2369 | 3-Cl-2-I-5-Me— | 2370 | 5-Cl-2-I-3-Me— |
| 2371 | 3-Br-2-I-5-Me— | 2372 | 5-Br-2-I-3-Me— | 2373 | 2,3-di-I-5-Me— |
| 2374 | 2,5-di-I-3-Me— | 2375 | 3-F-2-I-5-MeO— | 2376 | 5-F-2-I-3-MeO— |
| 2377 | 3-Cl-2-I-5-MeO— | 2378 | 5-Cl-2-I-3-MeO— | 2379 | 3-Br-2-I-5-MeO— |
| 2380 | 5-Br-2-I-3-MeO— | 2381 | 2,3-di-I-5-MeO— | 2382 | 2,5-di-I-3-MeO— |
| 2383 | 3-F-2-I-5-EtO— | 2384 | 5-F-2-I-3-EtO— | 2385 | 3-Cl-2-I-5-EtO— |
| 2386 | 5-Cl-2-I-3-EtO— | 2387 | 3-Br-2-I-5-EtO— | 2388 | 5-Br-2-I-3-EtO— |
| 2389 | 2,3-di-2-I-5-EtO— | 2390 | 2,5-di-I-3-EtO— | 2391 | 3-F-2-I-5-N=CCH$_2$O— |
| 2392 | 5-F-2-I-3-N=CCH$_2$O— | 2393 | 3-Cl-2-I-5-N=CCH$_2$O— | 2394 | 5-Cl-2-I-3-N=CCH$_2$O— |
| 2395 | 3-Br-2-I-5-N=CCH$_2$O— | 2396 | 5-Br-2-I-3-N=CCH$_2$O— | 2397 | 2,3-di-I-5-N=CCH$_2$O— |
| 2398 | 2,5-di-I-3-N=CCH$_2$O— | 2399 | 3-F-2-I-5-MeOCH$_2$O— | 2400 | 5-F-2-I-3-MeOCH$_2$O— |
| 2401 | 3-Cl-2-I-5-MeOCH$_2$O— | 2402 | 5-Cl-2-I-3-MeOCH$_2$O— | 2403 | 3-Br-2-I-5-MeOCH$_2$O— |
| 2404 | 5-Br-2-I-3-MeOCH$_2$O— | 2405 | 2,3-di-I-5-MeOCH$_2$O— | 2406 | 2,5-di-I-3-MeOCH$_2$O— |
| 2407 | 2-Me-3,5-di-MeO— | 2408 | 2-Me-3,5-di-EtO— | 2409 | 3,5-di-F-2-Me— |
| 2410 | 3,5-di-Cl-2-Me— | 2411 | 3,5-di-Br-2-Me— | 2412 | 3,5-di-I-2-Me— |
| 2413 | 2,3,5-tri-Me— | 2414 | 3-F-2,5-di-Me— | 2415 | 5-F-2,3-di-Me— |
| 2416 | 3-Cl-2,5-di-Me— | 2417 | 5-Cl-2,3-di-Me— | 2418 | 3-Br-2,5-di-Me— |
| 2419 | 5-Br-2,3-di-Me— | 2420 | 3-I-2,5-di-Me— | 2421 | 5-I-2,3-di-Me— |
| 2422 | 3-F-2-Me-5-MeO— | 2423 | 5-F-2-Me-3-MeO— | 2424 | 3-Cl-2-Me-5-MeO— |
| 2425 | 5-Cl-2-Me-3-MeO— | 2426 | 3-Br-2-Me-5-MeO— | 2427 | 5-Br-2-Me-3-MeO— |
| 2428 | 3-I-2-Me-5-MeO— | 2429 | 5-I-2-Me-3-MeO— | 2430 | 3-F-2-Me-5-EtO— |
| 2431 | 5-F-2-Me-3-EtO— | 2432 | 3-Cl-2-Me-5-EtO— | 2433 | 5-Cl-2-Me-3-EtO— |
| 2434 | 3-Br-2-Me-5-EtO— | 2435 | 5-Br-2-Me-3-EtO— | 2436 | 3-I-2-Me-5-EtO— |
| 2437 | 5-I-2-Me-3-EtO— | 2438 | 3-F-2-Me-5-N=CCH$_2$O— | 2439 | 5-F-2-Me-3-N=CCH$_2$O— |
| 2440 | 3-Cl-2-Me-5-N=CCH$_2$O— | 2441 | 5-Cl-2-Me-3-N=CCH$_2$O— | 2442 | 3-Br-2-Me-5-N=CCH$_2$O— |
| 2443 | 5-Br-2-Me-3-N=CCH$_2$O— | 2444 | 3-I-2-Me-5-N=CCH$_2$O— | 2445 | 5-I-2-Me-3-N=CCH$_2$O— |
| 2446 | 3-F-2-Me-5-MeOCH$_2$O— | 2447 | 5-F-2-Me-3-MeOCH$_2$O— | 2448 | 3-Cl-2-Me-5-MeOCH$_2$O— |
| 2449 | 5-Cl-2-Me-3-MeOCH$_2$O— | 2450 | 3-Br-2-Me-5-MeOCH$_2$O— | 2451 | 5-Br-2-Me-3-MeOCH$_2$O— |
| 2452 | 3-I-2-Me-5-MeOCH$_2$O— | 2453 | 5-I-2-Me-3-MeOCH$_2$O— | 2454 | 2,3,6-Tri-F— |
| 2455 | 2,6-di-Cl-3-F— | 2456 | 2-Cl-3,6-di-F— | 2457 | 6-Cl-2,3-di-F— |
| 2458 | 3-Cl-2,6-di-F— | 2459 | 2,3,6-Tri-Cl— | 2460 | 2,3-di-Cl-6-F— |
| 2461 | 3,6-di-Cl-2-F— | 2462 | 3-Br-2,6-di-F— | 2463 | 3-Br-2,6-di-Cl— |
| 2464 | 3-Br-2-Cl-6-F— | 2465 | 3-Br-6-Cl-2-F— | 2466 | 2,6-di-F-3-I— |
| 2467 | 2,6-di-Cl-3-I— | 2468 | 2-Cl-6-F-3-I— | 2469 | 6-Cl-2-F-3-I— |
| 2470 | 2,6-di-F-3-Me— | 2471 | 2,6-di-Cl-3-Me— | 2472 | 2-Cl-6-F-3-Me— |
| 2473 | 6-Cl-2-F-3-Me— | 2474 | 2,6-di-F-3-MeO— | 2475 | 2,6-di-Cl-3-MeO— |
| 2476 | 2-Cl-6-F-3-MeO— | 2477 | 6-Cl-2-F-3-MeO— | 2478 | 2,6-di-F-3-EtO— |
| 2479 | 2,6-di-Cl-3-EtO— | 2480 | 2-Cl-6-F-3-EtO— | 2481 | 6-Cl-2-F-3-EtO— |
| 2482 | 2,6-di-F-3-N=CCH$_2$O— | 2483 | 2,6-di-Cl-3-N=CCH$_2$O— | 2484 | 2-Cl-6-F-3-N=CCH$_2$O— |
| 2485 | 6-Cl-2-F-3-N=CCH$_2$O— | 2486 | 2,6-di-F-3-MeOCH$_2$O— | 2487 | 2,6-di-Cl-3-MeOCH$_2$O— |
| 2488 | 2-Cl-6-F-3-MeOCH$_2$O— | 2489 | 6-Cl-2-F-3-MeOCH$_2$O— | 2490 | 3,4,5-tri-F— |
| 2491 | 4-Cl-3,5-di-F— | 2492 | 4-Br-3,5-di-F— | 2493 | 3,5-di-F-4-I— |
| 2494 | 3,5-di-F-4-Me— | 2495 | 3,5-di-Cl-4-F— | 2496 | 3,4,5-tri-Cl— |
| 2497 | 4-Br-3,5-di-Cl— | 2498 | 3,5-di-Cl-4-I— | 2499 | 3,5-di-Cl-4-Me— |
| 2500 | 3,5-di-Br-4-F— | 2501 | 3,5-di-Br-4-Cl— | 2502 | 3,4,5-tri-Br— |
| 2503 | 3,5-di-Br-4-I— | 2504 | 3,5-di-Br-4-Me— | 2505 | 4-F-3,5-di-I— |
| 2506 | 4-Cl-3,5-di-I— | 2507 | 4-Br-3,5-di-I— | 2508 | 3,4,5-tri-I— |
| 2509 | 4-Me-3,5-di-I— | 2510 | 4-F-3,5-di-Me— | 2511 | 4-Cl-3,5-di-Me— |
| 2512 | 4-Br-3,5-di-Me— | 2513 | 4-I-3,5-di-Me— | 2514 | 3,4,5-tri-Me— |
| 2515 | 4-F-3,5-di-Me— | 2516 | 4-Cl-3,5-di-Me— | 2517 | 4-Br-3,5-di-Me— |
| 2518 | 4-I-3,5-di-Me— | 2519 | 4-MeO-3,5-di-Me— | 2520 | 4-F-3,5-di-MeO— |
| 2521 | 4-Cl-3,5-di-MeO— | 2522 | 4-Br-3,5-di-MeO— | 2523 | 4-I-3,5-di-MeO— |
| 2524 | 4-Me-3,5-di-MeO— | 2525 | 4-F-3,5-di-EtO— | 2526 | 4-Cl-3,5-di-EtO— |
| 2527 | 4-Br-3,5-di-EtO— | 2528 | 4-I-3,5-di-EtO— | 2529 | 4-Me-3,5-di-EtO— |
| 2530 | 2,3,4-tri-F— | 2531 | 2-Cl-3,4-di-F— | 2532 | 2-Br-3,4-di-F— |
| 2533 | 3,4-di-F-2-I— | 2534 | 3,4-di-F-2-Me— | 2535 | 2,4,5-tri-F— |
| 2536 | 2-Cl-4,5-di-F— | 2537 | 2-Br-4,5-di-F— | 2538 | 4,5-di-F-2-I— |
| 2539 | 4,5-di-F-2-Me— | 2540 | 2,4-di-F-3-Cl— | 2541 | 2,3-di-Cl-4-F— |
| 2542 | 2-Br-3-Cl-4-F— | 2543 | 3-Cl-4-F-2-I— | 2544 | 3-Cl-4-F-2-Me— |
| 2545 | 2,4-di-F-5-Cl— | 2546 | 2,5-di-Cl-4-F— | 2547 | 2-Br-5-Cl-4-F— |
| 2548 | 5-Cl-4-F-2-I— | 2549 | 5-Cl-4-F-2-Me— | 2550 | 2-F-3,4-di-Cl— |
| 2551 | 2,3,4-tri-Cl— | 2552 | 2-Br-3,4-di-Cl— | 2553 | di-3,4-Cl-2-I— |

TABLE 2-continued

| No. | (R2)n | No. | (R2)n | No. | (R2)n |
|---|---|---|---|---|---|
| 2554 | di-3,4-Cl-2-Me— | 2555 | 2-F-3,5-di-Cl— | 2556 | 2,3,5-tri-Cl— |
| 2557 | 2-Br-3,5-di-Cl— | 2558 | 3,5-di-Cl-2-I— | 2559 | 3,5-di-Cl-2-Me— |
| 2560 | 4-Cl-2,3-di-F— | 2561 | 2,4-di-Cl-3-F— | 2562 | 2-Br-4-Cl-3-F— |
| 2563 | 4-Cl-3-F-2-I— | 2564 | 4-Cl-3-F-2-Me— | 2565 | 4-Cl-2,5-di-F— |
| 2566 | 2,4-di-Cl-5-F— | 2567 | 2-Br-4-Cl-5-F— | 2568 | 4-Cl-5-F-2-I— |
| 2569 | 4-Cl-5-F-2-Me— | 2570 | 2,4-di-F-3-MeO— | 2571 | 2-Cl-4-F-3-MeO— |
| 2572 | 2-Br-4-F-3-MeO— | 2573 | 4-F-2-I-3-MeO— | 2574 | 4-F-2-Me-3-MeO— |
| 2575 | 2,4-F-5-MeO— | 2576 | 2-Cl-4-F-5-MeO— | 2577 | 2-Br-4-F-5-MeO— |
| 2578 | 4-F-2-I-5-MeO— | 2579 | 4-F-2-Me-5-MeO— | 2580 | 4-Cl-2-F-3-MeO— |
| 2581 | 2,4-di-Cl-3-MeO— | 2582 | 2-Br-4-Cl-3-MeO— | 2583 | 4-Cl-2-I-3-MeO— |
| 2584 | 4-Cl-2-Me-3-MeO— | 2585 | 4-Cl-2-F-5-MeO— | 2586 | 2,4-di-Cl-5-MeO— |
| 2587 | 2-Br-4-Cl-5-MeO— | 2588 | 4-Cl-2-I-5-MeO— | 2589 | 4-Cl-2-Me-5-MeO— |
| 2590 | 2,6-di-F-3,5-di-MeO— | 2591 | 2,6-di-Cl-3,5-di-MeO— | 2592 | 6-Cl-2-F-3,5-di-MeO— |
| 2593 | 6-Br-2-F-3,5-di-MeO— | 2594 | 2-Br-6-Cl-3,5-di-MeO— | 2595 | 2,3,4,5,-tetra-F— |
| 2596 | 2,3,5,6,-tetra-F— | 2597 | 2,3,4,5,6-penta-F— | 2598 | 2-Me$_3$SiCH$_2$CH$_2$OCH$_2$O— |
| 2599 | 3-Me$_3$SiCH$_2$CH$_2$OCH$_2$O— | 2600 | 4-Me$_3$SiCH$_2$CH$_2$OCH$_2$O— | 2601 | 2-F-3-Me$_3$SiCH$_2$CH$_2$OCH$_2$O— |
| 2602 | 2-F-4-Me$_3$SiCH$_2$CH$_2$OCH$_2$O— | 2603 | 2-F-5-Me$_3$SiCH$_2$CH$_2$OCH$_2$O— | 2604 | 2-F-6-Me$_3$SiCH$_2$CH$_2$OCH$_2$O— |
| 2605 | 2-Cl-3-Me$_3$SiCH$_2$CH$_2$OCH$_2$O— | 2606 | 2-Cl-4-Me$_3$SiCH$_2$CH$_2$OCH$_2$O— | 2607 | 2-Cl-5-Me$_3$SiCH$_2$CH$_2$OCH$_2$O— |
| 2608 | 2-Cl-6-Me$_3$SiCH$_2$CH$_2$OCH$_2$O— | 2609 | 2-Br-3-Me$_3$SiCH$_2$CH$_2$OCH$_2$O— | 2610 | 2-Br-4-Me$_3$SiCH$_2$CH$_2$OCH$_2$O— |
| 2611 | 2-Br-5-Me$_3$SiCH$_2$CH$_2$OCH$_2$O— | 2612 | 2-Br-6-Me$_3$SiCH$_2$CH$_2$OCH$_2$O— | 2613 | 2-I-3-Me$_3$SiCH$_2$CH$_2$OCH$_2$O— |
| 2614 | 2-I-4-Me$_3$SiCH$_2$CH$_2$OCH$_2$O— | 2615 | 2-I-5-Me$_3$SiCH$_2$CH$_2$OCH$_2$O— | 2616 | 2-I-6-Me$_3$SiCH$_2$CH$_2$OCH$_2$O— |
| 2617 | 2-Me-3-Me$_3$SiCH$_2$CH$_2$OCH$_2$O— | 2618 | 2-Me-4-Me$_3$SiCH$_2$CH$_2$OCH$_2$O— | 2619 | 2-Me-5-Me$_3$SiCH$_2$CH$_2$OCH$_2$O— |
| 2620 | 2-Me-6-Me$_3$SiCH$_2$CH$_2$OCH$_2$O— | | | | |

Hereinbelow, examples of the methods for producing the compounds represented by Formula (1) will be illustrated.

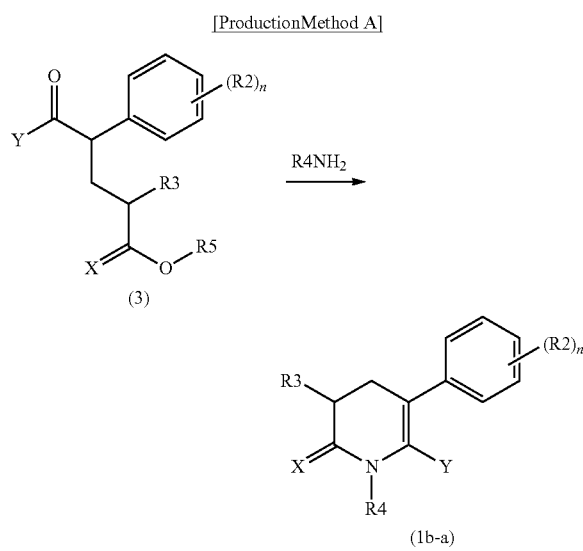

[ProductionMethod A]

In the formula, R4 represents a hydrogen atom, a hydroxy group, a cyano group, a C1-C6 alkyl group optionally substituted with substituent A, a C1-C6 haloalkyl group, a C3-C8 cycloalkyl group optionally substituted with substituent A, a C2-C6 alkenyl group optionally substituted with substituent A, a C2-C6 haloalkenyl group, a C2-C6 alkynyl group optionally substituted with substituent A, a C2-C6 haloalkynyl group, a C1-C6 alkoxy group optionally substituted with substituent A, a C1-C6 haloalkoxy group, a C3-C8 cycloalkoxy group optionally substituted with substituent A, a C2-C6 alkenyloxy group optionally substituted with substituent A, a C2-C6 haloalkenyloxy group, a C3-C6 alkynyloxy group optionally substituted with substituent A, a C3-C6 haloalkynyloxy group or an R10R11N— (wherein R10 and R11 each independently represents a hydrogen atom or a C1-C6 alkyl group), R5 represents a hydrogen atom or a C1-C6 alkyl group, and n, R2, R3, X and Y are the same as defined hereinabove.

Production Method A produces a compound represented by Formula (1b-a) which may be an inventive compound or may be an intermediate for an inventive compound. The production method includes reacting a compound represented by Formula (3) with R4NH$_2$ in the presence of an acid.

The R4NH$_2$ used in the reaction may be purchased from the market. The R4NH$_2$ may be in the form of a salt with an acidic compound such as hydrochloric acid or acetic acid, and is not particularly limited as long as the target reaction takes place.

In the reaction, the R4NH$_2$ is used in at least 1 equivalent weight relative to the compound represented by Formula (3). The amount is not particularly limited as long as this equivalent weight is satisfied and also the target reaction takes place, but is preferably 1 equivalent weight to 200 equivalent weights.

Examples of the acids used in the reaction include inorganic acids such as hydrochloric acid and sulfuric acid, and organic acids such as acetic acid, methanesulfonic acid and p-toluenesulfonic acid. The acid is not particularly limited as long as the target reaction takes place, but acetic acid is preferable. The use of an acid is not an absolute necessity when the R4NH$_2$ is used as a salt with an acidic compound.

In the reaction, the acid is used in at least 1 equivalent weight relative to the R4NH$_2$. The amount is not particularly limited as long as this equivalent weight is satisfied and also the target reaction takes place, but is preferably 1 equivalent weight to 200 equivalent weights. When the acid used is liquid, the acid may also serve as a solvent.

The reaction may involve a solvent, which however is not an absolute necessity.

The solvent used in the reaction is not particularly limited as long as the target reaction takes place. Examples include acidic solvents such as acetic acid and methanesulfonic acid, ether solvents such as diethyl ether, diisopropyl ether, methyl-t-butyl ether, dimethoxyethane, tetrahydrofuran and dioxane, alcohol solvents such as methanol, ethanol and isopropanol, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, and the like. These solvents may be used singly, or two or more may be used in combination in any ratio. As the solvents, among others, acidic solvents are preferable, and acetic acid is more preferable.

The amount of the solvent used in the reaction is not particularly limited as long as the target reaction takes place, but is usually 3 to 200 times by weight the amount of the compound represented by Formula (3).

The temperature of the reaction is not particularly limited as long as the target reaction takes place, but is usually 50° C. to 180° C., or is below the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. These solvents may be used singly, or two or more may be used in combination in any ratio. The liquid separation may be performed as many times as desired without limitation in accordance with the desired purity and yield.

The reaction mixture obtained above which includes the compound of Formula (1b-a) may be dehydrated with a desiccant such as sodium sulfate or magnesium sulfate, but this dehydration may be omitted.

The reaction mixture obtained above which includes the compound of Formula (1b-a) may be distilled to evaporate the solvent under reduced pressure as long as the compound is not decomposed.

The distilled reaction mixture which includes the compound of Formula (1b-a) may be purified with an appropriate solvent by a method such as washing, reprecipitation, recrystallization or column chromatography. The purification method may be selected appropriately in accordance with the desired purity.

A compound produced by Production Method A that is represented by Formula (1b-a) in which R4 is a hydrogen atom, namely, a compound represented by Formula (2), may be a useful intermediate for the production of a compound of Formula (1b) among the inventive compounds.

Specific examples of the intermediates represented by Formula (2) are shown by combinations of the structural formulas illustrated in Table 3 with (R2)n described in Table 2. Such compounds are only illustrative, and the scope of the invention is not limited thereto.

TABLE 3

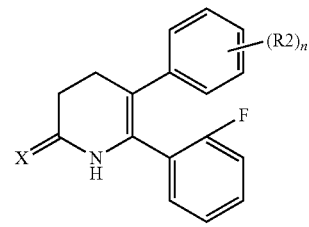

I-1

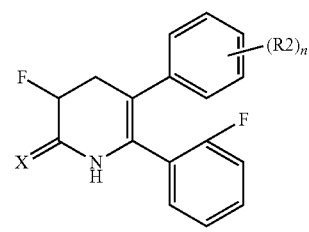

I-2

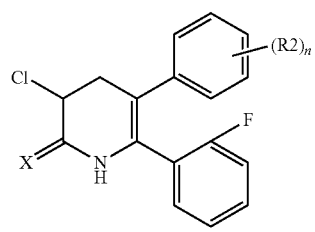

I-3

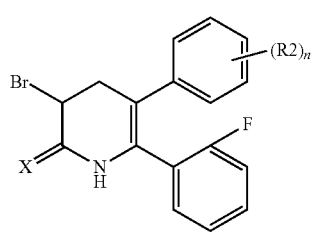

I-4

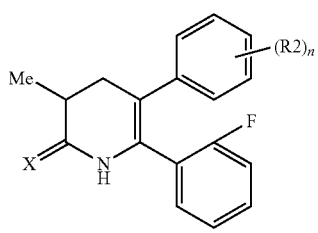

I-5

TABLE 3-continued
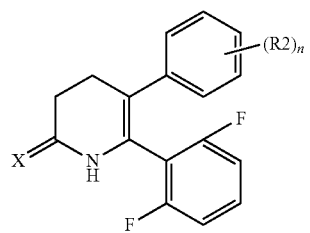 I-6
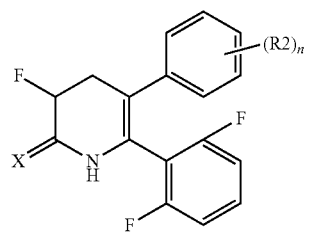 I-7
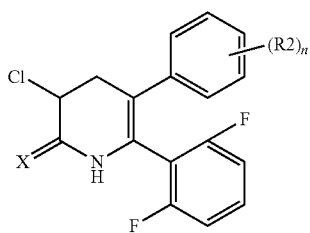 I-8
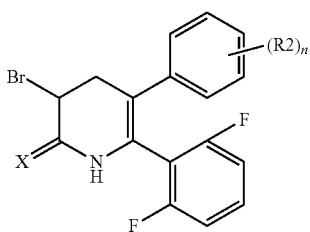 I-9
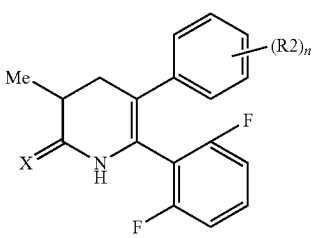 I-10
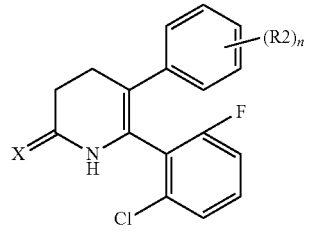 I-11
TABLE 3-continued
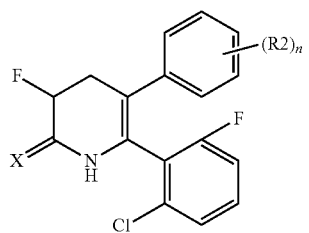 I-12
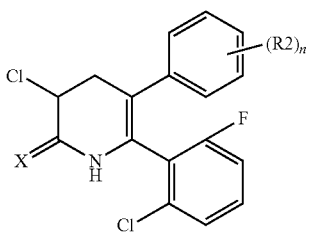 I-13
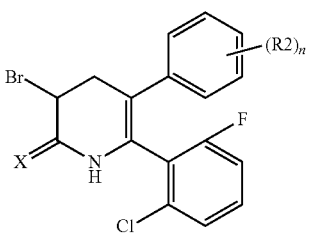 I-14
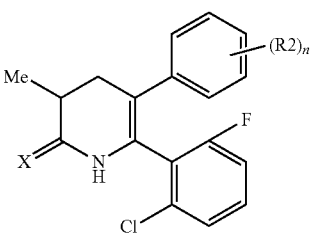 I-15
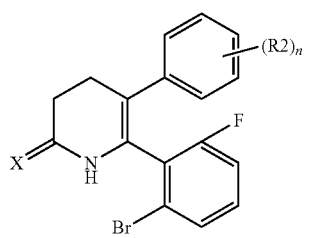 I-16
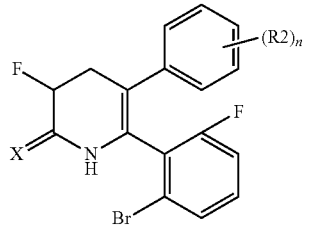 I-17

TABLE 3-continued
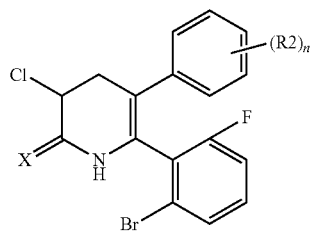 I-18
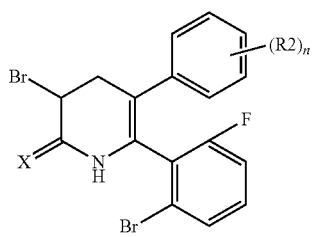 I-19
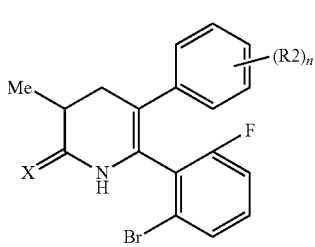 I-20
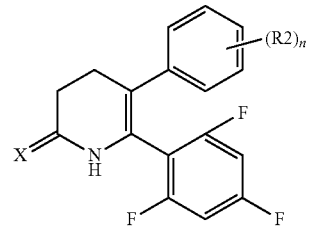 I-21
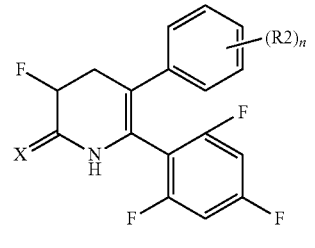 I-22
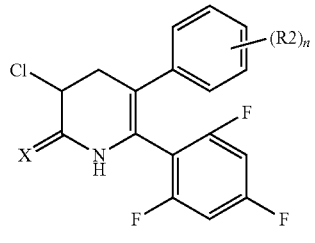 I-23
TABLE 3-continued
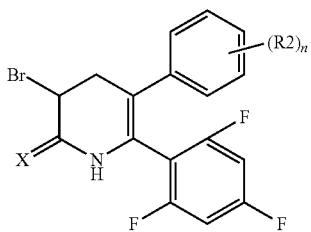 I-24
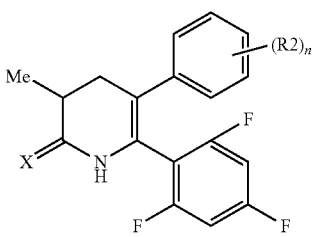 I-25
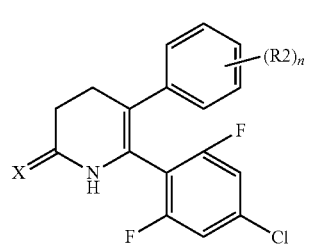 I-26
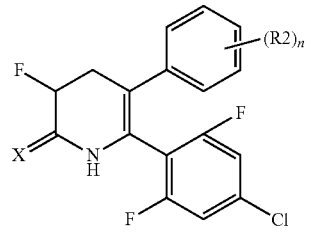 I-27
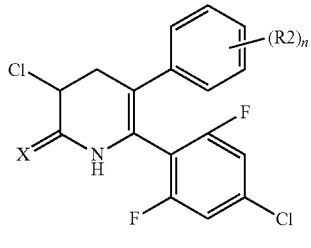 I-28
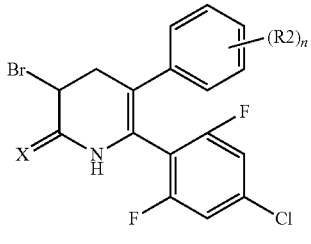 I-29

TABLE 3-continued
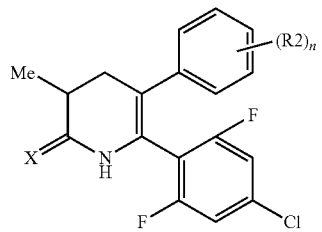 I-30
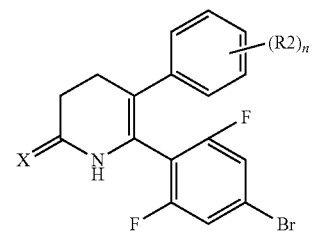 I-31
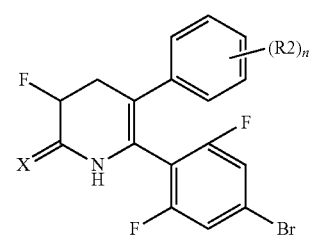 I-32
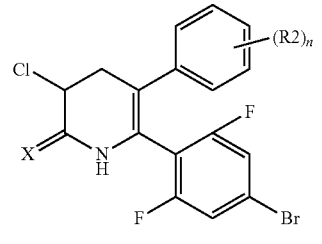 I-33
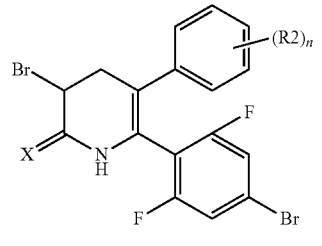 I-34
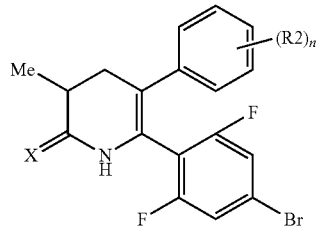 I-35
TABLE 3-continued
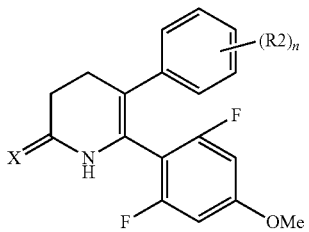 I-36
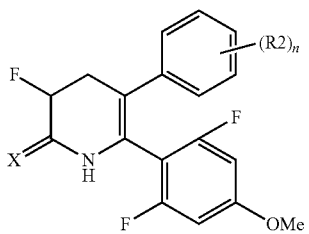 I-37
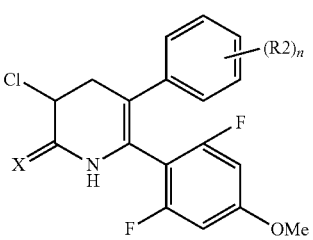 I-38
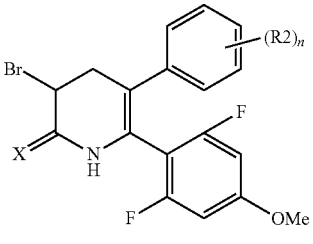 I-39
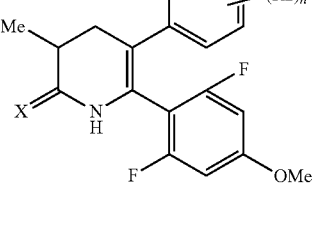 I-40
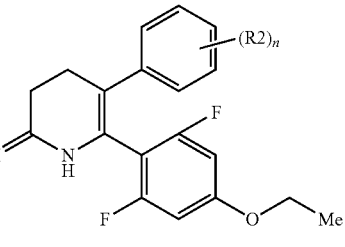 I-41

TABLE 3-continued
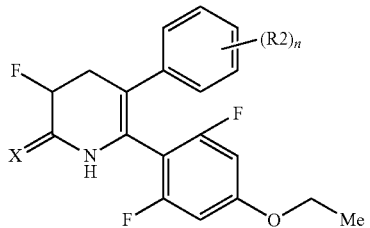 I-42
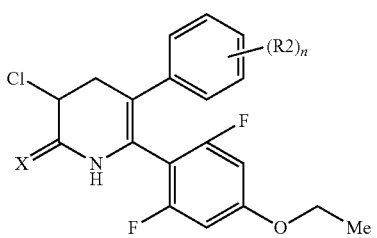 I-43
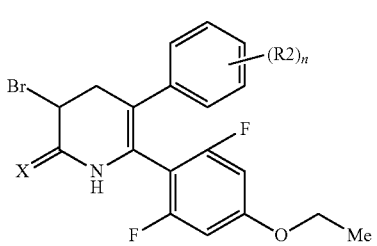 I-44
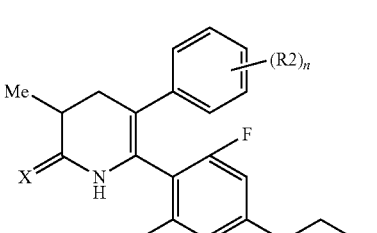 I-45
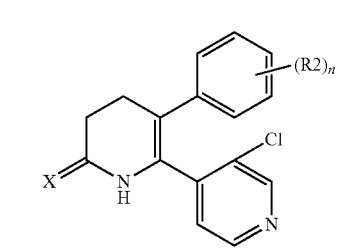 I-46
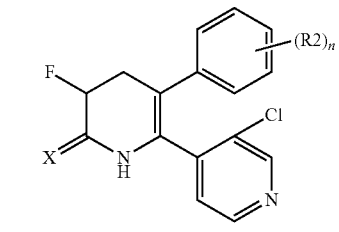 I-47
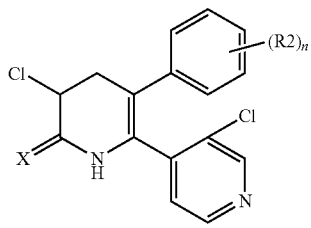 I-48
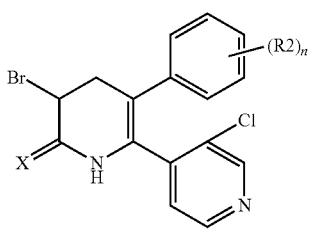 I-49
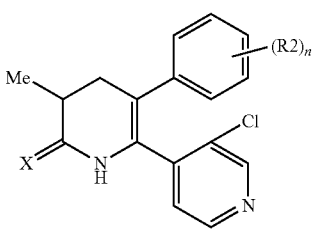 I-50
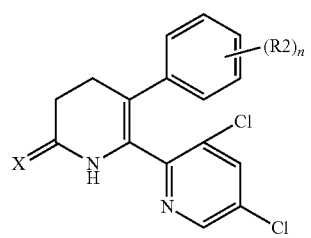 I-51
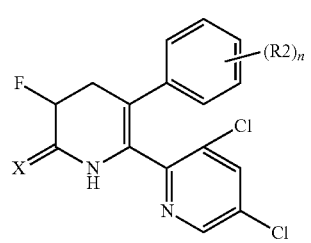 I-52
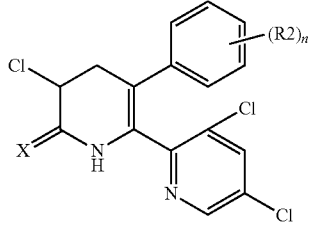 I-53

TABLE 3-continued
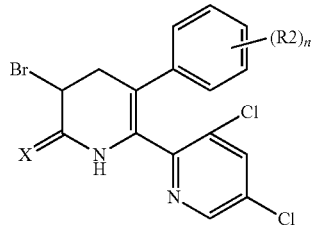 I-54
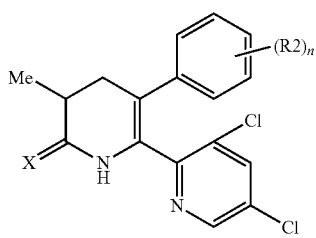 I-55
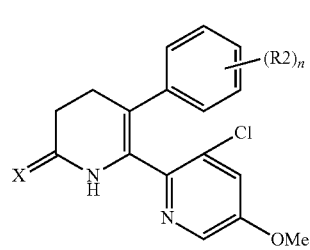 I-56
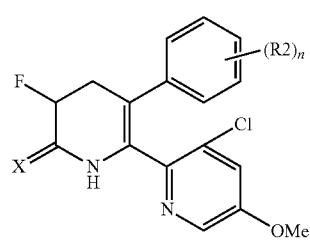 I-57
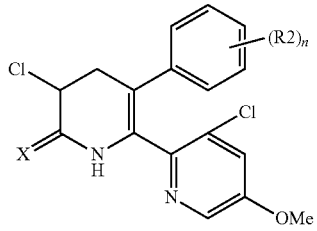 I-58
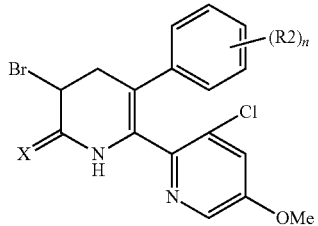 I-59
TABLE 3-continued
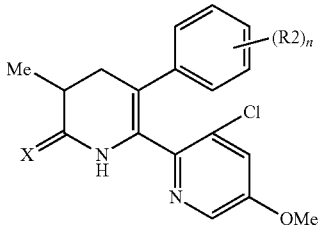 I-60
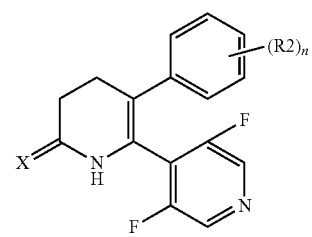 I-61
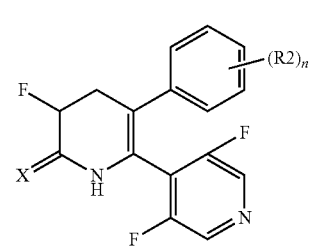 I-62
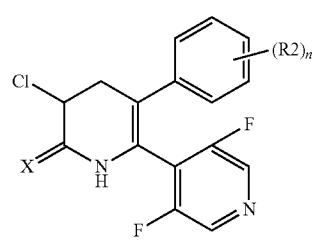 I-63
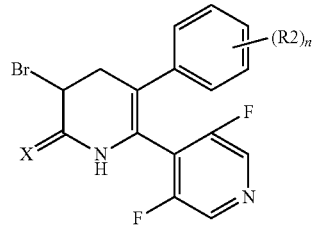 I-64
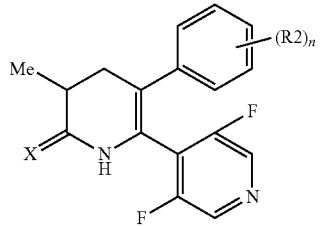 I-65

TABLE 3-continued
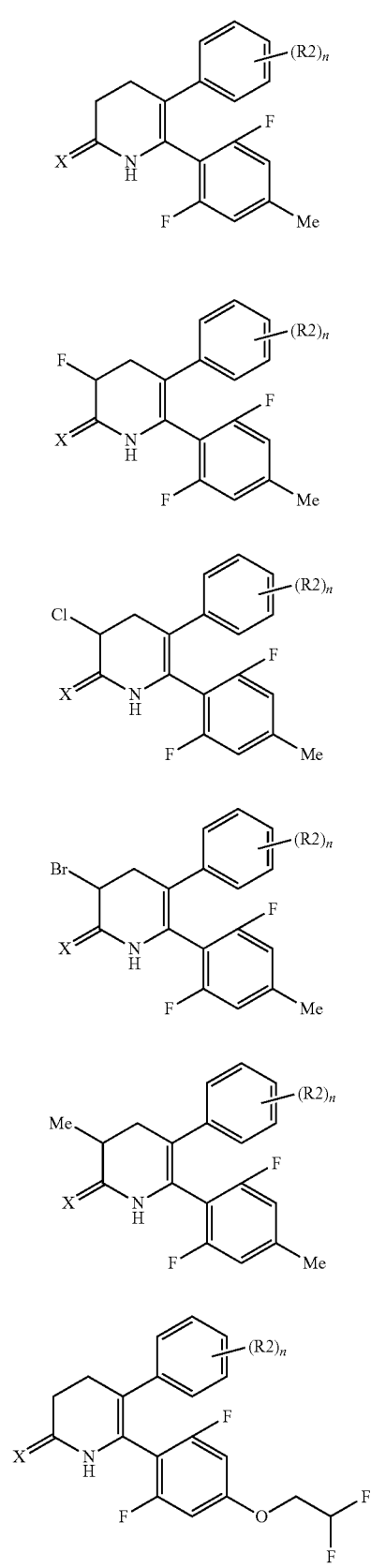
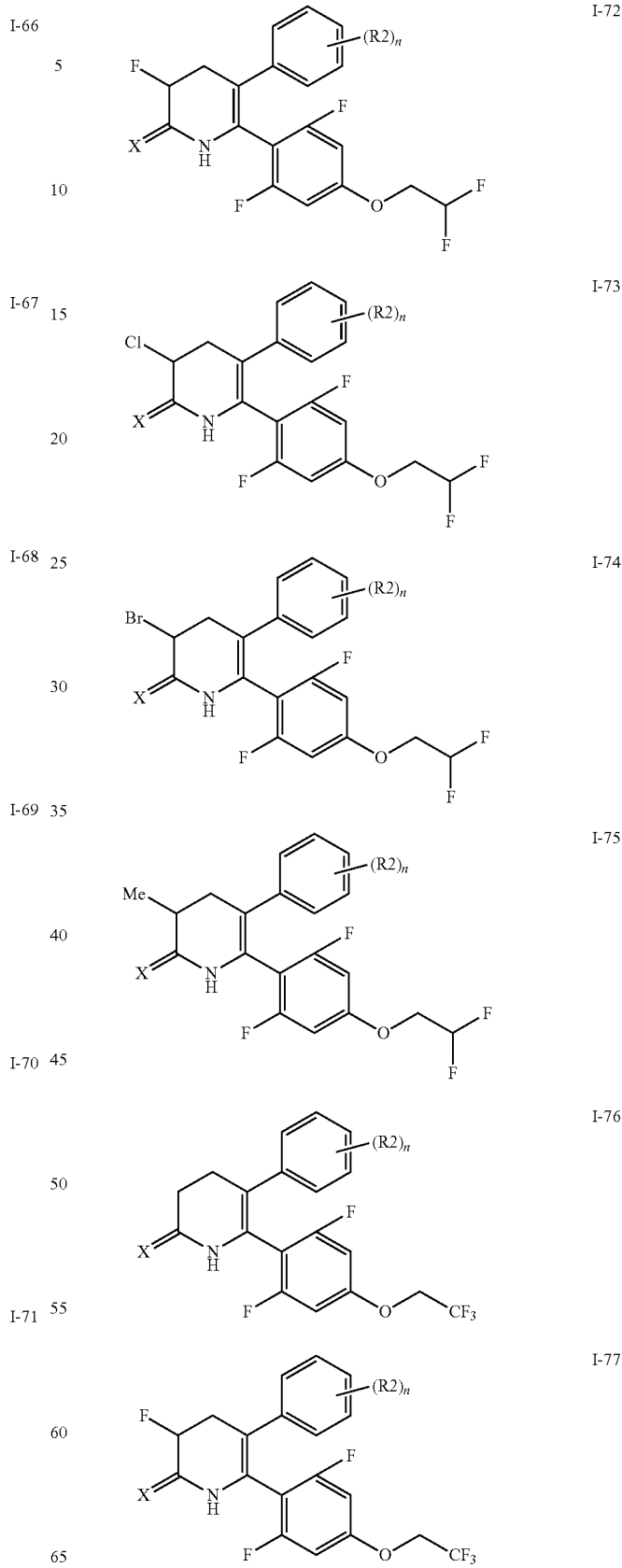

TABLE 3-continued
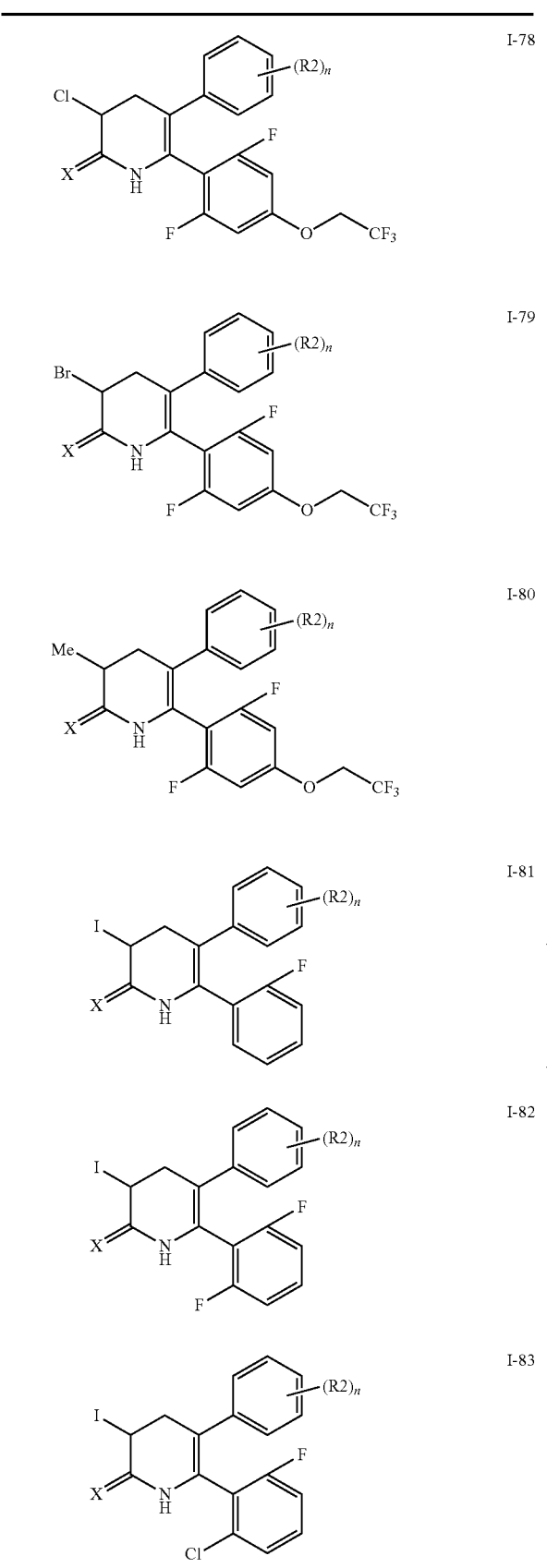
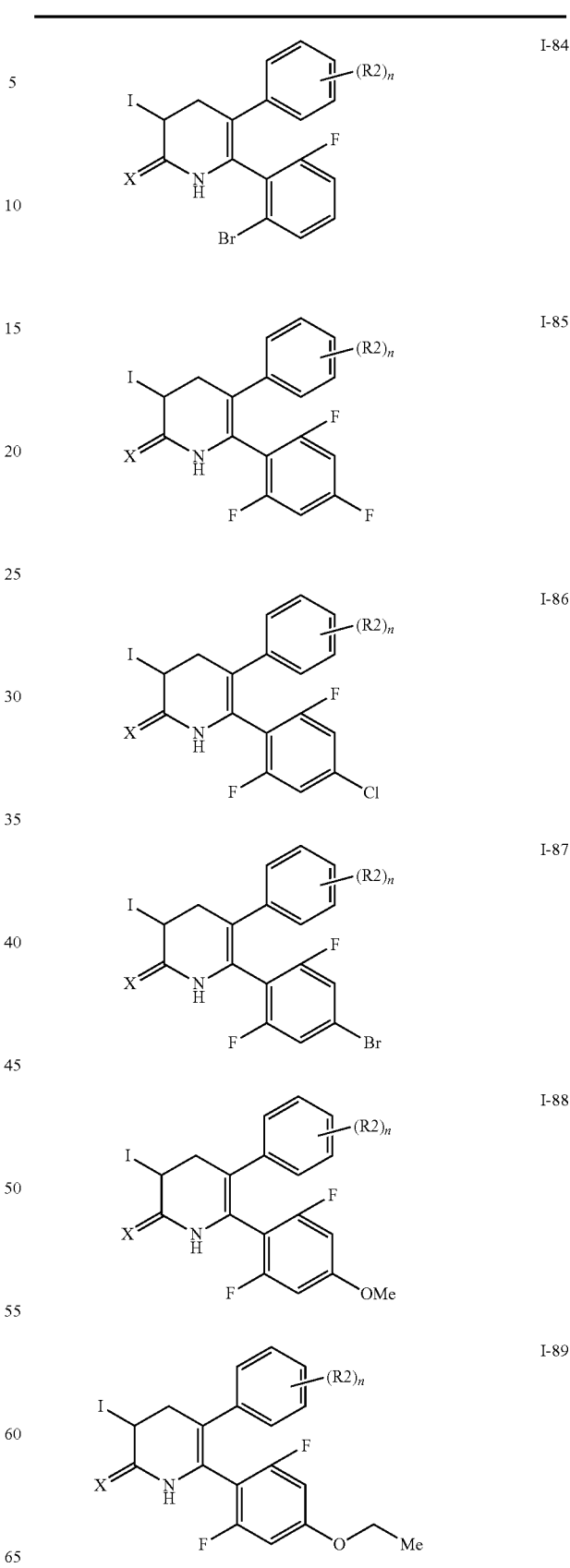

TABLE 3-continued

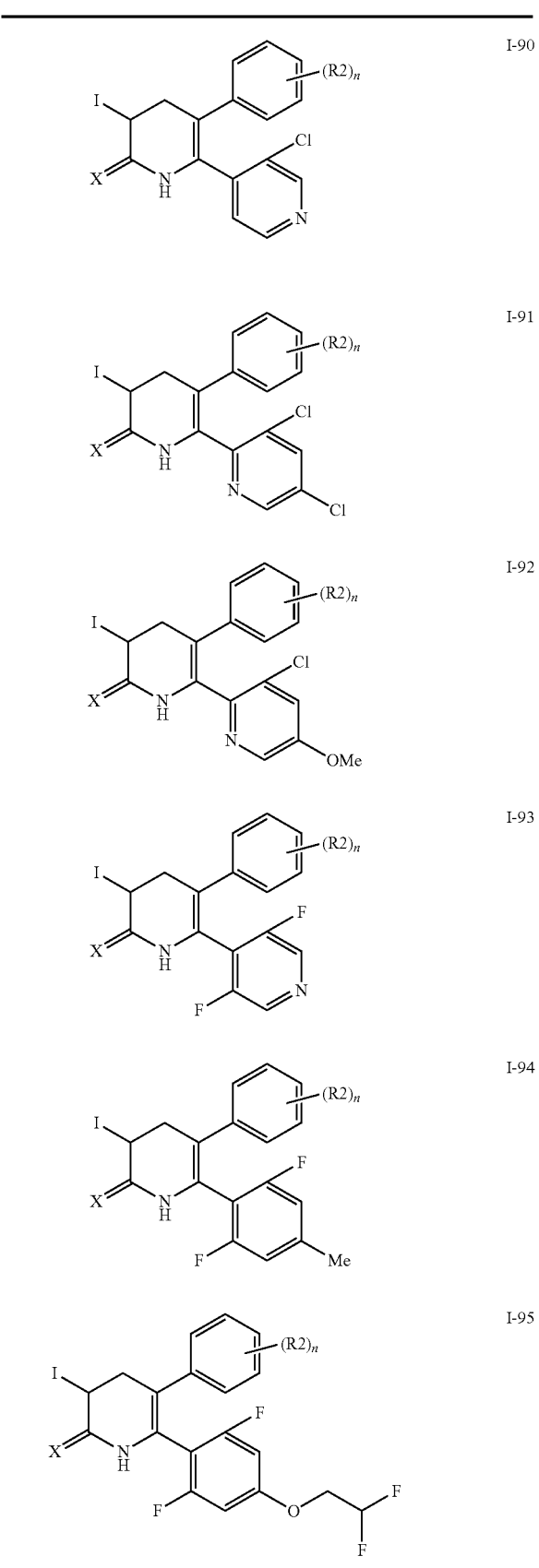

TABLE 3-continued

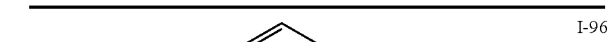
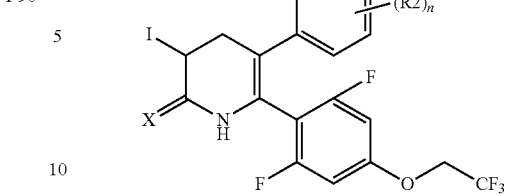

Illustrated below is a method for obtaining an inventive compound of Formula (1b) using a compound represented by Formula (2) as an intermediate.

[Production Method B]

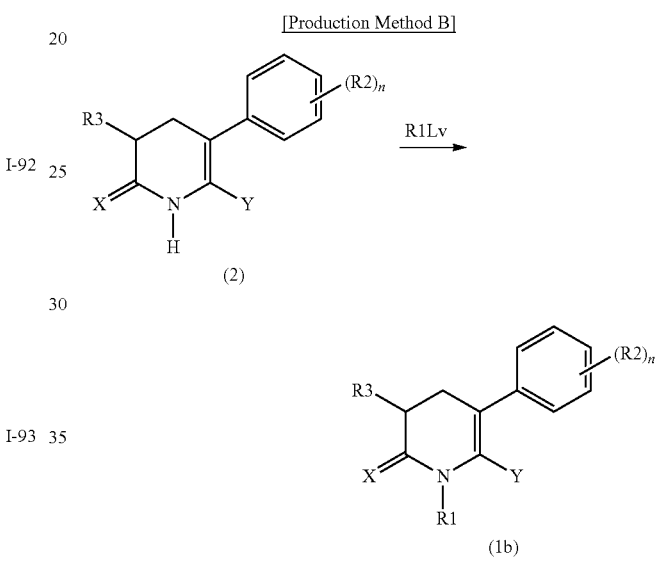

In the formula, Lv represents a leaving group such as a methanesulfonyl group, a trifluoromethanesulfonyl group, a p-toluenesulfonyl group or a halogen atom, and R1, R2, R3, X, Y and n are the same as defined hereinabove.

Production Method B produces a compound represented by Formula (1b). The production method includes reacting an intermediate represented by Formula (2) with R1Lv in a solvent in the presence of a base.

The R1Lv used in the reaction may be purchased from the market.

In the reaction, the R1Lv is used in at least 1 equivalent amount relative to the compound represented by Formula (2). The amount is not particularly limited as long as this equivalent amount is satisfied and also the target reaction takes place, but is preferably 1 equivalent amount to 10 equivalent amounts.

Examples of the bases used in the reaction include inorganic bases such as sodium hydroxide, potassium hydroxide, sodium carbonate, potassium carbonate, cesium carbonate and sodium hydride. The bases are not particularly limited thereto as long as the target reaction takes place.

In the reaction, the base is used in at least 1 equivalent amount relative to the compound represented by Formula (2). The amount is not particularly limited as long as this equivalent amount is satisfied and also the target reaction takes place, but is preferably 1 equivalent amount to 10 equivalent amounts.

The solvent used in the reaction is not particularly limited as long as the target reaction takes place. Examples include ether solvents such as diethyl ether, diisopropyl ether, methyl-t-butyl ether, dimethoxyethane, tetrahydrofuran and dioxane, alcohol solvents such as methanol, ethanol and isopropanol, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethylsulfoxide and sulfolane, ketone solvents such as acetone, methyl ethyl ketone and methyl isobutyl ketone, and the like. These solvents may be used singly, or two or more may be used in combination in any ratio.

The amount of the solvent used in the reaction is not particularly limited as long as the target reaction takes place, but is usually 3 to 200 times by weight the amount of the compound represented by Formula (2).

The temperature of the reaction is not particularly limited as long as the target reaction takes place, but is usually 0° C. to 150° C., or is below the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, aqueous solutions of sulfur-containing salts such as sodium thiosulfate and sodium sulfite, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. These solvents may be used singly, or two or more may be used in combination in any ratio. The liquid separation may be performed as many times as desired without limitation in accordance with the desired purity and yield.

The reaction mixture obtained above which includes the compound represented by Formula (1b) may be dehydrated with a desiccant such as sodium sulfate or magnesium sulfate, but this dehydration may be omitted.

The reaction mixture obtained above which includes the compound represented by Formula (1b) may be distilled to evaporate the solvent under reduced pressure as long as the compound is not decomposed.

The distilled reaction mixture which includes the compound represented by Formula (1b) may be purified in an appropriate solvent by a method such as washing, reprecipitation, recrystallization or column chromatography. The purification method may be selected appropriately in accordance with the desired purity.

[Production Method C]

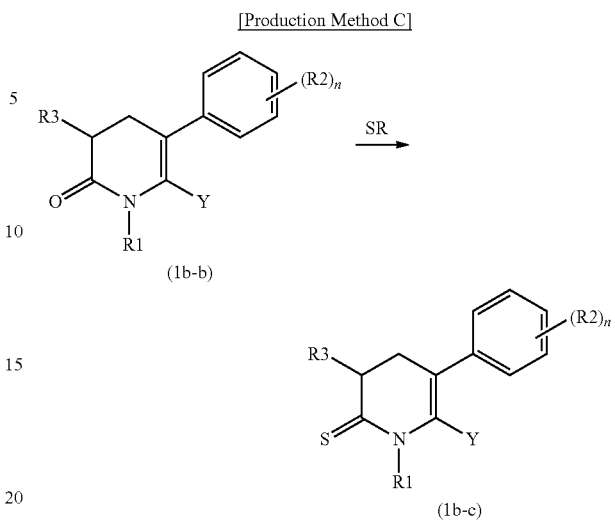

In the formula, SR represents a sulfidizing agent, and R1, R2, R3, Y and n are the same as defined hereinabove.

Production Method C produces a compound of Formula (1b-c) which belongs to the compounds represented by Formula (1b). The production method includes reacting a compound represented by Formula (1b-b) with a sulfidizing agent (SR) in a solvent.

An example of the sulfidizing agents used in the reaction is Lawesson's reagent (2,4-bis(4-methoxyphenyl)-1,3-dithia-2,4-diphosphetane-2,4-disulfide).

In the reaction, the sulfidizing agent is used in at least 0.5 equivalent amounts relative to the compound represented by Formula (1b-b). The amount is not particularly limited as long as this equivalent amount is satisfied and also the target reaction takes place, but is preferably 1 equivalent amount to 10 equivalent amounts.

The solvent used in the reaction is not particularly limited as long as the target reaction takes place. Examples include ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene, and the like. These solvents may be used singly, or two or more may be used in combination in any ratio.

The amount of the solvent used in the reaction is not particularly limited as long as the target reaction takes place, but is usually 3 to 200 times by weight the amount of the compound represented by Formula (1b-b).

The temperature of the reaction is not particularly limited as long as the target reaction takes place, but is usually 50° C. to 180° C., or is below the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. These solvents may be used singly, or two or more may be used in combination in any ratio. The liquid separation may be performed as many times as desired without limitation in accordance with the desired purity and yield. In the reaction, the liquid separation is not an absolute necessity.

The reaction mixture obtained above which includes the compound of Formula (1b-c) may be dehydrated with a desiccant such as sodium sulfate or magnesium sulfate, but this dehydration may be omitted.

The reaction mixture obtained above which includes the compound of Formula (1b-c) may be distilled to evaporate the solvent under reduced pressure as long as the compound is not decomposed.

The distilled reaction mixture which includes the compound of Formula (1b-c) may be purified with an appropriate solvent by a method such as washing, reprecipitation, recrystallization or column chromatography. The purification method may be selected appropriately in accordance with the desired purity.

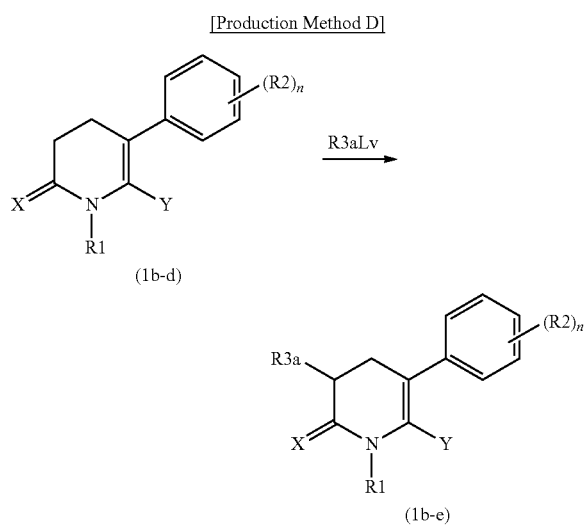

[Production Method D]

(1b-d)

(1b-e)

In the formula, R3a represents a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 haloalkenyl group, a C2-C6 alkynyl group optionally substituted with substituent C, or a C2-C6 haloalkynyl group, and Lv, R1, R2, X, Y and n are the same as defined hereinabove.

Production Method D produces a compound represented by Formula (1b-e), which belongs to the compounds represented by Formula (1b), wherein R3a represents a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 haloalkenyl group, a C2-C6 alkynyl group optionally substituted with substituent C, or a C2-C6 haloalkynyl group. The production method includes reacting a compound represented by Formula (1b-d) with R3aLv in a solvent in the presence of a base.

The R3aLv used in the reaction may be purchased from the market.

In the reaction, the R3aLv is used in at least 1 equivalent amount relative to the compound represented by Formula (1b-d). The amount is not particularly limited as long as this equivalent amount is satisfied and also the target reaction takes place, but is preferably 1 equivalent amount to 1.8 equivalent amounts.

Examples of the bases used in the reaction include metal hydrides such as sodium hydride, organolithiums such as methyllithium, butyllithium, sec-butyllithium, t-butyllithium and hexyllithium, and metal amides such as lithium diisopropylamide, hexamethyldisilazane lithium, hexamethyldisilazane sodium and hexamethyldisilazane potassium.

In the reaction, the base is used in at least 1 equivalent amount relative to the compound represented by Formula (1b-d). The amount is not particularly limited as long as this equivalent amount is satisfied and also the target reaction takes place, but is preferably 1 equivalent amount to 10 equivalent amounts.

The solvent used in the reaction is not particularly limited as long as the target reaction takes place. Examples include ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene, and the like. These solvents may be used singly, or two or more may be used in combination in any ratio.

The amount of the solvent used in the reaction is not particularly limited as long as the target reaction takes place, but is usually 3 to 200 times by weight the amount of the compound represented by Formula (1b-d).

The temperature of the reaction is not particularly limited as long as the target reaction takes place, but is usually −80° C. to 100° C., or is below the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, aqueous solutions of sulfur-containing salts such as sodium thiosulfate and sodium sulfite, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane and chloroform, hydrocarbon solvents such as hexane, heptane, cyclohexane and methylcyclohexane, and the like. These solvents may be used singly, or two or more may be used in combination in any ratio. The liquid separation may be performed as many times as desired without limitation in accordance with the desired purity and yield.

The reaction mixture obtained above which includes the compound of Formula (1b-e) may be dehydrated with a desiccant such as sodium sulfate or magnesium sulfate, but this dehydration may be omitted.

The reaction mixture obtained above which includes the compound of Formula (1b-e) may be distilled to evaporate the solvent under reduced pressure as long as the compound is not decomposed.

The distilled reaction mixture which includes the compound of Formula (1b-e) may be purified with an appropriate solvent by a method such as washing, reprecipitation, recrystallization or column chromatography. The purification method may be selected appropriately in accordance with the desired purity.

[Production Method E]

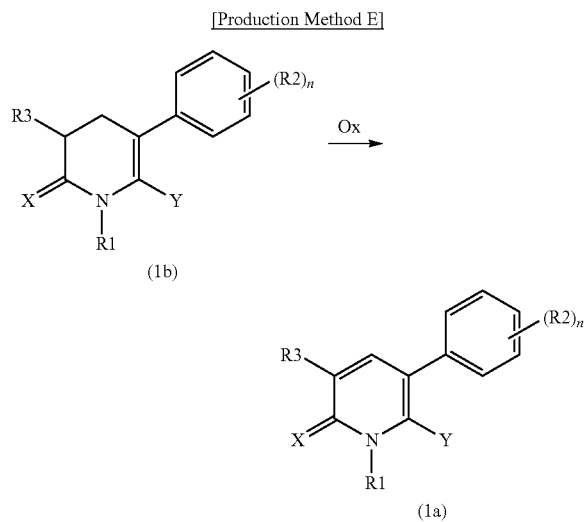

In the formula, Ox represents an oxidizer, and R1, R2, R3, X, Y and n are the same as defined hereinabove.

Production Method E produces a compound represented by Formula (1a). The production method includes reacting a compound represented by Formula (1b) with an oxidizer (Ox) in a solvent.

Examples of the oxidizers used in the reaction include metal oxides such as manganese dioxide, benzoquinones such as 2,3-dichloro-5,6-dicyano-p-benzoquinone, and combinations of radical initiators such as azobisisobutyronitrile and benzoyl peroxide with halogenating agents such as N-chlorosuccinimide, N-bromosuccinimide, N-iodosuccinimide, 1,3-dichloro-5,5-dimethylhydantoin, 1,3-dibromo-5,5-dimethylhydantoin and 1,3-diiodo-5,5-dimethylhydantoin.

Hereinbelow, the method will be described assuming that a metal oxide is used as the oxidizer.

In the reaction, the oxidizer is used in at least 1 equivalent amount relative to the compound represented by Formula (1b). The amount is not particularly limited as long as this equivalent amount is satisfied and also the target reaction takes place, but is usually 1 equivalent amount to 200 equivalent amounts.

The solvent used in the reaction is not particularly limited as long as the target reaction takes place. Examples include benzene based solvents such as benzene, toluene, xylene, mesitylene, chlorobenzene and dichlorobenzene, halogen solvents such as dichloromethane, dichloroethane, chloroform and carbon tetrachloride, and the like. These solvents may be used singly, or two or more may be used in combination in any ratio.

The amount of the solvent used in the reaction is not particularly limited as long as the target reaction takes place, but is usually 3 to 200 times by weight the amount of the compound represented by Formula (1b).

The temperature of the reaction is not particularly limited as long as the target reaction takes place, but is usually 0° C. to 150° C., or is below the boiling point of the solvent.

The reaction may be followed by a post treatment in which the undissolved metal is removed by filtration. Further, water or an appropriate aqueous solution may be added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. These solvents may be used singly, or two or more may be used in combination in any ratio. The liquid separation may be performed as many times as desired without limitation in accordance with the desired purity and yield. In the reaction, the liquid separation is not an absolute necessity.

The reaction mixture obtained above which includes the compound represented by Formula (1a) may be dehydrated with a desiccant such as sodium sulfate or magnesium sulfate, but this dehydration may be omitted.

The reaction mixture obtained above which includes the compound represented by Formula (1a) may be distilled to evaporate the solvent under reduced pressure as long as the compound is not decomposed.

The distilled reaction mixture which includes the compound of Formula (1a) may be purified in an appropriate solvent by a method such as washing, reprecipitation, recrystallization or column chromatography. The purification method may be selected appropriately in accordance with the desired purity.

Next, the method will be described assuming that one of benzoquinones is used as the oxidizer.

In the reaction, the oxidizer is used in at least 1 equivalent amount relative to the compound represented by Formula (1b). The amount is not particularly limited as long as this equivalent amount is satisfied and also the target reaction takes place, but is usually 1 equivalent amount to 20 equivalent amounts.

The solvent used in the reaction is not particularly limited as long as the target reaction takes place. Examples include benzene based solvents such as benzene, toluene, xylene, mesitylene, chlorobenzene and dichlorobenzene, halogen solvents such as dichloromethane, dichloroethane, chloroform and carbon tetrachloride, and the like. These solvents may be used singly, or two or more may be used in combination in any ratio.

The amount of the solvent used in the reaction is not particularly limited as long as the target reaction takes place, but is usually 3 to 200 times by weight the amount of the compound represented by Formula (1b).

The temperature of the reaction is not particularly limited as long as the target reaction takes place, but is usually 0° C. to 150° C., or is below the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. These solvents may be used singly, or two or more may be used in combination in any ratio. The liquid separation may be performed as many times as desired without limitation in accordance with the desired purity and yield. In the reaction, the liquid separation is not an absolute necessity.

The reaction mixture obtained above which includes the compound represented by Formula (1a) may be dehydrated with a desiccant such as sodium sulfate or magnesium sulfate, but this dehydration may be omitted.

The reaction mixture obtained above which includes the compound represented by Formula (1a) may be distilled to evaporate the solvent under reduced pressure as long as the compound is not decomposed.

The distilled reaction mixture which includes the compound represented by Formula (1a) may be purified in an appropriate solvent by a method such as washing, reprecipitation, recrystallization or column chromatography. The purification method may be selected appropriately in accordance with the desired purity.

Next, the method will be described assuming that a combination of a radical initiator and a halogenating agent is used as the oxidizer.

In the reaction, the radical initiator and the halogenating agent are used in at least 0.01 equivalent amounts and in at least 1.0 equivalent amount, respectively. Their amounts are not particularly limited as long as these equivalent amounts are satisfied and also the target reaction takes place, but preferably the radical initiator is used in 0.01 equivalent amount to 1 equivalent amount and the halogenating agent in 1 equivalent amount to 3 equivalent amounts.

The solvent used in the reaction is not particularly limited as long as the target reaction takes place. Examples include halogenated benzene based solvents such as chlorobenzene and dichlorobenzene, ester solvents such as ethyl acetate, isopropyl acetate and butyl acetate, halogen solvents such as dichloromethane, dichloroethane, chloroform and carbon tetrachloride, hydrocarbon solvents such as hexane, heptane, cyclohexane and methylcyclohexane, and the like. These solvents may be used singly, or two or more may be used in combination in any ratio.

The amount of the solvent used in the reaction is not particularly limited as long as the target reaction takes place, but is usually 3 to 200 times by weight the amount of the compound represented by Formula (1b).

The temperature of the reaction is not particularly limited as long as the target reaction takes place, but is usually 20° C. to 150° C., or is below the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, aqueous solutions of sulfur-containing salts such as sodium thiosulfate and sodium sulfite, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane and chloroform, hydrocarbon solvents such as hexane, heptane, cyclohexane and methylcyclohexane, and the like. These solvents may be used singly, or two or more may be used in combination in any ratio. The liquid separation may be performed as many times as desired without limitation in accordance with the desired purity and yield.

The reaction mixture obtained above which includes the compound represented by Formula (1a) may be dehydrated with a desiccant such as sodium sulfate or magnesium sulfate, but this dehydration may be omitted.

The reaction mixture obtained above which includes the compound represented by Formula (1a) may be distilled to evaporate the solvent under reduced pressure as long as the compound is not decomposed.

The distilled reaction mixture which includes the compound represented by Formula (1a) may be purified in an appropriate solvent by a method such as washing, reprecipitation, recrystallization or column chromatography. The purification method may be selected appropriately in accordance with the desired purity.

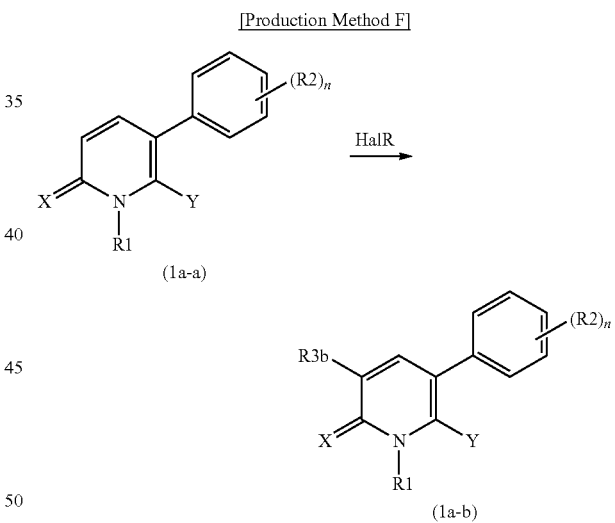

[Production Method F]

In the formula, R3b represents a halogen atom, HalR represents a halogenating agent, and R1, R2, X, Y and n are the same as defined hereinabove.

Production Method F produces a compound represented by Formula (1a-b), which belongs to the compounds represented by Formula (1a), wherein R3b is a halogen atom. The production method includes reacting a compound represented by Formula (1a-a) with a halogenating agent (HalR) in a solvent.

Examples of the halogenating agents used in the reaction include Selectfluor (N-fluoro-N'-triethylenediamine bis(tetrafluoroborate)), N-chlorosuccinimide, N-bromosuccinimide, N-iodosuccinimide, 1,3-dichloro-5,5-dimethylhydantoin, 1,3-dibromo-5,5-dimethylhydantoin, 1,3-diiodo-5,5-dimethylhydantoin, bromine, iodine and the like.

In the reaction, the halogenating agent is used in at least 1 equivalent amount relative to the compound represented by Formula (1a-a). The amount is not particularly limited as long as this equivalent amount is satisfied and also the target reaction takes place, but is preferably 1 equivalent amount to 10 equivalent amounts. Those halogenating agents containing hydantoin may be used in at least 0.5 equivalent amounts, and their amount is not particularly limited as long as this equivalent amount is satisfied and also the target reaction takes place, but is preferably 1 equivalent amount to 5 equivalent amounts.

When the halogenating agent is an iodinating agent, the reaction may involve an acid, for example, an inorganic acid such as hydrochloric acid or sulfuric acid, or an organic acid such as acetic acid, trifluoroacetic acid, methanesulfonic acid or trifluoromethanesulfonic acid.

Such an acid, which is added when the halogenating agent used in the reaction is an iodinating agent, is used in at least 0.01 equivalent amount relative to the compound represented by Formula (1a-a). The amount is not particularly limited as long as this equivalent amount is satisfied and also the target reaction takes place, but is preferably 0.1 equivalent amount to 3 equivalent amounts.

The solvent used in the reaction is not particularly limited as long as the target reaction takes place. Examples include acidic solvents such as sulfuric acid, acetic acid, trifluoroacetic acid, methanesulfonic acid and trifluoromethanesulfonic acid, ether solvents such as diethyl ether, diisopropyl ether, methyl-t-butyl ether, dimethoxyethane, tetrahydrofuran and dioxane, alcohol solvents such as methanol, ethanol and isopropanol, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, and the like. These solvents may be used singly, or two or more may be used in combination in any ratio.

The amount of the solvent used in the reaction is not particularly limited as long as the target reaction takes place, but is usually 3 to 200 times by weight the amount of the compound represented by Formula (1a-a).

The temperature of the reaction is not particularly limited as long as the target reaction takes place, but is usually 0° C. to 150° C., or is below the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, aqueous solutions of sulfur-containing salts such as sodium thiosulfate and sodium sulfite, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. These solvents may be used singly, or two or more may be used in combination in any ratio. The liquid separation may be performed as many times as desired without limitation in accordance with the desired purity and yield.

The reaction mixture obtained above which includes the compound of Formula (1a-b) may be dehydrated with a desiccant such as sodium sulfate or magnesium sulfate, but this dehydration may be omitted.

The reaction mixture obtained above which includes the compound of Formula (1a-b) may be distilled to evaporate the solvent under reduced pressure as long as the compound is not decomposed.

The distilled reaction mixture which includes the compound of Formula (1a-b) may be purified with an appropriate solvent by a method such as washing, reprecipitation, recrystallization or column chromatography. The purification method may be selected appropriately in accordance with the desired purity.

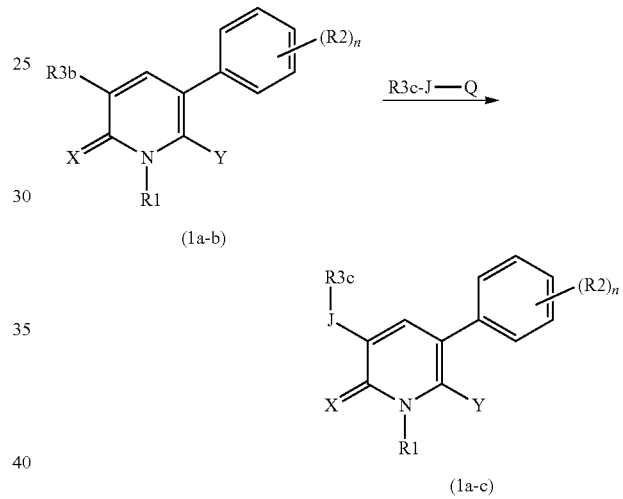

[Production Method G]

In the formula, R3c represents a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 haloalkenyl group, a C2-C6 alkynyl group optionally substituted with substituent C or a C2-C6 haloalkynyl group, J represents an oxygen atom or a sulfur atom, Q represents a hydrogen atom or a metal, and R1, R2, R3b, X, Y and n are the same as defined hereinabove.

Production Method G produces a compound represented by Formula (1a-c), which belongs to the compounds represented by Formula (1a), wherein R3c represents a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C, a C2-C6 haloalkenyl group, a C2-C6 alkynyl group optionally substituted with substituent C or a C2-C6 haloalkynyl group, and wherein J represents an oxygen atom or a sulfur atom. The production method includes obtaining the compound by coupling reaction that reacts a compound represented by Formula (1a-b) with R3c-J-Q in the presence of a transition metal.

In the compound represented by Formula (1a-b), R3b is preferably a chlorine atom, a bromine atom or an iodine atom.

The R3c-J-Q used in the reaction may be purchased from the market. Preferably, Q is a hydrogen atom or an alkali metal such as sodium or potassium.

In the reaction, the R3c-J-Q is used in at least 1 equivalent amount relative to the compound represented by Formula (1a-b). The amount is not particularly limited as long as this equivalent amount is satisfied and also the target reaction takes place. When Q is a hydrogen atom, the reagent may be used also as a solvent.

The transition metal used in the reaction may have a ligand. Examples of such metals include palladium materials such as palladium acetate, [1,1'-bis(diphenylphosphino)ferrocene]palladium dichloride, tris(dibenzylideneacetone)dipalladium, tetrakis(triphenylphosphine)palladium and bis(triphenylphosphine)palladium dichloride.

In the reaction, the transition metal is used in 0.001 equivalent amount to 1 equivalent amount relative to the compound represented by Formula (1a-b), but the amount is not particularly limited as long as the target reaction takes place.

To allow the reaction to proceed efficiently, a phosphine ligand may be added, with examples including triphenylphosphine, 1,1'-bis(diphenylphosphino)ferrocene, 2-dicyclohexylphosphino-2'4'6'-triisopropylbiphenyl, 2-di-t-butylphosphino-2'4'6'-triisopropylbiphenyl and the like.

In the reaction, the phosphine ligand is used in 0.001 equivalent amounts to 1 equivalent amount relative to the compound represented by Formula (1a-b), but the amount is not particularly limited as long as the target reaction takes place.

Examples of the bases used in the reaction include inorganic bases such as sodium carbonate, potassium carbonate and cesium carbonate, and organic bases such as triethylamine, tributylamine and diisopropylethylamine.

In the reaction, the base is used in at least 1 equivalent amount relative to the compound represented by Formula (1a-b). The amount is not particularly limited as long as this equivalent amount is satisfied and also the target reaction takes place, but is preferably 1 equivalent amount to 50 equivalent amounts.

The solvent used in the reaction is not particularly limited as long as the target reaction takes place. Examples include alcohol solvents represented by R3c-J-H (wherein R3c and J are the same as defined hereinabove), ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene, and the like. These solvents may be used singly, or two or more may be used in combination in any ratio.

The amount of the solvent used in the reaction is not particularly limited as long as the target reaction takes place, but is usually 3 to 200 times by weight the amount of the compound represented by Formula (1a-b).

The temperature of the reaction is not particularly limited as long as the target reaction takes place, but is usually 30° C. to 200° C., or is below the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. These solvents may be used singly, or two or more may be used in combination in any ratio. The liquid separation may be performed as many times as desired without limitation in accordance with the desired purity and yield. Insolubles may be removed by filtration, which however is not an absolute necessity.

The reaction mixture obtained above which includes the compound of Formula (1a-c) may be distilled to evaporate the solvent under reduced pressure as long as the compound is not decomposed.

The distilled reaction mixture which includes the compound of Formula (1a-c) may be purified with an appropriate solvent by a method such as washing, reprecipitation, recrystallization or column chromatography. The purification method may be selected appropriately in accordance with the desired purity.

[Production Method H]

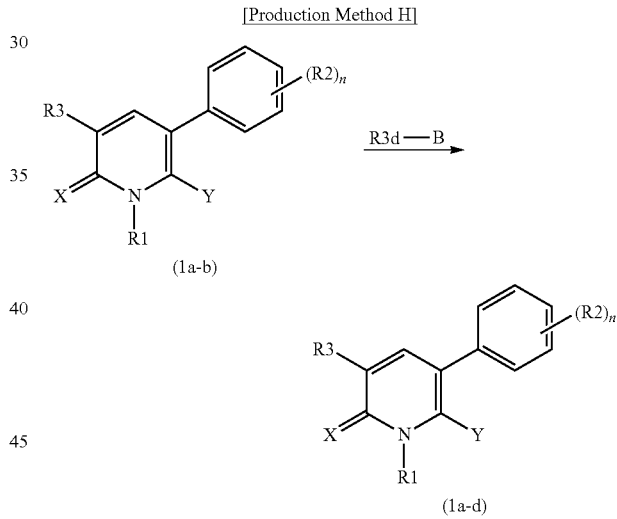

In the formula, R3d represents a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C or a C2-C6 haloalkenyl group, R3d-B represents an organoboronic acid, and R1, R2, R3b, X, Y and n are the same as defined hereinabove.

Production Method H produces a compound represented by Formula (1a-d), which belongs to the compounds represented by Formula (1a), wherein R3d is a C1-C6 alkyl group optionally substituted with substituent C, a C1-C6 haloalkyl group, a C3-C8 cycloalkyl group optionally substituted with substituent C, a C2-C6 alkenyl group optionally substituted with substituent C or a C2-C6 haloalkenyl group. The production method includes obtaining the compound by the Suzuki-Miyaura coupling that reacts a compound represented by Formula (1a-b) with an organoboronic acid (R3d-B).

In Formula (1a-b), R3b is preferably a chlorine atom, a bromine atom or an iodine atom.

The R3d-B used in the reaction indicates an organoboronic acid such as an organoboronic acid or an organoboronate ester, and may be purchased from the market.

In the reaction, the R3d-B is used in at least 1 equivalent amount relative to the compound represented by Formula (1a-b). The amount is not particularly limited as long as this equivalent weight is satisfied and also the target reaction takes place, but is preferably 1 equivalent amount to 10 equivalent amounts.

The transition metal used in the reaction is, among others, palladium, nickel or ruthenium, and may have a ligand. Palladium materials are preferable, with examples including palladium acetate, [1,1'-bis(diphenylphosphino)ferrocene] palladium dichloride, tris(dibenzylideneacetone)dipalladium, tetrakis(triphenylphosphine)palladium, bis(triphenylphosphine)palladium dichloride and the like.

In the reaction, the transition metal is used in 0.001 equivalent amount to 1 equivalent amount relative to the compound represented by Formula (1a-b), but the amount is not particularly limited as long as the target reaction takes place.

To allow the reaction to proceed efficiently, a phosphine ligand such as triphenylphosphine or tricyclohexylphosphine may be added.

In the reaction, the phosphine ligand is used in 0.001 equivalent amount to 1 equivalent amount relative to the compound represented by Formula (1a-b), but the amount is not particularly limited as long as the target reaction takes place.

Examples of the bases used in the reaction include inorganic bases such as sodium carbonate, potassium carbonate, cesium carbonate and tripotassium phosphate, metal alkoxides such as sodium methoxide, sodium ethoxide and potassium t-butoxide, and the like.

In the reaction, the base is used in at least 1 equivalent amount relative to the compound represented by Formula (1a-b). The amount is not particularly limited as long as this equivalent amount is satisfied and also the target reaction takes place, and is preferably 1 equivalent amount to 50 equivalent amounts.

The solvent used in the reaction is not particularly limited as long as the target reaction takes place. Examples include aqueous solvents, ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene, and the like. These solvents may be used singly, or two or more may be used in combination in any ratio.

The amount of the solvent used in the reaction is not particularly limited as long as the target reaction takes place, but is usually 3 to 200 times by weight the amount of the compound represented by Formula (1a-b).

The temperature of the reaction is not particularly limited as long as the target reaction takes place, but is usually 30° C. to 200° C., or is below the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. These solvents may be used singly, or two or more may be used in combination in any ratio. The liquid separation may be performed as many times as desired without limitation in accordance with the desired purity and yield. Insolubles may be removed by filtration, which however is not an absolute necessity.

The reaction mixture obtained above which includes the compound of Formula (1a-d) may be distilled to evaporate the solvent under reduced pressure as long as the compound is not decomposed.

The distilled reaction mixture which includes the compound of Formula (1a-d) may be purified with an appropriate solvent by a method such as washing, reprecipitation, recrystallization or column chromatography. The purification method may be selected appropriately in accordance with the desired purity.

[Production Method I]

In the formula, R3e represents a C2-C6 alkynyl group optionally substituted with substituent C or a C2-C6 haloalkynyl group, and R1, R2, R3b, X, Y and n are the same as defined hereinabove.

Production Method I produces a compound represented by Formula (1a-e), which belongs to the compounds represented by Formula (1a), wherein R3e is a C2-C6 alkynyl group optionally substituted with substituent C or a C2-C6 haloalkynyl group. The production method includes obtaining the compound by the Sonogashira coupling that reacts a compound represented by Formula (1a-b) with an alkyne-terminated compound.

In Formula (1a-b), R3b is preferably a chlorine atom, a bromine atom or an iodine atom.

The alkyne-terminated compound used in the reaction may be purchased from the market. Alternatively, trimethylsilylacetylene may be used as the alkyne-terminated compound. In this case, desilylation needs to be performed after the introduction of the trimethylsilylethynyl group into the compound represented by Formula (1a-b). The desilylation may be carried out with reference to non-patent literature such as Journal of the American Chemical Society, Vol. 131, No. 2, pp. 634-643 (2009) and Journal of Organometallic Chemistry, vol. 696, No. 25, pp 4039-4045 (2011).

In the reaction, the alkyne-terminated compound is used in at least 1 equivalent amount relative to the compound represented by Formula (1a-b). The amount is not particularly limited as long as this equivalent amount is satisfied and also the target reaction takes place, but is preferably 1 equivalent amount to 10 equivalent amounts.

The transition metal used in the reaction may have a ligand. An example of such materials is palladium materials such as palladium acetate, [1,1'-bis(diphenylphosphino)ferrocene]palladium dichloride, tris(dibenzylideneacetone)dipalladium, tetrakis(triphenylphosphine)palladium and bis(triphenylphosphine)palladium dichloride. Further, a copper material such as copper chloride, copper bromide or copper iodide is used at the same time.

In the reaction, the transition metals are used in such amounts that the amounts of the palladium material and the copper material are each at least 0.001 equivalent amount relative to the compound represented by Formula (1a-b). These amounts are not particularly limited as long as the above equivalent amounts are satisfied and also the target reaction takes place, but are preferably each 0.001 equivalent amounts to 1 equivalent amount.

Examples of the bases used in the reaction include organic amines such as triethylamine, tributylamine, isopropylamine, diethylamine, diisopropylamine and diisopropylethylamine, and inorganic bases such as sodium carbonate, potassium carbonate and cesium carbonate.

In the reaction, the base is used in at least 1 equivalent amount relative to the compound represented by Formula (1a-b). The amount is not particularly limited as long as this equivalent amount is satisfied and also the target reaction takes place, but is preferably 1 equivalent amount to 50 equivalent amounts. Those organic bases which are liquid may be used also as solvents.

To allow the reaction to proceed efficiently, a phosphine ligand such as tri-t-butylphosphine or 2-dicyclohexylphosphino-2'4'6'-triisopropylbiphenyl may be added. This addition, however, is not an absolute necessity.

In the reaction, the phosphine ligand is used in 0.001 equivalent amount to 1 equivalent amount relative to the compound represented by Formula (1a-b), but the amount is not particularly limited as long as this equivalent amount is satisfied and also the target reaction takes place.

The solvent used in the reaction is not particularly limited as long as the target reaction takes place. Examples include ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, organic amine solvents such as triethylamine, tributylamine, isopropylamine, diethylamine, diisopropylamine and diisopropylethylamine, and the like. These solvents may be used singly, or two or more may be used in combination in any ratio.

The amount of the solvent used in the reaction is not particularly limited as long as the target reaction takes place, but is usually 3 to 200 times by weight the amount of the compound represented by Formula (1a-b).

The temperature of the reaction is not particularly limited as long as the target reaction takes place, but is usually 0° C. to 150° C., or is below the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. These solvents may be used singly, or two or more may be used in combination in any ratio. The liquid separation may be performed as many times as desired without limitation in accordance with the desired purity and yield. Insolubles may be removed by filtration, which however is not an absolute necessity.

The reaction mixture obtained above which includes the compound of Formula (1a-e) may be distilled to evaporate the solvent under reduced pressure as long as the compound is not decomposed.

The distilled reaction mixture which includes the compound of Formula (1a-e) may be purified with an appropriate solvent by a method such as washing, reprecipitation, recrystallization or column chromatography. The purification method may be selected appropriately in accordance with the desired purity.

[Production Method J]

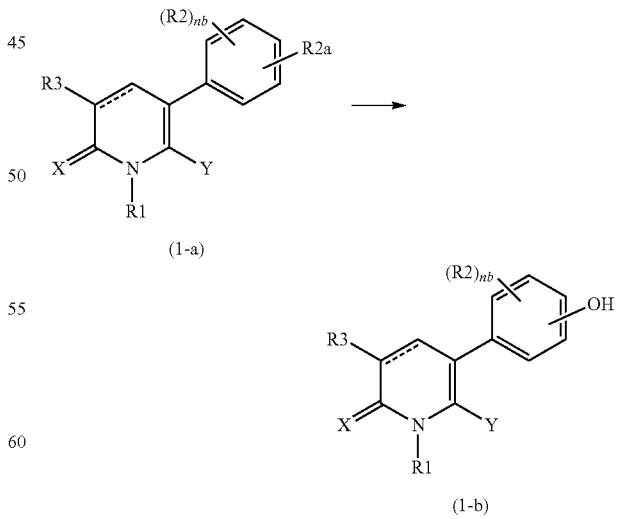

In the formula, R2a represents a C1-C6 alkoxy group, nb represents an integer of 0 to 4 (with the proviso that when nb is 2 or greater, the two or more R2's represent independent substituents), and R1, R2, R3, X, Y and the broken line are the same as defined hereinabove.

Production Method J produces a hydroxy group-containing compound represented by Formula (1-b), which belongs to the compounds represented by Formula (1). The production method includes reacting a compound of Formula (1-a) in which R2a is a C1-C6 alkoxy group with an acid.

Examples of the acids used in the reaction include boron halides such as boron trichloride and boron tribromide.

In the reaction, the acid is used in at least 1 equivalent amount relative to the compound represented by Formula (1-a). The amount is not particularly limited as long as the target reaction takes place, but is preferably 1 equivalent amount to 10 equivalent amounts.

The solvent used in the reaction is not particularly limited as long as the target reaction takes place. Examples include benzene based solvents such as benzene, toluene, xylene, mesitylene, chlorobenzene and dichlorobenzene, nitrile solvents such as acetonitrile, halogen solvents such as dichloromethane, dichloroethane, chloroform and carbon tetrachloride, hydrocarbon solvents such as hexane, heptane, cyclohexane and methylcyclohexane, and the like. These solvents may be used singly, or two or more may be used in combination in any ratio.

The amount of the solvent used in the reaction is not particularly limited as long as the target reaction takes place, but is usually 3 to 200 times by weight the amount of the compound represented by Formula (1-a).

The temperature of the reaction is not particularly limited as long as the target reaction takes place, but is usually −80° C. to 100° C., or is below the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. These solvents may be used singly, or two or more may be used in combination in any ratio. The liquid separation may be performed as many times as desired without limitation in accordance with the desired purity and yield.

The reaction mixture obtained above which includes the compound represented by Formula (1-b) may be dehydrated with a desiccant such as sodium sulfate or magnesium sulfate, but this dehydration may be omitted.

The reaction mixture obtained above which includes the compound represented by Formula (1-b) may be distilled to evaporate the solvent under reduced pressure as long as the compound is not decomposed.

The distilled reaction mixture which includes the compound represented by Formula (1-b) may be purified with an appropriate solvent by a method such as washing, reprecipitation, recrystallization or column chromatography. The purification method may be selected appropriately in accordance with the desired purity.

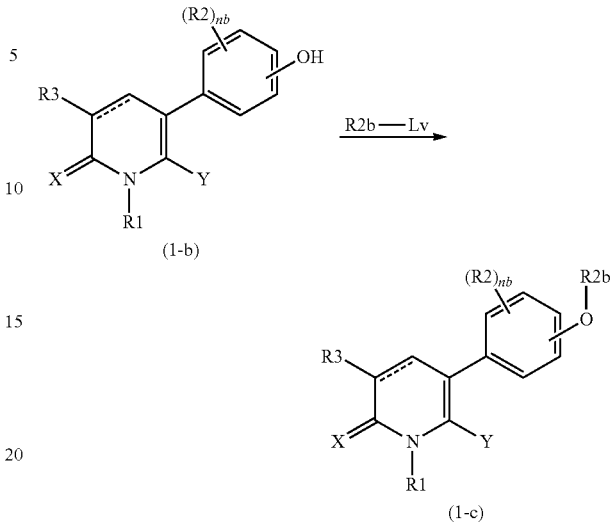

[Production Method K]

In the formula, R2b-O— represents a C1-C6 alkoxy group optionally substituted with substituent B, a C1-C6 haloalkoxy group, a C3-C8 cycloalkoxy group optionally substituted with substituent B, a C2-C6 alkenyloxy group optionally substituted with substituent B, a C2-C6 haloalkenyloxy group, a C3-C6 alkynyloxy group optionally substituted with substituent B, a C3-C6 haloalkynyloxy group or an R20C(=O)O— group, and Lv, R1, R2, R3, R20, X, Y, nb and the broken line are the same as defined hereinabove.

Production Method K produces a compound represented by Formula (1-c), which belongs to the compounds represented by Formula (1), wherein R2b-O— is a C1-C6 alkoxy group optionally substituted with substituent B, a C1-C6 haloalkoxy group, a C3-C8 cycloalkoxy group optionally substituted with substituent B, a C2-C6 alkenyloxy group optionally substituted with substituent B, a C2-C6 haloalkenyloxy group, a C3-C6 alkynyloxy group optionally substituted with substituent B, a C3-C6 haloalkynyloxy group or an R20C(=O)O— group (R20 is the same as defined hereinabove). The production method includes reacting a compound represented by Formula (1-b) with R2b-Lv in a solvent in the presence of a base.

The R2b-Lv used in the reaction may be purchased from the market.

In the reaction, the R2b-Lv is used in at least 1 equivalent amount relative to the compound represented by Formula (1-b). The amount is not particularly limited as long as this equivalent weight is satisfied and also the target reaction takes place, but is preferably 1 equivalent amount to 10 equivalent amounts.

Examples of the bases used in the reaction include inorganic bases such as sodium carbonate, potassium carbonate, cesium carbonate and sodium hydride, and organic bases such as triethylamine, tributylamine, diisopropylethylamine, pyridine, 4-dimethylaminopyridine, collidine and lutidine. The bases are not particularly limited as long as the target reaction takes place.

In the reaction, the base is used in at least 1 equivalent amount relative to the compound represented by Formula (1-b). The amount is not particularly limited as long as this equivalent amount is satisfied and also the target reaction takes place, but is preferably 1 equivalent amount to 10 equivalent amounts.

The solvent used in the reaction is not particularly limited as long as the target reaction takes place. Examples include ether solvents such as diethyl ether, diisopropyl ether, methyl-t-butyl ether, dimethoxyethane, tetrahydrofuran and dioxane, alcohol solvents such as methanol, ethanol and isopropanol, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethylsulfoxide and sulfolane, ketone solvents such as acetone, methyl ethyl ketone and methyl isobutyl ketone, and the like. These solvents may be used singly, or two or more may be used in combination in any ratio.

The amount of the solvent used in the reaction is not particularly limited as long as the target reaction takes place, but is usually 3 to 200 times by weight the amount of the compound represented by Formula (1-b).

The temperature of the reaction is not particularly limited as long as the target reaction takes place, but is usually −20° C. to 150° C., or is below the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, aqueous solutions of sulfur-containing salts such as sodium thiosulfate and sodium sulfite, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. These solvents may be used singly, or two or more may be used in combination in any ratio. The liquid separation may be performed as many times as desired without limitation in accordance with the desired purity and yield.

The reaction mixture obtained above which includes the compound represented by Formula (1-c) may be dehydrated with a desiccant such as sodium sulfate or magnesium sulfate, but this dehydration may be omitted.

The reaction mixture obtained above which includes the compound represented by Formula (1-c) may be distilled to evaporate the solvent under reduced pressure as long as the compound is not decomposed.

The distilled reaction mixture which includes the compound represented by Formula (1-c) may be purified with an appropriate solvent by a method such as washing, reprecipitation, recrystallization or column chromatography. The purification method may be selected appropriately in accordance with the desired purity.

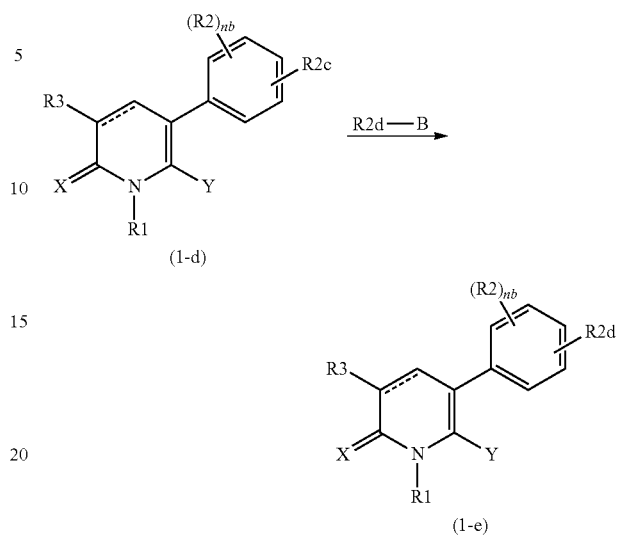

In the formula, R2c represents a halogen atom, R2d is a C1-C6 alkyl group optionally substituted with substituent B, a C1-C6 haloalkyl group, a C3-C8 cycloalkyl group optionally substituted with substituent B, a C2-C6 alkenyl group optionally substituted with substituent B or a C2-C6 haloalkenyl group, R2d-B is an organoboronic acid, and R1, R2, R3, nb, X, Y and the broken line are the same as defined hereinabove.

Production Method L produces a compound represented by Formula (1-e), which belongs to the compounds represented by Formula (1), wherein R2d is a C1-C6 alkyl group optionally substituted with substituent B, a C1-C6 haloalkyl group, a C3-C8 cycloalkyl group optionally substituted with substituent B, a C2-C6 alkenyl group optionally substituted with substituent B or a C2-C6 haloalkenyl group. The production method includes obtaining the compound by the Suzuki-Miyaura coupling that reacts a compound represented by Formula (1-d) with an organoboronic acid (R2d-B).

In Formula (1-d), R2c is preferably a chlorine atom, a bromine atom or an iodine atom.

Production Method L may be performed in accordance with Production Method H while replacing the compound represented by Formula (1a-b) and the R3d-B in Production Method H by the compound represented by Formula (1-d) and the R2d-B, respectively.

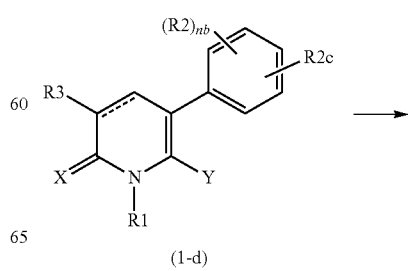

-continued

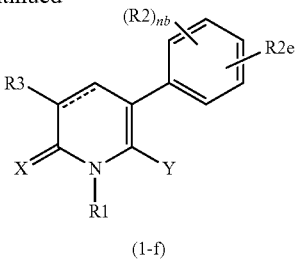

(1-f)

In the formula, R2e represents a C2-C6 alkynyl group optionally substituted with substituent B or a C2-C6 haloalkynyl group, and R1, R2, R2c, R3, nb, X, Y and the broken line are the same as defined hereinabove.

Production Method M produces a compound represented by Formula (1-f), which belongs to the compounds represented by Formula (1), wherein R2e is a C2-C6 alkynyl group optionally substituted with substituent B or a C2-C6 haloalkynyl group. The production method includes obtaining the compound by the Sonogashira coupling that reacts a compound represented by Formula (1-d) with an alkyne-terminated compound.

In the compound represented by Formula (1-d), R2c is preferably a chlorine atom, a bromine atom or an iodine atom.

Production Method M may be performed in accordance with Production Method I while replacing the compound represented by Formula (1a-b) in Production Method I by the compound represented by Formula (1-d).

[Production Method N]

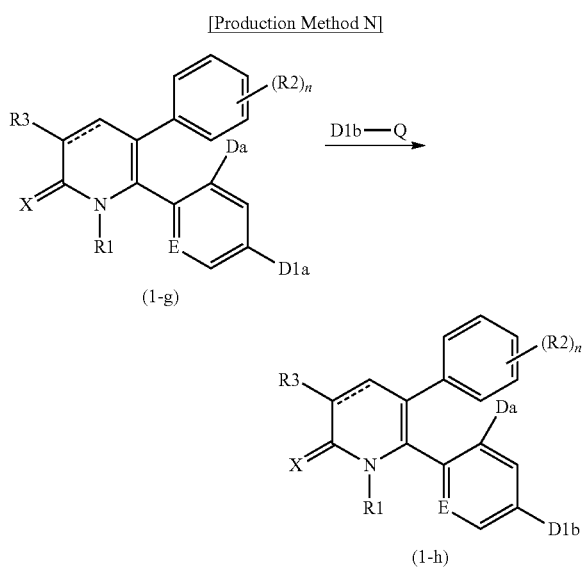

In the formula, Da represents a halogen atom, D1a represents a halogen atom, D1b represents a C1-C6 alkoxy group, a C1-C6 haloalkoxy group or a C3-C8 cycloalkoxy group, E represents a halogen-substituted carbon atom or a nitrogen atom, and R1, R2, R3, n, X, Q and the broken line are the same as defined hereinabove.

Production Method N produces a compound represented by Formula (1-h), which belongs to the compounds represented by Formula (1), wherein D1b is a C1-C6 alkoxy group, a C1-C6 haloalkoxy group or a C3-C8 cycloalkoxy group, and E is a halogen-substituted carbon atom or a nitrogen atom. The production method includes reacting a compound represented by Formula (1-g) with D1b-Q in a solvent.

The D1b-Q used in the reaction may be purchased from the market. Preferably, Q is a hydrogen atom or an alkali metal such as sodium or potassium.

In the reaction, the D1b-Q is used in at least 1 equivalent amount relative to the compound represented by Formula (1-g). The amount is not particularly limited as long as this equivalent amount is satisfied and also the target reaction takes place, but is preferably 1 equivalent amount to 30 equivalent amounts. When Q is a hydrogen atom, the reagent may be used also as a solvent.

The base used in the reaction is preferably an inorganic base such as sodium carbonate, potassium carbonate, cesium carbonate or sodium hydride. When Q is an alkali metal, the use of the base may be omitted.

In the reaction, the base is used in at least 1 equivalent weight relative to the compound represented by Formula (1-g). The amount is not particularly limited as long as this equivalent weight is satisfied and also the target reaction takes place, but is preferably 1 equivalent weight to 30 equivalent weights.

The solvent used in the reaction is not particularly limited as long as the target reaction takes place. Examples include alcohol solvents represented by D1b-H, ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethylsulfoxide and sulfolane, ketone solvents such as acetone, methyl ethyl ketone and methyl isobutyl ketone, and the like. These solvents may be used singly, or two or more may be used in combination in any ratio.

The amount of the solvent used in the reaction is not particularly limited as long as the target reaction takes place, but is usually 3 to 200 times by weight the amount of the compound represented by Formula (1-g).

The temperature of the reaction is not particularly limited as long as the target reaction takes place, but is usually 0° C. to 150° C., or is below the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. These solvents may be used singly, or two or more may be used in combination in any ratio. The liquid separation may be performed as many times as desired without limitation in accordance with the desired purity and yield.

The reaction mixture obtained above which includes the compound represented by Formula (1-h) may be dehydrated with a desiccant such as sodium sulfate or magnesium sulfate, but this dehydration may be omitted.

The reaction mixture obtained above which includes the compound represented by Formula (1-h) may be distilled to evaporate the solvent under reduced pressure as long as the compound is not decomposed.

The distilled reaction mixture which includes the compound represented by Formula (1-h) may be purified with an appropriate solvent by a method such as washing, reprecipitation, recrystallization or column chromatography. The purification method may be selected appropriately in accordance with the desired purity.

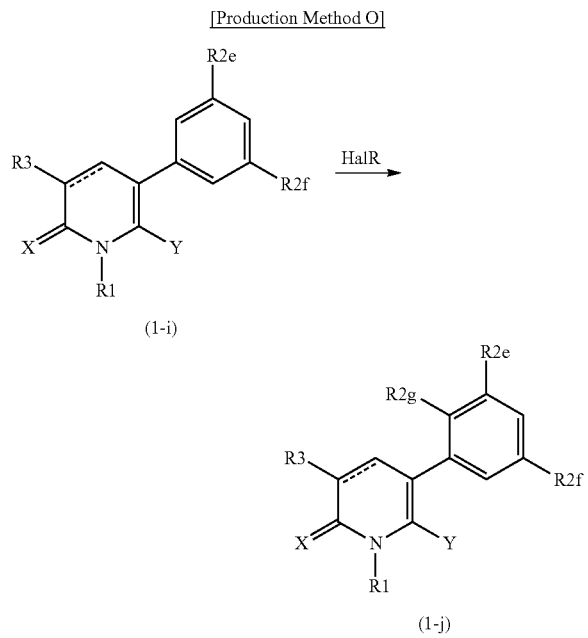

[Production Method O]

(1-i)

(1-j)

In the formula, R2e represents a C1-C6 alkoxy group optionally substituted with substituent B, R2f represents a C1-C6 alkoxy group optionally substituted with substituent B, R2g represents a halogen atom, and HalR, R1, R3, X, Y and the broken line are the same as defined hereinabove.

Production Method O produces a compound represented by Formula (1-j), which belongs to the compounds represented by Formula (1), wherein R2e is a C1-C6 alkoxy group optionally substituted with substituent B, R2f is a C1-C6 alkoxy group optionally substituted with substituent B, and R2g is a halogen atom. The production method includes reacting a compound represented by Formula (1-i) with a halogenating agent (HalR) in a solvent.

Examples of the halogenating agents used in the reaction include Selectfluor (N-fluoro-N'-triethylenediamine bis(tetrafluoroborate)), N-chlorosuccinimide, N-bromosuccinimide, N-iodosuccinimide, 1,3-dichloro-5,5-dimethylhydantoin, 1,3-dibromo-5,5-dimethylhydantoin, 1,3-diiodo-5,5-dimethylhydantoin, bromine, iodine and the like.

In the reaction, the halogenating agent is used in at least 1 equivalent amount relative to the compound represented by Formula (1-i). The amount is not particularly limited as long as this equivalent amount is satisfied and also the target reaction takes place, but is preferably 1 equivalent amount to 10 equivalent amounts. Those halogenating agents containing hydantoin may be used in at least 0.5 equivalent amounts, and their amount is not particularly limited as long as this equivalent amount is satisfied and also the target reaction takes place, but is preferably 1 equivalent amount to 5 equivalent amounts.

When the halogenating agent is an iodinating agent, the reaction may involve an acid, for example, an inorganic acid such as hydrochloric acid or sulfuric acid, or an organic acid such as acetic acid, trifluoroacetic acid, methanesulfonic acid or trifluoromethanesulfonic acid.

Such an acid, which is added when the halogenating agent used in the reaction is an iodinating agent, is used in at least 0.01 equivalent amount relative to the compound represented by Formula (1-i). The amount is not particularly limited as long as this equivalent amount is satisfied and also the target reaction takes place, but is preferably 0.1 equivalent amount to 3 equivalent amounts.

The solvent used in the reaction is not particularly limited as long as the target reaction takes place. Examples include acidic solvents such as sulfuric acid, acetic acid, trifluoroacetic acid, methanesulfonic acid and trifluoromethanesulfonic acid, ether solvents such as diethyl ether, diisopropyl ether, methyl-t-butyl ether, dimethoxyethane, tetrahydrofuran and dioxane, alcohol solvents such as methanol, ethanol and isopropanol, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, and the like. These solvents may be used singly, or two or more may be used in combination in any ratio.

The amount of the solvent used in the reaction is not particularly limited as long as the target reaction takes place, but is usually 3 to 200 times by weight the amount of the compound represented by Formula (1-i).

The temperature of the reaction is not particularly limited as long as the target reaction takes place, but is usually 0° C. to 150° C., or is below the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, aqueous solutions of sulfur-containing salts such as sodium thiosulfate and sodium sulfite, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. These solvents may be used singly, or two or more may be used in combination in any ratio. The liquid separation may be performed as many times as desired without limitation in accordance with the desired purity and yield.

The reaction mixture obtained above which includes the compound represented by Formula (1-j) may be dehydrated with a desiccant such as sodium sulfate or magnesium sulfate, but this dehydration may be omitted.

The reaction mixture obtained above which includes the compound represented by Formula (1-j) may be distilled to evaporate the solvent under reduced pressure as long as the compound is not decomposed.

The distilled reaction mixture which includes the compound represented by Formula (1-j) may be purified with an appropriate solvent by a method such as washing, reprecipitation, recrystallization or column chromatography. The purification method may be selected appropriately in accordance with the desired purity.

[Production Method P]

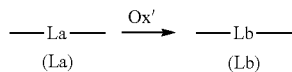

In the formula, La represents S, Lb represents SO or $SO_2$, and Ox' represents an oxidizer.

Production Method P produces a compound represented by Formula (1) in which any of R1, R2 and R3 includes Lb represented by Formula (Lb) that is SO or $SO_2$. The production method includes reacting a compound represented by Formula (1) in which R1, R2 or R3 includes La represented by Formula (La) that is S, with an oxidizer (Ox') in a solvent.

Examples of the oxidizers used in the reaction include peroxides such as hydrogen peroxide solution and meta-chloroperbenzoic acid. Further, transition metals such as sodium tungstate may be added.

The amount of the oxidizer used in the reaction for the production of SO is 1.0 equivalent amount to 1.2 equivalent amounts relative to the compound represented by Formula (La), and the amount for the production of $SO_2$ is 2 equivalent amounts to 10 equivalent amounts. When a transition metal is added, the amount thereof is 0.001 equivalent amount to 1 equivalent amount.

The solvent used in the reaction is not particularly limited as long as the target reaction takes place. Examples include aqueous solvents, acidic solvents such as acetic acid, benzene based solvents such as benzene, toluene, xylene, mesitylene, chlorobenzene and dichlorobenzene, nitrile solvents such as acetonitrile, halogen solvents such as dichloromethane, dichloroethane, chloroform and carbon tetrachloride, and the like. These solvents may be used singly, or two or more may be used in combination in any ratio.

The amount of the solvent used in the reaction is not particularly limited as long as the target reaction takes place, but is usually 3 to 200 times by weight the amount of the compound represented by Formula (1) having Formula (La).

The temperature of the reaction is not particularly limited as long as the target reaction takes place, but is usually −10° C. to 120° C., or is below the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, aqueous solutions of sulfur-containing salts such as sodium thiosulfate and sodium sulfite, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. These solvents may be used singly, or two or more may be used in combination in any ratio. The liquid separation may be performed as many times as desired without limitation in accordance with the desired purity and yield.

The reaction mixture obtained above which includes the compound represented by Formula (Lb) may be dehydrated with a desiccant such as sodium sulfate or magnesium sulfate, but this dehydration may be omitted.

The reaction mixture obtained above which includes the compound represented by Formula (Lb) may be distilled to evaporate the solvent under reduced pressure as long as the compound is not decomposed.

The distilled reaction mixture which includes the compound represented by Formula (Lb) may be purified in an appropriate solvent by a method such as washing, reprecipitation, recrystallization or column chromatography. The purification method may be selected appropriately in accordance with the desired purity.

Next, methods for synthesizing compounds represented by Formula (3) described in Production Method A will be described.

[Production Method Q]

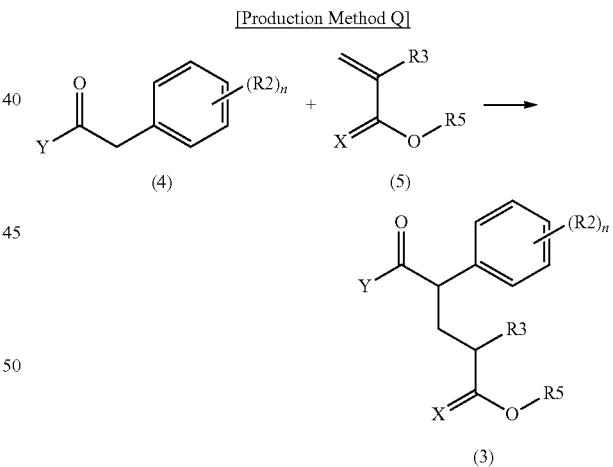

In the formula, R2, R3, R5, n, X and Y are the same as defined hereinabove.

Production Method Q produces an intermediate represented by Formula (3). The production method includes reacting a compound represented by Formula (4) with a compound represented by Formula (5) in a solvent in the presence of a base.

The compound represented by Formula (4) that is used in the reaction may be synthesized with reference to, for example, Green Chemistry, vol. 41, pp. 580-585 or The Journal of Organic Chemistry, vol. 65, No. 20, pp. 6458-6461 (2000).

The compound represented by Formula (5) that is used in the reaction may be purchased from the market.

In the reaction, the compound represented by Formula (5) is used in at least 1 equivalent amount relative to the compound represented by Formula (4). The amount is not particularly limited as long as this equivalent amount is satisfied and also the target reaction takes place, but is preferably 1 equivalent amount to 3 equivalent amounts.

Examples of the bases used in the reaction include inorganic bases such as sodium carbonate, potassium carbonate, cesium carbonate and tripotassium phosphate, metal alkoxides such as sodium methoxide, sodium ethoxide and potassium t-butoxide, and the like.

In the reaction, the base may be used in a catalytic amount. The amount is not particularly limited as long as this equivalent weight is satisfied and also the target reaction takes place, but is preferably 0.01 equivalent amount to 3 equivalent amounts.

Examples of the solvents used in the reaction include ether solvents such as diethyl ether, diisopropyl ether, methyl-t-butyl ether, dimethoxyethane, tetrahydrofuran and dioxane, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, sulfur solvents such as dimethylsulfoxide and sulfolane, ketone solvents such as acetone, methyl ethyl ketone and methyl isobutyl ketone, and the like. These solvents may be used singly, or two or more may be used in combination in any ratio.

The amount of the solvent used in the reaction is not particularly limited as long as the target reaction takes place, but is usually 3 to 200 times by weight the amount of the compound represented by Formula (4).

The temperature of the reaction is not particularly limited as long as the target reaction takes place, but is usually −50° C. to 150° C., or is below the boiling point of the solvent.

The reaction may be followed by a post treatment in which water or an appropriate aqueous solution is added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. These solvents may be used singly, or two or more may be used in combination in any ratio. The liquid separation may be performed as many times as desired without limitation in accordance with the desired purity and yield.

The reaction mixture obtained above which includes the compound represented by Formula (3) may be dehydrated with a desiccant such as sodium sulfate or magnesium sulfate, but this dehydration may be omitted.

The reaction mixture obtained above which includes the compound represented by Formula (3) may be distilled to evaporate the solvent under reduced pressure as long as the compound is not decomposed.

The distilled reaction mixture which includes the compound represented by Formula (3) may be purified with an appropriate solvent by a method such as washing, reprecipitation, recrystallization or column chromatography. The purification method may be selected appropriately in accordance with the desired purity.

[Production Method R]

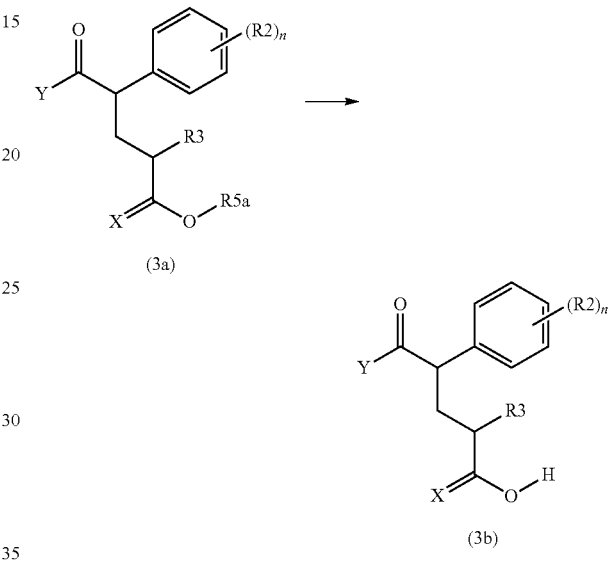

In the formula, R5a represents a C1-C6 alkyl group, and R2, R3, n, X and Y are the same as defined hereinabove.

Production Method R produces an intermediate represented by Formula (3b), which belongs to the compounds represented by Formula (3). The production method includes reacting a compound represented by Formula (3a) under acidic or basic conditions in a solvent.

First, the reaction under acidic conditions will be described.

Examples of the acids used in the reaction include inorganic acids such as hydrochloric acid, hydrobromic acid and phosphoric acid, and organic acids such as acetic acid, methanesulfonic acid, p-toluenesulfonic acid and trifluoroacetic acid. The acids are not particularly limited as long as the target reaction takes place.

The amount of the acid used in the reaction may be a catalytic amount. The amount is not particularly limited as long as this equivalent weight is satisfied and also the target reaction takes place, but is preferably not less than 0.01 equivalent amount relative to the compound represented by Formula (3a). Those acids which are liquid may be used also as solvents.

The solvent used in the reaction is not particularly limited as long as the target reaction takes place. Examples include aqueous solvents, acidic solvents such as acetic acid and methanesulfonic acid, ether solvents such as diethyl ether, diisopropyl ether, methyl-t-butyl ether, dimethoxyethane, tetrahydrofuran and dioxane, alcohol solvents such as methanol, ethanol and isopropanol, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, and the like. These solvents may be used singly, or two or more may be used in combination in any ratio.

The amount of the solvent used in the reaction is not particularly limited as long as the target reaction takes place, but is usually 3 to 200 times by weight the amount of the compound represented by Formula (3a).

The temperature of the reaction is not particularly limited as long as the target reaction takes place, but is usually 0° C. to 180° C., or is below the boiling point of the solvent.

Next, the reaction under basic conditions will be described.

Examples of the bases used in the reaction include inorganic bases such as lithium hydroxide, sodium hydroxide and potassium hydroxide. The bases are not particularly limited as long as the target reaction takes place.

In the reaction, the base is used in at least 1 equivalent weight relative to the compound represented by Formula (3a). The amount is not particularly limited as long as this equivalent weight is satisfied and also the target reaction takes place, but is preferably 1 equivalent weight to 30 equivalent weights.

The solvent used in the reaction is not particularly limited as long as the target reaction takes place. Examples include aqueous solvents, ether solvents such as diethyl ether, diisopropyl ether, methyl-t-butyl ether, dimethoxyethane, tetrahydrofuran and dioxane, alcohol solvents such as methanol, ethanol and isopropanol, benzene based solvents such as benzene, toluene, xylene, mesitylene, chlorobenzene and dichlorobenzene, ester solvents such as ethyl acetate, isopropyl acetate and butyl acetate, nitrile solvents such as acetonitrile, amide solvents such as N-methylpyrrolidone, N,N-dimethylformamide and N,N-dimethylacetamide, urea solvents such as 1,3-dimethyl-2-imidazolidinone, halogen solvents such as dichloromethane, dichloroethane, chloroform and carbon tetrachloride, and the like. These solvents may be used singly, or two or more may be used in combination in any ratio.

The amount of the solvent used in the reaction is not particularly limited as long as the target reaction takes place, but is usually 3 to 200 times by weight the amount of the compound represented by Formula (3a).

The temperature of the reaction is not particularly limited as long as the target reaction takes place, but is usually −20° C. to 180° C., or is below the boiling point of the solvent.

The reaction may be followed by a post treatment, which may be performed by a common method irrespective of whether the reaction conditions are acidic or basic. Water or an appropriate aqueous solution may be added to the reaction mixture to perform separation. The aqueous solution may be any of aqueous solutions of acids such as hydrochloric acid and sulfuric acid, aqueous solutions of alkalis such as potassium hydroxide, sodium hydroxide, sodium carbonate, potassium carbonate, sodium hydrogen carbonate and potassium hydrogen carbonate, and others such as brine. The liquid separation may optionally involve the addition of water-immiscible solvents, for example, benzene based solvents such as toluene, xylene, benzene, chlorobenzene and dichlorobenzene, ester solvents such as ethyl acetate, isopropyl acetate and butyl acetate, ether solvents such as diethyl ether, diisopropyl ether and methyl-t-butyl ether, halogen solvents such as dichloromethane, dichloroethane, chloroform and carbon tetrachloride, hydrocarbon solvents such as hexane, heptane, cyclohexane and methylcyclohexane, and the like. These solvents may be used singly, or two or more may be used in combination in any ratio. The liquid separation may be performed as many times as desired without limitation in accordance with the desired purity and yield.

The reaction mixture obtained above which includes the compound represented by Formula (3b) may be dehydrated with a desiccant such as sodium sulfate or magnesium sulfate, but this dehydration may be omitted.

The reaction mixture obtained above which includes the compound represented by Formula (3b) may be distilled to evaporate the solvent under reduced pressure as long as the compound is not decomposed.

The distilled reaction mixture which includes the compound represented by Formula (3b) may be purified in an appropriate solvent by a method such as washing, reprecipitation, recrystallization or column chromatography. The purification method may be selected appropriately in accordance with the desired purity.

The compound represented by Formula (3b) may be an isomer represented by Formula (3b'):

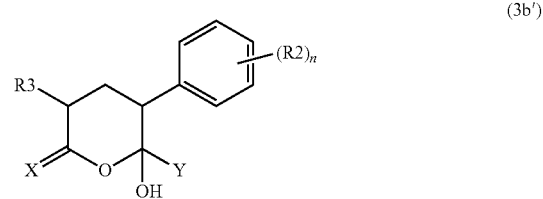

(3b')

(In the formula, R2, R3, n, X and Y are the same as defined hereinabove.)

The compound represented by Formula (3b') may be handled similarly to the compound represented by Formula (3b), and may be applied to Production Method A. The compound represented by Formula (3b') has an asymmetric carbon, and may be a single isomer or a mixture of isomers in an appropriate ratio. Further, a mixture of the compound represented by Formula (3b) and the compound represented by Formula (3b') may be used, and each of these compounds may be a single isomer or a mixture of isomers in an appropriate ratio.

The compounds represented by Formula (1) may be produced by appropriate combinations of Production Method A to Production Method R described hereinabove. Alternatively, the compounds represented by Formula (1) may be produced by appropriate combinations of known methods and Production Method A to Production Method R.

The compounds of the invention can protect plants from harmful organisms and thus may be used as pesticides. Specific examples of such use include fungicides, insecticides, herbicides and plant growth regulators, with fungicides being preferable.

The compounds of the present invention can be used as an agricultural and horticultural fungicide in farms, paddy fields, tea gardens, orchards, meadows, grasses, forests, gardens, roadside trees, etc. for prevention of plant diseases. A plant disease as used in the present invention refers to that in which systemic, abnormal pathological symptoms such as wilting, damping-off, yellowing, dwarfism, and spindly growth, or partial pathological symptoms such as spotting, leaf blight, mosaic pattern, leaf rolling, die back, root rot, club root, and knotting, are induced in plants such as crops, flowering plants, flowering trees and shrubs, and trees. In other words, a plant disease refers to that in which a plant becomes ill. Examples of pathogens that cause plant diseases mainly include fungi, bacteria, spiroplasmas, phytoplasmas, viruses, viroids, parasitic higher plants, nematodes and the like. The compounds of the present invention are effective against fungi, but which are not limitative.

Diseases caused by fungi are mainly fungal diseases. Examples of fungi (pathogens) that cause fungal diseases include *Plasmodiophora*, Oomycetes, Zygomycetes, Ascomycetes, Basidiomycetes and Deuteromycetes. Examples of *Plasmodiophora* include club root fungus, potato powdery scab fungus and beet necrotic yellow vein virus, examples of Oomycetes include blight fungus, downy mildew fungus, *Pythium* species and *Aphanomyces* species, examples of Zygomycetes include *Rhizopus* species, examples of Ascomycetes include peach leaf curl fungus, corn southern leaf blight fungus, rice blast fungus, powdery mildew fungus, anthracnose fungus, *fusarium* head blight fungus, bakanae fungus and stem rot fungus, examples of Basidiomycetes include rust fungus, smut fungus, violet root rot fungus, blister blight fungus and rice sheath blight fungus, and examples of Deuteromycetes include gray mold fungus, *Alternaria* species, *Fusarium* species, *Penicillium* species, *Rhizoctonia* species, southern blight fungus, and the like.

The compounds of the present invention are effective against various plant diseases. The following provides specific examples of disease names and pathogens thereof.

Rice: blast (*Magnaporthe grisea*), sheath blight (*Thanatephorus cucumeris*), brown sclerotial disease (*Ceratobasidium setariae*), brown small sclerotial disease (*Waitea circinata*), brown sheath blight (*Thanatephorus cucumeris*), globular sclerotial disease (*Sclerotium hydrophilum*), red sclerotial disease (*Waitea circinata*), black leaf blight (*Entyloma dactylidis*), stem rot (*Magnaporthe salvinii*), gray sclerotial disease (*Ceratobasidium cornigerum*), brown spot (*Cochliobolus miyabeanus*), cercospora leaf spot (*Sphaerulina oryzina*), bakanae disease (*Gibberella fujikuroi*), seedling blight (*Pythium* spp., *Fusarium* spp., *Trichoderma* spp., *Rhizopus* spp., *Rhizoctonia solani*, *Mucor* sp., *Phoma* sp.), seedling rot (*Pythium* spp., *Achlya* spp., *Dictyuchus* spp.), rice false smut (*Claviceps virens*), kernel smut (*Tilletia barclayana*), discolored rice grains (*Curvularia* spp., *Alternaria* spp.), crazy top (*Sclerophthora macrospora*), bacterial leaf blight (*Xanthomonas oryzae* pv. *oryzae*), bacterial brown stripe (*Acidovorax avenae* subsp. *avenae*), bacterial palea browning (*Erwinia ananas*), bacterial seeding blight (*Burkholderia plantarii*), bacterial grain rot (*Burkholderia glumae*), sheath brown rot (*Pseudomonas fuscovaginae*), bacterial halo blight (*Pseudomonas syringae* pv. *oryzae*), bacterial foot rot (*Erwinia chrysanthemi*), yellow dwarf (*Phytoplasma oryzae*), rice stripe (Rice stripe tenuivirus), rice dwarf (Rice dwarf reovirus); wheat and barley: powdery mildew (*Blumeria graminis* f. sp. *hordei*; f. sp. *tritici*), rust (*Puccinia striiformis, Puccinia graminis, Puccinia recondita, Puccinia hordei*), leaf blotch (*Pyrenophora graminea*), net blotch (*Pyrenophora teres*), *Fusarium* head blight (*Gibberella zeae, Fusarium culmorum, Fusarium avenaceum, Monographella nivalis*), *Typhula* snow blight (*Typhula incarnata, Typhula ishikariensis, Monographella nivalis*), loose smut (*Ustilago nuda*), stinking smut (*Tilletia caries, Tilletia controversa*), eye spot (*Pseudocercosporella herpotrichoides*), foot rot (*Ceratobasidium gramineum*), leaf scald (*Rhynchosporium secalis*), speckled leaf blotch (*Septoria tritici*), glume blotch (*Phaeosphaeria nodorum*), damping-off (*Fusarium* spp., *Pythium* spp., *Rhizoctonia* spp., *Septoria* spp., *Pyrenophora* spp.), take-all (*Gaeumannomyces graminis*), anthracnose (*Colletotrichum graminicola*), ergot (*Claviceps purpurea*), leaf spot (*Cochliobolus sativus*), bacterial black node (*Pseudomonas syringae* pv. *syringae*); corn: *Fusarium* blight (*Gibberella zeae*, etc.), damping-off (*Fusarium avenaceum, Penicillium* spp., *Pythium* spp., *Rhizoctonia* spp.), rust (*Puccinia sorghi*), brown spot (*Cochliobolus heterostrophus*), smut (*Ustilago maydis*), anthracnose (*Colletotrichum graminicola*), northern leaf spot (*Cochliobolus carbonum*), bacterial brown stripe (*Acidovorax avenae* subsp. *avenae*), bacterial stripe (*Burkholderia andropogonis*), bacterial stalk rot (*Erwinia chrysanthemi* pv. *zeae*), bacterial wilt (*Erwinia stewartii*); grapes: downy mildew (*Plasmopara viticola*), rust (*Physopella ampelopsidis*), powdery mildew (*Uncinula necator*), scab (*Elsinoe ampelina*), ripe rot (*Glomerella cingulata, Colletotrichum acutatum*), black rot (*Guignardia bidwellii*), *Phomopsis* leaf spot (*Phomopsis viticola*), fly speck (*Zygophiala jamaicensis*), gray mold (*Botrytis cinerea*), twig blight (*Diaporthe medusaea*), violet root rot (*Helicobasidium mompa*), white root rot (*Rosellinia necatrix*), crown gall (*Agrobacterium vitis*); apples: powdery mildew (*Podosphaera leucotricha*), black spot disease (*Venturia inaequalis*), *Alternaria* leaf spot (*Alternaria mali*), rust (*Gymnosporangium yamadae*), blossom blight (*Monilinia mali*), apple canker (*Valsa ceratosperma*), ring spot (*Botryosphaeria berengeriana*), anthracnose (*Colletotrichum acutatum, Glomerella cingulata*), fly speck (*Zygophiala jamaicensis*), sooty spot (*Gloeodes pomigena*), fruit spot (*Mycosphaerella pomi*), violet root rot (*Helicobasidium mompa*), white root rot (*Rosellinia necatrix*), canker (*Phomopsis mali, Diaporthe tanakae*), apple blotch (*Diplocarpon mali*), fire blight (*Erwinia amylovora*), crown gall (*Agrobacterium tumefaciens*), hairy root disease (*Agrobacterium rhizogenes*); Japanese pears: black spot (*Alternaria kikuchiana*), pear scab (*Venturia nashicola*), rust (*Gymnosporangium asiaticum*), ring spot (*Botryosphaeria berengeriana* f. sp. *piricola*), pear canker (*Phomopsis fukushii*), bacterial shoot blight (*Erwinia* sp.), crown gall (*Agrobacterium tumefaciens*), rusty canker (*Erwinia chrysanthemi* pv. *chrysanthemi*), bacterial petal blight (*Pseudononas syringae* pv. *syringae*); European pears: blight (*Phytophthora cactorum, Phytophthora syringae*), bacterial shoot blight (*Erwinia* sp.); peaches: black spot (*Cladosporium carpophilum*), *Phomopsis* rot (*Phomopsis* sp.), blight (*Phytophthora* sp.), anthracnose (*Colletotrichum gloeosporioides*), leaf curl (*Taphrina deformans*), bacterial shot hole (*Xhanthomonas campestris* pv. *pruni*), crown gall (*Agrobacterium tumefaciens*); cherries: anthracnose (*Glomerella cingulata*), young fruit sclerotial disease (*Monilinia kusanoi*), gray spot (*Monilinia fructicola*), crown gall (*Agrobacterium tumefaciens*), bacterial gummosis (*Pseudomonas syringae* pv. *syringae*): persimmons: anthracnose (*Glomerella cingulata*), leaf spot (*Cercospora kaki; Mycosphaerella nawae*), powdery mildew (*Phyllactinia kakikora*), crown gall (*Agrobacterium tumefaciens*); citrus fruits: melanose (*Diaporthe citri*), green mold disease (*Penicillium digitatum*), blue mold disease (*Penicillium italicum*), scab (*Elsinoe fawcettii*), brown rot (*Phytophthora citrophthora*), canker (*Xhanthomonas campestris* pv. *citri*), bacterial brown spot (*Pseudomonas syringae* pv. *syringae*), greening disease (*Liberibactor asiaticus*), crown gall (*Agrobacterium tumefaciens*); tomatoes, cucumbers, beans, strawberries, potatoes, cabbage, eggplants, lettuce and the like: gray mold (*Botrytis cinerea*); tomatoes, cucumbers, beans, strawberries, potatoes, rapeseed, cabbage, eggplants, lettuce, and the like: sclerotial disease (*Sclerotinia sclerotiorum*); various vegetables such as tomatoes, cucumbers, beans, Japanese radishes, watermelons, eggplants, rapeseed, green peppers, spinach, and beets: seedling damping-off (*Rhizoctonia* spp., *Pythium* spp., *Fusarium* spp., *Phythophthora* spp., *Sclerotinia sclerotiorum*, etc.); solanaceous plants: bacterial wilt (*Ralstonia solanacearum*); melons: downy mildew (*Pseudoperonospora cubensis*), powdery mildew (*Sphaerotheca fuliginea*), anthracnose (*Colletotrichum orbiculare*), gummy stem blight (*Didymella bryoniae*), stem rot (*Fusarium oxysporum*), late blight (*Phytophthora parasitica, Phytophthora melonis, Phytophthora nicotianae, Phytophthora drechsleri, Phytophthora capsici*, etc.), bacterial brown spot (*Xhanthomonas campestris* pv. *cucurbitae*), soft rot (*Erwinia carotovora* subsp. *carotovora*), bacterial spot (*Pseudomonas syringae* pv. *lachrymans*), marginal blight (*Pseudomonas marginalis* pv. *marginalis*), canker (*Streptomyces* sp.), hairy root disease (*Agrobacterium rhizogenes*), cucumber mosaic virus (Cucumber mosaic virus); tomatoes: ring spot (*Alternaria solani*), leaf mold (*Fulvia fulva*), late blight (*Phytophthora infestans*), wilt disease (*Fusarium oxysporum*), root rot (*Pythium myriotylum, Pythium dissotocum*), anthracnose (*Colletotrichum gloeosporioides*), canker (*Clavibacter michiganensis*), pith necrosis (*Pseudomonas corrugata*), bacterial black spot (*Pseudomonas viridiflava*), soft rot (*Erwinia carotovora* subsp. *carotovora*), bacterial leaf gall (*Crynebacterium* sp.), yellowing wilt (*Phytoplasma asteris*), yellow dwarfism (Tobacco leaf curl, subgroup III geminivirus); eggplants: powdery mildew (*Sphaerotheca fuliginea* etc.), leaf mold (*Mycovellosiella nattrassii*), blight (*Phytophthora infestans*), brown rot (*Phytophthora capsici*), bacterial brown spot (*Pseudomonas cichorii*), necrotic leaf spot (*Pseudomonas corrugata*), bacterial stem rot (*Erwinia chrysanthemi*), soft rot (*Erwinia carotovora* subsp. *carotovora*), bacterial spot (*Pseudomonas* sp.); Rapeseed: black spot (*Alternaria brassicae*), black rot (*Xhanthomonas campestris* pv. *campestris*), bacterial black spot (*Pseudomonas syringae* pv. *maculicola*), soft rot (*Erwinia carotovora*); cruciferous vegetables: black spot (*Alternaria brassicae* etc.), white spot (*Cercosporella brassicae*), black leg (*Phoma lingam*), club root (*Plasmodiophora brassicae*), downy mildew (*Peronospora parasitica*), black rot (*Xanthomonas campestris* pv. *campestris*), bacterial black spot (*Pseudomonas syringae* pv. *maculicola*), soft rot (*Erwinia carotovora* subsp. *carotovora*); cabbage: club foot (*Thanatephorus cucumeris*), yellowing wilt (*Fusarium oxysporum*), alternaria sooty spot (*Alternaria brassisicola*); Chinese cabbage: bottom rot (*Rhizoctonia solani*), yellowing (*Verticillium dahliae*); green onions: rust (*Puccinia allii*), black spot (*Alternaria porri*), southern blight (*Sclerotium rolfsii*), white rot (*Phytophthora porri*), black rot (*Sclerotium cepivorum*); onions: canker (*Curtobacterium flaccumfaciens*), soft rot (*Erwinia carotovora* subsp. *carotovora*), bacterial spot (*Pseudomonas syringae* pv. *syringae*), rot (*Erwinia rhapontici*), scale rot (*Burkholderia gladioli*), yellowing wilt (*Phytoplasma asteris*); garlic: soft rot (*Erwinia carotovora* subsp. *carotovora*), spring rot (*Pseudomonas marginalis* pv. *marginalis*); soybeans: purple seed stain (*Cercospora kikuchii*), scab (*Elsinoe glycines*), black spot (*Diaporthe phaseolorum*), Rhizoctonia root rot (*Rhizoctonia solani*), stem rot (*Phytophthora sojae*), downy mildew (*Peronospora manshurica*), rust (*Phakopsora pachyrhizi*), anthracnose (*Colletotrichum truncatum* etc.), leaf scald (*Xhantomonas campestris* pv. *glycinea*), bacterial spot (*Pseudomonas syringae* pv. *glycinea*); kidney beans: anthracnose (*Colletotrichum lindemuthianum*), bacterial wilt (*Ralstonia solanacearum*), halo blight (*Pseudomonas syringae* pv. *phaseolicola*), bacterial brown spot (*Pseudomonas viridiflava*), leaf scald (*Xhanthomonas campestris* pv. *phaseoli*); peanuts: leaf spot (*Mycosphaerella berkeleyi*), brown spot (*Mycosphaerella arachidis*), bacterial wilt (*Ralstonia solanacearum*); garden peas: powdery mildew (*Erysiphe pisi*), downy mildew (*Peronospora pisi*), bacterial stem blight (*Pseudomonas syringae* pv. *pisi*), bacterial stem rot (*Xhanthomonas campestris* pv. *pisi*); broad beans: downy mildew (*Peronospora viciae*), blight (*Phytophthora nicotianae*); potatoes: early blight (*Alternaria solani*), black scurf (*Thanatephorus cucumeris*), blight (*Phytophthora infestans*), silver scurf (*Helminthosporium solani*), soft rot (*Fusarium oxysporum, Fusarium solani*), powdery scab (*Spongospora subterranea*), bacterial wilt (*Ralstonia solanacearum*), black foot disease (*Erwinia carotovora* subsp. *atroseptica*), common scab (*Streptomyces scabies, Streptomyces acidiscabies*), soft rot (*Erwinia carotovora* subsp. *carotovora*), slimy rot (*Crostridium* spp.), ring rot (*Clavibacter michiganensis* subsp. *sepedonicus*); sweet potatoes: damping-off (*Streptomyces ipomoeae*); sugar beets: brown spot (*Cercospora beticola*), downy mildew (*Peronospora schachtii*), black root rot (*Aphanomyces cochioides*), leaf spot (*Phoma betae*), crown gall (*Agrobacterium tumefaciens*), scab (*Streptomyces scabies*), bacterial spot (*Pseudomonas syringae* pv. *aptata*); carrots: leaf blight (*Alternaria dauci*), bacterial gall (*Rhizobacter dauci*), crown gall (*Agrobacterium tumefaciens*), *Streptomyces* scab (*Streptomyces* spp.), soft rot (*Erwinia carotovora* subsp. *carotovora*); strawberries: powdery mildew (*Sphaerotheca aphanis* var. *aphanis*), blight (*Phytophthora nicotianae* etc.), anthracnose (*Glomerella cingulata*), fruit rot (*Pythium ultimum*), bacterial wilt (*Ralstonia solanacearum*), angular leaf spot (*Xhanthomonas campestris*), bacterial bud blight (*Pseudomonas marginalis* pv. *marginalis*); tea: net blister blight (*Exobasidium reticulatum*), white scab (*Elsinoe leucospila*), anthracnose (*Colletotrichum theae-sinensis*), ring spot (*Pestalotiopsis longiseta*), red blight (*Pseudomonas syringae* pv. *theae*), canker (*Xhanthomonas campestris* pv. *theicola*), witch's broom (*Pseudomonas* sp.); tobacco: red spot (*Alternaria alternata*), powdery mildew (*Erysiphe cichoracearum*), anthracnose (*Colletotrichum gloeosporioides*), blight (*Phytophthora nicotianae*), wildfire (*Pseudomonas syringae* pv. *tabaci*), bacterial leaf spot (*Pseudomonas syringae* pv. *mellea*), hollow root (*Erwinia carotovora* subsp. *carotovora*), bacterial wilt (*Ralstonia solanacearum*), Tobacco mosaic virus (Tobacco mosaic virus); coffee: rust (*Hemileia vastatrix*); banana: black sigatoka (*Mycosphaerella fijiensis*), panama disease (*Fusarium oxysporum* f. sp *cubense*); cotton: damping-off (*Fusarium oxysporum*), frosty mildew (*Ramularia areola*); sunflowers: sclerotial disease (*Sclerotinia sclerotiorum*), angular leaf spot (*Xhanthomonas campestris* pv. *malvacearum*), hollow root (*Erwinia carotovora* subsp. *carotovora*), bacterial spot (*Pseudomonas syringae* pv. *helianthi*); roses: black spot (*Diplocarpon rosae*), powdery mildew (*Sphaerotheca pannosa* etc.), blight (*Phytophthora megasperma*), downy mildew (*Peronospora sparsa*), crown gall (*Agrobacterium tumefaciens*); chrysanthemums: brown spot (*Septoria obesa*), white rust (*Puccinia horiana*), blight (*Phytophthora cactorum*), bacterial spot (*Pseudomonas cichorii*), soft rot (*Erwinia carotovora* subsp. *carotovora*), crown gall (*Agrobacterium tumefaciens*), hairy root disease (*Agrobacterium rhizogenes*), chrysanthemum virescence (*Phytoplasma aurantifolia*); grasses: brown patch disease (*Rhizoctonia solani*), dollar spot disease (*Sclerotinia homoeocarpa*), curvularia leaf blight (*Curvularia* sp.), rust (*Puccinia zoysiae*), helminthosporium leaf blight (*Cochliobolus* sp.), scald (*Rhynchosporium secalis*), take-all (*Gaeumannomyces*

*graminis*), anthracnose (*Colletotrichum* sp.), *typhula* brown snow blight (*Typhula incarnata*), *typhula* black snow blight (*Typhula ishikariensis*), Sclerotinia (*Myriosclerotinia borealis*), fairy ring disease (*Marasmius oreades* etc.), *Pythium* blight (*Pythium aphanidermatum* etc.), blast (*Pyricularia grisea*); and the like.

The compounds of the present invention may be used alone, but preferably can be used as a composition such as a powder, a water-dispersible powder, water-dispersible granules, a water-soluble powder, water-soluble granules, granules, an emulsion, a solution, a microemulsion, an aqueous suspension preparation, an aqueous emulsion preparation, or a suspoemulsion preparation by mixing with a solid carrier, liquid carrier, gas carrier, surfactant, adhesive agent, dispersant, stabilizer, or the like. The compositions are not limited thereto as long as the effects are demonstrated.

The followings show specific formulating examples, but which are not limitative.

Preparation Example 1: Flowable

The compound of the present invention (10 parts by mass), a sodium salt of naphthalene sulfonate formaldehyde condensate (5 parts by mass), polyoxyethylene aryl phenyl ether (1 part by mass), propylene glycol (5 parts by mass), a silicone antifoaming agent (0.1 parts by mass), xanthan gum (0.2 parts by mass), and ion exchanged water (78.7 parts by mass) are mixed to make a slurry. Further, the slurry is wet milled with Dyno-Mill KDL using glass beads having a diameter of 1.0 mm to obtain a flowable.

Preparation Example 2: Emulsion

The compound of the present invention (5 parts by mass) is dissolved in a mixed solution of xylene (40 parts by mass) and cyclohexane (35 parts by mass), to this solution is added Tween20 (20 parts by mass), and the solution is mixed to obtain an emulsion.

Preparation Example 3: Water-Dispersible Powder

The compound of the present invention (10 parts by mass), white carbon (10 parts by mass), polyvinyl alcohol (2 parts by mass), dioctyl sulfosuccinic acid, sodium salt (0.5 parts by mass), alkylbenzene sulfonic acid, sodium salt (5 parts by mass), calcined diatomaceous earth (10 parts by mass), and kaolinite clay (62.5 parts by mass) are mixed thoroughly, and the mixture is milled by the air mill to obtain a water-dispersible powder.

The method for applying the composition containing the compound of the present invention includes a method of bringing the composition into contact with a plant body or seeds, or a method of bringing cultivation soil containing the composition into contact with the roots or underground stem of a plant. Specific examples thereof include a treatment of spraying the composition onto the stem and leaves of a plant individual, an injection treatment, a treatment of seedling nursery boxes, a cell tray treatment, a treatment of spraying the composition to plant seeds, a plant seed coating treatment, a plant seed immersion treatment, a plant seed dressing treatment, a treatment of spraying the composition onto the surface of soil, a soil incorporation after a treatment of spraying the composition onto the surface of soil, a soil injection treatment, a soil incorporation after a soil injection treatment, a soil irrigation treatment, a soil incorporation after a soil irrigation treatment, etc. The composition demonstrates adequate effects when applied by any method usually used by a person skilled in the art.

A "plant" as used in the present invention refers to that which thrives by photosynthesis without moving. Specific examples thereof include rice, wheat, barley, corn, coffee, bananas, grapes, apples, pears, peaches, cherries, persimmons, citrus fruits, soybeans, kidney beans, cotton, strawberries, potatoes, cabbage, lettuce, tomatoes, cucumbers, eggplants, watermelons, sugar beets, spinach, field peas, squash, sugar cane, tobacco, green peppers, sweet potatoes, taro potatoes, konjak, cotton, sunflowers, roses, tulips, chrysanthemums, grasses, etc., and F1 hybrids thereof etc. In addition, gene recombinant crops that are created by genetic or other artificial manipulation that are inherently not present in nature are also included, examples of which include agricultural and horticultural crops such as soybeans, corn, cotton and the like which have been imparted with resistance to herbicides, rice, tobacco and the like acclimated to cold climates, and corn, cotton and the like which have been given the ability to produce insecticidal substances. Furthermore, trees such as pines, ash trees, ginkgos, maples, evergreen oaks, poplars, and zelkova trees are included. In addition, a "plant body" as used in the present invention refers to the generic term for all sites that compose the aforementioned plant individual, and examples thereof include the stems, leaves, roots, seeds, flowers, fruits and the like.

A "seed" as used in the present invention refers to that which is used for agricultural production storing nutrients for the germination of seedlings. Specific examples thereof include seeds of corn, soybeans, cotton, rice, sugar beets, wheat, barley, sunflowers, tomatoes, cucumbers, eggplants, spinach, field peas, squash, sugar cane, tobacco, green peppers, rape, etc., seeds of F1 hybrids thereof etc., seed tubers of taro potatoes, potatoes, sweet potatoes, konjak, etc., bulbs of edible lilies and tulips, seed bulbs of scallions, etc., seeds and tubers of gene recombinant crops, and the like.

Although the applied amount and applied concentration of the composition containing the compound of the present invention varies according to the target crop, target disease, degree of progression of the disease, formulation form of the compound, application method and various environmental conditions and the like, in the case of spraying or irrigation, the applied amount as the amount of active ingredient is suitably 0.1 g to 10,000 g per hectare and preferably 10 g to 1,000 g per hectare. In addition, the amount used in the case of seed treatment as the amount of active ingredient is 0.0001 g to 1000 g and preferably 0.001 g to 100 g per kg of seeds. In the case of using the composition containing the compound of the present invention for a stem and leaf spraying treatment to a plant individual, soil surface spraying treatment, soil injection treatment or soil irrigation treatment, the treatment may be carried out after having diluted to a suitable concentration in a suitable carrier. In the case of bringing the composition containing the compound of the present invention into contact with plant seeds, the seeds may be subjected to immersion, dressing, spraying or coating treatment after having diluted to a suitable concentration. Although the amount of the composition used in the case of immersion, dressing, spraying or coating treatment as the amount of the active ingredient is usually about 0.05% to 50% based on the dry weight of the plant seeds and is preferably 0.1% to 30%, the amount can be appropriately set according to the form of the composition and type of plant seeds targeted for treatment, and it is not limited to these ranges.

The composition containing the compound of the present invention can be mixed or used in combination with other agricultural chemicals as necessary, examples of which include agricultural chemicals such as fungicides, insecticides, miticides, nematicides, herbicides, biological pesticides and plant growth regulators, disease control agents containing nucleic acids as an active ingredient (WO 2014/062775), soil improvers, or fertilizing substances.

EXAMPLES

Although Synthesis Examples, Reference Examples and Test Examples are given below to explain the present invention in greater detail, the present invention is not limited thereto.

Synthesis Example 1

Step 1: Synthesis of 5-(2-chloro-5-methoxyphenyl)-6-(2,6-difluorophenyl)-3,4-dihydropyridine-2(1H)-one

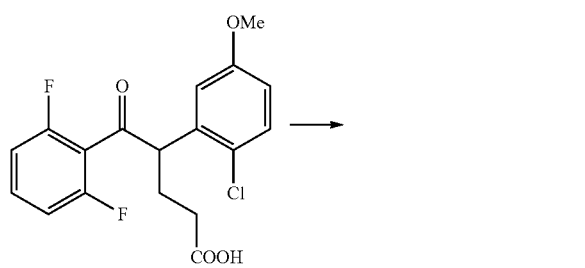

10 ml of an acetic acid solution containing 1.47 g of 4-(2-chloro-5-methoxyphenyl)-5-(2,6-difluorophenyl)-5-oxopentanoic acid and 6.75 g of ammonium acetate was allowed to react at 130° C. for 14 hours. After cooling to room temperature, to the reaction mixture were added ethyl acetate and water to separate the resulting mixture. To the obtained organic layer was added water, potassium carbonate was further added until bubble releasing subsided, and then the resulting mixture was separated. Subsequently, the organic layer was washed with brine and dried over sodium sulfate. After the solvent was distilled off under reduced pressure, the precipitate was washed with diisopropyl ether. The resulting purple solid was the title compound, which was 0.98 g in weight.

$^1$H-NMR (CDCl$_3$) δ: 7.25-7.21 (1H, m), 7.19 (1H, d, J=8.8 Hz), 6.83-6.76 (3H, m), 6.65 (1H, dd, J=8.8, 3.4 Hz), 6.53 (1H, d, J=3.4 Hz), 3.61 (3H, s), 2.91-2.76 (4H, m).

Step 2: Synthesis of 5-(2-chloro-5-methoxyphenyl)-6-(2,6-difluorophenyl)-1-ethyl-3,4-dihydropyridine-2(1H)-one (Compound No. 52)

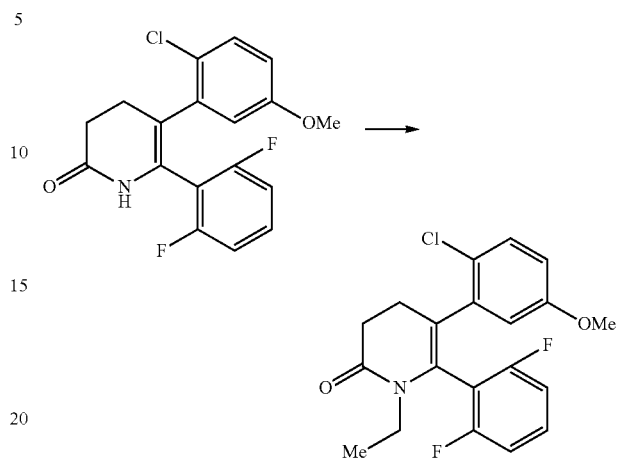

To 5 ml of a DMF solution containing 0.50 g of 5-(2-chloro-5-methoxyphenyl)-6-(2,6-difluorophenyl)-3,4-dihydropyridine-2(1H)-one were added 346 µl of ethyl iodide and 1.41 g of cesium carbonate, and the mixture was stirred at 60° C. for 2 hours. After cooling to room temperature, to the reaction mixture were added water and ethyl acetate to separate the resulting mixture. The obtained organic layer was sequentially washed with an aqueous sodium thiosulfate solution and brine and dried over sodium sulfate. After the solvent was distilled off under reduced pressure, the resulting residue was purified by silica gel column chromatography. The title compound was obtained as 0.54 g of a white solid.

Synthesis Example 2

Synthesis of 5-(2-chloro-5-methoxyphenyl)-6-(2,6-difluorophenyl)-1-ethylpyridine-2(1H)-one (Compound No. 53)

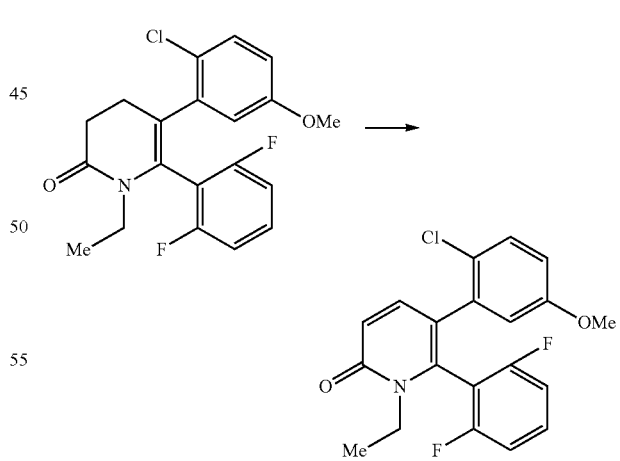

To 20 ml of a carbon tetrachloride solution containing 520 mg of 5-(2-chloro-5-methoxyphenyl)-6-(2,6-difluorophenyl)-1-ethyl-3,4-dihydropyridine-2(1 H)-one were added 258 mg of N-bromosuccinimide and 23 mg of azobisisobutyronitrile, and the mixture was stirred at 80° C. for 90 minutes. After cooling to room temperature, to the reaction mixture was added water, and carbon tetrachloride was distilled off under reduced pressure. After ethyl acetate was added thereto to separate the resulting mixture, the obtained organic layer was sequentially washed with an aqueous sodium thiosulfate solution and brine and dried over sodium sulfate. After the solvent was distilled off under reduced pressure, the resulting residue was purified by silica gel column chromatography. The title compound was obtained as 467 mg of a white solid.

Synthesis Example 3

Synthesis of 3-chloro-5-(2-chloro-5-methoxyphenyl)-6-(2,6-difluorophenyl)-1-ethylpyridine-2(1H)-one (Compound No. 54)

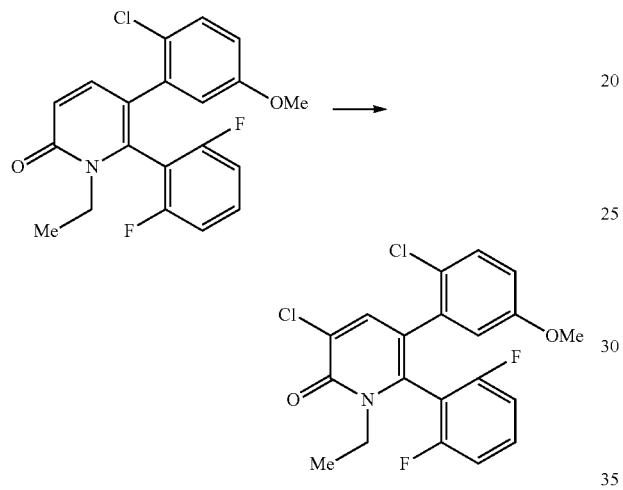

To 2 ml of a DMF solution containing 110 mg of 5-(2-chloro-5-methoxyphenyl)-6-(2,6-difluorophenyl)-1-ethylpyridine-2(1H)-one was added 43 mg of N-chlorosuccinimide, and the mixture was stirred at 70° C. for 1 hour.

After cooling to room temperature, to the reaction mixture were added ethyl acetate and water to separate the resulting mixture. The obtained organic layer was washed with brine and then dried over sodium sulfate. After the solvent was distilled off under reduced pressure, the resulting residue was purified by silica gel column chromatography. The title compound was obtained as 114 mg of a white solid.

Synthesis Example 4

Synthesis of 5-(2-chloro-5-hydroxyphenyl)-6-(2,6-difluorophenyl)-1-ethylpyridine-2(1H)-one (Compound No. 234)

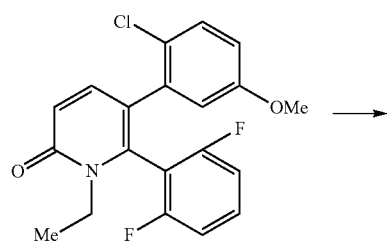

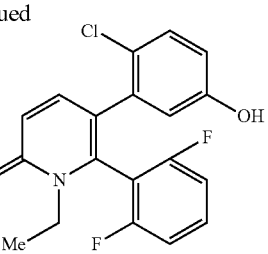

40 ml of a dichloromethane solution containing 4.0 g of 5-(2-chloro-5-methoxyphenyl)-6-(2,6-difluorophenyl)-1-ethylpyridine-2(1H)-one was ice-cooled, and 23.4 ml of a 1.0 mol/l solution of boron tribromide in dichloromethane was added dropwise thereto. After stirring for 30 minutes under ice cooling, to the reaction mixture was added water to separate the resulting mixture. The obtained organic layer was sequentially washed with an aqueous sodium thiosulfate solution and an aqueous saturated sodium bicarbonate solution and dried over sodium sulfate. After the solvent was distilled off under reduced pressure, the resulting residue was washed with hexane. The title compound was obtained as 3.9 g of a white solid.

Synthesis Example 5

Synthesis of 5-(2-chloro-5-(methoxymethoxy)phenyl)-6-(2,6-difluorophenyl)-1-ethylpyridine-2(1H)-one (Compound No. 97)

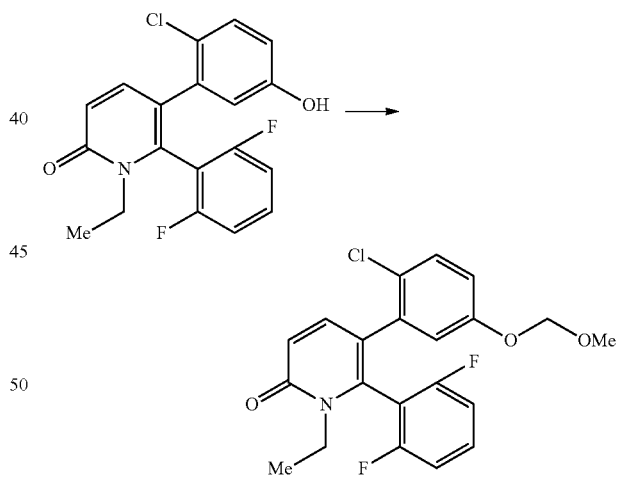

To a THF solution containing 0.08 g of sodium hydride (about 60% by weight, in a dispersed state in liquid paraffin) and 0.62 g of 5-(2-chloro-5-hydroxyphenyl)-6-(2,6-difluorophenyl)-1-ethylpyridine-2(1H)-one was added 0.08 g of chloromethyl methyl ether, and the mixture was stirred at room temperature for 3 hours. After to the reaction mixture were added water and ethyl acetate to separate the resulting mixture, the obtained organic layer was dried over magnesium sulfate. After the solvent was distilled off under reduced pressure, the resulting residue was purified by silica gel column chromatography. The title compound was obtained as 0.46 g of a white solid.

Synthesis Example 6

Synthesis of 3-chloro-5-(2-chloro-5-(methoxymethoxy)phenyl)-6-(2,6-difluorophenyl)-1-ethylpyridine-2(1H)-one (Compound No. 127)

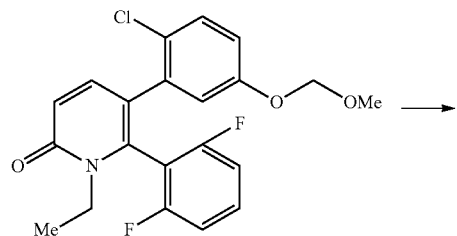

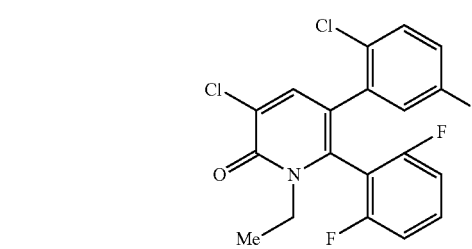

3 ml of a DMF solution containing 219 mg of 5-(2-chloro-5-(methoxymethoxy)phenyl)-6-(2,6-difluorophenyl)-1-ethylpyridine-2(1H)-one and 79 mg of N-chlorosuccinimide was stirred at 70° C. for 1 hour. After cooling to room temperature, to the reaction mixture were added an aqueous saturated sodium bicarbonate solution and ethyl acetate to separate the resulting mixture. The resulting organic layer was sequentially washed with an aqueous sodium thiosulfate solution and brine and dried over sodium sulfate. After the solvent was distilled off under reduced pressure, the resulting residue was purified by silica gel column chromatography. The title compound was obtained as 203 mg of a yellow gum.

Synthesis Example 7

Synthesis of 5-(2-chloro-5-methoxyphenyl)-1-(2,2-difluoroethyl)-6-(2,6-difluorophenyl)-3,4-dihydro-pyridine-2(1H)-one (Compound No. 192)

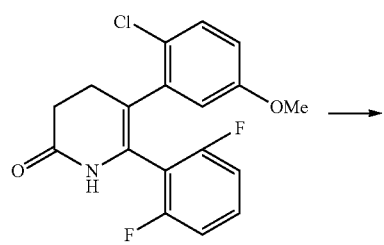

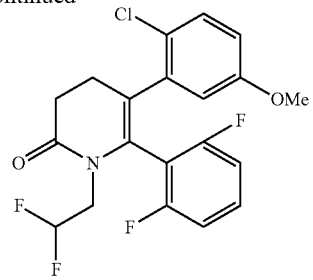

10 ml of a DMF solution containing 0.50 g of 5-(2-chloro-5-methoxyphenyl)-6-(2,6-difluorophenyl)-3,4-dihydropyridine-2(1H)-one, 0.68 g of 2,2-difluoroethyl p-toluenesulfonate, and 1.40 g of cesium carbonate was stirred at 80° C. for 4 hours. After to the reaction mixture were added water and ethyl acetate to separate the resulting mixture, the obtained organic layer was sequentially washed with 1N hydrochloric acid, an aqueous saturated sodium bicarbonate solution and brine and dried over sodium sulfate. After the solvent was distilled off under reduced pressure, the resulting residue was purified by silica gel column chromatography. The title compound was obtained as 0.48 g of a white solid.

Synthesis Example 8

Synthesis of 5-(2-chloro-5-methoxyphenyl)-1-(2,2-difluoroethyl)-6-(2,6-difluorophenyl)pyridine-2(1H)-one (Compound No. 194)

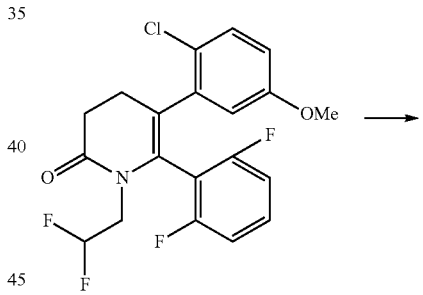

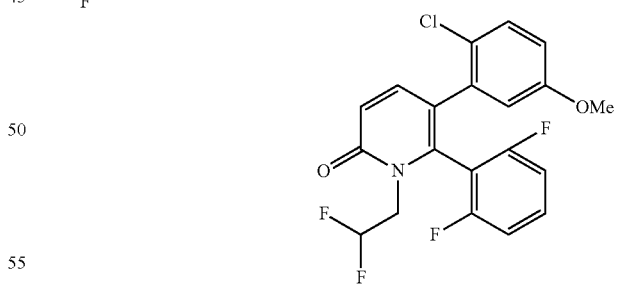

To 15 ml of a carbon tetrachloride solution containing 0.42 g of 5-(2-chloro-5-methoxyphenyl)-1-(2,2-difluoroethyl)-6-(2,6-difluorophenyl)-3,4-dihydro pyridine-2(1H)-one were added 190 mg of N-bromosuccinimide and 16 mg of azobisisobutyronitrile, and the mixture was stirred at 80° C. for 15 minutes. After cooling to room temperature, to the reaction mixture was added water, and carbon tetrachloride was distilled off under reduced pressure. After ethyl acetate was added thereto to separate the resulting mixture, the obtained organic layer was sequentially washed with an aqueous sodium thiosulfate solution and brine and dried over sodium sulfate. After the solvent was distilled off under reduced pressure, the resulting residue was purified by silica gel column chromatography. The title compound was obtained as 0.38 g of a white solid.

Synthesis Example 9

Synthesis of 3-bromo-5-(2-chloro-5-methoxyphenyl)-1-(2,2-difluoroethyl)-6-(2,6-difluorophenyl)pyridine-2(1H)-one (Compound No. 198)

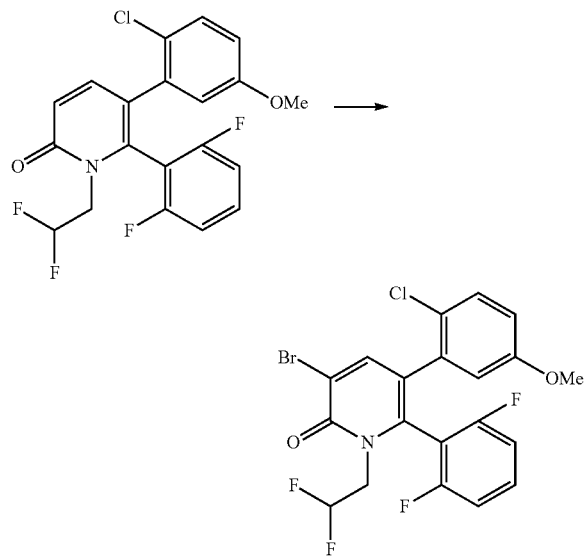 [SMILES: COc1ccc(Cl)c(C2=C(c3c(F)cccc3F)NC(=O)CC2)c1 ; COc1ccc(Cl)c(C2=C(c3c(F)cccc3F)N(CC(F)F)C(=O)CC2)c1]

5 ml of a DMF solution containing 125 mg of 5-(2-chloro-5-methoxyphenyl)-1-(2,2-difluoroethyl)-6-(2,6-difluorophenyl)pyridine-2(1H)-one and 65 mg of N-bromosuccinimide was stirred at 70° C. for 2 hours. 27 mg of N-bromosuccinimide was additionally added thereto, and the mixture was further stirred at 70° C. for 2 hours. After cooling to room temperature, to the reaction mixture were added water and ethyl acetate to separate the resulting mixture. The obtained organic layer was sequentially washed with an aqueous sodium thiosulfate solution and brine and dried over sodium sulfate. After the solvent was distilled off under reduced pressure, the resulting residue was purified by silica gel column chromatography. The title compound was obtained as 109 mg of an off-white solid.

Synthesis Example 10

Synthesis of 5-(2-chloro-5-methoxyphenyl)-6-(2,6-difluorophenyl)-1-ethyl-3-methyl-3,4-dihydropyridine-2(1H)-one

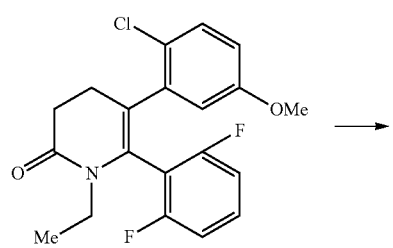

-continued

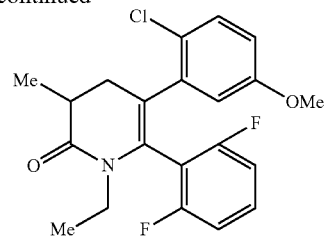

10 ml of a THF solution containing 500 mg of 5-(2-chloro-5-methoxyphenyl)-6-(2,6-difluorophenyl)-1-ethyl-3,4-dihydropyridine-2(1H)-one was cooled to −78° C., 1.33 ml of a 1.09 mol/l solution of lithium diisopropylamide in THF was added dropwise thereto, and the mixture was stirred at the same temperature for 30 minutes. Subsequently, 2 ml of a THF solution containing 82 μl of methyl iodide was added dropwise thereto, the mixture was stirred at −78° C. for 2 hours, and then the temperature was raised to room temperature. After further stirring at room temperature for 2 hours, to the reaction mixture were added a saturated aqueous ammonium chloride solution and ethyl acetate to separate the resulting mixture. The obtained organic layer was washed with brine and dried over sodium sulfate. After the solvent was distilled off under reduced pressure, the resulting residue was purified by silica gel column chromatography. The title compound was obtained as 101 mg of a white solid. And, the resulting title compound was a stereoisomeric mixture.

$^1$H-NMR (CDCl$_3$) δ: 7.24-7.17 (1H, m:mixture), 7.15-7.13 (1H, m:mixture), 6.87-6.71 (2H, m:mixture), 6.57-6.49 (2H, m:mixture), 3.70-3.14 (2H, m:mixture), 3.65 (3H, s:major), 3.58 (3H, s:minor), 2.98-2.70 (2H, m:mixture), 2.46-2.37 (1H, m:mixture), 1.35 (3H, d, J=6.7 Hz:minor), 1.33 (3H, d, J=7.0 Hz:major), 1.00-0.96 (3H, m). Stereoisomeric mixture ratio: about 57:43

Synthesis Example 11

Synthesis of 5-(2-chloro-5-methoxyphenyl)-6-(2,6-difluorophenyl)-1-ethyl-3-methylpyridine-2(1H)-one (Compound No. 329)

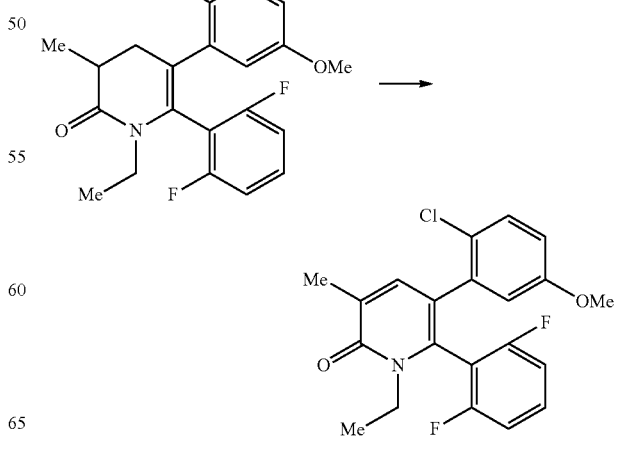

10 ml of a dichloromethane solution containing 413 mg of 5-(2-chloro-5-methoxyphenyl)-6-(2,6-difluorophenyl)-1-ethyl-3-methyl-3,4-dihydropyridine-2(1H)-one and 5.48 g of manganese dioxide was stirred for 11 hours under heating at reflux. Further, 1.83 g of manganese dioxide was added, and the mixture was stirred under heating at reflux for 3 hours. After cooling to room temperature, the reaction mixture was filtered over Celite. After the solvent was distilled off from the filtrate under reduced pressure, the resulting residue was purified by silica gel column chromatography. The title compound was obtained as 291 mg of a white solid.

Synthesis Example 12

Step 1: Synthesis of 5-(2-chloro-5-fluorophenyl)-6-(2,4,6-trifluorophenyl)-3,4-dihydropyridine-2(1H)-one

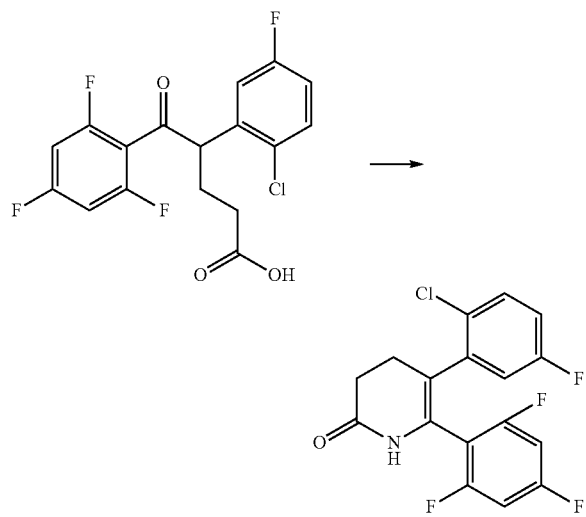

25 ml of an acetic acid solution containing 4.46 g of 4-(2-chloro-5-fluorophenyl)-5-oxo-5-(2,4,6-trifluorophenyl)pentanoic acid and 45.9 g of ammonium acetate was stirred at 130° C. for 2 hours. After cooling to room temperature, to the reaction mixture were added ethyl acetate and water to separate the resulting mixture. To the obtained organic layer was added water, and furthermore potassium carbonate was added until bubble releasing subsided, and the resulting mixture was separated. Subsequently, the organic layer was washed with brine and dried over sodium sulfate. The solvent was distilled off under reduced pressure, and the precipitate was washed with diisopropyl ether. The resulting white solid was the title compound, which was 2.24 g in weight. And, after the solvent of the filtrate formed after washing the precipitate was distilled off under reduced pressure, the resulting residue was purified by silica gel column chromatography. The white solid obtained from the filtrate was also the title compound, which was 0.46 g in weight.

$^1$H-NMR (CDCl$_3$) δ: 7.28-7.26 (1H, m), 7.18 (1H, br s), 6.86-6.83 (1H, m), 6.74-6.72 (1H, m), 6.61-6.59 (2H, br m), 2.85-2.74 (4H, br m).

Step 2: Synthesis of 5-(2-chloro-5-fluorophenyl)-1-ethyl-6-(2,4,6-trifluorophenyl)-3,4-dihydropyridine-2(1H)-one (Compound No. 320)

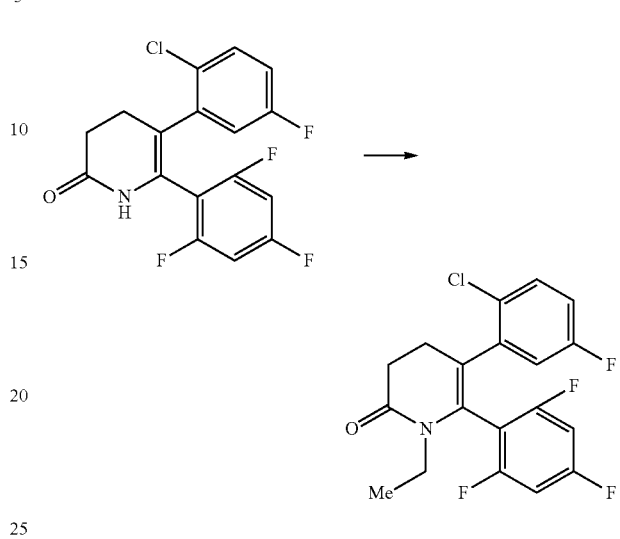

32 ml of a DMF solution containing 2.70 g of 5-(2-chloro-5-fluorophenyl)-6-(2,4,6-trifluorophenyl)-3,4-dihydropyridine-2(1H)-one, 7.42 g of cesium carbonate and 3.55 g of ethyl iodide was stirred at 55° C. for 2 hours. After cooling to room temperature, to the reaction mixture were added ethyl acetate and water to separate the resulting mixture. The obtained organic layer was washed with brine and dried over sodium sulfate. After the solvent was distilled off under reduced pressure, the resulting residue was purified by silica gel column chromatography. The title compound was obtained as 2.47 g of a reddish purple gum.

Synthesis Example 13

Synthesis of 5-(2-chloro-5-fluorophenyl)-1-ethyl-6-(2,4,6-trifluorophenyl)pyridine-2(1H)-one (Compound No. 321)

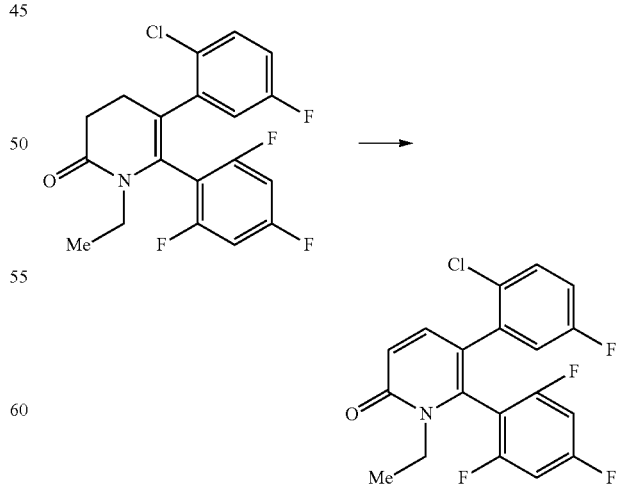

5 ml of a toluene solution containing 0.21 g of 5-(2-chloro-5-fluorophenyl)-1-ethyl-6-(2,4,6-trifluorophenyl)-3,4-dihydropyridine-2(1H)-one and 1.42 g of manganese dioxide was stirred at 90° C. for 5 hours. After cooling to room temperature, the reaction mixture was filtered over Celite. The solvent was distilled off from the filtrate under reduced pressure, and then the resulting residue was purified by silica gel column chromatography. The title compound was obtained as 0.14 g of a white solid.

Synthesis Example 14

Synthesis of 3-bromo-5-(2-chloro-5-fluorophenyl)-1-ethyl-6-(2,4,6-trifluorophenyl)pyridine-2(1H)-one (Compound No. 381)

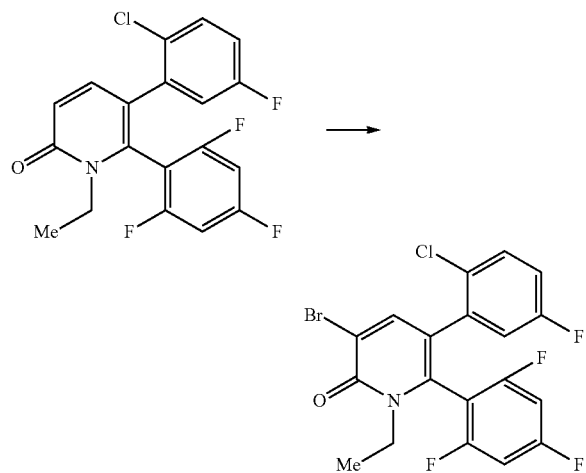

30 ml of a DMF solution containing 0.60 g of 5-(2-chloro-5-fluorophenyl)-1-ethyl-6-(2,4,6-trifluorophenyl)pyridine-2(1H)-one and 0.33 g of N-bromosuccinimide was stirred at 75° C. for 2.5 hours. Furthermore, 0.10 g of N-bromosuccinimide was added, and the mixture was stirred at 75° C. for 1.5 hours. After cooling to room temperature, to the reaction mixture were added water and ethyl acetate to separate the resulting mixture. The obtained organic layer was washed with brine and then dried over sodium sulfate. After the solvent was distilled off under reduced pressure, the resulting residue was purified by silica gel column chromatography. The title compound was obtained as 0.64 g of a white solid.

Synthesis Example 15

Synthesis of 5-(2-chloro-5-fluorophenyl)-1-ethyl-3-methyl-6-(2,4,6-trifluorophenyl)pyridine-2(1H)-one (Compound No. 461)

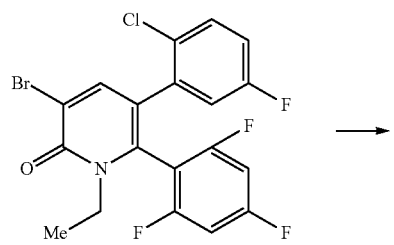

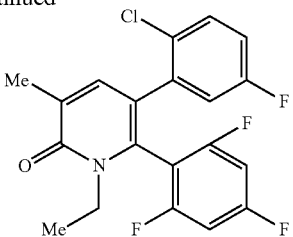

A mixed solution of 8 ml of toluene and 0.8 ml of water containing 250 mg of 3-bromo-5-(2-chloro-5-fluorophenyl)-1-ethyl-6-(2,4,6-trifluorophenyl)pyridine-2(1H)-one, 49 mg of methylboronic acid, 6 mg of palladium(II) acetate, 403 mg of tripotassium phosphate, and 15 mg of tricyclohexylphosphine was stirred at 100° C. for 7 hours. After cooling to room temperature, to the reaction mixture were added water and ethyl acetate to separate the resulting mixture. The obtained organic layer was washed with brine and then dried over sodium sulfate. After the solvent was distilled off under reduced pressure, the resulting residue was purified by silica gel column chromatography. The title compound was obtained as 116 mg of a white solid.

Synthesis Example 16

Synthesis of 3-bromo-5-(2-chloro-5-fluorophenyl)-6-(2,6-difluoro-4-methoxyphenyl)-1-ethylpyridine-2(1H)-one (Compound No. 476)

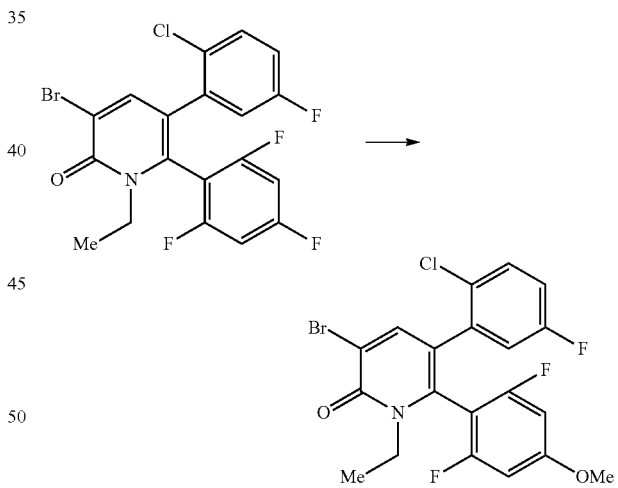

To 8 ml of a methanol solution of 300 mg of 3-bromo-5-(2-chloro-5-fluorophenyl)-1-ethyl-6-(2,4,6-trifluorophenyl)pyridine-2(1H)-one was added 0.63 ml of 28% by weight of sodium methoxide in methanol, and the mixture was stirred under heating at reflux for 13 hours. After cooling to room temperature, to the reaction mixture were added a saturated aqueous ammonium chloride solution and ethyl acetate to separate the resulting mixture. The obtained organic layer was washed with brine and dried over sodium sulfate. After the solvent was distilled off under reduced pressure, the resulting residue was purified by silica gel column chromatography. The title compound was obtained as 271 mg of a white solid.

Synthesis Example 17

Step 1: Synthesis of 5-(3,5-dimethoxyphenyl)-6-(2,4,6-trifluorophenyl)-3,4-dihydropyridine-2(1H)-one

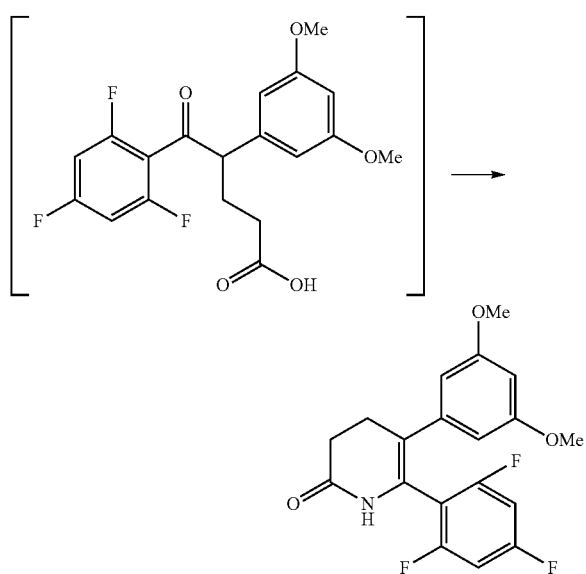

To the unpurified 4-(3,5-dimethoxyphenyl)-5-oxo-5-(2,4,6-trifluorophenyl)pentanoic acid obtained in Reference Example 3 were added 14.18 g of ammonium acetate and 15 ml of acetic acid, and the mixture was stirred at 120° C. for 10 hours. After cooling to room temperature, to the reaction mixture were added water and ethyl acetate to separate the resulting mixture. The obtained organic layer was sequentially washed with an aqueous saturated sodium bicarbonate solution and brine and dried over sodium sulfate. After the solvent was distilled off under reduced pressure, to the resulting solid was added isopropyl ether, and the solution was washed. The title compound was obtained as 0.99 g of a brown solid.

$^1$H-NMR (CDCl$_3$) δ: 6.68 (1H, s), 6.62 (2H, td, J=8.7, 1.4 Hz), 6.26 (1H, t, J=2.1 Hz), 6.16 (2H, d, J=2.1 Hz), 3.65 (6H, s), 2.87-2.86 (2H, m), 2.73-2.71 (2H, m).

Step 2: Synthesis of 5-(3,5-dimethoxyphenyl)-1-methyl-6-(2,4,6-trifluorophenyl)-3,4-dihydropyridine-2(1H)-one

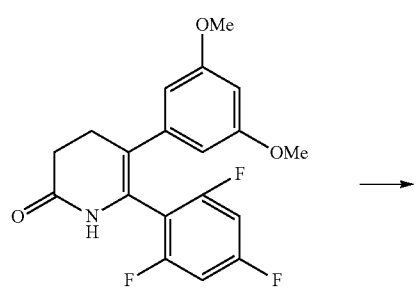

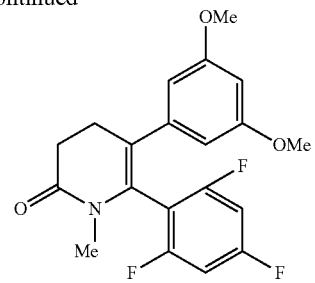

6 ml of a DMF solution containing 343 mg of 5-(3,5-dimethoxyphenyl)-6-(2,4,6-trifluorophenyl)-3,4-dihydropyridine-2(1H)-one, 176 μl of methyl iodide, and 1.85 g of cesium carbonate was stirred at room temperature for 3 hours. To the reaction mixture were added water and ethyl acetate to separate the resulting mixture. The obtained organic layer was sequentially washed with water, an aqueous sodium thiosulfate solution and brine, and dried over sodium sulfate. After the solvent was distilled off under reduced pressure, the resulting residue was purified by silica gel column chromatography. The title compound was obtained as 346 mg of a white solid.

$^1$H-NMR (CDCl$_3$) δ: 6.62-6.60 (2H, m), 6.23 (1H, t, J=2.1 Hz), 6.13 (2H, d, J=2.1 Hz), 3.65 (6H, s), 2.87 (3H, s), 2.76-2.74 (4H, m).

Synthesis Example 18

Synthesis of 5-(3,5-dimethoxyphenyl)-1-methyl-6-(2,4,6-trifluorophenyl)pyridine-2(1H)-one (Compound No. 134)

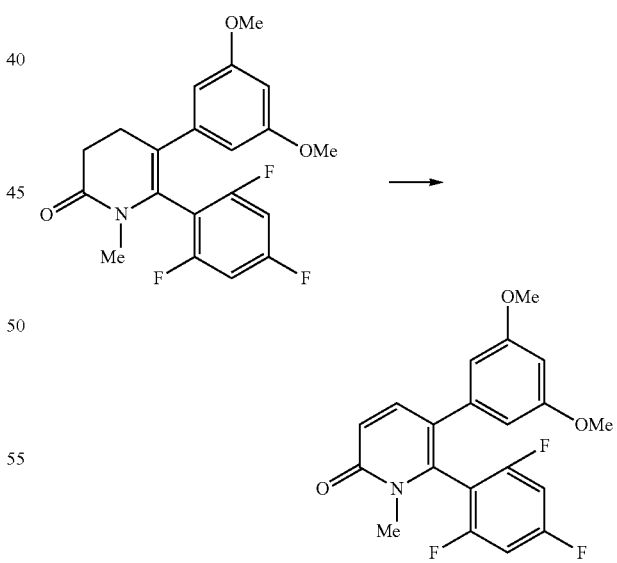

12 ml of a dichloromethane solution containing 320 mg of 5-(3,5-dimethoxyphenyl)-1-methyl-6-(2,4,6-trifluorophenyl)-3,4-dihydropyridine-2(1H)-one and 4.42 g of manganese dioxide was stirred under heating at reflux for 5 hours. After cooling to room temperature, the reaction mixture was filtered over Celite. After the solvent was distilled off from the filtrate under reduced pressure, the resulting residue was purified by silica gel column chromatography. The title compound was obtained as 263 mg of a white solid.

Synthesis Example 19

Synthesis of 5-(2-chloro-3,5-dimethoxyphenyl)-1-methyl-6-(2,4,6-trifluorophenyl)pyridine-2(1H)-one (Compound No. 136)

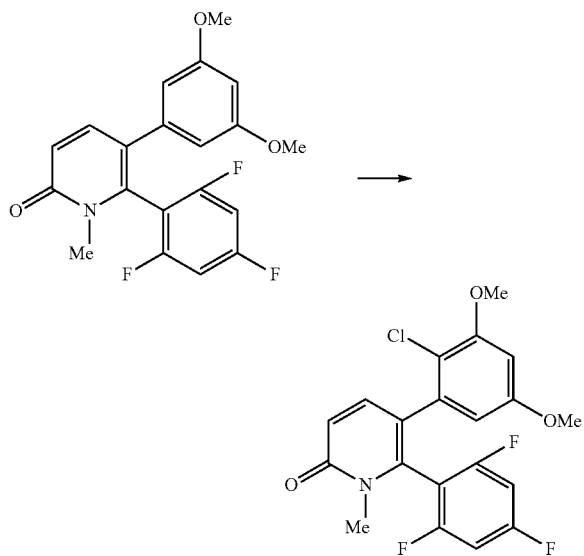

6 ml of a DMF solution containing 163 mg of 5-(3,5-dimethoxyphenyl)-1-methyl-6-(2,4,6-trifluorophenyl)pyridine-2(1H)-one and 64 mg of N-chlorosuccinimide was stirred at 80° C. for 5 hours. Further, 45 mg of N-chlorosuccinimide was added, and the mixture was stirred at 100° C. for 4 hours. After cooling to room temperature, to the reaction mixture were added water and ethyl acetate to separate the resulting mixture. The obtained organic layer was sequentially washed with an aqueous sodium thiosulfate solution and brine, and dried over sodium sulfate. After the solvent was distilled off under reduced pressure, the resulting residue was purified by silica gel column chromatography. The title compound was obtained as 150 mg of a white solid.

Reference Example 1

Step 1: Synthesis of 2-(2-chloro-5-methoxyphenyl)-1-(2,6-difluorophenyl)ethanone

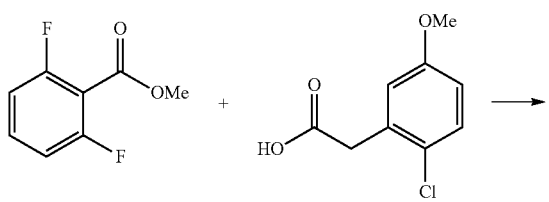

-continued

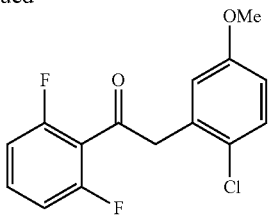

After 30 ml of a THF solution containing 2.05 g of 2-(2-chloro-5-methoxyphenyl)acetic acid was cooled to −78° C., 17.21 ml of 1.9 mol/L of a THF solution of hexamethyldisilazane sodium was added dropwise thereto at −50° C. or lower, and the mixture was stirred at −78° C. for 40 minutes. After 10 ml of a THF solution containing 1.76 g of methyl 2,6-difluorobenzoate was added dropwise thereto at −78° C., the temperature was allowed to warm to room temperature, and the mixture was stirred for 1.5 hours. To the reaction mixture was added a saturated aqueous ammonium chloride solution, the mixture was stirred, and then ethyl acetate was added to separate the resulting mixture. The obtained organic layer was washed with brine and dried over sodium sulfate. After the solvent was distilled off under reduced pressure, the resulting residue was purified by silica gel column chromatography to obtain the title compound as 2.58 g of a yellow oil.
$^1$H-NMR (CDCl$_3$) δ: 7.40-7.38 (1H, m), 7.28-7.27 (1H, m), 6.96-6.94 (2H, m), 6.83 (1H, d, J=3.1 Hz), 6.78 (1H, dd, J=8.9, 3.1 Hz), 4.27 (2H, s), 3.79 (3H, s).

Step 2: Synthesis of ethyl 4-(2-chloro-5-methoxyphenyl)-5-(2,6-difluorophenyl)-5-oxopentanoate

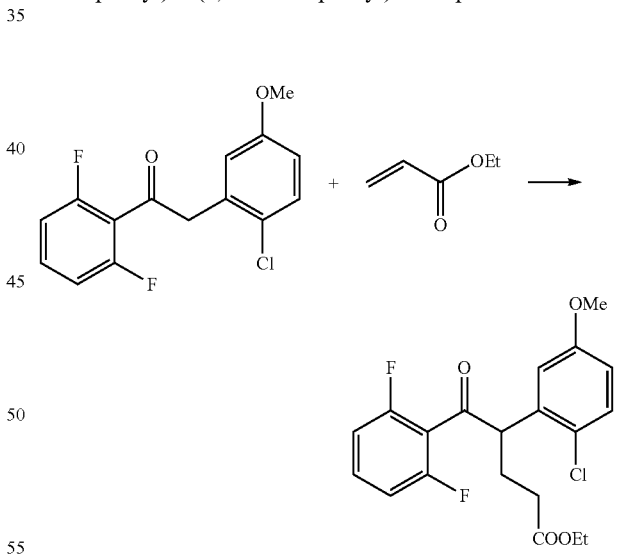

To 15 ml of a THF solution containing 1.30 g of 2-(2-chloro-5-methoxyphenyl)-1-(2,6-difluorophenyl)ethanone were added 98 mg of potassium t-butoxide and 525 μl of ethyl acrylate, and the mixture was stirred overnight under ice cooling. After to the reaction mixture were added 1N hydrochloric acid and ethyl acetate to separate the resulting mixture, the obtained organic layer was washed with brine and dried over sodium sulfate. After the solvent was distilled off under reduced pressure, the title compound was obtained as 1.69 g of a yellow oil, which was used in the next step without further purification.

¹H-NMR (CDCl₃) δ: 7.36-7.25 (1H, m), 7.19 (1H, d, J=8.9 Hz), 6.83 (2H, t, J=8.1 Hz), 6.74-6.71 (2H, m), 4.91 (1H, t, J=7.2 Hz), 4.13 (2H, q, J=7.1 Hz), 3.76 (3H, s), 2.57-2.53 (1H, m), 2.42-2.29 (2H, m), 2.16-2.07 (1H, m), 1.25 (3H, t, J=7.1 Hz).

Step 3: Synthesis of 4-(2-chloro-5-methoxyphenyl)-5-(2,6-difluorophenyl)-5-oxopentanoic Acid

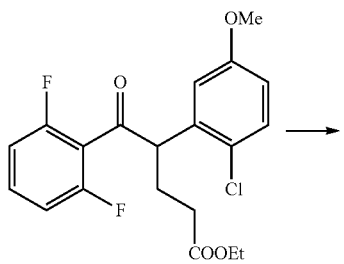

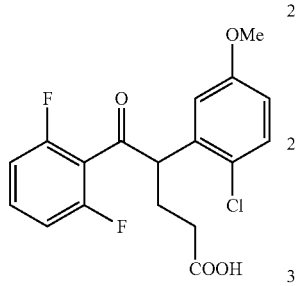

To a mixed solution of 40 ml of THF and 10 ml of water containing 1.69 g of ethyl 4-(2-chloro-5-methoxyphenyl)-5-(2,6-difluorophenyl)-5-oxopentanoate was added 0.74 g of lithium hydroxide monohydrate, and the mixture was stirred at 60° C. for 3 hours. After cooling to room temperature, the solvent of the reaction mixture was distilled off until the liquid volume was reduced by half. Water and diethyl ether were added thereto to separate the resulting mixture. To the obtained aqueous layer were added concentrated hydrochloric acid and ethyl acetate to separate the resulting mixture. The obtained organic layer was washed with brine and dried over sodium sulfate. Subsequently, after the solvent was distilled off under reduced pressure, the title compound was obtained as 1.47 g of a yellow gum, which was used in the next step without further purification.

¹H-NMR (CDCl₃) δ: 7.28-7.27 (1H, m), 7.19 (1H, d, J=8.6 Hz), 6.83 (2H, t, J=8.3 Hz), 6.75-6.74 (1H, m), 6.71 (1H, dd, J=8.6, 3.1 Hz), 4.92 (1H, t, J=7.3 Hz), 3.75 (3H, s), 2.60-2.34 (3H, m), 2.15-2.12 (1H, m).

Reference Example 2

Step 1: Synthesis of N'-(2-chloro-5-fluorobenzylidene)-4-methylbenzenesulfonylhydrazide

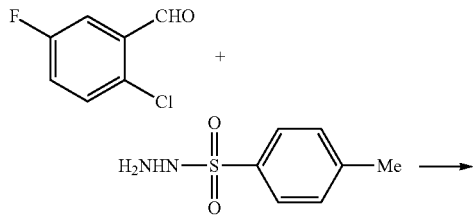

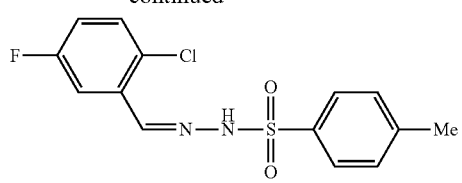

250 ml of an ethanol solution containing 25.43 g of 2-chloro-5-fluorobenzaldehyde and 29.87 g of 4-methylbenzenesulfonylhydrazide was stirred at room temperature for 4 hours. Subsequently, the reaction mixture was stirred under ice cooling for 1 hour, and then the precipitate was filtered to obtain 40.74 g of the title compound as a white solid.

¹H-NMR (CDCl₃) δ: 8.27 (1H, s), 8.10 (1H, d, J=1.8 Hz), 7.88 (21-1, d, J=8.2 Hz), 7.58 (1H, dd, J=9.2, 3.1 Hz), 7.34 (2H, d, J=8.2 Hz), 7.30-7.28 (1H, m), 7.02-6.99 (1H, m), 2.43 (3H, s).

Step 2: Synthesis of 2-(2-chloro-5-fluorophenyl)-1-(2,4,6-trifluorophenyl)ethanone

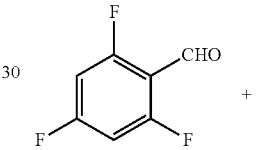

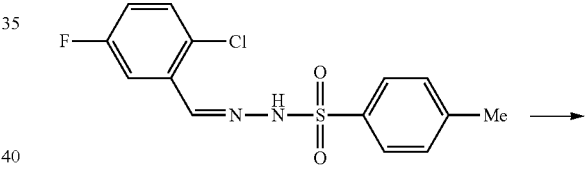

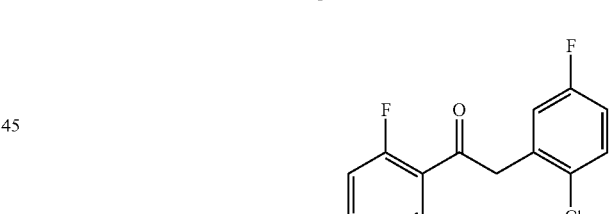

To 600 ml of an aqueous solution containing 4.0 g of sodium hydroxide were added 32.7 g of N'-(2-chloro-5-fluorobenzylidene)-4-methylbenzenesulfonylhydrazide and 8.0 g of 2,4,6-trifluorobenzaldehyde, and the mixture was stirred at 80° C. for 1 hour. After cooling to room temperature, to the reaction mixture were added ethyl acetate and 15.0 g of ammonium chloride, and the resulting mixture was stirred and separated. The obtained organic layer was washed with brine and dried over sodium sulfate. The solvent was distilled off under reduced pressure, and the resulting residue was purified by silica gel column chromatography. The title compound was obtained as 6.13 g of a pale yellow solid.

¹H-NMR (CDCl₃) δ: 7.36-7.34 (1H, m), 7.04-7.02 (1H, m), 6.98-6.96 (1H, m), 6.76-6.72 (2H, m) 4.26 (2H, s).

Step 3: Synthesis of ethyl 4-(2-chloro-5-fluorophenyl)-5-oxo-5-(2,4,6-trifluorophenyl)pentanoate

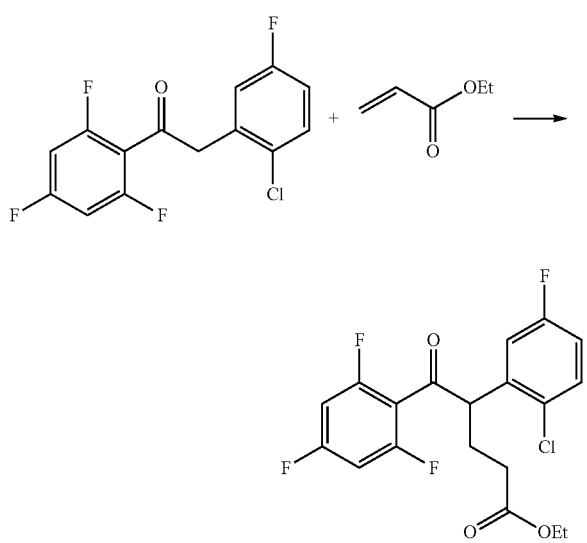

75 ml of a THF solution containing 6.13 g of 2-(2-chloro-5-fluorophenyl)-1-(2,4,6-trifluorophenyl)ethanone was ice-cooled, 0.45 g of potassium t-butoxide and 2.23 g of ethyl acrylate were added, and the mixture was stirred at room temperature for 8 hours. After to the reaction mixture was added 10% hydrochloric acid, water and ethyl acetate were added to separate the resulting mixture. The obtained organic layer was washed with brine and then dried over sodium sulfate. The solvent was distilled off under reduced pressure, and the resulting residue was purified by silica gel column chromatography. The title compound was obtained as 4.97 g of a pale yellow oil. $^1$H-NMR (CDCl$_3$) δ: 7.30 (1H, dd, J=8.9, 5.2 Hz), 7.01-6.98 (1H, m), 6.92-6.90 (1H, m), 6.66-6.60 (2H, m), 4.89 (1H, t, J=7.2 Hz), 4.13 (2H, q, J=7.2 Hz), 2.54-2.52 (1H, m), 2.35-2.31 (2H, m), 2.12-2.09 (1H, m), 1.25 (3H, t, J=7.2 Hz).

Step 4: Synthesis of 4-(2-chloro-5-fluorophenyl)-5-oxo-5-(2,4,6-trifluorophenyl)pentanoic Acid

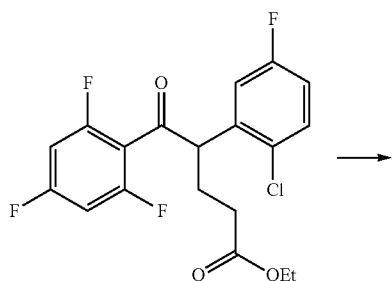

-continued

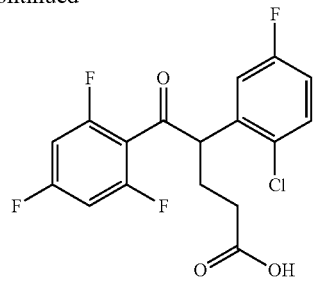

To 100 ml of a THF solution containing 4.97 g of ethyl 4-(2-chloro-5-fluorophenyl)-5-oxo-5-(2,4,6-trifluorophenyl)pentanoate were added 25 ml of water and 2.59 g of lithium hydroxide monohydrate, and the mixture was stirred at 60° C. for 2 hours. After cooling to room temperature, the solvent of the reaction mixture was distilled off under reduced pressure. Water and diethyl ether were added thereto to separate the resulting mixture. Subsequently, the obtained aqueous layer was acidified by adding concentrated hydrochloric acid and then extracted with ethyl acetate. The obtained organic layer was washed with brine and dried over sodium sulfate. The solvent was distilled off under reduced pressure, and the title compound was obtained as 4.46 g of a colorless transparent gum, which was used in the next step without further purification.

$^1$H-NMR (CDCl$_3$) δ: 7.32-7.29 (1H, m), 7.00-6.97 (1H, m), 6.94-6.89 (1H, m), 6.64-6.60 (2H, m), 4.89 (1H, t, J=7.2 Hz), 2.58-2.06 (4H, m).

Reference Example 3

Step 1: Synthesis of N'-(3,5-dimethoxybenzylidene)-4-methylbenzenesulfonylhydrazide

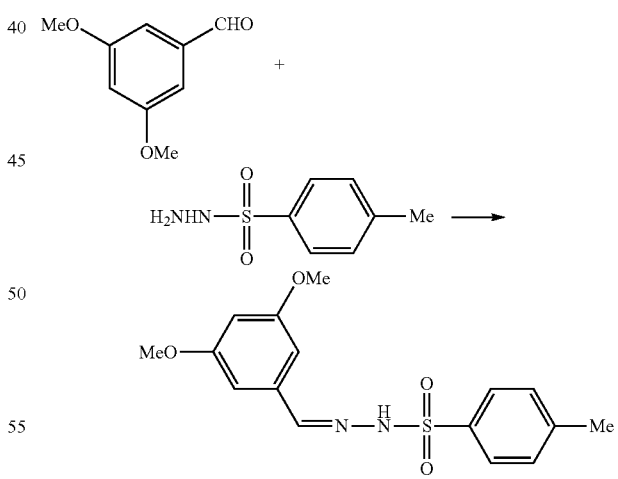

100 ml of an ethanol solution containing 10.0 g of 3,5-dimethoxybenzaldehyde and 11.2 g of 4-methylbenzenesulfonylhydrazide was stirred at room temperature for 5 hours. After the solvent of the resulting reaction mixture was distilled off under reduced pressure, the title compound was obtained as 20.0 g of a yellow solid.

$^1$H-NMR (CDCl$_3$) δ: 8.13 (1H, s), 7.87 (2H, d, J=7.8 Hz), 7.68 (1H, s), 7.30 (2H, d, J=7.8 Hz), 6.72 (2H, d, J=2.4 Hz), 6.46 (1H, t, J=2.4 Hz), 3.79 (6H, s), 2.40 (3H, s).

Step 2: Synthesis of 2-(3,5-dimethoxyphenyl)-1-(2,4,6-trifluorophenyl)ethanone

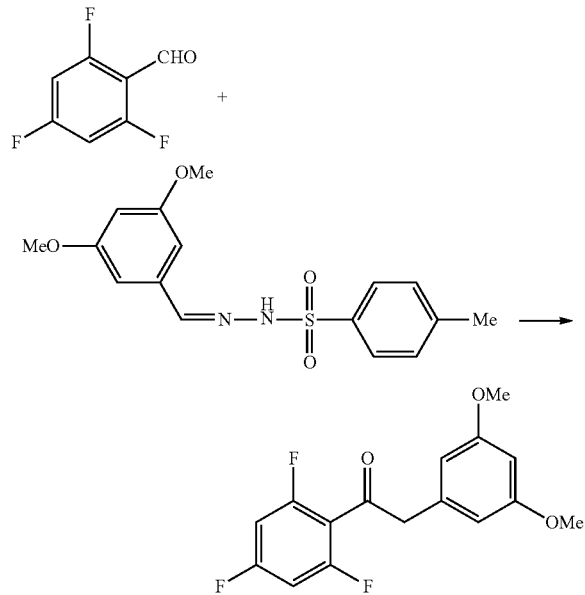

To 100 ml of an aqueous solution containing 6.68 g of N'-(3,5-dimethoxybenzylidene)-4-methylbenzenesulfonyl-hydrazide were added 20 ml of a solution of 0.80 g of sodium hydroxide dissolved in water and 1.60 g of 2,4,6-trifluorobenzaldehyde, and the mixture was stirred at 80° C. for 90 minutes. After cooling to room temperature, to the reaction mixture was added ethyl acetate to separate the resulting mixture. The obtained organic layer was sequentially washed with a saturated aqueous ammonium chloride solution and brine and dried over sodium sulfate. The solvent was distilled off under reduced pressure, and the resulting residue was purified by silica gel column chromatography. The title compound was obtained as 1.85 g of a yellow oil.

$^1$H-NMR (CDCl$_3$) δ: 6.68-6.66 (2H, m), 6.35 (3H, s), 4.06 (2H, s), 3.75 (6H, s).

Step 3: Synthesis of ethyl 4-(3,5-dimethoxyphenyl)-5-oxo-5-(2,4,6-trifluorophenyl)pentanoate

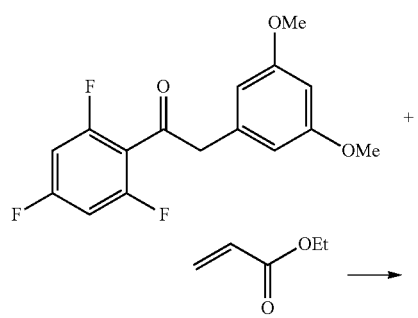

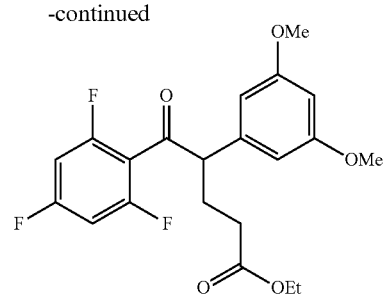

To 18 ml of a THF solution containing 1.85 g of 2-(3,5-dimethoxyphenyl)-1-(2,4,6-trifluorophenyl)ethanone were added 67 mg of potassium t-butoxide and 714 μl of ethyl acrylate, and the mixture was stirred under ice cooling overnight. To the reaction mixture were added a saturated aqueous ammonium chloride solution and ethyl acetate to separate the resulting mixture. The obtained organic layer was washed with brine and then dried over sodium sulfate. The solvent was distilled off under reduced pressure, and the resulting residue was purified by silica gel column chromatography. The title compound was obtained as 1.51 g of a brown oil.

$^1$H-NMR (CDCl$_3$) δ: 6.61-6.57 (2H, m), 6.31-6.29 (3H, m), 4.19 (1H, t, J=7.3 Hz), 4.13 (2H, q, J=7.1 Hz), 3.73 (6H, s), 2.49-2.47 (1H, m), 2.30 (2H, t, J=7.5 Hz), 2.09-2.07 (1H, m), 1.25 (3H, t, J=7.1 Hz)

Step 4: Synthesis of 4-(3,5-dimethoxyphenyl)-5-oxo-5-(2,4,6-trifluorophenyl)pentanoic Acid

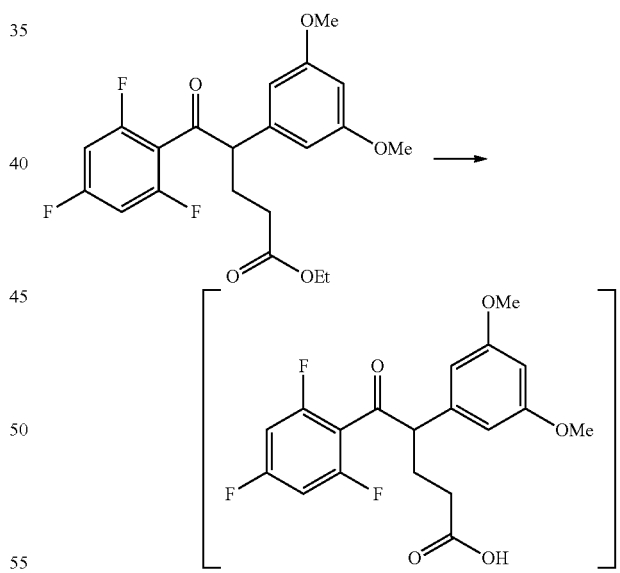

15 ml of an acetic acid solution containing 1.51 g of ethyl 4-(3,5-dimethoxyphenyl)-5-oxo-5-(2,4,6-trifluorophenyl) pentanoate and 3 ml of concentrated hydrochloric acid was stirred at 60° C. for 3 hours. After cooling to room temperature, to the reaction mixture were added water and ethyl acetate to separate the resulting mixture. The obtained organic layer was sequentially washed with water and brine and dried over sodium sulfate. The solvent was distilled off under reduced pressure, and the title compound was obtained, which was used in the next step without further purification.

Table 4 shows compounds synthesized according to the above-described Examples, but which are not limitative.

The structure A is depicted as follows.

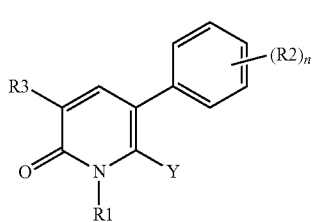

The structure B is depicted as follows.

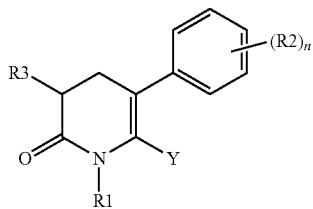

The structure C is depicted as follows.

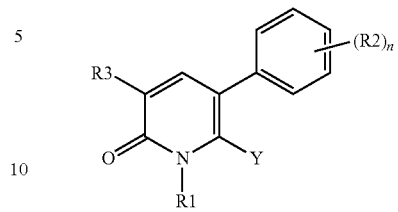

The structure D is depicted as follows.

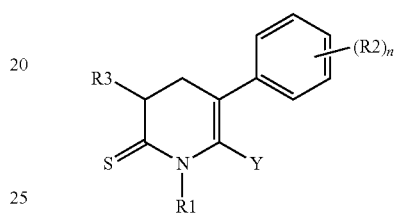

TABLE 4

| Compound | Structure | R1 | Y | (R2)n | R3 |
|---|---|---|---|---|---|
| 1 | B | Me | 3,5-di-Cl-2-Py | — | H |
| 2 | A | Me | 3,5-di-Cl-2-Py | — | H |
| 3 | B | Me | 3,5-di-Cl-2-Py | 2,6-di-F— | H |
| 4 | B | Et | 3,5-di-Cl-2-Py | 2,6-di-F— | H |
| 5 | A | Me | 3,5-di-Cl-2-Py | 2,6-di-F— | H |
| 6 | A | Et | 3,5-di-Cl-2-Py | 2,6-di-F— | H |
| 7 | A | Me | 3-Cl-5-MeO-2-Py | 2,6-di-F— | H |
| 8 | A | Et | 3-Cl-5-MeO-2-Py | 2,6-di-F— | H |
| 9 | A | Me | 3-Cl-5-MeO-2-Py | — | H |
| 10 | A | Et | 3,5-di-Cl-2-Py | — | H |
| 11 | A | Et | 3-Cl-5-MeO-2-Py | — | H |
| 12 | A | Me | 3-Cl-4-Py | — | H |
| 13 | A | Et | 3-Cl-4-Py | — | H |
| 14 | A | Et | 2,6-di-F—Ph | 3,5-di-MeO— | H |
| 15 | B | Et | 2,6-di-F—Ph | 3,5-di-MeO— | H |
| 16 | A | Et | 2,6-di-F—Ph | 2-Br-3,5-di-MeO— | H |
| 17 | B | Me | 2,6-di-F—Ph | 4-F— | H |
| 18 | B | Et | 2,6-di-F—Ph | 4-F— | H |
| 19 | A | Me | 2,6-di-F—Ph | 4-F— | H |
| 20 | A | Et | 2,6-di-F—Ph | 4-F— | H |
| 21 | B | Me | 3,5-di-Cl-2-Py | 4-F— | H |
| 22 | A | Me | 3,5-di-Cl-2-Py | 4-F— | Br |
| 23 | A | Me | 3,5-di-Cl-2-Py | 4-F— | H |
| 24 | B | Et | 3,5-di-Cl-2-Py | 4-F— | H |
| 25 | A | Et | 3,5-di-Cl-2-Py | 4-F— | Br |
| 26 | A | Et | 3,5-di-Cl-2-Py | 4-F— | H |
| 27 | B | Me | 2,6-di-F—Ph | 3,5-di-MeO— | H |
| 28 | A | Me | 2,6-di-F—Ph | 3,5-di-MeO— | H |
| 29 | A | Me | 2,6-di-F—Ph | 2-Br-3,5-di-MeO— | H |
| 30 | A | Me | 2,6-di-F—Ph | 2-Cl-3,5-di-MeO— | H |
| 31 | A | Me | 2,6-di-F—Ph | 4-Cl-3,5-di-MeO— | H |
| 32 | A | Et | 2,6-di-F—Ph | 2-Cl-3,5-di-MeO— | H |
| 33 | B | Et | 2,6-di-F-4-MeO—Ph | 2-Cl-4-F— | H |
| 34 | A | Et | 2,6-di-F-4-MeO—Ph | 2-Cl-4-F— | Br |
| 35 | A | Et | 2,6-di-F-4-MeO—Ph | 2-Cl-4-F— | H |
| 36 | B | Me | 2,6-di-F-4-MeO—Ph | 2-Cl-4-F— | H |
| 37 | A | Me | 2,6-di-F-4-MeO—Ph | 2-Cl-4-F— | H |
| 38 | A | Me | 2,6-di-F-4-MeO—Ph | 2-Cl-4-F— | Br |
| 39 | A | Et | 2,6-di-F—Ph | 4-Br-3,5-di-MeO— | H |
| 40 | A | Et | 2,6-di-F—Ph | 4-Cl-3,5-di-MeO— | H |
| 41 | A | Pr | 2,6-di-F—Ph | 3,5-di-MeO— | H |
| 42 | A | Pr | 2,6-di-F—Ph | 2-Br-3,5-di-MeO— | H |
| 43 | B | CH₂=CHCH₂— | 2,6-di-F-4-MeO—Ph | 2-Cl-4-F— | H |
| 44 | A | CH₂=CHCH₂— | 2,6-di-F-4-MeO—Ph | 2-Cl-4-F— | H |

TABLE 4-continued

| Compound | Structure | R1 | Y | (R2)n | R3 |
|---|---|---|---|---|---|
| 45 | A | FCH₂CH₂— | 2,6-di-F-4-MeO—Ph | 2-Cl-4-F— | H |
| 46 | A | Et | 2,6-di-F—Ph | — | H |
| 47 | A | Me | 2,6-di-F—Ph | — | H |
| 48 | A | Et | 2,6-di-F—Ph | — | Cl |
| 49 | A | Me | 2,6-di-F—Ph | — | Cl |
| 50 | A | Et | 2,6-di-F—Ph | — | Br |
| 51 | A | Me | 2,6-di-F—Ph | — | Br |
| 52 | B | Et | 2,6-di-F—Ph | 2-Cl-5-MeO— | H |
| 53 | A | Et | 2,6-di-F—Ph | 2-Cl-5-MeO— | H |
| 54 | A | Et | 2,6-di-F—Ph | 2-Cl-5-MeO— | Cl |
| 55 | A | Et | 2,6-di-F—Ph | 2-Cl-5-MeO— | Br |
| 56 | B | Me | 2,6-di-F—Ph | 2-Cl-5-MeO— | H |
| 57 | A | Me | 2,6-di-F—Ph | 2-Cl-5-MeO— | H |
| 58 | B | Et | 2,6-di-F—Ph | 2-Cl-4-F— | H |
| 59 | A | Et | 2,6-di-F—Ph | 2-Cl-4-F— | H |
| 60 | A | Me | 2,6-di-F—Ph | 2-Cl-5-MeO— | Cl |
| 61 | A | Me | 2,6-di-F—Ph | 2-Cl-5-MeO— | Br |
| 62 | A | Et | 2,6-di-F—Ph | 2-Cl-4-F— | Cl |
| 63 | A | Et | 2,6-di-F—Ph | 2-Cl-4-F— | Br |
| 64 | A | Me | 2,6-di-F—Ph | 2-Cl-4-F— | H |
| 65 | A | Et | 2,6-di-F—Ph | 2-Cl-3-MeO— | H |
| 66 | A | Et | 2,6-di-F—Ph | 2-Cl-3-MeO— | Br |
| 67 | A | Et | 2,6-di-F—Ph | 2-Br-6-Cl-3,5-di-MeO— | H |
| 68 | A | Et | 2,6-di-F—Ph | 2,6-di-Cl-3,5-di-MeO— | H |
| 69 | A | Et | 2,6-di-F—Ph | 2-Br-6-Cl-3,5-di-MeO— | Cl |
| 70 | A | Et | 2,6-di-F—Ph | 2-Br-6-Cl-3,5-di-MeO— | Br |
| 71 | A | Et | 2,6-di-F-4-MeO—Ph | 3,5-di-MeO— | H |
| 72 | A | Et | 2,6-di-F-4-MeO—Ph | 2-Br-3,5-di-MeO— | H |
| 73 | A | Et | 2,6-di-F-4-MeO—Ph | 2-Cl-3,5-di-MeO— | H |
| 74 | A | Et | 2,6-di-F—Ph | 2-Cl— | H |
| 75 | A | Et | 2,6-di-F—Ph | 2-Cl— | Cl |
| 76 | A | Et | 2,6-di-F—Ph | 2-Cl— | Br |
| 77 | A | Me | 2,6-di-F—Ph | 2-Cl— | H |
| 78 | A | Me | 2,6-di-F—Ph | 2-Cl— | Cl |
| 79 | A | Me | 2,6-di-F—Ph | 2-Cl— | Br |
| 80 | A | Me | 2,6-di-F-4-MeO—Ph | 3,5-di-MeO— | H |
| 81 | A | Me | 2,6-di-F-4-MeO—Ph | 2-Br-3,5-di-MeO— | H |
| 82 | A | Me | 2,6-di-F-4-MeO—Ph | 2-Cl-3,5-di-MeO— | H |
| 83 | A | Et | 2,6-di-F—Ph | 2,6-di-Cl-3,5-di-MeO— | Br |
| 84 | A | Et | 2,6-di-F—Ph | 2,6-di-Cl-3,5-di-MeO— | Cl |
| 85 | A | Et | 2,6-di-F—Ph | 2-Br— | H |
| 86 | A | Et | 2,6-di-F—Ph | 2-Br— | Cl |
| 87 | A | Et | 2,6-di-F—Ph | 2-Br— | Br |
| 88 | A | Et | 2,6-di-F—Ph | 2-F-5-MeO— | Br |
| 89 | A | Et | 2,6-di-F—Ph | 2-F-5-MeO— | H |
| 90 | A | Me | 2,6-di-F—Ph | 2-F-5-MeO— | Br |
| 91 | A | Me | 2,6-di-F—Ph | 2-F-5-MeO— | H |
| 92 | A | Et | 2,6-di-F—Ph | 2-F-5-MeO— | Cl |
| 93 | A | Me | 2,6-di-F—Ph | 2-F-5-MeO— | Cl |
| 94 | A | Me | 2,6-di-F—Ph | 2-Br— | H |
| 95 | A | Me | 2,6-di-F—Ph | 2-Br— | Cl |
| 96 | A | Me | 2,6-di-F—Ph | 2-Br— | Br |
| 97 | A | Et | 2,6-di-F—Ph | 2-Cl-5-MeOCH₂O— | H |
| 98 | A | Et | 2,6-di-F—Ph | 2-Cl-5-N≡CCH₂O— | H |
| 99 | A | Et | 2,6-di-F—Ph | 2-Cl-5-EtO— | H |
| 100 | A | Et | 2,6-di-F—Ph | 3-MeO— | H |
| 101 | A | Et | 2,6-di-F—Ph | 3-MeOCH₂O— | H |
| 102 | A | Et | 2,6-di-F—Ph | 3-N≡CCH₂O— | H |
| 103 | A | Et | 2,6-di-F—Ph | 3-EtO— | H |
| 104 | A | Et | 2,6-di-F—Ph | 2,6-di-F-3-MeO— | H |
| 105 | A | Et | 2,6-di-F—Ph | 2,6-di-F-3-MeO— | Br |
| 106 | A | Et | 2,6-di-F—Ph | 2,6-di-F-3-MeO— | Cl |
| 107 | A | Et | 2,6-di-F—Ph | 2-Cl-5-AcO— | H |
| 108 | A | Me | 2,6-di-F—Ph | 2,6-di-F-3-MeO— | H |
| 109 | A | Me | 2,6-di-F—Ph | 2,6-di-F-3-MeO— | Br |
| 110 | A | Me | 2,6-di-F—Ph | 2,6-di-F-3-MeO— | Cl |
| 111 | A | Et | 2,6-di-F—Ph | 2-I— | H |
| 112 | A | Et | 2,6-di-F—Ph | 2-I— | Cl |
| 113 | A | Et | 2,6-di-F—Ph | 2-I— | Br |
| 114 | A | Me | 2,6-di-F—Ph | 2-I— | H |
| 115 | A | Me | 2,6-di-F—Ph | 2-I— | Cl |
| 116 | A | Me | 2,6-di-F—Ph | 2-I— | Br |
| 117 | B | Et | 2,6-di-F—Ph | 2-Cl-3,5-di-MeO— | H |
| 118 | B | Et | 4-Cl-2,6-di-F—Ph | 3,5-di-MeO— | H |
| 119 | A | Et | 4-Cl-2,6-di-F—Ph | 3,5-di-MeO— | H |
| 120 | A | Et | 4-Cl-2,6-di-F—Ph | 2-Br-3,5-di-MeO— | H |
| 121 | A | Et | 4-Cl-2,6-di-F—Ph | 2-Cl-3,5-di-MeO— | H |
| 122 | A | Et | 4-Cl-2,6-di-F—Ph | 4-Cl-3,5-di-MeO— | H |

TABLE 4-continued

| Compound | Structure | R1 | Y | (R2)n | R3 |
|---|---|---|---|---|---|
| 123 | A | Et | 2,6-di-F—Ph | 2-MeO— | H |
| 124 | A | Et | 2,6-di-F—Ph | 5-Cl-2-MeO— | Cl |
| 125 | A | Et | 2,6-di-F—Ph | 5-Br-2-MeO— | Br |
| 126 | A | Et | 2,6-di-F—Ph | 2-Cl-5-MeOCH$_2$O— | Br |
| 127 | A | Et | 2,6-di-F—Ph | 2-Cl-5-MeOCH$_2$O— | Cl |
| 128 | A | Et | 2,6-di-F—Ph | 2-Cl-5-N≡CCH$_2$O— | Br |
| 129 | A | Et | 2,6-di-F—Ph | 2-Cl-5-N≡CCH$_2$O— | Cl |
| 130 | B | Et | 2,4,6-tri-F—Ph | 3,5-di-MeO— | H |
| 131 | A | Et | 2,4,6-tri-F—Ph | 3,5-di-MeO— | H |
| 132 | A | Et | 2,4,6-tri-F—Ph | 2-Br-3,5-di-MeO— | H |
| 133 | A | Et | 2,4,6-tri-F—Ph | 2-Cl-3,5-di-MeO— | H |
| 134 | A | Me | 2,4,6-tri-F—Ph | 3,5-di-MeO— | H |
| 135 | A | Me | 2,4,6-tri-F—Ph | 2-Br-3,5-di-MeO— | H |
| 136 | A | Me | 2,4,6-tri-F—Ph | 2-Cl-3,5-di-MeO— | H |
| 137 | A | Me | 2,6-di-F—Ph | 2-MeO— | H |
| 138 | A | Me | 2,6-di-F—Ph | 5-Cl-2-MeO— | Cl |
| 139 | A | Me | 2,6-di-F—Ph | 5-Br-2-MeO— | Br |
| 140 | A | Et | 2,6-di-F—Ph | 2-F— | H |
| 141 | A | Et | 2,6-di-F—Ph | 2-F— | Cl |
| 142 | A | Et | 2,6-di-F—Ph | 2-F— | Br |
| 143 | A | Me | 2,6-di-F—Ph | 2-F— | H |
| 144 | A | Me | 2,6-di-F—Ph | 2-F— | Cl |
| 145 | A | Me | 2,6-di-F—Ph | 2-F— | Br |
| 146 | A | Et | 2,6-di-F—Ph | 2-F$_3$C— | H |
| 147 | A | Et | 2,6-di-F—Ph | 2-F$_3$C— | Cl |
| 148 | A | Et | 2,6-di-F—Ph | 2-F$_3$C— | Br |
| 149 | B | Et | 2-Cl-6-F—Ph | 3,5-di-MeO— | H |
| 150 | A | Et | 2-Cl-6-F—Ph | 3,5-di-MeO— | H |
| 151 | A | Et | 2-Cl-6-F—Ph | 2-Br-3,5-di-MeO— | H |
| 152 | A | Et | 2-Cl-6-F—Ph | 2-Cl-3,5-di-MeO— | H |
| 153 | A | Et | 2,6-di-F—Ph | 3-F— | H |
| 154 | A | Et | 2,6-di-F—Ph | 3-F— | Cl |
| 155 | A | Et | 2,6-di-F—Ph | 3-F— | Br |
| 156 | B | Et | 2,6-di-F—Ph | 3-F— | H |
| 157 | A | Me | 2,6-di-F—Ph | 2-F$_3$C— | H |
| 158 | A | Me | 2,6-di-F—Ph | 2-F$_3$C— | Cl |
| 159 | A | Me | 2,6-di-F—Ph | 2-F$_3$C— | Br |
| 160 | A | Et | 2,6-di-F—Ph | 2-Me— | H |
| 161 | A | Et | 2,6-di-F—Ph | 2-Me— | Cl |
| 162 | A | Et | 2,6-di-F—Ph | 2-Me— | Br |
| 163 | B | Me | 2-Cl-6-F—Ph | 3,5-di-MeO— | H |
| 164 | A | Me | 2-Cl-6-F—Ph | 3,5-di-MeO— | H |
| 165 | A | Me | 2-Cl-6-F—Ph | 2-Br-3,5-di-MeO— | H |
| 166 | A | Me | 2-Cl-6-F—Ph | 2-Cl-3,5-di-MeO— | H |
| 167 | A | Et | 2-Cl-6-F—Ph | 2,6-di-Cl-3,5-di-MeO— | Cl |
| 168 | A | Me | 2,6-di-F—Ph | 3-F— | H |
| 169 | A | Me | 2,6-di-F—Ph | 3-F— | Cl |
| 170 | A | Me | 2,6-di-F—Ph | 3-F— | Br |
| 171 | A | Et | 2,6-di-F—Ph | 3-Cl— | H |
| 172 | B | Me | 2,6-di-F—Ph | 3-F— | H |
| 173 | B | Et | 2,6-di-F—Ph | 3-Cl— | H |
| 174 | B | Et | 2-Br-6-F—Ph | 3,5-di-MeO— | H |
| 175 | A | Et | 2-Br-6-F—Ph | 3,5-di-MeO— | H |
| 176 | A | Et | 2-Br-6-F—Ph | 2-Br-3,5-di-MeO— | H |
| 177 | A | Et | 2-Br-6-F—Ph | 2-Cl-3,5-di-MeO— | H |
| 178 | A | Et | 2,6-di-F—Ph | 3-Cl— | Cl |
| 179 | A | Et | 2,6-di-F—Ph | 3-Cl— | Br |
| 180 | A | Me | 2,6-di-F—Ph | 2-Me— | H |
| 181 | A | Me | 2,6-di-F—Ph | 2-Me— | Cl |
| 182 | A | Me | 2,6-di-F—Ph | 2-Me— | Br |
| 183 | A | Me | 2-Br-6-F—Ph | 3,5-di-MeO— | H |
| 184 | A | Me | 2-Br-6-F—Ph | 2-Br-3,5-di-MeO— | H |
| 185 | A | Me | 2-Br-6-F—Ph | 2-Cl-3,5-di-MeO— | H |
| 186 | B | Et | 4-Br-2,6-di-F—Ph | 3,5-di-MeO— | H |
| 187 | B | Me | 4-Br-2,6-di-F—Ph | 3,5-di-MeO— | H |
| 188 | A | Me | 2,6-di-F—Ph | 3-Cl— | H |
| 189 | A | Me | 2,6-di-F—Ph | 3-Cl— | Cl |
| 190 | A | Me | 2,6-di-F—Ph | 3-Cl— | Br |
| 191 | B | Me | 2,6-di-F—Ph | 3-Cl— | H |
| 192 | B | F$_2$CHCH$_2$— | 2,6-di-F—Ph | 2-Cl-5-MeO— | H |
| 193 | A | Et | 2,6-di-F—Ph | 2-Cl-5-MeOCH$_2$O— | H |
| 194 | A | F$_2$CHCH$_2$— | 2,6-di-F—Ph | 2-Cl-5-MeO— | H |
| 195 | A | Et | 2,6-di-F—Ph | 2-Cl-5-MeOCH$_2$O— | Cl |
| 196 | A | Et | 2,6-di-F—Ph | 2-Cl-5-MeOCH$_2$O— | Br |
| 197 | A | F$_2$CHCH$_2$— | 2,6-di-F—Ph | 2-Cl-5-MeO— | Cl |
| 198 | A | F$_2$CHCH$_2$— | 2,6-di-F—Ph | 2-Cl-5-MeO— | Br |
| 199 | A | Et | 4-Br-2,6-di-F—Ph | 3,5-di-MeO— | H |
| 200 | A | Et | 4-Br-2,6-di-F—Ph | 2-Br-3,5-di-MeO— | H |

TABLE 4-continued

| Compound | Structure | R1 | Y | (R2)n | R3 |
|---|---|---|---|---|---|
| 201 | A | Et | 4-Br-2,6-di-F—Ph | 2-Cl-3,5-di-MeO— | H |
| 202 | A | Et | 4-Br-2,6-di-F—Ph | 4-Cl-3,5-di-MeO— | H |
| 203 | A | Me | 4-Br-2,6-di-F—Ph | 3,5-di-MeO— | H |
| 204 | A | Me | 4-Br-2,6-di-F—Ph | 2-Br-3,5-di-MeO— | H |
| 205 | A | Me | 4-Br-2,6-di-F—Ph | 2-Cl-3,5-di-MeO— | H |
| 206 | A | Me | 4-Br-2,6-di-F—Ph | 4-Cl-3,5-di-MeO— | H |
| 207 | B | Et | 2,6-di-F—Ph | 3-Me— | H |
| 208 | B | Et | 2,6-di-F—Ph | 3-F$_3$CO— | H |
| 209 | A | Et | 2,6-di-F—Ph | 2-MeS— | H |
| 210 | A | Et | 2,6-di-F—Ph | 2-ClCH$_2$S— | Cl |
| 211 | A | Et | 2,6-di-F—Ph | 2-MeSO$_2$— | H |
| 212 | A | Et | 2,6-di-F—Ph | 2-Cl-5-cPrCH$_2$O— | H |
| 213 | A | F$_2$CHCH$_2$— | 2,6-di-F—Ph | 2-Cl-5-MeOCH$_2$O— | H |
| 214 | A | F$_2$CHCH$_2$— | 2,6-di-F—Ph | 2-Cl-5-EtO— | H |
| 215 | A | Et | 3,5-di-F-4-Py | 3,5-di-MeO— | H |
| 216 | A | Et | 3,5-di-F-4-Py | 2-Br-3,5-di-MeO— | H |
| 217 | A | Et | 2,6-di-F—Ph | 3-F3CO— | H |
| 218 | A | Et | 2,6-di-F—Ph | 3-F3CO— | Cl |
| 219 | A | Et | 2,6-di-F—Ph | 3-Me— | H |
| 220 | A | Et | 2,6-di-F—Ph | 3-Me— | Cl |
| 221 | A | Et | 2,6-di-F—Ph | 2-Cl-5-cPrCH$_2$O— | Cl |
| 222 | A | F$_2$CHCH$_2$— | 2,6-di-F—Ph | 2-Cl-5-MeOCH$_2$O— | Cl |
| 223 | A | F$_2$CHCH$_2$— | 2,6-di-F—Ph | 2-Cl-5-EtO— | Cl |
| 224 | A | Et | 3,5-di-F-4-Py | 2-Cl-3,5-di-MeO— | H |
| 225 | B | Et | 2-F—Ph | 3,5-di-MeO— | H |
| 226 | B | Me | 2-F—Ph | 3,5-di-MeO— | H |
| 227 | A | Me | 2-F—Ph | 3,5-di-MeO— | H |
| 228 | A | Me | 2-F—Ph | 2-Br-3,5-di-MeO— | H |
| 229 | A | Me | 2-F—Ph | 2-Cl-3,5-di-MeO— | H |
| 230 | A | Et | 2-F—Ph | 3,5-di-MeO— | H |
| 231 | A | Et | 2-F—Ph | 2-Br-3,5-di-MeO— | H |
| 232 | A | Et | 2-F—Ph | 2-Cl-3,5-di-MeO— | H |
| 233 | A | Me | 2-F—Ph | 2,6-di-Cl-3,5-di-MeO— | H |
| 234 | A | Et | 2,6-di-F—Ph | 2-Cl-5-HO— | H |
| 235 | A | Me | 2,6-di-F—Ph | 2-Cl-5-HO— | H |
| 236 | A | Me | 2,6-di-F—Ph | 2-Cl-5-N≡CCH$_2$O— | H |
| 237 | A | Me | 2,6-di-F—Ph | 2-Cl-5-EtO— | H |
| 238 | A | Me | 2,6-di-F—Ph | 2-Cl-5-cPrCH$_2$O— | H |
| 239 | A | Me | 2,6-di-F—Ph | 2-Cl-5-MeOCH$_2$O— | H |
| 240 | A | Me | 2,6-di-F—Ph | 2-Cl-5-MeOCH$_2$CH$_2$O— | H |
| 241 | A | Me | 2,6-di-F—Ph | 2-Cl-5-PrO— | H |
| 242 | A | Et | 2,6-di-F—Ph | 2-Cl-5-PrO— | H |
| 243 | A | Me | 2,6-di-F—Ph | 2-Cl-5-HC≡CCH$_2$O— | H |
| 244 | A | Et | 2,6-di-F—Ph | 2-Cl-5-HC≡CCH$_2$O— | H |
| 245 | A | Et | 2,6-di-F—Ph | 2-Cl-5-Me$_3$SiCH$_2$CH$_2$OCH$_2$O— | H |
| 246 | A | Me | 2,6-di-F—Ph | 2-Cl-5-Me$_3$SiCH$_2$CH$_2$OCH$_2$O— | H |
| 247 | A | Me | 4-EtO-2,6-di-F—Ph | 2-Cl-3,5-di-MeO— | H |
| 248 | A | Me | 4-tBuO-2,6-di-F—Ph | 2-Cl-3,5-di-MeO— | H |
| 249 | A | Me | 2,6-di-F-4-HO—Ph | 2-Cl-3,5-di-MeO— | H |
| 250 | A | Et | 2,6-di-F—Ph | 2-Cl-5-N≡CCH$_2$CH$_2$O— | H |
| 251 | A | Me | 2,6-di-F—Ph | 2-Cl-5-N≡CCH$_2$CH$_2$O— | H |
| 252 | A | Et | 2,6-di-F—Ph | 2-Cl-5-BuO— | H |
| 253 | A | Me | 2,6-di-F—Ph | 2-Cl-5-BuO— | H |
| 254 | A | Et | 2,6-di-F—Ph | 2-Cl-5-PentylO— | H |
| 255 | A | Me | 2,6-di-F—Ph | 2-Cl-5-PentylO— | H |
| 256 | A | Et | 2,6-di-F—Ph | 2-Cl-5-iPrO— | H |
| 257 | A | Me | 2,6-di-F—Ph | 2-Cl-5-iPrO— | H |
| 258 | A | Et | 2,6-di-F—Ph | 2-Cl-5-iBuO— | H |
| 259 | A | Me | 2,6-di-F—Ph | 2-Cl-5-iBuO— | H |
| 260 | A | Et | 2,6-di-F—Ph | 2-Cl-5-Me$_3$SiCH$_2$O— | H |
| 261 | A | Me | 2,6-di-F—Ph | 2-Cl-5-Me$_3$SiCH$_2$O— | H |
| 262 | A | Et | 2,6-di-F—Ph | 2-Cl-5-F$_3$CCH$_2$O— | H |
| 263 | A | Me | 2,6-di-F—Ph | 2-Cl-5-F$_3$CCH$_2$O— | H |
| 264 | A | Et | 2,6-di-F—Ph | 2-MeS(O)— | H |
| 265 | A | Et | 2,6-di-F—Ph | 4-Cl— | H |
| 266 | A | Et | 2,6-di-F—Ph | 4-Cl— | Cl |
| 267 | B | Et | 2,6-di-F—Ph | 4-Me— | H |
| 268 | B | Me | 2,6-di-F—Ph | 4-Me— | H |
| 269 | A | Et | 2,6-di-F—Ph | 4-Me— | H |
| 270 | A | Me | 2,6-di-F—Ph | 4-Me— | H |
| 271 | A | Et | 2,6-di-F—Ph | 4-Me— | Br |
| 272 | A | Et | 2,6-di-F—Ph | 4-Me— | Cl |
| 273 | A | Me | 2,6-di-F—Ph | 4-Me— | Br |
| 274 | A | Me | 2,6-di-F—Ph | 4-Me— | Cl |
| 275 | A | Et | 2,6-di-F—Ph | 2-Cl-5-Me$_3$SiCH$_2$CH$_2$CH$_2$O— | H |

TABLE 4-continued

| Compound | Structure | R1 | Y | (R2)n | R3 |
|---|---|---|---|---|---|
| 276 | A | Me | 2,6-di-F—Ph | 2-Cl-5-Me$_3$SiCH$_2$CH$_2$O— | H |
| 277 | A | Et | 2,6-di-F—Ph | 2-Cl-5-F$_2$CHCH$_2$O— | H |
| 278 | A | Me | 2,6-di-F—Ph | 2-Cl-5-F$_2$CHCH$_2$O— | H |
| 279 | A | Et | 2,6-di-F—Ph | 4-Cl— | Br |
| 280 | A | Me | 2,6-di-F—Ph | 4-Cl— | H |
| 281 | A | Me | 2,6-di-F-4-PrO—Ph | 2-Cl-3,5-di-MeO— | H |
| 282 | A | Me | 4-BuO-2,6-di-F—Ph | 2-Cl-3,5-di-MeO— | H |
| 283 | B | Et | 2,6-di-F—Ph | 3-F$_3$C— | H |
| 284 | A | Et | 2,6-di-F—Ph | 3-F$_3$C— | H |
| 285 | A | Me | 2,6-di-F—Ph | 4-Cl— | Cl |
| 286 | A | Me | 2,6-di-F—Ph | 4-Cl— | Br |
| 287 | A | Et | 2,6-di-F—Ph | 2-Cl-5-cPentylO— | H |
| 288 | A | Me | 2,6-di-F—Ph | 2-Cl-5-cPentylO— | H |
| 289 | A | Me | 2,6-di-F—Ph | 4-Br— | H |
| 290 | A | Me | 2,6-di-F—Ph | 4-Br— | Br |
| 291 | A | Me | 2,6-di-F—Ph | 4-Br— | Cl |
| 292 | A | Et | 2,6-di-F—Ph | 4-Br— | H |
| 293 | A | Et | 2,6-di-F—Ph | 4-Br— | Br |
| 294 | A | Et | 2,6-di-F—Ph | 4-Br— | Cl |
| 295 | A | Et | 2,6-di-F—Ph | 2-Cl-5-cHexylO— | H |
| 296 | A | Me | 2,6-di-F—Ph | 2-Cl-5-cHexylO— | H |
| 297 | A | Et | 2,6-di-F—Ph | 2-Cl-5-MeOC(=O)O— | H |
| 298 | A | Me | 2,6-di-F—Ph | 2-Cl-5-MeOC(=O)O— | H |
| 299 | A | Et | 2,6-di-F—Ph | 3-F3C— | Cl |
| 300 | B | Et | 2,6-di-F—Ph | 4-MeO— | H |
| 301 | A | Et | 2,6-di-F—Ph | 4-MeO— | H |
| 302 | A | Et | 2,6-di-F—Ph | 4-MeO— | Cl |
| 303 | A | Et | 2,6-di-F—Ph | 2-Cl-5-AcCH$_2$O— | H |
| 304 | A | Me | 2,6-di-F—Ph | 2-Cl-5-AcCH$_2$O— | H |
| 305 | A | Et | 2,6-di-F—Ph | 2-Cl-5-MeSCH$_2$O— | H |
| 306 | A | Me | 2,6-di-F—Ph | 2-Cl-5-MeSCH$_2$O— | H |
| 307 | A | Et | 2,6-di-F—Ph | 2-Cl-5-EtOC(=O)CH$_2$O— | H |
| 308 | A | Me | 2,6-di-F—Ph | 2-Cl-5-EtOC(=O)CH$_2$O— | H |
| 309 | A | Et | 2,6-di-F—Ph | 2-Cl-5-MeSO$_2$CH$_2$O— | H |
| 310 | A | Et | 2,6-di-F—Ph | 2-Cl-5-MeOCH$_2$CH$_2$O— | H |
| 311 | A | Me | 2,6-di-F—Ph | 2-Cl-5-MeOCH$_2$CH$_2$O— | H |
| 312 | A | Me | 2,6-di-F—Ph | 2-Cl-5-MeSO$_2$CH$_2$O— | H |
| 313 | A | Et | 2,6-di-F—Ph | 2-Cl-5-H$_2$C=CHCH$_2$O— | H |
| 314 | A | Me | 2,6-di-F—Ph | 2-Cl-5-H$_2$C=CHCH$_2$O— | H |
| 315 | A | Et | 2,6-di-F—Ph | 2-Cl-5-(1,3-dioxolan-2-yl)CH$_2$O— | H |
| 316 | A | Me | 2,6-di-F—Ph | 2-Cl-5-(1,3-dioxolan-2-yl)CH$_2$O— | H |
| 317 | A | Et | 2,6-di-F—Ph | 2-Cl-5-(1,3-dioxan-2-yl)CH$_2$CH$_2$O— | H |
| 318 | A | Me | 2,6-di-F—Ph | 2-Cl-5-(1,3-dioxan-2-yl)CH$_2$CH$_2$O— | H |
| 319 | A | Me | 4-(F$_3$CCH$_2$O)-2,6-di-F—Ph | 2-Cl-3,5-di-MeO— | H |
| 320 | B | Et | 2,4,6-tri-F—Ph | 2-Cl-5-F— | H |
| 321 | A | Et | 2,4,6-tri-F—Ph | 2-Cl-5-F— | H |
| 322 | A | Et | 2,4,6-tri-F—Ph | 2-Cl-5-F— | Cl |
| 323 | A | Et | 2,6-di-F—Ph | 2-Cl-5-cPentylCH$_2$O— | H |
| 324 | A | Me | 2,6-di-F—Ph | 2-Cl-5-cPentylCH$_2$O— | H |
| 325 | A | Et | 2,6-di-F—Ph | 2-Cl-5-EtOCH$_2$O— | H |
| 326 | A | Me | 2,6-di-F—Ph | 2-Cl-5-EtOCH$_2$O— | H |
| 327 | A | Et | 2,6-di-F—Ph | 3-Br— | H |
| 328 | A | Et | 2,6-di-F—Ph | 3-Br— | Cl |
| 329 | A | Et | 2,6-di-F—Ph | 2-Cl-5-MeO— | Me |
| 330 | A | Et | 2,6-di-F—Ph | 2-Cl-5-MeOCH$_2$CH$_2$OCH$_2$O— | H |
| 331 | A | Me | 2,6-di-F—Ph | 2-Cl-5-MeOCH$_2$CH$_2$OCH$_2$O— | H |
| 332 | A | Et | 2,6-di-F—Ph | 2,4-di-Cl— | H |
| 333 | A | Et | 2,6-di-F—Ph | 2,4-di-Cl— | Cl |
| 334 | B | F$_3$CCH$_2$— | 2,6-di-F—Ph | 2-Cl-3,5-di-MeO— | H |
| 335 | A | F$_3$CCH$_2$— | 2,6-di-F—Ph | 2-Cl-3,5-di-MeO— | H |
| 336 | B | F$_2$CHCH$_2$— | 2,6-di-F—Ph | 2-Cl-3,5-di-MeO— | H |
| 337 | A | F$_2$CHCH$_2$— | 2,6-di-F—Ph | 2-Cl-3,5-di-MeO— | H |
| 338 | A | Me | 4-(F$_2$CHCH$_2$O)-2,6-di-F—Ph | 2-Cl-3,5-di-MeO— | H |
| 339 | A | Me | 2,4,6-tri-F—Ph | 2-Cl-5-F— | H |
| 340 | A | Me | 2,4,6-tri-F—Ph | 2-Cl-5-F— | Cl |
| 341 | A | Et | 2,6-di-F—Ph | 3-N≡C— | H |
| 342 | B | Et | 2,4,6-tri-F—Ph | 2-Cl-3,5-di-MeO— | H |
| 343 | A | F$_2$CHCH$_2$— | 2,4,6-tri-F—Ph | 2-Cl-3,5-di-MeO— | H |
| 344 | A | Me | 2,6-di-F—Ph | 2-Et— | H |

TABLE 4-continued

| Compound | Structure | R1 | Y | (R2)n | R3 |
|---|---|---|---|---|---|
| 345 | A | F$_2$CHCH$_2$— | 2,6-di-F—Ph | 2,4-di-Cl— | H |
| 346 | A | Me | 2,6-di-F—Ph | 2,4-di-Cl— | H |
| 347 | A | F$_2$CHCH$_2$— | 2,6-di-F—Ph | 2,4-di-Cl— | Cl |
| 348 | A | Me | 2,6-di-F—Ph | 2,4-di-Cl— | Cl |
| 349 | A | Et | 2,6-di-F—Ph | 2,3-di-Cl— | H |
| 350 | A | Et | 2,6-di-F—Ph | 2,3-di-Cl— | Cl |
| 351 | A | Et | 2,6-di-F—Ph | 2-Cl-5-MeO— | HC≡C— |
| 352 | A | Et | 2,6-di-F—Ph | 2-Cl-5-MeO— | cPr |
| 353 | A | Et | 2,6-di-F—Ph | 3-N≡C— | Cl |
| 354 | A | Et | 2,4,6-tri-F—Ph | 2,5-di-Cl— | H |
| 355 | A | Et | 2,4,6-tri-F—Ph | 2,5-di-Cl— | Cl |
| 356 | B | Et | 2,6-di-F—Ph | 2-Cl-5-F— | H |
| 357 | B | Me | 2,6-di-F—Ph | 2-Cl-5-F— | H |
| 358 | A | Et | 2,6-di-F—Ph | 2-Cl-5-F— | H |
| 359 | A | Me | 2,6-di-F—Ph | 2-Cl-5-F— | H |
| 360 | A | Et | 2,6-di-F—Ph | 2-Cl-5-F— | Cl |
| 361 | A | Et | 2,6-di-F—Ph | 2-Cl-5-F— | Br |
| 362 | A | Me | 2,6-di-F—Ph | 2-Cl-5-F— | Cl |
| 363 | A | Me | 2,6-di-F—Ph | 2-Cl-5-F— | Br |
| 364 | A | Me | 2,6-di-F—Ph | 2,3-di-Cl— | H |
| 365 | A | Me | 2,6-di-F—Ph | 2,3-di-Cl— | Cl |
| 366 | A | F$_2$CHCH$_2$— | 2,6-di-F—Ph | 2,3-di-Cl— | H |
| 367 | A | F$_2$CHCH$_2$— | 2,6-di-F—Ph | 2,3-di-Cl— | Cl |
| 368 | A | Et | 2,6-di-F—Ph | 2,3,4,5,6-penta-F— | H |
| 369 | A | Et | 2,6-di-F—Ph | 2-Cl-5-MeO— | Et |
| 370 | A | Et | 2,6-di-F—Ph | 2-Cl-5-MeO— | Pr |
| 371 | A | Et | 2,6-di-F—Ph | 2-Cl-5-MeO— | MeO |
| 372 | A | Et | 2,6-di-F—Ph | 2,3,4,5,6-penta-F— | Cl |
| 373 | A | Me | 2,6-di-F—Ph | 2,3,4,5,6-penta-F— | H |
| 374 | A | Me | 2,6-di-F—Ph | 2,3,4,5,6-penta-F— | Cl |
| 375 | A | Et | 2,6-di-F—Ph | 2-Cl-5-MeO— | MeS |
| 376 | A | Et | 2,6-di-F—Ph | 2-Cl-5-EtO— | Cl |
| 377 | A | F$_3$CCH$_2$— | 2,4,6-tri-F—Ph | 2-Cl-3,5-di-MeO— | H |
| 378 | A | Et | 4-EtO-2,6-di-F—Ph | 2-Cl-3,5-di-MeO— | H |
| 379 | A | (E) FCH=CH— | 2,4,6-tri-F—Ph | 2-Cl-3,5-di-MeO— | H |
| 380 | A | (Z) FCH=CH— | 2,4,6-tri-F—Ph | 2-Cl-3,5-di-MeO— | H |
| 381 | A | Et | 2,4,6-tri-F—Ph | 2-Cl-5-F— | Br |
| 382 | A | Et | 2,6-di-F-4-MeO—Ph | 2-Cl-5-F— | H |
| 383 | A | F$_2$CHCH$_2$— | 2,6-di-F—Ph | 2,3,4,5,6-penta-F— | H |
| 384 | A | F$_2$CHCH$_2$— | 2,6-di-F—Ph | 2,3,4,5,6-penta-F— | Cl |
| 385 | A | Et | 2,6-di-F—Ph | 2-Cl-6-F— | H |
| 386 | A | Et | 2,6-di-F-4-MeO—Ph | 2-Cl-5-F— | Cl |
| 387 | A | Et | 2,6-di-F—Ph | 2-Cl-5-MeO— | MeSO$_2$ |
| 388 | B | F$_2$CHCH$_2$— | 2,6-di-F—Ph | 2-Cl-5-F— | H |
| 389 | B | Pr | 2,6-di-F—Ph | 2-Cl-5-MeO— | H |
| 390 | B | Bu | 2,6-di-F—Ph | 2-Cl-5-MeO— | H |
| 391 | A | F$_2$CHCH$_2$— | 2,6-di-F—Ph | 2-Cl-5-F— | H |
| 392 | A | F$_2$CHCH$_2$— | 2,6-di-F—Ph | 2-Cl-5-F— | Cl |
| 393 | A | F$_2$CHCH$_2$— | 2,6-di-F—Ph | 2-Cl-5-F— | Br |
| 394 | A | Bu | 2,6-di-F—Ph | 2-Cl-5-MeO— | H |
| 395 | A | Bu | 2,6-di-F—Ph | 2-Cl-5-MeO— | Cl |
| 396 | A | Bu | 2,6-di-F—Ph | 2-Cl-5-MeO— | Br |
| 397 | A | Et | 2,6-di-F—Ph | 2-Cl-6-F— | Cl |
| 398 | A | Me | 2,6-di-F—Ph | 2-Cl-6-F— | H |
| 399 | A | Pr | 2,6-di-F—Ph | 2-Cl-5-MeO— | H |
| 400 | A | Pr | 2,6-di-F—Ph | 2-Cl-5-MeO— | Cl |
| 401 | A | Pr | 2,6-di-F—Ph | 2-Cl-5-MeO— | Br |
| 402 | A | MeOCH$_2$— | 2,6-di-F—Ph | 2-Cl-5-MeO— | H |
| 403 | A | Et | 2,4,6-tri-F—Ph | 2-Cl-5-MeO— | H |
| 404 | A | Et | 2,4,6-tri-F—Ph | 2-Cl-5-MeO— | Cl |
| 405 | A | Me | 2,6-di-F—Ph | 2-Cl-6-F— | Cl |
| 406 | A | F$_2$CHCH$_2$— | 2,6-di-F—Ph | 2-Cl-6-F— | H |
| 407 | A | F$_2$CHCH$_2$— | 2,6-di-F—Ph | 2-Cl-6-F— | Cl |
| 408 | A | Et | 2,6-di-F—Ph | 4-Cl-2-F— | H |
| 409 | A | F$_3$CCH$_2$— | 2,6-di-F—Ph | 2-Cl-5-MeO— | H |
| 410 | A | F$_3$CCH$_2$— | 2,6-di-F—Ph | 2-Cl-5-MeO— | Cl |
| 411 | A | F$_3$CCH$_2$— | 2,6-di-F—Ph | 2-Cl-5-MeO— | Br |
| 412 | A | iPr | 2,6-di-F—Ph | 2-Cl-5-MeO— | H |
| 413 | A | iPr | 2,6-di-F—Ph | 2-Cl-5-MeO— | Cl |
| 414 | A | MeOCH$_2$— | 2,6-di-F—Ph | 2-Cl-5-MeO— | Cl |
| 415 | A | Me | 2,4,6-tri-F—Ph | 2-Cl-5-MeO— | H |
| 416 | A | Me | 2,4,6-tri-F—Ph | 2-Cl-5-MeO— | Cl |
| 417 | A | Et | 2,6-di-F—Ph | 4-Cl-2-F— | Cl |
| 418 | A | Me | 2,6-di-F—Ph | 4-Cl-2-F— | H |
| 419 | A | Me | 2,6-di-F—Ph | 4-Cl-2-F— | Cl |
| 420 | A | Et | 2,4,6-tri-F—Ph | 2-Cl— | H |
| 421 | A | Et | 2,4,6-tri-F—Ph | 2-Cl— | Cl |
| 422 | A | H$_2$N— | 2,6-di-F—Ph | 2-Cl-5-MeO— | H |

TABLE 4-continued

| Compound | Structure | R1 | Y | (R2)n | R3 |
|---|---|---|---|---|---|
| 423 | A | H₂N— | 2,6-di-F—Ph | 2-Cl-5-MeO— | Cl |
| 424 | A | Et | 2,4,6-tri-F—Ph | 2,5-di-F— | H |
| 425 | A | Et | 2,4,6-tri-F—Ph | 2,5-di-F— | Cl |
| 426 | A | Me | 2,4,6-tri-F—Ph | 2,5-di-F— | H |
| 427 | A | Me | 2,4,6-tri-F—Ph | 2,5-di-F— | Cl |
| 428 | A | F₂CHCH₂— | 2,6-di-F—Ph | 4-Cl-2-F— | H |
| 429 | A | F₂CHCH₂— | 2,6-di-F—Ph | 4-Cl-2-F— | Cl |
| 430 | A | Et | 2,6-di-F-4-MeO—Ph | 2-Cl— | H |
| 431 | A | Me | 2,4,6-tri-F—Ph | 2-Cl— | H |
| 432 | A | Me | 2,4,6-tri-F—Ph | 2-Cl— | Cl |
| 433 | A | Me | 2,6-di-F-4-MeO—Ph | 2-Cl— | H |
| 434 | A | Et | 2,6-di-F-4-MeO—Ph | 2-Cl— | Cl |
| 435 | A | Me | 2,6-di-F-4-MeO—Ph | 2-Cl— | Cl |
| 436 | B | Et | 2,6-di-F—Ph | 2,3,5-tri-F— | H |
| 437 | B | Me | 2,6-di-F—Ph | 2,3,5-tri-F— | H |
| 438 | A | Et | 2,6-di-F—Ph | 2,3,5-tri-F— | H |
| 439 | A | Me | 2,6-di-F—Ph | 2,3,5-tri-F— | H |
| 440 | A | Et | 2,6-di-F—Ph | 2,3,5-tri-F— | Cl |
| 441 | A | Et | 2,6-di-F—Ph | 2,3,5-tri-F— | Br |
| 442 | A | Me | 2,6-di-F—Ph | 2,3,5-tri-F— | Cl |
| 443 | A | Me | 2,6-di-F—Ph | 2,3,5-tri-F— | Br |
| 444 | A | Et | 2,6-di-F—Ph | 2,5-di-Cl— | H |
| 445 | A | Et | 2,6-di-F—Ph | 2,5-di-Cl— | Cl |
| 446 | A | Me | 2,6-di-F—Ph | 2,5-di-Cl— | H |
| 447 | A | Me | 2,6-di-F—Ph | 2,5-di-Cl— | Cl |
| 448 | A | F₂CHCH₂— | 2,6-di-F—Ph | 2,5-di-Cl— | H |
| 449 | A | F₂CHCH₂— | 2,6-di-F—Ph | 2,5-di-Cl— | Cl |
| 450 | A | Et | 2,6-di-F—Ph | 2,3,5-tri-Cl— | H |
| 451 | A | Et | 2,6-di-F—Ph | 2,3,5-tri-Cl— | Cl |
| 452 | A | Me | 2,6-di-F—Ph | 2,3,5-tri-Cl— | H |
| 453 | A | Me | 2,6-di-F—Ph | 2,3,5-tri-Cl— | Cl |
| 454 | A | F₂CHCH₂— | 2,6-di-F—Ph | 2,3,5-tri-Cl— | H |
| 455 | A | F₂CHCH₂— | 2,6-di-F—Ph | 2,3,5-tri-Cl— | Cl |
| 456 | B | HC≡C—CH₂— | 2,6-di-F—Ph | 2-Cl-5-MeO— | H |
| 457 | A | Me | 2,6-di-F—Ph | 2,3,5-tri-F— | Me |
| 458 | A | HC≡C—CH₂— | 2,6-di-F—Ph | 2-Cl-5-MeO— | H |
| 459 | A | Et | 2,6-di-F—Ph | 2,3,5-tri-F— | Me |
| 460 | A | N≡C—CH₂— | 2,6-di-F—Ph | 2-Cl-5-MeO— | H |
| 461 | A | Et | 2,4,6-tri-F—Ph | 2-Cl-5-F— | Me |
| 462 | A | HC≡C—CH₂— | 2,6-di-F—Ph | 2-Cl-5-MeO— | Cl |
| 463 | A | N≡C—CH₂— | 2,6-di-F—Ph | 2-Cl-5-MeO— | Cl |
| 464 | A | Et | 2,4,6-tri-F—Ph | 2,3,5-tri-F— | H |
| 465 | A | Et | 2,4,6-tri-F—Ph | 2,3,5-tri-F— | Cl |
| 466 | A | Me | 2,4,6-tri-F—Ph | 2,3,5-tri-F— | H |
| 467 | A | Me | 2,4,6-tri-F—Ph | 2,3,5-tri-F— | Cl |
| 468 | A | Et | 2,6-di-F-4-MeO—Ph | 2,5-di-F— | H |
| 469 | A | Et | 2,6-di-F-4-MeO—Ph | 2,5-di-F— | Cl |
| 470 | A | Et | 2,6-di-F—Ph | 2,5-di-Cl— | Me |
| 471 | A | Me | 2,6-di-F—Ph | 2,5-di-Cl— | Me |
| 472 | A | Et | 2,6-di-F—Ph | 3-Cl-2-F— | H |
| 473 | A | Et | 2,6-di-F—Ph | 3-Cl-2-F— | Cl |
| 474 | A | Me | 2,6-di-F—Ph | 3-Cl-2-F— | H |
| 475 | A | Me | 2,6-di-F—Ph | 3-Cl-2-F— | Cl |
| 476 | A | Et | 2,6-di-F-4-MeO—Ph | 2-Cl-5-F— | Br |
| 477 | B | Et | 2,6-di-F—Ph | 2,5-di-F— | H |
| 478 | A | Et | 2,6-di-F—Ph | 2,5-di-F— | H |
| 479 | A | Et | 2,6-di-F-4-MeO—Ph | 2-Cl-5-F— | Me |
| 480 | B | Me | 2,6-di-F—Ph | 2,5-di-F— | H |
| 481 | A | Et | 2,6-di-F—Ph | 2,5-di-F— | Cl |
| 482 | A | Et | 2,6-di-F—Ph | 2,5-di-F— | Br |
| 483 | A | Me | 2,6-di-F—Ph | 2,5-di-F— | H |
| 484 | A | Me | 2,6-di-F—Ph | 2,5-di-F— | Cl |
| 485 | A | Me | 2,6-di-F—Ph | 2,5-di-F— | Br |
| 486 | A | Et | 2,4,6-tri-F—Ph | 2-Cl-3-F— | H |
| 487 | A | Et | 2,4,6-tri-F—Ph | 2-Cl-3-F— | Br |
| 488 | A | Et | 2,4,6-tri-F—Ph | 2-Cl-3-F— | Cl |
| 489 | A | Et | 2,6-di-F-4-MeO—Ph | 2-Cl-3-F— | H |
| 490 | A | Et | 2,6-di-F-4-MeO—Ph | 2-Cl-3-F— | Cl |
| 491 | A | Me | 2,4,6-tri-F—Ph | 2-Cl-3-F— | H |
| 492 | A | Me | 2,6-di-F-4-MeO—Ph | 2-Cl-3-F— | H |
| 493 | A | Et | 2,6-di-F—Ph | 3-Cl-2-F— | Me |
| 494 | A | F₂CHCH₂— | 2,6-di-F—Ph | 3-Cl-2-F— | H |
| 495 | A | F₂CHCH₂— | 2,6-di-F—Ph | 3-Cl-2-F— | Cl |
| 496 | A | cPr | 2,6-di-F—Ph | 2-Cl-5-MeO— | H |
| 497 | A | Et | 2,6-di-F—Ph | 2,5-di-F— | Me |
| 498 | A | cPr | 2,6-di-F—Ph | 2-Cl-5-MeO— | Cl |
| 499 | A | Me | 2,6-di-F—Ph | 2,5-di-F— | Me |
| 500 | A | Me | 2,4,6-tri-F—Ph | 2-Cl-3-F— | Cl |

TABLE 4-continued

| Compound | Structure | R1 | Y | (R2)n | R3 |
|---|---|---|---|---|---|
| 501 | A | Et | 2,4,6-tri-F—Ph | 2-Cl-3-F— | Me |
| 502 | A | Et | 2,4,6-tri-F—Ph | 3-F-2-Me— | Me |
| 503 | A | Me | 2,4,6-tri-F—Ph | 2-Cl-3-F— | Br |
| 504 | A | Me | 2,6-di-F-4-MeO—Ph | 2-Cl-3-F— | Cl |
| 505 | A | Me | 2,4,6-tri-F—Ph | 2-Cl-3-F— | Me |
| 506 | A | Et | 2,6-di-F—Ph | 2-Cl-3-F— | H |
| 507 | A | Et | 2,6-di-F—Ph | 2-Cl-3-F— | Cl |
| 508 | A | Me | 2,6-di-F—Ph | 2-Cl-3-F— | H |
| 509 | A | Me | 2,6-di-F—Ph | 2-Cl-3-F— | Cl |
| 510 | A | F$_2$CHCH$_2$— | 2,6-di-F—Ph | 2-Cl-3-F— | H |
| 511 | A | F$_2$CHCH$_2$— | 2,6-di-F—Ph | 2-Cl-3-F— | Cl |
| 512 | A | Et | 2,6-di-F—Ph | 2-Cl-5-F— | F |
| 513 | A | Me | 2,6-di-F—Ph | 2-Cl-5-F— | F |
| 514 | B | Et | 2,4,6-tri-F—Ph | 2-F— | H |
| 515 | A | Et | 2,6-di-F-4-MeO—Ph | 2-Cl-3-F— | Me |
| 516 | A | Et | 2,6-di-F-4-MeO—Ph | 3-F-2-Me— | Me |
| 517 | A | Me | 2,6-di-F-4-MeO—Ph | 2-Cl-3-F— | Me |
| 518 | A | Et | 2,6-di-F—Ph | 2,3-di-F— | H |
| 519 | A | Et | 2,6-di-F—Ph | 2,3-di-F— | Cl |
| 520 | A | Et | 2,6-di-F—Ph | 2,3-di-F— | Br |
| 521 | A | F$_2$CHCH$_2$— | 2,6-di-F—Ph | 3-Cl-2-F— | Me |
| 522 | A | Et | 2,6-di-F—Ph | 5-Cl-2-F— | H |
| 523 | A | Et | 2,6-di-F—Ph | 5-Cl-2-F— | Cl |
| 524 | A | Me | 2,6-di-F—Ph | 5-Cl-2-F— | H |
| 525 | A | Me | 2,6-di-F—Ph | 5-Cl-2-F— | Cl |
| 526 | B | Me | 2,4,6-tri-F—Ph | 2-F— | H |
| 527 | A | Et | 2,4,6-tri-F—Ph | 2-F— | H |
| 528 | A | Me | 2,4,6-tri-F—Ph | 2-F— | H |
| 529 | A | Et | 2,4,6-tri-F—Ph | 2-F— | Cl |
| 530 | A | Et | 2,6-di-F-4-MeO—Ph | 2-F— | H |
| 531 | A | Et | 2,6-di-F-4-MeO—Ph | 2-F— | Cl |
| 532 | A | Et | 2,4,6-tri-F—Ph | 2-F— | Br |
| 533 | A | Et | 2,6-di-F—Ph | 2-Cl-5-MeO— | F |
| 534 | A | Et | 2,6-di-F—Ph | 2,3-di-F— | Me |
| 535 | A | Me | 2,6-di-F—Ph | 2,3-di-F— | H |
| 536 | A | Me | 2,6-di-F—Ph | 2,3-di-F— | Br |
| 537 | A | Me | 2,6-di-F—Ph | 2,3-di-F— | Cl |
| 538 | A | Me | 2,6-di-F—Ph | 2,3-di-F— | Me |
| 539 | A | F$_2$CHCH$_2$— | 2,6-di-F—Ph | 5-Cl-2-F— | H |
| 540 | A | F$_2$CHCH$_2$— | 2,6-di-F—Ph | 5-Cl-2-F— | Cl |
| 541 | A | Et | 2,6-di-F-4-MeO—Ph | 2-F— | Br |
| 542 | A | Et | 2,4,6-tri-F—Ph | 2-F— | Me |
| 543 | A | Me | 2,4,6-tri-F—Ph | 2-F— | Cl |
| 544 | A | Me | 2,6-di-F-4-MeO—Ph | 2-F— | H |
| 545 | A | Me | 2,4,6-tri-F—Ph | 2-F— | Br |
| 546 | A | Et | 2,6-di-F-4-MeO—Ph | 2,3,5-tri-F— | Cl |
| 547 | A | Et | 4-EtO-2,6-di-F—Ph | 2-Cl-5-F— | Cl |
| 548 | A | Et | 2,6-di-F-4-MeO—Ph | 2,3,5-tri-F— | H |
| 549 | A | Me | 2,6-di-F-4-MeO—Ph | 2,3,5-tri-F— | Cl |
| 550 | A | Me | 2,6-di-F-4-MeO—Ph | 2,3,5-tri-F— | H |
| 551 | A | Et | 2,6-di-F—Ph | 2-Cl-3,5-di-F— | H |
| 552 | A | Et | 2,6-di-F—Ph | 2-Cl-3,5-di-F— | Cl |
| 553 | A | Me | 2,6-di-F—Ph | 2-Cl-3,5-di-F— | H |
| 554 | A | Me | 2,6-di-F—Ph | 2-Cl-3,5-di-F— | Cl |
| 555 | A | F$_2$CHCH$_2$— | 2,6-di-F—Ph | 2-Cl-3,5-di-F— | H |
| 556 | A | F$_2$CHCH$_2$— | 2,6-di-F—Ph | 2-Cl-3,5-di-F— | Cl |
| 557 | A | Me | 2,4,6-tri-F—Ph | 2,3-di-F— | H |
| 558 | A | Et | 2,4,6-tri-F—Ph | 2,3-di-F— | H |
| 559 | A | Me | 2,4,6-tri-F—Ph | 2,3-di-F— | Cl |
| 560 | A | Me | 2,4,6-tri-F—Ph | 2,3-di-F— | Br |
| 561 | A | Me | 2,6-di-F-4-MeO—Ph | 2,3-di-F— | H |
| 562 | A | Me | 2,6-di-F-4-MeO—Ph | 2,3-di-F— | Cl |
| 563 | A | Me | 2,6-di-F-4-MeO—Ph | 2,3-di-F— | Br |
| 564 | A | Me | 2,4,6-tri-F—Ph | 2,3-di-F— | Me |
| 565 | A | Me | 2,6-di-F-4-MeO—Ph | 2,3-di-F— | Me |
| 566 | A | Et | 2,4,6-tri-F—Ph | 2,3-di-F— | Cl |
| 567 | A | Et | 2,4,6-tri-F—Ph | 2,3-di-F— | Br |
| 568 | A | Et | 2,4,6-tri-F—Ph | 2-F— | F |
| 569 | A | Et | 2,6-di-F-4-MeO—Ph | 2-F— | Me |
| 570 | A | Me | 2,6-di-F-4-MeO—Ph | 2-F— | Cl |
| 571 | A | Me | 2,4,6-tri-F—Ph | 2-F— | Me |
| 572 | A | Me | 2,6-di-F-4-MeO—Ph | 2-F— | Br |
| 573 | B | Et | 2,4,6-tri-F—Ph | 2-Cl-4-F— | H |
| 574 | B | Me | 2,4,6-tri-F—Ph | 2-Cl-4-F— | H |
| 575 | A | Et | 2,4,6-tri-F—Ph | 2-Cl-4-F— | H |
| 576 | A | Me | 2,4,6-tri-F—Ph | 2-Cl-4-F— | H |
| 577 | A | Et | 2,4,6-tri-F—Ph | 2-Cl-4-F— | Cl |
| 578 | A | Et | 2,4,6-tri-F—Ph | 2-Cl-4-F— | Br |

TABLE 4-continued

| Compound | Structure | R1 | Y | (R2)n | R3 |
|---|---|---|---|---|---|
| 579 | A | Et | 4-EtO-2,6-di-F—Ph | 2,3,5-tri-F— | H |
| 580 | A | Et | 4-EtO-2,6-di-F—Ph | 2,3,5-tri-F— | Cl |
| 581 | D | Et | 2,6-di-F—Ph | 2-Cl-5-MeO— | H |
| 582 | C | Et | 2,6-di-F—Ph | 2-Cl-5-MeO— | H |
| 583 | B | Et | 2,4,6-tri-F—Ph | 2-Cl-3,5-di-F— | H |
| 584 | A | Et | 2,4,6-tri-F—Ph | 2-Cl-3,5-di-F— | H |
| 585 | A | Et | 2,4,6-tri-F—Ph | 2-Cl-3,5-di-F— | Cl |
| 586 | A | Me | 2,4,6-tri-F—Ph | 2-Cl-3,5-di-F— | H |
| 587 | A | Me | 2,4,6-tri-F—Ph | 2-Cl-3,5-di-F— | Cl |
| 588 | A | Et | 2,6-di-F-4-MeO—Ph | 2,3-di-F— | H |
| 589 | A | Et | 2,6-di-F-4-MeO—Ph | 2,3-di-F— | Br |
| 590 | A | Et | 2,6-di-F-4-MeO—Ph | 2,3-di-F— | Cl |
| 591 | A | Me | 4-EtO-2,6-di-F—Ph | 2-F— | H |
| 592 | A | Et | 2,4,6-tri-F—Ph | 2-Cl-4-F— | F |
| 593 | A | Et | 2,6-di-F-4-MeO—Ph | 2-Cl-4-F— | Cl |
| 594 | A | Et | 2,4,6-tri-F—Ph | 2-Cl-4-F— | Me |
| 595 | A | Et | 4-EtO-2,6-di-F—Ph | 2-Cl-4-F— | Cl |
| 596 | A | Me | 2,4,6-tri-F—Ph | 2-Cl-4-F— | Cl |
| 597 | A | Me | 2,4,6-tri-F—Ph | 2-Cl-4-F— | Br |
| 598 | A | Me | 4-EtO-2,6-di-F—Ph | 2-F— | Cl |
| 599 | A | Et | 2,6-di-F-4-MeO—Ph | 2-Cl-4-F— | Me |
| 600 | A | Me | 2,6-di-F-4-MeO—Ph | 2-Cl-4-F— | Cl |
| 601 | A | Et | 4-Cl-2,6-di-F—Ph | 2-Cl-5-F— | H |
| 602 | A | Et | 4-Cl-2,6-di-F—Ph | 2-Cl-5-F— | Cl |
| 603 | A | Et | 4-Cl-2,6-di-F—Ph | 2-Cl-5-F— | Br |
| 604 | A | Me | 4-Cl-2,6-di-F—Ph | 2-Cl-5-F— | H |
| 605 | A | Me | 4-Cl-2,6-di-F—Ph | 2-Cl-5-F— | Cl |
| 606 | A | Me | 4-Cl-2,6-di-F—Ph | 2-Cl-5-F— | Br |
| 607 | A | F$_2$CHCH$_2$— | 2,4,6-tri-F—Ph | 2-Cl-3,5-di-F— | H |
| 608 | A | F$_2$CHCH$_2$— | 2,4,6-tri-F—Ph | 2-Cl-3,5-di-F— | Cl |
| 609 | A | Et | 2,4,6-tri-F—Ph | 2,3-di-F— | Me |
| 610 | A | Et | 2,6-di-F-4-MeO—Ph | 2,3-di-F— | Me |
| 611 | A | Et | 4-EtO-2,6-di-F—Ph | 2,3-di-F— | Me |
| 612 | A | Me | 4-EtO-2,6-di-F—Ph | 2-Cl-4-F— | H |
| 613 | A | Me | 2,4,6-tri-F—Ph | 2-Cl-4-F— | Me |
| 614 | B | Et | 2,4,6-tri-F—Ph | 2-Cl-3-F-5-MeO— | H |
| 615 | A | Et | 2,4,6-tri-F—Ph | 2-Cl-3-F-5-MeO— | H |
| 616 | A | Me | 4-EtO-2,6-di-F—Ph | 2-Cl-4-F— | Cl |
| 617 | A | Et | 2,4,6-tr-i-F—Ph | 2-Cl-3-F-5-MeO— | Cl |
| 618 | A | Et | 2,4,6-tri-F—Ph | 2-Cl-3-MeO— | H |
| 619 | A | Et | 2,4,6-tri-F—Ph | 2-Cl-3-MeO— | Cl |
| 620 | A | Et | 2,4,6-tri-F—Ph | 2-Cl-3-MeO— | Br |
| 621 | A | Me | 2,6-di-F-4-MeO—Ph | 2-Cl-4-F— | Me |
| 622 | B | Et | 2,4,6-tri-F—Ph | 4-Br-2-Cl— | H |
| 623 | A | Et | 2,6-di-F-4-MeO—Ph | 2-Cl-3-F-5-MeO— | H |
| 624 | A | Et | 2,4,6-tri-F—Ph | 4-Br-2-Cl— | H |
| 625 | A | Et | 2,4,6-tri-F—Ph | 4-Br-2-Cl— | Cl |
| 626 | A | Et | 2,4,6-tri-F—Ph | 2-Cl-4-Me— | H |
| 627 | A | Et | 2,6-di-F-4-MeO—Ph | 2-Cl-3-F-5-MeO— | Cl |
| 628 | A | Et | 2,4,6-tri-F—Ph | 2-Cl-4-Me— | Cl |
| 629 | A | Et | 2,6-di-F—Ph | 2,4-di-F— | H |
| 630 | A | Et | 2,6-di-F—Ph | 2,4-di-F— | Cl |
| 631 | A | Me | 2,6-di-F—Ph | 2,4-di-F— | H |
| 632 | A | Et | 2,4,6-tri-F—Ph | 2-Cl-3-MeO— | Me |
| 633 | A | Et | 2,6-di-F-4-MeO—Ph | 2-Cl-3-MeO— | H |
| 634 | A | Et | 4-EtO-2,6-di-F—Ph | 2-Cl-3-MeO— | H |
| 635 | A | Et | 2,4,6-tri-F—Ph | 2,4,5-tri-F— | H |
| 636 | A | Et | 2,4,6-tri-F—Ph | 2,4,5-tri-F— | Cl |
| 637 | A | Et | 2,6-di-F-4-MeO—Ph | 2,4,5-tri-F— | Cl |
| 638 | A | Et | 2,6-di-F-4-MeO—Ph | 2,4,5-tri-F— | H |
| 639 | A | Me | 2,4,6-tri-F—Ph | 2,4,5-tri-F— | H |
| 640 | A | Et | 2,6-di-F-4-MeO—Ph | 2-Cl-3-MeO— | Cl |
| 641 | A | Et | 4-EtO-2,6-di-F—Ph | 2-Cl-3-MeO— | Cl |
| 642 | A | Et | 2,6-di-F-4-MeO—Ph | 2-Cl-3-MeO— | Br |
| 643 | A | Et | 4-EtO-2,6-di-F—Ph | 2-Cl-3-MeO— | Br |
| 644 | A | Et | 2,6-di-F-4-MeO—Ph | 2-Cl-3-MeO— | Me |
| 645 | A | Et | 4-EtO-2,6-di-F—Ph | 2-Cl-3-MeO— | Me |
| 646 | A | Me | 2,6-di-F—Ph | 2,4-di-F— | Cl |
| 647 | A | F$_2$CHCH$_2$— | 2,6-di-F—Ph | 2,4-di-F— | H |
| 648 | A | F$_2$CHCH$_2$— | 2,6-di-F—Ph | 2,4-di-F— | Cl |
| 649 | C | Et | 2,4,6-tri-F—Ph | 2-Cl-3,5-di-F— | H |
| 650 | B | Et | 2,4,6-tri-F—Ph | 2-Br— | H |
| 651 | A | Et | 2,4,6-tri-F—Ph | 2-Br— | H |
| 652 | A | Et | 2,4,6-tri-F—Ph | 2-Br— | Cl |
| 653 | A | Me | 2,4,6-tri-F—Ph | 2,4,5-tri-F— | Cl |
| 654 | A | Me | 2,6-di-F-4-MeO—Ph | 2,4,5-tri-F— | H |
| 655 | A | Me | 2,6-di-F-4-MeO—Ph | 2,4,5-tri-F— | Cl |
| 656 | A | Et | 2,6-di-F-4-MeO—Ph | 2-Cl-3-F— | Br |

TABLE 4-continued

| Compound | Structure | R1 | Y | (R2)n | R3 |
|---|---|---|---|---|---|
| 657 | A | Et | 4-EtO-2,6-di-F—Ph | 2-Cl-3-F— | H |
| 658 | A | Et | 4-EtO-2,6-di-F—Ph | 2-Cl-3-F— | Cl |
| 659 | A | Et | 4-EtO-2,6-di-F—Ph | 2-Cl-3-F— | Br |
| 660 | A | Et | 4-EtO-2,6-di-F—Ph | 2-Cl-3-F— | Me |
| 661 | A | Me | 2,4,6-tri-F—Ph | 2-Cl-3-MeO— | H |
| 662 | A | Me | 2,4,6-tri-F—Ph | 2-Cl-3-MeO— | Br |
| 663 | A | Me | 2,6-di-F-4-MeO—Ph | 2-Cl-3-MeO— | H |
| 664 | A | Me | 4-EtO-2,6-di-F—Ph | 2-Cl-3-MeO— | H |
| 665 | A | Et | 2,6-di-F-4-MeO—Ph | 2-Cl-3,5-di-F— | H |
| 666 | A | Et | 2,6-di-F-4-MeO—Ph | 2-Cl-3,5-di-F— | Cl |
| 667 | A | Et | 2,6-di-F-4-MeO—Ph | 2-Br— | H |
| 668 | A | Et | 2,6-di-F-4-MeO—Ph | 2-Br— | Cl |
| 669 | A | Me | 2,6-di-F-4-MeO—Ph | 2-Cl-3-MeO— | Br |
| 670 | A | Me | 4-EtO-2,6-di-F—Ph | 2-Cl-3-MeO— | Br |
| 671 | A | Me | 2,4,6-tri-F—Ph | 2-Cl-3-MeO— | Me |
| 672 | A | Me | 2,6-di-F-4-MeO—Ph | 2-Cl-3-MeO— | Me |
| 673 | A | Me | 4-EtO-2,6-di-F—Ph | 2-Cl-3-MeO— | Me |
| 674 | A | Et | 2,4,6-tri-F—Ph | 3-F-2-Me— | H |
| 675 | A | Et | 2,4,6-tri-F—Ph | 3-F-2-Me— | Cl |
| 676 | A | Me | 2,6-di-F-4-MeO—Ph | 2-Cl-3,5-di-F— | H |
| 677 | A | Me | 2,6-di-F-4-MeO—Ph | 2-Cl-3,5-di-F— | Cl |
| 678 | A | F$_2$CHCH$_2$— | 2,6-di-F-4-MeO—Ph | 2-Cl-3,5-di-F— | H |
| 679 | A | F$_2$CHCH$_2$— | 2,6-di-F-4-MeO—Ph | 2-Cl-3,5-di-F— | Cl |
| 680 | A | Me | 4-Br-2,6-di-F—Ph | 2-Cl-5-F— | H |
| 681 | A | Me | 4-Br-2,6-di-F—Ph | 2-Cl-5-F— | Cl |
| 682 | A | Et | 2,4,6-tri-F—Ph | 3-F-2-Me— | Br |
| 683 | A | Et | 2,4,6-tri-F—Ph | 2-Cl— | Br |
| 684 | A | Et | 4-EtO-2,6-di-F—Ph | 2-Cl— | Cl |
| 685 | A | Et | 4-EtO-2,6-di-F—Ph | 2-Cl— | H |
| 686 | A | Et | 2,6-di-F-4-MeO—Ph | 2-Cl— | Br |
| 687 | A | Et | 2,4,6-tri-F—Ph | 2-Cl— | Me |
| 688 | A | Et | 2,4,6-tri-F—Ph | 2-Cl-3,5-di-F— | Br |
| 689 | A | Et | 2,4,6-tri-F—Ph | 2-Cl-3,5-di-F— | Me |
| 690 | A | Me | 2,6-di-F-4-Me—Ph | 2-Cl-5-F— | H |
| 691 | A | Me | 2,6-di-F-4-Me—Ph | 2-Cl-5-F— | Cl |
| 692 | A | Et | 4-Br-2,6-di-F—Ph | 2-Cl-5-F— | H |
| 693 | C | Et | 2,6-di-F-4-MeO—Ph | 2-Cl-3,5-di-F— | H |
| 694 | A | Me | 2,4,6-tri-F—Ph | 2-Cl-3,5-di-F— | Me |
| 695 | A | Et | 2,6-di-F-4-MeO—Ph | 2-Cl-3,5-di-F— | Br |
| 696 | C | Et | 2,4,6-tri-F—Ph | 2-Cl-3,5-di-MeO— | H |
| 697 | A | Et | 2,6-di-F-4-MeO—Ph | 3-F-2-Me— | H |
| 698 | A | Et | 4-EtO-2,6-di-F—Ph | 3-F-2-Me— | H |
| 699 | A | Et | 2,6-di-F-4-MeO—Ph | 3-F-2-Me— | Cl |
| 700 | A | Et | 4-EtO-2,6-di-F—Ph | 3-F-2-Me— | Cl |
| 701 | A | Et | 2,6-di-F-4-MeO—Ph | 2-Cl— | Me |
| 702 | A | Et | 4-EtO-2,6-di-F—Ph | 2-Cl— | Me |
| 703 | A | Et | 4-EtO-2,6-di-F—Ph | 2-Cl— | Br |
| 704 | B | N≡C— | 2,6-di-F—Ph | 2-Cl-5-MeO— | H |
| 705 | B | Me | 2,4,6-tri-F—Ph | 2-Cl— | H |
| 706 | A | Et | 4-Br-2,6-di-F—Ph | 2-Cl-5-F— | Cl |
| 707 | A | Et | 2,6-di-F-4-Me—Ph | 2-Cl-5-F— | H |
| 708 | A | Et | 2,6-di-F-4-Me—Ph | 2-Cl-5-F— | Cl |
| 709 | A | Et | 2,6-di-F-4-Me—Ph | 2-Cl-5-F— | Br |
| 710 | A | Et | 2,6-di-F-4-Me—Ph | 2-Cl-5-F— | Me |
| 711 | A | Et | 2,6-di-F-4-MeO—Ph | 3-F-2-Me— | Br |
| 712 | A | Et | 4-EtO-2,6-di-F—Ph | 3-F-2-Me— | Br |
| 713 | A | Et | 4-EtO-2,6-di-F—Ph | 3-F-2-Me— | Me |
| 714 | A | Et | 2,6-di-F-4-MeO—Ph | 2-Cl-3,5-di-F— | Me |
| 715 | C | Et | 2,4,6-tri-F—Ph | 2-Cl— | H |
| 716 | C | Et | 2,6-di-F-4-MeO—Ph | 2-Cl-3,5-di-MeO— | H |
| 717 | A | Me | 2,6-di-F-4-MeO—Ph | 2-Cl-3,5-di-F— | Br |
| 718 | C | Et | 2,6-di-F-4-MeO—Ph | 2-Cl— | H |
| 719 | A | N≡C— | 2,6-di-F—Ph | 2-Cl-5-MeO— | H |
| 720 | A | Me | 2,4,6-tri-F—Ph | 2-Cl— | Br |
| 721 | A | Me | 2,6-di-F-4-MeO—Ph | 2-Cl-5-MeO— | H |
| 722 | A | Me | 2,6-di-F-4-MeO—Ph | 2-Cl-5-MeO— | Cl |
| 723 | A | Me | 2,6-di-F-4-MeO—Ph | 2-Cl-5-MeO— | Br |
| 724 | A | Me | 2,6-di-F-4-MeO—Ph | 2-Cl-5-MeO— | Me |
| 725 | A | Me | 2,4,6-tri-F—Ph | 2-Cl-5-MeO— | Br |
| 726 | A | Me | 2,4,6-tri-F—Ph | 2-Cl-5-MeO— | Me |
| 727 | A | Et | 4-(F$_3$CCH$_2$O)-2,6-di-F—Ph | 2-Cl-3-F— | Cl |
| 728 | C | Et | 2,6-di-F—Ph | 2-Cl-3,5-di-MeO— | H |
| 729 | C | Et | 2,6-di-F—Ph | 2,3,5-tri-F— | H |
| 730 | A | Me | 4-EtO-2,6-di-F—Ph | 2-Cl— | H |
| 731 | A | Me | 2,4,6-tri-F—Ph | 2-Cl— | Me |
| 732 | A | Me | 2,6-di-F-4-MeO—Ph | 2-Cl— | Br |
| 733 | A | Me | 2,6-di-F-4-MeO—Ph | 2-Cl— | Me |
| 734 | A | Me | 4-EtO-2,6-di-F—Ph | 2-Cl— | Cl |

TABLE 4-continued

| Compound | Structure | R1 | Y | (R2)n | R3 |
|---|---|---|---|---|---|
| 735 | A | Et | 2,6-di-F—Ph | 2-Cl-4-MeO— | H |
| 736 | A | Et | 2,6-di-F—Ph | 2-Cl-4-MeO— | Cl |
| 737 | A | Et | 2,6-di-F—Ph | 2-Cl-4-MeO— | Br |
| 738 | C | Et | 2,4,6-tri-F—Ph | 2-Cl-5-F— | H |
| 739 | C | Et | 2,6-di-F-4-MeO—Ph | 2-Cl-5-F— | H |
| 740 | A | Me | 2,6-di-F—Ph | 2-Cl-4-MeO— | H |
| 741 | A | Et | 2,6-di-F—Ph | 2-Cl-4-MeO— | Me |
| 742 | A | Et | 2,4,6-tri-F—Ph | 2-Cl-4-MeO— | H |
| 743 | A | Me | 2,6-di-F—Ph | 2-Cl-4-MeO— | Cl |
| 744 | A | Me | 2,6-di-F—Ph | 2-Cl-4-MeO— | Br |
| 745 | A | Et | 2,6-di-F—Ph | 2-Cl-3-F— | Br |
| 746 | A | Et | 2,4,6-tri-F—Ph | 2-Cl-4-MeO— | Cl |
| 747 | A | Et | 2,4,6-tri-F—Ph | 2-Cl-4-MeO— | Br |
| 748 | A | Et | 2,6-di-F-4-MeO—Ph | 2-Cl-4-MeO— | Cl |
| 749 | A | Me | 2,6-di-F—Ph | 2-Cl-4-MeO— | Me |
| 750 | A | Et | 2,4,6-tri-F—Ph | 2-Cl-4-MeO— | Me |
| 751 | A | Et | 2,6-di-F-4-MeO—Ph | 2-Cl-4-MeO— | Me |
| 752 | A | Et | 2,6-di-F—Ph | 2-Cl-3-F— | Me |
| 753 | A | Me | 2,6-di-F—Ph | 2-Cl-3-F— | Br |
| 754 | A | Me | 2,6-di-F—Ph | 2-Cl-3-F— | Me |
| 755 | A | Et | 2,6-di-F-4-MeO—Ph | 2-Cl-4-MeO— | H |
| 756 | A | Me | 2,4,6-tri-F—Ph | 2-Cl-4-MeO— | H |
| 757 | A | Me | 2,4,6-tri-F—Ph | 2-Cl-5-F— | Br |
| 758 | A | Me | 2,4,6-tri-F—Ph | 2-Cl-5-F— | Me |
| 759 | A | Me | 2,6-di-F-4-MeO—Ph | 2-Cl-5-F— | Me |
| 760 | A | Me | 2,6-di-F-4-MeO—Ph | 2-Cl-5-F— | H |
| 761 | A | Me | 2,6-di-F-4-MeO—Ph | 2-Cl-5-F— | Cl |
| 762 | A | Et | 2,4,6-tri-F—Ph | — | H |
| 763 | A | Et | 2,6-di-F-4-MeO—Ph | — | H |
| 764 | A | Et | 2,4,6-tri-F—Ph | MeO— | Cl |
| 765 | A | Me | 2,6-di-F-4-MeO—Ph | 2-Cl-4-MeO— | H |
| 766 | A | Me | 2,4,6-tri-F—Ph | 2-Cl-4-MeO— | Cl |
| 767 | A | Me | 2,4,6-tri-F—Ph | 2-Cl-4-MeO— | Br |
| 768 | A | Et | 2,4,6-tri-F—Ph | 2-Cl-5-MeO— | Br |
| 769 | A | Et | 2,4,6-tri-F—Ph | 2-Cl-5-MeO— | Me |
| 770 | A | Et | 2,6-di-F-4-MeO—Ph | 2-Cl-5-MeO— | H |
| 771 | A | Et | 2,6-di-F-4-MeO—Ph | 2-Cl-5-MeO— | Me |
| 772 | A | Et | 2,6-di-F-4-MeO—Ph | 2-Cl-5-MeO— | Cl |
| 773 | A | Et | 2,6-di-F-4-MeO—Ph | — | Cl |
| 774 | A | Et | 2,4,6-tri-F—Ph | — | Br |
| 775 | A | Et | 2,6-di-F-4-MeO—Ph | — | Br |
| 776 | A | Me | 2,6-di-F-4-MeO—Ph | 2-Cl-4-MeO— | Cl |
| 777 | A | Me | 2,4,6-tri-F—Ph | — | H |
| 778 | A | Me | 2,6-di-F-4-MeO—Ph | — | H |
| 779 | A | Me | 2,4,6-tri-F—Ph | — | Cl |
| 780 | A | Me | 2,4,6-tri-F—Ph | — | Br |
| 781 | A | Me | 2,6-di-F-4-MeO—Ph | — | Cl |
| 782 | A | Me | 2,6-di-F-4-MeO—Ph | — | Br |
| 783 | A | Et | 2,6-di-F—Ph | 2-Cl-3-MeO— | Cl |
| 784 | A | Me | 2,6-di-F—Ph | 2-Cl-3-MeO— | H |
| 785 | A | Me | 2,6-di-F—Ph | 2-Cl-3-MeO— | Cl |
| 786 | A | Me | 2,6-di-F—Ph | 2-Cl-3-MeO— | Br |
| 787 | A | Me | 2,4,6-tri-F—Ph | 2-Cl-3-MeO— | Cl |
| 788 | A | Me | 2,6-di-F-4-MeO—Ph | 2-Cl-3-MeO— | Cl |
| 789 | A | Et | 2,4,6-tri-F—Ph | 3,5-di-F— | H |
| 790 | A | Et | 2,6-di-F-4-MeO—Ph | 3,5-di-F— | H |
| 791 | A | Et | 2,4,6-tri-F—Ph | 3,5-di-F— | Cl |
| 792 | A | Et | 2,4,6-tri-F—Ph | 2-Cl-5-HO— | Cl |
| 793 | A | Et | 2,4,6-tri-F—Ph | 2-Cl-5-EtO— | Cl |
| 794 | A | Et | 2,4,6-tri-F—Ph | 2-Cl-5-N≡CCH$_2$O— | Cl |
| 795 | A | Et | 2,4,6-tri-F—Ph | 2-Cl-5-MeOCH$_2$O— | Cl |
| 796 | A | Et | 2,6-di-F-4-MeO—Ph | 2-Cl-5-EtO— | Cl |
| 797 | A | Et | 2,4,6-tri-F—Ph | 3,5-di-F— | Br |
| 798 | A | Et | 2,6-di-F-4-MeO—Ph | 3,5-di-F— | Cl |
| 799 | A | Et | 2,6-di-F-4-MeO—Ph | 3,5-di-F— | Br |
| 800 | A | Me | 2,4,6-tri-F—Ph | 3,5-di-F— | H |
| 801 | A | Et | 2,6-di-F—Ph | 2-Cl-5-N≡CCH$_2$O— | Me |
| 802 | A | Et | 2,6-di-F—Ph | 2-Cl-5-EtO— | Me |
| 803 | A | Me | 2,6-di-F-4-MeO—Ph | 3,5-di-F— | H |
| 804 | A | Me | 2,4,6-tri-F—Ph | 3,5-di-F— | Cl |
| 805 | A | Me | 2,4,6-tri-F—Ph | 3,5-di-F— | Br |
| 806 | A | Et | 2,4,6-tri-F—Ph | 2-Cl-3-HO— | Cl |
| 807 | A | Me | 2,6-di-F-4-MeO—Ph | 3,5-di-F— | Cl |
| 808 | A | Me | 2,6-di-F-4-MeO—Ph | 3,5-di-F— | Br |
| 809 | A | Et | 2,4,6-tri-F—Ph | 2-Cl-3-EtO— | Cl |
| 810 | A | Et | 2,4,6-tri-F—Ph | 2-Cl-3-N≡CCH$_2$O— | Cl |
| 811 | A | Et | 2,4,6-tri-F—Ph | 2-Cl-3-MeOCH$_2$O— | Cl |
| 812 | A | Et | 2,4,6-tri-F—Ph | 2-Br-3,5-di-F— | H |

TABLE 4-continued

| Compound | Structure | R1 | Y | (R2)n | R3 |
|---|---|---|---|---|---|
| 813 | A | Et | 2,4,6-tri-F—Ph | 2-Br-3,5-di-F— | Cl |
| 814 | A | Et | 2,4,6-tri-F—Ph | 2-Br-3,5-di-F— | Br |
| 815 | A | Me | 2,4,6-tri-F—Ph | 2-Br-3,5-di-F— | H |
| 816 | A | Me | 2,4,6-tri-F—Ph | 2-Br-3,5-di-F— | Cl |
| 817 | A | Me | 2,4,6-tri-F—Ph | 2-Br-3,5-di-F— | Br |
| 818 | A | Et | 2,6-di-F-4-MeO—Ph | 2-Br-3,5-di-F— | H |
| 819 | A | Et | 2,6-di-F-4-MeO—Ph | 2-Br-3,5-di-F— | Cl |
| 820 | A | Et | 2,6-di-F-4-MeO—Ph | 2-Br-3,5-di-F— | Br |
| 821 | A | Et | 2,4,6-tri-F—Ph | 2-Cl— | I |
| 822 | A | Et | 2,6-di-F-4-MeO—Ph | 2-Cl— | I |
| 823 | A | Me | 2,6-di-F-4-MeO—Ph | 2-Br-3,5-di-F— | H |
| 824 | A | Me | 2,6-di-F-4-MeO—Ph | 2-Br-3,5-di-F— | Cl |
| 825 | A | Me | 2,6-di-F-4-MeO—Ph | 2-Br-3,5-di-F— | Br |

Next, Table 5 shows $^1$H-NMR data for the compounds in Table 4.

TABLE 5

| Compound | $^1$H-NMR |
|---|---|
| 1 | $^1$H-NMR (CDCl$_3$) δ: 8.46 (1H, d, J = 2.1 Hz), 7.64 (1H, d, J = 2.1 Hz), 7.13-7.11 (3H, m), 6.92-6.92 (2H, m), 2.84-2.77 (4H, m), 2.79 (3H, s). |
| 2 | $^1$H-NMR (CDCl$_3$) δ: 8.54 (1H, d, J = 2.1 Hz), 7.66 (1H, d, J = 2.1 Hz), 7.45 (1H, d, J = 9.5 Hz), 7.18-7.18 (3H, m), 7.04-7.02 (2H, m), 6.78 (1H, d, J = 9.5 Hz), 3.28 (3H, s). |
| 3 | $^1$H-NMR (CDCl$_3$) δ: 8.36 (1H, d, J = 2.1 Hz), 7.65 (1H, d, J = 2.1 Hz), 7.12-7.09 (1H, m), 6.76-6.70 (2H, m), 2.84 (3H, s), 2.78-2.69 (4H, m). |
| 4 | $^1$H-NMR (CDCl$_3$) δ: 8.39 (1H, d, J = 2.1 Hz), 7.62 (1H, d, J = 2.1 Hz), 7.11-7.09 (1H, m), 6.73-6.70 (2H, m), 3.60 (1H, dd, J = 14.1, 7.0 Hz), 3.19 (1H, dd, J = 14.1, 7.0 Hz), 2.78-2.68 (4H, m), 1.00 (3H, t, J = 7.0 Hz). |
| 5 | $^1$H-NMR (CDCl$_3$) δ: 8.47 (1H, d, J = 2.0 Hz), 7.71 (1H, d, J = 2.0 Hz), 7.33 (1H, d, J = 9.8 Hz), 7.19-7.16 (1H, m), 6.82-6.73 (3H, m), 3.32 (3H, s). |
| 6 | $^1$H-NMR (CDCl$_3$) δ: 8.52 (1H, d, J = 2.1 Hz), 7.65 (1H, d, J = 2.1 Hz), 7.30 (1H, dd, J = 9.5, 1.1 Hz), 7.20-7.17 (1H, m), 6.85-6.82 (1H, m), 6.77 (1H, d, J = 9.5 Hz), 6.70-6.68 (1H, m), 4.06 (1H, dd, J = 13.5, 7.0 Hz), 3.68 (1H, dd, J = 13.5, 7.0 Hz), 1.16 (3H, t, J = 7.0 Hz). |
| 7 | $^1$H-NMR (CDCl$_3$) δ: 8.20 (1H, d, J = 2.4 Hz), 7.32 (1H, d, J = 9.2 Hz), 7.17-7.14 (2H, m), 6.78-6.74 (3H, m), 3.85 (3H, s), 3.32 (3H, s). |
| 8 | $^1$H-NMR (CDCl$_3$) δ: 8.25 (1H, d, J = 2.8 Hz), 7.30 (1H, dd, J = 9.5, 0.9 Hz), 7.17-7.14 (1H, m), 7.10 (1H, d, J = 2.8 Hz), 6.83 (1H, t, J = 8.6 Hz), 6.74 (1H, d, J = 9.5 Hz), 6.68 (1H, t, J = 8.6 Hz), 4.05-4.02 (1H, m), 3.86 (3H, s), 3.77-3.75 (1H, m), 1.15 (3H, t, J = 7.0 Hz). |
| 9 | $^1$H-NMR (CDCl$_3$) δ: 8.26 (1H, d, J = 2.4 Hz), 7.45 (1H, d, J = 9.3 Hz), 7.19-7.13 (3H, m), 7.05-7.03 (2H, m), 6.75 (1H, d, J = 9.3 Hz), 3.86 (3H, s), 3.28 (3H, s). |
| 10 | $^1$H-NMR (CDCl$_3$) δ: 8.56 (1H, d, J = 2.1 Hz), 7.62 (1H, d, J = 2.1 Hz), 7.42 (1H, d, J = 9.2 Hz), 7.17-7.16 (3H, m), 7.03-7.00 (2H, m), 6.76 (1H, d, J = 9.2 Hz), 4.04-4.02 (1H, m), 3.63-3.60 (1H, m), 1.17 (3H, t, J = 7.0 Hz). |
| 11 | $^1$H-NMR (CDCl$_3$) δ: 8.29 (1H, d, J = 2.4 Hz), 7.42 (1H, d, J = 9.3 Hz), 7.16-7.14 (3H, m), 7.08 (1H, d, J = 2.4 Hz), 7.02-7.01 (2H, m), 6.74 (1H, d, J = 9.3 Hz), 4.04-3.97 (1H, m), 3.86 (3H, s), 3.70-3.67 (1H, m), 1.16 (3H, t, J = 7.1 Hz). |
| 12 | $^1$H-NMR (CDCl$_3$) δ: 8.66 (1H, s), 8.42 (1H, d, J = 4.6 Hz), 7.44 (1H, d, J = 9.5 Hz), 7.17-7.16 (3H, m), 7.02-6.99 (3H, m), 6.76 (1H, d, J = 9.5 Hz), 3.31 (3H, s). |
| 13 | $^1$H-NMR (CDCl$_3$) δ: 8.61 (1H, s), 8.44 (1H, d, J = 4.9 Hz), 7.41 (1H, d, J = 9.5 Hz), 7.16-7.16 (3H, m), 7.12 (1H, d, J = 4.9 Hz), 7.01-6.99 (2H, m), 6.74 (1H, d, J = 9.2 Hz), 4.25-4.22 (1H, m), 3.46-3.43 (1H, m), 1.12 (3H, t, J = 7.0 Hz). |
| 14 | $^1$H-NMR (CDCl$_3$) δ: 7.40 (1H, d, J = 9.5 Hz), 7.34 (1H, tt, J = 8.6, 6.1 Hz), 6.89 (2H, dd, J = 8.6, 7.2 Hz), 6.72 (1H, d, J = 9.5 Hz), 6.26 (1H, t, J = 2.3 Hz), 6.22 (2H, d, J = 2.3 Hz), 3.90 (2H, q, J = 7.1 Hz), 3.66 (6H, s), 1.14 (3H, t, J = 7.1 Hz). |
| 15 | $^1$H-NMR (CDCl$_3$) δ: 7.30-7.23 (1H, m), 6.83 (2H, dd, J = 8.6, 7.3 Hz), 6.20 (1H, t, J = 2.3 Hz), 6.13 (2H, d, J = 2.3 Hz), 3.62 (6H, s), 3.41 (2H, q, J = 7.1 Hz), 2.78-2.70 (4H, m), 0.96 (3H, t, J = 7.1 Hz). |
| 16 | $^1$H-NMR (CDCl$_3$) δ: 7.34-7.28 (2H, m), 6.90 (1H, t, J = 8.4 Hz), 6.83 (1H, t, J = 8.4 Hz), 6.73 (1H, d, J = 9.5 Hz), 6.30 (1H, d, J = 2.8 Hz), 6.28-6.27 (1H, m), 3.94-3.84 (2H, m), 3.81 (3H, s), 3.65 (3H, s), 1.16 (3H, t, J = 7.2 Hz). |
| 17 | $^1$H-NMR (CDCl$_3$) δ: 7.26 (1H, tt, J = 8.3, 6.4 Hz), 6.96-6.93 (2H, m), 6.84-6.79 (4H, m), 2.87 (3H, s), 2.78-2.73 (4H, m). |
| 18 | $^1$H-NMR (CDCl$_3$) δ: 7.26 (1H, tt, J = 8.3, 6.4 Hz), 6.95-6.92 (2H, m), 6.83-6.78 (4H, m), 3.41 (2H, q, J = 7.2 Hz), 2.74-2.72 (4H, m), 0.96 (3H, t, J = 7.2 Hz). |
| 19 | $^1$H-NMR (CDCl$_3$) δ: 7.38 (1H, d, J = 9.2 Hz), 7.34 (1H, tt, J = 8.3, 6.4 Hz), 7.02-7.00 (2H, m), 6.90-6.85 (4H, m), 6.75 (1H, d, J = 9.2 Hz), 3.38 (3H, s). |
| 20 | $^1$H-NMR (CDCl$_3$) δ: 7.36 (1H, d, J = 9.2 Hz), 7.33 (1H, tt, J = 8.4, 6.4 Hz), 7.03-7.01 (2H, m), 6.88-6.84 (4H, m), 6.73 (1H, d, J = 9.2 Hz), 3.90 (2H, q, J = 7.0 Hz), 1.14 (3H, t, J = 7.0 Hz). |
| 21 | $^1$H-NMR (CDCl$_3$) δ: 8.47 (1H, d, J = 2.1 Hz), 7.66 (1H, d, J = 2.1 Hz), 6.91-6.88 (2H, m), 6.82 (2H, t, J = 8.6 Hz), 2.79-2.77 (7H, m). |
| 22 | $^1$H-NMR (CDCl$_3$) δ: 8.55 (1H, d, J = 2.1 Hz), 7.84 (1H, s), 7.69 (1H, d, J = 2.1 Hz), 7.02-6.99 (2H, m), 6.88 (2H, t, J = 8.6 Hz), 3.34 (3H, s). |

TABLE 5-continued

| Compound | ¹H-NMR |
|---|---|
| 23 | ¹H-NMR (CDCl₃) δ: 8.55 (1H, d, J = 2.1 Hz), 7.68 (1H, d, J = 2.1 Hz), 7.40 (1H, d, J = 9.5 Hz), 7.00 (2H, dd, J = 8.7, 5.4 Hz), 6.87 (2H, t, J = 8.7 Hz), 6.77 (1H, d, J = 9.5 Hz), 3.27 (3H, s). |
| 24 | ¹H-NMR (CDCl₃) δ: 8.47 (1H, d, J = 2.1 Hz), 7.63 (1H, d, J = 2.1 Hz), 6.89-6.87 (2H, m), 6.82-6.80 (2H, m), 3.46 (1H, dq, J = 14.1, 7.0 Hz), 3.22 (1H, dq, J = 14.1, 7.0 Hz), 2.82-2.71 (4H, m), 0.98 (3H, t, J = 7.2 Hz). |
| 25 | ¹H-NMR (CDCl₃) δ: 8.57 (1H, d, J = 2.1 Hz), 7.82 (1H, s), 7.64 (1H, d, J = 2.1 Hz), 6.99-6.98 (2H, m), 6.88-6.86 (2H, m), 4.07 (1H, dq, J = 13.5, 7.2 Hz), 3.64 (1H, dq, J = 13.5, 7.2 Hz), 1.19 (3H, t, J = 7.2 Hz). |
| 26 | ¹H-NMR (CDCl₃) δ: 8.57 (1H, d, J = 2.1 Hz), 7.64 (1H, d, J = 2.1 Hz), 7.38 (1H, d, J = 9.5 Hz), 6.99-6.97 (2H, m), 6.88-6.84 (2H, m), 6.75 (1H, d, J = 9.5 Hz), 4.01 (1H, dq, J = 13.5, 7.0 Hz), 3.60 (1H, dq, J = 13.5, 7.0 Hz), 1.17 (3H, t, J = 7.0 Hz). |
| 27 | ¹H-NMR (CDCl₃) δ: 7.28-7.26 (1H, m), 6.84 (2H, dd, J = 8.6, 7.0 Hz), 6.21 (1H, t, J = 2.3 Hz), 6.14 (2H, d, J = 2.3 Hz), 3.61 (6H, s), 2.87 (3H, s), 2.80-2.72 (4H, m). |
| 28 | ¹H-NMR (CDCl₃) δ: 7.43 (1H, d, J = 9.2 Hz), 7.36-7.34 (1H, m), 6.90 (2H, dd, J = 8.3, 7.0 Hz), 6.74 (1H, d, J = 9.2 Hz), 6.27 (1H, t, J = 2.3 Hz), 6.21 (2H, d, J = 2.3 Hz), 3.65 (6H, s), 3.37 (3H, s). |
| 29 | ¹H-NMR (CDCl₃) δ: 7.34 (1H, d, J = 9.2 Hz), 7.31-7.29 (1H, m), 6.91 (1H, t, J = 8.4 Hz), 6.83 (1H, t, J = 8.4 Hz), 6.75 (1H, d, J = 9.2 Hz), 6.31 (1H, d, J = 2.8 Hz), 6.23 (1H, dd, J = 2.8, 1.5 Hz), 3.81 (3H, s), 3.63 (3H, s), 3.37 (3H, s). |
| 30 | ¹H-NMR (CDCl₃) δ: 7.36 (1H, d, J = 9.5 Hz), 7.32-7.30 (1H, m), 6.90 (1H, t, J = 8.4 Hz), 6.83 (1H, t, J = 8.4 Hz), 6.75 (1H, d, J = 9.5 Hz), 6.34 (1H, d, J = 2.8 Hz), 6.19 (1H, dd, J = 2.8, 1.2 Hz), 3.81 (3H, s), 3.63 (3H, s), 3.38 (3H, s). |
| 31 | ¹H-NMR (CDCl₃) δ: 7.44 (1H, d, J = 9.3 Hz), 7.38-7.36 (1H, m), 6.93-6.88 (2H, m), 6.76 (1H, d, J = 9.3 Hz), 6.30 (2H, s), 3.74 (6H, s), 3.38 (3H, s). |
| 32 | ¹H-NMR (CDCl₃) δ: 7.35-7.28 (2H, m), 6.90 (1H, t, J = 8.6 Hz), 6.83 (1H, t, J = 8.6 Hz), 6.73 (1H, d, J = 9.2 Hz), 6.32 (1H, d, J = 2.8 Hz), 6.24 (1H, dd, J = 2.8, 1.4 Hz), 3.96-3.94 (1H, m), 3.88-3.85 (1H, m), 3.80 (3H, s), 3.58 (3H, s), 1.15 (3H, t, J = 7.2 Hz). |
| 33 | ¹H-NMR (CDCl₃) δ: 7.03 (1H, dd, J = 8.6, 2.8 Hz), 7.00-6.98 (1H, m), 6.74 (1H, td, J = 8.6, 2.8 Hz), 6.36-6.34 (1H, m), 6.30-6.28 (1H, m), 3.74 (3H, s), 3.52-3.49 (1H, m), 3.35-3.32 (1H, m), 2.84-2.73 (2H, m), 2.70-2.65 (1H, m), 2.55-2.49 (1H, m), 0.98 (3H, t, J = 7.0 Hz). |
| 34 | ¹H-NMR (CDCl₃) δ: 7.71 (1H, s), 7.07-7.05 (2H, m), 6.80 (1H, td, J = 8.3, 2.4 Hz), 6.42-6.40 (1H, m), 6.38-6.35 (1H, m), 3.96 (2H, q, J = 7.1 Hz), 3.77 (3H, s), 1.17 (3H, t, J = 7.1 Hz). |
| 35 | ¹H-NMR (CDCl₃) δ: 7.27 (1H, d, J = 9.5 Hz), 7.06-7.04 (2H, m), 6.79 (1H, td, J = 8.3, 2.5 Hz), 6.71 (1H, d, J = 9.5 Hz), 6.42-6.40 (1H, m), 6.37-6.35 (1H, m), 3.93-3.90 (2H, m), 3.77 (3H, s), 1.15 (3H, t, J = 7.2 Hz). |
| 36 | ¹H-NMR (CDCl₃) δ: 7.04 (1H, dd, J = 8.6, 2.8 Hz), 6.98-6.97 (1H, m), 6.75-6.73 (1H, m), 6.38-6.35 (1H, m), 6.30-6.27 (1H, m), 3.74 (3H, s), 2.89 (3H, s), 2.85-2.77 (2H, m), 2.72-2.66 (1H, m), 2.55-2.52 (1H, m). |
| 37 | ¹H-NMR (CDCl₃) δ: 7.30 (1H, d, J = 9.2 Hz), 7.07 (1H, dd, J = 8.4, 2.6 Hz), 7.04-7.00 (1H, m), 6.80 (1H, td, J = 8.4, 2.6 Hz), 6.73 (1H, d, J = 9.2 Hz), 6.43-6.41 (1H, m), 6.37-6.35 (1H, m), 3.77 (3H, s), 3.39 (3H, s). |
| 38 | ¹H-NMR (CDCl₃) δ: 7.73 (1H, s), 7.07 (1H, dd, J = 8.6, 2.4 Hz), 7.04-7.02 (1H, m), 6.84-6.80 (1H, m), 6.41-6.37 (2H, m), 3.77 (3H, s), 3.45 (3H, s). |
| 39 | ¹H-NMR (CDCl₃) δ: 7.41 (1H, d, J = 9.5 Hz), 7.37-7.35 (1H, m), 6.91-6.89 (2H, m), 6.75 (1H, d, J = 9.5 Hz), 6.28 (2H, s), 3.92-3.88 (2H, m), 3.75 (6H, s), 1.16 (3H, t, J = 7.3 Hz). |
| 40 | ¹H-NMR (CDCl₃) δ: 7.41 (1H, d, J = 9.5 Hz), 7.37-7.35 (1H, m), 6.91-6.89 (2H, m), 6.75 (1H, d, J = 9.5 Hz), 6.31 (2H, s), 3.93-3.88 (2H, m), 3.76 (6H, s), 1.15 (3H, t, J = 7.0 Hz). |
| 41 | ¹H-NMR (CDCl₃) δ: 7.39 (1H, d, J = 9.3 Hz), 7.35-7.33 (1H, m), 6.89-6.87 (2H, m), 6.71 (1H, d, J = 9.3 Hz), 6.26 (1H, t, J = 2.4 Hz), 6.21 (2H, d, J = 2.4 Hz), 3.78-3.76 (2H, m), 3.66 (6H, s), 1.59-1.53 (2H, m), 0.74 (3H, t, J = 7.3 Hz). |
| 42 | ¹H-NMR (CDCl₃) δ: 7.32-7.30 (2H, m), 6.92-6.87 (1H, m), 6.84-6.80 (1H, m), 6.72 (1H, d, J = 9.3 Hz), 6.30 (1H, d, J = 2.9 Hz), 6.27-6.26 (1H, m), 3.85-3.83 (1H, m), 3.81 (3H, s), 3.72-3.66 (1H, m), 3.64 (3H, s), 1.61-1.57 (2H, m), 0.75 (3H, t, J = 7.3 Hz). |
| 43 | ¹H-NMR (CDCl₃) δ: 7.03 (1H, dd, J = 8.6, 2.8 Hz), 7.00-6.96 (1H, m), 6.74 (1H, td, J = 8.6, 2.8 Hz), 6.33-6.31 (1H, m), 6.25-6.23 (1H, m), 5.64-5.62 (1H, m), 4.97-4.95 (1H, m), 4.86-4.83 (1H, m), 4.18-4.15 (1H, m), 3.91-3.88 (1H, m), 3.73 (3H, s), 2.89-2.78 (2H, m), 2.74-2.69 (1H, m), 2.56-2.53 (1H, m). |
| 44 | ¹H-NMR (CDCl₃) δ: 7.29 (1H, d, J = 9.3 Hz), 7.06-7.03 (2H, m), 6.80-6.78 (1H, m), 6.73 (1H, d, J = 9.3 Hz), 6.39-6.37 (1H, m), 6.33-6.30 (1H, m), 5.81-5.71 (1H, m), 5.04-5.02 (1H, m), 4.79 (1H, d, J = 17.1 Hz), 4.59-4.56 (1H, m), 4.49-4.45 (1H, m), 3.76 (3H, s). |
| 45 | ¹H-NMR (CDCl₃) δ: 7.32 (1H, d, J = 9.3 Hz), 7.08-7.04 (2H, m), 6.81 (1H, td, J = 8.3, 2.6 Hz), 6.73 (1H, d, J = 9.3 Hz), 6.39-6.35 (2H, m), 4.62 (2H, dt, J = 47.3, 5.1 Hz), 4.19 (2H, dt, J = 24.1, 5.1 Hz), 3.76 (3H, s). |
| 46 | ¹H-NMR (CDCl₃) δ: 7.40 (1H, d, J = 9.5 Hz), 7.32-7.29 (1H, m), 7.17-7.15 (3H, m), 7.06-7.04 (2H, m), 6.85 (2H, dd, J = 8.5, 7.1 Hz), 6.73 (1H, d, J = 9.5 Hz), 3.91 (2H, q, J = 7.0 Hz), 1.14 (3H, t, J = 7.0 Hz). |
| 47 | ¹H-NMR (CDCl₃) δ: 7.43 (1H, d, J = 9.5 Hz), 7.33-7.30 (1H, m), 7.18-7.16 (3H, m), 7.05-7.04 (2H, m), 6.88-6.84 (2H, m), 6.75 (1H, d, J = 9.5 Hz), 3.38 (3H, s). |
| 48 | ¹H-NMR (CDCl₃) δ: 7.63 (1H, s), 7.32 (1H, tt, J = 8.6, 6.7 Hz), 7.18-7.16 (3H, m), 7.06-7.04 (2H, m), 6.86-6.85 (2H, m), 3.96 (2H, q, J = 7.0 Hz), 1.17 (3H, t, J = 7.0 Hz). |
| 49 | ¹H-NMR (CDCl₃) δ: 7.66 (1H, s), 7.34 (1H, tt, J = 8.6, 6.7 Hz), 7.19-7.17 (3H, m), 7.05-7.03 (2H, m), 6.87-6.86 (2H, m), 3.45 (3H, s). |
| 50 | ¹H-NMR (CDCl₃) δ: 7.84 (1H, s), 7.32 (1H, tt, J = 8.6, 6.7 Hz), 7.18-7.16 (3H, m), 7.06-7.04 (2H, m), 6.86-6.85 (2H, m), 3.96 (2H, q, J = 7.0 Hz), 1.17 (3H, t, J = 7.0 Hz). |
| 51 | ¹H-NMR (CDCl₃) δ: 7.86 (1H, s), 7.34 (1H, tt, J = 8.4, 6.7 Hz), 7.19-7.16 (3H, m), 7.05-7.03 (2H, m), 6.88-6.84 (2H, m), 3.45 (3H, s). |

TABLE 5-continued

| Compound | ¹H-NMR |
|---|---|
| 52 | ¹H-NMR (CDCl₃) δ: 7.22-7.21 (1H, m), 7.14 (1H, d, J = 8.9 Hz), 6.83 (1H, t, J = 8.6 Hz), 6.75 (1H, t, J = 8.6 Hz), 6.61 (1H, dd, J = 8.9, 3.1 Hz), 6.57-6.57 (1H, m), 3.63 (3H, s), 3.52-3.49 (1H, m), 3.35-3.32 (1H, m), 2.85-2.83 (2H, m), 2.72-2.69 (1H, m), 2.58-2.56 (1H, m), 0.99 (3H, t, J = 7.2 Hz). |
| 53 | ¹H-NMR (CDCl₃) δ: 7.33 (1H, d, J = 9.5 Hz), 7.31-7.30 (1H, m), 7.18 (1H, d, J = 8.9 Hz), 6.90 (1H, t, J = 8.4 Hz), 6.83 (1H, t, J = 8.4 Hz), 6.73 (1H, d, J = 9.5 Hz), 6.66 (1H, dd, J = 8.9, 3.1 Hz), 6.61-6.61 (1H, m), 3.94-3.87 (2H, m), 3.65 (3H, s), 1.16 (3H, t, J = 7.0 Hz). |
| 54 | ¹H-NMR (CDCl₃) δ: 7.57 (1H, s), 7.34-7.31 (1H, m), 7.18 (1H, d, J = 8.6 Hz), 6.90 (1H, t, J = 8.3 Hz), 6.84 (1H, t, J = 8.3 Hz), 6.68 (1H, dd, J = 8.6, 3.1 Hz), 6.61 (1H, dd, J = 3.1, 1.5 Hz), 3.96-3.95 (2H, m), 3.65 (3H, s), 1.18 (3H, t, J = 7.0 Hz). |
| 55 | ¹H-NMR (CDCl₃) δ: 7.77 (1H, s), 7.34-7.32 (1H, m), 7.17 (1H, d, J = 8.9 Hz), 6.90 (1H, t, J = 8.4 Hz), 6.84 (1H, t, J = 8.4 Hz), 6.68 (1H, dd, J = 8.9, 2.8 Hz), 6.61-6.61 (1H, m), 3.97-3.94 (2H, m), 3.65 (3H, s), 1.18 (3H, t, J = 7.0 Hz). |
| 56 | ¹H-NMR (CDCl₃) δ: 7.24-7.20 (1H, m), 7.15 (1H, d, J = 8.9 Hz), 6.84 (1H, t, J = 8.6 Hz), 6.76 (1H, t, J = 8.6 Hz), 6.61 (1H, dd, J = 8.9, 3.2 Hz), 6.56-6.55 (1H, m), 3.62 (3H, s), 2.89 (3H, s), 2.88-2.85 (2H, m), 2.75-2.69 (1H, m), 2.59-2.56 (1H, m). |
| 57 | ¹H-NMR (CDCl₃) δ: 7.36 (1H, d, J = 9.5 Hz), 7.34-7.30 (1H, m), 7.18 (1H, d, J = 8.9 Hz), 6.90 (1H, t, J = 8.4 Hz), 6.84 (1H, t, J = 8.4 Hz), 6.75 (1H, d, J = 9.5 Hz), 6.68 (1H, dd, J = 8.9, 3.1 Hz), 6.58 (1H, dd, J = 3.1, 1.5 Hz), 3.64 (3H, s), 3.39 (3H, s). |
| 58 | ¹H-NMR (CDCl₃) δ: 7.24-7.20 (1H, m), 7.02 (1H, dd, J = 8.6, 2.4 Hz), 7.00-6.97 (1H, m), 6.81 (1H, t, J = 8.4 Hz), 6.75 (1H, t, J = 8.4 Hz), 6.73-6.69 (1H, m), 3.52-3.49 (1H, m), 3.34-3.31 (1H, m), 2.87-2.76 (2H, m), 2.72-2.70 (1H, m), 2.56-2.53 (1H, m), 0.98 (3H, t, J = 7.0 Hz). |
| 59 | ¹H-NMR (CDCl₃) δ: 7.32-7.31 (2H, m), 7.05-7.04 (2H, m), 6.89 (1H, t, J = 8.4 Hz), 6.83 (1H, t, J = 8.4 Hz), 6.76-6.73 (2H, m), 3.97-3.83 (2H, m), 1.15 (3H, t, J = 7.0 Hz). |
| 60 | ¹H-NMR (CDCl₃) δ: 7.59 (1H, s), 7.35-7.32 (1H, m), 7.18 (1H, d, J = 8.9 Hz), 6.90 (1H, t, J = 8.6 Hz), 6.85 (1H, t, J = 8.6 Hz), 6.69 (1H, dd, J = 8.9, 3.1 Hz), 6.59-6.58 (1H, m), 3.65 (3H, s), 3.45 (3H, s). |
| 61 | ¹H-NMR (CDCl₃) δ: 7.79 (1H, s), 7.35-7.32 (1H, m), 7.18 (1H, d, J = 8.9 Hz), 6.90 (1H, t, J = 8.4 Hz), 6.85 (1H, t, J = 8.4 Hz), 6.69 (1H, dd, J = 8.9, 3.1 Hz), 6.58 (1H, dd, J = 3.1, 1.5 Hz), 3.65 (3H, s), 3.45 (3H, s). |
| 62 | ¹H-NMR (CDCl₃) δ: 7.53 (1H, s), 7.34-7.33 (1H, m), 7.07-7.04 (2H, m), 6.91-6.88 (1H, m), 6.86-6.84 (1H, m), 6.79-6.76 (1H, m), 3.97-3.94 (2H, m), 1.18 (3H, t, J = 7.2 Hz). |
| 63 | ¹H-NMR (CDCl₃) δ: 7.73 (1H, s), 7.34-7.32 (1H, m), 7.06-7.04 (2H, m), 6.91-6.87 (1H, m), 6.86-6.84 (1H, m), 6.79-6.75 (1H, m), 3.97-3.94 (2H, m), 1.18 (3H, t, J = 7.2 Hz). |
| 64 | ¹H-NMR (CDCl₃) δ: 7.34-7.31 (2H, m), 7.06 (1H, dd, J = 8.4, 2.6 Hz), 7.04-7.00 (1H, m), 6.89 (1H, t, J = 8.6 Hz), 6.84 (1H, t, J = 8.6 Hz), 6.78-6.75 (2H, m), 3.38 (3H, s). |
| 65 | ¹H-NMR (CDCl₃) δ: 7.32 (1H, d, J = 9.2 Hz), 7.29-7.25 (1H, m), 6.98 (1H, t, J = 8.1 Hz), 6.88 (1H, t, J = 8.4 Hz), 6.80 (1H, t, J = 8.4 Hz), 6.76-6.72 (2H, m), 6.69-6.67 (1H, m), 3.98-3.95 (1H, m), 3.88-3.80 (1H, m), 3.85 (3H, s), 1.16 (3H, t, J = 7.0 Hz). |
| 66 | ¹H-NMR (CDCl₃) δ: 7.75 (1H, s), 7.33-7.26 (1H, m), 6.99 (1H, t, J = 7.9 Hz), 6.90-6.85 (1H, m), 6.82-6.80 (1H, m), 6.78-6.76 (1H, m), 6.69-6.67 (1H, m), 3.97-3.92 (2H, m), 3.84 (3H, s), 1.18 (3H, t, J = 7.0 Hz). |
| 67 | ¹H-NMR (CDCl₃) δ: 7.34-7.25 (1H, m), 7.15 (1H, d, J = 9.5 Hz), 6.87-6.83 (1H, m), 6.82-6.80 (1H, m), 6.76 (1H, d, J = 9.5 Hz), 6.43 (1H, s), 4.02 (1H, dq, J = 14.5, 7.2 Hz), 3.90 (1H, dq, J = 14.5, 7.2 Hz), 3.86 (3H, s), 3.85 (3H, s), 1.14 (3H, t, J = 7.2 Hz). |
| 68 | ¹H-NMR (CDCl₃) δ: 7.31-7.28 (1H, m), 7.17 (1H, d, J = 9.5 Hz), 6.84-6.82 (2H, m), 6.76 (1H, d, J = 9.5 Hz), 6.45 (1H, s), 3.96 (2H, q, J = 7.0 Hz), 3.85 (6H, s), 1.14 (3H, t, J = 7.0 Hz). |
| 69 | ¹H-NMR (CDCl₃) δ: 7.39 (1H, s), 7.33-7.30 (1H, m), 6.88-6.80 (2H, m), 6.43 (1H, s), 4.05-3.96 (2H, m), 3.86-3.85 (6H, m), 1.16 (3H, t, J = 7.0 Hz). |
| 70 | ¹H-NMR (CDCl₃) δ: 7.59 (1H, s), 7.33-7.30 (1H, m), 6.88-6.80 (2H, m), 6.43 (1H, s), 4.07 (1H, dq, J = 13.9, 6.9 Hz), 3.94 (1H, dq, J = 13.9, 6.9 Hz), 3.86 (3H, s), 3.85 (3H, s), 1.16 (3H, t, J = 6.9 Hz). |
| 71 | ¹H-NMR (CDCl₃) δ: 7.38 (1H, d, J = 9.5 Hz), 6.70 (1H, d, J = 9.5 Hz), 6.43-6.40 (2H, m), 6.28 (1H, t, J = 2.1 Hz), 6.23 (2H, d, J = 2.1 Hz), 3.90 (2H, q, J = 7.1 Hz), 3.78 (3H, s), 3.68 (6H, s), 1.14 (3H, t, J = 7.1 Hz). |
| 72 | ¹H-NMR (CDCl₃) δ: 7.30 (1H, d, J = 9.5 Hz), 6.71 (1H, d, J = 9.5 Hz), 6.44-6.41 (1H, m), 6.36-6.34 (1H, m), 6.32 (1H, d, J = 2.8 Hz), 6.28 (1H, dd, J = 2.8, 1.7 Hz), 3.92-3.87 (2H, m), 3.82 (3H, s), 3.77 (3H, s), 3.67 (3H, s), 1.16 (3H, t, J = 7.0 Hz). |
| 73 | ¹H-NMR (CDCl₃) δ: 7.30 (1H, d, J = 9.2 Hz), 6.71 (1H, d, J = 9.2 Hz), 6.43-6.41 (1H, m), 6.37-6.34 (2H, m), 6.24 (1H, dd, J = 2.7, 1.5 Hz), 3.95-3.93 (1H, m), 3.88-3.86 (1H, m), 3.82 (3H, s), 3.76 (3H, s), 3.66 (3H, s), 1.16 (3H, t, J = 7.2 Hz). |
| 74 | ¹H-NMR (CDCl₃) δ: 7.33 (1H, d, J = 9.5 Hz), 7.31-7.25 (2H, m), 7.13-7.09 (1H, m), 7.09-7.04 (1H, m), 7.03-7.00 (1H, m), 6.88 (1H, t, J = 8.4 Hz), 6.80 (1H, t, J = 8.4 Hz), 6.73 (1H, d, J = 9.5 Hz), 3.99-3.92 (1H, m), 3.90-3.83 (1H, m), 1.16 (3H, t, J = 7.0 Hz). |
| 75 | ¹H-NMR (CDCl₃) δ: 7.57 (1H, s), 7.33-7.28 (2H, m), 7.14-7.11 (1H, m), 7.07-7.01 (2H, m), 6.88 (1H, t, J = 8.4 Hz), 6.82 (1H, t, J = 8.4 Hz), 4.02-3.90 (2H, m), 1.18 (3H, t, J = 7.0 Hz). |
| 76 | ¹H-NMR (CDCl₃) δ: 7.77 (1H, s), 7.33-7.27 (2H, m), 7.14-7.11 (1H, m), 7.07-7.01 (2H, m), 6.88 (1H, t, J = 8.4 Hz), 6.81 (1H, t, J = 8.4 Hz), 4.02-3.88 (2H, m), 1.18 (3H, t, J = 7.0 Hz). |
| 77 | ¹H-NMR (CDCl₃) δ: 7.36 (1H, d, J = 9.5 Hz), 7.32-7.26 (2H, m), 7.14-7.10 (1H, m), 7.03 (2H, d, J = 4.6 Hz), 6.88 (1H, t, J = 8.4 Hz), 6.81 (1H, t, J = 8.4 Hz), 6.75 (1H, d, J = 9.5 Hz), 3.39 (3H, s). |
| 78 | ¹H-NMR (CDCl₃) δ: 7.59 (1H, s), 7.34-7.26 (2H, m), 7.16-7.12 (1H, m), 7.05-7.04 (2H, m), 6.88 (1H, t, J = 8.4 Hz), 6.82 (1H, t, J = 8.4 Hz), 3.45 (3H, s). |
| 79 | ¹H-NMR (CDCl₃) δ: 7.79 (1H, s), 7.34-7.28 (2H, m), 7.15-7.12 (1H, m), 7.05-7.03 (2H, m), 6.88 (1H, t, J = 8.4 Hz), 6.82 (1H, t, J = 8.4 Hz), 3.46 (3H, s). |
| 80 | ¹H-NMR (CDCl₃) δ: 7.41 (1H, d, J = 9.5 Hz), 6.72 (1H, d, J = 9.5 Hz), 6.44-6.41 (2H, m), 6.29 (1H, t, J = 2.1 Hz), 6.22 (2H, d, J = 2.1 Hz), 3.78 (3H, s), 3.67 (6H, s), 3.37 (3H, s). |

TABLE 5-continued

| Compound | ¹H-NMR |
|---|---|
| 81 | ¹H-NMR (CDCl₃) δ: 7.32 (1H, d, J = 9.5 Hz), 6.72 (1H, d, J = 9.5 Hz), 6.45-6.42 (1H, m), 6.37-6.35 (1H, m), 6.33 (1H, d, J = 2.8 Hz), 6.24 (1H, dd, J = 2.8, 1.7 Hz), 3.83 (3H, s), 3.76 (3H, s), 3.66 (3H, s), 3.38 (3H, s). |
| 82 | ¹H-NMR (CDCl₃) δ: 7.33 (1H, d, J = 9.5 Hz), 6.72 (1H, d, J = 9.5 Hz), 6.44-6.42 (1H, m), 6.37-6.36 (2H, m), 6.21 (1H, dd, J = 2.6, 1.4 Hz), 3.83 (3H, s), 3.77 (3H, s), 3.66 (3H, s), 3.38 (3H, s). |
| 83 | ¹H-NMR (CDCl₃) δ: 7.61 (1H, s), 7.32-7.29 (1H, m), 6.85-6.83 (2H, m), 6.45 (1H, s), 4.01 (2H, q, J = 7.2 Hz), 3.85 (6H, s), 1.16 (3H, t, J = 7.2 Hz). |
| 84 | ¹H-NMR (CDCl₃) δ: 7.41 (1H, s), 7.32-7.29 (1H, m), 6.85-6.84 (2H, m), 6.45 (1H, s), 4.00 (2H, q, J = 7.0 Hz), 3.85 (6H, s), 1.16 (3H, t, J = 7.0 Hz). |
| 85 | ¹H-NMR (CDCl₃) δ: 7.50 (1H, d, J = 7.6 Hz), 7.33 (1H, d, J = 9.5 Hz), 7.31-7.25 (1H, m), 7.07 (2H, d, J = 4.3 Hz), 7.05-7.00 (1H, m), 6.89 (1H, t, J = 8.4 Hz), 6.80 (1H, t, J = 8.4 Hz), 6.73 (1H, d, J = 9.5 Hz), 3.99-3.91 (1H, m), 3.89-3.81 (1H, m), 1.16 (3H, t, J = 7.2 Hz). |
| 86 | ¹H-NMR (CDCl₃) δ: 7.56 (1H, s), 7.51 (1H, d, J = 7.3), 7.32-7.28 (1H, m), 7.08-7.03 (3H, m), 6.89 (1H, t, J = 8.4 Hz), 6.81 (1H, t, J = 8.4 Hz), 4.01-3.88 (2H, m), 1.19 (3H, t, J = 7.2 Hz). |
| 87 | ¹H-NMR (CDCl₃) δ: 7.77 (1H, s), 7.50 (1H, d, J = 7.6 Hz), 7.33-7.28 (1H, m), 7.08-7.03 (3H, m), 6.89 (1H, t, J = 8.4 Hz), 6.81 (1H, t, J = 8.4 Hz), 4.02-3.89 (2H, m), 1.19 (3H, t, J = 7.2 Hz). |
| 88 | ¹H-NMR (CDCl₃) δ: 7.80 (1H, d, J = 0.9 Hz), 7.37-7.32 (1H, m), 6.89-6.87 (2H, m), 6.83 (1H, t, J = 9.0 Hz), 6.70-6.66 (1H, m), 6.54 (1H, dd, J = 5.8, 3.1 Hz), 3.97 (2H, q, J = 7.0 Hz), 3.66 (3H, s), 1.17 (3H, t, J = 7.0 Hz). |
| 89 | ¹H-NMR (CDCl₃) δ: 7.37-7.31 (2H, m), 6.89-6.80 (3H, m), 6.73 (1H, d, J = 9.2 Hz), 6.68-6.66 (1H, m), 6.54 (1H, dd, J = 6.1, 3.1 Hz), 3.92 (2H, q, J = 7.0 Hz), 3.65 (3H, s), 1.15 (3H, t, J = 7.0 Hz). |
| 90 | ¹H-NMR (CDCl₃) δ: 7.82 (1H, d, J = 0.9 Hz), 7.37-7.34 (1H, m), 6.89-6.87 (2H, m), 6.83 (1H, t, J = 9.0 Hz), 6.71-6.68 (1H, m), 6.54-6.53 (1H, m), 3.66 (3H, s), 3.47 (3H, s). |
| 91 | ¹H-NMR (CDCl₃) δ: 7.39 (1H, dd, J = 9.2, 1.1 Hz), 7.35-7.32 (1H, m), 6.89-6.87 (2H, m), 6.83 (1H, t, J = 9.0 Hz), 6.75 (1H, d, J = 9.2 Hz), 6.69-6.67 (1H, m), 6.53 (1H, dd, J = 5.8, 3.1 Hz), 3.65 (3H, s), 3.40 (3H, s). |
| 92 | ¹H-NMR (CDCl₃) δ: 7.60 (1H, d, J = 0.9 Hz), 7.37-7.32 (1H, m), 6.89-6.87 (2H, m), 6.83 (1H, t, J = 9.0 Hz), 6.70-6.66 (1H, m), 6.54 (1H, dd, J = 5.8, 3.1 Hz), 3.97 (2H, q, J = 7.1 Hz), 3.66 (3H, s), 1.17 (3H, t, J = 7.1 Hz). |
| 93 | ¹H-NMR (CDCl₃) δ: 7.62 (1H, d, J = 0.9 Hz), 7.37-7.33 (1H, m), 6.89-6.87 (2H, m), 6.83 (1H, t, J = 9.0 Hz), 6.71-6.68 (1H, m), 6.54-6.53 (1H, m), 3.65 (3H, s), 3.46 (3H, s). |
| 94 | ¹H-NMR (CDCl₃) δ: 7.51 (1H, d, J = 9.2 Hz), 7.36 (1H, d, J = 9.5 Hz), 7.32-7.27 (1H, m), 7.09-7.02 (3H, m), 6.89 (1H, t, J = 8.4 1 Hz), 6.80 (1H, t, J = 8.4 Hz), 6.75 (1H, d, J = 9.5 Hz), 3.38 (3H, s). |
| 95 | ¹H-NMR (CDCl₃) δ: 7.58 (1H, s), 7.51 (1H, dd, J = 7.6, 1.2 Hz), 7.34-7.28 (1H, m), 7.10-7.02 (3H, m), 6.89 (1H, t, J = 8.4 Hz), 6.82 (1H, t, J = 8.4 Hz), 3.45 (3H, s). |
| 96 | ¹H-NMR (CDCl₃) δ: 7.79 (1H, s), 7.51 (1H, dd, J = 7.6, 1.5 Hz), 7.33-7.27 (1H, m), 7.10-7.02 (3H, m), 6.89 (1H, t, J = 8.4 Hz), 6.82 (1H, t, J = 8.4 Hz), 3.45 (3H, t, J = 7.2 Hz). |
| 97 | ¹H-NMR (CDCl₃) δ: 7.34(1H, d, J = 9.2 Hz), 7.33-7.28(1H, m), 7.18(1H, d, J = 9.2 Hz), 6.90(1H, t, J = 8.3 Hz), 6.82(1H, t, J = 8.3 Hz), 6.79-6.76(2H, m), 6.73(1H, d.J = 9.2 Hz), 5.01(1H, d, J = 7.0 Hz), 4.96(1H, d, J = 7.0 Hz), 4.00-3.81(2H, m), 3.38(3H, s), 1.16(3H, t, J = 7.0 Hz). |
| 98 | ¹H-NMR (CDCl₃) δ: 7.33-7.28 (3H, m), 6.94 (1H, t, J = 8.6 Hz), 6.85 (1H, t, J = 8.6 Hz), 6.78 (1H, dd, J = 8.9, 3.1 Hz), 6.75-6.72 (2H, m), 4.65 (1H, d, J = 16.2 Hz), 4.61 (1H, d, J = 16.2 Hz), 3.91 (2H, q, J = 7.1 Hz), 1.16 (3H, t, J = 7.1 Hz). |
| 99 | ¹H-NMR (CDCl₃) δ: 7.33 (1H, d, J = 9.5 Hz), 7.35-7.27(1H, m), 7.16(1H, d, J = 8.9 Hz), 6.89(1H, t, J = 8.6 Hz), 6.84(1H, t, J = 8.3 Hz), 6.73 (1H, d, J = 9.2 Hz), 6.65(1H, dd, J = 8.9 Hz, J = 3.1 Hz), 6.61-6.59(1H, m), 3.98-3.74(4H, m), 1.33(3H, t, J = 6.7 Hz), 1.16(3H, t, J = 7.0 Hz). |
| 100 | ¹H-NMR (CDCl₃) δ: 7.40(1H, d, J = 9.4 Hz), 7.37-7.28(1H, m), 7.07(1H, t, J = 7.9 Hz), 6.90-6.83(2H, m), 6.73(1H, d, J = 9.2 Hz), 6.72-6.58(3H, m), 3.90(2H, q.J = 7.3 Hz), 3.68(3H, s), 1.14(3H, t, J = 7.3 Hz). |
| 101 | ¹H-NMR (CDCl₃) δ: 7.40 (1H, d, J = 9.2 Hz), 7.39-7.28(2H, m), 7.09(1H, t, J = 8.0 Hz), 6.92-6.79(3H, m), 6.76-6.69(2H, m), 5.03 (2H, s), 3.90(2H, q, J = 7.0 Hz), 3.40(3H, s), 1.14(3H, t, J = 7.0 Hz). |
| 102 | ¹H-NMR (CDCl₃) δ: 7.38 (1H, d, J = 9.5 Hz), 7.38-7.30(1H, m), 7.15(1H, t, J = 8.3 Hz), 6.91-6.85(2H, m), 6.81-6.77(2H, m), 6.74 (1H, d, J = 9.2 Hz), 6.70-6.68(1H, m), 4.66(2H, s), 3.90(2H, q, J = 7.0 Hz), 1.15(3H, t, J = 7.0 Hz). |
| 103 | ¹H-NMR (CDCl₃) δ: 7.39 (1H, d, J = 9.2 Hz), 7.38-7.29(1H, m), 7.05(1H, t, J = 8.0 Hz), 6.92-6.81(2H, m), 6.72(1H, d, J = 9.5 Hz), 6.71-6.67(1H, m), 6.63-6.58 (2H, m), 3.93-3.85(4H, m), 1.35(3H, t, J = 7.0 Hz), 1.14(3H, t, J = 7.0 Hz). |
| 104 | ¹H-NMR (CDCl₃) δ: 7.35-7.33 (1H, m), 7.30 (1H, d, J = 9.5 Hz), 6.87-6.86 (2H, m), 6.77-6.75 (2H, m), 6.66 (1H, td, J = 8.8, 1.9 Hz), 3.98-3.93 (2H, m), 3.78 (3H, s), 1.14 (3H, t, J = 7.0 Hz). |
| 105 | ¹H-NMR (CDCl₃) δ: 7.74 (1H, s), 7.36-7.32 (1H, m), 6.88-6.86 (2H, m), 6.78-6.76 (1H, m), 6.67 (1H, td, J = 8.8, 2.0 Hz), 4.01-3.99 (2H, m), 3.78 (3H, s), 1.17 (3H, t, J = 7.0 Hz). |
| 106 | ¹H-NMR (CDCl₃) δ: 7.54 (1H, s), 7.35-7.33 (1H, m), 6.87 (2H, t, J = 8.0 Hz), 6.79-6.77 (1H, m), 6.67 (1H, td, J = 8.7, 1.8 Hz), 4.03-3.98 (2H, m), 3.78 (3H, s), 1.17 (3H, t, J = 7.2 Hz). |
| 107 | ¹H-NMR (CDCl₃) δ: 7.36-7.28(1H, m), 7.32 (1H, d, J = 9.5 Hz), 7.29(1H, d, J = 8.6 Hz), 6.92(1Ht.J = 8.6 Hz), 6.87-6.81(2H, m), 6.73(1H, d, J = 9.5 Hz), 3.97-3.84(2H, m), 2.24 (3H, s), 1.16(3H, t, J = 7.0 Hz). |
| 108 | ¹H-NMR (CDCl₃) δ: 7.37-7.29 (2H, m), 6.89-6.84 (2H, m), 6.78-6.76 (2H, m), 6.67 (1H, td, J = 8.9, 1.8 Hz), 3.78 (3H, s), 3.42 (3H, s). |
| 109 | ¹H-NMR (CDCl₃) δ: 7.77 (1H, s), 7.36-7.34 (1H, m), 6.89-6.87 (2H, m), 6.80-6.78 (1H, m), 6.68 (1H, td, J = 8.9, 2.1 Hz), 3.78 (3H, s), 3.49 (3H, s). |

TABLE 5-continued

| Compound | ¹H-NMR |
|---|---|
| 110 | ¹H-NMR (CDCl₃) δ: 7.57 (1H, s), 7.37-7.33 (1H, m), 6.89-6.87 (2H, m), 6.80-6.78 (1H, m), 6.68 (1H, td, J = 8.9, 1.8 Hz), 3.78 (3H, s), 3.48 (3H, s). |
| 111 | ¹H-NMR (CDCl₃) δ: 7.79 (1H, dd, J = 7.8, 1.1 Hz), 7.30 (1H, d, J = 9.5 Hz), 7.28-7.26 (1H, m), 7.11 (1H, dd, J = 7.6, 1.2 Hz), 7.07 (1H, ddd, J = 9.6, 4.8, 2.2 Hz), 6.89 (1H, t, J = 8.6 Hz), 6.85 (1H, ddd, J = 8.4, 6.6, 1.4 Hz), 6.8 (1H, t, J = 8.3 Hz), 6.74 (1H, d, J = 9.5 Hz), 3.94 (1H, td, J = 13.8, 6.9 Hz), 3.85 (1H, td, J = 13.8, 6.9 Hz), 1.17 (3H, t, J = 7.2 Hz). |
| 112 | ¹H-NMR (CDCl₃) δ: 7.79 (1H, dd, J = 8.1, 1.1 Hz), 7.31 (1H, ddd, J = 12.1, 6.9, 3.6 Hz), 7.11 (1H, td, J = 7.3, 1.2 Hz), 7.07 (1H, dt, J = 7.6, 1.8 Hz), 6.92-6.84 (2H, m), 6.84 (1H, tt, J = 8.4, 1.1 Hz), 3.94 (2H, dq, J = 27.0, 6.8 Hz), 1.19 (3H, t, J = 7.0 Hz). |
| 113 | ¹H-NMR (CDCl₃) δ: 7.79 (1H, dd, J = 8.0, 1.2 Hz), 7.30 (1H, tt, J = 8.4, 3.5 Hz), 7.11 (1H, td, J = 7.3, 1.2 Hz), 7.06 (1H, dt, J = 7.6, 1.8 Hz), 6.92-6.85 (2H, m), 6.81 (1H, t, J = 8.3 Hz), 3.95 (2H, m), 1.19 (3H, t, J = 7.0 Hz). |
| 114 | ¹H-NMR (CDCl₃) δ: 7.80 (1H, dd, J = 8.0, 1.2 Hz), 7.33 (1H, d, J = 9.5 Hz), 7.27-7.31 (1H, m), 7.10 (1H, td, J = 7.5, 1.2, Hz), 7.03 (1H, dt, J = 7.6, 1.7 Hz), 6.91-6.94 (2H, m), 6.80 (1H, t, J = 8.4 Hz), 6.76 (1H, d, J = 9.5 Hz), 3.38 (3H, s). |
| 115 | ¹H-NMR (CDCl₃) δ: 7.80 (1H, dd, J = 7.9, 1.2 Hz), 7.56 (1H, s), 7.31 (1H, tt, J = 8.5, 3.6 Hz), 7.12 (1H, td, J = 7.5, 1.2 Hz), 7.04 (1H, dt, J = 7.7, 1.7 Hz), 6.93-6.89 (m, 1H), 6.87 (1H, dd, J = 7.8, 1.7 Hz), 6.81 (1H, tt, J = 8.5, 1.0 Hz), 3.45 (3H, s). |
| 116 | ¹H-NMR (CDCl₃) δ: 7.80 (1H, dd, J = 7.9, 1.2 Hz), 7.76 (1H, s), 7.31 (1H, tt, J = 8.5, 3.6 Hz), 7.11 (1H, td, J = 7.5, 1.2 Hz), 7.03 (1H, dt, J = 7.7, 1.8 Hz), 6.92-6.89 (m, 1H), 6.88-6.85 (1H, m), 6.81 (1H, tt, J = 8.4, 1.0 Hz), 3.45 (3H, s). |
| 117 | ¹H-NMR (CDCl₃) δ: 7.21 (1H, tt, J = 8.3, 6.4 Hz), 6.83-6.81 (1H, m), 6.77-6.73 (1H, m), 6.28 (1H, d, J = 2.7 Hz), 6.20 (1H, dd, J = 2.7, 1.5 Hz), 3.79 (3H, s), 3.63 (3H, s), 3.50 (1H, dd, J = 14.3, 7.2 Hz), 3.32 (1H, dd, J = 14.3, 7.2 Hz), 2.91-2.80 (2H, m), 2.71-2.67 (1H, m), 2.59-2.51 (1H, m), 0.99 (3H, t, J = 7.2 Hz). |
| 118 | ¹H-NMR (CDCl₃) δ: 6.88 (2H, dd, J = 9.6, 2.9 Hz), 6.23 (1H, t, J = 2.3 Hz), 6.12 (2H, d, J = 2.3 Hz), 3.65 (6H, s), 3.40 (2H, q, J = 7.0 Hz), 2.73-2.71 (4H, m), 0.97 (3H, t, J = 7.2 Hz). |
| 119 | ¹H-NMR (CDCl₃) δ: 7.37 (1H, d, J = 9.5 Hz), 6.94-6.93 (2H, m), 6.72 (1H, d, J = 9.5 Hz), 6.30 (1H, t, J = 2.1 Hz), 6.20 (2H, d, J = 2.1 Hz), 3.87 (2H, q, J = 7.0 Hz), 3.69 (6H, s), 1.14 (3H, t, J = 7.0 Hz). |
| 120 | ¹H-NMR (CDCl₃) δ: 7.29 (1H, d, J = 9.5 Hz), 6.94 (1H, dt, J = 8.6, 1.8 Hz), 6.88 (1H, dt, J = 8.6, 1.8 Hz), 6.73 (1H, d, J = 9.5 Hz), 6.34 (1H, d, J = 2.1 Hz), 6.27-6.26 (1H, m), 3.88-3.86 (2H, m), 3.83 (3H, s), 3.68 (3H, s), 1.16 (3H, t, J = 7.2 Hz). |
| 121 | ¹H-NMR (CDCl₃) δ: 7.30 (1H, d, J = 9.5 Hz), 6.93 (1H, dt, J = 8.4, 1.8 Hz), 6.89 (1H, dt, J = 8.4, 1.8 Hz), 6.73 (1H, d, J = 9.5 Hz), 6.38 (1H, d, J = 2.7 Hz), 6.23 (1H, dd, J = 2.7, 1.8 Hz), 3.90-3.86 (2H, m), 3.83 (3H, s), 3.67 (3H, s), 1.16 (3H, t, J = 7.2 Hz). |
| 122 | ¹H-NMR (CDCl₃) δ: 7.39 (1H, d, J = 9.5 Hz), 6.96-6.94 (2H, m), 6.75 (1H, d, J = 9.5 Hz), 6.29 (2H, s), 3.87 (2H, q, J = 7.0 Hz), 3.77 (6H, s), 1.15 (3H, t, J = 7.0 Hz). |
| 123 | ¹H-NMR (CDCl₃) δ: 7.33 (1H, d, J = 9.5 Hz), 7.29-7.21 (1H, m), 7.14 (1H, ddd, J = 8.8, 7.1, 1.3 Hz), 6.99 (1H, d, J = 7.0 Hz), 6.82-6.74 (3H, m), 6.71-6.67 (2H, m), 4.05-3.79 (2H, brm, 3.63 (3H, s), 1.14 (3H, t, J = 7.0 Hz). |
| 124 | ¹H-NMR (CDCl₃) δ: 7.53 (1H, s), 7.32 (1H, tt, J = 8.5, 3.5 Hz), 7.10 (1H, dd, J = 8.9, 2.7 Hz), 6.99 (1H, d, J = 2.7 Hz), 6.85 (2H, t, J = 7.9 Hz), 6.61 (1H, d, J = 8.9 Hz), 4.00 (2H, brs), 3.62 (3H, s), 1.16 (3H, t, J = 7.2 Hz). |
| 125 | ¹H-NMR (CDCl₃) δ: 7.73 (1H, s), 7.32 (1H, tt, J = 8.4, 3.5 Hz), 7.24 (1H, dd, J = 8.9, 2.4 Hz), 7.13 (1H, d, J = 2.4 Hz), 6.85 (2H, t, J = 7.9 Hz), 6.56 (1H, d, J = 8.9 Hz), 3.96 (2H, brs), 3.62 (3H, s), 1.16 (3H, t, J = 7.0 Hz). |
| 126 | ¹H-NMR (CDCl₃) δ: 7.78 (1H, s), 7.34-7.30 (1H, m), 7.20-7.18 (1H, m), 6.91-6.89 (1H, m), 6.86-6.81 (1H, m), 6.80-6.78 (2H, m), 5.01 (1H, d, J = 7.0 Hz), 4.96 (1H, d, J = 7.0 Hz), 3.97-3.94 (2H, m), 3.38 (3H, s), 1.18 (3H, t, J = 7.2 Hz). |
| 127 | ¹H-NMR (CDCl₃) δ: 7.57 (1H, s), 7.34-7.30 (1H, m), 7.20-7.18 (1H, m), 6.90 (1H, t, J = 8.4 Hz), 6.84 (1H, t, J = 8.4 Hz), 6.80-6.79 (2H, m), 5.01 (1H, d, J = 7.0 Hz), 4.96 (1H, d, J = 7.0 Hz), 3.97-3.94 (2H, m), 3.38 (3H, s), 1.18 (3H, t, J = 7.0 Hz). |
| 128 | ¹H-NMR (CDCl₃) δ: 7.74 (1H, s), 7.36-7.34 (1H, m), 7.27 (2H, d, J = 8.9 Hz), 6.94 (1H, t, J = 8.4 Hz), 6.86 (1H, t, J = 8.4 Hz), 6.79 (1H, dd, J = 8.9, 3.1 Hz), 6.73 (1H, dd, J = 3.1, 1.5 Hz), 4.66 (1H, d, J = 16.2 Hz), 4.62 (1H, d, J = 16.2 Hz), 3.98-3.93 (2H, m), 1.18 (3H, t, J = 7.0 Hz). |
| 129 | ¹H-NMR (CDCl₃) δ: 7.54 (1H, s), 7.35-7.33 (1H, m), 7.27 (1H, d, J = 8.9 Hz), 6.94 (1H, t, J = 8.6 Hz), 6.86 (1H, t, J = 8.6 Hz), 6.79 (1H, dd, J = 8.9, 3.1 Hz), 6.73 (1H, dd, J = 3.1, 1.5 Hz), 4.66 (1H, d, J = 16.2 Hz), 4.62 (1H, d, J = 16.2 Hz), 3.97-3.94 (2H, m), 1.19 (3H, t, J = 7.2 Hz). |
| 130 | ¹H-NMR (CDCl₃) δ: 6.62-6.59 (2H, m), 6.23 (1H, t, J = 2.1 Hz), 6.12 (2H, d, J = 2.1 Hz), 3.65 (6H, s), 3.40 (2H, q, J = 7.1 Hz), 2.73-2.71 (4H, m), 0.97 (3H, t, J = 7.1 Hz). |
| 131 | ¹H-NMR (CDCl₃) δ: 7.38 (1H, d, J = 9.5 Hz), 6.72 (1H, d, J = 9.5 Hz), 6.67-6.65 (2H, m), 6.29 (1H, t, J = 2.1 Hz), 6.20 (2H, d, J = 2.1 Hz), 3.88 (2H, q, J = 7.1 Hz), 3.69 (6H, s), 1.15 (3H, t, J = 7.1 Hz). |
| 132 | ¹H-NMR (CDCl₃) δ: 7.30 (1H, d, J = 9.5 Hz), 6.73 (1H, d, J = 9.5 Hz), 6.67 (1H, tt, J = 8.7, 2.1 Hz), 6.61 (1H, tt, J = 8.7, 2.1 Hz), 6.33 (1H, d, J = 2.8 Hz), 6.26 (1H, dd, J = 2.8, 1.8 Hz), 3.91-3.84 (2H, m), 3.82 (3H, s), 3.67 (3H, s), 1.17 (3H, t, J = 7.0 Hz). |
| 133 | ¹H-NMR (CDCl₃) δ: 7.31 (1H, d, J = 9.5 Hz), 6.73 (1H, d, J = 9.5 Hz), 6.67 (1H, tt, J = 8.9, 2.1 Hz), 6.62 (1H, tt, J = 8.9, 2.1 Hz), 6.37 (1H, d, J = 2.8 Hz), 6.22 (1H, dd, J = 2.8, 1.8 Hz), 3.92-3.84 (2H, m), 3.83 (3H, s), 3.67 (3H, s), 1.16 (3H, t, J = 7.2 Hz). |
| 134 | ¹H-NMR (CDCl₃) δ: 7.41 (1H, d, J = 9.5 Hz), 6.74 (1H, d, J = 9.5 Hz), 6.68-6.66 (2H, m), 6.30 (1H, t, J = 2.3 Hz), 6.19 (2H, d, J = 2.3 Hz), 3.68 (6H, s), 3.37 (3H, s). |
| 135 | ¹H-NMR (CDCl₃) δ: 7.33 (1H, d, J = 9.5 Hz), 6.75 (1H, d, J = 9.5 Hz), 6.68 (1H, tt, J = 8.7, 2.1 Hz), 6.61 (1H, tt, J = 8.7, 2.1 Hz), 6.35 (1H, d, J = 2.7 Hz), 6.23 (1H, dd, J = 2.7, 1.8 Hz), 3.83 (3H, s), 3.67 (3H, s), 3.37 (3H, s). |

TABLE 5-continued

| Compound | ¹H-NMR |
|---|---|
| 136 | ¹H-NMR (CDCl₃) δ: 7.33 (1H, d, J = 9.5 Hz), 6.75 (1H, d, J = 9.5 Hz), 6.68-6.66 (1H, m), 6.63-6.62 (1H, m), 6.38 (1H, d, J = 2.8 Hz), 6.19 (1H, dd, J = 2.8, 1.8 Hz), 3.83 (3H, s), 3.67 (3H, s), 3.37 (3H, s). |
| 137 | ¹H-NMR (CDCl₃) δ: 7.37 (1H, d, J = 9.5 Hz), 7.29-7.23 (1H, m), 7.17-7.13 (1H, m), 6.99-6.97 (1H, m), 6.81-6.76 (3H, m), 6.73 (1H, d, J = 9.5 Hz), 6.70 (1H, d, J = 8.3 Hz), 3.62 (3H, s), 3.39 (3H, s). |
| 138 | ¹H-NMR (CDCl₃) δ: 7.31 (1H, tt, J = 8.4, 3.4 Hz), 7.26 (1H, s), 7.14 (1H, dd, J = 8.9, 2.8 Hz), 7.0 (1H, t, J = 2.3 Hz), 6.88-6.81 (2H, m), 6.64 (1H, d, J = 8.9 Hz), 3.66 (3H, s), 3.42 (3H, s). |
| 139 | ¹H-NMR (CDCl₃) δ: 7.76 (1H, s), 7.36-7.29 (1H, m), 7.27-7.24 (1H, m), 7.12 (1H, d, J = 2.4 Hz), 6.86 (2H, dd, J = 8.2, 7.6 Hz), 6.56 (1H, d, J = 8.9 Hz), 3.60 (3H, s), 3.46 (3H, s). |
| 140 | ¹H-NMR (CDCl₃) δ: 7.36 (H, d, J = 9.5 Hz), 7.31 (1H, tt, J = 8.4, 3.5 Hz), 7.18-7.13 (1H, m), 7.04-7.01 (1H, m), 6.96-6.93 (1H, m), 6.92-6.89 (1H, m), 6.86-6.83 (2H, m), 6.74 (1H, d, J = 9.5 Hz), 3.93 (2H, q, J = 7.0 Hz), 1.15 (3H, t, J = 7.0 Hz). |
| 141 | ¹H-NMR (CDCl₃) δ: 7.59 (1H, s), 7.32 (1H, tt, J = 8.4, 3.5 Hz), 7.20-7.15 (1H, m), 7.05-7.01 (1H, m), 6.97-6.94 (1H, m), 6.93-6.90 (1H, m), 6.85 (2H, dd, J = 8.5, 7.3 Hz), 3.98 (2H, q, J = 7.1 Hz), 1.17 (3H, t, J = 7.1 Hz). |
| 142 | ¹H-NMR (CDCl₃) δ: 7.80 (1H, s), 7.32 (1H, tt, J = 8.4, 3.5 Hz), 7.20-7.15 (1H, m), 7.05-7.01 (1H, m), 6.97-6.94 (1H, m), 6.93-6.89 (1H, m), 6.87-6.83 (2H, m), 3.98 (2H, q, J = 7.0 Hz), 1.17 (3H, t, J = 7.0 Hz). |
| 143 | ¹H-NMR (CDCl₃) δ: 7.38 (1H, dd, J = 9.3, 0.8 Hz), 7.31 (1H, tt, J = 8.4, 3.5 Hz), 7.20-7.14 (1H, m), 7.04-7.00 (1H, m), 6.97-6.94 (1H, m), 6.93-6.89 (1H, m), 6.87-6.83 (2H, m), 6.75 (1H, d, J = 9.2 Hz), 3.40 (3H, s). |
| 144 | ¹H-NMR (CDCl₃) δ: 7.62 (1H, s), 7.33 (1H, tt, J = 8.6, 3.5 Hz), 7.21-7.17 (1H, m), 7.05-7.01 (1H, m), 6.98-6.95 (1H, m), 6.94-6.91 (1H, m), 6.86 (2H, t, J = 8.0 Hz), 3.47 (3H, s). |
| 145 | ¹H-NMR (CDCl₃) δ: 7.82 (1H, s), 7.36-7.30 (1H, m), 7.21-7.16 (1H, m), 7.04-7.01 (1H, m), 6.98-6.95 (1H, m), 6.92 (1H, t, J = 8.9 Hz), 6.86 (2H, t, J = 8.0 Hz), 3.47 (3H, s). |
| 146 | ¹H-NMR (CDCl₃) δ: 7.60-7.59 (1H, m), 7.33-7.25 (4H, m), 7.22-7.18 (1H, m), 6.88 (1H, t, J = 8.4 Hz), 6.78 (1H, t, J = 8.4 Hz), 6.7 (1H, d, J = 9.5 Hz), 3.88 (2H, q, J = 7.1 Hz), 1.16 (3H, t, J = 7.1 Hz). |
| 147 | ¹H-NMR (CDCl₃) δ: 7.60-7.57 (1H, m), 7.55 (1H, s), 7.35-7.32 (2H, m), 7.31-7.28 (1H, m), 7.22-7.18 (1H, m), 6.88 (1H, t, J = 8.4 Hz), 6.80 (1H, t, J = 8.4 Hz), 3.98-3.88 (2H, m), 1.18 (3H, t, J = 7.2 Hz). |
| 148 | ¹H-NMR (CDCl₃) δ: 7.75 (1H, s), 7.60-7.57 (1H, m), 7.35-7.32 (2H, m), 7.31-7.28 (1H, m), 7.22-7.18 (1H, m), 6.88 (1H, t, J = 8.4 Hz), 6.80 (1H, t, J = 8.4 Hz), 3.9-3.87 (2H, m), 1.18 (3H, t, J = 7.0 Hz). |
| 149 | ¹H-NMR (CDCl₃) δ: 7.25-7.21 (1H, m), 7.18-7.16 (1H, m), 6.92-6.91 (1H, m), 6.20 (1H, t, J = 2.1 Hz), 6.14 (2H, d, J = 2.1 Hz), 3.66 (1H, dq, J = 14.1, 7.0 Hz), 3.61 (6H, s), 3.05 (1H, dq, J = 14.1, 7.0 Hz), 2.89-2.63 (4H, m), 0.97 (3H, t, J = 7.0 Hz). |
| 150 | ¹H-NMR (CDCl₃) δ: 7.40 (1H, d, J = 9.5 Hz), 7.33-7.27 (1H, m), 7.19 (1H, d, J = 8.0 Hz), 7.01-6.98 (1H, m), 6.73 (1H, d, J = 9.5 Hz), 6.25 (3H, s), 4.12 (1H, dq, J = 13.8, 7.0 Hz), 3.66 (6H, s), 3.61 (1H, dq, J = 13.8, 7.0 Hz), 1.14 (3H, t, J = 7.0 Hz). |
| 151 | Diastereomer-A (major) ¹H-NMR (CDCl₃) δ: 7.35 (1H, d, J = 9.5 Hz), 7.31-7.25 (1H, m), 7.23-7.21 (1H, m), 6.93-6.91 (1H, m), 6.73 (1H, d, J = 9.5 Hz), 6.36 (1H, d, J = 2.8 Hz), 6.30-6.29 (1H, m), 3.81 (3H, s), 3.76-3.71 (1H, m), 3.61 (3H, s), 3.40 (1H, dq, J = 13.4, 7.0 Hz), 1.15 (3H, t, J = 7.0 Hz).<br>Diastereomer-B (minor) ¹H-NMR (CDCl₃) δ: 7.40 (1H, d, J = 9.5 Hz), 7.31-7.25 (1H, m), 7.14-7.12 (1H, m), 7.05-7.03 (1H, m), 6.73 (1H, d, J = 9.5 Hz), 6.30-6.29 (1H, m), 6.27-6.25 (1H, m), 4.35 (1H, dq, J = 13.8, 7.0 Hz), 3.95-3.88 (1H, m), 3.81 (3H, s), 3.62 (3H, s), 1.19 (3H, t, J = 7.0 Hz).<br>Diastero ratio = 55/45 |
| 152 | Diastereomer-A (major) ¹H-NMR (CDCl₃) δ: 7.35 (1H, d, J = 9.5 Hz), 7.31-7.25 (1H, m), 7.23-7.22 (1H, m), 6.93-6.91 (1H, m), 6.73 (1H, d, J = 9.5 Hz), 6.34-6.31 (2H, m), 3.82 (3H, s), 3.76 (1H, dq, J = 13.6, 6.9 Hz), 3.61 (3H, s), 3.43 (1H, dq, J = 13.6, 6.9 Hz), 1.14 (3H, t, J = 6.9 Hz).<br>Diastereomer-B (minor) ¹H-NMR (CDCl₃) δ: 7.39 (1H, d, J = 9.5 Hz), 7.31-7.25 (1H, m), 7.13 (1H, d, J = 8.2 Hz), 7.05-7.03 (1H, m), 6.73 (1H, d, J = 9.5 Hz), 6.34-6.31 (1H, m), 6.22 (1H, dd, J = 2.7, 1.2 Hz), 4.34 (1H, dq, J = 13.6, 6.9 Hz), 3.91 (1H, dq, J = 13.6, 6.9 Hz), 3.82 (3H, s), 3.61 (3H, s), 1.18 (3H, t, J = 6.9 Hz).<br>Diastero ratio = 55/45 |
| 153 | ¹H-NMR (CDCl₃) δ: 7.36-7.34 (2H, m), 7.14-7.12 (1H, m), 6.88-6.85 (4H, m), 6.77 (1H, dt, J = 9.8, 2.1 Hz), 6.74 (1H, d, J = 9.2 Hz), 3.90 (2H, q, J = 7.0 Hz), 1.14 (3H, t, J = 7.0 Hz). |
| 154 | ¹H-NMR (CDCl₃) δ: 7.61 (1H, s), 7.37-7.35 (1H, m), 7.15-7.14 (1H, m), 6.91-6.83 (4H, m), 6.78 (1H, dt, J = 9.6, 2.1 Hz), 3.95 (2H, q, J = 7.0 Hz), 1.17 (3H, t, J = 7.0 Hz). |
| 155 | ¹H-NMR (CDCl₃) δ: 7.82 (1H, s), 7.37-7.35 (1H, m), 7.15-7.14 (1H, m), 6.91-6.83 (4H, m), 6.77 (1H, dt, J = 9.6, 2.1 Hz), 3.95 (2H, q, J = 7.0 Hz), 1.17 (3H, t, J = 7.0 Hz). |
| 156 | ¹H-NMR (CDCl₃) δ: 7.29-7.27 (1H, m), 7.08-7.07 (1H, m), 6.81-6.76 (4H, m), 6.67 (1H, dt, J = 10.0, 2.0 Hz), 3.42 (2H, q, J = 7.1 Hz), 2.78-2.71 (4H, m), 0.96 (3H, t, J = 7.1 Hz). |
| 157 | ¹H-NMR (CDCl₃) δ: 7.62-7.57 (1H, m), 7.34-7.30 (3H, m), 7.29-7.24 (1H, m), 7.18-7.16 (1H, m), 6.90-6.86 (1H, m), 6.80-6.76 (1H, m), 6.72 (1H, d, J = 9.5 Hz), 3.37 (3H, s). |
| 158 | ¹H-NMR (CDCl₃) δ: 7.61-7.58 (1H, m), 7.56 (1H, s), 7.36-7.33 (2H, m), 7.32-7.27 (1H, m), 7.19-7.17 (1H, m), 6.88 (1H, t, J = 8.4 Hz), 6.80 (H, t, J = 8.4 Hz), 3.43 (3H, s). |
| 159 | ¹H-NMR (CDCl₃) δ: 7.76 (1H, s), 7.16-7.57 (1H, m), 7.36-7.32 (2H, m), 7.31-7.26 (1H, m), 7.20-7.16 (1H, m), 6.88 (1H, t, J = 8.3 Hz). 6.80 (1H, t, J = 8.3 Hz), 3.43 (3H, s). |
| 160 | ¹H-NMR (CDCl₃) δ: 7.28-7.21 (2H, m), 7.10-7.08 (1H, m), 7.07-7.04 (1H, m), 6.96-6.90 (2H, m), 6.88 (1H, t, J = 8.4 Hz), 6.76 (1H, d, J = 8.6 Hz), 6.72 (1H, d, J = 9.5 Hz), 3.99-3.92 (1H, m), 3.87-3.80 (1H, m), 2.16 (3H, s), 1.16 (3H, t, J = 7.0 Hz). |

TABLE 5-continued

| Compound | ¹H-NMR |
|---|---|
| 161 | ¹H-NMR (CDCl₃) δ: 7.51 (1H, s), 7.30-7.23 (1H, m), 7.10-7.05 (2H, m), 6.96-6.91 (2H, m), 6.90-6.85 (1H, m), 6.79-6.75 (1H, m), 4.04-3.86 (2H, m), 2.17 (3H, s), 1.19 (3H, t, J = 7.0 Hz). |
| 162 | ¹H-NMR (CDCl₃) δ: 7.72 (1H, s), 7.30-7.23 (1H, m), 7.10-7.04 (2H, m), 6.96-6.91 (2H, m), 6.90-6.86 (1H, m), 6.79-6.75 (1H, m), 4.04-3.86 (2H, m), 2.17 (3H, s), 1.18 (3H, t, J = 7.0 Hz). |
| 163 | ¹H-NMR (CDCl₃) δ: 7.25-7.22 (1H, m), 7.18 (1H, d, J = 8.5 Hz), 6.93-6.92 (1H, m), 6.20 (1H, t, J = 2.3 Hz), 6.15 (2H, d, J = 2.3 Hz), 3.61 (6H, s), 2.88-2.86 (1H, m), 2.82 (3H, s), 2.78-2.66 (3H, m). |
| 164 | ¹H-NMR (CDCl₃) δ: 7.43 (1H, d, J = 9.5 Hz), 7.31 (1H, td, J = 8.2, 5.8 Hz), 7.21 (1H, dt, J = 8.2, 1.0 Hz), 6.99 (1H, td, J = 8.2, 1.1 Hz), 6.74 (1H, d, J = 9.5 Hz), 6.27-6.25 (3H, m), 3.66 (6H, s), 3.33 (3H, s). |
| 165 | Diastereomer-A(major) ¹H-NMR (CDCl₃) δ: 7.38 (1H, d, J = 9.5 Hz), 7.29-7.25 (2H, m), 6.92 (1H, td, J = 8.0, 1.6 Hz), 6.74 (1H, d, J = 9.5 Hz), 6.32 (1H, d, J = 3.1 Hz), 6.30 (1H, d, J = 3.1 Hz), 3.82 (3H, s), 3.60 (3H, s), 3.34 (3H, s).<br>Diastereomer-B (minor) ¹H-NMR (CDCl₃) δ: 7.41 (1H, d, J = 9.5 Hz), 7.31-7.27 (1H, m), 7.14-7.13 (1H, m), 7.04 (1H, td, J = 8.5, 0.9 Hz), 6.74 (1H, d, J = 9.5 Hz), 6.30 (1H, d, J = 2.7 Hz), 6.25 (1H, dd, J = 2.7, 1.2 Hz), 3.82 (3H, s), 3.61 (3H, s), 3.32 (3H, s).<br>Diastero ratio = 59/41 |
| 166 | Diastereomer-A(major) ¹H-NMR (CDCl₃) δ: 7.38 (1H, d, J = 9.5 Hz), 7.32-7.23 (2H, m), 6.92 (1H, td, J = 8.1, 1.6 Hz), 6.75 (1H, dd, J = 9.5, 1.2 Hz), 6.34 (1H, d, J = 2.7 Hz), 6.28 (1H, d, J = 2.7 Hz), 3.82 (3H, s), 3.60 (3H, s), 3.35 (3H, s).<br>Diastereomer-B(minor) ¹H-NMR (CDCl₃) δ: 7.41 (1H, d, J = 9.5 Hz), 7.32-7.23 (1H, m), 7.15-7.13 (1H, m), 7.04 (1H, t, J = 8.5 Hz), 6.75 (1H, dd, J = 9.5, 1.2 Hz), 6.34 (1H, d, J = 2.4 Hz), 6.21 (1H, m), 3.82 (3H, s), 3.61 (3H, s), 3.32 (3H, s).<br>Diastero ratio = 58/42 |
| 167 | ¹H-NMR (CDCl₃) δ: 7.42 (1H, s), 7.29-7.25 (1H, m), 7.15-7.14 (1H, m), 6.95 (1H, td, J = 8.5, 1.1 Hz), 6.47 (1H, s), 4.16 (1H, dq, J = 13.8, 7.0 Hz), 3.86 (6H, s), 3.82 (1H, dq, J = 13.8, 7.0 Hz), 1.16 (3H, t, J = 7.0 Hz). |
| 168 | ¹H-NMR (CDCl₃) δ: 7.40 (1H, d, J = 9.5 Hz), 7.38-7.33 (1H, m), 7.15-7.13 (1H, m), 6.91-6.85 (3H, m), 6.82 (1H, d, J = 8.0 Hz), 6.77-6.75 (2H, m), 3.38 (3H, s). |
| 169 | ¹H-NMR (CDCl₃) δ: 7.63 (1H, s), 7.38-7.37 (1H, m), 7.16-7.14 (1H, m), 6.92-6.87 (3H, m), 6.83 (1H, d, J = 8.0 Hz), 6.77 (1H, dt, J = 9.6, 2.1 Hz), 3.44 (3H, s). |
| 170 | ¹H-NMR (CDCl₃) δ: 7.84 (1H, s), 7.40-7.35 (1H, m), 7.16-7.14 (1H, m), 6.90-6.88 (3H, m), 6.83 (1H, d, J = 8.0 Hz), 6.77 (1H, dt, J = 9.6, 2.1 Hz), 3.45 (3H, s). |
| 171 | ¹H-NMR (CDCl₃) δ: 7.36-7.34 (2H, m), 7.13-7.07 (3H, m), 6.92-6.89 (3H, m), 6.74 (1H, d, J = 9.5 Hz), 3.90 (2H, q, J = 7.1 Hz), 1.14 (3H, t, J = 7.1 Hz). |
| 172 | ¹H-NMR (CDCl₃) δ: 7.32-7.24 (1H, m), 7.09-7.07 (1H, m), 6.86-6.74 (4H, m), 6.70-6.67 (1H, m), 2.87 (3H, s), 2.81-2.72 (4H, m). |
| 173 | ¹H-NMR (CDCl₃) δ: 7.29-7.28 (1H, m), 7.07-7.02 (2H, m), 6.97 (1H, t, J = 1.7 Hz), 6.84-6.82 (3H, m), 3.42 (2H, q, J = 7.1 Hz), 2.77-2.71 (4H, m), 0.96 (3H, t, J = 7.1 Hz). |
| 174 | ¹H-NMR (CDCl₃) δ: 7.36 (1H, d, J = 8.3 Hz), 7.17 (1H, td, J = 8.3, 5.8 Hz), 6.95 (1H, td, J = 8.3, 0.9 Hz), 6.20 (1H, t, J = 2.1 Hz), 6.16 (2H, d, J = 2.1 Hz), 3.73 (1H, dd, J = 14.2, 7.0 Hz), 3.62 (6H, s), 2.98 (1H, dd, J = 14.2, 7.0 Hz), 2.91-2.86 (1H, m), 2.80-2.74 (1H, m), 2.69-2.63 (2H, m), 0.98 (3H, t, J = 7.0 Hz). |
| 175 | ¹H-NMR (CDCl₃) δ: 7.40 (1H, d, J = 9.2 Hz), 7.36 (1H, d, J = 8.3 Hz), 7.23 (1H, td, J = 8.3, 6.0 Hz), 7.04 (1H, td, J = 8.3, 0.9 Hz), 6.73 (1H, d, J = 9.2 Hz), 6.27 (2H, d, J = 2.1 Hz), 6.26 (1H, t, J = 2.1 Hz), 4.18 (1H, dq, J = 13.6, 7.0 Hz), 3.66 (6H, s), 3.54 (1H, dq, J = 13.6, 7.0 Hz), 1.15 (3H, t, J = 7.0 Hz). |
| 176 | Diastereoisomer-A(major) ¹H-NMR (CDCl₃) δ: 7.42-7.39 (1H, m), 7.35 (1H, d, J = 9.5 Hz), 7.21-7.19 (1H, m), 6.96-6.94 (1H, m), 6.73 (1H, d, J = 9.5 Hz), 6.42 (1H, d, J = 2.7 Hz), 6.29 (1H, d, J = 2.7 Hz), 4.44 (1H, dq, J = 13.4, 7.0 Hz), 3.81 (3H, s), 3.61 (3H, s), 3.34 (1H, dq, J = 13.4, 7.0 Hz), 1.14 (3H, t, J = 7.0 Hz).<br>Diastereoisomer-B(minor) ¹H-NMR (CDCl₃) δ: 7.41 (1H, d, J = 9.5 Hz), 7.33-7.30 (1H, m), 7.24-7.17 (1H, m), 7.10-7.08 (1H, m), 6.73 (1H, d, J = 9.5 Hz), 6.30-6.29 (1H, m), 6.28-6.27 (1H, m), 3.99 (1H, dq, J = 13.6, 7.0 Hz), 3.82 (3H, s), 3.67 (1H, dq, J = 13.6, 7.0 Hz), 3.61 (3H, s), 1.20 (3H, t, J = 7.0 Hz).<br>Diastero ratio = 62/38 |
| 177 | Diatereomer-A(major) ¹H-NMR (CDCl₃) δ: 7.41-7.40 (1H, m), 7.36 (1H, d, J = 9.5 Hz), 7.22-7.20 (1H, m), 6.97-6.95 (1H, m), 6.74 (1H, d, J = 9.5 Hz), 6.38 (1H, d, J = 2.8 Hz), 6.32 (1H, d, J = 2.8 Hz), 4.43 (1H, dq, J = 13.6, 6.9 Hz), 3.82 (3H, s), 3.61 (3H, s), 3.36 (1H, dq, J = 13.6, 6.9 Hz), 1.14 (3H, t, J = 6.9 Hz).<br>Diastereomer-B(minor) ¹H-NMR (CDCl₃) δ: 7.41 (1H, d, J = 9.5 Hz), 7.33-7.31 (1H, m), 7.22-7.19 (1H, m), 7.11-7.07 (1H, m), 6.73 (1H, d, J = 9.5 Hz), 6.33 (1H, d, J = 2.8 Hz), 6.22 (1H, d, J = 2.8 Hz), 3.96 (1H, dd, J = 13.6, 7.0 Hz), 3.82 (3H, s), 3.71-3.66 (1H, m), 3.61 (3H, s), 1.20 (3H, t, J = 7.0 Hz).<br>Diastero ratio = 59/41 |
| 178 | ¹H-NMR (CDCl₃) δ: 7.60 (1H, s), 7.38-7.36 (1H, m), 7.16 (1H, dq, J = 8.1, 1.1 Hz), 7.10 (1H, t, J = 7.8 Hz), 7.07 (1H, t, J = 1.7 Hz), 6.94-6.88 (3H, m), 3.95 (2H, q, J = 7.1 Hz), 1.17 (3H, t, J = 7.1 Hz). |
| 179 | ¹H-NMR (CDCl₃) δ: 7.81 (1H, s), 7.38-7.36 (1H, m), 7.16-7.15 (1H, m), 7.10 (1H, t, J = 7.8 Hz), 7.06 (1H, t, J = 1.8 Hz), 6.94-6.88 (3H, m), 3.95 (2H, q, J = 7.1 Hz), 1.17 (3H, t, J = 7.1 Hz). |
| 180 | ¹H-NMR (CDCl₃) δ: 7.30 (1H, d, J = 9.2 Hz), 7.28-7.23 (1H, m), 7.11-7.05 (2H, m), 6.95-6.86 (3H, m), 6.78-3.73 (2H, m), 3.38 (3H, s), 2.16 (3H, s). |
| 181 | ¹H-NMR (CDCl₃) δ: 7.53 (1H, s), 7.30-7.24 (1H, m), 7.11-7.07 (2H, m), 6.96-6.87 (3H, m), 6.77 (1H, t, J = 8.6 Hz), 3.45 (3H, s), 2.17 (3H, s). |

TABLE 5-continued

| Compound | ¹H-NMR |
|---|---|
| 182 | ¹H-NMR (CDCl₃) δ: 7.73 (1H, s), 7.30-7.24 (1H, m), 7.11-7.07 (2H, m), 6.96-6.87 (3H, m), 6.77 (1H, t, J = 8.6 Hz), 3.45 (3H, s), 2.17 (3H, s). |
| 183 | ¹H-NMR (CDCl₃) δ: 7.43 (1H, d, J = 9.5 Hz), 7.39-7.37 (1H, m), 7.27-7.21 (1H, m), 7.05-7.03 (1H, m), 6.75 (1H, d, J = 9.5 Hz), 6.28-6.26 (3H, m), 3.66 (6H, s), 3.33 (3H, s). |
| 184 | Diastereomer-A(major) ¹H-NMR (CDCl₃) δ: 7.42 (1H, d, J = 8.0 Hz), 7.38 (1H, d, J = 9.5 Hz), 7.23-7.20 (1H, m), 6.96-6.95 (1H, m), 6.75 (1H, d, J = 9.5 Hz), 6.40 (1H, d, J = 2.8 Hz), 6.30 (1H, d, J = 2.8 Hz), 3.82 (3H, s), 3.61 (3H, s), 3.35 (3H, s).<br>Diastereomixture-B(minor) ¹H-NMR (CDCl₃) δ: 7.44 (1H, d, J = 9.5 Hz), 7.32 (1H, d, J = 8.3 Hz), 7.25-7.19 (1H, m), 7.11-7.07 (1H, m), 6.75 (1H, d, J = 9.5 Hz), 6.31 (1H, d, J = 2.8 Hz), 6.26 (1H, d, J = 2.8 Hz), 3.82 (3H, s), 3.61 (3H, s), 3.31 (3H, s).<br>Diastero ratio = 64/36 |
| 185 | Diastereomer-A(major) ¹H-NMR (CDCl₃) δ: 7.42 (1H, d, J = 8.0 Hz), 7.38 (1H, d, J = 9.5 Hz), 7.23-7.21 (1H, m), 6.97-6.95 (1H, m), 6.76 (1H, d, J = 9.5 Hz), 6.36 (1H, d, J = 2.8 Hz), 6.33 (1H, d, J = 2.8 Hz), 3.82 (3H, s), 3.60 (3H, s), 3.35 (3H, s).<br>Diastereomer-B(minor) ¹H-NMR (CDCl₃) δ: 7.43 (1H, d, J = 9.5 Hz), 7.32 (1H, d, J = 8.0 Hz), 7.23-7.21 (1H, m), 7.10-7.08 (1H, m), 6.75 (1H, d, J = 9.5 Hz), 6.34 (1H, d, J = 2.8 Hz), 6.21 (1H, d, J = 2.8 Hz), 3.83 (3H, s), 3.60 (3H, s), 3.31 (3H, s).<br>Diastero ratio = 63/37 |
| 186 | ¹H-NMR (CDCl₃) δ: 7.04-7.02 (2H, m), 6.23 (1H, t, J = 2.3 Hz), 6.11 (2H, d, J = 2.3 Hz), 3.65 (6H, s), 3.39 (2H, q, J = 7.0 Hz), 2.75-2.69 (4H, m), 0.96 (3H, t, J = 7.0 Hz). |
| 187 | ¹H-NMR (CDCl₃) δ: 7.06-7.03 (2H, m), 6.24 (1H, t, J = 2.3 Hz), 6.12 (2H, d, J = 2.3 Hz), 3.65 (6H, s), 2.86 (3H, s), 2.77-2.72 (4H, m). |
| 188 | ¹H-NMR (CDCl₃) δ: 7.38-7.35 (2H, m), 7.15 (1H, dt, J = 8.3, 1.6 Hz), 7.10 (1H, t, J = 7.8 Hz), 7.06 (1H, t, J = 1.8 Hz), 6.93-6.87 (3H, m), 6.75 (1H, d, J = 9.5 Hz), 3.38 (3H, s). |
| 189 | ¹H-NMR (CDCl₃) δ: 7.63 (1H, s), 7.39-7.37 (1H, m), 7.18-7.16 (1H, m), 7.11 (1H, t, J = 7.8 Hz), 7.06 (1H, t, J = 1.8 Hz), 6.92-6.90 (3H, m), 3.45 (3H, s). |
| 190 | ¹H-NMR (CDCl₃) δ: 7.83 (1H, s), 7.39-7.37 (1H, m), 7.17-7.16 (1H, m), 7.11 (1H, t, J = 7.8 Hz), 7.06 (1H, t, J = 1.8 Hz), 6.92-6.90 (3H, m), 3.45 (3H, s). |
| 191 | ¹H-NMR (CDCl₃) δ: 7.32-7.26 (1H, m), 7.06-7.04 (2H, m), 6.97 (1H, t, J = 1.8 Hz), 6.85-6.82 (3H, m), 2.87 (3H, s), 2.77-2.75 (4H, m). |
| 192 | ¹H-NMR (CDCl₃) δ: 7.26-7.24 (1H, m), 7.15 (1H, d, J = 8.9 Hz), 6.83 (1H, t, J = 8.6 Hz), 6.77 (1H, t, J = 8.6 Hz), 6.62 (1H, dd, J = 8.9, 3.1 Hz), 6.58 (1H, dd, J = 3.1, 1.4 Hz), 5.93 (1H, tt, J = 56.6, 4.4 Hz), 3.74-3.65 (2H, m), 3.64 (3H, s), 2.95-2.89 (1H, m), 2.87-2.81 (1H, m), 2.76-2.73 (1H, m), 2.67-2.61 (1H, m). |
| 193 | ¹H-NMR (CDCl₃) δ: 7.32-7.29 (2H, m), 7.16 (1H, d, J = 8.9 Hz), 6.89 (1H, t, J = 8.6 Hz), 6.83 (1H, t, J = 8.6 Hz), 6.74-6.70 (2H, m), 6.63-6.62 (1H, m), 4.00-3.97 (1H, m), 3.92-3.87 (3H, m), 3.71-3.64 (2H, m), 3.43 (3H, s), 1.16 (3H, t, J = 7.2 Hz). |
| 194 | ¹H-NMR (CDCl₃) δ: 7.41 (1H, d, J = 9.5 Hz), 7.36-7.33 (1H, m), 7.18 (1H, d, J = 8.9 Hz), 6.90 (1H, t, J = 8.6 Hz), 6.84 (1H, t, J = 8.6 Hz), 6.76 (1H, d, J = 9.5 Hz), 6.68 (1H, dd, J = 8.9, 3.1 Hz), 6.62 (1H, dd, J = 3.1, 1.5 Hz), 6.18 (1H, tt, J = 56.7, 4.5 Hz), 4.17 (2H, td, J = 12.9, 4.5 Hz), 3.65 (3H, s). |
| 195 | ¹H-NMR (CDCl₃) δ: 7.55 (1H, s), 7.34-7.30 (1H, m), 7.17 (1H, d, J = 8.9 Hz), 6.89 (1H, t, J = 8.4 Hz), 6.85 (1H, t, J = 8.4 Hz), 6.73 (1H, dd, J = 8.9, 3.1 Hz), 6.63 (1H, dd, J = 3.1, 1.7 Hz), 3.98-3.94 (3H, m), 3.89-3.86 (1H, m), 3.69-3.67 (2H, m), 3.43 (3H, s), 1.18 (3H, t, J = 7.0 Hz). |
| 196 | ¹H-NMR (CDCl₃) δ: 7.75 (1H, s), 7.33-7.30 (1H, m), 7.16 (1H, d, J = 8.9 Hz), 6.89 (1H, t, J = 7.9 Hz), 6.85 (1H, t, J = 7.9 Hz), 6.73 (1H, dd, J = 8.9, 3.1 Hz), 6.63 (1H, dd, J = 3.1, 1.5 Hz), 4.01-3.92 (3H, m), 3.89-3.85 (1H, m), 3.69-3.67 (2H, m), 3.43 (3H, s), 1.18 (3H, t, J = 7.0 Hz). |
| 197 | ¹H-NMR (CDCl₃) δ: 7.63 (1H, s), 7.36-7.33 (1H, m), 7.18 (1H, d, J = 8.9 Hz), 6.92-6.84 (2H, m), 6.70 (1H, dd, J = 8.9, 3.1 Hz), 6.62 (1H, dd, J = 3.1, 1.7 Hz), 6.20 (1H, tt, J = 56.6, 4.6 Hz), 4.23-4.19 (2H, m), 3.66 (3H, s). |
| 198 | ¹H-NMR (CDCl₃) δ: 7.84 (1H, s), 7.37-7.35 (1H, m), 7.18 (1H, d, J = 8.9 Hz), 6.91-6.84 (2H, m), 6.70 (1H, dd, J = 8.9, 2.9 Hz), 6.62 (1H, dd, J = 2.9, 1.7 Hz), 6.20 (1H, tt, J = 56.6, 4.4 Hz), 4.26-4.17 (2H, m), 3.66 (3H, s). |
| 199 | ¹H-NMR (CDCl₃) δ: 7.37 (1H, d, J = 9.5 Hz), 7.10-7.08 (2H, m), 6.72 (1H, d, J = 9.5 Hz), 6.30 (1H, t, J = 2.3 Hz), 6.20 (2H, d, J = 2.3 Hz), 3.86 (2H, q, J = 7.2 Hz), 3.69 (6H, s), 1.14 (3H, t, J = 7.2 Hz). |
| 200 | ¹H-NMR (CDCl₃) δ: 7.29 (1H, d, J = 9.2 Hz), 7.09 (1H, dt, J = 8.1, 1.6 Hz), 7.04 (1H, dt, J = 8.1, 1.6 Hz), 6.73 (1H, d, J = 9.2 Hz), 6.34 (1H, d, J = 2.8 Hz), 6.26-6.26 (1H, m), 3.88-3.86 (2H, m), 3.83 (3H, s), 3.68 (3H, s), 1.16 (3H, t, J = 7.0 Hz). |
| 201 | ¹H-NMR (CDCl₃) δ: 7.29 (1H, d, J = 9.5 Hz), 7.09 (1H, dt, J = 8.3, 1.8 Hz), 7.05 (1H, dt, J = 8.3, 1.8 Hz), 6.73 (1H, d, J = 9.5 Hz), 6.38 (1H, d, J = 2.8 Hz), 6.23-6.22 (1H, m), 3.88-3.86 (2H, m), 3.83 (3H, s), 3.68 (3H, s), 1.15 (3H, t, J = 7.0 Hz). |
| 202 | ¹H-NMR (CDCl₃) δ: 7.39 (1H, d, J = 9.5 Hz), 7.11-7.10 (2H, m), 6.75 (1H, d, J = 9.5 Hz), 6.29 (2H, s), 3.86 (2H, q, J = 7.0 Hz), 3.77 (6H, s), 1.15 (3H, t, J = 7.0 Hz). |
| 203 | ¹H-NMR (CDCl₃) δ: 7.40 (1H, d, J = 9.2 Hz), 7.11-7.10 (2H, m), 6.74 (1H, d, J = 9.2 Hz), 6.31 (1H, t, J = 2.1 Hz), 6.19 (2H, d, J = 2.1 Hz), 3.68 (6H, s), 3.36 (3H, s). |
| 204 | ¹H-NMR (CDCl₃) δ: 7.31 (1H, d, J = 9.5 Hz), 7.10 (1H, dt, J = 8.3, 1.5 Hz), 7.04 (1H, dt, J = 8.3, 1.5 Hz), 6.74 (1H, d, J = 9.5 Hz), 6.35 (1H, d, J = 2.8 Hz), 6.23 (1H, m), 3.84 (3H, s), 3.67 (3H, s), 3.36 (3H, s). |
| 205 | ¹H-NMR (CDCl₃) δ: 7.32 (1H, d, J = 9.5 Hz), 7.10 (1H, dt, J = 8.1, 1.7 Hz), 7.05 (1H, dt, J = 8.1, 1.7 Hz), 6.75 (1H, d, J = 9.5 Hz), 6.39 (1H, d, J = 2.7 Hz), 6.20 (1H, dd, J = 2.7, 1.5 Hz), 3.84 (3H, s), 3.67 (3H, s), 3.36 (3H, s). |
| 206 | ¹H-NMR (CDCl₃) δ: 7.42 (1H, d, J = 9.5 Hz), 7.13-7.11 (2H, m), 6.76 (1H, d, J = 9.5 Hz), 6.28 (2H, s), 3.76 (6H, s), 3.37 (3H, s). |

TABLE 5-continued

| Compound | ¹H-NMR |
|---|---|
| 207 | ¹H-NMR (CDCl₃) δ: 7.27-7.21 (1H, m), 6.99 (1H, t, J = 7.5 Hz), 6.89 (1H, d, J = 7.3 Hz), 6.81-6.78 (3H, m), 6.75 (1H, d, J = 7.6 Hz), 3.42 (2H, q, J = 7.1 Hz), 2.78-2.70 (4H, m), 2.18 (3H, s), 0.96 (3H, t, J = 7.1 Hz). |
| 208 | ¹H-NMR (CDCl₃) δ: 7.30-7.24 (1H, m), 7.17 (1H, t, J = 8.1 Hz), 6.95-6.93 (2H, m), 6.84-6.79 (3H, m), 3.42 (2H, q, J = 7.1 Hz), 2.79-2.72 (4H, m), 0.96 (3H, t, J = 7.1 Hz). |
| 209 | ¹H-NMR (CDCl₃) δ: 7.37 (1H, d, J = 9.5 Hz), 7.30-7.23 (1H, m), 7.17-7.12 (1H, m), 7.11-7.08 (1H, m), 6.97-6.94 (1H, m), 6.91-6.89 (1H, m), 6.87-6.85 (1H, m), 6.79 (1H, t, J-8.4 Hz), 6.72 (1H, d, J = 9.5 Hz), 3.90-3.81 (2H, m), 2.39 (3H, s), 1.16 (3H, t, J = 7.2 Hz). |
| 210 | ¹H-NMR (CDCl₃) δ: 7.58 (1H, s), 7.51 (1H, d, J = 8.0 Hz), 7.32-7.23 (2H, m), 7.07-7.06 (2H, m), 6.88 (1H, t, J = 8.4 Hz), 6.80 (1H, t, J = 8.4 Hz), 4.94 (2H, dd, J = 19.3, 12.2 Hz), 3.94 (2H, q, J = 7.0 Hz), 1.18 (3H, t, J = 7.0 Hz). |
| 211 | ¹H-NMR (CDCl₃) δ: 8.08 (1H, dd, J = 7.9, 1.5 Hz), 7.63 (1H, d, J = 9.5 Hz), 7.41-7.30 (3H, m), 7.20-7.17 (1H, m), 7.00-6.95 (1H, m), 6.79 (1H, t, J = 8.5 Hz), 6.73 (1H, d, J = 9.5 Hz), 4.02-3.94 (1H, m), 3.82-3.73 (1H, m), 2.98 (3H, s), 1.16 (3H, t, 7.0 Hz). |
| 212 | ¹H-NMR (CDCl₃) δ: 7.32-7.31 (2H, m), 7.16 (1H, d, J = 8.6 Hz), 6.88 (1H, t, J = 8.6 Hz), 6.83 (1H, t, J = 8.6 Hz), 6.72 (1H, d, J = 9.5 Hz), 6.68 (1H, dd, J = 8.6, 3.1 Hz), 6.59 (1H, dd, J = 3.1, 1.4 Hz), 3.96-3.83 (2H, m), 3.65-3.63 (1H, m), 3.58-3.56 (1H, m), 1.17-1.13 (4H, m), 0.62-0.61 (2H, m), 0.29-0.28 (2H, m). |
| 213 | ¹H-NMR (CDCl₃) δ: 7.42 (1H, d, J = 9.5 Hz), 7.37-7.31 (1H, m), 7.19 (1H, d, J = 8.9 Hz), 6.90 (1H, t, J = 8.4 Hz), 6.83 (1H, t, J = 8.4 Hz), 6.81-6.74 (3H, m), 6.17 (1H, tt, J = 56.6, 4.6 Hz), 5.01-4.96 (2H, m), 4.23-4.11 (2H, m), 3.37 (3H, s). |
| 214 | ¹H-NMR (CDCl₃) δ: 7.40 (1H, d, J = 9.5 Hz), 7.36-7.30 (1H, m), 7.16 (1H, d, J = 8.9 Hz), 6.91-6.83 (2H, m), 6.75 (1H, d, J = 9.5 Hz), 6.69-6.67 (1H, m), 6.61-6.60 (1H, m), 6.18 (1H, tt, J = 56.6, 4.5 Hz), 4.21-4.11 (2H, m), 3.93-3.89 (1H, m), 3.80-3.77 (1H, m), 1.33 (3H, t, J = 6.9 Hz). |
| 215 | ¹H-NMR (CDCl₃) δ: 8.37 (2H, s), 7.39 (1H, d, J = 9.5 Hz), 6.75 (1H, d, J = 9.5 Hz), 6.28 (1H, t, J = 2.4 Hz), 6.19 (2H, d, J = 2.4 Hz), 3.85 (2H, q, J = 7.1 Hz), 3.67 (6H, s), 1.15 (3H, t, J = 7.1 Hz). |
| 216 | ¹H-NMR (CDCl₃) δ: 8.37 (1H, s), 8.32 (1H, s), 7.31 (1H, d, J = 9.5 Hz), 6.76 (1H, d, J = 9.5 Hz), 6.32 (1H, d, J = 2.4 Hz), 6.26-6.26 (1H, m), 3.85 (2H, q, J = 7.2 Hz), 3.82 (3H, s), 3.67 (3H, s), 1.17 (3H, t, J = 7.2 Hz). |
| 217 | ¹H-NMR (CDCl₃) δ: 7.37-7.33 (2H, m), 7.22 (1H, t, J = 8.1 Hz), 7.03-7.01 (2H, m), 6.90-6.86 (3H, m), 6.75 (1H, d, J = 9.5 Hz), 3.91 (2H, q, J = 7.1 Hz), 1.14 (3H, t, J = 7.1 Hz). |
| 218 | ¹H-NMR (CDCl₃) δ: 7.62 (1H, s), 7.38-7.32 (1H, m), 7.24 (1H, t, J = 8.1 Hz), 7.05-7.02 (2H, m), 6.91-6.87 (3H, m), 3.96 (2H, q, J = 7.0 Hz), 1.17 (3H, t, J = 7.0 Hz). |
| 219 | ¹H-NMR (CDCl₃) δ: 7.39 (1H, d, J = 9.5 Hz), 7.32-7.30 (1H, m), 7.03 (1H, t, J = 7.5 Hz), 6.96 (1H, d, J = 7.3 Hz), 6.87-6.82 (4H, m), 6.72 (1H, d, J = 9.5 Hz), 3.91 (2H, q, J = 7.1 Hz), 2.21 (3H, s), 1.14 (3H, t, J = 7.1 Hz). |
| 220 | ¹H-NMR (CDCl₃) δ: 7.63 (1H, s), 7.34-7.32 (1H, m), 7.04 (1H, t, J = 7.6 Hz), 6.97 (1H, d, J = 7.3 Hz), 6.88-6.82 (4H, m), 3.95 (2H, q, J = 7.0 Hz), 2.22 (3H, s), 1.17 (3H, t, J = 7.0 Hz). |
| 221 | ¹H-NMR (CDCl₃) δ: 7.55 (1H, s), 7.34-7.31 (1H, m), 7.16 (1H, d, J = 8.9 Hz), 6.90-6.83 (2H, m), 6.69 (1H, dd, J = 8.9, 2.9 Hz), 6.60 (1H, dd, J = 2.8, 1.5 Hz), 3.95 (2H, q, J = 7.0 Hz), 3.65-3.63 (1H, m), 3.59-3.57 (1H, m), 1.19-1.17 (4H, m), 0.63-0.61 (2H, m), 0.30-0.28 (2H, m). |
| 222 | ¹H-NMR (CDCl₃) δ: 7.64 (1H, s), 7.36-7.35 (1H, m), 7.19 (1H, d, J = 8.6 Hz), 6.90 (1H, t, J = 8.6 Hz), 6.85 (1H, t, J = 8.6 Hz), 6.83-6.79 (2H, m), 6.19 (1H, tt, J = 56.6, 4.5 Hz), 5.02 (1H, d, J = 7.0 Hz), 4.97 (1H, d, J = 7.0 Hz), 4.25-4.17 (2H, m), 3.38 (3H, s). |
| 223 | ¹H-NMR (CDCl₃) δ: 7.62 (1H, s), 7.37-7.35 (1H, m), 7.16 (1H, d, J = 8.9 Hz), 6.90-6.86 (2H, m), 6.70-6.68 (1H, m), 6.62-6.61 (1H, m), 6.20 (1H, tt, J = 56.6, 4.4 Hz), 4.27-4.16 (2H, m), 3.93-3.88 (1H, m), 3.82-3.78 (1H, m), 1.34 (3H, t, J = 7.0 Hz). |
| 224 | ¹H-NMR (CDCl₃) δ: 8.37 (1H, s), 8.33 (1H, s), 7.31 (1H, d, J = 9.5 Hz), 6.76 (1H, d, J = 9.5 Hz), 6.36 (1H, d, J = 2.8 Hz), 6.22-6.22 (1H, m), 3.86 (2H, q, J = 7.0 Hz), 3.82 (3H, s), 3.67 (3H, s), 1.16 (3H, t, J = 7.0 Hz). |
| 225 | ¹H-NMR (CDCl₃) δ: 7.30-7.28 (1H, m), 7.09-7.01 (3H, m), 6.17 (1H, t, J = 2.4 Hz), 6.06 (2H, d, J = 2.4 Hz), 3.61-3.54 (7H, m), 3.28-3.25 (1H, m), 2.84-2.67 (4H, m), 0.95 (3H, t, J = 7.2 Hz). |
| 226 | ¹H-NMR (CDCl₃) δ: 7.30-7.27 (1H, m), 7.06-7.01 (3H, m), 6.17 (1H, t, J = 2.3 Hz), 6.07 (2H, d, J = 2.3 Hz), 3.57 (6H, s), 2.88-2.86 (4H, m), 2.72-2.69 (3H, m). |
| 227 | ¹H-NMR (CDCl₃) δ: 7.45 (1H, d, J = 9.5 Hz), 7.39-7.34 (1H, m), 7.13-7.11 (1H, m), 7.07 (1H, td, J = 7.3, 1.2 Hz), 7.01 (1H, td, J = 7.3, 1.7 Hz), 6.71 (1H, d, J = 9.5 Hz), 6.23 (1H, t, J = 2.3 Hz), 6.15 (2H, d, J = 2.3 Hz), 3.62 (6H, s), 3.36 (3H, s). |
| 228 | Diastereomer-A(major) ¹H-NMR (CDCl₃) δ: 7.32-7.30 (2H, m), 7.11-7.06 (2H, m), 7.01 (1H, td, J = 7.5, 1.2 Hz), 6.71 (1H, d, J = 9.5 Hz), 6.27 (1H, d, J = 2.8 Hz), 6.14 (1H, d, J = 2.8 Hz), 3.82 (3H, s), 3.59 (3H, s), 3.35 (3H, s).<br>Diastereomer-B (minor) ¹H-NMR (CDCl₃) δ: 7.33-7.30 (2H, m), 7.11-7.06 (2H, m), 7.01 (1H, td, J = 7.5, 1.2 Hz), 6.71 (1H, d, J = 9.5 Hz), 6.30 (1H, d, J = 2.8 Hz), 6.21 (1H, d, J = 2.8 Hz), 3.79 (3H, s), 3.66 (3H, s), 3.37 (3H, s).<br>Diastero ratio = 82/18 |
| 229 | Diastereomer-A(major) ¹H-NMR (CDCl₃) δ: 7.33-7.30 (2H, m), 7.09-7.00 (3H, m), 6.71 (1H, d, J = 9.5 Hz), 6.31 (1H, d, J = 2.8 Hz), 6.10 (1H, d, J = 2.8 Hz), 3.82 (3H, s), 3.58 (3H, s), 3.35 (3H, s).<br>Diastereomer-B (minor) ¹H-NMR (CDCl₃) δ: 7.33-7.30 (2H, m), 7.09-7.00 (3H, m), 6.71 (1H, d, J = 9.5 Hz), 6.33 (1H, d, J = 2.8 Hz), 6.19 (1H, d, J = 2.8 Hz), 3.79 (3H, s), 3.66 (3H, s), 3.37 (3H, s).<br>Diastero ratio = 79/21 |
| 230 | ¹H-NMR (CDCl₃) δ: 7.41 (1H, d, J = 9.5 Hz), 7.38-7.33 (1H, m), 7.11-7.06 (3H, m), 6.69 (1H, d, J = 9.5 Hz), 6.22 (1H, t, J = 2.8 Hz), 6.16 (2H, d, J = 2.8 Hz), 4.04 (1H, dd, J = 13.6, 7.0 Hz), 3.76 (1H, dd, J = 13.6, 7.0 Hz), 3.63 (6H, s), 1.13 (3H, t, J = 7.0 Hz). |

TABLE 5-continued

| Compound | ¹H-NMR |
| --- | --- |
| 231 | Diastereomer-A(major) ¹H-NMR (CDCl₃) δ: 7.31-7.27 (2H, m), 7.17-7.16 (1H, m), 7.08-7.03 (2H, m), 6.69 (1H, d, J = 9.2 Hz), 6.27-6.25 (2H, m), 4.03-3.97 (1H, m), 3.80 (3H, s), 3.74 (1H, dd, J = 13.9, 7.0 Hz), 3.63 (3H, s), 1.15 (3H, t, J = 7.0 Hz).<br>Diastereomer-B (minor) ¹H-NMR (CDCl₃) δ: 7.31-7.27 (2H, m), 7.17-7.16 (1H, m), 7.08-7.03 (2H, m), 6.74 (1H, d, J = 9.5 Hz), 6.27-6.27 (1H, m), 6.14 (1H, d, J = 2.8 Hz), 4.03-3.97 (1H, m), 3.88 (3H, s), 3.81 (3H, s), 3.75-3.72 (1H, m), 1.12 (3H, t, J = 7.0 Hz).<br>Diastero ratio = 86/14 |
| 232 | Diastereomer-A(major) ¹H-NMR (CDCl₃) δ: 7.33-7.24 (2H, m), 7.14-7.08 (1H, m), 7.06-6.98 (2H, m), 6.69 (1H, d, J = 9.5 Hz), 6.30 (1H, d, J = 2.8 Hz), 6.21 (1H, dd, J = 2.8, 1.2 Hz), 4.06-3.94 (1H, m), 3.80 (3H, s), 3.77-3.70 (1H, m), 3.62 (3H, s), 1.15 (3H, t, J = 7.0 Hz).<br>Diastereomer-B (minor) ¹H-NMR (CDCl₃) δ: 7.33-7.25 (2H, m), 7.13-7.11 (1H, m), 7.06-6.99 (2H, m), 6.69 (1H, d, J = 9.5 Hz), 6.30 (1H, d, J = 2.8 Hz), 6.11 (1H, d, J = 2.8 Hz), 4.02-3.99 (1H, m), 3.87 (3H, s), 3.82 (3H, s), 3.76-3.72 (1H, m), 1.13 (3H, t, J = 7.0 Hz).<br>Diastero ratio = 82/18 |
| 233 | ¹H-NMR (CDCl₃) δ: 7.32-7.29 (1H, m), 7.18-7.15 (1H, m), 7.14 (1H, d, J = 9.5 Hz), 7.08-7.06 (1H, m), 6.97 (1H, td, J = 7.6, 1.2 Hz), 6.74 (1H, d, J = 9.5 Hz), 6.42 (1H, s), 3.90 (3H, s), 3.81 (3H, s), 3.39 (3H, d, J = 1.2 Hz). |
| 234 | ¹H-NMR (DMSO-D₆) δ: 9.66 (1H, br s), 7.54-7.51 (1H, m), 7.41 (1H, d, J = 9.5 Hz), 7.22 (1H, t, J = 8.7 Hz), 7.15 (1H, d, J = 8.9 Hz), 7.12 (1H, t, J = 8.7 Hz), 6.63-6.58 (2H, m), 6.47 (1H, dd, J = 3.1, 1.5 Hz), 3.78-3.73 (2H, m), 1.01 (3H, t, J = 7.0 Hz). |
| 235 | ¹H-NMR (DMSO-D₆) δ: 9.64 (1H, br s), 7.53-7.51 (1H, m), 7.43 (1H, d, J = 9.2 Hz), 7.20 (1H, t, J = 8.7 Hz), 7.16-7.09 (2H, m), 6.64-6.59 (2H, m), 6.46-6.45 (1H, m), 3.22 (3H, s). |
| 236 | ¹H-NMR (CDCl₃) δ: 7.33-7.29 (3H, m), 6.93 (1H, t, J = 8.4 Hz), 6.85 (1H, t, J = 8.4 Hz), 6.79 (1H, dd, J = 8.9, 3.1 Hz), 6.76 (1H, d, J = 9.5 Hz), 6.70 (1H, dd, J = 3.1, 1.2 Hz), 4.64 (1H, d, J = 15.9 Hz), 4.60 (1H, d, J = 15.9 Hz), 3.39 (3H, s). |
| 237 | ¹H-NMR (CDCl₃) δ: 7.35 (1H, d, J = 9.2 Hz), 7.33-7.30 (1H, m), 7.17 (1H, d, J = 8.9 Hz), 6.90 (1H, t, J = 8.6 Hz), 6.84 (1H, t, J = 8.6 Hz), 6.75 (1H, d, J = 9.2 Hz), 6.67 (1H, dd, J = 8.9, 3.1 Hz), 6.57 (1H, dd, J = 3.1, 1.4 Hz), 3.91-3.89 (1H, m), 3.77-3.75 (1H, m), 3.38 (3H, s), 1.32 (3H, t, J = 7.0 Hz). |
| 238 | ¹H-NMR (CDCl₃) δ: 7.35-7.30 (2H, m), 7.17 (1H, d, J = 8.9 Hz), 6.88 (1H, t, J = 8.6 Hz), 6.84 (1H, t, J = 8.6 Hz), 6.74 (1H, d, J = 9.5 Hz), 6.69 (1H, dd, J = 8.9, 3.1 Hz), 6.57 (1H, m), 3.63 (1H, dd, J = 10.1, 7.0 Hz), 3.57-3.55 (1H, m), 3.38 (3H, s), 1.18-1.13 (1H, m), 0.62-0.60 (2H, m), 0.29-0.27 (2H, m). |
| 239 | ¹H-NMR (CDCl₃) δ: 7.37 (1H, d, J = 9.5 Hz), 7.33-7.30 (1H, m), 7.20 (1H, d, J = 8.9 Hz), 6.91 (1H, t, J = 8.4 Hz), 6.83 (1H, t, J = 8.4 Hz), 6.79 (1H, dd, J = 8.9, 2.9 Hz), 6.75-6.74 (2H, m), 5.00 (1H, d, J = 6.7 Hz), 4.94 (1H, d, J = 6.7 Hz), 3.38 (3H, s), 3.36 (3H, s). |
| 240 | ¹H-NMR (CDCl₃) δ: 7.33-7.30 (2H, m), 7.17 (1H, d, J = 8.9 Hz), 6.89 (1H, t, J = 8.4 Hz), 6.84 (1H, t, J = 8.4 Hz), 6.75-6.71 (2H, m), 6.60-6.60 (1H, m), 3.99-3.97 (1H, m), 3.87-3.83 (1H, m), 3.69-3.66 (2H, m), 3.42 (3H, s), 3.38 (3H, s). |
| 241 | ¹H-NMR (CDCl₃) δ: 7.36 (1H, d, J = 9.5 Hz), 7.33-7.30 (1H, m), 7.16 (1H, d, J = 8.6 Hz), 6.89 (1H, t, J = 8.4 Hz), 6.84 (1H, t, J = 8.4 Hz), 6.75 (1H, d, J = 9.5 Hz), 6.67 (1H, dd, J = 8.6, 3.1 Hz), 6.57 (1H, dd, J = 3.1, 1.2 Hz), 3.78-3.76 (1H, m), 3.67-3.66 (1H, m), 3.39 (3H, s), 1.72-1.69 (2H, m), 0.97 (3H, t, J = 7.5 Hz). |
| 242 | ¹H-NMR (CDCl₃) δ: 7.33-7.30 (2H, m), 7.16 (1H, d, J = 8.9 Hz), 6.89 (1H, t, J = 8.4 Hz), 6.83 (1H, t, J = 8.4 Hz), 6.73 (1H, d, J = 9.2 Hz), 6.65 (1H, dd, J = 8.9, 2.9 Hz), 6.60 (1H, dd, J = 2.9, 1.4 Hz), 3.93-3.88 (2H, m), 3.80-3.77 (1H, m), 3.68-3.66 (1H, m), 1.72-1.70 (2H, m), 1.16 (3H, t, J = 7.2 Hz), 0.98 (3H, t, J = 7.3 Hz). |
| 243 | ¹H-NMR (CDCl₃) δ: 7.36-7.29 (2H, m), 7.21 (1H, d, J = 8.6 Hz), 6.90 (1H, t, J = 8.6 Hz), 6.84 (1H, t, J = 8.6 Hz), 6.77-6.75 (2H, m), 6.69-6.68 (1H, m), 4.51 (2H, d, J = 2.3 Hz), 3.38 (3H, s), 2.50 (1H, t, J = 2.3 Hz). |
| 244 | ¹H-NMR (CDCl₃) δ: 7.33-7.29 (2H, m), 7.20 (1H, d, J = 8.9 Hz), 6.90 (1H, t, J = 8.6 Hz), 6.83 (1H, t, J = 8.6 Hz), 6.74-6.72 (3H, m), 4.51 (2H, d, J = 2.4 Hz), 3.92-3.89 (2H, m), 2.51 (1H, t, J = 2.4 Hz), 1.16 (3H, t, J = 7.2 Hz). |
| 245 | ¹H-NMR (CDCl₃) δ: 7.33 (1H, d, J = 9.2 Hz), 7.31-7.28 (1H, m), 7.17 (1H, d, J = 9.2 Hz), 6.88 (1H, t, J = 8.3 Hz), 6.82 (1H, t, J = 8.3 Hz), 6.79-6.78 (2H, m), 6.72 (1H, d, J = 9.2 Hz), 5.04-5.00 (2H, m), 3.92-3.88 (2H, m), 3.68-3.64 (2H, m), 1.15 (3H, t, J = 7.0 Hz), 0.93-0.91 (2H, m), −0.01 (9H, s). |
| 246 | ¹H-NMR (CDCl₃) δ: 7.36 (1H, d, J = 9.5 Hz), 7.33-7.29 (1H, m), 7.19 (1H, d, J = 8.9 Hz), 6.89 (1H, t, J = 8.4 Hz), 6.84 (1H, t, J = 8.4 Hz), 6.81 (1H, dd, J = 8.9, 3.1 Hz), 6.76-6.75 (2H, m), 5.04 (1H, d, J = 7.0 Hz), 5.00 (1H, d, J = 7.0 Hz), 3.68-3.64 (2H, m), 3.39 (3H, s), 0.93-0.91 (2H, m), −0.01 (9H, s). |
| 247 | ¹H-NMR (CDCl₃) δ: 7.33 (1H, d, J = 9.2 Hz), 6.72 (1H, d, J = 9.2 Hz), 6.41 (1H, d, J = 10.7 Hz), 6.36 (1H, d, J = 2.8 Hz), 6.34 (1H, d, J = 10.7 Hz), 6.20 (1H, d, J = 2.8 Hz), 3.95 (2H, q, J = 7.0 Hz), 3.83 (3H, s), 3.65 (3H, s), 3.38 (3H, s), 1.40 (3H, t, J = 7.0 Hz). |
| 248 | ¹H-NMR (CDCl₃) δ: 7.35 (1H, d, J = 9.5 Hz), 6.73 (1H, d, J = 9.5 Hz), 6.51 (1H, dt, J = 10.7, 1.8 Hz), 6.43 (1H, dt, J = 10.7, 1.8 Hz), 6.34 (1H, d, J = 2.8 Hz), 6.16 (1H, dd, J = 2.8, 1.4 Hz), 3.82 (3H, s), 3.63 (3H, s), 3.41 (3H, s), 1.35 (9H, s). |
| 249 | ¹H-NMR (DMSO-D₆) δ: 7.39 (1H, d, J = 9.5 Hz), 6.59 (1H, d, J = 9.5 Hz), 6.57 (1H, d, J = 2.8 Hz), 6.53-6.51 (1H, m), 6.40-6.39 (1H, m), 6.15 (1H, d, J = 2.8 Hz), 3.80 (3H, s), 3.63 (3H, s), 3.23 (3H, s). |
| 250 | ¹H-NMR (CDCl₃) δ: 7.35-7.31 (2H, m), 7.21 (1H, d, J = 8.9 Hz), 6.92 (1H, t, J = 8.4 Hz), 6.85 (1H, t, J = 8.4 Hz), 6.74 (1H, d, J = 9.5 Hz), 6.69 (1H, dd, J = 8.9, 2.9 Hz), 6.62 (1H, m), 4.08-4.06 (1H, m), 3.97-3.87 (3H, m), 2.76 (2H, t, J = 6.3 Hz), 1.16 (3H, t, J = 7.0 Hz). |
| 251 | ¹H-NMR (CDCl₃) δ: 7.35-7.34 (2H, m), 7.22 (1H, d, J = 8.9 Hz), 6.93 (1H, t, J = 8.4 Hz), 6.86 (1H, t, J = 8.4 Hz), 6.75 (1H, dd, J = 9.5, 0.9 Hz), 6.71 (1H, dd, J = 8.9, 3.1 Hz), 6.60-6.59 (1H, m), 4.08-4.06 (1H, m), 3.95-3.93 (1H, m), 3.39 (3H, s), 2.76 (2H, t, J = 6.3 Hz). |
| 252 | ¹H-NMR (CDCl₃) δ: 7.33 (1H, d, J = 9.2 Hz), 7.32-7.30 (1H, m), 7.15 (1H, d, J = 8.9 Hz), 6.88 (1H, t, J = 8.4 Hz), 6.83 (1H, t, J = 8.4 Hz), 6.73 (1H, d, J = 9.2 Hz), 6.65 (1H, dd, J = 8.9, |

TABLE 5-continued

| Compound | ¹H-NMR |
|---|---|
| | 3.1 Hz), 6.60 (1H, dd, J = 3.1, 1.5 Hz), 3.91-3.84 (3H, m), 3.73-3.69 (1H, m), 1.69-1.64 (2H, m), 1.43-1.41 (2H, m), 1.16 (3H, t, J = 7.0 Hz), 0.95 (3H, t, J = 7.3 Hz). |
| 253 | ¹H-NMR (CDCl₃) δ: 7.36 (1H, d, J = 9.2 Hz), 7.32-7.29 (1H, m), 7.16 (1H, d, J = 8.9 Hz), 6.89 (1H, t, J = 8.4 Hz), 6.84 (1H, t, J = 8.4 Hz), 6.74 (1H, d, J = 9.2 Hz), 6.66 (1H, dd, J = 8.9, 3.1 Hz), 6.56 (1H, dd, J = 3.1, 1.5 Hz), 3.83-3.80 (1H, m), 3.71-3.68 (1H, m), 3.38 (3H, s), 1.70-1.63 (2H, m), 1.44-1.40 (2H, m), 0.94 (3H, t, J = 7.3 Hz). |
| 254 | ¹H-NMR (CDCl₃) δ: 7.33 (1H, d, J = 9.2 Hz), 7.32-7.28 (1H, m), 7.15 (1H, d, J = 8.9 Hz), 6.88 (1H, t, J = 8.4 Hz), 6.83 (1H, t, J = 8.4 Hz), 6.73 (1H, d, J = 9.2 Hz), 6.65 (1H, dd, J = 8.9, 3.1 Hz), 6.59 (1H, dd, J = 3.1, 1.4 Hz), 3.93-3.88 (2H, m), 3.83-3.80 (1H, m), 3.71-3.68 (1H, m), 1.72-1.66 (2H, m), 1.37-1.35 (4H, m), 1.16 (3H, t, J = 7.2 Hz), 0.93 (3H, t, J = 7.2 Hz). |
| 255 | ¹H-NMR (CDCl₃) δ: 7.36 (1H, d, J = 9.2 Hz), 7.33-7.30 (1H, m), 7.16 (1H, d, J = 8.9 Hz), 6.89 (1H, t, J = 8.4 Hz), 6.84 (1H, t, J = 8.4 Hz), 6.75 (1H, d, J = 9.2 Hz), 6.66 (1H, dd, J = 8.9, 3.1 Hz), 6.57-6.56 (1H, m), 3.82-3.80 (1H, m), 3.69-3.67 (1H, m), 3.39 (3H, s), 1.69-1.67 (2H, m), 1.37-1.35 (4H, m), 0.92 (3H, t, J = 7.0 Hz). |
| 256 | ¹H-NMR (CDCl₃) δ: 7.32 (2H, d, J = 9.2 Hz), 7.31-7.29 (1H, m), 7.15 (1H, d, J = 8.9 Hz), 6.88 (1H, t, J = 8.4 Hz), 6.84 (1H, t, J = 8.4 Hz), 6.73 (1H, d, J = 9.2 Hz), 6.65 (1H, dd, J = 8.9, 3.1 Hz), 6.60 (1H, dd, J = 3.1, 1.5 Hz), 4.34-4.28 (1H, m), 3.92-3.88 (2H, m), 1.24 (3H, d, J = 6.1 Hz), 1.18 (3H, d, J = 6.1 Hz), 1.16 (3H, t, J = 7.0 Hz). |
| 257 | ¹H-NMR (CDCl₃) δ: 7.35 (1H, d, J = 9.5 Hz), 7.33-7.29 (1H, m), 7.16 (1H, d, J = 8.9 Hz), 6.88 (1H, t, J = 8.4 Hz), 6.85 (1H, t, J = 8.4 Hz), 6.74 (1H, d, J = 9.5 Hz), 6.66 (1H, dd, J = 8.9, 3.1 Hz), 6.57 (1H, dd, J = 3.1, 1.5 Hz), 4.31-4.29 (1H, m), 3.38 (3H, s), 1.23 (3H, d, J = 6.1 Hz), 1.16 (3H, d, J = 6.1 Hz). |
| 258 | ¹H-NMR (CDCl₃) δ: 7.33 (1H, d, J = 9.2 Hz), 7.32-7.28 (1H, m), 7.15 (1H, d, J = 8.6 Hz), 6.88 (1H, t, J = 8.6 Hz), 6.83 (1H, t, J = 8.6 Hz), 6.73 (1H, d, J = 9.5 Hz), 6.65 (1H, dd, J = 8.6, 3.1 Hz), 6.60 (1H, dd, J = 3.1, 1.4 Hz), 3.93-3.89 (2H, m), 3.58 (1H, dd, J = 9.0, 6.6 Hz), 3.47 (1H, dd, J = 9.0, 6.6 Hz), 2.00-1.95 (1H, m), 1.16 (3H, t, J = 7.0 Hz), 0.96 (6H, d, J = 6.7 Hz). |
| 259 | ¹H-NMR (CDCl₃) δ: 7.36 (1H, d, J = 9.5 Hz), 7.32-7.30 (1H, m), 7.16 (1H, d, J = 8.9 Hz), 6.89 (1H, t, J = 8.6 Hz), 6.84 (1H, t, J = 8.6 Hz), 6.75 (1H, d, J = 9.5 Hz), 6.67 (1H, dd, J = 8.9, 3.1 Hz), 6.56 (1H, dd, J = 3.1, 1.2 Hz), 3.57 (1H, dd, J = 9.0, 6.6 Hz), 3.45 (1H, dd, J = 9.0, 6.6 Hz), 3.39 (3H, s), 1.99-1.94 (1H, m), 0.95 (6H, d, J = 6.7 Hz). |
| 260 | ¹H-NMR (CDCl₃) δ: 7.33 (1H, d, J = 9.5 Hz), 7.31-7.29 (1H, m), 7.14 (1H, d, J = 8.6 Hz), 6.87 (1H, t, J = 8.4 Hz), 6.83 (1H, t, J = 8.4 Hz), 6.72 (1H, d, J = 9.5 Hz), 6.70-6.67 (2H, m), 3.92-3.89 (2H, m), 3.44 (1H, d, J = 12.5 Hz), 3.31 (1H, d, J = 12.5 Hz), 1.16 (3H, t, J = 7.0 Hz), 0.10 (9H, s). |
| 261 | ¹H-NMR (CDCl₃) δ: 7.36 (1H, d, J = 9.5 Hz), 7.32-7.30 (1H, m), 7.15 (1H, d, J = 8.9 Hz), 6.88 (1H, t, J = 8.6 Hz), 6.83 (1H, t, J = 8.6 Hz), 6.74 (1H, d, J = 9.5 Hz), 6.71 (1H, dd, J = 8.9, 3.1 Hz), 6.64 (1H, dd, J = 3.1, 1.2 Hz), 3.44 (1H, d, J = 12.5 Hz), 3.39 (3H, s), 3.29 (1H, d, J = 12.5 Hz), 0.10 (9H, s). |
| 262 | ¹H-NMR (CDCl₃) δ: 7.36-7.30 (1H, m), 7.31 (1H, d, J = 9.5 Hz), 7.23 (1H, d, J = 8.9 Hz), 6.91 (1H, t, J = 8.4 Hz), 6.84 (1H, t, J = 8.4 Hz), 6.75-6.73 (2H, m), 6.66 (1H, dd, J = 3.1, 1.2 Hz), 4.23-4.19 (1H, m), 4.15-4.12 (1H, m), 3.92-3.89 (2H, m), 1.16 (3H, t, J = 7.2 Hz). |
| 263 | ¹H-NMR (CDCl₃) δ: 7.34-7.33 (2H, m), 7.24 (1H, d, J = 8.9 Hz), 6.91 (1H, t, J = 8.4 Hz), 6.85 (1H, t, J = 8.4 Hz), 6.76-6.74 (2H, m), 6.64 (1H, dd, J = 3.1, 1.2 Hz), 4.22-4.19 (1H, m), 4.14-4.11 (1H, m), 3.39 (3H, s). |
| 264 | ¹H-NMR (CDCl₃), mixture of 2 diastereoisomers, δ: 8.05-8.02 (1H, m, one diastereoisomer), 7.90 (1H, dd, J = 8.0, 0.9 Hz, one diastereoisomer), 7.52 (1H, d, J = 9.2 Hz, one diastereoisomer), 7.47-7.15 (7H, m, two diastereoisomers), 7.13 (1H, d, J = 9.2 Hz, one diastereoisomer), 7.06-7.01 (2H, m, two diastereoisomers), 6.91 (1H, t, J = 8.4 Hz, one diastereoisomer), 6.81-6.72 (4H, m, two diastereoisomers), 4.14-4.07 (1H, m, one diastereoisomer), 4.01-.95 (1H, m, one diastereoisomer), 3.81-3.72 (2H, m, two diastereoisomers), 2.63 (3H, s, one diastereoisomer), 2.60 (3H, s, one diastereoisomer.), 1.15 (6H, t, J = 7.0 Hz, two diastereoisomers ). Diastero ratio = 50/50 |
| 265 | ¹H-NMR (CDCl₃) δ7.39-7.31 (2H, m), 7.14 (2H, d, J = 8.9 Hz), 6.98 (2H, d, J = 8.9 Hz), 6.88 (2H, td, J = 8.9, 1.9 Hz), 6.73 (1H, d, J = 9.2 Hz), 3.90 (2H, q, J = 7.0 Hz), 1.14 (3H, t, J = 7.0 Hz). |
| 266 | ¹H-NMR (CDCl₃) δ: 7.58 (1H, s), 7.37 (1H, tt, J = 8.4, 7.2 Hz), 7.15 (2H, d, J = 8.5 Hz), 6.98 (2H, d, J = 8.5 Hz), 6.89 (2H, dd, J = 8.4, 7.2 Hz), 3.95 (2H, q, J = 7.0 Hz), 1.16 (3H, t, J = 7.0 Hz). |
| 267 | ¹H-NMR (CDCl₃) δ: 7.26-7.24 (1H, m), 6.92 (2H, d, J = 8.0 Hz), 6.85 (2H, d, J = 8.0 Hz), 6.81-6.79 (2H, m), 3.41 (2H, q, J = 7.0 Hz), 2.77-2.69 (4H, m), 2.23 (3H, s), 0.96 (3H, t, J = 7.0 Hz). |
| 268 | ¹H-NMR (CDCl₃) δ: 7.26-7.24 (1H, m), 6.93 (2H, d, J = 8.0 Hz), 6.86 (2H, d, J = 8.0 Hz), 6.82-6.80 (2H, m), 2.86 (3H, s), 2.78-2.73 (4H, m), 2.23 (3H, s). |
| 269 | ¹H-NMR (CDCl₃) δ: 7.38 (1H, d, J = 9.5 Hz), 7.33-7.30 (1H, m), 6.96 (2H, d, J = 8.3 Hz), 6.93 (2H, d, J = 8.3 Hz), 6.86 (2H, dd, J = 8.4, 7.2 Hz), 6.72 (1H, d, J = 9.5 Hz), 3.90 (2H, q, J = 7.0 Hz), 2.24 (3H, s), 1.14 (3H, t, J = 7.0 Hz). |
| 270 | ¹H-NMR (CDCl₃) δ: 7.41 (1H, d, J = 9.5 Hz), 7.33 (1H, tt, J = 8.4, 6.4 Hz), 6.97 (2H, d, J = 8.0 Hz), 6.92 (2H, d, J = 8.0 Hz), 6.89-6.85 (2H, m), 6.74 (1H, d, J = 9.5 Hz), 3.37 (3H, s), 2.25 (3H, s). |
| 271 | ¹H-NMR (CDCl₃) δ: 7.82 (1H, s), 7.33 (1H, tt, J = 8.4, 6.4 Hz), 6.98-6.91 (4H, m), 6.86 (2H, dd, J = 8.4, 7.0 Hz), 3.95 (2H, q, J = 7.1 Hz), 2.25 (3H, s), 1.16 (3H, t, J = 7.1 Hz). |
| 272 | ¹H-NMR (CDCl₃) δ: 7.61 (1H, s), 7.33-7.31 (1H, m), 6.98-6.91 (4H, m), 6.86 (2H, dd, J = 8.4, 7.2 Hz), 3.95 (2H, q, J = 7.1 Hz), 2.25 (3H, s), 1.16 (3H, t, J = 7.1 Hz). |
| 273 | ¹H-NMR (CDCl₃) δ: 7.85 (1H, s), 7.35-7.33 (1H, m), 6.98-6.92 (4H, m), 6.87 (2H, dd, J = 8.6, 7.1 Hz), 3.44 (3H, s), 2.25 (3H, s). |
| 274 | 1H-NMR (CDCl3) δ: 7.64 (1H, s), 7.34 (1H, tt, J = 8.6, 7.0 Hz), 6.98 (2H, d, J = 8.2 Hz), 6.92 (2H, d, J = 8.2 Hz), 6.88 (2H, dd, J = 8.6, 7.0 Hz), 3.44 (3H, s), 2.25 (3H, s). |

TABLE 5-continued

| Compound | ¹H-NMR |
|---|---|
| 275 | ¹H-NMR (CDCl₃) δ: 7.32 (1H, d, J = 9.5 Hz), 7.31-7.29 (1H, m), 7.15 (1H, d, J = 8.9 Hz), 6.88 (1H, t, J = 8.4 Hz), 6.83 (1H, t, J = 8.4 Hz), 6.72 (1H, d, J = 9.5 Hz), 6.65 (1H, dd, J = 8.9, 3.1 Hz), 6.59 (1H, dd, J = 3.1, 1.5 Hz), 3.92-3.88 (2H, m), 3.79-3.75 (1H, m), 3.66-3.63 (1H, m), 1.71-1.69 (2H, m), 1.16 (3H, t, J = 7.2 Hz), 0.56-0.52 (2H, m), 0.01 (9H, s). |
| 276 | ¹H-NMR (CDCl₃) δ: 7.35 (1H, d, J = 9.5 Hz), 7.33-7.30 (1H, m), 7.16 (1H, d, J = 8.9 Hz), 6.88 (1H, t, J = 8.6 Hz), 6.84 (1H, t, J = 8.6 Hz), 6.74 (1H, d, J = 9.5 Hz), 6.66 (1H, dd, J = 8.9, 3.1 Hz), 6.57 (1H, dd, J = 3.1, 1.5 Hz), 3.77-3.76 (1H, m), 3.64-3.63 (1H, m), 3.38 (3H, s), 1.70-1.69 (2H, m), 0.56-0.51 (2H, m), 0.01 (9H, s). |
| 277 | ¹H-NMR (CDCl₃) δ: 7.33-7.31 (2H, m), 7.21 (1H, d, J = 8.9 Hz), 6.91 (1H, t, J = 8.4 Hz), 6.84 (1H, t, J = 8.4 Hz), 6.75-6.69 (2H, m), 6.64-6.63 (1H, m), 5.98 (1H, tt, J = 55.1, 4.1 Hz), 4.08-3.87 (4H, m), 1.16 (3H, t, J = 7.2 Hz). |
| 278 | ¹H-NMR (CDCl₃) δ: 7.35-7.32 (1H, m), 7.34 (1H, d, J = 9.5 Hz), 7.22 (1H, d, J = 8.9 Hz), 6.92 (1H, t, J = 8.4 Hz), 6.85 (1H, t, J = 8.4 Hz), 6.75 (1H, d, J = 9.5 Hz), 6.72 (1H, dd, J = 8.9, 3.1 Hz), 6.60 (1H, dd, J = 3.1, 1.5 Hz), 5.98 (1H, tt, J = 54.9, 4.1 Hz), 4.07-3.90 (2H, m), 3.39 (3H, s). |
| 279 | ¹H-NMR (CDCl₃) δ: 7.79 (1H, s), 7.37 (1H, tt, J = 8.6, 3.5 Hz), 7.15 (2H, d, J = 8.3 Hz), 6.98 (2H, d, J = 8.6 Hz), 6.89 (2H, dd, J = 8.4, 7.2 Hz), 3.95 (2H, q, J = 7.0 Hz), 1.16 (3H, t, J = 7.0 Hz). |
| 280 | ¹H-NMR (CDCl₃) δ: 7.39-7.33 (2H, m), 7.15 (2H, d, J = 8.6 Hz), 6.98 (2H, d, J = 8.3 Hz), 6.89 (2H, dt, J = 12.4, 4.8 Hz), 6.75 (1H, d, J = 9.2 Hz), 3.37 (3H, s). |
| 281 | ¹H-NMR (CDCl₃) δ: 7.33 (1H, d, J = 9.5 Hz), 6.72 (1H, d, J = 9.5 Hz), 6.42-6.41 (1H, m), 6.37 (1H, d, J = 2.8 Hz), 6.35-6.33 (1H, m), 6.21 (1H, dd, J = 2.8, 1.2 Hz), 3.85-3.84 (5H, m), 3.65 (3H, s), 3.38 (3H, s), 1.79-1.78 (2H, m), 1.02 (3H, t, J = 7.3 Hz). |
| 282 | ¹H-NMR (CDCl₃) δ: 7.33 (1H, d, J = 9.5 Hz), 6.72 (1H, d, J = 9.5 Hz), 6.42-6.40 (1H, m), 6.37 (1H, d, J = 2.8 Hz), 6.35-6.33 (1H, m), 6.21 (1H, dd, J = 2.8, 1.2 Hz), 3.88 (2H, t, J = 6.6 Hz), 3.83 (3H, s), 3.65 (3H, s), 3.38 (3H, s), 1.75-1.72 (2H, m), 1.47-1.44 (2H, m), 0.97 (3H, t, J = 7.3 Hz). |
| 283 | ¹H-NMR (CDCl₃) δ: 7.32-7.26 (3H, m), 7.18-7.17 (2H, m), 6.83-6.80 (2H, m), 3.44 (2H, q, J = 7.1 Hz), 2.82-2.73 (4H, m), 0.97 (3H, t, J = 7.1 Hz). |
| 284 | ¹H-NMR (CDCl₃) δ: 7.43-7.26 (6H, m), 6.87 (2H, dd, J = 8.4, 7.2 Hz), 6.76 (1H, d, J = 9.2 Hz), 3.92 (2H, q, J = 7.2 Hz), 1.15 (3H, t, J = 7.2 Hz). |
| 285 | ¹H-NMR (CDCl₃) δ: 7.61 (1H, s), 7.38 (1H, tt, J = 8.6, 3.5 Hz), 7.16 (2H, d, J = 8.6 Hz), 6.98 (2H, dd, J = 8.6 Hz), 6.90 (2H, dd, J = 8.4, 7.2 Hz), 3.44 (3H, s). |
| 286 | ¹H-NMR (CDCl₃) δ: 7.81 (1H, s), 7.38 (1H, tt, J = 8.5, 3.5 Hz), 7.16 (2H, dt, J = 8.7, 2.3 Hz), 6.98 (2H, dt, J = 8.9, 2.3 Hz), 6.89 (2H, tt, J = 10.1, 1.8 Hz), 3.44 (3H, s). |
| 287 | ¹H-NMR (CDCl₃) δ: 7.34-7.28 (1H, m), 7.32 (1H, d, J = 9.5 Hz), 7.14 (1H, d, J = 8.6 Hz), 6.89 (1H, t, J = 8.4 Hz), 6.84 (1H, t, J = 8.4 Hz), 6.73 (1H, d, J = 9.5 Hz), 6.63 (1H, dd, J = 8.6, 3.1 Hz), 6.57 (1H, dd, J = 3.1, 1.5 Hz), 4.53-4.52 (1H, m), 3.94-3.86 (2H, m), 1.82-1.57 (8H, m), 1.16 (3H, t, J = 7.2 Hz). |
| 288 | ¹H-NMR (CDCl₃) δ: 7.35 (1H, d, J = 9.5 Hz), 7.32-7.30 (1H, m), 7.15 (1H, d, J = 8.6 Hz), 6.89 (1H, t, J = 8.4 Hz), 6.84 (1H, t, J = 8.4 Hz), 6.75 (1H, d, J = 9.2 Hz), 6.64 (1H, dd, J = 8.6, 3.1 Hz), 6.54 (1H, dd, J = 3.1, 1.4 Hz), 4.53-4.51 (1H, m), 3.38 (3H, s), 1.81-1.56 (8H, m). |
| 289 | ¹H-NMR (CDCl₃) δ: 7.37-7.36 (2H, m), 7.30 (2H, d, J = 8.6 Hz), 6.91-6.89 (4H, m), 6.75 (1H, d, J = 9.2 Hz), 3.37 (3H, s). |
| 290 | ¹H-NMR (CDCl₃) δ: 7.81 (1H, s), 7.40-7.36 (1H, m), 7.31 (2H, d, J = 8.6 Hz), 6.91-6.89 (4H, m), 3.44 (3H, s). |
| 291 | ¹H-NMR (CDCl₃) δ: 7.60 (1H, s), 7.40-7.36 (1H, m), 7.31 (2H, d, J = 8.3 Hz), 6.93-6.88 (4H, m), 3.44 (3H, s). |
| 292 | ¹H-NMR (CDCl₃) δ: 7.39-7.28 (4H, m), 6.94-6.86 (4H, m), 6.73 (1H, d, J = 9.5 Hz), 3.89 (2H, q, J = 7.1 Hz), 1.14 (3H, t, J = 7.1 Hz). |
| 293 | ¹H-NMR (CDCl₃) δ: 7.79 (1H, s), 7.38-7.36 (1H, m), 7.31 (2H, d, J = 8.3 Hz), 6.94-6.87 (4H, m), 3.94 (2H, q, J = 7.1 Hz), 1.16 (3H, t, J = 7.1 Hz). |
| 294 | ¹H-NMR (CDCl₃) δ: 7.58 (1H, s), 7.41-7.34 (1H, m), 7.31 (2H, d, J = 8.6 Hz), 6.92-6.89 (4H, m), 3.94 (2H, q, J = 7.1 Hz), 1.16 (3H, t, J = 7.1 Hz). |
| 295 | ¹H-NMR (CDCl₃) δ: 7.33 (1H, d, J = 9.5 Hz), 7.32-7.30 (1H, m), 7.15 (1H, d, J = 8.7 Hz), 6.88 (1H, t, J = 8.4 Hz), 6.84 (1H, t, J = 8.4 Hz), 6.73 (1H, d, J = 9.5 Hz), 6.66 (1H, dd, J = 8.7, 2.9 Hz), 6.60 (1H, dd, J = 2.9, 1.4 Hz), 3.95-3.89 (3H, m), 1.76-1.40 (10H, m), 1.16 (3H, t, J = 7.0 Hz). |
| 296 | ¹H-NMR (CDCl₃) δ: 7.36 (1H, d, J = 9.5 Hz), 7.32-7.30 (1H, m), 7.16 (1H, d, J = 8.9 Hz), 6.89 (1H, t, J = 8.6 Hz), 6.84 (1H, t, J = 8.6 Hz), 6.75 (1H, d, J = 9.5 Hz), 6.67 (1H, dd, J = 8.9, 3.1 Hz), 6.57 (1H, dd, J = 3.1, 1.2 Hz), 3.99-3.96 (1H, m), 3.38 (3H, s), 1.74-1.37 (10H, m). |
| 297 | ¹H-NMR (CDCl₃) δ: 7.31 (3H, tt, J = 9.6, 3.0 Hz), 6.96-6.90 (3H, m), 6.83 (1H, t, J = 8.4 Hz), 6.74 (1H, d, J = 9.5 Hz), 3.93-3.88 (2H, m), 3.88 (3H, s), 1.16 (3H, t, J = 7.2 Hz). |
| 298 | ¹H-NMR (CDCl₃) δ: 7.36-7.30 (3H, m), 6.97 (1H, dd, J = 8.9, 2.8 Hz), 6.92-6.90 (2H, m), 6.84 (1H, t, J = 8.4 Hz), 6.75 (1H, d, J = 9.5 Hz), 3.87 (3H, s), 3.39 (3H, s). |
| 299 | ¹H-NMR (CDCl₃) δ: 7.64 (1H, s), 7.44 (1H, d, J = 7.3 Hz), 7.35-7.31 (4H, m), 6.90-6.86 (2H, m), 3.97 (2H, q, J = 7.2 Hz), 1.18 (3H, t, J = 7.2 Hz). |
| 300 | ¹H-NMR (CDCl₃) δ: 7.26-7.23 (1H, m), 6.89 (2H, d, J = 8.6 Hz), 6.80 (2H, t, J = 7.8 Hz), 6.65 (2H, d, J = 8.9 Hz), 3.72 (3H, s), 3.41 (2H, q, J = 7.0 Hz), 2.74-2.71 (4H, m), 0.95 (3H, t, J = 7.0 Hz). |
| 301 | ¹H-NMR (CDCl₃) δ: 7.37 (1H, d, J = 9.2 Hz), 7.32-7.31 (1H, m), 6.97-6.96 (2H, m), 6.86 (2H, dd, J = 8.4, 7.2 Hz), 6.72-6.69 (3H, m), 3.90 (2H, q, J = 7.2 Hz), 3.73 (3H, s), 1.14 (3H, t, J = 7.2 Hz). |
| 302 | ¹H-NMR (CDCl₃) δ: 7.61 (1H, s), 7.34-7.32 (1H, m), 6.96 (2H, dt, J = 9.4, 2.5 Hz), 6.88-6.86 (2H, m), 6.69 (2H, dt, J = 9.3, 2.6 Hz), 3.94 (2H, q, J = 7.2 Hz), 3.73 (3H, s), 1.16 (3H, t, J = 7.2 Hz). |
| 303 | ¹H-NMR (CDCl₃) δ: 7.32-7.31 (1H, m), 7.31 (1H, d, J = 9.5 Hz), 7.20 (1H, d, J = 8.9 Hz), 6.91 (1H, t, J = 8.4 Hz), 6.84 (1H, t, J = 8.4 Hz), 6.73 (1H, d, J = 9.5 Hz), 6.69 (1H, dd, J = 8.9, |

TABLE 5-continued

| Compound | ¹H-NMR |
|---|---|
| | 3.1 Hz), 6.55 (1H, dd, J = 3.1, 1.5 Hz), 4.42 (1H, d, J = 16.8 Hz), 4.37 (1H, d, J = 16.8 Hz), 3.92-3.87 (2H, m), 2.20 (3H, s), 1.16 (3H, t, J = 7.0 Hz). |
| 304 | ¹H-NMR (CDCl₃) δ: 7.34-7.32 (2H, m), 7.21 (1H, d, J = 8.9 Hz), 6.92 (1H, t, J = 8.4 Hz), 6.85 (1H, t, J = 8.4 Hz), 6.75 (1H, d, J = 9.2 Hz), 6.70 (1H, dd, J = 8.9, 3.1 Hz), 6.53 (1H, dd, J = 3.1, 1.4 Hz), 4.41 (1H, d, J = 16.8 Hz), 4.35 (1H, d, J = 16.8 Hz), 3.38 (3H, s), 2.19 (3H, s). |
| 305 | ¹H-NMR (CDCl₃) δ: 7.33 (1H, d, J = 9.2 Hz), 7.33-7.30 (1H, m), 7.21 (1H, d, J = 8.9 Hz), 6.91 (1H, t, J = 8.4 Hz), 6.84 (1H, t, J = 8.4 Hz), 6.73-6.72 (2H, m), 6.68-6.67 (1H, m), 4.98 (1H, d, J = 11.9 Hz), 4.96 (1H, d, J = 11.9 Hz), 3.93-3.87 (2H, m), 2.17 (3H, s), 1.16 (3H, t, J = 7.2 Hz). |
| 306 | ¹H-NMR (CDCl₃) δ: 7.36 (1H, d, J = 9.5 Hz), 7.33-7.30 (1H, m), 1.12 (1H, d, J = 8.5 Hz), 6.91 (1H, t, J = 8.4 Hz), 6.84 (1H, t, J = 8.4 Hz), 6.74 (2H, dd, J = 9.0, 3.4 Hz), 6.65 (1H, m), 4.98 (1H, d, J = 11.9 Hz), 4.94 (1H, d, J = 11.9 Hz), 3.38 (3H, s), 2.16 (3H, s). |
| 307 | ¹H-NMR (CDCl₃) δ: 7.33-7.31 (2H, m), 7.19 (1H, d, J = 8.9 Hz), 6.91 (1H, t, J = 8.4 Hz), 6.84 (1H, t, J = 8.4 Hz), 6.73-6.71 (2H, m), 6.59 (1H, dd, J = 3.1, 1.5 Hz), 4.43 (2H, s), 4.27 (2H, q, J = 7.1 Hz), 3.91-3.89 (2H, m), 1.30 (3H, t, J = 7.1 Hz), 1.16 (3H, t, J = 7.1 Hz). |
| 308 | ¹H-NMR (CDCl₃) δ: 7.34-7.31 (1H, m), 7.34 (1H, d, J = 9.5 Hz), 7.20 (1H, d, J = 8.9 Hz), 6.91 (1H, t, J = 8.6 Hz), 6.84 (1H, t, J = 8.6 Hz), 6.76-6.71 (2H, m), 6.57 (1H, dd, J = 3.1, 1.5 Hz), 4.42 (2H, s), 4.26 (2H, q, J = 7.2 Hz), 3.38 (3H, s), 1.30 (3H, t, J = 7.2 Hz). |
| 309 | ¹H-NMR (CDCl₃) δ: 7.34-7.32 (1H, m), 7.31 (1H, d, J = 9.5 Hz), 7.26 (3H, d, J = 8.9 Hz), 6.93 (1H, t, J = 8.4 Hz), 6.87-6.83 (2H, m), 6.78 (1H, dd, J = 2.9, 1.4 Hz), 6.74 (1H, d, J = 9.5 Hz), 4.80 (1H, d, J = 12.2 Hz), 4.73 (1H, d, J = 12.2 Hz), 3.93-3.87 (2H, m), 2.96 (3H, s), 1.16 (3H, t, J = 7.2 Hz). |
| 310 | ¹H-NMR (CDCl₃) δ: 7.33-7.27 (1H, m), 7.33 (1H, d, J = 9.2 Hz), 7.16 (1H, d, J = 8.9 Hz), 6.89 (1H, t, J = 8.4 Hz), 6.83 (1H, t, J = 8.4 Hz), 6.73 (1H, d, J = 9.2 Hz), 6.66 (1H, dd, J = 8.9, 3.1 Hz), 6.61 (1H, dd, J = 3.1, 1.2 Hz), 3.96-3.78 (4H, m), 3.49-3.48 (2H, m), 3.34 (3H, s), 1.98-1.93 (2H, m), 1.16 (3H, t, J = 7.0 Hz). |
| 311 | ¹H-NMR (CDCl₃) δ: 7.35 (1H, d, J = 9.5 Hz), 7.32-7.30 (1H, m), 7.17 (1H, d, J = 8.9 Hz), 6.90 (1H, t, J = 8.4 Hz), 6.84 (1H, t, J = 8.4 Hz), 6.75 (1H, d, J = 9.5 Hz), 6.67 (1H, dd, J = 8.9, 3.1 Hz), 6.58 (1H, dd, J = 3.1, 1.4 Hz), 3.93-3.90 (1H, m), 3.80-3.78 (1H, m), 3.48 (2H, t, J = 6.1 Hz), 3.39 (3H, s), 3.34 (3H, s), 1.97-1.92 (2H, m). |
| 312 | ¹H-NMR (CDCl₃) δ: 7.36-7.32 (2H, m), 7.27-7.26 (1H, m), 6.93 (1H, t, J = 8.4 Hz), 6.88-6.84 (2H, m), 6.76-6.75 (2H, m), 4.79 (1H, d, J = 12.2 Hz), 4.72 (1H, d, J = 12.2 Hz), 3.39 (3H, s), 2.95 (3H, s). |
| 313 | ¹H-NMR (CDCl₃) δ: 7.32 (1H, d, J = 9.5 Hz), 7.32-7.30 (1H, m), 7.17 (1H, d, J = 8.9 Hz), 6.89 (1H, t, J = 8.4 Hz), 6.83 (1H, t, J = 8.4 Hz), 6.73 (1H, d, J = 9.5 Hz), 6.68 (1H, dd, J = 8.9, 3.1 Hz), 6.62 (1H, dd, J = 3.1, 1.5 Hz), 5.99-5.91 (1H, m), 5.34-5.30 (1H, m), 5.27-5.25 (1H, m), 4.40-4.38 (1H, m), 4.32-4.31 (1H, m), 3.94-3.88 (2H, m), 1.16 (3H, t, J = 7.0 Hz). |
| 314 | ¹H-NMR (CDCl₃) δ: 7.35 (1H, d, J = 9.2 Hz), 7.32-7.31 (1H, m), 7.18 (1H, d, J = 8.9 Hz), 6.90 (1H, t, J = 8.6 Hz), 6.84 (1H, t, J = 8.6 Hz), 6.75 (1H, d, J = 9.2 Hz), 6.69 (1H, dd, J = 8.9, 3.1 Hz), 6.59 (1H, dd, J = 3.1, 1.4 Hz), 5.98-5.90 (1H, m), 5.34-5.29 (1H, m), 5.26-5.24 (1H, m), 4.40-4.37 (1H, m), 4.32-4.29 (1H, m), 3.38 (3H, s). |
| 315 | ¹H-NMR (CDCl₃) δ: 7.33-7.29 (1H, m), 7.31 (1H, d, J = 9.5 Hz), 7.17 (1H, d, J = 8.9 Hz), 6.89 (1H, t, J = 8.4 Hz), 6.83 (1H, t, J = 8.4 Hz), 6.73-6.71 (2H, m), 6.64-6.63 (1H, m), 5.19 (1H, t, J = 4.0 Hz), 4.05-4.00 (2H, m), 3.99-3.87 (5H, m), 3.77 (1H, dd, J = 10.2, 4.0 Hz), 1.16 (3H, t, J = 7.2 Hz). |
| 316 | ¹H-NMR (CDCl₃) δ: 7.34-7.29 (1H, m), 7.34 (1H, d, J = 9.5 Hz), 7.18 (1H, d, J = 8.9 Hz), 6.89 (1H, t, J = 8.6 Hz), 6.84 (1H, t, J = 8.6 Hz), 6.75-6.72 (2H, m), 6.62-6.61 (1H, m), 5.19 (1H, t, J = 4.0 Hz), 4.03-4.01 (2H, m), 3.98-3.94 (2H, m), 3.89 (1H, dd, J = 10.1, 4.0 Hz), 3.76 (1H, dd, J = 10.1, 4.0 Hz), 3.38 (3H, s). |
| 317 | ¹H-NMR (CDCl₃) δ: 7.33 (1H, d, J = 9.2 Hz), 7.32-7.29 (1H, m), 7.16 (1H, d, J = 8.9 Hz), 6.90 (1H, t, J = 8.4 Hz), 6.83 (1H, t, J = 8.4 Hz), 6.73 (1H, d, J = 9.2 Hz), 6.66 (1H, dd, J = 8.9, 2.9 Hz), 6.61 (1H, dd, J = 2.9, 1.4 Hz), 4.70 (1H, t, J = 5.2 Hz), 4.12-4.10 (2H, m), 3.96-3.75 (6H, m), 2.12-2.05 (1H, m), 1.99-1.97 (2H, m), 1.38-1.35 (1H, m), 1.16 (3H, t, J = 7.0 Hz). |
| 318 | ¹H-NMR (CDCl₃) δ: 7.35 (1H, d, J = 9.5 Hz), 7.32-7.30 (1H, m), 7.17 (1H, d, J = 8.9 Hz), 6.90 (1H, t, J = 8.6 Hz), 6.83 (1H, t, J = 8.6 Hz), 6.74 (1H, d, J = 9.5 Hz), 6.67 (1H, dd, J = 8.9, 3.1 Hz), 6.58 (1H, dd, J = 3.1, 1.2 Hz), 4.70 (1H, t, J = 5.2 Hz), 4.12-4.09 (2H, m), 3.94-3.92 (1H, m), 3.79-3.77 (3H, m), 3.39 (3H, s), 1.98-1.96 (2H, m), 1.38-1.35 (1H, m). |
| 319 | ¹H-NMR (CDCl₃) δ: 7.32 (1H, d, J = 9.5 Hz), 6.74 (1H, d, J = 9.5 Hz), 6.51 (1H, dt, J = 10.0, 2.0 Hz), 6.42 (1H, dt, J = 10.0, 2.0 Hz), 6.38 (1H, d, J = 2.8 Hz), 6.21 (1H, dd, J = 2.8, 1.7 Hz), 4.29 (2H, q, J = 7.8 Hz), 3.83 (3H, s), 3.67 (3H, s), 3.37 (3H, s). |
| 320 | ¹H-NMR (CDCl₃) δ: 7.24 (1H, dd, J = 8.9, 5.2 Hz), 6.83-6.81 (1H, m), 6.76-6.74 (1H, m), 6.63-6.61 (1H, m), 6.56-6.54 (1H, m), 3.44-3.39 (2H, m), 2.89-2.54 (4H, m), 0.99 (3H, t, J = 7.0 Hz). |
| 321 | ¹H-NMR (CDCl₃) δ: 7.30-7.27 (2H, m), 6.90-6.61 (5H, m), 3.90 (2H, q, J = 6.9 Hz), 1.16 (3H, t, J = 6.9 Hz). |
| 322 | ¹H-NMR (CDCl₃) δ: 7.53 (1H, s), 7.29 (1H, dd, J = 8.9, 5.2 Hz), 6.92-6.90 (1H, m), 6.82-6.80 (1H, m), 6.71 (1H, tt, J = 8.7, 2.0 Hz), 6.64 (1H, tt, J = 8.7, 2.0 Hz), 3.99-3.90 (2H, m), 1.19 (3H, t, J = 7.0 Hz). |
| 323 | ¹H-NMR (CDCl₃) δ: 7.34-7.28 (1H, m), 7.33 (1H, d, J = 9.5 Hz), 7.15 (1H, d, J = 8.9 Hz), 6.88 (1H, t, J = 8.6 Hz), 6.83 (1H, t, J = 8.6 Hz), 6.73 (1H, d, J = 9.5 Hz), 6.65 (1H, dd, J = 8.9, 3.1 Hz), 6.60 (1H, dd, J = 3.1, 1.4 Hz), 3.97-3.84 (2H, m), 3.69 (1H, dd, J = 9.0, 7.0 Hz), 3.57 (1H, dd, J = 9.0, 7.0 Hz), 2.27-2.22 (1H, m), 1.79-1.74 (2H, m), 1.64-1.54 (4H, m), 1.28-1.26 (2H, m), 1.16 (3H, t, J = 7.0 Hz). |
| 324 | ¹H-NMR (CDCl₃) δ: 7.36 (1H, d, J = 9.5 Hz), 7.33-7.30 (1H, m), 7.16 (1H, d, J = 8.9 Hz), 6.89 (1H, t, J = 8.6 Hz), 6.84 (1H, t, J = 8.6 Hz), 6.74 (1H, d, J = 9.5 Hz), 6.67 (1H, dd, J = 8.9, 2.8 Hz), 6.57 (1H, dd, J = 2.8, 1.2 Hz), 3.68 (1H, dd, J = 9.0, 6.9 Hz), 3.55 (1H, dd, J = 9.0, 6.9 Hz), 3.39 (3H, s), 2.24 (1H, t, J = 7.3 Hz), 1.78-1.77 (2H, m), 1.63-1.56 (4H, m), 1.29-1.25 (2H, m). |

TABLE 5-continued

| Compound | ¹H-NMR |
|---|---|
| 325 | ¹H-NMR (CDCl₃) δ: 7.33 (1H, d, J = 9.2 Hz), 7.33-7.27 (1H, m), 7.19-7.17 (1H, m), 6.89 (1H, t, J = 8.4 Hz), 6.83 (1H, t, J = 8.4 Hz), 6.80-6.77 (2H, m), 6.73 (1H, d, J = 9.2 Hz), 5.05 (1H, d, J = 7.0 Hz), 5.02 (1H, d, J = 7.0 Hz), 3.92-3.88 (2H, m), 3.63 (2H, q, J = 7.1 Hz), 1.20-1.14 (6H, m). |
| 326 | ¹H-NMR (CDCl₃) δ: 7.36 (1H, d, J = 9.5 Hz), 7.32-7.30 (1H, m), 7.19 (1H, d, J = 8.9 Hz), 6.89 (1H, t, J = 8.4 Hz), 6.83 (1H, t, J = 8.4 Hz), 6.80 (1H, dd, J = 8.9, 2.9 Hz), 6.76-6.74 (2H, m), 5.05 (1H, d, J = 7.0 Hz), 5.01 (1H, d, J = 7.0 Hz), 3.62 (2H, q, J = 7.0 Hz), 3.38 (3H, s), 1.18 (3H, t, J = 7.0 Hz). |
| 327 | ¹H-NMR (CDCl₃) δ: 7.37-7.35 (2H, m), 7.30-7.28 (1H, m), 7.22 (1H, t, J = 1.7 Hz), 7.03 (1H, t, J = 7.6 Hz), 6.98-6.97 (1H, m), 6.92-6.87 (2H, m), 6.73 (1H, d, J = 9.5 Hz), 3.90 (2H, q, J = 7.1 Hz), 1.14 (3H, t, J = 7.1 Hz). |
| 328 | ¹H-NMR (CDCl₃) δ: 7.60 (1H, s), 7.38-7.36 (1H, m), 7.32-7.30 (1H, m), 7.22 (1H, t, J = 1.7 Hz), 7.05-7.03 (1H, m), 6.99-6.97 (1H, m), 6.93-6.88 (2H, m), 3.95 (2H, q, J = 7.1 Hz), 1.17 (3H, t, J = 7.1 Hz). |
| 329 | 1H-NMR (CDCl3) δ: 7.30-7.28 (1H, m), 7.23 (1H, s), 7.17 (1H, d, J = 8.9 Hz), 6.88 (1H, t, J = 8.3 Hz), 6.82 (1H, t, J = 8.3 Hz), 6.65 (1H, dd, J = 8.9, 3.1 Hz), 6.63-6.61 (1H, m), 3.93-3.90 (2H, m), 3.65 (3H, s), 2.25 (3H, s), 1.16 (3H, t, J = 7.0 Hz). |
| 330 | ¹H-NMR (CDCl₃) δ: 7.32 (1H, d, J = 9.5 Hz), 7.31-7.28 (1H, m), 7.18 (1H, d, J = 8.5 Hz), 6.89 (1H, t, J = 8.5 Hz), 6.85-6.78 (3H, m), 6.73 (1H, d, J = 9.5 Hz), 5.10 (1H, d, J = 7.0 Hz), 5.07 (1H, d, J = 7.0 Hz), 3.91-3.89 (2H, m), 3.74-3.71 (2H, m), 3.54-3.51 (2H, m), 3.37 (3H, s), 1.16 (3H, t, J = 7.0 Hz). |
| 331 | ¹H-NMR (CDCl₃) δ: 7.35 (1H, d, J = 9.5 Hz), 7.33-7.29 (1H, m), 7.19 (1H, d, J = 8.9 Hz), 6.89 (1H, t, J = 8.4 Hz), 6.85-6.81 (2H, m), 6.75-6.74 (2H, m), 6.73 (1H, d, J = 9.5 Hz), 5.09 (1H, d, J = 7.0 Hz), 5.06 (1H, d, J = 7.0 Hz), 3.73-3.71 (2H, m), 3.53-3.51 (2H, m), 3.38 (3H, s), 3.36 (3H, s). |
| 332 | ¹H-NMR (CDCl₃)δ: 7.36-7.30 (2H, m), 7.28 (1H, d, J = 9.5 Hz), 7.03-6.97 (2H, m), 6.90 (1H, t, J = 8.5 Hz), 6.85 (1H, t, J = 8.5 Hz), 3.96-3.83 (2H, m), 1.15 (3H, t, J = 7.0 Hz). |
| 333 | ¹H-NMR (CDCl₃) δ: 7.51 (1H, s), 7.37-7.31 (2H, m), 7.08-6.99 (2H, m), 6.91-6.83 (2H, m), 4.01-3.91 (2H, m), 1.18 (3H, t, J = 7.0 Hz). |
| 334 | ¹H-NMR (CDCl₃) δ: 7.27-7.23 (1H, m), 6.82 (1H, t, J = 8.4 Hz), 6.77 (1H, t, J = 8.4 Hz), 6.31 (1H, d, J = 2.4 Hz), 6.19-6.17 (1H, br m), 4.07 (2H, br s), 3.80 (3H, s), 3.63 (3H, s), 2.97-2.91 (1H, m), 2.87-2.82 (1H, m), 2.78-2.72 (1H, m), 2.67-2.61 (1H, m). |
| 335 | ¹H-NMR (CDCl₃) δ: 7.38-7.30 (1H, m), 6.90-6.82 (2H, m), 6.77 (1H, d, J = 9.5 Hz), 6.35 (1H, d, J = 2.7 Hz), 6.24-6.21 (1H, br m), 4.62 (2H, br s), 3.81 (3H, s), 3.65 (3H, s). |
| 336 | ¹H-NMR (CDCl₃) δ: 7.26-7.22 (1H, m), 6.82 (1H, tt, J = 8.4, 1.5 Hz), 6.77 (1H, tt, J = 8.4, 1.5 Hz), 6.30 (1H, d, J = 2.7 Hz), 6.21 (1H, dd, J = 2.7, 1.8 Hz), 5.92 (1H, tt, J = 56.6, 4.6 Hz), 3.79 (3H, s), 3.68 (2H, tt, J = 13.4, 4.6 Hz), 3.63 (3H, s), 2.98-2.59 (4H, m). |
| 337 | ¹H-NMR (CDCl₃) δ: 7.39 (1H, d, J = 9.5 Hz), 7.38-7.30 (1H, m), 6.89 (1H, t, J = 8.5 Hz), 6.84 (1H, t, J = 8.5 Hz), 6.75 (1H, d, J = 9.5 Hz), 6.35 (1H, d, J = 2.7 Hz), 6.24 (1H, dd, J = 2.7, 1.5 Hz), 6.18 (1H, tt, J = 56.8, 4.5 Hz), 4.19-4.10 (2H, m), 3.81 (3H, s), 3.64 (3H, s). |
| 338 | ¹H-NMR (CDCl₃) δ: 7.32 (1H, d, J = 9.5 Hz), 6.73 (1H, d, J = 9.5 Hz), 6.47 (1H, dt, J = 10.5, 2.0 Hz), 6.42-6.39 (1H, m), 6.37 (1H, d, J = 2.7 Hz), 6.21 (1H, dd, J = 2.7, 1.5 Hz), 6.06 (1H, tt, J = 55.2, 4.0 Hz), 4.12 (2H, dt, J = 4.0, 12.8 Hz), 3.83 (3H, s), 3.66 (3H, s), 3.37 (3H, s). |
| 339 | ¹H-NMR (CDCl₃) δ: 7.32-7.29 (2H, m), 6.91-6.88 (1H, m), 6.79-6.77 (2H, m), 6.73-6.61 (2H, m), 3.38 (3H, s). |
| 340 | ¹H-NMR (CDCl₃) δ: 7.54 (1H, s), 7.29 (1H, dd, J = 9.0, 5.0 Hz), 6.93-6.91 (1H, m), 6.81-6.79 (1H, m), 6.73-6.62 (2H, m), 3.45 (3H, s). |
| 341 | ¹H-NMR (CDCl₃) δ: 7.46-7.45 (1H, m), 7.40-7.33 (3H, m), 7.30-7.29 (2H, m), 6.90 (2H, dd, J = 8.4, 7.2 Hz), 6.76 (1H, d, J = 9.5 Hz), 3.91 (2H, q, J = 7.2 Hz), 1.15 (3H, t, J = 7.2 Hz). |
| 342 | ¹H-NMR (CDCl₃) δ: 6.61-6.51 (2H, m), 6.31 (1H, d, J = 2.7 Hz), 6.19 (1H, m), 3.81 (3H, s), 3.67 (3H, s), 3.46 (1H, dq, J = 14.3, 7.2 Hz), 3.35 (1H, dq, J = 14.3, 7.2 Hz), 2.91-2.52 (4H, m), 0.99 (3H, t, J = 7.2 Hz). |
| 343 | ¹H-NMR (CDCl₃) δ: 7.37 (1H, d, J = 9.5 Hz), 6.76 (1H, d, J = 9.5 Hz), 6.69-6.59 (2H, m), 6.38 (1H, d, J = 2.7 Hz), 6.23 (1H, dd, J = 2.7, 2.0 Hz), 6.17 (1H, tt, J = 56.8, 4.6 Hz), 4.16-4.12 (2H, m), 3.83 (3H, s), 3.68 (3H, s). |
| 344 | ¹H-NMR (CDCl₃) δ: 7.29 (1H, d, J = 9.2 Hz), 7.26-7.22 (1H, m), 7.16-7.11 (2H, m), 6.95 (2H, d, J = 3.7 Hz), 6.86 (1H, t, J = 8.4 Hz), 6.78-6.72 (2H, m), 3.37 (3H, s), 2.56-2.41 (2H, m), 1.14 (3H, t, J = 7.5 Hz). |
| 345 | ¹H-NMR (CDCl₃) δ: 7.33-7.32 (3H, m), 7.04 (1H, dd, J = 8.3, 2.1 Hz), 7.00 (1H, dd, J = 8.3, 1.5 Hz), 6.89 (1H, t, J = 8.6 Hz), 6.85 (1H, t, J = 8.6 Hz), 6.75 (1H, d, J = 9.5 Hz), 6.16 (1H, tt, J = 56.7, 4.5 Hz), 4.23-4.10 (2H, m). |
| 346 | ¹H-NMR (CDCl₃) δ: 7.36-7.29 (3H, m), 7.03 (1H, dd, J = 8.3, 2.1 Hz), 6.97 (1H, dd, J = 8.3, 1.2 Hz), 6.90 (1H, t, J = 8.4 Hz), 6.85 (1H, t, J = 8.4 Hz), 6.75 (1H, d, J = 9.5 Hz), 3.38 (3H, s). |
| 347 | ¹H-NMR (CDCl₃) δ: 7.58 (1H, s), 7.38 (1H, tt, J = 8.4, 3.5 Hz), 7.33 (1H, d, J = 2.1 Hz), 7.06 (1H, dd, J = 8.3, 2.1 Hz), 7.01 (1H, dd, J = 8.3, 1.8 Hz), 6.92-6.85 (2H, m), 6.18 (1H, tt, J = 56.4, 4.4 Hz), 4.21 (2H, m). |
| 348 | ¹H-NMR (CDCl₃) δ: 7.53 (1H, s), 7.38-7.32 (2H, m), 7.04 (1H, dd, J = 8.4, 2.0 Hz), 6.98 (1H, dd, J = 8.4, 1.5 Hz), 6.88 (2H, dt, J = 21.0, 8.4 Hz), 3.44 (3H, s). |
| 349 | ¹H-NMR (CDCl₃) δ: 7.33-7.27 (3H, m), 7.00-6.94 (2H, m), 6.88 (1H, t, J = 8.4 Hz), 6.83 (1H, t, J = 8.3 Hz), 6.73 (1H, d, J = 9.5 Hz), 3.99-3.90 (1H, m), 3.89-3.82 (1H, m), 1.16 (3H, t, J = 7.0 Hz). |
| 350 | ¹H-NMR (CDCl₃) δ: 7.54 (1H, s), 7.35-7.29 (2H, m), 7.01-6.96 (2H, m), 6.91-6.83 (2H, m), 4.00-3.88 (2H, m), 1.18 (3H, t, J = 7.2 Hz). |
| 351 | ¹H-NMR (CDCl₃) δ: 7.61 (1H, s), 7.34-7.31 (1H, m), 7.17 (1H, d, J = 8.9 Hz), 6.89 (1H, t, J = 8.4 Hz), 6.84 (1H, t, J = 8.4 Hz), 6.67 (1H, dd, J = 8.9, 3.1 Hz), 6.61 (1H, dd, J = 3.1, 1.5 Hz), 3.94-3.92 (2H, m), 3.65 (3H, s), 3.38 (3H, s), 1.18 (3H, t, J = 7.2 Hz). |
| 352 | ¹H-NMR (CDCl₃) δ: 7.31-7.28 (1H, m), 7.16 (1H, d, J = 8.9 Hz), 6.88 (1H, t, J = 8.4 Hz), 6.83 (1H, s), 6.81 (1H, t, J = 8.4 Hz), 6.65 (1H, dd, J = 8.9, 3.1 Hz), 6.59 (1H, dd, J = 3.1, 1.2 |

TABLE 5-continued

| Compound | ¹H-NMR |
|---|---|
| | Hz), 3.95-3.90 (2H, m), 3.64 (3H, s), 2.31-2.28 (1H, m), 1.17 (3H, t, J = 7.0 Hz), 1.01-1.00 (2H, m), 0.72-0.67 (2H, m). |
| 353 | ¹H-NMR (CDCl₃) δ: 7.58 (1H, s), 7.49-7.47 (1H, m), 7.41-7.38 (1H, m), 7.34 (1H, m), 7.32-7.31 (2H, m), 6.92-6.89 (2H, m), 3.96 (2H, q, J = 7.2 Hz), 1.17 (3H, t, J = 7.2 Hz). |
| 354 | ¹H-NMR (CDCl₃) δ: 7.28 (1H, d, J = 9.2 Hz), 7.25 (1H, d, J = 8.5 Hz), 7.13 (1H, dd, J = 8.5, 2.7 Hz), 7.06 (1H, dd, J = 2.4, 1.5 Hz), 6.75-6.69 (2H, m), 6.63-6.61 (1H, m), 3.90 (2H, q, J = 7.0 Hz), 1.16 (3H, t, J = 7.0 Hz). |
| 355 | ¹H-NMR (CDCl₃) δ: 7.52 (1H, s), 7.26 (1H, d, J = 8.3 Hz), 7.16 (1H, dd, J = 8.6, 2.8 Hz), 7.07 (1H, t, J = 2.0 Hz), 6.72 (1H, tt, J = 8.6, 2.1 Hz), 6.64 (1H, tt, J = 8.6, 2.1 Hz), 4.01-3.89 (2H, m), 1.19 (3H, t, J = 7.0 Hz). |
| 356 | ¹H-NMR (CDCl₃) δ: 7.23-7.22 (2H, m), 6.86-6.83 (1H, m), 6.78-6.76 (3H, m), 3.51-3.33 (2H, m), 2.78-2.65 (4H, m), 0.98 (3H, t, J = 7.2 Hz). |
| 357 | ¹H-NMR (CDCl₃) δ: 7.27-7.21 (2H, m), 6.86 (1H, t, J = 8.6 Hz), 6.80-6.73 (3H, m), 2.89 (3H, s), 2.87-2.82 (2H, m), 2.73-2.70 (1H, m), 2.61-2.55 (1H, m). |
| 358 | ¹H-NMR (CDCl₃) δ: 7.33 (1H, tt, J = 8.4, 6.7 Hz), 7.30 (1H, dd, J = 9.5 Hz), 7.25 (1H, dd, J = 8.6, 4.9 Hz), 6.92 (1H, t, J = 8.4 Hz), 6.86-6.79 (3H, m), 6.74 (1H, d, J = 9.5 Hz), 3.93-3.88 (2H, m), 1.16 (3H, t, J = 7.0 Hz). |
| 359 | ¹H-NMR (CDCl₃) δ: 7.34 (1H, tt, J = 8.6, 6.7 Hz), 7.33 (1H, d, J = 9.5 Hz), 7.26 (1H, dd, J = 8.9, 5.2 Hz), 6.92 (1H, t, J = 8.6 Hz), 6.87-6.83 (2H, m), 6.79-6.77 (1H, m), 6.75 (1H, d, J = 9.5 Hz), 3.38 (3H, s). |
| 360 | ¹H-NMR (CDCl₃) δ: 7.54 (1H, s), 7.35 (1H, tt, J = 8.6, 6.7 Hz), 7.26 (1H, dd, J = 8.4, 5.5 Hz), 6.93 (1H, t, J = 8.6 Hz), 6.88-6.80 (3H, m), 3.95 (2H, q, J = 7.0 Hz), 1.18 (3H, t, J = 7.0 Hz). |
| 361 | ¹H-NMR (CDCl₃) δ: 7.74 (1H, s), 7.35 (1H, tt, J = 8.5, 6.7 Hz), 7.26 (1H, dd, J = 8.9, 4.9 Hz), 6.95-6.90 (1H, m), 6.88-6.80 (3H, m), 3.95 (2H, q, J = 7.2 Hz), 1.18 (3H, t, J = 7.2 Hz). |
| 362 | ¹H-NMR (CDCl₃) δ: 7.56 (1H, s), 7.36 (1H, tt, J = 8.4, 6.7 Hz), 7.27 (1H, dd, J = 9.3, 4.7 Hz), 6.92-6.87 (3H, m), 6.81-6.79 (1H, m), 3.45 (3H, s). |
| 363 | ¹H-NMR (CDCl₃) δ: 7.76 (1H, s), 7.35 (1H, tt, J = 8.9, 6.7 Hz), 7.26 (1H, dd, J = 8.6, 5.2 Hz), 6.94-6.84 (3H, m), 6.79 (1H, ddd, J = 8.6, 3.1, 1.5 Hz), 3.45 (3H, s). |
| 364 | ¹H-NMR (CDCl₃) δ: 7.35-7.26 (3H, m), 7.00-6.95 (2H, m), 6.89 (1H, tt, J = 8.5, 1.1 Hz), 6.84 (1H, tt, J = 8.4, 1.1 Hz), 6.76 (1H, d, J = 9.5 Hz), 3.38 (3H, s). |
| 365 | ¹H-NMR (CDCl₃) δ: 7.56 (1H, s), 7.36-7.30 (2H, m), 7.01-6.95 (2H, m), 6.92-6.83 (2H, m), 3.45 (3H, s). |
| 366 | ¹H-NMR (CDCl₃) δ: 7.38-7.29 (3H, m), 6.99 (2H, dd, J = 4.3, 1.2 Hz), 6.91-6.83 (2H, m), 6.77 (1H, d, J = 9.5 Hz), 6.17 (1H, tt, J = 56.6, 4.5 Hz), 4.21-4.11 (2H, m). |
| 367 | ¹H-NMR (CDCl₃) δ: 7.60 (1H, s), 7.39-7.31 (2H, m), 7.03-6.99 (2H, m), 6.91-6.85 (2H, m), 6.19 (1H, tt, J = 56.4, 4.5 Hz), 4.21 (2H, td, J = 12.8, 4.4 Hz). |
| 368 | ¹H-NMR (CDCl₃) δ: 7.41 (1H, tt, J = 8.5, 3.6 Hz), 7.24 (1H, d, J = 9.5 Hz), 6.94 (2H, dd, J = 8.5, 7.3 Hz), 6.77 (1H, d, J = 9.5 Hz), 3.95 (2H, q, J = 7.2 Hz), 1.14 (3H, t, J = 7.2 Hz). |
| 369 | ¹H-NMR (CDCl₃) δ: 7.31-7.28 (1H, m), 7.19 (1H, s), 7.17 (1H, d, J = 8.9 Hz), 6.88 (1H, t, J = 8.4 Hz), 6.82 (1H, t, J = 8.4 Hz), 6.66 (1H, dd, J = 8.9, 3.1 Hz), 6.63 (1H, dd, J = 3.1, 1.2 Hz), 3.93-3.90 (2H, m), 3.65 (3H, s), 2.68 (2H, q, J = 7.4 Hz), 1.25 (3H, t, J = 7.4 Hz), 1.16 (3H, t, J = 7.0 Hz). |
| 370 | ¹H-NMR (CDCl₃) δ: 7.31-7.28 (1H, m), 7.18 (1H, s), 7.17 (1H, d, J = 8.6 Hz), 6.88 (1H, t, J = 8.6 Hz), 6.81 (1H, t, J = 8.6 Hz), 6.65 (1H, dd, J = 8.6, 3.1 Hz), 6.62 (1H, dd, J = 3.1, 1.2 Hz), 3.93-3.88 (2H, m), 3.64 (3H, s), 2.65-2.59 (2H, m), 1.71-1.68 (2H, m), 1.15 (3H, t, J = 7.0 Hz), 1.02 (3H, t, J = 7.5 Hz). |
| 371 | ¹H-NMR (CDCl₃) δ: 7.30-7.27 (1H, m), 7.18 (1H, dd, J = 8.1, 1.1 Hz), 6.88 (1H, t, J = 8.4 Hz), 6.81 (1H, t, J = 8.4 Hz), 6.68-6.63 (3H, m), 3.95-3.91 (2H, m), 3.87 (3H, s), 3.65 (3H, s), 1.16 (3H, t, J = 7.2 Hz). |
| 372 | ¹H-NMR (CDCl₃) δ: 7.49 (1H, s), 7.43 (1H, tt, J = 8.4, 3.5 Hz), 6.95 (2H, dd, J = 8.5, 7.3 Hz), 4.00 (2H, q, J = 7.1 Hz), 1.17 (3H, t, J = 7.2 Hz). |
| 373 | ¹H-NMR (CDCl₃) δ: 7.42 (1H, tt, J = 8.5, 3.6 Hz), 7.27 (1H, d, J = 9.5 Hz), 6.94 (2H, dd, J = 8.4, 7.5 Hz), 6.79 (1H, d, J = 9.5 Hz), 3.42 (3H, s). |
| 374 | ¹H-NMR (CDCl₃) δ: 7.51 (1H, s), 7.44 (1H, tt, J = 8.6, 3.5 Hz), 6.95 (2H, t, J = 8.0 Hz), 3.48 (3H, s). |
| 375 | ¹H-NMR (CDCl₃) δ: 7.31-7.29 (1H, m), 7.18 (1H, d, J = 8.6 Hz), 6.96 (1H, s), 6.88 (1H, t, J = 8.4 Hz), 6.82 (1H, t, J = 8.4 Hz), 6.67 (1H, dd, J = 8.6, 3.1 Hz), 6.65 (1H, dd, J = 2.9, 1.4 Hz), 3.95-3.90 (2H, m), 3.65 (3H, s), 2.38 (3H, s), 1.17 (3H, t, J = 7.0 Hz). |
| 376 | ¹H-NMR (CDCl₃) δ: 7.56 (1H, s), 7.34-7.31 (1H, m), 7.16 (1H, d, J = 8.6 Hz), 6.89 (1H, t, J = 8.6 Hz), 6.85 (1H, t, J = 8.6 Hz), 6.67 (1H, dd, J = 8.6, 3.1 Hz), 6.60 (1H, dd, J = 3.1, 1.5 Hz), 3.96-3.91 (3H, m), 3.79-3.77 (1H, m), 1.33 (3H, t, J = 6.9 Hz), 1.18 (3H, t, J = 7.2 Hz). |
| 377 | ¹H-NMR (CDCl₃) δ: 7.34 (1H, d, J = 9.5 Hz), 6.78 (1H, d, J = 9.5 Hz), 6.65-6.62 (2H, m), 6.39 (1H, d, J = 2.7 Hz), 6.23 (1H, br s), 4.66 (1H, br s), 4.53 (1H, br s), 3.83 (3H, s), 3.68 (3H, s). |
| 378 | ¹H-NMR (CDCl₃) δ: 7.30 (1H, d, J = 9.5 Hz), 6.70 (1H, d, J = 9.5 Hz), 6.40 (1H, dt, J = 10.8, 1.9 Hz), 6.35 (1H, d, J = 2.8 Hz), 6.33 (1H, dd, J = 10.8, 1.9 Hz), 6.24 (1H, dd, J = 2.8, 1.5 Hz), 3.96-3.95 (3H, m), 3.85 (1H, dd, J = 13.8, 7.0 Hz), 3.82 (3H, s), 3.65 (3H, s), 1.40 (3H, t, J = 7.0 Hz), 1.16 (3H, t, J = 7.0 Hz). |
| 379 | ¹H-NMR (CDCl₃) δ: 7.34 (1H, d, J = 9.5 Hz), 7.26 (1H, dd, J = 80.2, 11.0 Hz), 6.75 (1H, d, J = 9.5 Hz), 6.64-6.61 (2H, m), 6.41 (1H, t, J = 11.0 Hz), 6.39 (1H, d, J = 2.8 Hz), 6.19 (1H, dd, J = 2.8, 1.5 Hz), 3.83 (3H, s), 3.67 (3H, s). |
| 380 | ¹H-NMR (CDCl₃) δ: 7.38 (1H, d, J = 9.5 Hz), 6.75 (1H, d, J = 9.5 Hz), 6.57-6.55 (2H, m), 6.45 (1H, dd, J = 76.3, 3.7 Hz), 6.40 (1H, d, J = 2.8 Hz), 6.24-6.23 (1H, m), 6.01 (1H, dd, J = 30.2, 3.7 Hz), 3.83 (3H, s), 3.67 (3H, s). |
| 381 | ¹H-NMR (CDCl₃) δ: 7.73 (1H, s), 7.29 (1H, dd, J = 8.9, 5.2 Hz), 6.92-6.90 (1H, m), 6.82-6.80 (1H, m), 6.70 (1H, tt, J = 8.7, 2.0 Hz), 6.64 (1H, tt, J = 8.7, 2.0 Hz), 3.98-3.90 (2H, m), 1.18 (3H, t, J = 7.2 Hz). |

TABLE 5-continued

| Compound | ¹H-NMR |
|---|---|
| 382 | ¹H-NMR (CDCl₃) δ: 7.28-7.26 (2H, m), 6.89-6.83 (1H, m), 6.83-6.78 (1H, m), 6.72 (1H, d, J = 9.5 Hz), 6.45 (1H, dt, J = 10.5, 2.0 Hz), 6.36 (1H, dt, J = 10.5, 2.0 Hz), 3.93-3.88 (2H, m), 3.77 (3H, s), 1.16 (3H, t, J = 7.0 Hz). |
| 383 | ¹H-NMR (CDCl₃) δ: 7.44 (1H, tt, J = 8.6, 3.5 Hz), 7.32 (1H, d, J = 9.5 Hz), 6.94 (2H, dd, J = 8.6, 7.6 Hz), 6.81 (1H, d, J = 9.5 Hz), 6.12 (1H, tt, J = 56.6, 4.5 Hz), 4.22 (2H, td, J = 12.8, 4.5 Hz). |
| 384 | ¹H-NMR (CDCl₃) δ: 7.56 (1H, s), 7.47 (1H, tt, J = 8.4, 3.5 Hz), 6.96 (2H, dd, J = 8.6, 7.6 Hz), 6.14 (1H, tt, J = 56.4, 4.5 Hz), 4.27 (2H, td, J = 12.6, 4.5 Hz). |
| 385 | ¹H-NMR (CDCl₃) δ: 7.32-7.26 (2H, m), 7.13-7.07 (2H, m), 6.89 (1H, t, J = 8.4 Hz), 6.82-6.78 (2H, m), 6.76 (1H, d, J = 9.5 Hz), 4.10-4.03 (1H, m), 3.88-3.81 (1H, m), 1.15 (3H, t, J = 7.0 Hz). |
| 386 | ¹H-NMR (CDCl₃) δ: 7.52 (1H, s), 7.29-7.28 (1H, m), 6.89-6.87 (1H, m), 6.83-6.81 (1H, m), 6.45 (1H, dt, J = 10.8, 1.8 Hz), 6.37 (1H, dt, J = 10.8, 1.8 Hz), 3.96 (2H, q, J = 7.2 Hz), 3.77 (3H, s), 1.18 (3H, t, J = 7.2 Hz). |
| 387 | ¹H-NMR (CDCl₃) δ: 8.20 (1H, s), 7.39-7.36 (1H, m), 7.18 (1H, d, J = 8.9 Hz), 6.94-6.87 (2H, m), 6.70 (1H, dd, J = 8.9, 3.1 Hz), 6.61 (1H, dd, J = 2.9, 1.7 Hz), 3.99 (2H, dt, J = 21.7, 7.0 Hz), 3.67 (3H, s), 3.42 (3H, s), 1.21 (3H, t, J = 7.2 Hz). |
| 388 | ¹H-NMR (CDCl₃) δ: 7.29-7.26 (1H, m), 7.22 (1H, dd, J = 8.6, 5.2 Hz), 6.86 (1H, t, J = 8.6 Hz), 6.82-6.76 (3H, m), 5.92 (1H, tt, J = 56.4, 4.5 Hz), 3.74-3.63 (2H, m), 2.95-2.89 (1H, m), 2.85-2.82 (1H, m), 2.77-2.74 (1H, m), 2.67-2.61 (1H, m). |
| 389 | ¹H-NMR (CDCl₃) δ: 7.21 (1H, tt, J = 8.5, 6.4 Hz), 7.14 (1H, d, J = 8.9 Hz), 6.82 (1H, t, J = 8.5 Hz), 6.74 (1H, t, J = 8.5 Hz), 6.60 (1H, dd, J = 8.9, 3.1 Hz), 6.54 (1H, dd, J = 3.1, 1.2 Hz), 3.62 (3H, s), 3.47-3.43 (1H, m), 3.21-3.17 (1H, m), 2.87-2.83 (2H, m), 2.73-2.69 (1H, m), 2.60-2.52 (1H, m), 1.45-1.38 (2H, m), 0.74 (3H, t, J = 7.5 Hz). |
| 390 | ¹H-NMR (CDCl₃) δ: 7.21 (1H, tt, J = 8.5, 6.4 Hz), 7.14 (1H, d, J = 8.5 Hz), 6.82 (1H, t, J = 8.5 Hz), 6.74 (1H, t, J = 8.5 Hz), 6.60 (1H, dd, J = 8.5, 3.1 Hz), 6.55 (1H, dd, J = 3.1, 1.2 Hz), 3.62 (3H, s), 3.50-3.43 (1H, m), 3.27-3.20 (1H, m), 2.90-2.51 (4H, m), 1.43-1.32 (2H, m), 1.14 (2H, td, J = 14.8, 7.3 Hz), 0.74 (3H, t, J = 7.3 Hz). |
| 391 | ¹H-NMR (CDCl₃) δ: 7.40-7.32 (2H, m), 7.28-7.24 (1H, m), 6.93-6.91 (1H, m), 6.89-6.80 (3H, m), 6.76 (1H, d, J = 9.5 Hz), 6.16 (1H, tt, J = 56.6, 4.5 Hz), 4.17 (2H, td, J = 13.0, 4.5 Hz). |
| 392 | ¹H-NMR (CDCl₃) δ: 7.60 (1H, s), 7.38 (1H, tt, J = 8.5, 6.4 Hz), 7.27 (1H, dd, J = 9.3, 4.7 Hz), 6.94-6.81 (4H, m), 6.18 (1H, tt, J = 56.5, 4.5 Hz), 4.26-4.17 (2H, m). |
| 393 | ¹H-NMR (CDCl₃) δ: 7.80 (1H, s), 7.38 (1H, tt, J = 8.5, 6.4 Hz), 7.27 (1H, dd, J = 9.3, 4.9 Hz), 6.94-6.81 (4H, m), 6.18 (1H, tt, J = 56.5, 4.5 Hz), 4.26-4.16 (2H, m). |
| 394 | ¹H-NMR (CDCl₃) δ: 7.33-7.30 (2H, m), 7.17 (1H, d, J = 8.5 Hz), 6.89 (1H, t, J = 8.5 Hz), 6.82 (1H, t, J = 8.5 Hz), 6.72 (1H, d, J = 9.5 Hz), 6.66 (1H, dd, J = 8.5, 3.1 Hz), 6.60 (1H, dd, J = 3.1, 1.4 Hz), 3.85-3.75 (2H, m), 3.64 (3H, s), 1.59-1.49 (2H, m), 1.18-1.15 (2H, m), 0.72 (3H, t, J = 7.5 Hz). |
| 395 | ¹H-NMR (CDCl₃) δ: 7.56 (1H, s), 7.32 (1H, tt, J = 8.4, 6.4 Hz), 7.17 (1H, d, J = 8.9 Hz), 6.89 (1H, t, J = 8.4 Hz), 6.84 (1H, t, J = 8.4 Hz), 6.68 (1H, dd, J = 8.9, 3.1 Hz), 6.61 (1H, dd, J = 3.1, 1.5 Hz), 3.88-3.84 (2H, m), 3.65 (3H, s), 1.59-1.52 (2H, m), 1.19-1.15 (2H, m), 0.73 (3H, t, J = 7.3 Hz). |
| 396 | ¹H-NMR (CDCl₃) δ: 7.76 (1H, s), 7.32 (1H, tt, J = 8.5, 6.4 Hz), 7.17 (1H, d, J = 8.9 Hz), 6.89 (1H, t, J = 8.5 Hz), 6.84 (1H, t, J = 8.5 Hz), 6.68 (1H, dd, J = 8.9, 3.1 Hz), 6.61 (1H, dd, J = 3.1, 1.5 Hz), 3.89-3.85 (2H, m), 3.65 (3H, s), 1.58-1.55 (2H, m), 1.20-1.12 (2H, m), 0.73 (3H, t, J = 7.3 Hz). |
| 397 | ¹H-NMR (CDCl₃) δ: 7.52 (1H, s), 7.32 (1H, tt, J = 8.4, 3.6 Hz), 7.15-7.10 (2H, m), 6.90 (1H, t, J = 8.4 Hz), 6.83-6.78 (2H, m), 4.14-4.07 (1H, m), 3.95-3.87 (1H, m), 1.18 (3H, t, J = 7.2 Hz). |
| 398 | ¹H-NMR (CDCl₃) δ: 7.34-7.28 (2H, m), 7.15-7.10 (2H, m), 6.89 (1H, tt, J = 8.6, 1.0 Hz), 6.83-6.79 (2H, m), 6.77 (1H, d, J = 9.2 Hz), 3.42 (3H, s). |
| 399 | ¹H-NMR (CDCl₃) δ: 7.35-7.29 (2H, m), 7.17 (1H, d, J = 8.9 Hz), 6.89 (1H, t, J = 8.5 Hz), 6.82 (1H, t, J = 8.5 Hz), 6.72 (1H, d, J = 9.2 Hz), 6.66 (1H, dd, J = 8.9, 3.1 Hz), 6.60 (1H, dd, J = 3.1, 1.5 Hz), 3.86-3.82 (1H, m), 3.77-3.70 (1H, m), 3.64 (3H, s), 1.62-1.53 (2H, m), 0.75 (3H, t, J = 7.5 Hz). |
| 400 | ¹H-NMR (CDCl₃) δ: 7.56 (1H, s), 7.36-7.30 (1H, m), 7.17 (1H, d, J = 8.9 Hz), 6.89 (1H, t, J = 8.4 Hz), 6.84 (1H, t, J = 8.4 Hz), 6.68 (1H, dd, J = 8.9, 3.1 Hz), 6.60 (1H, dd, J = 3.1, 1.4 Hz), 3.87-3.79 (2H, m), 3.65 (3H, s), 1.62-1.58 (2H, m), 0.76 (3H, t, J = 7.3 Hz). |
| 401 | ¹H-NMR (CDCl₃) δ: 7.76 (1H, s), 7.33 (1H, tt, J = 8.5, 6.4 Hz), 7.17 (1H, d, J = 8.9 Hz), 6.89 (1H, t, J = 8.5 Hz), 6.84 (1H, t, J = 8.5 Hz), 6.68 (1H, dd, J = 8.5, 3.1 Hz), 6.60 (1H, dd, J = 3.1, 1.5 Hz), 3.83 (2H, q, J = 7.6 Hz), 3.65 (3H, s), 1.63-1.56 (2H, m), 0.76 (3H, t, J = 7.3 Hz). |
| 402 | ¹H-NMR (CDCl₃) δ: 7.36 (1H, d, J = 9.5 Hz), 7.30-7.27 (1H, m), 7.19 (1H, d, J = 8.9 Hz), 6.86 (1H, t, J = 8.4 Hz), 6.78 (1H, t, J = 8.4 Hz), 6.73 (1H, d, J = 9.5 Hz), 6.68 (1H, dd, J = 8.9, 3.1 Hz), 6.63 (1H, dd, J = 3.1, 0.9 Hz), 5.30-5.29 (2H, m), 3.65 (3H, s), 3.33 (3H, s). |
| 403 | ¹H-NMR (CDCl₃) δ: 7.31 (1H, d, J = 9.5 Hz), 7.20 (1H, d, J = 8.9 Hz), 6.75-6.60 (5H, m), 3.90 (2H, q, J = 7.2 Hz), 3.68 (3H, s), 1.16 (3H, t, J = 7.2 Hz). |
| 404 | ¹H-NMR (CDCl₃) δ: 7.55 (1H, s), 7.20 (1H, d, J = 8.9 Hz), 6.72 (1H, dd, J = 8.9, 3.1 Hz), 6.69-6.60 (3H, m), 3.97-3.92 (2H, m), 3.68 (3H, s), 1.19 (3H, t, J = 7.0 Hz). |
| 405 | ¹H-NMR (CDCl₃) δ: 7.54 (1H, s), 7.36-7.29 (1H, m), 7.16-7.14 (2H, m), 6.91-6.88 (1H, m), 6.85-6.80 (2H, m), 3.49 (3H, s). |
| 406 | ¹H-NMR (CDCl₃) δ: 7.37-7.30 (2H, m), 7.16-7.11 (2H, m), 6.91-6.87 (1H, m), 6.84-6.77 (3H, m), 6.14 (1H, tdd, J = 56.6, 4.9, 3.9 Hz), 4.42-4.33 (1H, m), 4.13-4.05 (1H, m). |
| 407 | ¹H-NMR (CDCl₃) δ: 7.59 (1H, s), 7.35 (1H, tt, J = 8.5, 3.7 Hz), 7.17-7.14 (2H, m), 6.90 (1H, t, J = 8.2 Hz), 6.85-6.81 (2H, m), 6.16 (1H, tt, J = 56.9, 4.4 Hz), 4.43-4.37 (1H, m), 4.20-4.10 (1H, m). |
| 408 | ¹H-NMR (CDCl₃) δ: 7.35 (1H, tt, J = 8.4, 3.5 Hz), 7.30 (1H, dd, J = 9.5, 0.9 Hz), 6.97-6.94 (3H, m), 6.88 (2H, dd, J = 8.6, 7.3 Hz), 6.73 (1H, d, J = 9.2 Hz), 3.91 (2H, q, J = 7.0 Hz), 1.14 (3H, t, J = 6.9 Hz). |

TABLE 5-continued

| Compound | ¹H-NMR |
|---|---|
| 409 | ¹H-NMR (CDCl₃) δ: 7.37 (1H, d, J = 9.5 Hz), 7.35-7.33 (1H, m), 7.17 (1H, d, J = 8.9 Hz), 6.88 (1H, t, J = 8.6 Hz), 6.84 (1H, t, J = 8.6 Hz), 6.78 (1H, d, J = 9.5 Hz), 6.69 (1H, dd, J = 8.9, 3.1 Hz), 6.62-6.60 (1H, m), 4.63 (2H, s), 3.66 (3H, s). |
| 410 | ¹H-NMR (CDCl₃) δ: 7.60 (1H, s), 7.36 (1H, tt, J = 8.6, 6.4 Hz), 7.17 (1H, d, J = 8.9 Hz), 6.91-6.84 (2H, m), 6.71 (1H, dd, J = 8.9, 3.1 Hz), 6.63-6.61 (1H, m), 4.73 (1H, s), 4.61 (1H, s), 3.66 (3H, s). |
| 411 | ¹H-NMR (CDCl₃) δ: 7.81 (1H, s), 7.36 (1H, tt, J = 8.6, 6.4 Hz), 7.17 (1H, d, J = 8.9 Hz), 6.88-6.86 (2H, m), 6.70 (1H, dd, J = 8.9, 3.1 Hz), 6.63-6.61 (1H, m), 4.73 (1H, s), 4.61 (1H, s), 3.66 (3H, s). |
| 412 | ¹H-NMR (CDCl₃) δ: 7.29-7.27 (2H, m), 7.15 (1H, d, J = 8.9 Hz), 6.87 (1H, t, J = 8.6 Hz), 6.81 (1H, t, J = 8.6 Hz), 6.65-6.63 (2H, m), 6.61 (1H, dd, J = 3.1, 1.7 Hz), 4.13-3.95 (1H, m), 3.65 (3H, s), 1.60-1.59 (6H, m). |
| 413 | ¹H-NMR (CDCl₃) δ: 7.52 (1H, s), 7.32-7.29 (1H, m), 7.16 (1H, d, J = 8.9 Hz), 6.87 (1H, t, J = 8.5 Hz), 6.82 (1H, t, J = 8.5 Hz), 6.66 (1H, dd, J = 8.9, 3.1 Hz), 6.61 (1H, dd, J = 3.1, 1.8 Hz), 4.09-4.06 (1H, m), 3.65 (3H, s), 1.61-1.59 (6H, m). |
| 414 | ¹H-NMR (CDCl₃) δ: 7.59 (1H, s), 7.30-7.28 (1H, m), 7.19 (1H, d, J = 8.9 Hz), 6.86 (1H, t, J = 8.4 Hz), 6.79 (1H, t, J = 8.4 Hz), 6.69 (1H, dd, J = 8.9, 3.1 Hz), 6.64 (1H, dd, J = 3.1, 1.2 Hz), 5.38 (1H, d, J = 10.4 Hz), 5.32 (1H, d, J = 10.4 Hz), 3.65 (3H, s), 3.36 (3H, s). |
| 415 | ¹H-NMR (CDCl₃) δ: 7.34 (1H, d, J = 9.5 Hz), 7.20 (1H, d, J = 8.9 Hz), 6.75 (1H, d, J = 9.5 Hz), 6.71 (1H, dd, J = 8.9, 3.1 Hz), 6.67-6.62 (2H, m), 6.58 (1H, dd, J = 2.9, 1.7 Hz), 3.68 (3H, s), 3.38 (3H, s). |
| 416 | ¹H-NMR (CDCl₃) δ: 7.57 (1H, s), 7.20 (1H, d, J = 8.9 Hz), 6.73 (1H, dd, J = 8.9, 3.1 Hz), 6.70-6.61 (2H, m), 6.59 (1H, dd, J = 3.1, 1.5 Hz), 3.68 (3H, s), 3.45 (3H, s). |
| 417 | ¹H-NMR (CDCl₃) δ: 7.54 (1H, s), 7.37 (1H, tt, J = 8.6, 3.6 Hz), 6.99-6.94 (3H, m), 6.89 (2H, dd, J = 8.6, 7.3 Hz), 3.97 (2H, q, J = 7.1 Hz), 1.16 (3H, t, J = 7.0 Hz). |
| 418 | ¹H-NMR (CDCl₃) δ: 7.39-7.32 (2H, m), 6.98-6.95 (3H, m), 6.88 (2H, dd, J = 8.5, 7.3 Hz), 6.75 (1H, d, J = 9.5 Hz), 3.39 (3H, s). |
| 419 | ¹H-NMR (CDCl₃) δ: 7.57 (1H, d, J = 0.6 Hz), 7.38 (1H, tt, J = 8.6, 3.5 Hz), 6.99-6.96 (3H, m), 6.89 (2H, dd, J = 8.4, 7.5 Hz), 3.46 (3H, s). |
| 420 | ¹H-NMR (CDCl₃) δ: 7.33-7.30 (2H, m), 7.16-7.14 (1H, m), 7.09-7.02 (2H, m), 6.74 (1H, d, J = 9.5 Hz), 6.65 (1H, tt, J = 8.9, 2.1 Hz), 6.58 (1H, tt, J = 8.9, 2.1 Hz), 3.93-3.87 (2H, m), 1.16 (3H, t, J = 7.0 Hz). |
| 421 | ¹H-NMR (CDCl₃) δ: 7.56 (1H, s), 7.33-7.32 (1H, m), 7.18-7.16 (1H, m), 7.10-7.04 (2H, m), 6.67-6.63 (1H, m), 6.61-6.59 (1H, m), 3.95 (2H, q, J = 7.1 Hz), 1.19 (3H, t, J = 7.1 Hz). |
| 422 | ¹H-NMR (CDCl₃) δ: 7.41 (1H, d, J = 9.5 Hz), 7.31 (1H, tt, J = 8.6, 6.4 Hz), 7.20 (1H, d, J = 8.9 Hz), 6.88 (1H, t, J = 8.6 Hz), 6.83-6.82 (2H, m), 6.70 (1H, dd, J = 8.9, 3.1 Hz), 6.59 (1H, dd, J = 3.1, 1.2 Hz), 5.10 (2H, s), 3.64 (3H, s). |
| 423 | ¹H-NMR (CDCl₃) δ: 7.62 (1H, s), 7.32 (1H, tt, J = 8.5, 6.4 Hz), 7.20 (1H, d, J = 8.9 Hz), 6.87-6.83 (2H, m), 6.72 (1H, dd, J = 8.9, 3.1 Hz), 6.60 (1H, dd, J = 3.1, 1.2 Hz), 5.16 (2H, s), 3.65 (3H, s). |
| 424 | ¹H-NMR (CDCl₃) δ: 7.32 (1H, dd, J = 9.5, 0.6 Hz), 6.91-6.88 (2H, m), 6.77-6.74 (2H, m), 6.70-6.64 (2H, m), 3.91 (2H, q, J = 7.1 Hz), 1.15 (3H, t, J = 7.1 Hz). |
| 425 | ¹H-NMR (CDCl₃) δ: 7.56 (1H, d, J = 0.9 Hz), 6.93-6.90 (2H, m), 6.78-6.76 (1H, m), 6.70-6.65 (2H, m), 3.96 (2H, q, J = 7.1 Hz), 1.17 (3H, t, J = 7.1 Hz). |
| 426 | ¹H-NMR (CDCl₃) δ: 7.35 (1H, dd, J = 9.5, 0.9 Hz), 6.91-6.89 (2H, m), 6.78-6.76 (2H, m), 6.69-6.66 (2H, m), 3.39 (3H, s). |
| 427 | ¹H-NMR (CDCl₃) δ: 7.58 (1H, s), 6.94-6.90 (2H, m), 6.79-6.77 (1H, m), 6.70-6.66 (2H, m), 3.46 (3H, s). |
| 428 | ¹H-NMR (CDCl₃) δ: 7.41-7.37 (2H, m), 6.98-6.96 (3H, m), 6.88 (2H, dd, J = 8.4, 7.5 Hz), 6.77 (1H, d, J = 9.5 Hz), 6.14 (1H, tt, J = 56.6, 4.5 Hz), 4.19 (2H, td, J = 12.8, 4.5 Hz). |
| 429 | ¹H-NMR (CDCl₃) δ: 7.61 (1H, s), 7.40 (1H, tt, J = 8.5, 3.5 Hz), 7.01-6.96 (3H, m), 6.89 (2H, t, J = 7.9 Hz), 6.16 (1H, tt, J = 56.6, 4.4 Hz), 4.23 (2H, td, J = 12.7, 4.4 Hz). |
| 430 | ¹H-NMR (CDCl₃) δ: 7.32-7.29 (2H, m), 7.14-7.12 (1H, m), 7.06-7.05 (2H, m), 6.72 (1H, d, J = 9.2 Hz), 6.42-6.39 (1H, m), 6.34-6.32 (1H, m), 3.98-3.95 (1H, m), 3.89-3.87 (1H, m), 3.75 (3H, s), 1.16 (3H, t, J = 7.0 Hz). |
| 431 | ¹H-NMR (CDCl₃) δ: 7.35 (1H, d, J = 9.5 Hz), 7.33-7.32 (1H, m), 7.16 (1H, td, J = 7.6, 1.8 Hz), 7.08 (1H, td, J = 7.6, 1.2 Hz), 7.03-7.02 (1H, m), 6.76 (1H, d, J = 9.5 Hz), 6.67-6.63 (1H, m), 6.61-6.57 (1H, m), 3.39 (3H, s). |
| 432 | ¹H-NMR (CDCl₃) δ: 7.58 (1H, s), 7.34-7.32 (1H, m), 7.18 (1H, td, J = 7.6, 1.8 Hz), 7.10 (1H, td, J = 7.6, 1.2 Hz), 7.05-7.03 (1H, m), 6.68-6.58 (2H, m), 3.45 (3H, s). |
| 433 | ¹H-NMR (CDCl₃) δ: 7.35-7.31 (2H, m), 7.16-7.13 (1H, m), 7.08-7.02 (2H, m), 6.73 (1H, d, J = 9.2 Hz), 6.42-6.40 (1H, m), 6.35-6.32 (1H, m), 3.75 (3H, s), 3.39 (3H, s). |
| 434 | ¹H-NMR (CDCl₃) δ: 7.55 (1H, s), 7.33-7.31 (1H, m), 7.16-7.14 (1H, m), 7.07-7.06 (2H, m), 6.41-6.39 (1H, m), 6.35-6.32 (1H, m), 3.98-3.96 (2H, m), 3.75 (3H, s), 1.18 (3H, t, J = 7.0 Hz). |
| 435 | ¹H-NMR (CDCl₃) δ: 7.57 (1H, s), 7.33-7.31 (1H, m), 7.18-7.14 (1H, m), 7.09-7.07 (1H, m), 7.05-7.04 (1H, m), 6.42-6.39 (1H, m), 6.36-6.33 (1H, m), 3.75 (3H, s), 3.46 (3H, s). |
| 436 | ¹H-NMR (CDCl₃) δ: 7.29 (1H, tt, J = 8.6, 6.4 Hz), 6.86-6.82 (2H, m), 6.70-6.68 (1H, m), 6.43-6.41 (1H, m), 3.43 (2H, q, J = 7.1 Hz), 2.77-2.69 (4H, m), 0.97 (3H, t, J = 7.1 Hz). |
| 437 | ¹H-NMR (CDCl₃) δ: 7.30 (1H, tt, J = 8.6, 6.4 Hz), 6.86-6.83 (2H, m), 6.72-6.67 (1H, m), 6.43-6.41 (1H, m), 2.89 (3H, s), 2.78-2.71 (4H, m) |
| 438 | ¹H-NMR (CDCl₃) δ: 7.38 (1H, tt, J = 8.6, 6.4 Hz), 7.31 (1H, dd, J = 9.5, 0.9 Hz), 6.92-6.91 (2H, m), 6.79-6.72 (2H, m), 6.58-6.55 (1H, m), 3.92 (2H, q, J = 7.0 Hz), 1.14 (3H, t, J = 7.0 Hz). |
| 439 | ¹H-NMR (CDCl₃) δ: 7.39 (1H, tt, J = 8.4, 6.4 Hz), 7.34 (1H, dd, J = 9.5, 0.9 Hz), 6.93-6.91 (2H, m), 6.80-6.75 (2H, m), 6.57-6.55 (1H, m), 3.40 (3H, s). |
| 440 | ¹H-NMR (CDCl₃) δ: 7.55 (1H, s), 7.40 (1H, tt, J = 8.4, 6.4 Hz), 6.94-6.92 (2H, m), 6.82-6.75 (1H, m), 6.59-6.56 (1H, m), 3.97 (2H, q, J = 7.0 Hz), 1.17 (3H, t, J = 7.0 Hz). |

TABLE 5-continued

| Compound | ¹H-NMR |
|---|---|
| 441 | ¹H-NMR (CDCl₃) δ: 7.76 (1H, s), 7.40 (1H, tt, J = 8.4, 6.4 Hz), 6.93-6.91 (2H, m), 6.82-6.75 (1H, m), 6.59-6.56 (1H, m), 3.97 (2H, q, J = 7.1 Hz), 1.17 (3H, t, J = 7.1 Hz). |
| 442 | ¹H-NMR (CDCl₃) δ: 7.57 (1H, s), 7.41 (1H, tt, J = 8.4, 6.4 Hz), 6.94-6.92 (2H, m), 6.84-6.77 (1H, m), 6.59-6.56 (1H, m), 3.46 (3H, s). |
| 443 | ¹H-NMR (CDCl₃) δ: 7.78 (1H, s), 7.41 (1H, tt, J = 8.6, 6.4 Hz), 6.94-6.92 (2H, m), 6.83-6.77 (1H, m), 6.59-6.57 (1H, m), 3.46 (3H, s). |
| 444 | ¹H-NMR (CDCl₃) δ: 7.37-7.29 (2H, m), 7.23 (1H, d, J = 8.2 Hz), 7.10-7.06 (2H, m), 6.94 (1H, t, J = 8.4 Hz), 6.83 (1H, t, J = 8.4 Hz), 6.74 (1H, d, J = 9.5 Hz), 3.98-3.93 (2H, m), 1.16 (3H, t, J = 7.3 Hz). |
| 445 | ¹H-NMR (CDCl₃) δ: 7.54 (1H, s), 7.35 (1H, tt, J = 8.6, 3.5 Hz), 7.23 (1H, d, J = 8.6 Hz), 7.11 (1H, dd, J = 8.6, 2.4 Hz), 7.08-7.06 (1H, m), 6.95 (1H, t, J = 8.4 Hz), 6.85 (1H, t, J = 8.4 Hz), 3.96 (2H, q, J = 7.1 Hz), 1.18 (3H, t, J = 7.1 Hz). |
| 446 | ¹H-NMR (CDCl₃) δ: 7.37-7.31 (2H, m), 7.23 (1H, d, J = 8.6 Hz), 7.10 (1H, dd, J = 8.6, 2.4 Hz), 7.05-7.03 (1H, m), 6.94 (1H, t, J = 8.4 Hz), 6.85 (1H, t, J = 8.4 Hz), 6.76 (1H, d, J = 9.2 Hz), 3.39 (3H, s). |
| 447 | ¹H-NMR (CDCl₃) δ: 7.55 (1H, s), 7.36 (1H, tt, J = 8.4, 3.5 Hz), 7.24 (1H, d, J = 8.6 Hz), 7.13 (1H, dd, J = 8.6, 2.8 Hz), 7.06-7.04 (1H, m), 6.94 (1H, t, J = 8.6 Hz), 6.86 (1H, t, J = 8.6 Hz), 3.45 (3H, s). |
| 448 | ¹H-NMR (CDCl₃) δ: 7.40-7.33 (2H, m), 7.23 (1H, d, J = 8.5 Hz), 7.11 (1H, dd, J = 8.5, 2.7 Hz), 7.10-7.06 (1H, m), 6.96-6.91 (1H, m), 6.87-6.82 (1H, m), 6.77 (1H, d, J = 9.5 Hz), 6.16 (1H, tt, J = 56.6, 4.5 Hz), 4.26-4.11 (2H, m). |
| 449 | ¹H-NMR (CDCl₃) δ: 7.60 (1H, s), 7.39 (1H, tt, J = 8.4, 3.5 Hz), 7.24 (1H, d, J = 8.9 Hz), 7.14 (1H, dd, J = 8.6, 2.4 Hz), 7.10-7.08 (1H, m), 6.94 (1H, t, J = 8.4 Hz), 6.87 (1H, t, J = 8.4 Hz), 6.19 (1H, tt, J = 56.4, 4.5 Hz), 4.26-4.18 (2H, m). |
| 450 | ¹H-NMR (CDCl₃) δ: 7.41-7.32 (1H, m), 7.30 (1H, d, J = 2.4 Hz), 7.28-7.25 (1H, m), 7.00 (1H, dd, J = 2.4, 1.2 Hz), 6.99-6.93 (1H, m), 6.90-6.84 (1H, m), 6.74 (1H, d, J = 9.5 Hz), 3.97-3.82 (2H, m), 1.16 (3H, t, J = 7.2 Hz). |
| 451 | ¹H-NMR (CDCl₃) δ: 7.51 (1H, s), 7.43-7.34 (1H, m), 7.32 (1H, d, J = 2.4 Hz), 7.01 (1H, dd, J = 2.4, 1.5 Hz), 6.96 (1H, t, J = 8.4 Hz), 6.89 (1H, t, J = 8.4 Hz), 3.95 (2H, q, J = 7.0 Hz), 1.18 (3H, t, J = 7.0 Hz). |
| 452 | ¹H-NMR (CDCl₃) δ: 7.40-7.33 (1H, m), 7.32 (1H, d, J = 2.4 Hz), 7.29 (1H, d, J = 9.5 Hz), 6.98-6.94 (2H, m), 6.88 (1H, t, J = 8.4 Hz), 6.76 (1H, d, J = 9.5 Hz), 3.38 (3H, s). |
| 453 | ¹H-NMR (CDCl₃) δ: 7.53 (1H, s), 7.42-7.35 (1H, m), 7.34 (1H, d, J = 2.4 Hz), 6.99 (1H, dd, J = 2.4, 1.5 Hz), 6.98-6.94 (1H, m), 6.92-6.87 (1H, m), 3.45 (3H, s). |
| 454 | ¹H-NMR (CDCl₃) δ: 7.42-7.36 (1H, m), 7.35-7.33 (2H, m), 7.01 (1H, dd, J = 2.3, 1.7 Hz), 6.95 (1H, t, J = 8.4 Hz), 6.88 (1H, t, J = 8.4 Hz), 6.77 (1H, d, J = 9.5 Hz), 6.16 (1H, tt, J = 56.6, 4.5 Hz), 4.16 (2H, td, J = 12.9, 4.5 Hz). |
| 455 | ¹H-NMR (CDCl₃) δ: 7.58 (1H, s), 7.45-7.38 (1H, m), 7.35 (1H, d, J = 2.4 Hz), 7.03 (1H, dd, J = 2.4, 1.5 Hz), 6.96 (1H, t, J = 8.6 Hz), 6.90 (1H, t, J = 8.6 Hz), 6.18 (1H, tt, J = 56.4, 4.4 Hz), 4.28-4.13 (2H, m). |
| 456 | ¹H-NMR (CDCl₃) δ: 7.27-7.21 (1H, m), 7.15 (1H, d, J = 8.6 Hz), 6.83 (1H, t, J = 8.4 Hz), 6.75 (1H, t, J = 8.4 Hz), 6.62 (1H, dd, J = 8.6, 3.1 Hz), 6.61-6.60 (1H, m), 4.26 (1H, dd, J = 17.7, 2.4 Hz), 4.17 (1H, dd, J = 17.7, 2.4 Hz), 3.64 (3H, s), 2.93-2.83 (2H, m), 2.78-2.72 (1H, m), 2.65-2.59 (1H, m), 2.03 (1H, t, J = 2.4 Hz). |
| 457 | ¹H-NMR (CDCl₃) δ: 7.37 (1H, tt, J = 8.5, 6.4 Hz), 7.23 (1H, m), 6.91 (2H, dd, J = 8.5, 7.3 Hz), 6.80-6.73 (1H, m), 6.58-6.55 (1H, m), 3.40 (3H, s), 2.26 (3H, d, J = 1.2 Hz). |
| 458 | ¹H-NMR (CDCl₃) δ: 7.37 (1H, d, J = 9.5 Hz), 7.34 (1H, tt, J = 8.6, 6.4 Hz), 7.19 (1H, d, J = 8.9 Hz), 6.90 (1H, t, J = 8.6 Hz), 6.83 (1H, t, J = 8.6 Hz), 6.77 (1H, d, J = 9.5 Hz), 6.68 (1H, dd, J = 8.9, 3.1 Hz), 6.62 (1H, dd, J = 3.1, 1.2 Hz), 4.70-4.70 (2H, m), 3.65 (3H, s), 2.11 (1H, t, J = 2.6 Hz). |
| 459 | ¹H-NMR (CDCl₃) δ: 7.36 (1H, tt, J = 8.6, 6.4 Hz), 7.21 (1H, m), 6.90 (2H, dd, J = 8.6, 7.2 Hz), 6.76-6.74 (1H, m), 6.58-6.55 (1H, m), 3.92 (2H, q, J = 7.0 Hz), 2.25 (3H, d, J = 1.2 Hz), 1.14 (3H, t, J = 7.0 Hz). |
| 460 | ¹H-NMR (CDCl₃) δ: 7.43 (1H, d, J = 9.5 Hz), 7.41 (1H, tt, J = 8.6, 6.4 Hz), 7.20 (1H, d, J = 8.9 Hz), 6.98 (1H, t, J = 8.6 Hz), 6.91 (1H, t, J = 8.6 Hz), 6.80 (1H, d, J = 9.5 Hz), 6.71 (1H, dd, J = 8.9, 3.1 Hz), 6.61 (1H, dd, J = 3.1, 1.5 Hz), 4.85 (1H, d, J = 17.1 Hz), 4.72 (1H, d, J = 17.1 Hz), 3.66 (3H, s). |
| 461 | ¹H-NMR (CDCl₃) δ: 7.27 (1H, dd, J = 8.6, 5.5 Hz), 7.18 (1H, m), 6.87 (1H, td, J = 8.6, 3.3 Hz), 6.80 (1H, ddd, J = 8.9, 3.3, 1.2 Hz), 6.68 (1H, tt, J = 8.6, 2.1 Hz), 6.61 (1H, tt, J = 8.6, 2.1 Hz), 3.93-3.89 (2H, m), 2.25 (3H, d, J = 0.9 Hz), 1.16 (3H, t, J = 7.0 Hz). |
| 462 | ¹H-NMR (CDCl₃) δ: 7.59 (1H, s), 7.39-7.32 (1H, m), 7.19 (1H, d, J = 8.9 Hz), 6.90 (1H, t, J = 8.4 Hz), 6.85 (1H, t, J = 8.4 Hz), 6.70 (1H, dd, J = 8.9, 3.1 Hz), 6.63 (1H, dd, J = 3.1, 1.5 Hz), 4.78 (1H, dd, J = 17.4, 2.6 Hz), 4.72 (1H, dd, J = 17.4, 2.6 Hz), 3.66 (3H, s), 2.14 (1H, t, J = 2.6 Hz). |
| 463 | ¹H-NMR (CDCl₃) δ: 7.64 (1H, s), 7.43 (1H, tt, J = 8.4, 6.4 Hz), 7.20 (1H, d, J = 8.9 Hz), 6.98 (1H, t, J = 8.4 Hz), 6.92 (1H, t, J = 8.4 Hz), 6.74-6.71 (1H, m), 6.62 (1H, dd, J = 3.1, 1.5 Hz), 4.91 (1H, d, J = 17.1 Hz), 4.74 (1H, d, J = 17.1 Hz), 3.66 (3H, s). |
| 464 | ¹H-NMR (CDCl₃) δ: 7.30 (1H, dd, J = 9.3, 0.8 Hz), 6.84-6.79 (1H, m), 6.76 (1H, d, J = 9.3 Hz), 6.72-6.68 (2H, m), 6.58-6.56 (1H, m), 3.91 (2H, q, J = 7.0 Hz), 1.15 (3H, t, J = 7.0 Hz). |
| 465 | ¹H-NMR (CDCl₃) δ: 7.54 (1H, d, J = 0.9 Hz), 6.87-6.80 (1H, m), 6.74-6.68 (2H, m), 6.60-6.57 (1H, m), 3.96 (2H, q, J = 7.0 Hz), 1.17 (3H, t, J = 7.0 Hz). |
| 466 | ¹H-NMR (CDCl₃) δ: 7.33 (1H, dd, J = 9.5, 0.6 Hz), 6.85-6.79 (1H, m), 6.78 (1H, d, J = 9.5 Hz), 6.73-6.68 (2H, m), 6.59-6.57 (1H, m), 3.39 (3H, s). |
| 467 | ¹H-NMR (CDCl₃) δ: 7.56 (1H, s), 6.87-6.82 (1H, m), 6.74-6.69 (2H, m), 6.61-6.58 (1H, m), 3.46 (3H, s). |
| 468 | ¹H-NMR (CDCl₃) δ: 7.31 (1H, dd, J = 9.5, 0.9 Hz), 6.93-6.83 (2H, m), 6.77-6.75 (1H, m), 6.72 (1H, d, J = 9.2 Hz), 6.41 (2H, d, J = 9.2 Hz), 3.93 (2H, q, J = 7.2 Hz), 3.78 (3H, s), 1.14 (3H, t, J = 7.2 Hz). |

TABLE 5-continued

| Compound | ¹H-NMR |
|---|---|
| 469 | 1H-NMR (CDCl3) δ: 7.55 (1H, d, J = 0.9 Hz), 6.92-6.89 (2H, m), 6.79-6.74 (1H, m), 6.42 (2H, d, J = 9.2 Hz), 3.98 (2H, q, J = 7.1 Hz), 3.78 (3H, s), 1.17 (3H, t, J = 7.1 Hz). |
| 470 | ¹H-NMR (CDCl₃) δ: 7.32 (1H, tt, J = 8.4, 3.5 Hz), 7.21 (1H, d, J = 9.2 Hz), 7.19 (1H, d, J = 1.2 Hz), 7.09-7.06 (2H, m), 6.92 (1H, t, J = 8.4 Hz), 6.83 (1H, t, J = 8.4 Hz), 3.92 (2H, q, J = 7.0 Hz), 2.26-2.24 (3H, m), 1.16 (3H, t, J = 7.0 Hz). |
| 471 | ¹H-NMR (CDCl₃) δ: 7.32 (1H, tt, J = 8.6, 3.5 Hz), 7.22-7.19 (2H, m), 7.09 (1H, dd, J = 8.6, 2.4 Hz), 7.06-7.03 (1H, m), 6.91 (1H, t, J = 8.4 Hz), 6.84 (1H, t, J = 8.4 Hz), 3.40 (3H, s), 2.26-2.25 (3H, m). |
| 472 | ¹H-NMR (CDCl₃) δ: 7.37-7.31 (2H, m), 7.23-7.20 (1H, m), 6.95-6.91 (1H, m), 6.88 (3H, t, J = 8.0 Hz), 6.74 (1H, d, J = 9.5 Hz), 3.92 (2H, q, J = 7.0 Hz), 1.15 (3H, t, J = 7.0 Hz). |
| 473 | ¹H-NMR (CDCl₃) δ: 7.57 (1H, s), 7.35 (1H, tt, J = 8.4, 3.5 Hz), 7.26-7.21 (1H, m), 6.96-6.86 (4H, m), 3.97 (2H, q, J = 7.0 Hz), 1.17 (3H, t, J = 7.0 Hz). |
| 474 | ¹H-NMR (CDCl₃) δ: 7.38-7.31 (2H, m), 7.25-7.21 (1H, m), 6.94-6.90 (2H, m), 6.88-6.85 (2H, m), 6.76 (1H, d, J = 9.2 Hz), 3.40 (3H, s). |
| 475 | ¹H-NMR (CDCl₃) δ: 7.59 (1H, s), 7.36 (1H, tt, J = 8.4, 3.5 Hz), 7.27-7.23 (1H, m), 6.94-6.87 (4H, m), 3.46 (3H, s). |
| 476 | ¹H-NMR (CDCl₃) δ: 7.72 (1H, s), 7.29-7.27 (1H, m), 6.88 (1H, ddd, J = 8.9, 8.0, 3.1 Hz), 6.82 (1H, ddd, J = 8.9, 3.1, 1.5 Hz), 6.45 (1H, dt, J = 10.8, 1.9 Hz), 6.37 (1H, dt, J = 10.8, 1.9 Hz), 3.96 (2H, q, J = 7.2 Hz), 3.77 (3H, s), 1.18 (3H, t, J = 7.2 Hz). |
| 477 | ¹H-NMR (CDCl₃) δ: 7.27 (1H, tt, J = 8.6, 6.4 Hz), 6.90-6.74 (4H, m), 6.63-6.59 (1H, m), 3.43 (2H, q, J = 7.0 Hz), 2.77-2.69 (4H, m), 0.97 (3H, t, J = 7.0 Hz). |
| 478 | ¹H-NMR (CDCl₃) δ: 7.37-7.33 (2H, m), 6.91-6.82 (4H, m), 6.77-6.73 (2H, m), 3.92 (2H, q, J = 7.1 Hz), 1.14 (3H, t, J = 7.1 Hz). |
| 479 | ¹H-NMR (CDCl₃) δ: 7.27-7.25 (1H, m), 7.17 (1H, d, J = 1.2 Hz), 6.87-6.80 (2H, m), 6.43 (1H, dt, J = 10.7, 2.0 Hz), 6.36 (1H, dt, J = 10.7, 2.0 Hz), 3.92 (2H, q, J = 7.1 Hz), 3.77 (3H, s), 2.24 (3H, d, J = 1.2 Hz), 1.15 (3H, t, J = 7.1 Hz). |
| 480 | ¹H-NMR (CDCl₃) δ: 7.27 (1H, tt, J = 8.5, 6.4 Hz), 6.90-6.75 (4H, m), 6.63-6.59 (1H, m), 2.89 (3H, s), 2.76-2.73 (4H, m). |
| 481 | ¹H-NMR (CDCl₃) δ: 7.57 (1H, d, J = 0.9 Hz), 7.37 (1H, tt, J = 8.6, 6.4 Hz), 6.92-6.86 (4H, m), 6.78-6.74 (1H, m), 3.97 (2H, q, J = 7.1 Hz), 1.17 (3H, t, J = 7.1 Hz). |
| 482 | ¹H-NMR (CDCl₃) δ: 7.78 (1H, d, J = 0.9 Hz), 7.37 (1H, tt, J = 8.4, 6.4 Hz), 6.90-6.87 (4H, m), 6.78-6.75 (1H, m), 3.97 (2H, q, J = 7.2 Hz), 1.17 (3H, t, J = 7.2 Hz). |
| 483 | ¹H-NMR (CDCl₃) δ: 7.38-7.34 (2H, m), 6.91-6.85 (4H, m), 6.77-6.74 (2H, m), 3.40 (3H, s). |
| 484 | ¹H-NMR (CDCl₃) δ: 7.59 (1H, d, J = 0.9 Hz), 7.38 (1H, tt, J = 8.6, 6.4 Hz), 6.90-6.89 (4H, m), 6.77-6.75 (1H, m), 3.46 (3H, s). |
| 485 | ¹H-NMR (CDCl₃) δ: 7.80 (1H, d, J = 0.6 Hz), 7.38 (1H, tt, J = 8.6, 6.4 Hz), 6.90-6.88 (4H, m), 6.78-6.74 (1H, m), 3.47 (3H, s). |
| 486 | ¹H-NMR (CDCl₃) δ: 7.30 (1H, d, J = 9.5 Hz), 7.07-7.00 (2H, m), 6.87-6.85 (1H, m), 6.75 (1H, d, J = 9.5 Hz), 6.66 (1H, tt, J = 8.7, 2.0 Hz), 6.61 (1H, tt, J = 8.7, 2.0 Hz), 3.97-3.83 (2H, m), 1.16 (3H, t, J = 7.0 Hz). |
| 487 | ¹H-NMR (CDCl₃) δ: 7.74 (1H, s), 7.09-7.02 (2H, m), 6.88-6.85 (1H, m), 6.69-6.61 (2H, m), 3.97-3.93 (2H, m), 1.19 (3H, t, J = 7.0 Hz). |
| 488 | ¹H-NMR (CDCl₃) δ: 7.53 (1H, s), 7.09-7.02 (2H, m), 6.88-6.86 (1H, m), 6.69-6.61 (2H, m), 3.96-3.94 (2H, m), 1.19 (3H, t, J = 7.0 Hz). |
| 489 | ¹H-NMR (CDCl₃) δ: 7.29 (1H, d, J = 9.5 Hz), 7.05-6.98 (2H, m), 6.88-6.86 (1H, m), 6.72 (1H, d, J = 9.5 Hz), 6.43-6.40 (1H, m), 6.36-6.34 (1H, m), 3.99-3.84 (2H, m), 3.76 (3H, s), 1.16 (3H, t, J = 7.0 Hz). |
| 490 | ¹H-NMR (CDCl₃) δ: 7.52 (1H, s), 7.07-6.99 (2H, m), 6.89-6.87 (1H, m), 6.42-6.39 (1H, m), 6.37-6.34 (1H, m), 4.01-3.93 (2H, m), 3.76 (3H, s), 1.18 (3H, t, J = 7.2 Hz). |
| 491 | ¹H-NMR (CDCl₃) δ: 7.32 (1H, d, J = 9.5 Hz), 7.08-7.01 (2H, m), 6.85-6.83 (1H, m), 6.77 (1H, d, J = 9.5 Hz), 6.69-6.60 (2H, m), 3.39 (3H, s). |
| 492 | ¹H-NMR (CDCl₃) δ: 7.31 (1H, d, J = 9.2 Hz), 7.07-6.98 (2H, m), 6.86-6.83 (1H, m), 6.74 (1H, d, J = 9.2 Hz), 6.43-6.40 (1H, m), 6.37-6.34 (1H, m), 3.76 (3H, s), 3.39 (3H, s). |
| 493 | ¹H-NMR (CDCl₃) δ: 7.35-7.28 (1H, m), 7.25-7.19 (2H, m), 6.95-6.91 (1H, m), 6.89-6.80 (3H, m), 3.93 (2H, q, J = 7.0 Hz), 2.26-2.24(3H, m), 1.14 (3H, t, J = 7.0 Hz). |
| 494 | ¹H-NMR (CDCl₃) δ: 7.42-7,33 (2H, m), 6.96-6.85 (4H, m), 6.77 (1H, d, J = 9.5 Hz), 6.15 (1H, tt, J = 56.6, 4.5 Hz), 4.22-4.15 (2H, m). |
| 495 | ¹H-NMR (CDCl₃) δ: 7.64 (1H, s), 7.39 (1H, tt, J = 8.6, 3.6 Hz), 7.28-7.25 (1H, m), 6.97-6.87 (4H, m), 6.17 (1H, tt, J = 56.6, 4.5 Hz), 4.26-4.20 (2H, m). |
| 496 | ¹H-NMR (CDCl₃) δ: 7.33-7.25 (2H, m), 7.18 (1H, d, J = 8.9 Hz), 6.86 (1H, t, J = 8.6 Hz), 6.80 (1H, t, J = 8.6 Hz), 6.69-6.67 (2H, m), 6.53 (1H, dd, J = 3.1, 1.5 Hz), 3.62 (3H, s), 2.93-2.91 (1H, m), 0.90-0.61 (4H, m). |
| 497 | ¹H-NMR (CDCl₃) δ: 7.33 (1H, tt, J = 8.4, 6.4 Hz), 7.23 (1H, m), 6.89-6.81 (4H, m), 6.77-6.74 (1H, m), 3.93 (2H, q, J = 7.0 Hz), 2.25 (3H, d, J = 1.2 Hz), 1.14 (3H, t, J = 7.0 Hz). |
| 498 | ¹H-NMR (CDCl₃) δ: 7.54 (1H, s), 7.31 (1H, tt, J = 8.6, 6.4 Hz), 7.18 (1H, d, J = 8.9 Hz), 6.86 (1H, t, J = 8.6 Hz), 6.81 (1H, t, J = 8.6 Hz), 6.69 (1H, dd, J = 8.9, 3.1 Hz), 6.54 (1H, dd, J = 3.1, 1.7 Hz), 3.63 (3H, s), 3.00-2.99 (1H, m), 0.90-0.66 (4H, m). |
| 499 | ¹H-NMR (CDCl₃) δ: 7.34 (1H, tt, J = 8.4, 6.4 Hz), 7.25 (1H, m), 6.89-6.83 (4H, m), 6.76-6.74 (1H, m), 3.40 (3H, s), 2.26 (3H, d, J = 1.2 Hz). |
| 500 | ¹H-NMR (CDCl₃) δ: 7.55 (1H, s), 7.10-7.03 (2H, m), 6.87-6.84 (1H, m), 6.69-6.61 (2H, m), 3.45 (3H, s). |
| 501 | ¹H-NMR (CDCl₃) δ: 7.19-7.18 (1H, m), 7.06-6.99 (2H, m), 6.87-6.85 (1H, m), 6.66-6.58 (2H, m), 3.96-3.85 (2H, m), 2.25 (3H, d, J = 1.2 Hz), 1.16 (3H, t, J = 7.0 Hz). |
| 502 | ¹H-NMR (CDCl₃) δ: 7.13 (1H, m), 6.93 (1H, td, J = 7.8, 5.9 Hz), 6.88-6.83 (1H, m), 6.74 (1H, d, J = 7.8 Hz), 6.64 (1H, tt, J = 8.7, 2.1 Hz), 6.56 (1H, tt, J = 8.7, 2.1 Hz), 3.99-3.81 (2H, m), 2.25 (3H, d, J = 0.9 Hz), 2.06 (3H, d, J = 1.8 Hz), 1.16 (3H, t, J = 7.2 Hz). |
| 503 | ¹H-NMR (CDCl₃) δ: 7.76 (1H, s), 7.09-7.03 (2H, m), 6.86-6.84 (1H, m), 6.69-6.61 (2H, m), 3.46 (3H, s). |

TABLE 5-continued

| Compound | ¹H-NMR |
|---|---|
| 504 | ¹H-NMR (CDCl₃) δ: 7.55 (1H, s), 7.10-7.01 (2H, m), 6.88-6.85 (1H, m), 6.43-6.35 (2H, m), 3.77 (3H, s), 3.46 (3H, s). |
| 505 | ¹H-NMR (CDCl₃) δ: 7.21 (1H, d, J = 1.2 Hz), 7.07-7.00 (2H, m), 6.85-6.83 (1H, m), 6.66-6.59 (2H, m), 3.39 (3H, s), 2.26 (3H, d, J = 1.2 Hz). |
| 506 | ¹H-NMR (CDCl₃) δ: 7.34-7.28 (2H, m), 7.03-6.95 (2H, m), 6.91-6.80 (3H, m), 6.74 (1H, d, J = 9.2 Hz), 3.98-3.83 (2H, m), 1.16 (3H, t, J = 7.2 Hz). |
| 507 | ¹H-NMR (CDCl₃) δ: 7.54 (1H, s), 7.32 (1H, m), 7.05-6.97 (2H, m), 6.91-6.81 (3H, m), 4.01-3.90 (2H, m), 1.18 (3H, t, J = 7.0 Hz). |
| 508 | ¹H-NMR (CDCl₃) δ: 7.35-7.28 (2H, m), 7.03-6.96 (2H, m), 6.91-6.86 (1H, m), 6.85-6.80 (2H, m), 6.76 (1H, d, J = 9.5 Hz), 3.39 (3H, s). |
| 509 | ¹H-NMR (CDCl₃) δ: 7.56 (1H, s), 7.34 (1H, m), 7.05-6.98 (2H, m), 6.91-6.88 (1H, m), 6.86-6.82 (2H, m), 3.45 (3H, s). |
| 510 | ¹H-NMR (CDCl₃) δ: 7.38 (1H, d, J = 9.2 Hz), 7.37-7.30 (1H, m), 7.05-6.98 (2H, m), 6.90-6.86 (2H, m), 6.85-6.82 (1H, m), 6.77 (1H, d, J = 9.2 Hz), 6.17 (1H, tt, J = 56.6, 4.5 Hz), 4.25-4.10 (2H, m). |
| 511 | ¹H-NMR (CDCl₃) δ: 7.61 (1H, s), 7.36 (1H, m), 7.07-6.99 (2H, m), 6.91-6.83 (3H, m), 6.19 (1H, tt, J = 56.5, 4.6 Hz), 4.25-4.17 (2H, m). |
| 512 | ¹H-NMR (CDCl₃) δ: 7.35 (1H, tt, J = 8.5, 6.4 Hz), 7.27 (1H, dd, J = 8.9, 5.0 Hz), 7.13 (1H, d, J = 9.5 Hz), 6.93 (1H, t, J = 8.4 Hz), 6.89-6.80 (3H, m), 3.98-3.92 (2H, m), 1.17 (3H, t, J = 7.0 Hz). |
| 513 | ¹H-NMR (CDCl₃) δ: 7.35 (1H, tt, J = 8.5, 6.4 Hz), 7.27 (1H, dd, J = 8.9, 5.2 Hz), 7.15 (1H, d, J = 9.5 Hz), 6.93 (1H, t, J = 8.5 Hz), 6.88-6.86 (2H, m), 6.80 (1H, ddd, J = 8.9, 3.1, 1.2 Hz), 3.44 (3H, s). |
| 514 | ¹H-NMR (CDCl₃) δ: 7.14-7.09 (1H, m), 6.94-6.90 (3H, m), 6.57-6.55 (2H, m), 3.42 (2H, q, J = 7.2 Hz), 2.75-2.69 (4H, m), 0.98 (3H, t, J = 7.2 Hz). |
| 515 | ¹H-NMR (CDCl₃) δ: 7.18 (1H, d, J = 1.2 Hz), 7.05-6.96 (2H, m), 6.88-6.86 (1H, m), 6.41-6.38 (1H, m), 6.36-6.33 (1H, m), 3.99-3.86 (2H, m), 3.76 (3H, s), 2.24 (3H, d, J = 1.2 Hz), 1.15 (3H, t, J = 7.0 Hz). |
| 516 | ¹H-NMR (CDCl₃) δ: 7.12 (1H, d, J = 1.2 Hz), 6.93 (1H, td, J = 7.7, 5.9 Hz), 6.85-6.82 (1H, m), 6.76 (1H, d, J = 7.7 Hz), 6.41-6.38 (1H, m), 6.33-6.30 (1H, m), 3.98-3.85 (2H, m), 3.74 (3H, s), 2.24 (3H, d, J = 1.2 Hz), 2.06-2.05 (3H, m), 1.16 (3H, t, J = 7.2 Hz). |
| 517 | ¹H-NMR (CDCl₃) δ: 7.20 (1H, d, J = 1.1 Hz), 7.06-6.98 (2H, m), 6.86-6.84 (1H, m), 6.41-6.39 (1H, m), 6.36-6.33 (1H, m), 3.76 (3H, s), 3.40 (3H, s), 2.25 (3H, d, J = 1.1 Hz). |
| 518 | ¹H-NMR (CDCl₃) δ: 7.37-7.31 (2H, m), 7.02-6.96 (1H, m), 6.90-6.85 (3H, m), 6.79 (1H, dd, J = 7.6, 6.1 Hz), 6.75 (1H, d, J = 9.2 Hz), 3.93 (2H, q, J = 7.1 Hz), 1.15 (3H, t, J = 7.1 Hz). |
| 519 | ¹H-NMR (CDCl₃) δ: 7.58 (1H, d, J = 0.9 Hz), 7.38-7.32 (1H, m), 7.04-6.98 (2H, m), 6.92-6.87 (3H, m), 6.82-6.79 (1H, m), 3.98 (2H, q, J = 7.1 Hz), 1.17 (3H, t, J = 7.1 Hz). |
| 520 | ¹H-NMR (CDCl₃) δ: 7.78 (1H, d, J = 0.6 Hz), 7.38-7.32 (1H, m), 7.04-6.98 (1H, m), 6.92-6.86 (3H, m), 6.82-6.79 (1H, m), 3.98 (2H, q, J = 7.1 Hz), 1.17 (3H, t, J = 7.1 Hz). |
| 521 | ¹H-NMR (CDCl₃) δ: 7.35 (1H, m), 7.30-7.28 (1H, m), 7.25-7.21 (1H, m), 6.96-6.85 (4H, m), 6.16 (1H, tt, J = 56.6, 4.5 Hz), 4.23-4.15 (2H, m), 2.26 (3H, d, J = 1.2 Hz). |
| 522 | ¹H-NMR (CDCl₃) δ: 7.38-7.31 (2H, m), 7.13-7.09 (1H, m), 7.04-7.01 (1H, m), 6.91-6.84 (3H, m), 6.74 (1H, d, J = 9.5 Hz), 3.92 (2H, q, J = 7.1 Hz), 1.14 (3H, t, J = 7.1 Hz). |
| 523 | ¹H-NMR (CDCl₃) δ: 7.56 (1H, s), 7.37 (1H, m), 7.15-7.12 (1H, m), 7.05-7.03 (1H, m), 6.92-6.85 (3H, m), 3.97 (2H, q, J = 7.0 Hz), 1.17 (3H, t, J = 7.0 Hz). |
| 524 | ¹H-NMR (CDCl₃) δ: 7.39-7.33 (2H, m), 7.14-7.11 (1H, m), 7.04-7.01 (1H, m), 6.91-6.84 (3H, m), 6.76 (1H, d, J = 9.5 Hz), 3.40 (3H, s). |
| 525 | ¹H-NMR (CDCl₃) δ: 7.58 (1H, s), 7.38 (1H, m), 7.17-7.13 (1H, m), 7.05-7.02 (1H, m), 6.92-6.84 (3H, m), 3.46 (3H, s). |
| 526 | ¹H-NMR (CDCl₃) δ: 7.16-7.10 (1H, m), 6.95-6.93 (1H, m), 6.90-6.89 (2H, m), 6.58-6.56 (2H, m), 2.89 (3H, s), 2.75-2.73 (4H, br m). |
| 527 | ¹H-NMR (CDCl₃) δ: 7.35 (1H, dd, J = 9.2, 0.8 Hz), 7.22-7.17 (1H, m), 7.03 (1H, td, J = 7.5, 1.9 Hz), 6.99 (1H, td, J = 7.5, 1.1 Hz), 6.96-6.92 (1H, m), 6.75 (1H, d, J = 9.2 Hz), 6.65-6.60 (2H, m), 3.92 (2H, q, J = 7.0 Hz), 1.15 (3H, t, J = 7.0 Hz). |
| 528 | ¹H-NMR (CDCl₃) δ: 7.37 (1H, dd, J = 9.5, 0.9 Hz), 7.22-7.19 (1H, m), 7.03-7.00 (2H, m), 6.95-6.93 (1H, m), 6.76 (1H, d, J = 9.5 Hz), 6.66-6.60 (2H, m), 3.40 (3H, s). |
| 529 | ¹H-NMR (CDCl₃) δ: 7.59 (1H, d, J = 0.6 Hz), 7.22-7.21 (1H, m), 7.05-7.03 (1H, m), 7.00 (1H, td, J = 7.3, 1.2 Hz), 6.96-6.93 (1H, m), 6.65-6.61 (2H, m), 3.97 (2H, q, J = 7.0 Hz), 1.17 (3H, t, J = 7.0 Hz). |
| 530 | ¹H-NMR (CDCl₃) δ: 7.34 (1H, dd, J = 9.5, 0.9 Hz), 7.20-7.15 (1H, m), 7.04-7.02 (1H, m), 6.98-6.96 (1H, m), 6.95-6.93 (1H, m), 6.72 (1H, d, J = 9.5 Hz), 6.39-6.37 (2H, m), 3.94 (2H, q, J = 7.0 Hz), 3.76 (3H, s), 1.14 (3H, t, J = 7.0 Hz). |
| 531 | ¹H-NMR (CDCl₃) δ: 7.58 (1H, d, J = 0.7 Hz), 7.22-7.17 (1H, m), 7.05-7.02 (1H, m), 6.99-6.97 (1H, m), 6.96-6.93 (1H, m), 6.39-6.36 (2H, m), 3.99 (2H, q, J = 7.1 Hz), 3.76 (3H, s), 1.17 (3H, t, J = 7.1 Hz). |
| 532 | ¹H-NMR (CDCl₃) δ: 7.79 (1H, s), 7.24-7.19 (1H, m), 7.04-6.99 (2H, m), 6.95-6.93 (1H, m), 6.66-6.60 (2H, m), 3.97 (2H, q, J = 7.0 Hz), 1.17 (3H, t, J = 7.0 Hz). |
| 533 | ¹H-NMR (CDCl₃) δ: 7.33 (1H, tt, J = 8.3, 6.4 Hz), 7.18 (1H, d, J = 8.9 Hz), 7.15 (1H, d, J = 9.5 Hz), 6.90 (1H, t, J = 8.3 Hz), 6.84 (1H, t, J = 8.3 Hz), 6.68 (1H, dd, J = 8.9, 3.1 Hz), 6.62 (1H, dd, J = 3.1, 1.5 Hz), 4.02-3.87 (2H, m), 3.65 (3H, s), 1.18 (3H, t, J = 7.1 Hz). |
| 534 | ¹H-NMR (CDCl₃) δ: 7.35-7.28 (1H, m), 7.23 (1H, t, J = 0.9 Hz), 7.01-6.94 (1H, m), 6.89-6.84 (3H, m), 6.81-6.77 (1H, m), 3.93 (2H, q, J = 7.0 Hz), 2.25 (3H, d, J = 0.9 Hz), 1.14 (3H, t, J = 7.0 Hz). |
| 535 | ¹H-NMR (CDCl₃) δ: 7.38-7.31 (2H, m), 7.03-6.96 (1H, m), 6.92-6.86 (3H, m), 6.81-6.75 (2H, m), 3.40 (3H, s). |
| 536 | ¹H-NMR (CDCl₃) δ: 7.80 (1H, d, J = 0.7 Hz), 7.40-7.33 (1H, m), 7.06-6.99 (1H, m), 6.94-6.87 (3H, m), 6.82-6.78 (1H, m), 3.47 (3H, s). |

TABLE 5-continued

| Compound | ¹H-NMR |
|---|---|
| 537 | ¹H-NMR (CDCl₃) δ: 7.60 (1H, br s), 7.39-7.34 (1H, m), 7.05-7.00 (1H, m), 6.93-6.87 (3H, m), 6.82-6.78 (1H, m), 3.47 (3H, s). |
| 538 | ¹H-NMR (CDCl₃) δ: 7.36-7.30 (1H, m), 7.26 (1H, m), 7.02-6.96 (1H, m), 6.90-6.85 (3H, m), 6.81-6.77 (1H, m), 3.41 (3H, s), 2.26 (3H, d, J = 0.9 Hz). |
| 539 | ¹H-NMR (CDCl₃) δ: 7.41-7.35 (2H, m), 7.15-7.12 (1H, m), 7.05-7.02 (1H, m), 6.91-6.85 (3H, m), 6.77 (1H, d, J = 9.5 Hz), 6.14 (1H, tt, J = 56.6, 4.5 Hz), 4.22-4.16 (2H, m). |
| 540 | ¹H-NMR (CDCl₃) δ: 7.63 (1H, s), 7.44-7.36 (1H, m), 7.18-7.14 (1H, m), 7.06-7.03 (1H, m), 6.93-6.85 (3H, m), 6.16 (1H, tt, J = 56.4, 4.5 Hz), 4.27-4.20 (2H, m). |
| 541 | ¹H-NMR (CDCl₃) δ: 7.78 (1H, d, J = 0.9 Hz), 7.21-7.17 (1H, m), 7.04 (1H, td, J = 7.6, 1.6 Hz), 6.98 (1H, td, J = 7.6, 1.1 Hz), 6.96-6.92 (1H, m), 6.39-6.37 (2H, m), 3.99 (2H, q, J = 7.0 Hz), 3.76 (3H, s), 1.17 (3H, t, J = 7.0 Hz). |
| 542 | ¹H-NMR (CDCl₃) δ: 7.24 (1H, t, J = 1.2 Hz), 7.21-7.16 (1H, m), 7.03 (1H, td, J = 7.5, 1.6 Hz), 6.98 (1H, td, J = 7.5, 1.2 Hz), 6.95-6.91 (1H, m), 6.63-6.59 (2H, m), 3.92 (2H, q, J = 7.1 Hz), 2.25 (3H, d, J = 1.2 Hz), 1.15 (3H, t, J = 7.1 Hz). |
| 543 | ¹H-NMR (CDCl₃) δ: 7.60 (1H, d, J = 0.7 Hz), 7.25-7.20 (1H, m), 7.03-7.00 (2H, m), 6.97-6.92 (1H, m), 6.67-6.61 (2H, m), 3.46 (3H, s). |
| 544 | ¹H-NMR (CDCl₃) δ: 7.37 (1H, dd, J = 9.5, 1.0 Hz), 7.21-7.15 (1H, m), 7.05-7.01 (1H, m), 7.00-6.96 (1H, m), 6.96-6.92 (1H, m), 6.73 (1H, d, J = 9.5 Hz), 6.40-6.37 (2H, m), 3.76 (3H, s), 3.40 (3H, s). |
| 545 | ¹H-NMR (CDCl₃) δ: 7.81 (1H, d, J = 0.7 Hz), 7.25-7.20 (1H, m), 7.03-7.01 (2H, m), 6.95-6.93 (1H, m), 6.66-6.61 (2H, m), 3.47 (3H, s). |
| 546 | ¹H-NMR (CDCl₃) δ: 7.53 (1H, d, J = 0.9 Hz), 6.83-6.78 (1H, m), 6.59-6.57 (1H, m), 6.44 (2H, dd, J = 11.9, 2.8 Hz), 3.98 (2H, q, J = 7.1 Hz), 3.80 (3H, s), 1.17 (3H, t, J = 7.1 Hz). |
| 547 | ¹H-NMR (CDCl₃) δ: 7.52 (1H, s), 7.29-7.27 (1H, m), 6.89-6.87 (1H, m), 6.82 (1H, dq, J = 8.7, 1.4 Hz), 6.43 (1H, dt, J = 10.8, 1.9 Hz), 6.35 (1H, dt, J = 10.8, 1.9 Hz), 3.96 (4H, q, J = 7.0 Hz), 1.40 (3H, t, J = 7.0 Hz), 1.18 (3H, t, J = 7.0 Hz). |
| 548 | ¹H-NMR (CDCl₃) δ: 7.29 (1H, dd, J = 9.5, 0.9 Hz), 6.81-6.76 (1H, m), 6.73 (1H, d, J = 9.2 Hz), 6.58-6.56 (1H, m), 6.44 (2H, dd, J = 11.9, 2.8 Hz), 3.93 (2H, q, J = 7.1 Hz), 3.80 (3H, s), 1.14 (3H, t, J = 7.1 Hz). |
| 549 | ¹H-NMR (CDCl₃) δ: 7.55 (1H, d, J = 0.9 Hz), 6.84-6.79 (1H, m), 6.59-6.57 (1H, m), 6.45 (2H, dd, J = 11.9, 2.8 Hz), 3.80 (3H, s), 3.46 (3H, s). |
| 550 | ¹H-NMR (CDCl₃) δ: 7.32 (1H, dd, J = 9.5, 0.9 Hz), 6.82-6.77 (1H, m), 6.74 (1H, d, J = 9.5 Hz), 6.58-6.55 (1H, m), 6.44 (2H, dd, J = 12.2, 2.8 Hz), 3.80 (3H, s), 3.40 (3H, s). |
| 551 | ¹H-NMR (CDCl₃) δ: 7.38-7.32 (1H, m), 7.27 (1H, d, J = 9.8 Hz), 6.94 (1H, t, J = 8.4 Hz), 6.87 (1H, t, J = 8.4 Hz), 6.78-6.73 (2H, m), 6.68-6.65 (1H, m), 3.96-3.84 (2H, m), 1.16 (3H, t, J = 7.0 Hz). |
| 552 | ¹H-NMR (CDCl₃) δ: 7.51 (1H, s), 7.41-7.33 (1H, m), 6.95 (1H, t, J = 8.4 Hz), 6.88 (1H, t, J = 8.4 Hz), 6.81-6.76 (1H, m), 6.69-6.66 (1H, m), 3.95 (2H, q, J = 7.1 Hz), 1.18 (3H, t, J = 7.1 Hz). |
| 553 | ¹H-NMR (CDCl₃) δ: 7.40-7.32 (1H, m), 7.30 (1H, d, J = 9.3 Hz), 6.94 (1H, t, J = 8.4 Hz), 6.87 (1H, t, J = 8.4 Hz), 6.80-6.75 (2H, m), 6.66-6.62 (1H, m), 3.38 (3H, s). |
| 554 | ¹H-NMR (CDCl₃) δ: 7.53 (1H, s), 7.42-7.34 (1H, m), 6.94 (1H, t, J = 8.4 Hz), 6.89 (1H, t, J = 8.4 Hz), 6.82-6.75 (1H, m), 6.67-6.64 (1H, m), 3.45 (3H, s). |
| 555 | ¹H-NMR (CDCl₃) δ: 7.41-7.37 (1H, m), 7.35 (1H, d, J = 9.5 Hz), 6.94 (1H, t, J = 8.4 Hz), 6.88 (1H, t, J = 8.4 Hz), 6.81-6.77 (2H, m), 6.69-6.66 (1H, m), 6.16 (1H, tt, J = 56.6, 4.4 Hz), 4.19-4.13 (2H, m). |
| 556 | ¹H-NMR (CDCl₃) δ: 7.58 (1H, s), 7.44-7.37 (1H, m), 6.96-6.87 (2H, m), 6.83-6.78 (1H, m), 6.71-6.67 (1H, m), 6.18 (1H, tt, J = 56.5, 4.5 Hz), 4.26-4.16 (2H, m). |
| 557 | ¹H-NMR (CDCl₃) δ: 7.35 (1H, dd, J = 9.3, 0.8 Hz), 7.07-7.01 (1H, m), 6.96-6.92 (1H, m), 6.81-6.76 (2H, m), 6.68-6.64 (2H, m), 3.40 (3H, s). |
| 558 | ¹H-NMR (CDCl₃) δ: 7.33 (1H, dd, J = 9.2, 0.9 Hz), 7.06-7.00 (1H, m), 6.95-6.90 (1H, m), 6.81-6.77 (1H, m), 6.75 (1H, d, J = 9.2 Hz), 6.68-6.63 (2H, m), 3.91 (2H, q, J = 7.2 Hz), 1.15 (3H, t, J = 7.2 Hz). |
| 559 | ¹H-NMR (CDCl₃) δ: 7.59 (1H, d, J = 0.6 Hz), 7.09-7.04 (1H, m), 6.98-6.94 (1H, m), 6.83-6.79 (1H, m), 6.69-6.65 (2H, m), 3.46 (3H, s). |
| 560 | ¹H-NMR (CDCl₃) δ: 7.79 (1H, s), 7.09-7.04 (1H, m), 6.98-6.94 (1H, m), 6.83-6.79 (1H, m), 6.69-6.65 (2H, m), 3.47 (3H, s). |
| 561 | ¹H-NMR (CDCl₃) δ: 7.35 (1H, dd, J = 9.3, 1.0 Hz), 7.05-6.98 (1H, m), 6.95-6.89 (1H, m), 6.81-6.77 (1H, m), 6.74 (1H, d, J = 9.3 Hz), 6.42-6.38 (2H, m), 3.78 (3H, s), 3.40 (3H, s). |
| 562 | ¹H-NMR (CDCl₃) δ: 7.58 (1H, d, J = 0.7 Hz), 7.07-7.00 (1H, m), 6.96-6.91 (1H, m), 6.82-6.78 (1H, m), 6.43-6.39 (2H, m), 3.78 (3H, s), 3.47 (3H, s). |
| 563 | ¹H-NMR (CDCl₃) δ: 7.78 (1H, d, J = 0.6 Hz), 7.07-7.01 (1H, m), 6.96-6.91 (1H, m), 6.82-6.79 (1H, m), 6.41 (2H, dd, J = 12.2, 2.8 Hz), 3.78 (3H, s), 3.47 (3H, s). |
| 564 | ¹H-NMR (CDCl₃) δ: 7.25-7.24 (1H, m), 7.06-6.99 (1H, m), 6.96-6.90 (1H, m), 6.81-6.77 (1H, m), 6.67-6.62 (2H, m), 3.40 (3H, s), 2.26 (3H, d, J = 1.2 Hz). |
| 565 | ¹H-NMR (CDCl₃) δ: 7.25-7.23 (1H, m), 7.04-6.97 (1H, m), 6.93-6.88 (1H, m), 6.81-6.77 (1H, m), 6.41-6.37 (2H, m), 3.77 (3H, s), 3.41 (3H, s), 2.25 (3H, d, J = 1.2 Hz). |
| 566 | ¹H-NMR (CDCl₃) δ: 7.57 (1H, d, J = 0.6 Hz), 7.08-7.03 (1H, m), 6.97-6.92 (1H, m), 6.82-6.79 (1H, m), 6.69-6.64 (2H, m), 3.97 (2H, q, J = 7.0 Hz), 1.18 (3H, t, J = 7.0 Hz). |
| 567 | ¹H-NMR (CDCl₃) δ: 7.77 (1H, s), 7.08-7.03 (1H, m), 6.97-6.92 (1H, m), 6.82-6.79 (1H, m), 6.68-6.64 (2H, m), 3.97 (2H, q, J = 7.0 Hz), 1.17 (3H, t, J = 7.0 Hz). |
| 568 | ¹H-NMR (CDCl₃) δ: 7.25-7.19 (1H, m), 7.16 (1H, d, J = 9.3 Hz), 7.01-6.97 (3H, m), 6.66-6.60 (2H, m), 3.96 (2H, q, J = 7.1 Hz), 1.17 (3H, t, J = 7.1 Hz). |
| 569 | ¹H-NMR (CDCl₃) δ: 7.24 (1H, m), 7.19-7.13 (1H, m), 7.03 (1H, td, J = 7.5, 1.8 Hz), 6.98-6.91 (2H, m), 6.38-6.35 (2H, m), 3.94 (2H, q, J = 7.1 Hz), 3.75 (3H, s), 2.24 (3H, d, J = 1.0 Hz), 1.14 (3H, t, J = 7.1 Hz). |
| 570 | ¹H-NMR (CDCl₃) δ: 7.60 (1H, d, J = 0.7 Hz), 7.23-7.18 (1H, m), 7.04 (1H, td, J = 7.6, 1.8 Hz), 7.01-6.98 (1H, m), 6.97-6.92 (1H, m), 6.40-6.37 (2H, m), 3.76 (3H, s), 3.47 (3H, s). |

TABLE 5-continued

| Compound | ¹H-NMR |
|---|---|
| 571 | ¹H-NMR (CDCl₃) δ: 7.28-7.25 (1H, m), 7.21-7.18 (1H, m), 7.03 (1H, td, J = 7.4, 2.0 Hz), 6.99 (1H, td, J = 7.4, 1.2 Hz), 6.93 (1H, ddd, J = 9.7, 8.2, 1.2 Hz), 6.64-6.59 (2H, m), 3.41 (3H, s), 2.26 (3H, d, J = 1.0 Hz). |
| 572 | ¹H-NMR (CDCl₃) δ: 7.80 (1H, d, J = 1.0 Hz), 7.23-7.17 (1H, m), 7.04 (1H, td, J = 7.4, 2.1 Hz), 7.01-6.97 (1H, m), 6.94 (1H, ddd, J = 9.7, 8.3, 1.2 Hz), 6.40-6.37 (2H, m), 3.76 (3H, s), 3.47 (3H, s). |
| 573 | ¹H-NMR (CDCl₃) δ: 7.04 (1H, dd, J = 8.6, 2.8 Hz), 6.98 (1H, ddd, J = 7.9, 6.1, 1.8 Hz), 6.76 (1H, td, J = 7.9, 2.8 Hz), 6.59 (1H, tt, J = 8.9, 2.1 Hz), 6.54 (1H, tt, J = 8.9, 2.1 Hz), 3.47 (1H, dq, J = 14.1, 7.0 Hz), 3.35 (1H, dq, J = 14.1, 7.0 Hz), 2.87-2.52 (4H, m), 0.99 (3H, t, J = 7.0 Hz). |
| 574 | ¹H-NMR (CDCl₃) δ: 7.05 (1H, dd, J = 8.6, 2.8 Hz), 6.97 (1H, ddd, J = 8.3, 6.1, 1.8 Hz), 6.76 (1H, td, J = 8.3, 2.8 Hz), 6.60 (1H, tt, J = 8.7, 2.1 Hz), 6.54 (1H, tt, J = 8.7, 2.1 Hz), 2.89 (3H, s), 2.87-2.77 (2H, m), 2.72-2.69 (1H, m), 2.59-2.55 (1H, m). |
| 575 | ¹H-NMR (CDCl₃) δ: 7.28 (1H, d, J = 9.2 Hz), 7.07 (1H, dd, J = 8.6, 2.8 Hz), 7.05-7.02 (1H, m), 6.81 (1H, ddd, J = 8.6, 8.0, 2.8 Hz), 6.74 (1H, d, J = 9.2 Hz), 6.67-6.62 (2H, m), 3.91-3.88 (2H, m), 1.16 (3H, t, J = 7.0 Hz). |
| 576 | ¹H-NMR (CDCl₃) δ: 7.30 (1H, d, J = 9.5 Hz), 7.08 (1H, dd, J = 8.5, 2.5 Hz), 7.02 (1H, ddd, J = 8.5, 6.0, 1.8 Hz), 6.82 (1H, ddd, J = 8.6, 8.0, 2.5 Hz), 6.76 (1H, d, J = 9.5 Hz), 6.69-6.61 (2H, m), 3.38 (3H, s). |
| 577 | ¹H-NMR (CDCl₃) δ: 7.52 (1H, s), 7.08 (1H, dd, J = 8.4, 2.6 Hz), 7.05 (1H, ddd, J = 8.6, 6.1, 1.8 Hz), 6.82 (1H, ddd, J = 8.6, 8.0, 2.6 Hz), 6.69-6.61 (2H, m), 3.96-3.93 (2H, m), 1.18 (3H, t, J = 7.0 Hz). |
| 578 | ¹H-NMR (CDCl₃) δ: 7.72 (1H, s), 7.08 (1H, dd, J = 8.6, 2.6 Hz), 7.04 (1H, ddd, J = 8.6, 6.1, 1.8 Hz), 6.82 (1H, ddd, J = 8.6, 8.0, 2.6 Hz), 6.69-6.62 (2H, m), 3.96-3.93 (2H, m), 1.18 (3H, t, J = 7.0 Hz). |
| 579 | ¹H-NMR (CDCl₃) δ: 7.29 (1H, dd, J = 9.5, 0.9 Hz), 6.81-6.75 (1H, m), 6.73 (1H, d, J = 9.5 Hz), 6.58-6.55 (1H, m), 6.43-6.40 (2H, m), 3.99 (2H, q, J = 7.0 Hz), 3.93 (2H, q, J = 7.0 Hz), 1.42 (3H, t, J = 7.0 Hz), 1.14 (3H, t, J = 7.0 Hz). |
| 580 | ¹H-NMR (CDCl₃) δ: 7.53 (1H, d, J = 0.6 Hz), 6.83-6.78 (1H, m), 6.59-6.57 (1H, m), 6.43-6.41 (2H, m), 4.01-3.96 (4H, m), 1.42 (3H, t, J = 7.0 Hz), 1.17 (3H, t, J = 7.0 Hz). |
| 581 | ¹H-NMR (CDCl₃) δ: 7.23-7.21 (1H, m), 7.15 (1H, d, J = 8.8 Hz), 6.84 (1H, t, J = 8.5 Hz), 6.78 (1H, t, J = 8.5 Hz), 6.62 (1H, dd, J = 8.8, 3.2 Hz), 6.56-6.54 (1H, m), 4.19-4.11 (1H, m), 3.97-3.90 (1H, m), 3.64 (3H, s), 3.44-3.36 (1H, m), 3.31-3.23 (1H, m), 2.75-2.68 (1H, m), 2.50-2.42 (1H, m), 1.10 (3H, t, J = 7.1 Hz). |
| 582 | ¹H-NMR (CDCl₃) δ: 7.85 (1H, d, J = 9.0 Hz), 7.38-7.30 (1H, m), 7.18 (1H, d, J = 9.0 Hz), 7.14 (1H, d, J = 9.0 Hz), 6.94-6.89 (1H, m), 6.88-6.83 (1H, m), 6.69 (1H, dd, J = 8.9, 3.1 Hz), 6.59-6.58 (1H, m), 4.64-4.52 (2H, m), 3.65 (3H, s), 1.28 (3H, t, J = 7.2 Hz). |
| 583 | ¹H-NMR (CDCl₃) δ: 6.74 (1H, td, J = 8.5, 2.9 Hz), 6.66-6.55 (3H, m), 3.49-3.42 (1H, m), 3.40-3.33 (1H, m), 2.88-2.82 (1H, m), 2.79-2.74 (1H, m), 2.72-2.67 (1H, m), 2.60-2.54 (1H, m), 0.99 (3H, t, J = 7.2 Hz). |
| 584 | ¹H-NMR (CDCl₃) δ: 7.26 (1H, d, J = 9.5 Hz), 6.81 (1H, td, J = 8.5, 2.9 Hz), 6.75 (1H, d, J = 9.5 Hz), 6.73-6.69 (1H, m), 6.67-6.63 (2H, m), 3.89 (2H, q, J = 7.0 Hz), 1.16 (3H, t, J = 7.0 Hz). |
| 585 | ¹H-NMR (CDCl₃) δ: 7.50 (1H, s), 6.83 (1H, td, J = 8.4, 3.0 Hz), 6.74-6.69 (1H, m), 6.69-6.65 (2H, m), 3.98-3.90 (2H, m), 1.19 (3H, t, J = 7.0 Hz). |
| 586 | ¹H-NMR (CDCl₃) δ: 7.28 (1H, d, J = 9.5 Hz), 6.82 (1H, td, J = 8.4, 2.9 Hz), 6.77 (1H, d, J = 9.5 Hz), 6.74-6.62 (3H, m), 3.38 (3H, s). |
| 587 | ¹H-NMR (CDCl₃) δ: 7.52 (1H, s), 6.84 (1H, td, J = 8.4, 2.8 Hz), 6.74-6.64 (3H, m), 3.45 (3H, s). |
| 588 | ¹H-NMR (CDCl₃) δ: 7.32 (1H, dd, J = 9.4, 0.9 Hz), 7.03-6.98 (1H, m), 6.93-6.88 (1H, m), 6.81-6.78 (1H, m), 6.73 (1H, d, J = 9.4 Hz), 6.41-6.38 (2H, m), 3.93 (2H, q, J = 7.1 Hz), 3.78 (3H, s), 1.14 (3H, t, J = 7.1 Hz). |
| 589 | ¹H-NMR (CDCl₃) δ: 7.76 (1H, d, J = 0.9 Hz), 7.06-7.00 (1H, m), 6.95-6.90 (1H, m), 6.82-6.79 (1H, m), 6.42-6.39 (2H, m), 3.99 (2H, q, J = 7.0 Hz), 3.78 (3H, s), 1.17 (3H, t, J = 7.0 Hz). |
| 590 | ¹H-NMR (CDCl₃) δ: 7.56 (1H, d, J = 0.6 Hz), 7.06-7.00 (1H, m), 6.95-6.90 (1H, m), 6.82-6.79 (1H, m), 6.42-6.39 (2H, m), 3.98 (2H, q, J = 7.1 Hz), 3.78 (3H, s), 1.17 (3H, t, J = 7.1 Hz). |
| 591 | ¹H-NMR (CDCl₃) δ: 7.37 (1H, dd, J = 9.5, 0.9 Hz), 7.20-7.16 (1H, m), 7.03 (1H, td, J = 7.6, 2.1 Hz), 6.98-6.94 (2H, m), 6.73 (1H, d, J = 9.5 Hz), 6.37-6.35 (2H, m), 3.95 (2H, q, J = 7.0 Hz), 3.40 (3H, s), 1.39 (3H, t, J = 7.0 Hz). |
| 592 | ¹H-NMR (CDCl₃) δ: 7.10 (1H, d, J = 9.3 Hz), 7.07-7.04 (2H, m), 6.82 (1H, ddd, J = 8.8, 8.1, 2.8 Hz), 6.67 (1H, tt, J = 8.6, 2.1 Hz), 6.63 (1H, tt, J = 8.6, 2.1 Hz), 3.94 (2H, q, J = 7.1 Hz), 1.17 (3H, t, J = 7.1 Hz). |
| 593 | ¹H-NMR (CDCl₃) δ: 7.51 (1H, s), 7.08-7.03 (2H, m), 6.81 (1H, ddd, J = 8.8, 8.1, 2.8 Hz), 6.43-6.39 (1H, m), 6.39-6.34 (1H, m), 3.96 (2H, q, J = 7.2 Hz), 3.77 (3H, s), 1.17 (3H, t, J = 7.2 Hz). |
| 594 | ¹H-NMR (CDCl₃) δ: 7.17 (1H, q, J = 0.9 Hz), 7.06-7.03 (2H, m), 6.80 (1H, td, J = 8.3, 2.7 Hz), 6.66-6.59 (2H, m), 3.90 (2H, q, J = 7.2 Hz), 2.25 (3H, d, J = 0.9 Hz), 1.15 (3H, t, J = 7.2 Hz). |
| 595 | ¹H-NMR (CDCl₃) δ: 7.51 (1H, s), 7.08-7.03 (2H, m), 6.80 (1H, ddd, J = 8.8, 8.0, 2.8 Hz), 6.39 (1H, dt, J = 10.8, 2.0 Hz), 6.34 (1H, dt, J = 10.8, 2.0 Hz), 3.97-3.95 (4H, m), 1.40 (3H, t, J = 7.1 Hz), 1.17 (3H, t, J = 7.1 Hz). |
| 596 | ¹H-NMR (CDCl₃) δ: 7.54 (1H, s), 7.08 (1H, dd, J = 8.4, 2.8 Hz), 7.04 (1H, ddd, J = 8.0, 6.1, 1.8 Hz), 6.84 (1H, ddd, J = 8.8, 8.0, 2.8 Hz), 6.67-6.65 (2H, m), 3.45 (3H, s). |
| 597 | ¹H-NMR (CDCl₃) δ: 7.74 (1H, s), 7.08 (1H, dd, J = 8.3, 2.8 Hz), 7.06-7.01 (1H, m), 6.84 (1H, ddd, J = 8.9, 8.0, 2.8 Hz), 6.68 (1H, dt, J = 8.5, 2.1 Hz), 6.63 (1H, dt, J = 8.5, 2.1 Hz), 3.45 (3H, s). |
| 598 | ¹H-NMR (CDCl₃) δ: 7.60 (1H, d, J = 1.0 Hz), 7.21-7.17 (1H, m), 7.04-6.92 (3H, m), 6.38-6.35 (2H, m), 3.95 (2H, q, J = 7.0 Hz), 3.47 (3H, s), 1.39 (3H, t, J = 7.0 Hz). |

TABLE 5-continued

| Compound | ¹H-NMR |
|---|---|
| 599 | ¹H-NMR (CDCl₃) δ: 7.16 (1H, q, J = 0.9 Hz), 7.06-7.03 (2H, m), 6.78 (1H, td, J = 8.3, 2.7 Hz), 6.40 (1H, dt, J = 10.7, 1.8 Hz), 6.35 (1H, dt, J = 10.6, 1.9 Hz), 3.93-3.90 (2H, m), 3.77 (3H, s), 2.24 (3H, d, J = 0.9 Hz), 1.15 (3H, t, J = 7.0 Hz). |
| 600 | ¹H-NMR (CDCl₃) δ: 7.53 (1H, s), 7.08 (1H, dd, J = 8.4, 2.8 Hz), 7.03 (1H, ddd, J = 8.0, 6.0, 1.7 Hz), 6.82 (1H, ddd, J = 8.8, 8.0, 2.8 Hz), 6.41 (1H, dt, J = 10.8, 1.9 Hz), 6.37 (1H, dt, J = 10.8, 1.9 Hz), 3.77 (3H, s), 3.45 (3H, s). |
| 601 | ¹H-NMR (CDCl₃) δ: 7.30-7.27 (2H, m), 6.97 (1H, dt, J = 8.4, 1.8 Hz), 6.92-6.88 (2H, m), 6.80 (1H, m), 6.74 (1H, d, J = 9.2 Hz), 3.92-3.85 (2H, m), 1.16 (3H, t, J = 7.0 Hz). |
| 602 | ¹H-NMR (CDCl₃) δ: 7.52 (1H, s), 7.29 (1H, dd, J = 8.8, 5.1 Hz), 6.97 (1H, dt, J = 8.5, 1.8 Hz), 6.93-6.90 (2H, m), 6.82 (1H, m), 4.01-3.86 (2H, m), 1.18 (3H, t, J = 7.1 Hz). |
| 603 | ¹H-NMR (CDCl₃) δ: 7.73 (1H, s), 7.29 (1H, dd, J = 8.9, 5.2 Hz), 6.97 (1H, dt, J = 8.4, 1.8 Hz), 6.94-6.90 (2H, m), 6.81 (1H, m), 4.00-3.87 (2H, m), 1.18 (3H, t, J = 7.2 Hz). |
| 604 | ¹H-NMR (CDCl₃) δ: 7.31-7.28 (2H, m), 6.97 (1H, dt, J = 8.6, 1.7 Hz), 6.93-6.89 (2H, m), 6.79 (1H, m), 6.76 (1H, d, J = 9.5 Hz), 3.37 (3H, s). |
| 605 | ¹H-NMR (CDCl₃) δ: 7.54 (1H, s), 7.29 (1H, dd, J = 8.9, 5.2 Hz), 6.97 (1H, m), 6.95-6.91 (2H, m), 6.81 (1H, m), 3.44 (3H, s). |
| 606 | ¹H-NMR (CDCl₃) δ: 7.74 (1H, s), 7.29 (1H, dd, J = 8.8, 5.1 Hz), 6.98-6.90 (3H, m), 6.81 (1H, m), 3.44 (3H, s). |
| 607 | ¹H-NMR (CDCl₃) δ: 7.33 (1H, d, J = 9.5 Hz), 6.83 (1H, td, J = 8.4, 2.8 Hz), 6.78 (1H, d, J = 9.5 Hz), 6.74-6.63 (3H, m), 6.15 (1H, tt, J = 56.6, 4.5 Hz), 4.22-4.09 (2H, m). |
| 608 | ¹H-NMR (CDCl₃) δ: 7.57 (1H, s), 6.86 (1H, td, J = 8.3, 2.9 Hz), 6.73-6.65 (3H, m), 6.17 (1H, tt, J = 56.4, 4.5 Hz), 4.29-4.10 (2H, m). |
| 609 | ¹H-NMR (CDCl₃) δ: 7.23-7.22 (1H, m), 7.05-6.99 (1H, m), 6.94-6.89 (1H, m), 6.81-6.78 (1H, m), 6.66-6.62 (2H, m), 3.92 (2H, q, J = 7.0 Hz), 2.25 (3H, d, J = 0.9 Hz), 1.15 (3H, t, J = 7.0 Hz). |
| 610 | ¹H-NMR (CDCl₃) δ: 7.22-7.21 (1H, m), 7.03-6.96 (1H, m), 6.92-6.86 (1H, m), 6.82-6.77 (1H, m), 6.41-6.37 (2H, m), 3.94 (2H, q, J = 7.1 Hz), 3.77 (3H, s), 2.24 (3H, d, J = 1.2 Hz), 1.14 (3H, t, J = 7.1 Hz). |
| 611 | ¹H-NMR (CDCl₃) δ: 7.22-7.21 (1H, m), 7.03-6.96 (1H, m), 6.92-6.86 (1H, m), 6.82-6.77 (1H, m), 6.39-6.35 (2H, m), 3.99-3.91 (4H, m), 2.24 (3H, d, J = 1.0 Hz), 2.05 (1H, s), 1.40 (3H, t, J = 7.0 Hz), 1.14 (3H, t, J = 7.1 Hz). |
| 612 | ¹H-NMR (CDCl₃) δ: 7.30 (1H, d, J = 9.5 Hz), 7.07 (1H, dd, J = 8.6, 2.8 Hz), 7.03-7.00 (1H, m), 6.80 (1H, td, J = 8.3, 2.8 Hz), 6.73 (1H, d, J = 9.5 Hz), 6.40 (1H, dt, J = 11.0, 1.8 Hz), 6.34 (1H, dt, J = 11.0, 1.8 Hz), 3.96 (2H, q, J = 7.0 Hz), 3.39 (3H, s), 1.40 (3H, t, J = 7.0 Hz). |
| 613 | ¹H-NMR (CDCl₃) δ: 7.19 (1H, d, J = 1.2 Hz), 7.07 (1H, dd, J = 8.3, 2.8 Hz), 7.04-7.00 (1H, m), 6.81 (1H, ddd, J = 8.6, 8.0, 2.8 Hz), 6.66-6.64 (1H, m), 6.61-6.60 (1H, m), 3.39 (3H, s), 2.25 (3H, d, J = 1.2 Hz). |
| 614 | ¹H-NMR (CDCl₃) δ: 6.61 (1H, tt, J = 8.3, 2.8 Hz), 6.58-6.55 (1H, m), 6.53 (1H, dd, J = 10.5, 2.9 Hz), 6.39-6.38 (1H, m), 3.67 (3H, s), 3.47-3.44 (1H, m), 3.39-3.34 (1H, m), 2.89-2.82 (1H, m), 2.79-2.75 (1H, m), 2.71-2.68 (1H, m), 2.59-2.53 (1H, m), 0.99 (3H, t, J = 7.2 Hz). |
| 615 | ¹H-NMR (CDCl₃) δ: 7.29 (1H, d, J = 9.5 Hz), 6.74 (1H, d, J = 9.5 Hz), 6.71-6.62 (2H, m), 6.59 (1H, dd, J = 10.4, 3.1 Hz), 6.44-6.43 (1H, m), 3.91-3.85 (2H, m), 3.68 (3H, s), 1.16 (3H, t, J = 7.0 Hz). |
| 616 | ¹H-NMR (CDCl₃) δ: 7.53 (1H, s), 7.07 (1H, dd, J = 8.6, 2.8 Hz), 7.03 (1H, ddd, J = 8.6, 6.1, 1.7 Hz), 6.82 (1H, ddd, J = 8.6, 8.0, 2.8 Hz), 6.39 (1H, dt, J = 10.8, 1.8 Hz), 6.35 (1H, dt, J = 10.8, 1.8 Hz), 3.96 (2H, q, J = 7.0 Hz), 3.45 (3H, s), 1.40 (3H, t, J = 7.0 Hz). |
| 617 | ¹H-NMR (CDCl₃) δ: 7.52 (1H, s), 6.71-6.64 (2H, m), 6.61 (1H, dd, J = 10.4, 2.8 Hz), 6.45-6.44 (1H, m), 3.98-3.92 (2H, m), 3.69 (3H, s), 1.19 (3H, t, J = 7.0 Hz). |
| 618 | ¹H-NMR (CDCl₃) δ: 7.31 (1H, d, J = 9.2 Hz), 7.03 (1H, dd, J = 8.3, 8.0 Hz), 6.79 (1H, dd, J = 8.3, 1.4 Hz), 6.74 (1H, d, J = 9.2 Hz), 6.67-6.63 (2H, m), 6.58 (1H, tt, J = 8.7, 2.1 Hz), 3.96-3.83 (5H, m), 1.16 (3H, t, J = 7.0 Hz). |
| 619 | ¹H-NMR (CDCl₃) δ: 7.54 (1H, s), 7.04 (1H, dd, J = 8.3, 7.6 Hz), 6.81 (1H, dd, J = 8.3, 1.2 Hz), 6.68-6.63 (2H, m), 6.59 (1H, tt, J = 8.6, 2.0 Hz), 3.99-3.90 (2H, m), 3.86 (3H, s), 1.18 (3H, t, J = 7.0 Hz). |
| 620 | ¹H-NMR (CDCl₃) δ: 7.74 (1H, s), 7.04 (1H, dd, J = 8.3, 7.8 Hz), 6.81 (1H, dd, J = 8.3, 1.2 Hz), 6.68-6.57 (3H, m), 4.01-3.89 (2H, m), 3.86 (3H, s), 1.18 (3H, t, J = 7.1 Hz). |
| 621 | ¹H-NMR (CDCl₃) δ: 7.19 (1H, d, J = 1.2 Hz), 7.06 (1H, dd, J = 8.6, 2.8 Hz), 7.04-7.01 (1H, m), 6.80 (1H, td, J = 8.3, 2.5 Hz), 6.40 (1H, dt, J = 10.7, 1.8 Hz), 6.36 (1H, dt, J = 10.5, 1.9 Hz), 3.76 (3H, s), 3.39 (3H, s), 2.25 (3H, d, J = 1.2 Hz). |
| 622 | ¹H-NMR (CDCl₃) δ: 7.46 (1H, d, J = 2.0 Hz), 7.16 (1H, dd, J = 8.3, 2.0 Hz), 6.87 (1H, dd, J = 8.3, 2.0 Hz), 6.63-6.52 (2H, m), 3.51-3.44 (1H, m), 3.38-3.31 (1H, m), 2.75-2.62 (4H, m), 0.98 (3H, t, J = 7.1 Hz). |
| 623 | ¹H-NMR (CDCl₃) δ: 7.28 (1H, d, J = 9.5 Hz), 6.72 (1H, d, J = 9.5 Hz), 6.57 (1H, dd, J = 10.4, 3.1 Hz), 6.46-6.42 (2H, m), 6.38 (1H, dt, J = 10.4, 2.0 Hz), 3.92-3.87 (2H, m), 3.78 (3H, s), 3.68 (3H, s), 1.16 (3H, t, J = 7.0 Hz). |
| 624 | ¹H-NMR (CDCl₃) δ: 7.50 (1H, d, J = 2.0 Hz), 7.26 (1H, d, J = 9.5 Hz), 7.21 (1H, dd, J = 8.3, 2.0 Hz), 6.92 (1H, dd, J = 8.3, 2.0 Hz), 6.74 (1H, d, J = 9.5 Hz), 6.70-6.60 (2H, m), 3.90-3.87 (2H, m), 1.15 (3H, t, J = 7.1 Hz). |
| 625 | ¹H-NMR (CDCl₃) δ: 7.51 (1H, d, J = 1.8 Hz), 7.50 (1H, s), 7.23 (1H, dd, J = 8.3, 1.8 Hz), 6.93 (1H, dd, J = 8.3, 1.8 Hz), 6.70-6.62 (2H, m), 3.94 (2H, q, J = 7.0 Hz), 1.18 (3H, t, J = 7.0 Hz). |
| 626 | ¹H-NMR (CDCl₃) δ: 7.30 (1H, d, J = 9.5 Hz), 7.13 (1H, dd, J = 1.7, 0.9 Hz), 6.91 (1H, dd, J = 7.8, 1.7 Hz), 6.86 (1H, ddd, J = 7.8, 1.7, 0.9 Hz), 6.72 (1H, d, J = 9.5 Hz), 6.65 (1H, tt, J = 8.7, 2.1 Hz), 6.59 (1H, tt, J = 8.7, 2.1 Hz), 3.94-3.84 (2H, m), 2.26 (3H, s), 1.15 (3H, t, J = 7.0 Hz). |
| 627 | ¹H-NMR (CDCl₃) δ: 7.51 (1H, s), 6.59 (1H, dd, J = 10.4, 2.8 Hz), 6.47-6.45 (1H, m), 6.43-6.39 (2H, m), 3.96 (2H, q, J = 7.1 Hz), 3.78 (3H, s), 3.68 (3H, s), 1.18 (3H, t, J = 7.1 Hz). |

TABLE 5-continued

| Compound | ¹H-NMR |
|---|---|
| 628 | ¹H-NMR (CDCl₃) δ: 7.53 (1H, s), 7.14 (1H, m), 6.92 (1H, dd, J = 8.0, 1.8 Hz), 6.88-6.86 (1H, m), 6.66 (1H, tt, J = 8.7, 2.1 Hz), 6.61 (1H, tt, J = 8.7, 2.1 Hz), 3.96-3.93 (2H, m), 2.27 (3H, s), 1.18 (3H, t, J = 7.0 Hz). |
| 629 | ¹H-NMR (CDCl₃) δ: 7.37-7.30 (2H, m), 7.04-6.98 (1H, m), 6.87 (2H, dd, J = 8.4, 7.2 Hz), 6.73 (1H, d, J = 9.3 Hz), 6.71-6.65 (2H, m), 3.92 (2H, q, J = 7.1 Hz), 1.14 (3H, t, J = 7.1 Hz). |
| 630 | ¹H-NMR (CDCl₃) δ: 7.55 (1H, s), 7.38-7.31 (1H, m), 7.04-6.98 (1H, m), 6.88 (2H, dd, J = 8.5, 7.3 Hz), 6.73-6.66 (2H, m), 3.97 (2H, q, J = 7.1 Hz), 1.17 (3H, t, J = 7.1 Hz). |
| 631 | ¹H-NMR (CDCl₃) δ: 7.38-7.31 (2H, m), 7.03-6.97 (1H, m), 6.87 (2H, dd, J = 8.3, 7.3 Hz), 6.75 (1H, d, J = 9.3 Hz), 6.73-6.65 (2H, m), 3.39 (3H, s). |
| 632 | ¹H-NMR (CDCl₃) δ: 7.20-7.19 (1H, m), 7.02 (1H, dd, J = 8.3, 7.6 Hz), 6.78 (1H, dd, J = 8.3, 1.5 Hz), 6.67 (1H, ddd, J = 7.6, 1.7, 1.5 Hz), 6.63 (1H, tt, J = 8.9, 2.1 Hz), 6.57 (1H, tt, J = 8.7, 2.1 Hz), 3.96-3.85 (5H, m), 2.24 (3H, d, J = 1.2 Hz), 1.16 (3H, t, J = 7.2 Hz). |
| 633 | ¹H-NMR (CDCl₃) δ: 7.30 (1H, d, J = 9.3 Hz), 7.02 (1H, dd, J = 8.4, 7.6 Hz), 6.78 (1H, dd, J = 8.4, 1.5 Hz), 6.72 (1H, d, J = 9.3 Hz), 6.68 (1H, dt, J = 7.6, 1.5 Hz), 6.42-6.39 (1H, m), 6.34-6.31 (1H, m), 4.00-3.93 (1H, m), 3.90-3.82 (4H, m), 3.75 (3H, s), 1.16 (3H, t, J = 7.0 Hz). |
| 634 | ¹H-NMR (CDCl₃) δ: 7.30 (1H, d, J = 9.5 Hz), 7.01 (1H, dd, J = 8.3, 7.6 Hz), 6.78 (1H, dd, J = 8.3, 1.5 Hz), 6.71 (1H, d, J = 9.5 Hz), 6.68 (1H, dt, J = 7.6, 1.5 Hz), 6.40-6.37 (1H, m), 6.32-6.29 (1H, m), 4.00-3.92 (3H, m), 3.90-3.82 (4H, m), 1.38 (3H, t, J = 7.0 Hz), 1.15 (3H, t, J = 7.2 Hz). |
| 635 | ¹H-NMR (CDCl₃) δ: 7.28 (1H, dd, J = 9.5, 0.6 Hz), 6.91-6.88 (1H, m), 6.83-6.81 (1H, m), 6.75 (1H, d, J = 9.5 Hz), 6.71-6.67 (2H, m), 3.90 (2H, q, J = 7.1 Hz), 1.14 (3H, t, J = 7.1 Hz). |
| 636 | ¹H-NMR (CDCl₃) δ: 7.53 (1H, d, J = 0.5 Hz), 6.93-6.89 (1H, m), 6.85-6.82 (1H, m), 6.73-6.67 (2H, m), 3.95 (2H, q, J = 7.1 Hz), 1.17 (3H, t, J = 7.1 Hz). |
| 637 | ¹H-NMR (CDCl₃) δ: 7.52 (1H, d, J = 0.7 Hz), 6.93-6.80 (2H, m), 6.45-6.42 (2H, m), 3.97 (2H, q, J = 7.1 Hz), 3.80 (3H, s), 1.16 (3H, t, J = 7.1 Hz). |
| 638 | ¹H-NMR (CDCl₃) δ: 7.28-7.27 (1H, m), 6.91-6.79 (2H, m), 6.72 (1H, d, J = 9.5 Hz), 6.44-6.42 (2H, m), 3.92 (2H, q, J = 7.1 Hz), 3.80 (3H, s), 1.14 (3H, t, J = 7.1 Hz). |
| 639 | ¹H-NMR (CDCl₃) δ: 7.31 (1H, dd, J = 9.5, 0.6 Hz), 6.93-6.79 (2H, m), 6.76 (1H, d, J = 9.2 Hz), 6.72-6.68 (2H, m), 3.39 (3H, s). |
| 640 | ¹H-NMR (CDCl₃) δ: 7.53 (1H, s), 7.03 (1H, dd, J = 8.3, 7.6 Hz), 6.79 (1H, dd, J = 8.3, 1.5 Hz), 6.70-6.67 (1H, m), 6.42-6.39 (1H, m), 6.35-6.32 (1H, m), 4.03-3.89 (2H, m), 3.86 (3H, s), 3.75 (3H, s), 1.18 (3H, t, J = 7.0 Hz). |
| 641 | ¹H-NMR (CDCl₃) δ: 7.53 (1H, s), 7.03 (1H, dd, J = 8.3, 7.8 Hz), 6.79 (1H, dd, J = 8.3, 1.2 Hz), 6.69-6.67 (1H, m), 6.40-6.37 (1H, m), 6.33-6.30 (1H, m), 4.03-3.90 (4H, m), 3.86 (3H, s), 1.38 (3H, t, J = 7.0 Hz), 1.18 (3H, t, J = 7.2 Hz). |
| 642 | ¹H-NMR (CDCl₃) δ: 7.73 (1H, s), 7.03 (1H, dd, J = 8.3, 7.7 Hz), 6.79 (1H, dd, J = 8.3, 1.5 Hz), 6.69-6.67 (1H, m), 6.42-6.39 (1H, m), 6.35-6.32 (1H, m), 4.02-3.90 (2H, m), 3.86 (3H, s), 3.75 (3H, s), 1.18 (3H, t, J = 7.0 Hz). |
| 643 | ¹H-NMR (CDCl₃) δ: 7.73 (1H, s), 7.03 (1H, dd, J = 8.3, 7.6 Hz), 6.79 (1H, dd, J = 8.3, 1.5 Hz), 6.68 (1H, dt, J = 7.6, 1.5 Hz), 6.40-6.37 (1H, m), 6.33-6.30 (1H, m), 4.03-3.89 (4H, m), 3.86 (3H, s), 1.38 (3H, t, J = 7.0 Hz), 1.17 (3H, t, J = 7.0 Hz). |
| 644 | ¹H-NMR (CDCl₃) δ: 7.19 (1H, m), 7.01 (1H, dd, J = 8.3, 7.7 Hz), 6.77 (1H, dd, J = 8.3, 1.5 Hz), 6.69 (1H, ddd, J = 7.7, 1.6, 1.5 Hz), 6.40-6.37 (1H, m), 6.34-6.31 (1H, m), 3.99-3.84 (5H, m), 3.75 (3H, s), 2.24 (3H, d, J = 0.9 Hz), 1.15 (3H, t, J = 7.2 Hz). |
| 645 | ¹H-NMR (CDCl₃) δ: 7.19 (1H, d, J = 1.2 Hz), 7.01 (1H, dd, J = 8.3, 7.9 Hz), 6.77 (1H, dd, J = 8.3, 1.2 Hz), 6.69 (1H, ddd, J = 7.9, 1.4, 1.2 Hz), 6.39-6.36 (1H, m), 6.31-6.29 (1H, m), 3.98-3.86 (7H, m), 2.23 (3H, d, J = 0.9 Hz), 1.38 (3H, t, J = 7.0 Hz), 1.15 (3H, t, J = 7.0 Hz). |
| 646 | ¹H-NMR (CDCl₃) δ: 7.57 (1H, d, J = 0.7 Hz), 7.39-7.32 (1H, m), 7.04-6.98 (1H, m), 6.88 (2H, dd, J = 8.4, 7.4 Hz), 6.74-6.66 (2H, m), 3.46 (3H, s). |
| 647 | ¹H-NMR (CDCl₃) δ: 7.40-7.34 (2H, m), 7.04-6.99 (1H, m), 6.88 (2H, dd, J = 8.6, 7.3 Hz), 6.76 (1H, d, J = 9.2 Hz), 6.73-6.66 (2H, m), 6.15 (1H, tt, J = 56.6, 4.5 Hz), 4.21-4.15 (2H, m). |
| 648 | ¹H-NMR (CDCl₃) δ: 7.62 (1H, d, J = 0.7 Hz), 7.42-7.35 (1H, m), 7.06-7.00 (1H, m), 6.89 (2H, dd, J = 8.4, 7.4 Hz), 6.76-6.66 (2H, m), 6.17 (1H, tt, J = 56.5, 4.5 Hz), 4.26-4.19 (2H, m). |
| 649 | ¹H-NMR (CDCl₃) δ: 7.85 (1H, d, J = 9.2 Hz), 7.05 (1H, d, J = 9.2 Hz), 6.86-6.82 (1H, m), 6.76-6.72 (1H, m), 6.71-6.64 (2H, m), 4.59-4.91 (2H, m), 1.27 (3H, t, J = 7.0 Hz). |
| 650 | ¹H-NMR (CDCl₃) δ: 7.47 (1H, dd, J = 8.2, 1.3 Hz), 7.10-6.99 (3H, m), 6.60-6.49 (2H, m), 3.50-3.43 (1H, m), 3.40-3.33 (1H, m), 2.95-2.79 (2H, m), 2.71-2.68 (1H, m), 2.61-2.53 (1H, m), 0.99 (3H, t, J = 7.1 Hz). |
| 651 | ¹H-NMR (CDCl₃) δ: 7.52 (1H, ddd, J = 7.5, 1.5, 0.7 Hz), 7.32 (1H, d, J = 9.3 Hz), 7.11-7.06 (3H, m), 6.74 (1H, d, J = 9.3 Hz), 6.66 (1H, tt, J = 8.8, 2.1 Hz), 6.58 (1H, tt, J = 8.8, 2.1 Hz), 3.93-3.86 (2H, m), 1.17 (3H, t, J = 7.1 Hz). |
| 652 | ¹H-NMR (CDCl₃) δ: 7.55 (1H, s), 7.54-7.52 (1H, m), 7.15-7.04 (3H, m), 6.66 (1H, tt, J = 8.8, 2.1 Hz), 6.60 (1H, tt, J = 8.8, 2.1 Hz), 3.96-3.93 (2H, m), 1.19 (3H, t, J = 7.1 Hz). |
| 653 | ¹H-NMR (CDCl₃) δ: 7.55 (1H, s), 6.93-6.91 (1H, m), 6.85-6.82 (1H, m), 6.73-6.69 (2H, m), 3.46 (3H, s). |
| 654 | ¹H-NMR (CDCl₃) δ: 7.30 (1H, dd, J = 9.5, 0.9 Hz), 6.90-6.87 (1H, m), 6.83-6.80 (1H, m), 6.73 (1H, d, J = 9.5 Hz), 6.45-6.42 (2H, m), 3.80 (3H, s), 3.39 (3H, s). |
| 655 | ¹H-NMR (CDCl₃) δ: 7.53 (1H, d, J = 0.7 Hz), 6.93-6.80 (2H, m), 6.45-6.42 (2H, m), 3.80 (3H, s), 3.46 (3H, s). |
| 656 | ¹H-NMR (CDCl₃) δ: 7.73 (1H, s), 7.07-6.99 (2H, m), 6.88-6.87 (1H, m), 6.42-6.34 (2H, m), 4.01-3.93 (2H, m), 3.76 (3H, s), 1.18 (3H, t, J = 7.0 Hz). |
| 657 | ¹H-NMR (CDCl₃) δ: 7.29 (1H, d, J = 9.3 Hz), 7.06-6.97 (2H, m), 6.88-6.85 (1H, m), 6.72 (1H, d, J = 9.3 Hz), 6.41-6.31 (2H, m), 4.00-3.84 (4H, m), 1.39 (3H, t, J = 7.0 Hz), 1.15 (3H, t, J = 7.1 Hz). |
| 658 | ¹H-NMR (CDCl₃) δ: 7.52 (1H, s), 7.08-6.99 (2H, m), 6.89-6.86 (1H, m), 6.41-6.32 (2H, m), 4.04-3.90 (4H, m), 1.39 (3H, t, J = 7.0 Hz), 1.18 (3H, t, J = 7.1 Hz). |
| 659 | ¹H-NMR (CDCl₃) δ: 7.72 (1H, s), 7.08-6.99 (2H, m), 6.89-6.86 (1H, m), 6.40-6.32 (2H, m), 4.04-3.90 (4H, m), 1.39 (3H, t, J = 7.0 Hz), 1.18 (3H, t, J = 7.1 Hz). |

TABLE 5-continued

| Compound | ¹H-NMR |
|---|---|
| 660 | ¹H-NMR (CDCl₃) δ: 7.18 (1H, d, J = 1.2 Hz), 7.05-6.96 (2H, m), 6.88-6.86 (1H, m), 6.39-6.31 (2H, m), 3.99-3.86 (4H, m), 2.24 (3H, d, J = 1.2 Hz), 1.39 (3H, t, J = 7.0 Hz), 1.15 (3H, t, J = 7.0 Hz). |
| 661 | ¹H-NMR (CDCl₃) δ: 7.33 (1H, d, J = 9.4 Hz), 7.04 (1H, dd, J = 8.4, 8.0 Hz), 6.80 (1H, dd, J = 8.4, 1.4 Hz), 6.75 (1H, d, J = 9.4 Hz), 6.68-6.63 (2H, m), 6.59 (1H, tt, J = 8.9, 2.1 Hz), 3.87 (3H, s), 3.38 (3H, s). |
| 662 | ¹H-NMR (CDCl₃) δ: 7.76 (1H, s), 7.07-7.03 (1H, m), 6.82 (1H, dd, J = 8.3, 1.5 Hz), 6.68-6.57 (3H, m), 3.87 (3H, s), 3.45 (3H, s). |
| 663 | ¹H-NMR (CDCl₃) δ: 7.32 (1H, d, J = 9.4 Hz), 7.04-7.00 (1H, m), 6.79 (1H, dd, J = 8.3, 1.2 Hz), 6.72 (1H, d, J = 9.4 Hz), 6.65 (1H, dt, J = 7.7, 1.5 Hz), 6.43-6.39 (1H, m), 6.35-6.31 (1H, m), 3.87 (3H, s), 3.75 (3H, s), 3.38 (3H, s). |
| 664 | ¹H-NMR (CDCl₃) δ: 7.32 (1H, d, J = 9.5 Hz), 7.02 (1H, dd, J = 8.3, 7.8 Hz), 6.78 (1H, dd, J = 8.3, 1.4 Hz), 6.72 (1H, d, J = 9.5 Hz), 6.65 (1H, dt, J = 7.8, 1.4 Hz), 6.41-6.37 (1H, m), 6.33-6.29 (1H, m), 3.94 (2H, q, J = 7.0 Hz), 3.86 (3H, s), 3.38 (3H, s), 1.38 (3H, t, J = 7.0 Hz). |
| 665 | ¹H-NMR (CDCl₃) δ: 7.25 (1H, d, J = 9.5 Hz), 6.79 (1H, td, J = 8.5, 3.1 Hz), 6.73 (1H, d, J = 9.5 Hz), 6.68-6.65 (1H, m), 6.47-6.44 (1H, m), 6.40-6.37 (1H, m), 3.95-3.87 (2H, m), 3.79 (3H, s), 1.15 (3H, t, J = 7.2 Hz). |
| 666 | ¹H-NMR (CDCl₃) δ: 7.49 (1H, s), 6.81 (1H, td, J = 8.5, 3.0 Hz), 6.69-6.66 (1H, m), 6.47-6.44 (1H, m), 6.41-6.38 (1H, m), 3.96 (2H, q, J = 7.0 Hz), 3.79 (3H, s), 1.18 (3H, t, J = 7.0 Hz). |
| 667 | ¹H-NMR (CDCl₃) δ: 7.53-7.50 (1H, m), 7.31 (1H, d, J = 9.3 Hz), 7.10-7.03 (3H, m), 6.72 (1H, d, J = 9.3 Hz), 6.41 (1H, dt, J = 10.7, 2.0 Hz), 6.33 (1H, dt, J = 10.7, 2.0 Hz), 3.95-3.88 (2H, m), 3.75 (3H, s), 1.16 (3H, t, J = 7.1 Hz). |
| 668 | ¹H-NMR (CDCl₃) δ: 7.54 (1H, s), 7.53-7.51 (1H, m), 7.13-7.04 (3H, m), 6.41 (1H, dt, J = 10.7, 2.0 Hz), 6.34 (1H, dt, J = 10.7, 2.0 Hz), 3.98-3.94 (2H, m), 3.75 (3H, s), 1.18 (3H, t, J = 7.1 Hz). |
| 669 | ¹H-NMR (CDCl₃) δ: 7.75 (1H, s), 7.04 (1H, dd, J = 8.4, 7.8 Hz), 6.80 (1H, dd, J = 8.4, 1.6 Hz), 6.66 (1H, dt, J = 7.8, 1.6 Hz), 6.42-6.39 (1H, m), 6.36-6.33 (1H, m), 3.86 (3H, s), 3.75 (3H, s), 3.45 (3H, s). |
| 670 | ¹H-NMR (CDCl₃) δ: 7.75 (1H, s), 7.04 (1H, dd, J = 8.3, 7.6 Hz), 6.80 (1H, dd, J = 8.3, 1.4 Hz), 6.66 (1H, dt, J = 7.6, 1.4 Hz), 6.40-6.37 (1H, m), 6.33-6.30 (1H, m), 3.94 (2H, q, J = 7.0 Hz), 3.86 (3H, s), 3.45 (3H, s), 1.38 (3H, t, J = 7.0 Hz). |
| 671 | ¹H-NMR (CDCl₃) δ: 7.22 (1H, q, J = 1.2 Hz), 7.03 (1H, dd, J = 8.3, 7.6 Hz), 6.79 (1H, dd, J = 8.3, 1.5 Hz), 6.66-6.56 (3H, m), 3.86 (3H, s), 3.39 (3H, s), 2.25 (3H, d, J = 1.2 Hz). |
| 672 | ¹H-NMR (CDCl₃) δ: 7.21-7.21 (1H, m), 7.02 (1H, dd, J = 8.3, 7.7 Hz), 6.78 (1H, dd, J = 8.3, 1.5 Hz), 6.66 (1H, dt, J = 7.7, 1.5 Hz), 6.41-6.38 (1H, m), 6.34-6.31 (1H, m), 3.86 (3H, s), 3.75 (3H, s), 3.39 (3H, s), 2.24 (3H, d, J = 1.2 Hz). |
| 673 | ¹H-NMR (CDCl₃) δ: 7.21 (1H, m), 7.02 (1H, dd, J = 8.3, 7.7 Hz), 6.77 (1H, dd, J = 8.3, 1.2 Hz), 6.66 (1H, ddd, J = 7.7, 1.4, 1.2 Hz), 6.39-6.36 (1H, m), 6.32-6.29 (1H, m), 3.94 (2H, q, J = 7.0 Hz), 3.86 (3H, s), 3.39 (3H, s), 2.24 (3H, d, J = 0.9 Hz), 1.38 (3H, t, J = 7.0 Hz). |
| 674 | ¹H-NMR (CDCl₃) δ: 7.23 (1H, d, J = 9.2 Hz), 6.96-6.92 (1H, m), 6.89-6.85 (1H, m), 6.75-6.73 (2H, m), 6.66 (1H, tt, J = 8.7, 2.1 Hz), 6.57 (1H, tt, J = 8.9, 2.1 Hz), 3.98-3.91 (1H, m), 3.86-3.79 (1H, m), 2.06 (3H, d, J = 1.8 Hz), 1.16 (3H, t, J = 7.2 Hz). |
| 675 | ¹H-NMR (CDCl₃) δ: 7.47 (1H, s), 7.00-6.86 (2H, m), 6.76-6.73 (1H, m), 6.66 (1H, tt, J = 8.7, 2.1 Hz), 6.59 (1H, tt, J = 8.8, 2.1 Hz), 4.02-3.85 (2H, m), 2.07 (3H, d, J = 1.7 Hz), 1.19 (3H, t, J = 7.1 Hz). |
| 676 | ¹H-NMR (CDCl₃) δ: 7.28 (1H, d, J = 9.3 Hz), 6.80 (1H, td, J = 8.5, 2.9 Hz), 6.74 (1H, d, J = 9.3 Hz), 6.66-6.63 (1H, m), 6.47-6.43 (1H, m), 6.41-6.37 (1H, m), 3.79 (3H, s), 3.39 (3H, s). |
| 677 | ¹H-NMR (CDCl₃) δ: 7.51 (1H, s), 6.82 (1H, td, J = 8.4, 3.2 Hz), 6.67-6.65 (1H, m), 6.46-6.44 (1H, m), 6.41-6.39 (1H, m), 3.79 (3H, s), 3.45 (3H, s). |
| 678 | ¹H-NMR (CDCl₃) δ: 7.32 (1H, d, J = 9.5 Hz), 6.83-6.78 (1H, m), 6.75 (1H, d, J = 9.5 Hz), 6.70-6.66 (1H, m), 6.46-6.43 (1H, m), 6.41-6.37 (1H, m), 6.16 (1H, tt, J = 56.6, 4.5 Hz), 4.22-4.11 (2H, m), 3.79 (3H, s). |
| 679 | ¹H-NMR (CDCl₃) δ: 7.56 (1H, s), 6.85-6.81 (1H, m), 6.71-6.68 (1H, m), 6.46-6.43 (1H, dt, J = 10.8, 1.8 Hz), 6.42-6.39 (1H, m), 6.18 (1H, tt, J = 56.6, 4.5 Hz), 4.28-4.17 (2H, m), 3.80 (3H, s). |
| 680 | ¹H-NMR (CDCl₃) δ: 7.30-7.28 (2H, m), 7.12 (1H, dt, J = 8.1, 1.7 Hz), 7.07 (1H, dt, J = 8.1, 1.6 Hz), 6.92-6.90 (1H, m), 6.79 (1H, m), 6.76 (1H, d, J = 9.5 Hz), 3.37 (3H, s). |
| 681 | ¹H-NMR (CDCl₃) δ: 7.54 (1H, s), 7.29 (1H, dd, J = 8.9, 5.2 Hz), 7.12 (1H, dt, J = 8.2, 1.6 Hz), 7.08 (1H, dt, J = 8.2, 1.6 Hz), 6.94-6.92 (1H, m), 6.81 (1H, m), 3.44 (3H, s). |
| 682 | ¹H-NMR (CDCl₃) δ: 7.68 (1H, s), 6.98-6.93 (1H, m), 6.90-6.86 (1H, m), 6.75-6.73 (1H, m), 6.66 (1H, tt, J = 8.7, 2.1 Hz), 6.59 (1H, tt, J = 8.9, 2.1 Hz), 4.01-3.87 (2H, m), 2.07 (3H, d, J = 1.8 Hz), 1.19 (3H, t, J = 7.0 Hz). |
| 683 | ¹H-NMR (CDCl₃) δ: 7.76 (1H, s), 7.32 (1H, dd, J = 8.0, 1.2 Hz), 7.17 (1H, ddd, J = 8.0, 7.3, 1.8 Hz), 7.08 (1H, td, J = 7.3, 1.2 Hz), 7.05 (1H, dt, J = 7.3, 1.8 Hz), 6.65 (1H, tt, J = 8.9, 2.1 Hz), 6.60 (1H, tt, J = 8.9, 2.1 Hz), 3.95 (2H, q, J = 7.0 Hz), 1.19 (3H, t, J = 7.0 Hz). |
| 684 | ¹H-NMR (CDCl₃) δ: 7.55 (1H, s), 7.33-7.31 (1H, m), 7.16-7.14 (1H, m), 7.07-7.06 (2H, m), 6.38 (1H, dt, J = 10.8, 1.8 Hz), 6.32 (1H, dt, J = 10.8, 1.8 Hz), 3.98-3.94 (4H, m), 1.38 (3H, t, J = 7.0 Hz), 1.18 (3H, t, J = 7.0 Hz). |
| 685 | ¹H-NMR (CDCl₃) δ: 7.32-7.30 (2H, m), 7.14-7.12 (1H, m), 7.06-7.05 (2H, m), 6.71 (1H, d, J = 9.5 Hz), 6.39 (1H, dt, J = 10.7, 2.0 Hz), 6.31 (1H, dt, J = 10.7, 2.0 Hz), 3.94-3.90 (4H, m), 1.38 (3H, t, J = 7.1 Hz), 1.16 (3H, t, J = 7.1 Hz). |
| 686 | ¹H-NMR (CDCl₃) δ: 7.75 (1H, s), 7.32 (1H, dd, J = 7.8, 1.2 Hz), 7.16-7.14 (1H, m), 7.07-7.06 (2H, m), 6.40 (1H, dt, J = 10.7, 1.8 Hz), 6.34 (1H, dt, J = 10.7, 1.8 Hz), 4.00-3.94 (2H, m), 3.75 (3H, s), 1.18 (3H, t, J = 7.2 Hz). |
| 687 | ¹H-NMR (CDCl₃) δ: 7.32-7.30 (1H, m), 7.21 (1H, q, J = 1.1 Hz), 7.15-7.13 (1H, m), 7.08-7.06 (2H, m), 6.65-6.55 (2H, m), 3.92-3.89 (2H, m), 2.25 (3H, d, J = 1.1 Hz), 1.16 (3H, t, J = 7.1 Hz). |

TABLE 5-continued

| Compound | ¹H-NMR |
| --- | --- |
| 688 | ¹H-NMR (CDCl₃) δ: 7.71 (1H, s), 6.83 (1H, td, J = 8.4, 3.1 Hz), 6.74-6.69 (1H, m), 6.69-6.65 (2H, m), 3.98-3.90 (2H, m), 1.18 (3H, t, J = 7.2 Hz). |
| 689 | ¹H-NMR (CDCl₃) δ: 7.15 (1H, d, J = 1.2 Hz), 6.80 (1H, td, J = 8.5, 2.8 Hz), 6.72-6.61 (3H, m), 3.94-3.85 (2H, m), 2.25 (3H, d, J = 1.2 Hz), 1.16 (3H, t, J = 7.1 Hz). |
| 690 | ¹H-NMR (CDCl₃) δ: 7.31 (1H, d, J = 9.2 Hz), 7.28-7.26 (1H, m), 6.88-6.86 (1H, m), 6.79 (1H, m), 6.74-6.72 (2H, m), 6.65 (1H, d, J = 9.2 Hz), 3.38 (3H, s), 2.32 (3H, s). |
| 691 | ¹H-NMR (CDCl₃) δ: 7.54 (1H, s), 7.29-7.26 (1H, m), 6.90-6.88 (1H, m), 6.80 (1H, m), 6.73 (1H, d, J = 9.5 Hz), 6.66 (1H, d, J = 9.5 Hz), 3.44 (3H, s), 2.33 (3H, s). |
| 692 | ¹H-NMR (CDCl₃) δ: 7.30-7.27 (2H, m), 7.13 (1H, dt, J = 8.1, 1.7 Hz), 7.06 (1H, dt, J = 8.0, 1.6 Hz), 6.91-6.89 (1H, m), 6.80 (1H, m), 6.74 (1H, d, J = 9.5 Hz), 3.92-3.83 (2H, m), 1.16 (3H, t, J = 7.1 Hz). |
| 693 | ¹H-NMR (CDCl₃) δ: 7.84 (1H, d, J = 8.9 Hz), 7.05 (1H, d, J = 8.9 Hz), 6.82 (1H, td, J = 8.4, 2.8 Hz), 6.67-6.64 (1H, m), 6.48-6.46 (1H, m), 6.42-6.39 (1H, m), 4.60-4.54 (2H, m), 3.80 (3H, s), 1.27 (3H, t, J = 7.0 Hz). |
| 694 | ¹H-NMR (CDCl₃) δ: 7.17 (1H, d, J = 1.2 Hz), 6.81 (1H, td, J = 8.5, 3.0 Hz), 6.71-6.63 (3H, m), 3.39 (3H, s), 2.26 (3H, d, J = 1.2 Hz). |
| 695 | ¹H-NMR (CDCl₃) δ: 7.69 (1H, s), 6.81 (1H, td, J = 8.4, 3.2 Hz), 6.69-6.67 (1H, m), 6.47-6.44 (1H, m), 6.39-6.37 (1H, m), 3.96 (2H, q, J = 7.0 Hz), 3.79 (3H, s), 1.18 (3H, t, J = 7.0 Hz). |
| 696 | ¹H-NMR (CDCl₃) δ: 7.84 (1H, d, J = 8.9 Hz), 7.11 (1H, d, J = 8.9 Hz), 6.71-6.62 (2H, m), 6.38 (1H, d, J = 2.8 Hz), 6.19-6.18 (1H, m), 4.60-4.51 (2H, m), 3.83 (3H, s), 3.68 (3H, s), 1.28 (3H, t, J = 7.1 Hz). |
| 697 | ¹H-NMR (CDCl₃) δ: 7.22 (1H, d, J = 9.4 Hz), 6.96-6.91 (1H, m), 6.87-6.83 (1H, m), 6.77-6.75 (1H, m), 6.71 (1H, d, J = 9.4 Hz), 6.42-6.39 (1H, m), 6.33-6.30 (1H, m), 3.99-3.83 (2H, m), 3.75 (3H, s), 2.06 (3H, d, J = 2.1 Hz), 1.16 (3H, t, J = 7.2 Hz). |
| 698 | ¹H-NMR (CDCl₃) δ: 7.21 (1H, d, J = 9.5 Hz), 6.96-6.91 (1H, m), 6.87-6.83 (1H, m), 6.77-6.75 (1H, m), 6.71 (1H, d, J = 9.5 Hz), 6.40-6.37 (1H, m), 6.31-6.28 (1H, m), 3.99-3.83 (4H, m), 2.05 (3H, d, J = 2.1 Hz), 1.38 (3H, t, J = 7.0 Hz), 1.16 (3H, t, J = 7.2 Hz). |
| 699 | ¹H-NMR (CDCl₃) δ: 7.46 (1H, s), 6.98-6.92 (1H, m), 6.89-6.84 (1H, m), 6.78-6.75 (1H, m), 6.40 (1H, m), 6.33 (1H, m), 4.03-3.89 (2H, m), 3.75 (3H, s), 2.06 (3H, d, J = 2.0 Hz), 1.18 (3H, t, J = 7.1 Hz). |
| 700 | ¹H-NMR (CDCl₃) δ: 7.45 (1H, s), 6.98-6.92 (1H, m), 6.89-6.84 (1H, m), 6.78-6.75 (1H, m), 6.40-6.36 (1H, m), 6.32-6.29 (1H, m), 4.03-3.91 (4H, m), 2.06 (3H, d, J = 2.0 Hz), 1.38 (3H, t, J = 7.0 Hz), 1.18 (3H, t, J = 7.1 Hz). |
| 701 | ¹H-NMR (CDCl₃) δ: 7.32-7.29 (1H, m), 7.21 (1H, q, J = 1.1 Hz), 7.13-7.11 (1H, m), 7.07-7.04 (2H, m), 6.39 (1H, ddd, J = 10.5, 2.4, 1.4 Hz), 6.32 (1H, ddd, J = 10.5, 2.4, 1.4 Hz), 3.96-3.90 (2H, m), 3.74 (3H, s), 2.24 (3H, d, J = 1.1 Hz), 1.15 (3H, t, J = 7.1 Hz). |
| 702 | ¹H-NMR (CDCl₃) δ: 7.31-7.29 (1H, m), 7.20 (1H, q, J = 1.0 Hz), 7.13-7.11 (1H, m), 7.07-7.04 (2H, m), 6.37 (1H, dt, J = 10.6, 2.0 Hz), 6.30 (1H, dt, J = 10.6, 2.0 Hz), 3.94-3.92 (4H, m), 2.24 (3H, d, J = 1.0 Hz), 1.38 (3H, t, J = 7.1 Hz), 1.15 (3H, t, J = 7.1 Hz). |
| 703 | ¹H-NMR (CDCl₃) δ: 7.75 (1H, s), 7.33-7.30 (1H, m), 7.16-7.14 (1H, m), 7.07-7.06 (2H, m), 6.38 (1H, dt, J = 10.6, 1.9 Hz), 6.31 (1H, dt, J = 10.6, 1.9 Hz), 3.97-3.94 (4H, m), 1.38 (3H, t, J = 7.0 Hz), 1.18 (3H, t, J = 7.1 Hz). |
| 704 | ¹H-NMR (CDCl₃) δ: 7.25-7.19 (2H, m), 6.78 (2H, t, J = 8.5 Hz), 6.69 (1H, dd, J = 8.9, 3.1 Hz), 6.62 (1H, d, J = 3.2 Hz), 3.64 (3H, s), 2.93-2.65 (4H, m). |
| 705 | ¹H-NMR (CDCl₃) δ: 7.29 (1H, dd, J = 8.0, 1.2 Hz), 7.10 (1H, ddd, J = 8.0, 7.3, 1.7 Hz), 7.03 (1H, td, J = 7.3, 1.2 Hz), 6.98 (1H, dt, J = 7.3, 1.7 Hz), 6.59 (1H, tt, J = 8.9, 2.1 Hz), 6.51 (1H, tt, J = 8.9, 2.1 Hz), 2.89 (3H, s), 2.89-2.81 (2H, m), 2.73-2.70 (1H, m), 2.62-2.55 (1H, m). |
| 706 | ¹H-NMR (CDCl₃) δ: 7.52 (1H, s), 7.29 (1H, dd, J = 8.8, 5.1 Hz), 7.13 (1H, dt, J = 8.1, 1.7 Hz), 7.07 (1H, dt, J = 8.0, 1.6 Hz), 6.93-6.91 (1H, m), 6.82 (1H, dq, J = 8.5, 1.5 Hz), 4.01-3.85 (2H, m), 1.18 (3H, t, J = 7.1 Hz). |
| 707 | ¹H-NMR (CDCl₃) δ: 7.29-7.26 (2H, m), 6.88-6.79 (2H, m), 6.74-6.71 (2H, m), 6.64 (1H, d, J = 9.3 Hz), 3.95-3.85 (2H, m), 2.32 (3H, s), 1.15 (3H, t, J = 7.1 Hz). |
| 708 | ¹H-NMR (CDCl₃) δ: 7.52 (1H, s), 7.29-7.26 (1H, m), 6.88-6.86 (1H, m), 6.82 (1H, dq, J = 8.9, 1.4 Hz), 6.73 (1H, d, J = 9.5 Hz), 6.65 (1H, d, J = 9.2 Hz), 3.95 (2H, q, J = 7.0 Hz), 2.32 (3H, s), 1.17 (3H, t, J = 7.0 Hz). |
| 709 | ¹H-NMR (CDCl₃) δ: 7.73 (1H, s), 7.28-7.26 (1H, m), 6.88-6.86 (1H, m), 6.83-6.80 (1H, m), 6.73 (1H, d, J = 9.5 Hz), 6.65 (1H, d, J = 9.3 Hz), 3.95 (2H, q, J = 7.1 Hz), 2.32 (3H, s), 1.17 (3H, t, J = 7.1 Hz). |
| 710 | ¹H-NMR (CDCl₃) δ: 7.26-7.24 (1H, m), 7.18 (1H, d, J = 1.0 Hz), 6.85-6.81 (2H, m), 6.70 (1H, d, J = 9.3 Hz), 6.63 (1H, d, J = 9.3 Hz), 3.90 (2H, q, J = 7.1 Hz), 2.31 (3H, s), 2.24 (3H, d, J = 1.0 Hz), 1.15 (3H, t, J = 7.1 Hz). |
| 711 | ¹H-NMR (CDCl₃) δ: 7.67 (1H, s), 6.97-6.93 (1H, m), 6.88-6.85 (1H, m), 6.77-6.75 (1H, m), 6.42-6.39 (1H, m), 6.34-6.31 (1H, m), 4.02-3.90 (2H, m), 3.75 (3H, s), 2.07 (3H, d, J = 2.1 Hz), 1.18 (3H, t, J = 7.0 Hz). |
| 712 | ¹H-NMR (CDCl₃) δ: 7.66 (1H, s), 6.95 (1H, td, J = 7.9, 6.0 Hz), 6.88-6.84 (1H, m), 6.77-6.75 (1H, m), 6.39-6.36 (1H, m), 6.32-6.29 (1H, m), 4.01-3.90 (4H, m), 2.06 (3H, d, J = 2.1 Hz), 1.38 (3H, t, J = 7.0 Hz), 1.18 (3H, t, J = 7.0 Hz). |
| 713 | ¹H-NMR (CDCl₃) δ: 7.11 (1H, m), 6.93 (1H, td, J = 7.9, 5.9 Hz), 6.86-6.81 (1H, m), 6.77-6.75 (1H, m), 6.39-6.35 (1H, m), 6.30-6.27 (1H, m), 3.99-3.84 (4H, m), 2.24 (3H, d, J = 1.2 Hz), 2.05-2.05 (3H, m), 1.38 (3H, t, J = 7.0 Hz), 1.15 (3H, t, J = 7.1 Hz). |
| 714 | ¹H-NMR (CDCl₃) δ: 7.14 (1H, d, J = 1.2 Hz), 6.77 (1H, td, J = 8.5, 2.8 Hz), 6.69-6.65 (1H, m), 6.45-6.42 (1H, m), 6.39-6.35 (1H, m), 3.91 (2H, q, J = 7.1 Hz), 3.78 (3H, s), 2.24 (3H, d, J = 1.2 Hz), 1.15 (3H, t, J = 7.1 Hz). |
| 715 | ¹H-NMR (CDCl₃) δ: 7.85 (1H, d, J = 8.8 Hz), 7.33 (1H, m), 7.19 (1H, m), 7.13 (1H, d, J = 8.8 Hz), 7.09 (1H, m), 7.04-7.01 (1H, m), 6.70-6.59 (2H, m), 4.61-4.54 (2H, m), 1.28 (3H, t, J = 7.1 Hz). |

TABLE 5-continued

| Compound | ¹H-NMR |
|---|---|
| 716 | ¹H-NMR (CDCl₃) δ: 7.83 (1H, d, J = 8.9 Hz), 7.11 (1H, d, J = 8.9 Hz), 6.44-6.41 (1H, m), 6.39-6.36 (2H, m), 6.21-6.20 (1H, m), 4.65-4.50 (2H, m), 3.83 (3H, s), 3.78 (3H, s), 3.67 (3H, s), 1.28 (3H, t, J = 7.5 Hz). |
| 717 | ¹H-NMR (CDCl₃) δ: 7.71 (1H, s), 6.82 (1H, td, J = 8.4, 2.9 Hz), 6.68-6.64 (1H, m), 6.46-6.43 (1H, m), 6.42-6.38 (1H, m), 3.79 (3H, s), 3.45 (3H, s). |
| 718 | ¹H-NMR (CDCl₃) δ: 7.84 (1H, d, J = 8.8 Hz), 7.33 (1H, dd, J = 7.9, 1.1 Hz), 7.18-7.14 (1H, m), 7.12 (1H, d, J = 8.8 Hz), 7.10-7.06 (1H, m), 7.0-5-7.02 (1H, m), 6.43-6.39 (1H, m), 6.36-6.33 (1H, m), 4.66-4.55 (2H, m), 3.76 (3H, s), 1.28 (3H, t, J = 7.1 Hz). |
| 719 | ¹H-NMR (CDCl₃) δ: 7.45 (1H, d, J = 9.5 Hz), 7.33 (1H, tt, J = 8.4, 6.4 Hz), 7.27 (1H, d, J = 8.7 Hz), 6.85 (2H, t, J = 8.7 Hz), 6.77 (1H, dd, J = 8.7, 3.1 Hz), 6.61 (1H, d, J = 3.1 Hz), 6.46 (1H, d, J = 9.5 Hz), 3.64 (3H, s). |
| 720 | ¹H-NMR (CDCl₃) δ: 7.78 (1H, s), 7.33 (1H, dd, J = 8.1, 1.2 Hz), 7.18 (1H, td, J = 7.6, 2.0 Hz), 7.10 (1H, td, J = 7.6, 1.2 Hz), 7.03 (1H, dt, J = 7.6, 2.0 Hz), 6.67-6.58 (2H, m), 3.46 (3H, s). |
| 721 | ¹H-NMR (CDCl₃) δ: 7.34 (1H, d, J = 9.3 Hz), 7.20 (1H, d, J = 8.8 Hz), 6.73-6.70 (2H, m), 6.59 (1H, dd, J = 2.9, 1.5 Hz), 6.43 (1H, dt, J = 10.8, 2.0 Hz), 6.37 (1H, dt, J = 10.6, 1.9 Hz), 3.77 (3H, s), 3.66 (3H, s), 3.39 (3H, s). |
| 722 | ¹H-NMR (CDCl₃) δ: 7.57 (1H, s), 7.20 (1H, d, J = 8.6 Hz), 6.71 (1H, dd, J = 8.9, 3.1 Hz), 6.60-6.59 (1H, m), 6.44-6.41 (1H, m), 6.39-6.37 (1H, m), 3.77 (3H, s), 3.67 (3H, s), 3.45 (3H, s). |
| 723 | ¹H-NMR (CDCl₃) δ: 7.77 (1H, s), 7.20 (1H, d, J = 8.8 Hz), 6.71 (1H, dd, J = 8.9, 3.1 Hz), 6.60-6.59 (1H, m), 6.42-6.38 (2H, m), 3.77 (3H, s), 3.67 (3H, s), 3.45 (3H, s). |
| 724 | ¹H-NMR (CDCl₃) δ: 7.23 (1H, d, J = 1.0 Hz), 7.19 (1H, d, J = 8.8 Hz), 6.69 (1H, dd, J = 8.8, 3.2 Hz), 6.60-6.59 (1H, m), 6.41-6.36 (2H, m), 3.76 (3H, s), 3.66 (3H, s), 3.39 (3H, s), 2.25 (3H, d, J = 1.2 Hz). |
| 725 | ¹H-NMR (CDCl₃) δ: 7.77 (1H, s), 7.20 (1H, d, J = 8.9 Hz), 6.73 (1H, dd, J = 8.9, 3.1 Hz), 6.67-6.64 (2H, m), 6.59 (1H, m), 3.69 (3H, s), 3.45 (3H, s). |
| 726 | ¹H-NMR (CDCl₃) δ: 7.23 (1H, d, J = 1.0 Hz), 7.19 (1H, d, J = 8.8 Hz), 6.70 (1H, dd, J = 8.9, 3.1 Hz), 6.68-6.58 (3H, m), 3.68 (3H, s), 3.39 (3H, s), 2.26 (3H, d, J = 1.0 Hz). |
| 727 | ¹H-NMR (CDCl₃) δ: 7.53 (1H, s), 7.09-7.01 (2H, m), 6.88 (1H, dq, J = 7.4, 1.5 Hz), 6.51-6.48 (1H, m), 6.45-6.42 (1H, m), 4.29 (2H, q, J = 7.8 Hz), 3.95 (2H, q, J = 7.1 Hz), 1.18 (3H, t, J = 7.1 Hz). |
| 728 | ¹H-NMR (CDCl₃) δ: 7.85 (1H, d, J = 8.9 Hz), 7.37-7.32 (1H, m), 7.13 (1H, d, J = 8.9 Hz), 6.92 (1H, t, J = 8.4 Hz), 6.86 (1H, t, J = 8.4 Hz), 6.35 (1H, d, J = 2.8 Hz), 6.21-6.20 (1H, m), 4.65-4.60 (1H, m), 4.55-4.48 (1H, m), 3.81 (3H, s), 3.65 (3H, s), 1.28 (3H, t, J = 7.2 Hz). |
| 729 | ¹H-NMR (CDCl₃) δ: 7.85 (1H, d, J = 9.0 Hz), 7.45-7.37 (1H, m), 7.10 (1H, d, J = 9.0 Hz), 6.94 (2H, dd, J = 8.9, 7.0 Hz), 6.83-6.77 (1H, m), 6.58-6.55 (1H, m), 4.61-4.55 (2H, m), 1.25 (3H, t, J = 7.1 Hz). |
| 730 | ¹H-NMR (CDCl₃) δ: 7.34-7.32 (2H, m), 7.16-7.12 (1H, m), 7.08-7.02 (2H, m), 6.73 (1H, d, J = 9.5 Hz), 6.39 (1H, dt, J = 10.9, 1.8 Hz), 6.31 (1H, dt, J = 10.9, 1.8 Hz), 3.94 (2H, q, J = 7.0 Hz), 3.39 (3H, s), 1.38 (3H, t, J = 7.0 Hz). |
| 731 | ¹H-NMR (CDCl₃) δ: 7.31 (1H, dd, J = 8.0, 1.2 Hz), 7.23 (1H, d, J = 1.2 Hz), 7.15 (1H, ddd, J = 8.0, 7.5, 1.8 Hz), 7.08 (1H, td, J = 7.5, 1.2 Hz), 7.03 (1H, dt, J = 7.5, 1.8 Hz), 6.65-6.56 (2H, m), 3.40 (3H, s), 2.26 (3H, d, J = 1.2 Hz). |
| 732 | ¹H-NMR (CDCl₃) δ: 7.77 (1H, s), 7.32 (1H, dd, J = 8.1, 1.2 Hz), 7.17-7.15 (1H, m), 7.08 (1H, td, J = 7.6, 1.2 Hz), 7.04 (1H, dt, J = 7.6, 1.8 Hz), 6.40 (1H, dt, J = 10.6, 2.0 Hz), 6.35 (1H, dt, J = 10.6, 2.0 Hz), 3.75 (3H, s), 3.46 (3H, s). |
| 733 | ¹H-NMR (CDCl₃) δ: 7.31 (1H, dd, J = 8.1, 1.2 Hz), 7.23 (1H, d, J = 1.0 Hz), 7.14-7.12 (1H, m), 7.07-7.04 (2H, m), 6.39 (1H, dt, J = 10.6, 2.0 Hz), 6.33 (1H, dt, J = 10.6, 2.0 Hz), 3.74 (3H, s), 3.40 (3H, s), 2.25 (3H, d, J = 1.0 Hz). |
| 734 | ¹H-NMR (CDCl₃) δ: 7.57 (1H, s), 7.32 (1H, dd, J = 8.1, 1.2 Hz), 7.17-7.15 (1H, m), 7.08 (1H, td, J = 7.6, 1.2 Hz), 7.04 (1H, dt, J = 7.6, 1.7 Hz), 6.38 (1H, dt, J = 10.7, 2.0 Hz), 6.32 (1H, dt, J = 10.7, 2.0 Hz), 3.94 (2H, q, J = 7.0 Hz), 3.46 (3H, s), 1.38 (3H, t, J = 7.0 Hz). |
| 735 | ¹H-NMR (CDCl₃) δ: 7.32-7.27 (2H, m), 6.95 (1H, dd, J = 8.6, 1.5 Hz), 6.88 (1H, t, J = 8.4 Hz), 6.84-6.80 (2H, m), 6.71 (1H, d, J = 9.5 Hz), 6.57 (1H, dd, J = 8.6, 2.8 Hz), 3.92-3.90 (1H, m), 3.89-3.82 (1H, m), 3.73 (3H, s), 1.15 (3H, t, J = 7.0 Hz). |
| 736 | ¹H-NMR (CDCl₃) δ: 7.54 (1H, s), 7.34-7.21 (1H, m), 6.95 (1H, dd, J = 8.5, 1.7 Hz), 6.89 (1H, t, J = 8.4 Hz), 6.85-6.81 (2H, m), 6.57 (1H, dd, J = 8.5, 2.7 Hz), 4.00-3.89 (2H, m), 3.73 (3H, s), 1.17 (3H, t, J = 7.1 Hz). |
| 737 | ¹H-NMR (CDCl₃) δ: 7.75 (1H, s), 7.34-7.28 (1H, m), 6.95 (1H, dd, J = 8.6, 1.8 Hz), 6.84-6.81 (1H, m), 6.83 (2H, dd, J = 9.5, 7.0 Hz), 6.57 (1H, dd, J = 8.6, 2.8 Hz), 3.99-3.90 (2H, m), 3.73 (3H, s), 1.17 (3H, t, J = 7.2 Hz). |
| 738 | ¹H-NMR (CDCl₃) δ: 7.85 (1H, d, J = 9.0 Hz), 7.30 (1H, dd, J = 9.0, 5.1 Hz), 7.09 (1H, d, J = 9.0 Hz), 6.94-6.89 (1H, m), 6.80-6.77 (1H, m), 6.72 (1H, tt, J = 8.7, 2.1 Hz), 6.65 (1H, tt, J = 8.7, 2.1 Hz), 4.61-4.51 (2H, m), 1.27 (3H, t, J = 7.0 Hz). |
| 739 | ¹H-NMR (CDCl₃) δ: 7.84 (1H, d, J = 8.9 Hz), 7.29 (1H, dd, J = 8.9, 5.2 Hz), 7.09 (1H, d, J = 8.9 Hz), 6.91-6.87 (1H, m), 6.81-6.78 (1H, m), 6.47-6.49 (1H, m), 6.39-6.36 (1H, m), 4.61-4.56 (2H, m), 3.78 (3H, s), 1.27 (3H, t, J = 7.0 Hz). |
| 740 | ¹H-NMR (CDCl₃) δ: 7.34-7.28 (2H, m), 6.94-6.86 (2H, m), 6.84-6.80 (2H, m), 6.73 (1H, d, J = 9.3 Hz), 6.58 (1H, dd, J = 8.5, 2.7 Hz), 3.73 (3H, s), 3.38 (3H, s). |
| 741 | ¹H-NMR (CDCl₃) δ: 7.31-7.20 (2H, m), 6.96 (1H, d, J = 8.5 Hz), 6.88-6.79 (3H, m), 6.57 (1H, d, J = 8.5 Hz), 3.96-3.85 (2H, m), 3.72 (3H, s), 2.25 (3H, s), 1.15 (3H, t, J = 7.0 Hz). |
| 742 | ¹H-NMR (CDCl₃) δ: 7.30 (1H, d, J = 9.2 Hz), 6.94 (1H, dd, J = 8.6, 1.8 Hz), 6.86 (1H, d, J = 2.4 Hz), 6.72 (1H, d, J = 9.2 Hz), 6.67-6.63 (1H, m), 6.62-6.58 (2H, m), 3.93-3.84 (2H, m), 3.75 (3H, s), 1.15 (3H, t, J = 7.0 Hz). |
| 743 | ¹H-NMR (CDCl₃) δ: 7.56 (1H, s), 7.35-7.29 (1H, m), 6.93 (1H, dd, J = 8.6, 1.5 Hz), 6.89 (1H, t, J = 8.4 Hz), 6.85-6.82 (2H, m), 6.59 (1H, dd, J = 8.6, 2.4 Hz), 3.73 (3H, s), 3.44 (3H, s). |
| 744 | ¹H-NMR (CDCl₃) δ: 7.77 (1H, s), 7.35-7.29 (1H, m), 6.93 (1H, dd, J = 8.6, 1.8 Hz), 6.89 (1H, t, J = 8.4 Hz), 6.85-6.82 (2H, m), 6.59 (1H, dd, J = 8.6, 2.8 Hz), 3.73 (3H, s), 3.45 (3H, s). |

TABLE 5-continued

| Compound | ¹H-NMR |
|---|---|
| 745 | ¹H-NMR (CDCl₃) δ: 7.75 (1H, s), 7.35-7.29 (1H, m), 7.05-6.97 (2H, m), 6.91-6.82 (3H, m), 4.02-3.90 (2H, m), 1.18 (3H, t, J = 7.0 Hz). |
| 746 | ¹H-NMR (CDCl₃) δ: 7.53 (1H, s), 6.94 (1H, dd, J = 8.5, 2.0 Hz), 6.85 (1H, d, J = 2.4 Hz), 6.69-6.59 (3H, m), 3.94 (2H, q, J = 7.1 Hz), 3.75 (3H, s), 1.18 (3H, t, J = 7.1 Hz). |
| 747 | ¹H-NMR (CDCl₃) δ: 7.74 (1H, s), 6.94 (1H, dd, J = 8.6, 1.8 Hz), 6.85 (1H, d, J = 2.8 Hz), 6.67-6.60 (3H, m), 3.94 (2H, q, J = 7.1 Hz), 3.75 (3H, s), 1.18 (3H, t, J = 7.1 Hz). |
| 748 | ¹H-NMR (CDCl₃) δ: 7.52 (1H, s), 6.96 (1H, dd, J = 8.6, 1.8 Hz), 6.85 (1H, d, J = 2.8 Hz), 6.61 (1H, dd, J = 8.6, 2.8 Hz), 6.42-6.39 (1H, m), 6.37-6.34 (1H, m), 4.00-3.91 (2H, m), 3.77 (3H, s), 3.75 (3H, s), 1.17 (3H, t, J = 7.0 Hz). |
| 749 | ¹H-NMR (CDCl₃) δ: 7.31-7.25 (1H, m), 7.22 (1H, d, J = 1.2 Hz), 6.93 (1H, dd, J = 8.6, 1.5 Hz), 6.88-6.80 (3H, m), 6.58 (1H, dd, J = 8.6, 2.8 Hz), 3.73 (3H, s), 3.39 (3H, s), 2.25 (3H, s). |
| 750 | ¹H-NMR (CDCl₃) δ: 7.19 (1H, m), 6.94 (1H, dd, J = 8.6, 1.8 Hz), 6.85 (1H, d, J = 2.8 Hz), 6.66-6.58 (3H, m), 3.90 (2H, q, J = 7.1 Hz), 3.75 (3H, s), 2.24 (3H, d, J = 1.2 Hz), 1.15 (3H, t, J = 7.1 Hz). |
| 751 | ¹H-NMR (CDCl₃) δ: 7.18 (1H, m), 6.96 (1H, dd, J = 8.6, 1.5 Hz), 6.85 (1H, d, J = 2.8 Hz), 6.60 (1H, dd, J = 8.6, 2.8 Hz), 6.40-6.38 (1H, m), 6.35-6.33 (1H, m), 3.95-3.87 (2H, m), 3.76 (3H, s), 3.75 (3H, s), 2.23 (3H, d, J = 0.9 Hz), 1.15 (3H, t, J = 7.0 Hz). |
| 752 | ¹H-NMR (CDCl₃) δ: 7.32-7.25 (1H, m), 7.20-7.19 (1H, m), 7.02-6.94 (2H, m), 6.88-6.79 (3H, m), 3.99-3.84 (2H, m), 2.26 (3H, d, J = 1.2 Hz), 1.16 (3H, t, J = 7.1 Hz). |
| 753 | ¹H-NMR (CDCl₃) δ: 7.77 (1H, s), 7.37-7.30 (1H, m), 7.06-6.98 (2H, m), 6.91-6.82 (3H, m), 3.46 (3H, s). |
| 754 | ¹H-NMR (CDCl₃) δ: 7.33-7.28 (1H, m), 7.22 (1H, d, J = 0.9 Hz), 7.03-6.96 (2H, m), 6.89-6.80 (3H, m), 3.40 (3H, s), 2.26 (3H, d, J = 0.9 Hz). |
| 755 | ¹H-NMR (CDCl₃) δ: 7.29 (1H, d, J = 9.3 Hz), 6.95 (1H, dd, J = 8.5, 1.5 Hz), 6.85 (1H, d, J = 2.4 Hz), 6.69 (1H, d, J = 9.3 Hz), 6.60 (1H, dd, J = 8.5, 2.7 Hz), 6.43-6.39 (1H, m), 6.36-6.33 (1H, m), 3.97-3.84 (2H, m), 3.76 (3H, s), 3.75 (3H, s), 1.15 (3H, t, J = 7.1 Hz). |
| 756 | ¹H-NMR (CDCl₃) δ: 7.32 (1H, d, J = 9.3 Hz), 6.92 (1H, dd, J = 8.5, 1.7 Hz), 6.86 (1H, d, J = 2.7 Hz), 6.74 (1H, d, J = 9.3 Hz), 6.64-6.62 (3H, m), 3.75 (3H, s), 3.38 (3H, s). |
| 757 | ¹H-NMR (CDCl₃) δ: 7.75 (1H, s), 7.29 (1H, dd, J = 8.9, 4.9 Hz), 6.93-6.91 (1H, m), 6.80 (1H, dq, J = 8.6, 1.5 Hz), 6.72-6.63 (2H, m), 3.45 (3H, s). |
| 758 | ¹H-NMR (CDCl₃) δ: 7.28-7.26 (1H, m), 7.20 (1H, d, J = 1.2 Hz), 6.89-6.88 (1H, m), 6.79 (1H, dq, J = 8.8, 1.5 Hz), 6.69-6.60 (2H, m), 3.39 (3H, s), 2.26 (3H, d, J = 1.2 Hz). |
| 759 | ¹H-NMR (CDCl₃) δ: 7.27-7.26 (1H, m), 7.19 (1H, m), 6.87-6.85 (1H, m), 6.80-6.79 (1H, m), 6.43 (1H, dt, J = 10.6, 1.9 Hz), 6.37 (1H, dt, J = 10.6, 1.9 Hz), 3.77 (3H, s), 3.40 (3H, s), 2.25 (3H, d, J = 0.9 Hz). |
| 760 | ¹H-NMR (CDCl₃) δ: 7.31 (1H, d, J = 9.5 Hz), 7.29-7.26 (1H, m), 6.89-6.87 (1H, m), 6.80-6.78 (1H, m), 6.74 (1H, d, J = 9.5 Hz), 6.46-6.44 (1H, m), 6.38-6.36 (1H, m), 3.78 (3H, s), 3.39 (3H, s). |
| 761 | ¹H-NMR (CDCl₃) δ: 7.54 (1H, s), 7.29 (1H, m), 6.91-6.89 (1H, m), 6.81-6.79 (1H, m), 6.46-6.43 (1H, m), 6.39-6.37 (1H, m), 3.78 (3H, s), 3.45 (3H, s). |
| 762 | ¹H-NMR (CDCl₃) δ: 7.39 (1H, d, J = 9.4 Hz), 7.21-7.18 (3H, m), 7.05-7.02 (2H, m), 6.74 (1H, d, J = 9.4 Hz), 6.65-6.60 (2H, m), 3.90 (2H, q, J = 7.1 Hz), 1.15 (3H, t, J = 7.1 Hz). |
| 763 | ¹H-NMR (CDCl₃) δ: 7.38 (1H, d, J = 9.2 Hz), 7.21-7.15 (3H, m), 7.06-7.04 (2H, m), 6.72 (1H, d, J = 9.2 Hz), 6.40-6.37 (2H, m), 3.92 (2H, q, J = 7.1 Hz), 3.76 (3H, s), 1.14 (3H, t, J = 7.1 Hz). |
| 764 | ¹H-NMR (CDCl₃) δ: 7.62 (1H, s), 7.22-7.19 (3H, m), 7.05-7.03 (2H, m), 6.66-6.61 (2H, m), 3.95 (2H, q, J = 7.1 Hz), 1.17 (3H, t, J = 7.1 Hz). |
| 765 | ¹H-NMR (CDCl₃) δ: 7.31 (1H, d, J = 9.5 Hz), 6.93 (1H, dd, J = 8.6, 1.5 Hz), 6.86 (1H, d, J = 2.8 Hz), 6.71 (1H, d, J = 9.5 Hz), 6.61 (1H, dd, J = 8.6, 2.8 Hz), 6.42-6.40 (1H, m), 6.36-6.34 (1H, m), 3.77 (3H, s), 3.75 (3H, s), 3.38 (3H, s). |
| 766 | ¹H-NMR (CDCl₃) δ: 7.55 (1H, s), 6.93 (1H, dd, J = 8.5, 1.7 Hz), 6.86 (1H, d, J = 2.7 Hz), 6.69-6.60 (3H, m), 3.76 (3H, s), 3.44 (3H, s). |
| 767 | ¹H-NMR (CDCl₃) δ: 7.75 (1H, s), 6.93 (1H, dd, J = 8.6, 1.8 Hz), 6.85 (1H, d, J = 2.4 Hz), 6.67-6.60 (3H, m), 3.76 (3H, s), 3.45 (3H, s). |
| 768 | ¹H-NMR (CDCl₃) δ: 7.76 (1H, s), 7.20 (1H, d, J = 8.8 Hz), 6.73-6.60 (4H, m), 3.97-3.92 (2H, m), 3.69 (3H, s), 1.18 (3H, t, J = 7.1 Hz). |
| 769 | ¹H-NMR (CDCl₃) δ: 7.20-7.19 (2H, m), 6.70-6.59 (4H, m), 3.91-3.89 (2H, m), 3.68 (3H, s), 2.25 (3H, d, J = 1.2 Hz), 1.16 (3H, t, J = 7.0 Hz). |
| 770 | ¹H-NMR (CDCl₃) δ: 7.31 (1H, d, J = 9.5 Hz), 7.19 (1H, d, J = 8.9 Hz), 6.71-6.69 (2H, m), 6.62-6.61 (1H, m), 6.44-6.42 (1H, m), 6.37-6.35 (1H, m), 3.98-3.85 (2H, m), 3.77 (3H, s), 3.67 (3H, s), 1.16 (3H, t, J = 7.0 Hz). |
| 771 | ¹H-NMR (CDCl₃) δ: 7.20-7.18 (2H, m), 6.68 (1H, dd, J = 8.8, 3.2 Hz), 6.63-6.62 (1H, m), 6.42-6.40 (1H, m), 6.37-6.34 (1H, m), 3.92 (2H, q, J = 7.1 Hz), 3.76 (3H, s), 3.67 (3H, s), 2.24 (3H, d, J = 1.0 Hz), 1.16 (3H, t, J = 7.1 Hz). |
| 772 | ¹H-NMR (CDCl₃) δ: 7.55 (1H, s), 7.19 (1H, d, J = 8.6 Hz), 6.70 (1H, dd, J = 8.9, 3.1 Hz), 6.62 (1H, dd, J = 2.9, 1.4 Hz), 6.43 (1H, dt, J = 10.6, 2.0 Hz), 6.37 (1H, dt, J = 10.6, 1.9 Hz), 3.96 (2H, q, J = 7.1 Hz), 3.77 (3H, s), 3.68 (3H, s), 1.18 (3H, t, J = 7.1 Hz). |
| 773 | ¹H-NMR (CDCl₃) δ: 7.62 (1H, s), 7.23-7.17 (3H, m), 7.08-7.03 (2H, m), 6.41-6.36 (2H, m), 3.97 (2H, q, J = 7.1 Hz), 3.76 (3H, s), 1.17 (3H, t, J = 7.1 Hz). |
| 774 | ¹H-NMR (CDCl₃) δ: 7.83 (1H, s), 7.22-7.19 (3H, m), 7.05-7.02 (2H, m), 6.66-6.60 (2H, m), 3.95 (2H, q, J = 7.1 Hz), 1.17 (3H, t, J = 7.1 Hz). |
| 775 | ¹H-NMR (CDCl₃) δ: 7.82 (1H, s), 7.23-7.17 (3H, m), 7.07-7.04 (2H, m), 6.41-6.36 (2H, m), 3.97 (2H, q, J = 7.1 Hz), 3.76 (3H, s), 1.16 (3H, t, J = 7.1 Hz). |
| 776 | ¹H-NMR (CDCl₃) δ: 7.54 (1H, s), 6.94 (1H, dd, J = 8.6, 1.5 Hz), 6.86 (1H, d, J = 2.4 Hz), 6.62 (1H, dd, J = 8.6, 2.4 Hz), 6.42-6.39 (1H, m), 6.37-6.34 (1H, m), 3.77 (3H, s), 3.76 (3H, s), 3.45 (3H, s). |

TABLE 5-continued

| Compound | ¹H-NMR |
|---|---|
| 777 | ¹H-NMR (CDCl₃) δ: 7.42 (1H, d, J = 9.3 Hz), 7.22-7.19 (3H, m), 7.04-7.02 (2H, m), 6.76 (1H, d, J = 9.3 Hz), 6.67-6.61 (2H, m), 3.38 (3H, s). |
| 778 | ¹H-NMR (CDCl₃) δ: 7.42 (1H, d, J = 9.2 Hz), 7.22-7.16 (3H, m), 7.06-7.04 (2H, m), 6.74 (1H, d, J = 9.2 Hz), 6.41-6.37 (2H, m), 3.76 (3H, s), 3.39 (3H, s). |
| 779 | ¹H-NMR (CDCl₃) δ: 7.65 (1H, s), 7.23-7.20 (3H, m), 7.04-7.02 (2H, m), 6.68-6.61 (2H, m), 3.45 (3H, s). |
| 780 | ¹H-NMR (CDCl₃) δ: 7.85 (1H, s), 7.23-7.20 (3H, m), 7.05-7.01 (2H, m), 6.67-6.62 (2H, m), 3.45 (3H, s). |
| 781 | ¹H-NMR (CDCl₃) δ: 7.64 (1H, s), 7.22-7.19 (3H, m), 7.06-7.04 (2H, m), 6.42-6.38 (2H, m), 3.77 (3H, s), 3.45 (3H, s). |
| 782 | ¹H-NMR (CDCl₃) δ: 7.85 (1H, s), 7.23-7.17 (3H, m), 7.07-7.03 (2H, m), 6.41-6.37 (2H, m), 3.77 (3H, s), 3.46 (3H, s). |
| 783 | ¹H-NMR (CDCl₃) δ: 7.55 (1H, s), 7.33-7.27 (1H, m), 7.01-6.98 (1H, m), 6.90-6.86 (1H, m), 6.83-6.80 (1H, m), 6.77 (1H, dd, J = 8.4, 1.4 Hz), 6.69-6.67 (1H, m), 4.02-3.87 (2H, m), 3.85 (3H, s), 1.18 (3H, t, J = 7.2 Hz). |
| 784 | ¹H-NMR (CDCl₃) δ: 7.35 (1H, d, J = 9.3 Hz), 7.32-7.25 (1H, m), 7.01-6.97 (1H, m), 6.91-6.86 (1H, m), 6.82-6.73 (3H, m), 6.66-6.63 (1H, m), 3.85 (3H, s), 3.38 (3H, s). |
| 785 | ¹H-NMR (CDCl₃) δ: 7.57 (1H, s), 7.34-7.28 (1H, m), 7.02-6.99 (1H, m), 6.90-6.87 (1H, m), 6.84-6.80 (1H, m), 6.79-6.77 (1H, m), 6.66-6.64 (1H, m), 3.85 (3H, s), 3.44 (3H, s). |
| 786 | ¹H-NMR (CDCl₃) δ: 7.77 (1H, s), 7.35-7.27 (1H, m), 7.03-6.99 (1H, m), 6.91-6.86 (1H, m), 6.84-6.77 (2H, m), 6.65 (1H, dt, J = 7.7, 1.5 Hz), 3.85 (3H, s), 3.45 (3H, s). |
| 787 | ¹H-NMR (CDCl₃) δ: 7.56 (1H, s), 7.05 (1H, dd, J = 8.3, 7.6 Hz), 6.82 (1H, dd, J = 8.3, 1.2 Hz), 6.68-6.58 (3H, m), 3.87 (3H, s), 3.44 (3H, s). |
| 788 | ¹H-NMR (CDCl₃) δ: 7.55 (1H, s), 7.06-7.02 (1H, m), 6.80 (1H, dd, J = 8.4, 1.4 Hz), 6.67-6.65 (1H, m), 6.42-6.39 (1H, m), 6.36-6.33 (1H, m), 3.87 (3H, s), 3.75 (3H, s), 3.45 (3H, s). |
| 789 | ¹H-NMR (CDCl₃) δ: 7.33 (1H, d, J = 9.5 Hz), 6.75-6.63 (4H, m), 6.61-6.55 (2H, m), 3.88 (2H, q, J = 7.1 Hz), 1.15 (3H, t, J = 7.1 Hz). |
| 790 | ¹H-NMR (CDCl₃) δ: 7.32 (1H, d, J = 9.5 Hz), 6.72 (1H, d, J = 9.5 Hz), 6.67-6.57 (3H, m), 6.47-6.42 (2H, m), 3.90 (2H, q, J = 7.1 Hz), 3.80 (3H, s), 1.14 (3H, t, J = 7.1 Hz). |
| 791 | ¹H-NMR (CDCl₃) δ: 7.57 (1H, s), 6.74-6.66 (3H, m), 6.62-6.57 (2H, m), 3.93 (2H, q, J = 7.0 Hz), 1.17 (3H, t, J = 7.0 Hz). |
| 792 | ¹H-NMR (CDCl₃) δ: 7.56 (1H, s), 7.15 (1H, d, J = 8.6 Hz), 6.71 (1H, dd, J = 8.6, 3.1 Hz), 6.69-6.62 (2H, m), 6.53 (1H, dd, J = 3.1, 1.8 Hz), 5.91 (1H, brs), 3.97-3.94 (2H, m), 1.18 (3H, t, J = 7.2 Hz). |
| 793 | ¹H-NMR (CDCl₃) δ: 7.54 (1H, s), 7.18 (1H, d, J = 8.8 Hz), 6.72-6.59 (4H, m), 3.96-3.89 (3H, m), 3.83-3.81 (1H, m), 1.36 (3H, t, J = 7.0 Hz), 1.18 (3H, t, J = 7.2 Hz). |
| 794 | ¹H-NMR (CDCl₃) δ: 7.52 (1H, s), 7.30 (1H, d, J = 8.8 Hz), 6.83 (1H, dd, J = 8.8, 3.1 Hz), 6.74-6.62 (3H, m), 4.70 (1H, d, J = 16.4 Hz), 4.65 (1H, d, J = 16.4 Hz), 3.99-3.92 (2H, m), 1.19 (3H, t, J = 7.1 Hz). |
| 795 | ¹H-NMR (CDCl₃) δ: 7.56 (1H, s), 7.21 (1H, d, J = 8.8 Hz), 6.83 (1H, dd, J = 8.8, 3.1 Hz), 6.76 (1H, dd, J = 3.1, 1.6 Hz), 6.70-6.60 (2H, m), 5.06 (1H, d, J = 7.0 Hz), 4.98 (1H, d, J = 7.0 Hz), 3.96-3.93 (2H, m), 3.39 (3H, s), 1.18 (3H, t, J = 7.1 Hz). |
| 796 | ¹H-NMR (CDCl₃) δ: 7.54 (1H, s), 7.18 (1H, d, J = 8.8 Hz), 6.69 (1H, dd, J = 8.8, 2.9 Hz), 6.60 (1H, dd, J = 2.9, 1.7 Hz), 6.41-6.37 (2H, m), 3.96-3.94 (3H, m), 3.83-3.80 (1H, m), 3.76 (3H, s), 1.35 (3H, t, J = 7.0 Hz), 1.18 (3H, t, J = 7.2 Hz). |
| 797 | ¹H-NMR (CDCl₃) δ: 7.78 (1H, s), 6.73-6.66 (3H, m), 6.62-6.57 (2H, m), 3.93 (2H, q, J = 7.1 Hz), 1.17 (3H, t, J = 7.1 Hz). |
| 798 | ¹H-NMR (CDCl₃) δ: 7.56 (1H, s), 6.69-6.57 (3H, m), 6.47-6.42 (2H, m), 3.95 (2H, q, J = 7.1 Hz), 3.80 (3H, s), 1.16 (3H, t, J = 7.1 Hz). |
| 799 | ¹H-NMR (CDCl₃) δ: 7.77 (1H, s), 6.66 (1H, tt, J = 9.0, 2.3 Hz), 6.63-6.58 (2H, m), 6.46-6.43 (2H, m), 3.96 (2H, q, J = 7.1 Hz), 3.80 (3H, s), 1.16 (3H, t, J = 7.1 Hz). |
| 800 | ¹H-NMR (CDCl₃) δ: 7.36 (1H, d, J = 9.5 Hz), 6.77-6.64 (4H, m), 6.61-6.55 (2H, m), 3.37 (3H, s). |
| 801 | ¹H-NMR (CDCl₃) δ: 7.34-7.28 (1H, m), 7.26-7.25 (1H, m), 7.20-7.19 (1H, m), 6.93-6.90 (1H, m), 6.86-6.82 (1H, m), 6.76 (1H, dd, J = 8.6, 3.1 Hz), 6.73-6.72 (1H, m), 4.66-4.59 (2H, m), 3.95-3.88 (2H, m), 2.26 (3H, d, J = 1.2 Hz), 1.16 (3H, t, J = 7.1 Hz). |
| 802 | ¹H-NMR (CDCl₃) δ: 7.33-7.25 (1H, m), 7.22 (1H, d, J = 1.2 Hz), 7.15 (1H, d, J = 8.5 Hz), 6.89-6.80 (2H, m), 6.64 (1H, dd, J = 8.5, 2.9 Hz), 6.61-6.60 (1H, m), 3.96-3.87 (3H, m), 3.82-3.74 (1H, m), 2.25 (3H, d, J = 1.2 Hz), 1.33 (3H, t, J = 7.1 Hz), 1.16 (3H, t, J = 7.1 Hz). |
| 803 | ¹H-NMR (CDCl₃) δ: 7.35 (1H, d, J = 9.5 Hz), 6.74 (1H, d, J = 9.5 Hz), 6.67-6.56 (3H, m), 6.48-6.43 (2H, m), 3.80 (3H, s), 3.38 (3H, s). |
| 804 | ¹H-NMR (CDCl₃) δ: 7.59 (1H, s), 6.75-6.67 (3H, m), 6.61-6.56 (2H, m), 3.44 (3H, s). |
| 805 | ¹H-NMR (CDCl₃) δ: 7.81 (1H, s), 6.76-6.68 (3H, m), 6.62-6.57 (2H, m), 3.45 (3H, s). |
| 806 | ¹H-NMR (CDCl₃) δ: 7.54 (1H, s), 7.01-6.98 (1H, m), 6.91 (1H, dd, J = 8.2, 1.6 Hz), 6.70-6.58 (3H, m), 5.66 (1H, s), 4.02-3.87 (2H, m), 1.19 (3H, t, J = 7.1 Hz). |
| 807 | ¹H-NMR (CDCl₃) δ: 7.59 (1H, s), 6.67 (1H, tt, J = 8.9, 2.3 Hz), 6.63-6.57 (2H, m), 6.48-6.43 (2H, m), 3.80 (3H, s), 3.44 (3H, s). |
| 808 | ¹H-NMR (CDCl₃) δ: 7.79 (1H, s), 6.67 (1H, tt, J = 8.9, 2.3 Hz), 6.62-6.56 (2H, m), 6.48-6.43 (2H, m), 3.80 (3H, s), 3.44 (3H, s). |
| 809 | ¹H-NMR (CDCl₃) δ: 7.54 (1H, s), 7.00 (1H, dd, J = 8.3, 7.8 Hz), 6.79 (1H, dd, J = 8.3, 1.5 Hz), 6.68-6.57 (3H, m), 4.08-3.86 (4H, m), 1.45 (3H, t, J = 7.0 Hz), 1.18 (3H, t, J = 7.1 Hz). |
| 810 | ¹H-NMR (CDCl₃) δ: 7.53 (1H, s), 7.12 (1H, dd, J = 8.3, 7.8 Hz), 6.97 (1H, dd, J = 8.3, 1.5 Hz), 6.85 (1H, dt, J = 7.8, 1.5 Hz), 6.69-6.60 (2H, m), 4.85-4.78 (2H, m), 3.99-3.91 (2H, m), 1.19 (3H, t, J = 7.1 Hz). |
| 811 | ¹H-NMR (CDCl₃) δ: 7.55 (1H, s), 7.07-6.99 (2H, m), 6.73 (1H, dt, J = 7.3, 1.8 Hz), 6.68-6.57 (2H, m), 5.22 (1H, d, J = 6.8 Hz), 5.19 (1H, d, J = 6.8 Hz), 3.99-3.90 (2H, m), 3.49 (3H, s), 1.19 (3H, t, J = 7.1 Hz). |

TABLE 5-continued

| Compound | $^1$H-NMR |
|---|---|
| 812 | $^1$H-NMR (CDCl$_3$) δ: 7.26 (1H, d, J = 9.5 Hz), 6.80-6.63 (5H, m), 3.92-3.85 (2H, m), 1.16 (3H, t, J = 7.2 Hz). |
| 813 | $^1$H-NMR (CDCl$_3$) δ: 7.49 (1H, s), 6.81 (1H, td, J = 8.3, 3.1 Hz), 6.76-6.64 (3H, m), 3.96-3.91 (2H, m), 1.19 (3H, t, J = 7.0 Hz). |
| 814 | $^1$H-NMR (CDCl$_3$) δ: 7.70 (1H, s), 6.80 (1H, td, J = 8.2, 2.8 Hz), 6.76-6.63 (3H, m), 3.95-3.92 (2H, m), 1.19 (3H, t, J = 7.1 Hz). |
| 815 | $^1$H-NMR (CDCl$_3$) δ: 7.28 (1H, d, J = 10.0 Hz), 6.82-6.70 (3H, m), 6.68-6.63 (2H, m), 3.38 (3H, s). |
| 816 | $^1$H-NMR (CDCl$_3$) δ: 7.51 (1H, s), 6.82 (1H, td, J = 8.3, 3.1 Hz), 6.73 (1H, tt, J = 8.7, 2.1 Hz), 6.68-6.66 (2H, m), 3.44 (3H, s). |
| 817 | $^1$H-NMR (CDCl$_3$) δ: 7.71 (1H, s), 6.81 (1H, td, J = 8.3, 2.8 Hz), 6.74-6.72 (1H, m), 6.69-6.65 (2H, m), 3.45 (3H, s). |
| 818 | $^1$H-NMR (CDCl$_3$) δ: 7.25 (1H, d, J = 9.5 Hz), 6.76-6.70 (3H, m), 6.48-6.46 (1H, m), 6.39-6.37 (1H, m), 3.93-3.88 (2H, m), 3.79 (3H, s), 1.16 (3H, t, J = 7.0 Hz). |
| 819 | $^1$H-NMR (CDCl$_3$) δ: 7.48 (1H, s), 6.78 (1H, td, J = 8.3, 3.1 Hz), 6.71-6.68 (1H, m), 6.48-6.46 (1H, m), 6.40-6.38 (1H, m), 3.95 (2H, q, J = 7.1 Hz), 3.79 (3H, s), 1.18 (3H, t, J = 7.1 Hz). |
| 820 | $^1$H-NMR (CDCl$_3$) δ: 7.69 (1H, s), 6.78 (1H, td, J = 8.3, 2.8 Hz), 6.71-6.68 (1H, m), 6.47 (1H, dt, J = 10.7, 1.8 Hz), 6.39 (1H, dt, J = 10.5, 2.0 Hz), 3.96 (2H, q, J = 7.1 Hz), 3.79 (3H, s), 1.18 (3H, t, J = 7.1 Hz). |
| 821 | $^1$H-NMR (CDCl$_3$) δ: 7.99 (1H, s), 7.32 (1H, dd, J = 8.1, 1.2 Hz), 7.18-7.16 (1H, m), 7.08-7.04 (2H, m), 6.67-6.57 (2H, m), 3.95 (2H, q, J = 7.1 Hz), 1.18 (3H, t, J = 7.1 Hz). |
| 822 | $^1$H-NMR (CDCl$_3$) δ: 7.98 (1H, s), 7.32-7.30 (1H, m), 7.15-7.14 (1H, m), 7.08-7.05 (2H, m), 6.40 (1H, ddd, J = 10.7, 2.5, 1.6 Hz), 6.34 (1H, ddd, J = 10.4, 2.5, 1.6 Hz), 4.00-3.94 (2H, m), 3.75 (3H, s), 1.17 (3H, t, J = 7.2 Hz). |
| 823 | $^1$H-NMR (CDCl$_3$) δ: 7.27 (1H, d, J = 6.1 Hz), 6.79-6.73 (2H, m), 6.68-6.65 (1H, m), 6.48-6.45 (1H, m), 6.40-6.37 (1H, m), 3.79 (3H, s), 3.38 (3H, s). |
| 824 | $^1$H-NMR (CDCl$_3$) δ: 7.50 (1H, s), 6.79 (1H, td, J = 8.3, 3.1 Hz), 6.69-6.66 (1H, m), 6.48-6.45 (1H, m), 6.41-6.39 (1H, m), 3.79 (3H, s), 3.45 (3H, s). |
| 825 | $^1$H-NMR (CDCl$_3$) δ: 7.70 (1H, s), 6.79 (1H, td, J = 8.2, 2.8 Hz), 6.69-6.66 (1H, m), 6.48-6.45 (1H, m), 6.41-6.38 (1H, m), 3.79 (3H, s), 3.45 (3H, s). |

The followings specifically show that the compounds of the present invention are effective against plant diseases, but the compounds of the present invention are not limited thereto.

[Test Example A] Blast on Rice

Seeds of a test plant (rice variety: Sachikaze) were planted followed by cultivating until the second leaves appeared. In the test, dilutions were obtained by dissolving the compounds of the present invention in mixed solution of dimethyl sulfoxide-methanol (a volume ratio: 9/1) and diluting them with well water so that the concentration reached to 250 ppm. The dilutions were sprayed to the plants (2.5 ml/pot). After the sprayed dilutions were dried, a conidial suspension (1-2×10$^5$ conidia/ml) of Magnaporthe grisea was inoculated to the plants by spraying. After the inoculation, the plants were kept in the mist chamber for about 24 hours at room temperature of 20° C. to 23° C. to promote the onset of disease. Disease development was investigated 6-10 days after inoculation, and the effects were evaluated.

[Test Example B] Gray Mold on Tomato

Seeds of a test plant (tomato variety: Oogata Fukuju) were planted followed by cultivating until three to five first leaves (true leaves) appeared. In the test, dilutions were obtained by dissolving the compounds of the present invention in mixed solution of dimethyl sulfoxide-methanol (a volume ratio: 9/1) and diluting them with well water so that the concentration reached to 250 ppm. The dilutions were sprayed to the plants (2.5 ml/pot). After the sprayed dilutions were dried, a conidial suspension (4-8×10$^5$ conidia/ml) of Botrytis cinerea was inoculated to the plants by spraying. After the inoculation, the plants were kept in the mist chamber for about 48 hours at room temperature of 20° C. to 23° C. to promote the onset of disease. Disease development was investigated 2-3 days after inoculation, and the effects were evaluated.

[Test Example C] Alternaria Sooty Spot on Cabbage

Seeds of a test plant (cabbage variety: Shikidori) were planted followed by cultivating until the cotyledons extended. In the test, dilutions were obtained by dissolving the compounds of the present invention in mixed solution of dimethyl sulfoxide-methanol (a volume ratio: 9/1) and diluting them with well water so that the concentration reached to 250 ppm. The dilutions were sprayed to the plants (2.5 ml/pot). After the sprayed dilutions were dried, a conidial suspension (4-8×10$^5$ conidia/ml) of Alternaia brassicicola was inoculated to the plants by spraying. After the inoculation, the plants were kept in the mist chamber for about 48 hours at room temperature of 20° C. to 23° C. to promote the onset of disease. Disease development was investigated 2-3 days after inoculation, and the effects were evaluated.

[Test Example D] Powdery Mildew on Barley

Seeds of a test plant (barley variety: Akashinriki) were planted followed by cultivating until the first leaves appeared. In the test, dilutions were obtained by dissolving the compounds of the present invention in mixed solution of dimethyl sulfoxide-methanol (a volume ratio: 9/1) and diluting them with well water so that the concentration reached to 250 ppm. The dilutions were sprayed to the plants (2.5 ml/pot). After the sprayed dilutions were dried, conidia of Blumeria graminis f sp. hordei were inoculated to the plants by shaking off. Disease development was investigated 6-10 days after the inoculation, and the effects were evaluated.

[Test Example E] Brown Rust on Wheat

Seeds of a test plant (wheat variety: Norin 61) were planted followed by cultivating until the first leaves appeared. In the test, dilutions were obtained by dissolving the compounds of the present invention in mixed solution of dimethyl sulfoxide-methanol (a volume ratio: 9/1) and diluting them with well water so that the concentration reached to 250 ppm. The dilutions were sprayed to the plants (2.5 ml/pot). After the sprayed dilutions were dried, a conidial suspension (1-2×10$^5$ conidia/ml) of *Puccinia recondita* was inoculated to the plants by spraying. After the inoculation, the plants were kept in the mist chamber for about 24 hours at room temperature of 20° C. to 23° C. to promote the onset of disease. Disease development was investigated 7-10 days after inoculation, and the effects were evaluated.

[Test Example F] Late Blight on Tomato

Seeds of a test plant (tomato variety: Oogata Fukuju) were planted followed by cultivating until three to five first leaves appeared. In the test, dilutions were obtained by dissolving the compounds of the present invention in mixed solution of dimethyl sulfoxide-methanol (a volume ratio: 9/1) and diluting them with well water so that the concentration reached to 250 ppm. The dilutions were sprayed to the plants (2.5 ml/pot). After the sprayed dilutions were dried, a zoosporangia suspension (4-8×10$^3$ zoosporangia/ml) of *Phytophthora infestans* was inoculated to the plants by spraying. After the inoculation, the plants were kept in the mist chamber for about 24 hours at room temperature of 20° C. to promote the onset of disease. Disease development was investigated 5-10 days after inoculation, and the effects were evaluated.

[Test Example G] Downy Mildew on Vine

Seeds of a test plant (grape variety: Neomuscat) were planted followed by cultivating until three to four first leaves appeared. In the test, dilutions were obtained by dissolving the compounds of the present invention in mixed solution of dimethyl sulfoxide-methanol (a volume ratio: 9/1) and diluting them with well water so that the concentration reached to 250 ppm. The dilutions were sprayed to the plants (2.5 ml/pot). After the sprayed dilutions were dried, a zoosporangia suspension (1-2×10$^4$ zoosporangia/ml) of *Plasmopara viticola* was inoculated to the plants by spraying. After the inoculation, the plants were kept in the mist chamber for about 24 hours at room temperature of 20° C. to promote the onset of disease. Disease development was investigated 7-10 days after inoculation, and the effects were evaluated.

[Test Example H] Anthracnose on Cucumber

Seeds of a test plant (cucumber variety: Sagami Hanjiro) were planted followed by cultivating until the first leaves appeared. In the test, dilutions were obtained by dissolving the compounds of the present invention in mixed solution of dimethyl sulfoxide-methanol (a volume ratio: 9/1) and diluting them with well water so that the concentration reached to 250 ppm. The dilutions were sprayed to the plants (2.5 ml/pot). After the sprayed dilutions were dried, a conidial suspension (2-4×10$^5$ conidia/ml) of *Colletotrichum orbiculare* was inoculated to the plants by spraying. After the inoculation, the plants were kept in the mist chamber for about 24 hours at room temperature of 20° C. to 23° C. to promote the onset of disease. Disease development was investigated 6-10 days after inoculation, and the effects were evaluated.

Disease development in Test Examples described above was evaluated in increments of 0.05 by setting 0 as no incidence of disease and 3 as disease development of a plant of untreated group. Furthermore, control values were calculated according to the following calculation formula based on disease development.

Control value=100{1−(n/3)}    <Preventive Value> n=Disease development of each treated group

Table 6 shows a summary of test results described above. In the table, H shows more than 50% of control values and L shows 50% or less of control values. Further, nt shows that no test was performed.

TABLE 6

| Compound | Test A | Test B | Test C | Test D | Test E | Test F | Test G | Test H |
|---|---|---|---|---|---|---|---|---|
| 1 | H | H | H | H | H | L | L | nt |
| 2 | H | H | H | H | H | L | H | nt |
| 3 | nt | L | L | H | H | nt | nt | nt |
| 4 | nt | L | L | H | H | nt | nt | nt |
| 5 | nt | H | H | H | H | nt | nt | nt |
| 6 | H | H | H | H | H | nt | nt | nt |
| 7 | nt | H | H | L | H | nt | nt | nt |
| 8 | nt | H | H | H | H | nt | nt | nt |
| 9 | nt | H | H | H | H | nt | nt | nt |
| 10 | nt | H | H | H | H | nt | nt | nt |
| 11 | nt | H | H | H | H | nt | nt | nt |
| 12 | nt | L | L | H | H | nt | nt | nt |
| 13 | nt | H | H | H | H | nt | nt | nt |
| 14 | nt | H | H | L | H | nt | nt | nt |
| 15 | nt | H | H | H | H | nt | nt | nt |
| 16 | H | H | H | H | H | nt | nt | nt |
| 17 | nt | H | L | H | H | nt | nt | nt |
| 18 | nt | H | H | H | H | nt | nt | nt |
| 19 | nt | H | H | H | H | nt | nt | nt |
| 20 | nt | H | H | H | H | nt | nt | nt |
| 21 | nt | H | H | H | H | nt | nt | nt |
| 22 | nt | H | H | H | H | nt | nt | nt |
| 23 | nt | H | H | H | H | nt | nt | nt |
| 24 | nt | H | H | H | H | nt | nt | nt |
| 25 | nt | H | H | H | H | nt | nt | nt |
| 26 | nt | H | H | H | H | nt | nt | nt |
| 27 | nt | L | H | L | H | nt | nt | nt |
| 28 | nt | H | H | L | H | nt | nt | nt |

TABLE 6-continued

| Compound | Test A | Test B | Test C | Test D | Test E | Test F | Test G | Test H |
|---|---|---|---|---|---|---|---|---|
| 29 | nt | H | H | H | H | nt | nt | nt |
| 30 | nt | H | H | H | H | nt | nt | nt |
| 31 | nt | H | H | H | H | nt | nt | nt |
| 32 | H | H | H | H | H | H | H | H |
| 33 | nt | H | H | H | H | nt | nt | nt |
| 34 | nt | H | H | H | H | nt | nt | nt |
| 35 | nt | H | H | H | H | nt | nt | nt |
| 36 | nt | H | H | H | H | nt | nt | nt |
| 37 | nt | H | H | H | H | nt | nt | nt |
| 38 | nt | H | H | H | H | nt | nt | nt |
| 39 | nt | H | H | H | H | nt | nt | nt |
| 40 | nt | H | H | H | H | nt | nt | nt |
| 41 | nt | L | L | L | H | nt | nt | nt |
| 42 | nt | H | H | H | H | nt | nt | nt |
| 43 | nt | L | H | H | H | nt | nt | nt |
| 44 | nt | H | H | H | H | nt | nt | nt |
| 45 | nt | H | H | H | H | nt | nt | nt |
| 46 | nt | H | H | H | H | nt | nt | nt |
| 47 | nt | H | H | H | H | nt | nt | nt |
| 48 | nt | L | H | L | L | nt | nt | nt |
| 49 | nt | H | H | L | H | nt | nt | nt |
| 50 | nt | H | H | L | L | nt | nt | nt |
| 51 | nt | H | H | L | H | nt | nt | nt |
| 52 | nt | H | H | H | H | nt | nt | nt |
| 53 | nt | H | H | H | H | nt | nt | nt |
| 54 | H | H | H | H | H | L | H | H |
| 55 | nt | H | H | H | H | nt | nt | nt |
| 56 | nt | H | H | H | H | nt | nt | nt |
| 57 | nt | H | H | H | H | nt | nt | nt |
| 58 | nt | H | H | H | H | nt | nt | nt |
| 59 | nt | H | H | H | H | nt | nt | nt |
| 60 | nt | H | H | H | H | nt | nt | nt |
| 61 | nt | H | H | H | H | nt | nt | nt |
| 62 | nt | H | H | H | H | nt | nt | nt |
| 63 | nt | H | H | H | H | nt | nt | nt |
| 64 | nt | H | H | H | H | nt | nt | nt |
| 65 | nt | H | H | H | H | nt | nt | nt |
| 66 | nt | H | H | H | H | nt | nt | nt |
| 67 | nt | H | H | L | H | nt | nt | nt |
| 68 | nt | H | H | H | H | nt | nt | nt |
| 69 | nt | H | L | L | L | nt | nt | nt |
| 70 | nt | H | L | L | L | nt | nt | nt |
| 71 | nt | H | H | H | H | nt | nt | nt |
| 72 | nt | H | H | H | H | nt | nt | nt |
| 73 | nt | H | H | H | H | nt | nt | nt |
| 74 | nt | H | H | H | H | nt | nt | nt |
| 75 | nt | H | H | H | H | nt | nt | nt |
| 76 | nt | H | H | H | H | nt | nt | nt |
| 77 | nt | H | H | H | H | nt | nt | nt |
| 78 | nt | H | H | H | H | nt | nt | nt |
| 79 | nt | H | H | H | H | nt | nt | nt |
| 80 | nt | H | H | H | H | nt | nt | nt |
| 81 | nt | H | H | H | H | nt | nt | nt |
| 82 | nt | H | H | H | H | nt | nt | nt |
| 83 | nt | H | L | L | H | nt | nt | nt |
| 84 | nt | H | L | L | L | nt | nt | nt |
| 85 | nt | H | H | H | H | nt | nt | nt |
| 86 | nt | H | H | H | H | nt | nt | nt |
| 87 | nt | H | H | H | H | nt | nt | nt |
| 88 | nt | H | H | H | H | nt | nt | nt |
| 89 | nt | H | H | H | H | nt | nt | nt |
| 90 | nt | H | H | H | H | nt | nt | nt |
| 91 | nt | H | H | H | H | nt | nt | nt |
| 92 | nt | H | H | H | H | nt | nt | nt |
| 93 | nt | H | H | H | H | nt | nt | nt |
| 94 | nt | H | H | H | H | nt | nt | nt |
| 95 | nt | H | H | H | H | nt | nt | nt |
| 96 | nt | H | H | H | H | nt | nt | nt |
| 97 | H | H | H | H | H | L | H | H |
| 98 | H | H | H | H | H | L | H | H |
| 99 | H | H | H | H | H | L | H | H |
| 100 | nt | H | H | H | H | nt | nt | nt |
| 101 | H | H | H | H | H | L | H | H |
| 102 | H | H | H | H | H | L | H | H |
| 103 | H | H | H | H | H | L | H | nt |
| 104 | nt | H | H | H | H | nt | nt | nt |
| 105 | nt | H | H | H | H | nt | nt | nt |
| 106 | nt | H | H | H | H | nt | nt | nt |

TABLE 6-continued

| Compound | Test A | Test B | Test C | Test D | Test E | Test F | Test G | Test H |
|---|---|---|---|---|---|---|---|---|
| 107 | nt | H | H | H | H | nt | nt | nt |
| 108 | nt | H | H | H | H | nt | nt | nt |
| 109 | nt | H | H | L | H | nt | nt | nt |
| 110 | nt | H | H | H | H | nt | nt | nt |
| 111 | nt | H | H | H | H | nt | nt | nt |
| 112 | nt | H | H | H | H | nt | nt | nt |
| 113 | nt | H | H | H | H | nt | nt | nt |
| 114 | nt | H | L | L | H | nt | nt | nt |
| 115 | nt | L | L | L | H | nt | nt | nt |
| 116 | nt | L | L | H | H | nt | nt | nt |
| 117 | nt | H | H | H | H | nt | nt | nt |
| 118 | nt | H | H | H | H | nt | nt | nt |
| 119 | nt | H | H | H | H | nt | nt | nt |
| 120 | nt | H | H | H | H | nt | nt | nt |
| 121 | nt | H | H | H | H | nt | nt | nt |
| 122 | nt | H | H | H | H | nt | nt | nt |
| 123 | nt | H | H | H | H | nt | nt | nt |
| 124 | nt | H | H | H | H | nt | nt | nt |
| 125 | nt | H | H | L | H | nt | nt | nt |
| 126 | H | H | H | H | H | L | H | nt |
| 127 | H | H | H | H | H | L | H | nt |
| 128 | H | H | H | H | H | L | H | nt |
| 129 | H | H | H | H | H | L | H | nt |
| 130 | nt | H | H | H | H | nt | nt | nt |
| 131 | nt | H | H | H | H | nt | nt | nt |
| 132 | nt | H | H | H | H | nt | nt | nt |
| 133 | nt | H | H | H | H | nt | nt | nt |
| 134 | nt | H | H | H | H | nt | nt | nt |
| 135 | nt | H | H | H | H | nt | nt | nt |
| 136 | H | H | H | H | H | H | H | H |
| 137 | nt | H | H | H | H | nt | nt | nt |
| 138 | nt | L | L | H | H | nt | nt | nt |
| 139 | nt | H | H | L | H | nt | nt | nt |
| 140 | nt | H | H | H | H | nt | nt | nt |
| 141 | nt | H | H | H | H | nt | nt | nt |
| 142 | nt | H | H | H | H | nt | nt | nt |
| 143 | H | H | H | H | H | L | H | H |
| 144 | H | H | H | H | H | L | H | H |
| 145 | H | H | H | H | H | H | H | H |
| 146 | H | L | L | H | H | L | L | L |
| 147 | L | L | L | L | H | L | L | L |
| 148 | H | L | L | L | L | L | L | L |
| 149 | H | H | H | H | H | L | H | H |
| 150 | L | H | L | L | H | L | L | L |
| 151 | H | H | H | H | H | L | H | H |
| 152 | H | H | H | H | H | L | H | H |
| 153 | H | H | H | H | H | H | H | H |
| 154 | H | H | H | H | H | L | L | L |
| 155 | H | H | H | H | H | L | L | L |
| 156 | H | H | H | H | H | H | H | H |
| 157 | H | H | H | H | H | L | H | H |
| 158 | H | L | H | L | L | L | L | L |
| 159 | H | L | L | L | H | L | L | L |
| 160 | H | H | H | H | H | H | H | H |
| 161 | H | H | H | H | H | L | L | L |
| 162 | H | H | H | H | L | L | L | L |
| 163 | H | H | L | L | H | L | H | L |
| 164 | H | H | H | L | H | L | L | H |
| 165 | H | H | H | H | H | H | H | H |
| 166 | H | H | H | H | H | H | H | H |
| 167 | H | L | L | L | L | L | L | L |
| 168 | H | H | H | H | H | H | H | H |
| 169 | H | H | H | L | H | L | L | H |
| 170 | H | H | H | H | H | L | H | H |
| 171 | H | H | H | H | H | L | H | H |
| 172 | H | H | H | H | H | H | L | L |
| 173 | H | H | H | H | H | H | H | L |
| 174 | H | H | H | L | H | L | H | L |
| 175 | H | H | L | L | L | L | L | H |
| 176 | H | H | H | H | H | H | H | H |
| 177 | H | H | H | H | H | L | H | H |
| 178 | H | L | H | L | L | L | L | L |
| 179 | H | L | H | L | L | L | L | L |
| 180 | H | H | H | H | H | H | L | H |
| 181 | H | H | H | L | H | L | L | L |
| 182 | H | H | H | L | H | L | L | L |
| 183 | H | H | L | L | H | L | L | L |
| 184 | H | H | H | H | H | H | H | H |

TABLE 6-continued

| Compound | Test A | Test B | Test C | Test D | Test E | Test F | Test G | Test H |
|---|---|---|---|---|---|---|---|---|
| 185 | H | H | H | H | H | H | L | H |
| 186 | H | H | H | L | H | H | H | L |
| 187 | H | H | H | L | H | H | H | L |
| 188 | H | H | H | H | H | L | H | L |
| 189 | H | H | H | H | H | L | H | L |
| 190 | H | H | H | H | H | L | H | L |
| 191 | L | L | H | H | H | L | L | L |
| 192 | H | H | L | H | H | L | L | L |
| 193 | H | H | H | H | H | L | H | H |
| 194 | H | H | H | H | H | L | L | H |
| 195 | H | H | H | H | H | L | H | H |
| 196 | H | H | H | H | H | L | H | H |
| 197 | H | H | H | H | H | L | H | H |
| 198 | H | H | H | H | H | L | H | H |
| 199 | H | H | H | L | H | L | L | H |
| 200 | H | H | H | H | H | H | H | H |
| 201 | H | H | H | H | H | H | H | H |
| 202 | H | H | H | L | H | L | H | H |
| 203 | H | H | H | L | H | L | L | H |
| 204 | H | H | H | H | H | H | H | H |
| 205 | H | H | H | H | H | H | H | H |
| 206 | H | H | H | L | H | L | H | H |
| 207 | H | L | H | H | H | L | L | L |
| 208 | H | L | L | L | L | L | L | L |
| 209 | H | H | H | H | H | L | H | L |
| 210 | H | H | H | L | L | L | L | L |
| 211 | nt | L | H | L | L | nt | nt | nt |
| 212 | H | H | H | H | H | L | H | L |
| 213 | H | H | H | H | H | L | L | H |
| 214 | H | H | H | H | H | L | L | H |
| 215 | H | H | H | H | H | L | H | H |
| 216 | H | H | H | H | H | H | H | H |
| 217 | H | L | H | H | H | L | H | L |
| 218 | H | L | H | H | H | L | L | L |
| 219 | H | H | H | H | H | L | L | L |
| 220 | H | L | L | L | L | L | L | L |
| 221 | H | H | H | H | H | L | L | H |
| 222 | H | H | H | H | H | L | H | H |
| 223 | H | H | H | H | H | L | H | H |
| 224 | H | H | H | H | H | H | H | H |
| 225 | H | H | H | L | H | L | H | L |
| 226 | H | H | H | L | H | H | H | H |
| 227 | nt | H | H | L | H | nt | nt | nt |
| 228 | nt | H | H | L | H | nt | nt | nt |
| 229 | nt | H | H | L | H | nt | nt | nt |
| 230 | H | H | H | H | H | H | H | H |
| 231 | H | H | H | H | H | H | H | H |
| 232 | H | H | H | H | H | L | L | H |
| 233 | H | H | L | H | H | H | H | L |
| 234 | H | H | H | L | H | L | H | H |
| 235 | H | H | L | L | H | L | L | L |
| 236 | H | H | H | H | H | L | H | H |
| 237 | H | H | L | H | H | L | L | H |
| 238 | H | H | H | H | H | L | H | H |
| 239 | H | H | H | H | H | H | H | H |
| 240 | H | H | H | H | H | L | H | H |
| 241 | H | H | H | H | H | L | H | H |
| 242 | H | H | H | H | H | L | L | H |
| 243 | H | H | H | H | H | L | H | H |
| 244 | H | H | H | H | H | L | L | H |
| 245 | L | H | H | H | L | L | L | L |
| 246 | L | H | H | H | H | L | L | L |
| 247 | H | H | H | H | H | H | H | H |
| 248 | H | H | H | L | H | L | H | L |
| 249 | L | H | H | L | H | L | L | H |
| 250 | H | H | H | L | H | L | H | H |
| 251 | H | H | H | L | H | L | H | H |
| 252 | H | L | H | H | L | L | L | H |
| 253 | H | H | H | H | L | L | H | H |
| 254 | H | L | H | H | L | L | H | L |
| 255 | L | L | H | L | L | L | L | L |
| 256 | H | H | H | H | H | L | L | H |
| 257 | H | H | H | H | H | L | L | L |
| 258 | L | L | H | H | L | L | H | H |
| 259 | H | L | H | L | L | L | L | L |
| 260 | L | L | H | H | L | L | L | H |
| 261 | L | L | H | L | L | L | L | L |
| 262 | H | H | H | H | H | L | H | H |

TABLE 6-continued

| Compound | Test A | Test B | Test C | Test D | Test E | Test F | Test G | Test H |
|---|---|---|---|---|---|---|---|---|
| 263 | H | H | H | L | H | L | H | H |
| 264 | H | H | L | L | L | L | L | L |
| 265 | H | H | H | H | H | L | H | H |
| 266 | H | L | H | L | L | L | L | L |
| 267 | H | L | H | H | H | L | L | L |
| 268 | H | L | L | H | H | L | H | L |
| 269 | H | H | H | H | H | L | H | H |
| 270 | H | H | H | H | H | L | L | L |
| 271 | H | H | H | H | H | L | H | H |
| 272 | H | H | H | H | H | L | H | H |
| 273 | H | H | H | H | H | L | H | L |
| 274 | H | H | H | H | H | L | H | H |
| 275 | L | L | H | L | L | L | L | L |
| 276 | L | L | H | L | L | L | L | L |
| 277 | H | H | H | H | H | L | H | H |
| 278 | H | H | H | H | H | L | H | H |
| 279 | H | L | H | H | H | L | L | L |
| 280 | H | H | H | H | H | L | H | H |
| 281 | H | H | H | H | H | L | H | H |
| 282 | H | H | H | L | H | L | L | H |
| 283 | L | H | L | H | L | L | L | L |
| 284 | L | H | L | H | L | L | L | L |
| 285 | H | H | H | H | H | nt | L | H |
| 286 | H | H | H | L | H | L | H | L |
| 287 | H | H | H | H | L | L | H | L |
| 288 | L | H | L | L | L | L | L | L |
| 289 | H | H | H | H | H | L | L | L |
| 290 | H | H | H | L | H | L | H | H |
| 291 | H | H | H | H | H | L | H | H |
| 292 | H | H | H | H | H | L | L | H |
| 293 | H | H | H | H | H | L | L | H |
| 294 | H | H | H | H | H | L | H | L |
| 295 | L | H | L | L | L | L | L | L |
| 296 | L | H | L | L | L | L | L | L |
| 297 | H | H | H | H | H | L | L | H |
| 298 | H | H | H | H | H | L | L | H |
| 299 | H | H | H | H | H | L | L | L |
| 300 | H | H | H | H | H | L | L | L |
| 301 | H | H | H | H | H | H | L | H |
| 302 | H | H | H | H | H | L | L | H |
| 303 | H | H | H | H | H | L | L | H |
| 304 | H | H | H | H | H | L | L | L |
| 305 | H | H | H | H | H | L | L | H |
| 306 | H | H | H | L | H | L | L | H |
| 307 | L | H | L | L | H | L | L | L |
| 308 | L | H | L | L | H | L | L | L |
| 309 | L | H | H | L | H | L | L | H |
| 310 | H | H | H | H | L | L | L | L |
| 311 | H | H | H | H | H | L | L | L |
| 312 | L | H | L | L | H | L | L | L |
| 313 | H | H | H | H | H | L | L | H |
| 314 | H | H | H | H | H | L | H | H |
| 315 | H | H | H | H | H | H | H | L |
| 316 | H | H | L | H | H | L | L | L |
| 317 | H | H | H | H | H | L | L | L |
| 318 | H | H | L | L | H | L | L | L |
| 319 | H | H | H | H | H | H | L | H |
| 320 | nt | H | H | H | H | nt | nt | nt |
| 321 | H | H | H | H | H | H | H | H |
| 322 | H | H | H | H | H | L | L | H |
| 323 | H | H | L | H | L | L | L | L |
| 324 | L | L | H | L | L | L | L | L |
| 325 | H | H | H | H | H | L | L | H |
| 326 | H | H | H | H | H | L | L | H |
| 327 | H | L | L | L | L | L | L | L |
| 328 | H | L | L | L | L | L | L | L |
| 329 | H | H | H | H | H | L | H | H |
| 330 | H | H | L | H | H | H | H | H |
| 331 | H | H | L | H | H | H | H | H |
| 332 | H | H | H | H | H | L | H | H |
| 333 | H | L | L | H | H | L | L | L |
| 334 | nt | H | L | H | H | nt | nt | nt |
| 335 | H | H | H | H | H | L | H | H |
| 336 | H | H | H | H | H | L | H | H |
| 337 | H | H | H | H | H | H | H | H |
| 338 | H | H | H | L | H | H | H | H |
| 339 | H | H | H | H | H | H | H | H |
| 340 | H | H | H | H | H | L | L | H |

TABLE 6-continued

| Compound | Test A | Test B | Test C | Test D | Test E | Test F | Test G | Test H |
|---|---|---|---|---|---|---|---|---|
| 341 | H | L | L | L | L | L | L | L |
| 342 | H | H | H | H | H | L | L | H |
| 343 | H | H | H | H | H | H | H | H |
| 344 | H | H | L | H | H | L | L | L |
| 345 | H | H | H | H | H | H | H | H |
| 346 | H | H | H | L | L | L | L | L |
| 347 | H | H | H | H | H | L | L | H |
| 348 | H | L | L | L | L | L | L | L |
| 349 | H | H | H | H | H | H | H | H |
| 350 | H | H | H | H | H | L | L | L |
| 351 | H | H | H | H | H | L | L | H |
| 352 | H | H | H | L | L | L | L | L |
| 353 | H | H | L | L | L | L | L | L |
| 354 | H | H | H | H | H | L | H | H |
| 355 | H | H | H | H | H | L | L | H |
| 356 | H | H | H | H | H | H | H | H |
| 357 | H | H | H | H | H | H | H | H |
| 358 | H | H | H | H | H | H | H | H |
| 359 | H | H | H | H | H | H | H | H |
| 360 | H | H | H | H | H | L | L | H |
| 361 | H | H | L | L | H | L | L | L |
| 362 | H | H | H | H | H | L | H | H |
| 363 | H | H | H | H | H | L | H | H |
| 364 | H | H | H | H | H | L | L | H |
| 365 | H | H | H | H | H | L | L | H |
| 366 | H | H | H | H | H | L | L | H |
| 367 | H | H | H | H | H | L | L | L |
| 368 | H | H | H | H | H | L | L | H |
| 369 | H | H | H | H | H | L | L | H |
| 370 | H | H | H | L | L | L | L | L |
| 371 | H | H | L | H | H | L | L | H |
| 372 | H | L | H | L | H | L | L | L |
| 373 | H | H | L | L | H | L | L | L |
| 374 | H | H | H | H | H | L | L | H |
| 375 | H | H | H | L | H | L | H | H |
| 376 | H | H | H | H | H | L | H | H |
| 377 | H | H | H | H | H | L | H | H |
| 378 | H | H | H | H | H | L | H | H |
| 379 | H | H | H | H | H | H | H | H |
| 380 | H | H | H | H | H | L | H | H |
| 381 | H | H | H | H | H | L | L | H |
| 382 | H | H | H | H | H | L | L | H |
| 383 | H | L | L | L | L | L | L | L |
| 384 | H | L | L | H | H | L | L | L |
| 385 | H | H | H | H | H | H | H | H |
| 386 | H | H | H | H | H | L | L | H |
| 387 | H | L | L | L | L | L | L | L |
| 388 | H | H | L | H | L | L | H | H |
| 389 | H | L | L | H | L | L | L | L |
| 390 | nt | L | L | H | L | L | L | L |
| 391 | H | H | H | H | H | L | L | H |
| 392 | H | H | H | H | H | L | L | H |
| 393 | H | H | L | H | H | L | L | H |
| 394 | H | L | L | H | H | L | H | L |
| 395 | H | L | L | L | L | L | L | L |
| 396 | H | L | L | L | L | L | L | L |
| 397 | H | H | H | H | H | L | H | H |
| 398 | H | H | H | H | H | L | H | H |
| 399 | H | H | H | H | H | L | H | H |
| 400 | H | H | H | H | H | L | H | H |
| 401 | H | H | H | H | H | L | L | H |
| 402 | H | H | H | H | H | L | H | H |
| 403 | H | H | H | H | H | L | L | H |
| 404 | H | H | H | H | H | L | H | H |
| 405 | H | H | H | H | H | L | L | H |
| 406 | H | H | H | H | H | L | H | H |
| 407 | H | H | H | H | H | L | H | H |
| 408 | H | H | H | H | H | L | L | L |
| 409 | H | H | L | H | H | L | L | L |
| 410 | H | H | H | H | H | L | L | H |
| 411 | H | H | H | H | H | L | L | H |
| 412 | nt | H | H | H | H | nt | nt | nt |
| 413 | H | L | H | H | H | L | L | H |
| 414 | nt | H | H | H | H | nt | nt | nt |
| 415 | H | H | H | H | H | H | L | H |
| 416 | H | H | H | H | H | L | L | H |
| 417 | H | L | H | H | H | L | L | L |
| 418 | H | H | H | L | H | L | L | H |

TABLE 6-continued

| Compound | Test A | Test B | Test C | Test D | Test E | Test F | Test G | Test H |
|---|---|---|---|---|---|---|---|---|
| 419 | H | L | H | L | H | L | L | L |
| 420 | H | H | H | H | H | H | H | H |
| 421 | H | H | H | H | H | L | L | H |
| 422 | H | H | H | L | H | H | L | L |
| 423 | H | H | H | L | H | L | H | H |
| 424 | H | H | H | H | H | H | L | H |
| 425 | H | H | H | H | H | L | L | H |
| 426 | H | H | H | H | H | L | L | H |
| 427 | H | H | H | H | H | L | L | H |
| 428 | H | H | H | H | H | L | H | H |
| 429 | nt | L | H | H | H | nt | nt | nt |
| 430 | H | H | H | H | H | L | H | H |
| 431 | H | H | H | H | H | H | H | H |
| 432 | H | H | H | H | H | H | H | H |
| 433 | H | H | H | H | H | L | L | H |
| 434 | H | H | H | H | H | L | H | H |
| 435 | H | H | H | H | H | L | H | H |
| 436 | L | H | L | H | H | L | L | H |
| 437 | L | H | L | H | H | L | L | H |
| 438 | H | H | H | H | H | L | L | H |
| 439 | H | H | H | H | H | L | L | H |
| 440 | H | H | H | H | H | L | L | H |
| 441 | H | H | H | H | H | L | L | H |
| 442 | H | H | H | L | H | L | L | H |
| 443 | H | H | H | L | H | L | L | H |
| 444 | H | H | H | H | H | L | L | H |
| 445 | H | H | H | H | L | L | L | H |
| 446 | H | H | H | H | H | L | H | H |
| 447 | H | H | H | H | H | L | L | H |
| 448 | H | H | L | H | L | L | L | H |
| 449 | H | H | H | H | H | L | L | H |
| 450 | H | H | H | H | L | L | L | H |
| 451 | H | H | H | H | H | L | L | H |
| 452 | H | H | H | H | H | L | L | H |
| 453 | H | H | H | H | H | L | L | H |
| 454 | H | H | H | H | H | L | H | H |
| 455 | H | H | H | H | H | L | L | H |
| 456 | H | H | H | H | H | L | L | H |
| 457 | H | H | H | H | H | L | H | H |
| 458 | H | H | L | L | L | L | L | H |
| 459 | H | H | H | H | H | L | L | H |
| 460 | H | H | H | H | H | L | L | L |
| 461 | H | H | H | H | H | L | H | H |
| 462 | H | H | H | H | H | L | H | H |
| 463 | H | H | H | H | H | L | H | H |
| 464 | H | H | H | H | H | L | L | H |
| 465 | H | H | H | H | H | L | L | H |
| 466 | H | H | H | H | H | L | L | H |
| 467 | H | H | H | H | H | L | L | H |
| 468 | H | H | H | H | H | H | H | H |
| 469 | H | H | H | H | H | L | L | H |
| 470 | H | H | H | H | H | L | H | H |
| 471 | H | H | H | H | H | L | H | H |
| 472 | H | H | H | H | H | L | H | H |
| 473 | H | L | H | L | L | L | L | L |
| 474 | H | H | H | H | H | L | L | H |
| 475 | H | H | H | H | H | L | L | H |
| 476 | H | H | H | H | H | L | L | H |
| 477 | H | H | H | H | H | H | L | L |
| 478 | H | H | H | H | H | H | H | H |
| 479 | H | H | H | H | H | L | H | H |
| 480 | H | H | L | L | L | L | L | L |
| 481 | H | H | H | H | H | L | L | H |
| 482 | H | L | H | L | H | L | L | L |
| 483 | H | H | H | H | H | H | H | H |
| 484 | H | H | H | H | H | L | H | H |
| 485 | H | H | H | H | H | H | L | H |
| 486 | H | H | H | H | H | H | H | H |
| 487 | H | H | H | H | H | L | L | H |
| 488 | H | H | H | H | H | L | L | H |
| 489 | H | H | H | H | H | H | H | H |
| 490 | H | H | H | H | H | L | L | H |
| 491 | H | H | H | H | H | L | L | H |
| 492 | H | H | H | H | H | L | L | H |
| 493 | H | H | H | H | H | L | L | H |
| 494 | H | L | H | H | L | L | L | L |
| 495 | H | L | L | L | L | L | L | L |
| 496 | H | H | H | H | H | L | L | H |

TABLE 6-continued

| Compound | Test A | Test B | Test C | Test D | Test E | Test F | Test G | Test H |
|---|---|---|---|---|---|---|---|---|
| 497 | H | H | H | H | H | L | L | H |
| 498 | H | H | H | H | H | L | H | H |
| 499 | H | H | H | H | H | L | H | H |
| 500 | H | H | H | H | H | L | H | H |
| 501 | H | H | H | H | H | H | H | H |
| 502 | nt | H | H | H | H | nt | nt | nt |
| 503 | H | H | H | H | H | L | H | H |
| 504 | H | H | H | H | H | L | H | H |
| 505 | H | H | H | H | H | L | H | H |
| 506 | H | H | H | H | H | L | H | H |
| 507 | H | H | H | H | H | L | H | H |
| 508 | H | H | H | H | H | H | H | H |
| 509 | H | H | H | H | H | L | H | H |
| 510 | H | H | H | H | H | L | H | H |
| 511 | H | H | H | H | H | L | H | H |
| 512 | H | H | H | H | H | L | H | H |
| 513 | H | H | H | H | H | L | H | H |
| 514 | H | H | H | H | H | L | L | H |
| 515 | nt | H | nt | H | H | nt | nt | nt |
| 516 | nt | H | nt | H | H | nt | nt | nt |
| 517 | H | H | H | H | H | L | H | H |
| 518 | H | H | H | H | H | H | L | H |
| 519 | H | H | H | H | H | L | L | H |
| 520 | H | H | H | H | H | L | L | H |
| 521 | H | H | H | H | H | L | L | L |
| 522 | H | H | H | L | L | L | L | H |
| 523 | H | H | L | L | H | L | L | L |
| 524 | H | H | H | L | H | L | L | L |
| 525 | H | H | L | L | H | L | L | L |
| 526 | L | H | H | H | L | L | H | H |
| 527 | H | H | H | H | H | L | H | H |
| 528 | H | H | H | H | H | H | H | H |
| 529 | H | H | H | H | H | L | H | H |
| 530 | H | H | H | H | H | L | H | H |
| 531 | H | H | H | H | H | L | L | H |
| 532 | H | H | H | H | H | L | H | H |
| 533 | H | H | H | H | H | L | L | H |
| 534 | H | H | H | H | H | L | L | H |
| 535 | H | H | H | H | H | L | L | H |
| 536 | H | H | H | H | H | L | L | H |
| 537 | H | H | H | H | H | L | L | H |
| 538 | H | H | H | H | H | H | H | H |
| 539 | H | H | H | H | H | H | H | H |
| 540 | H | H | H | H | H | L | L | H |
| 541 | H | H | H | H | H | L | L | H |
| 542 | H | H | H | H | H | H | H | H |
| 543 | H | H | H | H | H | L | H | H |
| 544 | H | H | H | H | H | L | L | H |
| 545 | H | H | H | H | H | L | L | H |
| 546 | H | H | H | H | H | L | L | H |
| 547 | H | H | H | H | H | L | L | H |
| 548 | H | H | H | H | H | L | L | H |
| 549 | H | H | H | H | H | L | L | H |
| 550 | H | H | H | H | H | L | H | H |
| 551 | H | H | H | H | H | L | L | H |
| 552 | H | H | H | H | H | L | L | H |
| 553 | H | H | H | H | H | H | H | H |
| 554 | H | H | H | H | H | L | L | H |
| 555 | H | H | H | H | H | L | L | H |
| 556 | H | H | H | H | H | L | L | H |
| 557 | H | H | H | H | H | L | H | H |
| 558 | H | H | H | H | H | L | H | H |
| 559 | H | H | H | H | H | L | L | H |
| 560 | H | H | H | H | H | L | L | H |
| 561 | H | H | H | H | H | L | H | H |
| 562 | H | H | H | H | H | L | L | H |
| 563 | H | H | H | H | H | L | L | H |
| 564 | H | H | H | H | H | L | H | H |
| 565 | H | H | H | H | H | L | H | H |
| 566 | H | H | H | H | H | L | H | H |
| 567 | H | H | H | H | H | L | H | H |
| 568 | H | H | H | H | H | L | H | H |
| 569 | H | H | H | H | H | L | H | H |
| 570 | H | H | H | H | H | L | H | H |
| 571 | H | H | H | H | H | H | H | H |
| 572 | H | H | H | H | H | L | H | H |
| 573 | H | H | H | H | H | L | L | H |
| 574 | H | H | H | H | H | H | H | H |

TABLE 6-continued

| Compound | Test A | Test B | Test C | Test D | Test E | Test F | Test G | Test H |
|---|---|---|---|---|---|---|---|---|
| 575 | H | H | H | H | H | L | H | H |
| 576 | H | H | H | H | H | L | H | H |
| 577 | H | H | H | H | H | L | L | H |
| 578 | H | H | H | H | H | L | L | H |
| 579 | H | H | H | H | H | L | H | H |
| 580 | H | H | H | H | H | L | L | H |
| 581 | H | H | H | H | H | L | H | H |
| 582 | H | H | H | H | H | L | H | H |
| 583 | H | H | H | H | H | L | H | H |
| 584 | H | H | H | H | H | L | H | H |
| 585 | H | H | H | H | H | L | L | H |
| 586 | H | H | H | H | H | L | L | H |
| 587 | H | H | H | H | H | L | L | H |
| 588 | H | H | H | H | H | L | H | H |
| 589 | H | H | H | H | H | L | L | H |
| 590 | H | H | H | H | H | L | L | H |
| 591 | H | H | H | H | H | L | H | H |
| 592 | H | H | H | H | H | L | L | H |
| 593 | H | H | H | H | H | L | H | H |
| 594 | H | H | H | H | H | L | H | H |
| 595 | H | H | H | H | H | L | H | H |
| 596 | H | H | H | H | H | L | L | H |
| 597 | H | H | H | H | H | L | L | H |
| 598 | H | H | H | H | H | L | H | H |
| 599 | H | H | H | H | H | L | H | H |
| 600 | H | H | H | H | H | L | H | H |
| 601 | H | H | H | H | H | L | L | H |
| 602 | H | H | H | H | H | L | L | H |
| 603 | H | L | H | H | H | L | L | L |
| 604 | H | H | H | H | H | L | L | H |
| 605 | H | H | H | H | H | L | L | H |
| 606 | H | H | H | H | H | L | L | H |
| 607 | H | H | H | H | H | L | L | H |
| 608 | H | H | H | H | H | L | L | H |
| 609 | H | H | H | H | H | L | L | H |
| 610 | H | H | H | H | H | L | L | H |
| 611 | H | H | H | H | H | L | H | H |
| 612 | H | H | H | H | H | H | L | H |
| 613 | H | H | H | H | H | L | L | H |
| 614 | H | H | H | H | H | L | L | H |
| 615 | H | H | H | H | H | L | L | H |
| 616 | H | H | H | H | H | L | H | H |
| 617 | H | H | H | H | H | L | L | H |
| 618 | H | H | H | H | H | L | H | H |
| 619 | H | H | H | H | H | L | L | H |
| 620 | H | H | H | H | H | L | L | H |
| 621 | H | H | H | H | H | L | L | H |
| 622 | H | L | H | H | H | L | L | H |
| 623 | H | H | H | H | H | L | L | H |
| 624 | H | H | H | H | H | H | H | H |
| 625 | H | H | H | H | H | L | L | H |
| 626 | H | H | H | H | H | L | H | H |
| 627 | H | H | H | H | H | L | L | H |
| 628 | H | H | H | H | H | L | L | H |
| 629 | H | H | H | H | H | L | H | H |
| 630 | H | H | H | H | H | L | H | H |
| 631 | H | H | H | H | H | L | L | H |
| 632 | H | H | H | H | H | L | L | H |
| 633 | H | H | H | H | H | H | H | H |
| 634 | H | H | H | H | H | H | H | H |
| 635 | H | H | H | H | H | L | H | H |
| 636 | H | H | H | L | H | L | L | H |
| 637 | H | H | H | H | H | L | H | H |
| 638 | H | H | H | H | H | L | H | H |
| 639 | H | H | H | H | H | L | H | H |
| 640 | H | H | H | H | H | L | H | H |
| 641 | H | H | H | H | H | L | H | H |
| 642 | H | H | H | H | H | H | H | H |
| 643 | H | H | H | H | H | L | H | H |
| 644 | H | H | H | H | H | L | H | H |
| 645 | H | H | H | H | H | L | H | H |
| 646 | H | H | H | L | H | L | L | H |
| 647 | H | H | H | H | H | H | H | H |
| 648 | H | H | H | H | H | L | L | H |
| 649 | H | H | H | H | H | L | H | H |
| 650 | H | H | H | H | H | L | L | H |
| 651 | H | H | H | H | H | L | H | H |
| 652 | H | H | H | H | H | L | L | H |

TABLE 6-continued

| Compound | Test A | Test B | Test C | Test D | Test E | Test F | Test G | Test H |
|---|---|---|---|---|---|---|---|---|
| 653 | H | H | H | L | H | L | L | H |
| 654 | H | H | H | H | H | H | L | H |
| 655 | H | H | H | L | H | L | L | H |
| 656 | H | H | H | H | H | L | L | H |
| 657 | H | H | H | H | H | L | L | H |
| 658 | H | H | H | H | H | L | L | H |
| 659 | H | H | H | H | H | L | L | H |
| 660 | H | H | H | H | H | H | H | H |
| 661 | H | H | H | H | H | H | H | H |
| 662 | H | H | H | L | H | L | L | H |
| 663 | H | H | H | H | H | H | H | H |
| 664 | H | H | H | H | H | H | H | H |
| 665 | H | H | H | H | H | L | L | H |
| 666 | H | H | H | H | H | L | H | H |
| 667 | H | H | H | H | H | L | H | H |
| 668 | H | H | H | H | H | L | H | H |
| 669 | H | H | H | L | H | L | L | H |
| 670 | H | H | H | L | H | H | H | H |
| 671 | H | H | H | H | H | L | H | H |
| 672 | H | H | H | H | H | L | H | H |
| 673 | H | H | H | H | H | L | H | H |
| 674 | H | H | H | H | H | L | H | H |
| 675 | H | H | H | H | H | L | H | H |
| 676 | H | H | H | H | H | L | H | H |
| 677 | H | H | H | H | H | L | H | H |
| 678 | H | H | H | H | H | L | H | H |
| 679 | H | H | H | H | H | L | L | H |
| 680 | H | H | H | L | H | L | L | H |
| 681 | H | H | H | H | H | L | L | H |
| 682 | H | H | H | H | H | L | L | H |
| 683 | H | H | H | H | H | L | L | H |
| 684 | H | H | H | H | H | L | H | H |
| 685 | H | H | H | H | H | L | H | H |
| 686 | H | H | H | H | H | L | H | H |
| 687 | H | H | H | H | H | L | H | H |
| 688 | H | H | H | H | H | L | L | H |
| 689 | H | H | H | H | H | L | H | H |
| 690 | H | H | H | L | H | L | L | H |
| 691 | H | H | H | H | H | L | H | H |
| 692 | H | H | H | H | H | L | L | L |
| 693 | H | H | H | H | H | L | H | H |
| 694 | H | H | H | H | H | L | H | H |
| 695 | H | H | H | H | H | L | H | H |
| 696 | H | H | H | H | H | L | H | H |
| 697 | H | H | H | H | H | L | H | H |
| 698 | H | H | H | H | H | L | H | H |
| 699 | H | H | H | H | H | L | L | H |
| 700 | H | H | H | H | H | L | H | H |
| 701 | H | H | H | H | H | L | H | H |
| 702 | H | H | H | H | H | L | H | H |
| 703 | H | H | H | H | H | L | H | H |
| 704 | L | L | L | L | L | H | H | L |
| 705 | H | H | L | H | H | L | L | H |
| 706 | L | L | L | L | H | L | L | L |
| 707 | L | H | L | L | H | L | L | L |
| 708 | L | L | L | L | H | L | L | L |
| 709 | L | H | L | L | L | L | L | L |
| 710 | H | H | H | H | H | L | L | H |
| 711 | H | H | H | H | H | L | H | H |
| 712 | H | H | H | H | H | L | H | H |
| 713 | H | H | H | H | H | L | H | H |
| 714 | H | H | H | H | H | L | H | H |
| 715 | H | H | H | H | H | L | H | H |
| 716 | H | H | H | H | H | L | H | H |
| 717 | H | H | H | H | H | L | H | H |
| 718 | H | H | H | H | H | L | H | H |
| 719 | H | H | H | H | H | L | H | H |
| 720 | H | H | H | H | H | L | H | H |
| 721 | H | H | H | H | H | L | L | H |
| 722 | H | H | H | H | H | L | H | H |
| 723 | H | H | H | H | H | L | H | H |
| 724 | H | H | H | L | H | L | L | H |
| 725 | H | H | H | H | H | L | L | H |
| 726 | H | H | H | H | H | L | L | H |
| 727 | H | H | H | H | L | L | L | H |
| 728 | H | H | H | H | H | L | H | H |
| 729 | H | H | H | H | H | L | L | H |
| 730 | H | H | H | H | H | L | L | H |

TABLE 6-continued

| Compound | Test A | Test B | Test C | Test D | Test E | Test F | Test G | Test H |
|---|---|---|---|---|---|---|---|---|
| 731 | H | H | H | H | H | H | H | H |
| 732 | H | H | H | L | H | L | L | H |
| 733 | H | H | H | H | H | L | H | H |
| 734 | H | H | H | H | H | L | H | H |
| 735 | H | H | H | H | H | L | H | H |
| 736 | H | H | H | H | H | L | H | H |
| 737 | H | H | H | L | H | L | H | H |
| 738 | H | H | H | H | H | L | L | H |
| 739 | H | H | H | H | H | L | H | H |
| 740 | H | H | H | L | H | L | H | H |
| 741 | H | H | H | H | H | L | H | H |
| 742 | H | H | H | H | H | L | H | H |
| 743 | H | H | H | H | H | L | L | L |
| 744 | H | L | L | L | H | L | L | L |
| 745 | H | H | H | H | H | L | H | H |
| 746 | H | H | H | H | H | L | L | H |
| 747 | H | H | H | H | H | L | L | H |
| 748 | H | L | H | L | H | L | L | L |
| 749 | L | H | H | L | H | L | L | L |
| 750 | H | H | H | H | H | L | H | H |
| 751 | H | H | H | H | H | L | L | H |
| 752 | H | H | H | H | H | L | H | H |
| 753 | H | H | H | H | H | L | H | H |
| 754 | H | H | H | H | H | L | L | H |
| 755 | H | H | H | H | H | L | H | H |
| 756 | H | H | H | H | H | L | H | H |
| 757 | H | H | H | H | H | L | H | H |
| 758 | H | H | H | H | H | H | H | H |
| 759 | H | H | H | H | H | L | L | H |
| 760 | H | H | H | H | H | L | L | H |
| 761 | H | H | H | H | H | L | L | H |
| 762 | H | H | H | H | H | H | H | H |
| 763 | H | H | H | H | H | H | H | H |
| 764 | H | H | H | H | H | L | L | H |
| 765 | H | H | H | L | H | L | L | H |
| 766 | H | H | H | L | H | L | L | H |
| 767 | H | H | H | L | H | L | L | H |
| 768 | H | H | H | H | H | L | H | H |
| 769 | H | H | H | H | H | L | L | H |
| 770 | H | H | H | L | H | L | L | H |
| 771 | H | H | H | H | H | L | H | H |
| 772 | H | H | H | H | H | H | H | H |
| 773 | H | H | H | H | H | L | H | H |
| 774 | H | H | H | H | H | L | L | H |
| 775 | H | H | H | L | H | L | L | H |
| 776 | H | L | L | L | L | L | L | L |
| 777 | H | H | H | H | H | L | H | H |
| 778 | H | H | H | H | H | L | H | H |
| 779 | H | H | H | H | H | L | H | H |
| 780 | H | H | H | H | H | L | L | H |
| 781 | H | H | H | H | H | L | H | H |
| 782 | H | H | H | H | H | L | H | H |
| 783 | H | H | H | H | H | L | H | H |
| 784 | H | H | H | H | H | L | H | H |
| 785 | H | H | H | H | H | H | H | H |
| 786 | H | H | H | H | H | H | H | H |
| 787 | H | H | H | L | H | L | L | H |
| 788 | H | H | H | L | H | L | L | H |
| 789 | H | H | H | H | H | L | L | H |
| 790 | H | H | H | H | H | L | H | H |
| 791 | H | H | H | H | H | L | L | H |
| 792 | H | H | H | L | H | H | H | H |
| 793 | H | H | H | H | H | L | L | H |
| 794 | H | H | H | H | H | L | H | H |
| 795 | H | H | H | H | H | L | H | H |
| 796 | H | H | H | H | H | L | H | H |
| 797 | H | H | H | H | H | L | L | H |
| 798 | H | H | H | H | H | L | L | H |
| 799 | H | H | H | H | H | L | H | H |
| 800 | H | H | H | H | H | L | H | H |
| 801 | H | H | H | H | H | L | H | H |
| 802 | H | H | H | H | H | L | H | H |
| 803 | H | H | H | H | H | H | H | H |
| 804 | H | H | H | H | H | L | L | H |
| 805 | H | H | H | H | H | L | L | H |
| 806 | H | H | H | H | H | H | H | H |
| 807 | H | H | H | L | H | L | L | H |
| 808 | H | H | H | L | H | L | L | H |

TABLE 6-continued

| Compound | Test A | Test B | Test C | Test D | Test E | Test F | Test G | Test H |
|---|---|---|---|---|---|---|---|---|
| 809 | H | H | H | L | H | L | L | H |
| 810 | H | H | H | L | H | L | H | H |
| 811 | H | H | H | L | H | L | L | H |
| 812 | H | H | H | H | H | L | H | H |
| 813 | H | H | H | H | H | L | L | H |
| 814 | H | H | H | H | H | L | L | H |
| 815 | H | H | H | H | H | L | L | H |
| 816 | H | H | H | H | H | L | L | H |
| 817 | H | H | H | H | H | L | L | H |
| 818 | H | H | H | H | H | L | H | H |
| 819 | H | H | H | H | H | H | H | H |
| 820 | H | H | H | H | H | L | H | H |
| 821 | H | H | H | H | H | L | H | H |
| 822 | H | H | H | L | H | L | L | H |
| 823 | H | H | H | H | H | L | L | H |
| 824 | H | H | H | H | H | L | H | H |
| 825 | H | H | H | H | H | L | H | H |

INDUSTRIAL APPLICABILITY

The pyridone compounds of the inventive are novel and can treat or prevent plant diseases, thus being valuable as pesticides.

The entire contents of Japanese Patent Application No. 2015-201578 (filed: Oct. 9, 2015) are incorporated herein by reference.

All publications, patent applications and technical standards mentioned in the present specification are herein incorporated by reference to the same extent as if each individual publication, patent application or technical standard was specifically and individually indicated to be incorporated by reference.

The invention claimed is:

1. A compound represented by Formula (1), or a salt thereof:

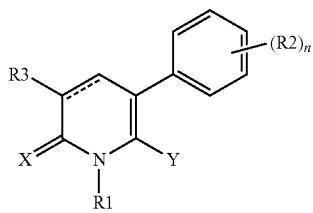

wherein R1 represents a hydroxy group,
a cyano group,
a C1-C6 alkyl group optionally substituted with substituent A,
a C1-C6 haloalkyl group,
a C3-C8 cycloalkyl group optionally substituted with substituent A,
a C2-C6 alkenyl group optionally substituted with substituent A,
a C2-C6 haloalkenyl group,
a C2-C6 alkynyl group optionally substituted with substituent A,
a C2-C6 haloalkynyl group,
a C1-C6 alkoxy group optionally substituted with substituent A,
a C1-C6 haloalkoxy group,
a C3-C8 cycloalkoxy group optionally substituted with substituent A,
a C2-C6 alkenyloxy group optionally substituted with substituent A,
a C2-C6 haloalkenyloxy group,
a C3-C6 alkynyloxy group optionally substituted with substituent A,
a C3-C6 haloalkynyloxy group, or
an R10R11N— (wherein R10 and R11 each independently represents a hydrogen atom or a C1-C6 alkyl group);
R2 represents a halogen atom,
a hydroxy group,
a cyano group,
a nitro group,
a C1-C6 alkyl group optionally substituted with substituent B,
a C1-C6 haloalkyl group,
a C3-C8 cycloalkyl group optionally substituted with substituent B,
a C2-C6 alkenyl group optionally substituted with substituent B,
a C2-C6 haloalkenyl group,
a C2-C6 alkynyl group optionally substituted with substituent B,
a C2-C6 haloalkynyl group,
a C1-C6 alkoxy group optionally substituted with substituent B,
a C1-C6 haloalkoxy group,
a C3-C8 cycloalkoxy group optionally substituted with substituent B,
a C2-C6 alkenyloxy group optionally substituted with substituent B,
a C2-C6 haloalkenyloxy group,
a C3-C6 alkynyloxy group optionally substituted with substituent B,
a C3-C6 haloalkynyloxy group,
an R20C(=O)— (wherein R20 represents a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or an R21R22N— (wherein R21 and R22 each independently represents a hydrogen atom, a C1-C6 alkyl group optionally substituted with substituent B1, a C1-C6 haloalkyl group or a C3-C8 cycloalkyl group, or R21 and R22 in combination with the nitrogen atom to which they are bonded form an aziridinyl group, an azetidinyl group, a pyrrolidinyl group, a piperidinyl group, a homopiperidinyl group or an azocanyl group)), an R20C(═O)O— (wherein R20 is the same as defined hereinabove),
a 3 to 6-membered ring group containing 1 to 2 oxygen atoms,
an R23-L2- (wherein R23 represents a C1-C6 alkyl group or a C1-C6 haloalkyl group, and L2 is S, SO or SO$_2$),
an R21R22N— (wherein R21 and R22 are the same as defined hereinabove), or
an R24C(═O)N(R25)- (wherein R24 represents a hydrogen atom, a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or an R21R22N— (wherein R21 and R22 are the same as defined hereinabove), and R25 represents a hydrogen atom, a C1-C6 alkyl group optionally substituted with substituent B1, a C1-C6 haloalkyl group or a C3-C8 cycloalkyl group);
R3 represents a hydrogen atom,
a halogen atom,
a nitro group,
a C1-C6 alkyl group optionally substituted with substituent C,
a C1-C6 haloalkyl group,
a C3-C8 cycloalkyl group optionally substituted with substituent C,
a C1-C6 alkoxy group optionally substituted with substituent C,
a C1-C6 haloalkoxy group,
a C2-C6 alkenyl group optionally substituted with substituent C,
a C2-C6 haloalkenyl group,
a C2-C6 alkynyl group optionally substituted with substituent C,
a C2-C6 haloalkynyl group,
an R30-L3- (wherein R30 has the same definition as R23, and L3 has the same definition as L2),
an R31R32N— (wherein R31 and R32 have the same definition as R21 and R22), or
an R33C(═O)— (wherein R33 represents a C1-C6 alkyl group, a C1-C6 haloalkyl group or a C3-C8 cycloalkyl group);
n represents an integer of 0 to 5 (with the proviso that when n is 2 or greater, the two or more R2's represent independent substituents);
X represents an oxygen atom or a sulfur atom;
Y represents a phenyl group, a pyridyl group, a pyridazinyl group, a pyrimidinyl group, a pyrazinyl group, a triazinyl group, a tetrazinyl group, a thienyl group, a thiazolyl group, an isothiazolyl group or a thiadiazolyl group,
the phenyl group is substituted with substituent D at an ortho position and is further substituted with 0 to 4 independent substituents D1 appropriately,
the pyridyl group, the pyrazinyl group, the pyrimidinyl group, the pyridazinyl group, the triazinyl group or the tetrazinyl group is substituted with substituent D at an ortho position and is further substituted with 0 to 3 independent substituents D1 appropriately,
the thienyl group, the thiazolyl group, the isothiazolyl group or the thiadiazolyl group is substituted with substituent D at an ortho position and is further substituted with 0 to 2 independent substituents D1 appropriately;
the bond with a broken line indicates a double bond or a single bond,
the substituent A is at least one selected from the group consisting of:

a hydroxy group, a cyano group, a C3-C8 cycloalkyl group, a C1-C6 alkoxy group, a C1-C6 haloalkoxy group, a C3-C8 cycloalkoxy group, an R12R13N— (wherein R12 and R13 each independently represents a hydrogen atom, a C1-C6 alkyl group, a C1-C6 haloalkyl group or a C3-C8 cycloalkyl group, or R12 and R13 in combination with the nitrogen atom to which they are bonded form an aziridinyl group, an azetidinyl group, a pyrrolidinyl group, a piperidinyl group, a homopiperidinyl group or an azocanyl group), and an R14-L1- (wherein R14 represents a C1-C6 alkyl group or a C1-C6 haloalkyl group, and L1 represents S, SO or SO$_2$);
the substituent B is at least one selected from the group consisting of:
a hydroxy group, a cyano group, a C3-C8 cycloalkyl group, a C1-C6 alkoxy group, a C1-C6 haloalkoxy group, a C3-C8 cycloalkoxy group, a C2-C6 alkoxyalkoxy group, an R21R22N— (wherein R21 and R22 are the same as defined hereinabove), an R23-L2- (wherein R23 and L2 are the same as defined hereinabove), an R26R27R28Si— (wherein R26, R27 and R28 each independently represents a C1-C6 alkyl group), an R26R27R28Si—(CH$_2$)s-O— (wherein s represents an integer of 1 to 3, and R26, R27 and R28 are the same as defined hereinabove), an R20C(═O)— (wherein R20 is the same as defined hereinabove) and a 3 to 6-membered ring group containing 1 to 2 oxygen atoms;
the substituent B1 is at least one selected from the group consisting of:
a cyano group, a C1-C6 alkoxy group, a C1-C6 haloalkoxy group and a C3-C8 cycloalkoxy group;
the substituent C is at least one selected from the group consisting of:
a hydroxy group, a cyano group, a C3-C8 cycloalkyl group, a C1-C6 alkoxy group, a C1-C6 haloalkoxy group, a C3-C8 cycloalkoxy group, an R31R32N— (wherein R31 and R32 have the same definition as R21 and R22) and an R30-L3- (wherein R30 has the same definition as R14, and L3 has the same definition as L1);
the substituent D is at least one selected from the group consisting of:
a halogen atom, a C1-C6 alkyl group, a C1-C6 haloalkyl group, a C1-C6 alkoxy group and a C1-C6 haloalkoxy group; and
the substituent D1 is at least one selected from the group consisting of:
a hydroxy group, a halogen atom, a C1-C6 alkyl group, a C1-C6 haloalkyl group, a C3-C8 cycloalkyl group, a C1-C6 alkoxy group, a C1-C6 haloalkoxy group and a C3-C8 cycloalkoxy group.

2. The compound or salt thereof according to claim 1, wherein
R1 represents a cyano group,
a C1-C6 alkyl group optionally substituted with substituent A,
a C1-C6 haloalkyl group,
a C3-C8 cycloalkyl group optionally substituted with substituent A,
a C2-C6 alkenyl group optionally substituted with substituent A,
a C2-C6 haloalkenyl group,
a C2-C6 alkynyl group optionally substituted with substituent A, or an R10R11N— (wherein R10 and R11 each independently represents a hydrogen atom or a C1-C6 alkyl group);

R2 represents a halogen atom,
a hydroxy group,
a cyano group,
a C1-C6 alkyl group optionally substituted with substituent B,
a C1-C6 haloalkyl group,
a C1-C6 alkoxy group optionally substituted with substituent B,
a C1-C6 haloalkoxy group,
a C3-C8 cycloalkoxy group optionally substituted with substituent B,
a C2-C6 alkenyloxy group optionally substituted with substituent B,
a C3-C6 alkynyloxy group optionally substituted with substituent B,
an R20C(=O)O— (wherein R20 represents a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or an R21R22N— (wherein R21 and R22 each independently represents a hydrogen atom, a C1-C6 alkyl group optionally substituted with substituent B1, a C1-C6 haloalkyl group or a C3-C8 cycloalkyl group, or R21 and R22 in combination with the nitrogen atom to which they are bonded form an aziridinyl group, an azetidinyl group, a pyrrolidinyl group, a piperidinyl group, a homopiperidinyl group or an azocanyl group), or
an R23-L2- (wherein R23 represents a C1-C6 alkyl group or a C1-C6 haloalkyl group, and L2 represents S, SO or SO$_2$);

R3 represents a hydrogen atom,
a halogen atom,
a C1-C6 alkyl group optionally substituted with substituent C,
a C3-C8 cycloalkyl group optionally substituted with substituent C,
a C1-C6 alkoxy group optionally substituted with substituent C,
a C2-C6 alkynyl group optionally substituted with substituent C, or
an R30-L3- (wherein R30 has the same definition as R23, and L3 has the same definition as L2);

Y represents a phenyl group or a pyridyl group,
the phenyl group is substituted with substituent D at an ortho position and is further substituted with 0 to 4 independent substituents D1 appropriately, and
the pyridyl group is substituted with substituent D at an ortho position and is further substituted with 0 to 3 independent substituents a1 appropriately.

3. The compound or salt thereof according to claim 2, wherein
R1 represents a C1-C6 alkyl group optionally substituted with substituent A, or a C1-C6 haloalkyl group;
R2 represents a halogen atom, a C1-C6 alkyl group optionally substituted with substituent B, or a C1-C6 alkoxy group optionally substituted with substituent B; and
R3 represents a hydrogen atom, a halogen atom, or a C1-C6 alkyl group optionally substituted with substituent C.

4. A compound represented by Formula (2), or a salt thereof:

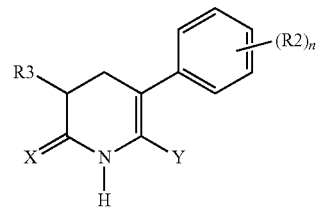

(2)

wherein R2 represents a halogen atom,
a hydroxy group,
a cyano group,
a nitro group,
a C1-C6 alkyl group optionally substituted with substituent B,
a C1-C6 haloalkyl group,
a C3-C8 cycloalkyl group optionally substituted with substituent B,
a C2-C6 alkenyl group optionally substituted with substituent B,
a C2-C6 haloalkenyl group,
a C2-C6 alkynyl group optionally substituted with substituent B,
a C2-C6 haloalkynyl group,
a C1-C6 alkoxy group optionally substituted with substituent B,
a C1-C6 haloalkoxy group,
a C3-C8 cycloalkoxy group optionally substituted with substituent B,
a C2-C6 alkenyloxy group optionally substituted with substituent B,
a C2-C6 haloalkenyloxy group,
a C3-C6 alkynyloxy group optionally substituted with substituent B,
a C3-C6 haloalkynyloxy group,
an R20C(=O)— (wherein R20 represents a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or an R21R22N— (wherein R21 and R22 each independently represents a hydrogen atom, a C1-C6 alkyl group optionally substituted with substituent B1, a C1-C6 haloalkyl group or a C3-C8 cycloalkyl group, or R21 and R22 in combination with the nitrogen atom to which they are bonded form an aziridinyl group, an azetidinyl group, a pyrrolidinyl group, a piperidinyl group, a homopiperidinyl group or an azocanyl group)),
an R20C(=O)O— (wherein R20 is the same as defined hereinabove),
a 3 to 6-membered ring group containing 1 to 2 oxygen atoms,
an R23-L2- (wherein R23 represents a C1-C6 alkyl group or a C1-C6 haloalkyl group, and L2 represents S, SO or SO$_2$),
an R21R22N— (wherein R21 and R22 are the same as defined hereinabove), or
an R24C(=O)N(R25)- (wherein R24 represents a hydrogen atom, a C1-C6 alkyl group, a C1-C6 haloalkyl group, a C3-C8 cycloalkyl group, a C1-C6 alkoxy group, a C1-C6 haloalkoxy group, a C3-C8 cycloalkoxy group or an R21R22N— (wherein R21 and R22 are the same as defined hereinabove), and R25 represents a hydrogen atom, a C1-C6 alkyl group optionally substituted with substituent B1, a C1-C6 haloalkyl group or a C3-C8 cycloalkyl group);

R3 represents a hydrogen atom,
a halogen atom,
a nitro group,
a C1-C6 alkyl group optionally substituted with substituent C,
a C1-C6 haloalkyl group,
a C3-C8 cycloalkyl group optionally substituted with substituent C,
a C1-C6 alkoxy group optionally substituted with substituent C,
a C1-C6 haloalkoxy group,
a C2-C6 alkenyl group optionally substituted with substituent C,
a C2-C6 haloalkenyl group,
a C2-C6 alkynyl group optionally substituted with substituent C,
a C2-C6 haloalkynyl group,
an R30-L3- (wherein R30 has the same definition as R23, and L3 has the same definition as L2),
an R31R32N— (wherein R31 and R32 have the same definition as R21 and R22), or
an R33C(=O)— (wherein R33 represents a C1-C6 alkyl group, a C1-C6 haloalkyl group or a C3-C8 cycloalkyl group);
n represents an integer of 0 to 5 (with the proviso that when n is 2 or greater, the two or more R2's represent independent substituents);
X represents an oxygen atom or a sulfur atom;
Y represents a phenyl group, a pyridyl group, a pyridazinyl group, a pyrimidinyl group, a pyrazinyl group, a triazinyl group, a tetrazinyl group, a thienyl group, a thiazolyl group, an isothiazolyl group or a thiadiazolyl group,
the phenyl group is substituted with substituent D at an ortho position and is further substituted with 0 to 4 independent substituents D1 appropriately, the pyridyl group, the pyrazinyl group, the pyrimidinyl group, the pyridazinyl group, the triazinyl group or the tetrazinyl group is substituted with substituent D at an ortho position and is further substituted with 0 to 3 independent substituents D1 appropriately, and the thienyl group, the thiazolyl group, the isothiazolyl group or the thiadiazolyl group is substituted with substituent D at an ortho position and is further substituted with 0 to 2 independent substituents D1 appropriately,
the substituent B is at least one selected from the group consisting of:
a hydroxy group, a cyano group, a C3-C8 cycloalkyl group, a C1-C6 alkoxy group, a C1-C6 haloalkoxy group, a C3-C8 cycloalkoxy group, a C2-C6 alkoxyalkoxy group, an R21R22N— (wherein R21 and R22 are the same as defined hereinabove), an R23-L2- (wherein R23 and L2 are the same as defined hereinabove), an R26R27R28Si— (wherein R26, R27 and R28 each independently represents a C1-C6 alkyl group), an R26R27R28Si—(CH$_2$)s-O— (wherein s represents an integer of 1 to 3, and R26, R27 and R28 are the same as defined hereinabove), an R20C(=O)— (wherein R20 is the same as defined hereinabove) and a 3 to 6-membered ring group containing 1 to 2 oxygen atoms;
the substituent B1 is at least one selected from the group consisting of:
a cyano group, a C1-C6 alkoxy group, a C1-C6 haloalkoxy group and a C3-C8 cycloalkoxy group;
the substituent C is at least one selected from the group consisting of:
a hydroxy group, a cyano group, a C3-C8 cycloalkyl group, a C1-C6 alkoxy group, a C1-C6 haloalkoxy group, a C3-C8 cycloalkoxy group, an R31R32N— (wherein R31 and R32 have the same definition as R21 and R22) and an R30-L3- (wherein R30 has the same definition as R23, and L3 has the same definition as L2);
the substituent D is at least one selected from the group consisting of:
a halogen atom, a C1-C6 alkyl group, a C1-C6 haloalkyl group, a C1-C6 alkoxy group and a C1-C6 haloalkoxy group; and
the substituent D1 is at least one selected from the group consisting of:
a hydroxy group, a halogen atom, a C1-C6 alkyl group, a C1-C6 haloalkyl group, a C3-C8 cycloalkyl group, a C1-C6 alkoxy group, a C1-C6 haloalkoxy group and a C3-C8 cycloalkoxy group.

5. An agricultural and horticultural pest control agent comprising the compound or salt thereof described in claim 1 as an active ingredient.

6. An agricultural and horticultural fungicide comprising the compound or salt thereof described in claim 1 as an active ingredient.

7. A method for treating or preventing a plant disease, comprising applying the agricultural and horticultural pest control agent described in claim 5 to a plant, a plant seed, or a soil for plant cultivation.

* * * * *